US006291514B1

(12) United States Patent
Illig et al.

(10) Patent No.: US 6,291,514 B1
(45) Date of Patent: Sep. 18, 2001

(54) HETEROARYL AMIDINES, METHYLAMIDINES AND GUANIDINES, PREPARATION THEREOF, AND USE THEREOF AS PROTEASE INHIBITORS

(75) Inventors: Carl R. Illig, Phoenixville; Nalin L. Subasinghe, West Chester; James B. Hoffman, Ardmore; Kenneth J. Wilson, Exton; M. Jonathan Rudolph, Doylestown; Juan José Marugán, Exton, all of PA (US)

(73) Assignee: 3-Dimensional Pharmaceuticals, Inc., Exton, PA (US)

( * ) Notice: Subject to any disclaimer, the term of this patent is extended or adjusted under 35 U.S.C. 154(b) by 0 days.

(21) Appl. No.: 09/372,748

(22) Filed: Aug. 11, 1999

Related U.S. Application Data

(63) Continuation-in-part of application No. 09/247,062, filed on Feb. 9, 1999.
(60) Provisional application No. 60/074,110, filed on Feb. 9, 1998.

(51) Int. Cl.[7] .................... A61K 31/38; A61K 31/425; A61K 31/47; A61K 31/44; C07D 333/36; C07D 409/00; C07D 277/04; C07D 215/38; C07D 411/00

(52) U.S. Cl. .................... 514/447; 514/444; 514/370; 514/314; 514/342; 549/68; 549/60; 548/198; 546/162; 546/280.4

(58) Field of Search .................... 549/68, 60; 514/447, 514/444, 370, 314, 342; 548/198; 546/162, 280.4

(56) References Cited

U.S. PATENT DOCUMENTS

| | | | |
|---|---|---|---|
| 4,220,654 | 9/1980 | Bolhofer et al. | 424/273 |
| 4,239,769 | * 12/1980 | Price et al. | 424/274 |
| 4,424,367 | * 1/1984 | Pelosi et al. | 549/74 |
| 4,634,783 | 1/1987 | Fugii et al. | 549/475 |
| 4,745,222 | 5/1988 | LeTourneau et al. | 564/305 |
| 4,906,282 | 3/1990 | Rorer | 71/92 |
| 4,912,199 | 3/1990 | Lown et al. | 530/331 |
| 5,084,466 | 1/1992 | Alig et al. | 514/353 |
| 5,874,472 | * 2/1999 | Shearer et al. | 514/565 |
| 6,057,342 | * 5/2000 | Fevig et al. | 514/340 |

FOREIGN PATENT DOCUMENTS

| | | |
|---|---|---|
| 24 58 973 A1 | 6/1976 | (DE). |
| 34 27 865 | 2/1986 | (DE). |
| 42 30 755 A1 | 3/1994 | (DE). |

(List continued on next page.)

OTHER PUBLICATIONS

Billström, A. et al., "The urokinase inhibitor p-aminobenzamidine inhibits growth of a human prostate tumor in SCID mice," *Int. J. Cancer* 61:542–547 (1995).

Bridges, A. J. et al., "The Synthesis of Three 4–Substituted Benzo[b]thiophene–2–Carboxamidines as Potent and Selective Inhibitors of Urokinase," *Bioorg. & Med. Chem.* 1:403–410 (1993).

Carmeliet, P. et al., "Urokinase but Not Tissue Plasminogen Activator Mediates Arterial Neointima Formation in Mice," *Circ. Res.* 81:829–839 (Nov. 1997).

Carmeliet, P. et al., "Inhibitory Role of Plasminogen Activator Inhibitor–1 in Arterial Wound Healing and Neointima Formation. A Gene Targeting and Gene Transfer Study in Mice," *Circulation* 96:3180–3191 (Nov. 1997).

Garrigues, B., "Synthesis of 5–functionalized 2–tert–butylthiophenes," CA 119:203252 (1993).

Rosowsky, A., et al., "Brominated trimetrexate analogs as inhibitors of Pneumocystis carinii and Toxoplasma gondii dihydrofolate reductase," *J. Heterocycl. Chem.* 33 (6):1959–1966 (1996).

English language abstract of Document AP5, DE 34 27 865, Derwent World Patents Index, Accession No. 1986–035121.

Lucas, A. et al., "Virus–Encoded Serine Proteinase Inhibitor SERP–1 Inhibits Atherosclerotic Plaque Development After Balloon Angioplasty," *Circulation* 94:2890–2900 (1996).

Rabbani, S.A. et al., "Prevention of prostrate–cancer metastasis in vivo by a novel synthetic inhibitor of urokinase–type plasminogen activator (uPA)," *Int. J. Cancer* 63:840–845 (1995).

Towle, M. J. et al., "Inhibition of Urokinase by 4–substituted Benzo[b]thiophene–2–carboxamidines: An Important New Class of Selective Synthetic Urokinase Inhibitor," *Cancer Res.* 53:2553–2559 (1993).

(List continued on next page.)

*Primary Examiner*—Deborah C. Lambkin
(74) *Attorney, Agent, or Firm*—Sterne, Kessler, Goldstein & Fox P.L.L.C.

(57) ABSTRACT

The present invention is directed to compounds of Formula I:

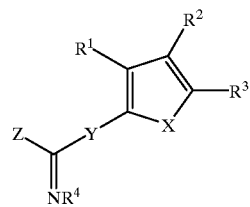

wherein X is O, S or $NR^7$ and $R^1$–$R^7$, Y and Z are set forth in the specification, as well as hydrates, solvates or pharmaceutically acceptable salts thereof. Also described are methods for preparing the compounds of Formula I. The novel compounds of the present invention are potent inhibitors of proteases, especially trypsin-like serine proteases, such as chymotrypsin, trypsin, plasmin and urokinase. Certain of the compounds exhibit direct, selective inhibition of urokinase, or are intermediates useful for forming compounds having such activity.

60 Claims, No Drawings

FOREIGN PATENT DOCUMENTS

| | | |
|---|---|---|
| 43 38 948 A1 | 5/1995 | (DE) . |
| 0 352 832 A1 | 1/1990 | (EP) . |
| 0 393 936 A1 | 10/1990 | (EP) . |
| 0 482 717 A1 | 4/1992 | (EP) . |
| 0 568 289 A2 | 11/1993 | (EP) . |
| 0 672 658 A1 | 9/1995 | (EP) . |
| 0 794 068 A1 | 9/1997 | (EP) . |
| 4-356029 | 12/1992 | (JP) . |
| 7-33729 | 2/1995 | (JP) . |
| 10-95771 | 4/1998 | (JP) . |
| 7415285 | 6/1975 | (NL) . |
| WO 92/14707 | 9/1992 | (WO) . |
| WO 93/06118 | 4/1993 | (WO) . |
| WO 93/16036 | 8/1993 | (WO) . |
| WO 94/28014 | 12/1994 | (WO) . |
| WO 95/00505 | 1/1995 | (WO) . |
| WO 95/04732 | 2/1995 | (WO) . |
| WO 95/11014 | 4/1995 | (WO) . |
| WO 96/22288 | 7/1996 | (WO) . |
| WO 96/40679 | 12/1996 | (WO) . |
| WO 98/37075 | 8/1998 | (WO) . |
| WO 99/32477 | 7/1999 | (WO) . |
| WO 99/40072 | 8/1999 | (WO) . |
| WO 99/40088 | 8/1999 | (WO) . |
| WO 99/50254 | 10/1999 | (WO) . |
| WO 99/50257 | 10/1999 | (WO) . |
| WO 99/50263 | 10/1999 | (WO) . |

OTHER PUBLICATIONS

Wang, Y. et al., "Amiloride modulates urokinase gene expression at both transcription and post–transcription levels in human colon cancer cells," *Clin. Exp. Metastasis* *13*:196–202 (1995).

Garrigues, B. et al., "Synthèse de 2–tert–butylthiophénes substituès en position 5," *Bull. Soc. Chim. Fr. 130*:58–63 (1993).

HCaplus database, American Chemical Society, English language abstract for Garrigues, B. et al., "Synthèse de 2–tert–butylthiophènes substitués en position 5," *Bull. Soc. Chim. Fr. 130*:58–63 (1993).

American Chemical Society STN Database Chemical Abstracts Service, Enriz, R. D. et al., "Theoretical Study of Cimetidine and Rigid Analogs," Database Accession No. 115:7781 (1991).

\* cited by examiner

HETEROARYL AMIDINES, METHYLAMIDINES AND GUANIDINES, PREPARATION THEREOF, AND USE THEREOF AS PROTEASE INHIBITORS

This application is a continuation-in-part of U.S. application Ser. No. 09/247,062, filed Feb. 9, 1999, herein fully incorporated by reference, which application claims benefit under 35 U.S.C. § 119(e) of U.S. Provisional Application No. 60/074,110, filed Feb. 9, 1998.

BACKGROUND OF THE INVENTION

1. Field of the Invention

The present invention relates to novel heteroaryl compounds that function as enzyme inhibitors, and particularly to a new class of non-peptidic inhibitors of proteolytic enzymes such as urokinase (uPa).

2. Related Art

Proteases are enzymes that cleave proteins at single, specific peptide bonds. Proteases can be classified into four generic classes: serine, thiol or cysteinyl, acid or aspartyl, and metalloproteases (Cuypers et al., *J. Biol. Chem.* 257:7086 (1982)). Proteases are essential to a variety of biological activities, such as digestion, formation and dissolution of blood clots, reproduction and the immune reaction to foreign cells and organisms. Aberrant proteolysis is associated with a number of disease states in man and other mammals. The human neutrophil proteases, elastase and cathepsin G, have been implicated as contributing to disease states marked by tissue destruction. These disease states include emphysema, rheumatoid arthritis, corneal ulcers and glomerular nephritis. (Barret, in *Enzyme Inhibitors as Drugs*, Sandler, ed., University Park Press, Baltimore, (1980)). Additional proteases such as plasmin, C-1 esterase, C-3 convertase, urokinase and tissue-type plasminogen activators, acrosin, and kallikreins play key roles in normal biological functions of mammals. In many instances, it is beneficial to disrupt the function of one or more proteolytic enzymes in the course of therapeutically treating a mammal.

Serine proteases include such enzymes as elastase (human leukocyte), cathepsin G, plasmin, C-1 esterase, C-3 convertase, urokinase and tissue-type plasminogen activators, acrosin, chymotrypsin, trypsin, thrombin, factor Xa and kallikreins.

Human leukocyte elastase is released by polymorphonuclear leukocytes at sites of inflammation and thus is a contributing cause for a number of disease states. Cathepsin G is another human neutrophil serine protease. Compounds with the ability to inhibit the activity of these enzymes are expected to have an anti-inflammatory effect useful in the treatment of gout, rheumatoid arthritis and other inflammatory diseases, and in the treatment of emphysema. Chymotrypsin and trypsin are digestive enzymes. Inhibitors of these enzymes are useful in treating pancreatitis. Inhibitors of urokinase plasminogen activator are useful in treating excessive cell growth disease states, such as benign prostatic hypertrophy, prostatic carcinoma and psoriasis.

Urokinase (urinary-type plasminogen activator or uPA; International Union of Biochemistry Classification Number: EC3.4.21.31) is a proteolytic enzyme which is highly specific for a single peptide bond in plasminogen. It is a multidomain serine protease, having a catalytic "B" chain (amino acids (aa) 144–411), and an amino-terminal fragment ("ATF", aa 1–143) consisting of a growth factor-like domain (4–43) and a Kringle domain (aa 47–135). The uPA Kringle domain appears to bind heparin, but not fibrin, lysine, or aminohexanoic acid. The growth factor-like domain bears some similarity to the structure of epidermal growth factor (EGF) and is thus also referred to as "EGF-like" domain. The single chain pro-uPA is activated by plasmin, cleaving the chain into a two-chain active form that is stabilized by a disulfide bond.

Cleavage of the peptide bond in plasminogen by urokinase ("plasminogen activation") results in the formation of a potent general protease, plasmin. Many cell types use urokinase as a key initiator of plasmin-mediated proteolytic degradation or modification of extracellular support structures (e.g., the extracellular matrix (ECM) and the basement membrane (BM)). Cells exist, move, and interact with each other in tissues and organs within the physical framework provided by the ECM and BM. Movement of cells within the ECM or across the BM requires local proteolytic degradation or modification of these structures, allowing cells to "invade" into adjacent areas that were previously unavailable.

Central to the ability of urokinase to mediate cellular migration and invasiveness is the existence of specific high affinity urokinase receptors (uPARs) which concentrate urokinase on the cell surface, leading to the generation of locally high plasmin concentrations between cells and ECM or BM (Blasi, F., et al., *Cell Biol.* 104:801–804 (1987); Roldan, A. L., et al., *EMBO J.* 9:467–74 (1990)). The binding interaction is apparently mediated by the EGF-like domain (Rabbani, S. A., et al., *J. Biol. Chem.* 267:14151–56 (1992)). Cleavage of pro-uPA into active uPA is accelerated when pro-uPA and plasminogen are receptor-bound. Thus, plasmin activates pro-uPA, which in turn activates more plasmin by cleaving plasminogen. This positive feedback cycle is apparently limited to the receptor-based proteolysis on the cell surface, since a large excess of protease inhibitors is found in plasma, including $\alpha_2$ antiplasmin, PAI-1 and PAI-2. High plasmin concentrations between invasive cells and ECM or BM are necessary in order to overcome inhibitory effect of these ubiquitous plasmin inhibitors. Thus, it is cell surface receptor-bound urokinase, and not simply free urokinase secreted by cells, which plays the predominant role in initiating cellular invasiveness.

Plasmin can activate or degrade extracellular proteins such as fibrinogen, fibronectin, and zymogens, including matrix metalloproteinases. Plasminogen activators thus can regulate extracellular proteolysis, fibrin clot lysis, tissue remodeling, developmental cell and smooth muscle cell migration, inflammation, and metastasis. Cellular invasiveness initiated by urokinase is central to a wide variety of normal and disease-state physiological processes (reviewed in Blasi, F., et al., *J. Cell Biol.* 104:801–804(1987); Dano, K., et al.,*Adv. Cancer Res.*44:139–266 (1985); Littlefield, B. A., *Ann. N. Y. Acad. Sci.* 622:167–175 (1991); Saksela, O., *Biochim. Biophys. Acta* 823:35–65 (1985); Testa, J. E., and Quigley, J. P., *Cancer Metast. Rev.* 9:353–367 (1990)). Such processes include, but are not limited to, angiogenesis (neovascularization), bone restructuring, embryo implantation in the uterus, infiltration of immune cells into inflammatory sites, ovulation, spermatogenesis, tissue remodeling during wound repair, restenosis and organ differentiation, fibrosis, local invasion of tumors into adjacent areas, metastatic spread of tumor cells from primary to secondary sites, and tissue destruction in arthritis. Inhibitors of urokinase therefore have mechanism-based anti-angiogenic, anti-arthritic, anti-inflammatory, anti-restenotic, anti-invasive, anti-metastatic, anti-osteoporotic, anti-retinopathic (for angiogenesis-dependent retinopathies), contraceptive, and tumoristatic activities. Inhibitors of urokinase are useful agents in the treatment of a variety of disease states, including but not limited to, benign prostatic hypertrophy, prostatic carcinoma and psoriasis.

Beneficial effects of urokinase inhibitors have been reported using anti-urokinase monoclonal antibodies and certain other known urokinase inhibitors. For instance, anti-urokinase monoclonal antibodies have been reported to block tumor cell invasiveness in vitro (Hollas, W., et al., *Cancer Res.* 51:3690–3695, (1991); Meissauer, A., et al., *Exp. Cell Res.* 192:453–459 (1991)), tumor metastasis and invasion in vivo (Ossowski, L., *J. Cell Biol.* 107:2437–2445 (1988); Ossowski, L., et al., *J. Cancer Res.* 51:274–81 (1991)), and angiogenesis in vivo (Jerdan, J. A., et al., *J. Cell Biol.* 115[3 Pt 2]:402a (1991)). In addition, amiloride, a known urokinase inhibitor of only moderate potency, has been reported to inhibit tumor metastasis in vivo (Kellen, J. A., et al., *Anticancer Res.* 8:1373–1376 (1988)) and angiogenesis/capillary network information in vitro (Alliegro, M. A., et al., *J. Cell Biol.* 115[3 Pt 2]:402a (1991)).

Urokinase plays a significant role in vascular wound healing and arterial neointima formation after injury, most likely affecting cellular migration. Urokinase mediates plasmin proteolysis, which in turn promotes vascular wound-healing and associated neointima formation (Carmeliet et al., *Circ. Res.* 81:829–839 (November 1997), Lupu et al., *Fibrinolysis* 10 Supp 2:33–35 (1996)). A viral serine proteinase inhibitor, SERP-1, has been employed to reduce plaque formation after primary balloon angioplasty in rabbits. This activity has been attributed to the inhibition by SERP-1 of cellular proteinases, such as plasmin or urokinase (Lucas et al., *Circulation* 94:2890–2900 (1996)).

A need continues for non-peptidic compounds that are potent and selective urokinase inhibitors, and which possess greater bioavailability and fewer side-effects than currently available urokinase inhibitors. Accordingly, new classes of potent urokinase inhibitors, characterized by potent inhibitory capacity and low toxicity, are potentially valuable therapeutic agents for a variety of conditions.

SUMMARY OF THE INVENTION

The present invention is broadly directed to the use of heteroaryl amidines, methylamidines and guanidines having Formula I (below) as protease inhibitors, preferably as urokinase inhibitors.

Compounds of the present invention exhibit anti-urokinase activity via direct, selective inhibition of urokinase, or are intermediates useful for forming compounds having such activity. Compounds of the present invention inhibit urokinase and are, therefore, useful anti-angiogenic, anti-arthritic, anti-inflammatory, anti-restenotic, anti-invasive, anti-metastatic, anti-osteoporotic, anti-retinopathic (for angiogenesis-dependent retinopathies), contraceptive, and tumoristatic treatment agents. For example, such treatment agents are useful in the treatment of a variety of disease states, including but not limited to, benign prostatic hypertrophy, prostatic carcinoma, tumor metastasis and psoriasis.

Also provided are methods to inhibit extracellular proteolysis, methods to treat benign prostatic hypertrophy, prostatic carcinoma, tumor metastasis, psoriasis, and other conditions by administering the compound of Formula I.

A number of the heteroaryl compounds described herein are novel compounds. Therefore, the present invention is also directed to novel compounds of Formula I.

Further provided are pharmaceutical compositions comprising a compound of Formula I and one or more pharmaceutically acceptable carriers or diluents and said pharmaceutical compositions further comprising a thrombolytic agent such as tissue plasminogen activator and streptokinase.

Further provided are methods of synthesizing compounds of Formula I.

DETAILED DESCRIPTION OF THE PREFERRED EMBODIMENTS

The present invention is broadly directed to a method of inhibiting proteases, particularly serine proteases, by contacting a serine protease with a compound of the general Formula I:

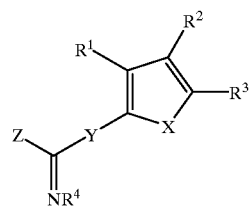

or a solvate, hydrate or pharmaceutically acceptable salt thereof, wherein:

X is O, S or $NR^7$, where $R^7$ is hydrogen, alkyl, aralkyl, hydroxy($C_{2-4}$)alkyl, or alkoxy($C_{2-4}$)alkyl;

Y is a direct covalent bond, $CH_2$ or NH;

Z is $NR^5R^6$, hydrogen or alkyl, provided that Y is NH whenever Z is hydrogen or alkyl;

$R^1$ is hydrogen, amino, hydroxy, halogen, cyano, $C_{1-4}$ alkyl or —$CH_2R$, where R is hydroxy, amino or $C_{1-3}$ alkoxy;

$R^2$ and $R^3$ are independently:
  i. hydrogen;
  ii. halogen;
  iii. hydroxy;
  iv. nitro;
  v. cyano;
  vi. amino, monoalkylamino, dialkylamino, monoarylamino, diarylamino, monoalkylmonoarylamino, monoaralkylamino, diaralkylamino, monoalkylmonoaralkylamino, monoheterocycleamino, diheterocycleamino, monoalkylmonoheterocycleamino, alkoxycarbonylamino, aralkoxycarbonylamino, aryloxycarbonylamino, alkylsulfonylamino, aralkylsulfonylamino, aralkenylsulfonylamino, arylsulfonylamino, heteroarylsulfonylamino, di(aralkylsulfonyl)amino, di(aralkenylsulfonyl)amino, di(arylsulfonyl)amino, or di-(heteroarylsulfonyl)amino, formylamino, alkanoylamino, alkenoylamino, alkynoylamino, aroylamino, aralkanoylamino, aralkenoylamino, heteroaroylamino, heteroaralkanoylamino, H(S)CNH—, or thioacylamino, wherein any of the aryl or heteroaryl containing groups can be optionally substituted on the aromatic ring and wherein any of the heterocycle containing groups can be optionally ring substituted;
  vii. aminocarbonyl, monoalkylaminocarbonyl, dialkylaminocarbonyl, acyl, aminoacyl, monoarylaminocarbonyl, diarylaminocarbonyl or monoalkylmonoarylaminocarbonyl;

viii. aminothiocarbonyl, monoalkylaminothiocarbonyl, dialkylaminothiocarbonyl, thioacyl or aminothioacyl;
ix. aminocarbonylamino, mono- and dialkylaminocarbonylamino, mono- and diarylaminocarbonylamino, or mono- and diaralkylaminocarbonylamino;
x. aminocarbonyloxy, mono- and dialkylaminocarbonyloxy, mono- and diarylaminocarbonyloxy, mono- and diaralkylaminocarbonyloxy;
xi. aminosulfonyl, mono- and dialkylaminosulfonyl, mono- and diarylaminosulfonyl, or mono- and diaralkylaminosulfonyl;
xii. alkoxy, or alkylthio, wherein the alkyl portion of each group may be optionally substituted,
xiii. aralkoxy, aryloxy, heteroaryloxy, aralkylthio, arylthio, or heteroarylthio, wherein the aryl portion of each group can be optionally substituted;
xiv. alkylsulfonyl, wherein the alkyl portion can be optionally substituted;
xv. aralkylsulfonyl, aralkenylsulfonyl, arylsulfonyl or heteroarylsulfonyl, wherein the aryl portion of each group can be optionally substituted;
xvi. alkenyl, or alkynyl;
xvii. optionally substituted aryl;
xviii. optionally substituted alkyl;
xix. optionally substituted aralkyl;
xx. optionally substituted heterocycle; or
xxi. optionally substituted cycloalkyl; and $R^4$, $R^5$ and $R^6$ are independently hydrogen, $C_{1-4}$ alkyl, aryl, hydroxyalkyl, aminoalkyl, monoalkylamino $(C_{2-10})$alkyl, dialkylamino$(C_{2-10})$alkyl, carboxyalkyl, cyano, amino, alkoxy, or hydroxy, or —$CO_2R^w$, where $R^w$ is alkyl, cycloalkyl, phenyl, benzyl,

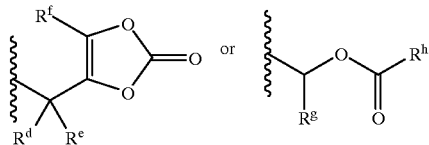

where $R^d$ and $R^e$ are independently hydrogen, $C_{1-6}$ alkyl, $C_{2-6}$ alkenyl or phenyl, $R^f$ is hydrogen, $C_{1-6}$ alkyl, $C_{2-6}$ alkenyl or phenyl, $R^g$ is hydrogen, $C_{1-6}$ alkyl, $C_{2-6}$ alkenyl or phenyl, and $R^h$ is aralkyl or $C_{1-6}$ alkyl.

The present invention is also directed to novel compounds of Formula I, where X, Y and $R^1$–$R^6$ are as defined above; provided that at least one of $R^2$ or $R^3$ is selected from the group consisting of:
(a) an optionally substituted alkyl group, preferably $C_1$–$C_6$ alkyl, more preferably $C_1$–$C_3$;
(b) alkoxy, aryloxy, alkylthio or arylthio, any of which is optionally substituted;
(c) optionally substituted $C_6$–$C_{14}$ aryl, or optionally substituted aralkyl, except that $R^3$ is not nitrophenyl or aminophenyl, when $R^1$ and $R^2$ are both hydrogen or methyl;
(d) optionally substituted heterocycle; and
(e) optionally substituted cycloalkyl.

When an alkyl-containing group, heterocyclic-containing group or aryl-containing group of $R^2$ or $R^3$ is optionally substituted, the optional substituents can be 1 to 4 non-hydrogen substituents, provided that the resulting compound is stable. Values of optional substituents on alkyl groups are halogen, hydroxy, thiol, amino, monoalkylamino, dialkylamino, formylamino, aminoiminomethyl, acylamino, aminoacyl, mono- or di-alkylaminocarbonyl, thiocarbonylamino, thioacylamino, aminothiocarbonyl, alkoxy, aryloxy, aminocarbonyloxy, mono- or di-alkylaminocarbonyloxy, mono- or diarylaminocarbonyloxy, mono- or diaralkylaminocarbonyloxy, alkylsulfonyl, arylsulfonyl, aralkylsulfonyl, alkylsulfonylamino, arylsulfonylamino, aralkylsulfonylamino, alkoxycarbonylamino, aralkoxycarbonylamino, aryloxycarbonylamino, mono- or di-alkylaminothiocarbonyl, aralkoxy, carboxy, carboxyalkyl, alkoxycarbonyl, alkoxycarbonylalkyl, nitro, cyano, trifluoromethyl, alkylthio and arylthio.

Preferred values of optional substituents on an alkyl group are chloro, hydroxy, amino, mono($C_{1-4}$)alkylamino, di($C_{1-4}$) alkylamino, formylamino, $C_{2-6}$ acylamino, aminocarbonyl, $C_{2-8}$ aminoacyl, $C_{1-6}$ alkoxy, $C_{6-14}$ aryloxy, carboxy, carboxy($C_{1-6}$)alkyl, $C_{2-8}$ alkoxycarbonyl, nitro, cyano, trifluoromethyl, $C_{1-6}$ alkylthio, $C_{6-14}$ arylthio, Cl-$_6$ alkylsulfonylamino, $C_{7-15}$ aralkylsulfonylamino, $C_{6-10}$ arylsulfonylamino, mono- or di($C_{1-6}$) alkylaminocarbonyloxy, mono- or di($C_{6-10}$) arylaminocarbonyloxy, mono- or di($C_{7-15}$) aralkylcarbonyloxy, $C_{1-6}$ alkoxycarbonylamino, $C_7$–$C_{15}$ aralkoxycarbonylamino, and $C_6$–$C_{10}$ aryloxycarbonylamino.

Preferred values of optional substituents on aryl-containing and heterocyclic-containing groups include chloro, hydroxy, amino, mono($C_{1-4}$) alkylamino, di($C_{1-4}$) alkylamino, formylamino, $C_{2-6}$ acylamino, aminocarbonyl, $C_{2-8}$ aminoacyl, $C_{3-7}$ cycloalkyl, $C_{1-6}$ alkyl, $C_{1-6}$ alkoxy, $C_{6-14}$ aryloxy, carboxy, carboxy($C_{1-6}$)alkyl, $C_{2-8}$ alkoxycarbonyl, nitro, cyano, trifluoromethyl, $C_{1-6}$ alkylthio, $C_{6-14}$ arylthio, $C_{6-14}$ aryl, substituted phenyl, tetrazolyl, thienyl (further optionally substituted by one, two or three of chloro, hydroxy, $C_{1-4}$ alkyl, $C_{1-4}$ alkoxy, amino or carboxy), 3,4-methylenedioxy, 3,4-ethylenedioxy, 3,4-propylenedioxy, $C_{1-6}$ alkylsulfonylamino, $C_{7-15}$ aralkylsulfonylamino, $C_{1-6}$ arylsulfonylamino, $C_{1-6}$ alkyl/sulfonyl, $C_{6-10}$ arylsulfonyl, mono- or di($C_{1-6}$) alkylaminocarbonyloxy, mono- or di-$C_{6-10}$ arylaminocarbonyloxy, mono- or di-($C_{7-15}$) aralkylcarbonyloxy, $C_{1-6}$ alkoxycarbonylamino, $C_7$–$C_{15}$ aralkoxycarbonylamino, $C_6$–$C_{10}$ aryloxycarbonylamino, $C_{2-6}$ thioacylamino, aminothiocarbonyl, and $C_{2-8}$ aminothioacyl.

Preferred values of $R^1$ include hydrogen, amino, hydroxy and fluoro.

A preferred value of $R^2$ is Formula II:

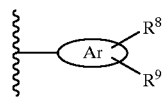

II where Ar is phenyl, thiazolyl, thiazolinyl, oxazolyl, isothiazolyl, isoxazolyl, imidazolyl, pyridyl, pyrimidinyl, pyrazinyl, thienyl (thiophenyl), pyrrolyl, oxazolinyl and benzothienyl.

Preferred values of $R^3$ include $C_{1-4}$ alkyl (optionally substituted), halogen, amino, acylamino, $C_{1-6}$ alkylthio (such as methylthio or ethylthio), $C_{1-6}$ alkoxy (such as methoxy and ethoxy), trifluoromethyl, methylsulfonyl, and benzylthio.

A preferred value of X is divalent sulfur (S).

Preferred values of Y are a covalent bond or —NH—, most preferably a covalent bond.

Preferred values of $R^4$, $R^5$ and $R^6$ in Formula I are hydrogen, hydroxy, cyano, $C_{1-6}$ alkyl, or $C_{1-6}$ alkoxy. Suitable values of $R^4$, $R^5$ and $R^6$ include hydrogen, methyl, ethyl, propyl, n-butyl, hydroxy, methoxy, and ethoxy. In the most preferred embodiments, $R^4$, $R^5$ and $R^6$ are each hydrogen.

Preferred values of $R^4$, $R^5$ and $R^6$ in Formula I also include prodrugs such as —$CO_2R^w$, where $R^w$, in each instance, is preferably one of $C_{1-4}$alkyl, $C_{4-7}$cycloalkyl or benzyloxycarbonyl. Suitable values of $R^4$, $R^5$ and $R^6$ include hydrogen, methyl, ethyl, propyl, n-butyl, hydroxy, methoxy, ethoxy, cyano, —$CO_2CH_3$, —$O_2CH_2CH_3$ and —$CO_2CH_2CH_2CH_3$. In the most preferred embodiments, $R^4$, $R^5$ and $R^6$ are each hydrogen.

Also preferred at $R^4$, $R^5$ and $R^6$ is the group —$CO_2R^w$, where $R_w$ is one of

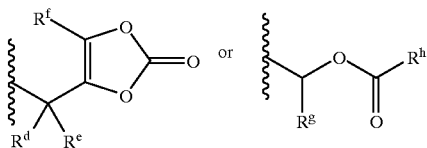

where $R^d$–$R^h$ are defined as above. When $R^4$, $R^5$ and $R^6$ are —$CO_2R^w$, where $R^w$ is one of one of these moieties, the resulting compounds are prodrugs that possess desirable formulation and bioavailability characteristics. A preferred value for each of $R^d$, $R^e$ and $R^g$ is hydrogen, $R^f$ is methyl, and preferred values for $R^h$ include benzyl and tert-butyl.

Preferred values of $R^7$ include hydrogen, $C_{1-6}$ alkyl, $C_{6-10}$ ar($C_{1-4}$)alkyl, and $C_{2-6}$ hydroxyalkyl. Suitable values are hydrogen, methyl, ethyl, and benzyl.

The term "alkyl" as employed herein by itself or as part of another group refers to both straight and branched chain radicals of up to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl.

The term "alkenyl" is used herein to mean a straight or branched chain radical of 2–20 carbon atoms, unless the chain length is limited thereto, including, but not limited to, ethenyl, 1-propenyl, 2-propenyl, 2-methyl-1-propenyl, 1-butenyl, 2-butenyl, and the like. Preferably, the alkenyl chain is 2 to 10 carbon atoms in length, more preferably, 2 to 8 carbon atoms in length most preferably from 2 to 4 carbon atoms in length.

The term "alkynyl" is used herein to mean a straight or branched chain radical of 2–20 carbon atoms, unless the chain length is limited thereto, wherein there is at least one triple bond between two of the carbon atoms in the chain, including, but not limited to, acetylene, 1-propylene, 2-propylene, and the like. Preferably, the alkynyl chain is 2 to 10 carbon atoms in length, more preferably, 2 to 8 carbon atoms in length, most preferably from 2 to 4 carbon atoms in length.

In all instances herein where there is an alkenyl or alkynyl moiety as a substituent group, the unsaturated linkage, i.e., the vinylene or acetylene linkage is preferably not directly attached to a nitrogen, oxygen or sulfur moiety.

The term "alkylthio" as employed herein by itself or as part of another group refers to a straight or branched chain radical of 1 to 20 carbon atoms, unless the chain length is limited thereto, bonded to a sulfur atom, including, but not limited to, methylthio, ethylthio, n-propylthio, isopropylthio, and the like. Preferably the alkylthio chain is 1 to 10 carbon atoms in length, more preferably 1 to 8 carbon atoms in length.

The term "alkoxy" as employed herein by itself or as part of another group refers to a straight or branched chain radical of 1 to 20 carbon atoms, unless the chain length is limited thereto, bonded to an oxygen atom, including, but not limited to, methoxy, ethoxy, n-propoxy, isopropoxy, and the like. Preferably the alkoxy chain is 1 to 10 carbon atoms in length, more preferably 1 to 8 carbon atoms in length.

The term "cycloalkyl" as employed herein by itself or as part of another group refers to cycloalkyl groups containing 3 to 9 carbon atoms. Typical examples are cyclopropyl, cyclobutyl, cyclopentyl, cyclohexyl, cycloheptyl, cyclooctyl and cyclononyl.

The term "halogen" or "halo" as employed herein by itself or as part of another group refers to chlorine, bromine, fluorine or iodine with chlorine being preferred.

The term "acyl" as employed herein by itself or as part of another group refers to the group —$C(O)R^g$ where $R^g$ is alkyl, alkenyl, alkynyl, aryl, aralkyl, aralkenyl, heteroaryl, heteroarylalkyl or heteroarylalkenyl. Preferred acyl groups are alkanoyl, aralkanoyl and aroyl groups (—$C(O)R^g$ where $R^g$ is $C_{1-8}$ alkyl, $C_{6-10}$ aryl($C_{1-4}$)alkyl or $C_{6-10}$ aryl).

The term "thioacyl" as employed herein by itself or as part of another group refers to the group —$C(S)R^g$ where $R^g$ is alkyl, alkenyl, alkynyl, aryl, aralkyl, aralkenyl, heteroaryl, heteroarylalkyl or heteroarylalkenyl, preferably $C_{1-8}$ alkyl.

The term "thiocarbonyl" as employed herein by itself or as part of another group refers to the group —$C(S)$—.

The term "monoalkylamine" as employed herein by itself or as part of another group refers to an amino group which is substituted with one alkyl group having from 1 to 6 carbon atoms.

The term "dialkylamine" as employed herein by itself or as part of another group refers to an amino group which is substituted with two alkyl groups, each having from 1 to 6 carbon atoms The term "aryl" as employed herein by itself or as part of another group refers to monocyclic or bicyclic aromatic groups containing from 6 to 14 carbons in the ring portion, preferably 6–10 carbons in the ring portion, such as phenyl, naphthyl or tetrahydronaphthyl.

The term "aralkyl" or "arylalkyl" as employed herein by itself or as part of another group refers to $C_{1-6}$alkyl groups as discussed above having an aryl substituent, such as benzyl, phenylethyl or 2-naphthylmethyl.

The terms "heterocyclic," "heterocyclo" or "heterocycle" as employed herein by themselves or as part of larger groups refers to a saturated or wholly or partially unsaturated 3–7 membered monocyclic, or 7–10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable. Especially useful are rings containing one oxygen or sulfur, one to three nitrogen atoms, or one oxygen or sulfur combined with one or two nitrogen atoms. Examples of such heterocyclic groups include piperidinyl, piperazinyl, 2-oxopiperazinyl, 2-oxopiperidinyl, 2-oxopyrrolodinyl, 2 -oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, indanyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

The term "heteroatom" is used herein to mean an oxygen atom ("O"), a sulfur atom ("S") or a nitrogen atom ("N"). It will be recognized that when the heteroatom is nitrogen, it may form an $NR^yR^z$ moiety, wherein $R^y$ and $R^z$ are, independently from one another, hydrogen or $C_1$ to $C_8$ alkyl, or together with the nitrogen to which they are bound, form a saturated or unsaturated 5-, 6-, or 7-membered ring.

The term "heteroaryl" as employed herein refers to groups having 5 to 14 ring atoms; 6, 10 or 14π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2, 3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The expression "prodrug" denotes a derivative of a known direct acting drug, which derivative has enhanced delivery characteristics and therapeutic value as compared to the drug, and is transformed into the active drug by an enzymatic or chemical process. Useful prodrugs are those where $R^4$, $R^5$ and/or $R^6$ are —$CO_2R^w$, where $R^w$ is defined above. See, U.S. Pat. No. 5,466,811 and Saulnier et al., *Bioorg. Med. Chem. Lett.* 4:1985–1990 (1994).

The term "substituted", as used herein, means that one or more hydrogens of the designated moiety are replaced with a selection from the indicated group, provided that no atom's normal valency is exceeded, and that the substitution results in a stable compound. When a substituent is keto (i.e., =O), then 2 hydrogens attached to an atom of the moiety are replaced.

By "stable compound" or "stable formula" is meant herein a compound that is sufficiently robust to survive isolation to a useful degree of purity from a reaction mixture and formulation into an efficacious therapeutic agent.

A first preferred group of compounds falling within the scope of the present invention include compounds of Formula I wherein X is sulfur or oxygen; Y is a covalent bond or —NH—; $R^1$ is hydrogen, amino, hydroxy or halogen; $R^4$, $R^5$ and $R^6$ are independently hydrogen, $C_{1-4}$ alkyl, amino, cyano, $C_{1-4}$ alkoxy or hydroxy, and are preferably all hydrogen; one of $R^2$ or $R^3$ is hydrogen, $C_{1-6}$ alkyl (optionally substituted with hydroxy, amino, carboxy or aminocarbonyl), $C_{1-6}$ alkylthio or $C_{1-6}$ alkoxy; and the other of $R^2$ or $R^3$ is aminoacyl, acylamino, aminosulfonyl, sulfonylamino, aminocarbonylamino, alkoxycarbonylamino, optionally substituted oxazolyl, optionally substituted isoxazolyl, optionally substituted benzothienyl, optionally substituted furanyl, optionally substituted pyrazolyl or optionally substituted pyridyl.

Specific compounds within the scope of the invention include the compounds described in the Examples, such as the following:

4-[4-(4-chlorophenyl)thiazol-2-yl]-5-methylthiothiophene-2-carboxamidine;
4-phenyl-5-methylthiothiophene-2-carboxamidine;
4-[4-(2,4-dichlorophenyl)thiazol-2-yl]-5-methylthiothiophene-2-carboxamidine;
4-(4-methylthiazol-2-yl)-5-methylthiothiophene-2-carboxamidine; methyl 4-[4-(4-phenylphenyl)thiazol-2-yl]-5-methylthiothiophene-2-carboxylate;
4-[4-(3-methoxyphenyl)thiazol-2-yl]-5-methylthiothiophene-2-carboxamidine,
4-[4-(3-hydroxyphenyl)thiazol-2-yl]-5-methylthiothiophene-2-carboxamidine,
4-(4-phenylthiazol-2-yl)-5-methylthiothiophene-2-carboxamidine,
4-[4-(4-nitrophenyl)thiazol-2-yl]-5-methylthiothiophene-2-carboxamidine,
4-[4-(3,4-ethylenedioxyphenyl)thiazol-2-yl]-5-methylthiothiophene-2-carboxamidine,
4-[4-(3,4-propylenedioxyphenyl)thiazol-2-yl]-5-methylthiothiophene-2-carboxamidine,
4-[4-(4-(naphth-2-yl)thiazol-2-yl]-5-methylthiothiophene-2-carboxamidine,
4-isopropylsulfonyl-5-methylthiothiophene-2-carboxamidine;
4-phenyl-5-methylthiothiophene-2-carboxamidine;
4-[4-(4-chlorophenyl)thiazol-2-yl]-5-methylthiothiophene-2-carboxamidine;
4-[4-(4-phenylphenyl)thiazol-2-yl]-5-methylthiothiophene-2-carboxamidine;
4-[4-(4-methoxyphenyl)thiazol-2-yl]-5-methylthiothiophene-2-carboxamidine;
4-(2-naphthylthiazol-2-yl)-5-methylthiothiophene-2-carboxamidine;
4-[4-(4-chloro-3-methylphenyl)thiazol-2-yl]-5-methylthiothiophene-2-carboxamidine;
4-(5-methyl-4-phenylthiazol-2-yl)-5-methylthiothiophene-2-carboxamidine;
4-[4-(4-chloro-3-nitrophenyl)thiazol-2-yl]-5-methylthiothiophene-2-carboxamidine;
4-(5-phenyloxazol-2-yl)-5-methylthiothiophene-2-carboxamidine;
4-[4-(3-fluoro-5-trifluoromethylphenyl)-5-methylthiazol-2-yl]-5-methylthiothiophene-2-carboxamidine;
4-[4-(3,5-bis(trifluoromethyl)phenyl)-5-methyl-thiazol-2-yl]-5-methylthiothiophene-2-carboxamidine;
4-[4-(3-fluoro-5-trifluoromethylphenyl)thiazol-2-yl]-5-methylthiothiophene-2-carboxamidine;
4-[4-(3-bromophenyl)thiazol-2-yl]-5-methylthiothiophene-2-carboxamidine;
4-[4-(3,4-methylenedioxyphenyl)thiazol-2-yl]-5-methylthiothiophene-2-carboxamidine;
4-[4-(4-methylphenyl)thiazol-2-yl]-5-methylthiothiophene-2-carboxamidine;
4-[4-(3,5-bis(trifluoromethyl)phenyl)thiazol-2-yl]-5-methylthiothiophene-2-carboxamidine;
4-[4-(2-methoxyphenyl)thiazol-2-yl]-5-methylthiothiophene-2-carboxamidine;
4-(4-phenylimidazol-2-yl)-5-methylthiothiophene-2-carboxamidine;
4-[4-(2,4-dimethoxyphenyl)thiazol-2-yl]-5-methylthiothiophene-2-carboxamidine;
4-(4-benzylthiazol-2-yl)-5-methylthiothiophene-2-carboxamidine;
4-[4-(3,4-dichlorophenyl)thiazol-2-yl]-5-methylthiothiophene-2-carboxamidine;
4-[4-(3-methylphenyl)thiazol-2-yl]-5-methylthiothiophene-2-carboxamidine;

4-[4-(3,5-dimethoxyphenyl)thiazo-2-yl]-5-methylthiothiophene-2-carboxamidine;
4-[4-(2-methylphenyl)thiazol-2-yl]-5-methylthiothiophene-2-carboxamidine;
4-[4-(2,5-dimethoxyphenyl)thiazol-2-yl]-5-methylthiothiophene-2-carboxamidine;
4-(4,5-diphenylthiazol-2-yl)-5-methylthiothiophene-2-carboxamidine;
4-(2-phenyl)thiazol-4-yl-5-methylthiothiophene-2-carboxamidine;
4-[4-(2-chloro-3-pyridyl)thiazol-2-yl]-5-methylthiothiophene-2-carboxamidine;
4-[4-phenoxymethyl)thiazol-2-yl]-5-methylthiothiophene-2-carboxamidine;
4-(4-cyclohexylthiazol-2-yl)-5-methylthiothiophene-2-carboxamidine;
4-[4-(4-chlorophenyl)thiazol-2-yl]-5-methylthiothiophene-2-carboxamidine;
4-[4-(2-hydroxyphenyl)thiazol-2-yl]-5-methylthiothiophene-2-carboxamidine;
4-[4-(3-trifluoromethoxyphenyl)thiazol-2-yl]-5-methylthiothiophene-2-carboxamidine;
4-[4-chloro-4-pyridyl)thiazol-2-yl]-5-methylthiothiophene-2-carboxamidine;
4-(5-phenyl-2-pyridyl)-5-methylthiothiophene-2-carboxamidine;
4-[2-(2-chloro phenylamino)thiazol-4-yl]-5-methylthiothiophene-2-carboxamidine;
4-[2-(3-methoxyphenylamino)thiazol-4-yl]-5-methylthiothiophene-2-carboxamidine;
4-[2-(phenylamino)thiazol-4-yl]-5-methylthiothiophene-2-carboxamidine;
4-[2-(2,5-dimethoxyphenylamino)thiazol-4-yl]-5-methylthiothiophene-2-carboxamidine;
4-(2-aminothiazol-4-yl)-5-methylthiothiophene-2-carboxamidine;
4-[2-(4-chloro-2-methylphenylamino)thiazol-4-yl]-5-methylthiothiophene-2-carboxamidine;
4-[2-(4-dimethylaminophenylamino)thiazol-4-yl]-5-methylthiothiophene-2-carboxamidine;
4-[2-(4-methoxyphenylamino)thiazol-4-yl]-5-methylthiothiophene-2-carboxamidine;
4-[4-(4-hydroxy-3-methoxyphenyl)thiazol-2-yl]-5-methylthiothiophene-2-carboxamidine;
4-[4-(3-hydroxy-4-methoxyphenyl)thiazol-2-yl]-5-methylthiothiophene-2-carboxamidine;
4-[2-(2-fluorophenylamino)thiazol-4-yl]-5-methylthiothiophene-2-carboxamidine;
4-[2-(2,4,5-trimethylphenyl)aminothiazol-4-yl]-5-methylthiothiophene-2-carboxamidine;
4-[2-(3-chloro-2-methylphenyl)aminothiazol-4-yl]-5-methylthiothiophene-2-carboxamidine;
4-[2-(2-isopropylphenyl)aminothiazol-4-yl]-5-methylthiothiophene-2-carboxamidine;
4-[2-(4-benzyloxyphenyl)aminothiazol-4-yl]-5-methylthiothiophene-2-carboxamidine;
4-[2-(2-bromophenyl)aminothiazol-4-yl]-5-methylthiothiophene-2-carboxamidine;
4-[2-(2,5-dichlorophenyl)aminothiazol-4-yl]-5-methylthiothiophene-2-carboxamidine;
4-[2-(2-bromo-4-methylphenyl)aminothiazol-4-yl]-5-methylthiothiophene-2-carboxamidine;
4-[2-(2,3-dichlorophenyl)aminothiazol-4-yl]-5-methylthiothiophene-2-carboxamidine;
4-[2-(3,4,5-trimethoxyphenyl)aminothiazol-4-yl]-5-methylthiothiophene-2-carboxamidine;
4-[2-(2-piperidinylethyl)aminothiazol-4yl]-5-methylthiothiophene-2-carboxamidine;
4-[2-(4-methylphenyl)aminothiazol-4-yl]-5-methylthiothiophene-2-carboxamidine;
4-(4-phenyloxazol-2-yl)-5-methylthiothiophene-2-carboxamidine;
4-[2-(diphenylmethyl)aminothiazol-4-yl]-5-methylthiothiophene-2-carboxamidine; and
4-[2-(3-phenylpropyl)aminothiazol-4-yl]-5-methylthiothiophene-2-carboxamidine, as well as pharmaceutically acceptable salts thereof, for example the hydrochloride, hydrobromide and acetate salts thereof, or a prodrug thereof.

A second preferred group of compounds falling within the scope of the present invention include compounds of Formula I wherein X is sulfur or oxygen; Y is a covalent bond or —NH—; Z is $NR^5R^6$; $R^1$ is hydrogen, amino, hydroxy or halogen; $R^4$, $R^5$ and $R^6$ are independently hydrogen, $C_{1-4}$ alkyl, amino, $C_{1-4}$ alkoxy or hydroxy, and are preferably all hydrogen; one of $R^2$ or $R^3$ is hydrogen, $C_{1-6}$ alkylthio, $C_{1-6}$ alkyl optionally substituted with OH, $NH_2$, COOH or aminocarbonyl, or $C_{1-6}$ alkoxy; and the other of $R^2$ or $R^3$ is:

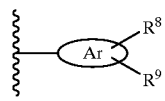

II where:
Ar is a group selected from the group consisting of phenyl, thiazolyl, thiazolinyl, oxazolyl, isothiazolyl, isoxazolyl, furanyl, imidazolyl, pyridyl, pyrimidinyl, pyrazinyl, thienyl (thiophenyl), tetrazolyl, pyrrolyl, pyrazolyl, oxadiazolyl, oxazolinyl, isoxazolinyl, imidazolinyl, triazolyl, pyrrolinyl, benzothiazolyl, benzothienyl, benzimidazolyl, 1,3-oxazolidin-2-onyl, imidazolin-2-onyl (preferably phenyl, thiazolyl, thiazolinyl, oxazolyl, isothiazolyl, isoxazolyl, imidazolyl, pyridyl, pyrimidinyl, thienyl, pyrrolyl, oxazolinyl and benzothienyl), any of which can optionally include an exocyclic =O (keto) or =$NR^v$ (imino) group, where $R^v$ is alkyl, aryl, aralkyl, alkylamino, arylimino or aralkylimino; and $R^8$ and $R^9$ are independently selected from the group consisting of hydrogen, halogen, amino, mono($C_{1-4}$) alkylamino, di($C_{1-4}$)alkylamino, arylamino, mono- and di-($C_{6-14}$)arylamino, mono- and di-($C_{6-14}$)ar($C_{1-6}$) alkylarnino, formylamino, $C_{2-6}$ acylamino, aminocarbonyl, $C_{2-8}$ aminoacyl, $C_{2-6}$ thioacylamino, aminothiocarbonyl, $C_{2-8}$ aminothioacyl, $C_{1-6}$ alkyl, $C_{3-8}$ cycloalkyl, $C_{1-6}$ alkoxy, carboxy, carboxy($C_{1-6}$) alkyl, $C_{2-8}$ alkoxycarbonyl, nitro, cyano, trifluoromethyl, thiazolyl, thiazolinyl, oxazolyl, isothiazolyl, isoxazolyl, furanyl, imidazolyl, pyridyl, pyrimidinyl, pyrazinyl, thienyl (thiophenyl), tetrazolyl, pyrrolyl, pyrazolyl, oxadiazolyl, oxazolinyl, isoxazolinyl, imidazolinyl, triazolyl, pyrrolinyl, benzothiazolyl, benzothienyl, benzimidazolyl, 1,3-oxazolidin-2-onyl, imidazolin-2-onyl, $C_{6-14}$ aryloxy, $C_{1-6}$ alkylthio, $C_{6-14}$ arylthio, $C_{6-14}$ aryl, or $C_{6-14}$ ar($C_{1-6}$)alkyl, wherein the aforementioned heteroaryl groups and the aryl portions of $C_{6-14}$ aryloxy, mono- and di $C_{6-14}$ aryl amino, mono- and di-$C_{6-14}$ ar($C_{1-6}$) alkylamino, $C_{6-14}$ arylthio, $C_{6-14}$ ar($C_{1-6}$)alkyl, and $C_{6-14}$ aryl can be further optionally substituted, preferably by one, two or three of halogen, hydroxy, amino, mono($C_{1-4}$)alkylamino, di($C_{1-4}$)alkylamino, formylamino, $C_{1-4}$acylamino, $C_{1-4}$aminoacyl, mono- or di-($C_{1-4}$)alkylaminocarbonyl, thiocarbonylamino, $C_{1-4}$thioacylamino, aminothiocarbonyl, $C_{1-4}$alkoxy, $C_{6-10}$aryloxy, aminocarbonyloxy, mono- or di($C_{1-4}$) alkylaminocarbonyloxy, mono- or di($C_{6-10}$) arylaminocarbonyloxy, mono- or di($C_{7-15}$) aralkylaminocarbonyloxy, $C_{1-4}$alkylsulfonyl, $C_{6-10}$arylsulfonyl, ($C_{7-15}$)aralkylsulfonyl, $C_{1-4}$alkylsulfonylamino, $C_{6-10}$arylsulfonylamino, ($C_{7-15}$)aralkylsulfonylamino, aminosulfonyl, mono- and di-alkylaminosulfonyl, mono- and di-arylaminosulfonyl, mono- and di-aralkylaminosulfonyl, $C_{1-4}$ alkoxycarbonylamino, $C_{7-15}$aralkoxycarbonylamino, $C_{6-10}$aryloxycarbonylamino, mono- or di-($C_{1-4}$) alkylaminothiocarbonyl, $C_{7-15}$aralkoxy, carboxy, carboxy($C_{1-4}$)alkyl, $C_{1-4}$alkoxycarbonyl, $C_{1-4}$alkoxycarbonylalkyl, carboxy($C_{1-4}$)alkoxy, alkoxycarbonylalkoxy, nitro, cyano, trifluoromethyl, $C_{1-4}$alkylthio and $C_{6-10}$arylthio, or by 3,4-methylenedioxy, 3,4-ethylenedioxy, and 3,4-propylenedioxy.

Preferred values of $R^8$ and $R^9$ are halogen, $C_{1-6}$ alkyl, $C_{1-6}$ alkoxy, hydroxy, nitro, trifluoromethyl, $C_{6-10}$ aryl (further optionally substituted by one or two of chloro, halogen, $C_{1-6}$ alkyl, $C_{1-6}$ alkoxy, hydroxy, nitro, trifluoromethyl, carboxy, 3,4-methylenedioxy, 3,4-ethylenedioxy, 3,4-propylenedioxy, or amino), 4-phenylphenyl (biphenyl), $C_{1-6}$ aminoalkyl, carboxy, $C_{1-6}$ alkyl, 3,4-methylenedioxy, 3,4-ethylenedioxy, 3,4-propylenedioxy, amino, $C_{1-6}$ alkanoylamino, $C_{6-14}$ aroylamino, $C_{1-6}$ hydroxyalkyl, thienyl (further optionally substituted by one or two of chloro, amino, methyl, methoxy, or hydroxy) and tetrazolyl. More preferably, $R^2$ is thienyl, oxazolyl, or thiazolyl, optionally substituted by any of the aforementioned groups.

Examples of preferred $R^8$ and $R^9$ groups include 4-chlorophenyl, 2,4-dichlorophenyl, methyl, 4-nitrophenyl, 3-nitrophenyl, 4-methoxyphenyl, 3-methoxyphenyl, 2-methoxyphenyl, 3-(2,4-dimethylthien-5-yl)phenyl, 3-hydroxyphenyl, 5-(carboxymethyl)thien-2-yl, phenyl, 3,4-ethylenedioxyphenyl, 3,4-propylenedioxyphenyl, naphth-2-yl, 3-phenyl-4-(tetrazol-5-yl)phenyl, 2,4-dichlorophenyl), 4-phenylphenyl, 3-methoxyphenyl, 3-hydroxyphenyl, 3-phenylphenyl, phenylthiomethyl, 2-chloro-4,5-dimethoxyphenyl, 4-chloro-3-methylphenyl, 5-methyl-4-phenyl, 4-chloro-3-nitrophenyl, 3-fluoro-5-trifluoromethylphenyl, 3,5-bis(trifluoromethyl), 3-fluoro-5-trifluoromethylphenyl, 3-bromophenol, 3,4-methylenedioxyphenyl, 4-methylphenyl, 3-methylphenyl, 3,5-bis(trifluoromethyl)phenyl, 2-methoxyphenyl, 6-phenyl-2-pyridyl, 2,4-dimethoxyphenyl, 3,4-dimethoxyphenyl, benzyl, 3,4-dichlorophenyl, 3-methylphenyl, 3,5-dimethoxyphenyl, 2-methylphenyl, 2,5-dimethoxyphenyl, 2-chloro-3-pyridyl, phenoxymethyl, cyclohexyl, 2-hydroxyphenyl, 3-trifluoromethoxyphenyl, 2-chloro-4-pyridyl, 3-chloro-4-pyridyl, 2-chlorophenylamino, 3-methoxyphenylamino, phenylamino, 2,5-dimethoxyphenylamino, amino, 4-chloro-2-methylphenylamino, 4-dimethylaminophenylamino, 4-methoxyphenylamino, 4-hydroxy-3-methoxyphenyl, 3-hydroxy-4-methoxyphenyl, 2-fluorophenylamino, 2,4,5-trimethylphenylamino, 3-chloro-2-methylphenylamino, 2-isopropylphenylamino, 4-benzyloxyphenylamino, 2-bromophenylamino, 2,5-dichlorophenylamino, 2-bromo-4-methylphenylamino, 2,3-dichlorophenylamino, 3,4,5-trimethoxyphenylamino, 2-piperidinylethylamino, 4-methylphenylamino, 2-thienyl, 2-5,6,7,8-tetrahydronaphthyl, 3-(2-phenoxyacetic acid)phenyl, 2-(2-phenoxyacetic acid)phenyl, diphenylmethylamino, 3-phenylpropylamino, 3-phenylphenyl, phenylthiomethyl, 2-chloro-4,5-dimethoxyphenyl, and isopropyl.

A third preferred group of compounds are those of Formula I wherein:

X is sulfur;

Y is a covalent bond;

Z is $NR^5R^6$;

$R^1$ is hydrogen;

$R^3$ is methylthio or methyl;

$R^4$, $R^5$ and $R^6$ are all hydrogen; and $R^2$ is Formula II, where Ar is phenyl, thiazolyl, oxazolyl, benzothienyl, pyridyl, or imidazolyl; and $R^8$ and $R^9$ are independently hydrogen, or $C_{6-10}$ aryl or heterocycle, optionally substituted by one, two or three of chloro, hydroxy, $C_{1-4}$ alkyl, $C_{3-6}$ cycloalkyl, $C_{1-4}$ alkoxy, amino, carboxy, phenyl, naphthyl, biphenyl, hydroxyphenyl, methoxyphenyl, dimethoxyphenyl, carboxyalkoxyphenyl, alkoxycarbonylalkoxy, carboxyethoxy, alkylsulfonylaminophenyl, arylsulfonylaminophenyl, acylsulfonylaminophenyl, aralkylsulfonylaminophenyl, heteroarylsulfonylaminophenyl where the heteroaryl portion is optionally halo or $C_{1-6}$alkyl substituted, chlorophenyl, dichlorophenyl, aminophenyl, carboxyphenyl, nitrophenyl, or by 3,4-methylenedioxy, 3,4-ethylenedioxy, and 3,4-propylenedioxy.

A fourth preferred group of compounds are those of Formula I wherein:

X is sulfur;

Y is a direct covalent bond;

Z is $NR^5R^6$;

$R^1$ is hydrogen;

$R^2$ is alkyl, ar(alkyl), alkylsulfonyl, —$SO_2$-alkyl, amido, amidino, or

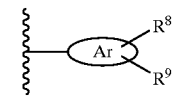

II where

Ar is an aromatic or heteroaromatic group selected from the group consisting of phenyl, thiazolyl, oxazolyl, imidazolyl and pyridyl;

$R^8$ and $R^9$ are independently selected from the group consisting of hydrogen, carboxy, phenyl, naphthyl, alkyl, pyridyl, oxazolyl, furanyl, cycloalkyl and amino, any of which may be optionally substituted with 1 to 3 substituents independently selected from the group consisting of halogen, alkyl, haloalkyl, alkaryl, heteroaryl, phenyl, naphthyl, alkoxy, aryloxy, hydroxy, amino nitro, thiophenyl, benzothiophenyl, fluorenyl, 3,4-ethylenedioxy, 3,4-methylenedioxy, 3,4-propylenedioxy, arylsulfonamido, alkylsulfonamido and aryloxy, each of said 1 to 3 substituents may be further optionally substituted with one or more groups selected from alkoxy, haloalkyl, halogen, alkyl, amino, acetyl, hydroxy, dialkylamino, dialkylamino acyl, monoalkylaminoacyl, —$SO_2$-heteroaryl, —$SO_2$-aryl, or aryl;

$R^3$ is —$SO_2$-alkyl, trifluoromethyl, S(O)-alkyl, hydrogen, alkoxy, alkylthio, alkyl, aralkylthio; and $R^4$, $R^5$, $R^6$ are hydrogen.

Preferred compounds of this embodiment are those where Ar is a thiazolyl, preferably thiazol-2-yl or thiazol-4-yl, and at least one of $R^8$ and $R^9$ is substituted phenyl, most preferably on the 4-position of the thiazol-2-yl group. Also preferred are compounds where $R^2$ is a 4-phenylthiazol-2-yl group wherein said phenyl is further optionally substituted, and $R^3$ is methylthio.

A fifth preferred group of compounds are those of Formula III:

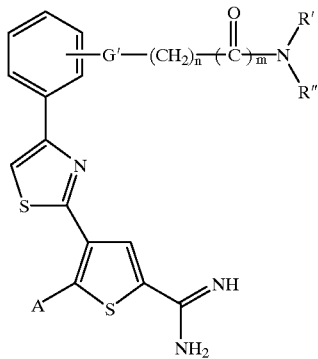

or a pharmaceutically acceptable salt or prodrug thereof, where

A is methylthio or methyl;
G' is —O—, —S—, —NH—, or a covalent bond;
n is an integer from 1–10, preferably from 1–6;
m is an integer from 0–1; and
R' and R" are independently selected from hydrogen, alkyl, aryl or aralkyl, or R' and R" are taken together with the N atom to which they are attached form a 3–8 membered heterocyclic ring, optionally containing an additional O, N, or S atom, and when said 3–8 membered heterocyclic ring contains an additional N atom, said additional N atom is optionally substituted by hydrogen, $C_{1-4}$alkyl, $C_{6-10}$aryl, $C_{6-10}$ar($C_{1-4}$)alkyl, acyl, alkoxycarbonyl or benzyloxycarbonyl.

Most preferred compounds of Formula III are those for which R' and R", taken together with the N atom to which they are attached, form a ring selected from piperazinyl, pyrrolidinyl, piperidinyl or morpholinyl, which are further optionally substituted with 1 to 4 non-hydrogen substituents selected from halogen, hydroxy, amino, monoalkylamino, dialkylamino, formylamino, acylamino, aminoacyl, mono- or di-alkylaminocarbonyl, thiocarbonylamino, thioacylamino, aminothiocarbonyl, alkoxy, aryloxy, aminocarbonyloxy, mono- or di-alkylaminocarbonyloxy, mono- or diarylaminocarbonyloxy, mono- or diarakylaminocarbonyloxy, alkylsulfonyl, arylsulfonyl, aralkylsulfonyl, alkylsulfonylamino, arylsulfonylamino, arakylsulfonylamino, alkoxycarbonylamino, aralkoxycarbonylamino, aryloxycarbonylamino, mono- or di-alkylaminothiocarbonyl, aralkoxy, carboxy, carboxyalkyl, alkoxycarbonyl, alkoxycarbonylalkyl, nitro, cyano, trifluoromethyl, alkylthio and arylthio, where each of these substituents has the preferred values set forth for Formulae I and II above.

Examples of preferred compounds of Formula III include:
5-methylthio-4-[4-(3-{[N-(2-morpholin-4-ylethyl) carbamoyl]methoxy}phenyl)(1,3-thiazol-2-yl)] thiophene-2-carboxamidine,
5-methylthio-4-{4-[3-(2-morpholin-4-yl-2-oxoethoxy) phenyl](1,3-thiazol-2-yl)}thiophene-2-carboxamidine,
5-methylthio-4-{4-[3-(2-oxo-2-piperazinylethoxy)phenyl] (1,3-thiazol-2-yl)}thiophene-2-carboxamidine,
4-[4-(3-{[N-(2-aminoethyl)carbamoyl]methoxy}phenyl)(1, 3-thiazol-2-yl)]-5-methylthiothiophene-2-carboxamidine,
4-(4-{3-[2-(4-acetylpiperazinyl)-2-oxoethoxy]phenyl}(1,3-thiazol-2-yl))-5-methylthiothiophene-2-carboxamidine,
4-(4-{3-[2-(4-methylpiperazinyl)-2-oxoethoxy]phenyl}(1, 3-thiazol-2-yl))-5-methylthiothiophene-2-carboxamidine,
the compound described in Example 151,
5-methylthio-4-[4-(3-{2-oxo-2-[4-benzylpiperazinyl] ethoxy}phenyl)(1,3-thiazol-2-yl)]thiophene-2-carboxamidine,
(D,L)-4-(4-{3-[2-(3-aminopyrrolidinyl)-2-oxoethoxy] phenyl}(1,3-thiazol-2-yl))-5-methylthiothiophene-2-carboxamidine,
5-methylthio-4-{4-[3-(2-oxo-2-piperidylethoxy)phenyl](1, 3-thiazol-2-yl)}thiophene-2-carboxamidine,
(D,L)-ethyl 1-(2-{3-[2-(5-amidino-2-methylthio-3-thienyl)-1,3-thiazol-4-yl]phenoxy}acetyl)piperidine-2-carboxylate,
5-methylthio-4-{4-[3-(2-oxo-2-pyrrolidinylethoxy)phenyl] (1,3-thiazol-2-yl)}thiophene-2-carboxamidine,
5-methylthio-4-[4-(3-{2-oxo-2-[4-benzylpiperidyl] ethoxy}phenyl)(1,3-thiazol-2-yl)]thiophene-2-carboxamidine,
(D,L)-4-(4-{3-[2-(3-methylpiperidyl)-2-oxoethoxy]phenyl} (1,3-thiazol-2-yl))-5-methylthiothiophene-2-carboxamidine,
4-(4-{3-[2-(4-methylpiperidyl)-2-oxoethoxy]phenyl}(1,3-thiazol-2-yl))-5-methylthiothiophene-2-carboxamidine,
4-(4-{3-[2-(2-azabicyclo[4.4.0]dec-2-yl)-2-oxoethoxy] phenyl}(1,3-thiazol-2-yl))-5-methylthiothiophene-2-carboxamidine,
(D,L)-ethyl 1-(2-{3-[2-(5-amidino-2-methylthio-3-thienyl)-1,3-thiazol-4-yl]phenoxy }acetyl)piperidine-3-carboxylate,
5-methylthio-4-{4-[3-(2-oxo-2-(1,2,3,4-tetrahydroquinolyl) ethoxy)phenyl](1,3-thiazol-2-yl)}thiophene-2-carboxamidine,
ethyl 1-(2-{3-[2-(5-amidino-2-methylthio-3-thienyl)-1,3-thiazol-4-yl]phenoxy}acetyl)piperidine-4-carboxylate,
4-(4-{3-[2-((3R)-3-hydroxypiperidyl)-2-oxoethoxy] phenyl}(1,3-thiazol-2-yl))-5-methylthiothiophene-2-carboxamidine,
D,L-4-(4-{3-[2-(2-ethylpiperidyl)-2-oxoethoxy]phenyl}(1, 3-thiazol-2-yl))-5-methylthiothiophene-2-carboxamidine,
4-(4-{3-[2-((3 S)-3-hydroxypyrrolidinyl)-2-oxoethoxy] phenyl}(1,3-thiazol-2-yl))-5-methylthiothiophene-2-carboxamidine,
D,L-4-[4-(3-{2-[3-(hydroxymethyl)piperidyl]-2-oxoethoxy}phenyl)(1,3-thiazol-2-yl)]-5-methylthiothiophene-2-carboxamidine,
4-{4-[3-(2-{(2R)-2-[(phenylamino)methyl]pyrrolidinyl}-2-oxoethoxy)phenyl](1,3-thiazol-2-yl)}-5-methylthiothiophene-2-carboxamidine,
4-[4-(3-{2-[(3R)-3-(methoxymethyl)pyrrolidinyl]-2-oxoethoxy}phenyl)(1,3-thiazol-2-yl)]-5-methylthiothiophene-2-carboxamidine,
1-(2-{3-[2-(5-amidino-2-methylthio-3-thienyl)-1,3-thiazol -4-yl]phenoxy}acetyl)piperidine-3-carboxamide, and
2-{3-[2-(5-{[(tert-butoxy)carbonylamino]iminomethyl}-2-methyl-3-thienyl)-1,3-thiazol-4-yl]phenoxy}acetic acid;
or pharmaceutically acceptable salts or prodrugs thereof.

A sixth preferred group of compounds are those of Formula IV:

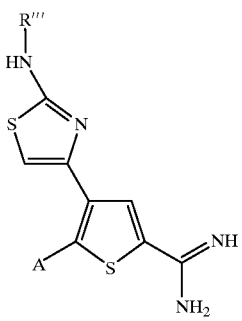

IV or a pharmaceutically acceptable salt or prodrug thereof, where

A is methylthio or methyl; and

R''' is hydrogen, $C_{6-14}$aryl, $C_{1-6}$alkyl, $C_{1-6}$alkoxy ($C_{6-14}$) aryl, amino($C_{6-14}$)aryl, monoalkylamino($C_{6-14}$)aryl, dialkylamino($C_{6-14}$)aryl, $C_{6-10}$ar($C_{1-6}$)alkyl, heterocycle($C_{2-6}$)alkyl such as morpholinoalkyl, piperazinylalkyl and the like, $C_{1-6}$alk($C_{6-14}$)aryl, amino($C_{1-6}$)alkyl, mono($C_{1-6}$)alkylamino($C_{1-6}$)alkyl, di($C_{1-6}$)alkylamino($C_{1-6}$)alkyl, hydroxy($C_{6-14}$)aryl, or hydroxy($C_{1-6}$)alkyl, where the aryl and heterocyclic rings can be further optionally substituted by 1–4 non-hydrogen substituents selected from halogen, hydroxy, amino, mono($C_{1-6}$)alkylamino, di($C_{1-6}$)alkylamino, formylamino, ($C_{1-6}$)acylamino, amino($C_{1-6}$)acyl, mono- or di-($C_{1-6}$)alkylaminocarbonyl, thiocarbonylamino, ($C_{1-6}$)thioacylamino, aminothiocarbonyl, ($C_{1-6}$)alkoxy, ($C_{6-10}$)aryloxy, aminocarbonyloxy, mono- or di-($C_{1-6}$)alkylaminocarbonyloxy, mono- or di-($C_{6-10}$)arylaminocarbonyloxy, mono- or di($C_{6-10}$)ar($C_{1-6}$)alkylaminocarbonyloxy, ($C_{1-6}$)alkylsulfonyl, ($C_{6-10}$)arylsulfonyl, ($C_{6-10}$)ar($C_{1-6}$)alkylsulfonyl, ($C_{1-6}$)alkylsulfonylamino, $C_{6-10}$ arylsulfonylamino, ($C_{6\ 10}$)ar($C_{1-6}$)alkylsulfonylamino,($C_{1-6}$)alkoxycarbonylamino, ($C_{6-10}$)ar($C_{1-6}$)alkoxycarbonylamino, $C_{6-10}$aryloxycarbonylamino, mono- or di-($C_{1-6}$)alkylaminothiocarbonyl, ($C_{6-10}$)ar($C_{1-6}$)alkoxy, carboxy, ($C_{1-6}$)carboxyalkyl, $C_{1-6}$alkoxycarbonyl, ($C_{1-6}$)alkoxycarbonyl($C_{1-6}$)alkyl, nitro, cyano, trifluoromethyl, ($C_{1-6}$)alkylthio and $C_{6-10}$arylthio.

Examples of preferred compounds of Formula IV include:

4-{2-[(3-methoxyphenyl)amino](1,3-thiazol-4-yl)}-5-methylthiothiophene-2-carboxamidine, 4-{2-[(4-methoxyphenyl)amino](1,3-thiazol-4-yl)}-5-methylthiothiophene-2-carboxamidine, 4-(2-{[4-(dimethylamino)phenyl]amino}(1,3-thiazol-4-yl))-5-methylthiothiophene-2-carboxamidine, 4-{2-[(4-chloro-2-methylphenyl)amino](1,3-thiazol-4-yl)}-5-methylthiothiophene-2-carboxamidine, 4-(2-[(diphenylmethyl)amino](1,3-thiazol-4-yl)}-5-methylthiothiophene-2-carboxamidine, 5-methylthio-4-{2-[(3-phenylpropyl)amino](1,3-thiazol-4-yl)}thiophene-2-carboxamidine, 5-methylthio-4-{2-[(2,4,5-trimethylphenyl)amino](1,3-thiazol-4-yl)}thiophene-2-carboxamidine, 4-{2-[(2-fluorophenyl)amino](1,3-thiazol-4-yl)}-5-methylthiothiophene-2-carboxamidine, 4-{2-[(3-chloro-2-methylphenyl)amino](1,3-thiazol-4-yl)}-5-methylthiothiophene-2-carboxamidine, 4-(2-{[2-(methylethyl)phenyl]amino}(1,3-thiazol-4-yl))-5-methylthiothiophene-2-carboxamidine, 5-methylthio-4-(2-{[4-(phenylmethoxy)phenyl]amino}(1,3-thiazol-4-yl))thiophene-2-carboxamidine, 4-{(2-[(2-bromophenyl)amino](1,3-thiazol-4-yl)}-5-methylthiothiophene-2-carboxamidine, 4-{2-[(2,6-dichlorophenyl)amino](1,3-thiazol-4-yl)}-5-methylthiothiophene-2-carboxamidine, 4-{2-[(2-bromo-4-methylphenyl)amino](1,3-thiazol-4-yl)}-5-methylthiothiophene-2-carboxamidine, 5-methylthio-4-{2-[(2-morpholin-4-ylethyl)amino](1,3-thiazol-4-yl)}thiophene-2-carboxamidine, 4-{2-[(2,3-dichlorophenyl)amino](1,3-thiazol-4-yl)}-5-methylthiothiophene-2-carboxamidine, 5-methylthio-4-{2-[(3,4,5-trimethoxyphenyl)amino](1,3-thiazol-4-yl)}thiophene-2-carboxamidine, 5-methylthio-4-{2-[(2-piperidylethyl)amino](1,3-thiazol-4-yl)}thiophene-2-carboxamidine, 4-(2-{[(4-methylphenyl)methyl]amino}(1,3-thiazol-4-yl))-5-methylthiothiophene-2-carboxamidine, 4-(2-{[4-(4-chlorophenoxy)phenyl]amino}(1,3-thiazol-4-yl))-5-methylthiothiophene-2-carboxamidine, 4-(2-{[4-phenoxyphenyl]amino}(1,3-thiazol-4-yl))-5-methylthiothiophene-2-carboxamidine, 5-methylthio-4-(2-{[4-(phenylamino)phenyl]amino}(1,3-thiazol-4-yl))thiophene-2-carboxamidine, 5-methylthio-4-(2-{[4-benzylphenyl]amino}(1,3-thiazol-4-yl))thiophene-2-carboxamidine, 5-methylthio-4-(2-{[4-(piperidylsulfonyl)phenyl]amino}(1,3-thiazol-4-yl))thiophene-2-carboxamidine, 5-methylthio-4-[2-(3-quinolylamino)(1,3-thiazol-4-yl)]thiophene-2-carboxamidine, 5-methylthio-4-[2-(2-naphthylamino)(1,3-thiazol-4-yl)]thiophene-2-carboxamidine, 4-[2-(2H-benzo[3,4-d]1,3-dioxolan-5-ylamino)(1,3-thiazol-4-yl)]-5-methylthiothiophene-2-carboxamidine, 4-{2-[(7-bromofluoren-2-yl)amino](1,3-thiazol-4-yl)}-5-methylthiothiophene-2-carboxamidine, 4-{2-[(4-cyclohexylphenyl)amino](1,3-thiazol-4-yl)}-5-methylthiothiophene-2-carboxamidine, 5-methylthio-4-(2-{[4-(phenyldiazenyl)phenyl]amino}(1,3-thiazol-4-yl))thiophene-2-carboxamidine, 5-methylthio 4-(2-{[3-(hydroxymethyl)phenyl]amino}(1,3-thiazol-4-yl))-thiophene-2-carboxamidine, 4-[2-({3-[(3-methylpiperidyl)methyl]phenyl}amino)(1,3-thiazol-4-yl)]-5-methylthiothiophene-2-carboxamidine, 4-{2-[(3-hydroxyphenyl)amino](1,3-thiazol-4-yl)}-5-methylthiothiophene-2-carboxamidine, 4-(2-{[4-(carbamoylmethoxy)phenyl]amino}(1,3-thiazol-4-yl))-5-methylthiothiophene-2-carboxamidine, 5-methyl-4-{2-[(3,4,5-trimethoxyphenyl)amino](1,3-thiazol-4-yl)}thiophene-2-carboxamidine, 5-methyl-4-{2-[(4-phenoxyphenyl)amino](1,3-thiazol-4-yl)}thiophene-2-carboxamidine, 5-methyl-4-[2-(phenylamino)(1,3-thiazol-4-yl)]thiophene-2-carboxamidine, and 4-(4-isoxazol-5-yl(1,3-thiazol-2-yl))-5-methylthiothiophene-2-carboxamidine;

as well as pharmaceutically acceptable salts and prodrugs thereof.

A seventh preferred group of compounds are compounds of Formula I, or a pharmaceutically acceptable salt or prodrug thereof, wherein:

X is sulfur or oxygen, preferably sulfur;

Y is a covalent bond or —NH—, preferably a covalent bond;

Z is $NR^5R^6$;

$R^1$ is hydrogen, amino, hydroxy or halogen, preferably hydrogen;

$R^4$, $R^5$ and $R^6$ are independently hydrogen, $C_{1-4}$ alkyl, amino, $C_{1-4}$ alkoxy or hydroxy, and are preferably all hydrogen;

$R^3$ is hydrogen, $C_{1-6}$ alkylthio, $C_{1-6}$ alkyl optionally substituted with OH, $NH_2$ COOH or aminocarbonyl, or $C_{1-6}$ alkoxy, preferably methylthio or methyl; and $R^2$ is alkylsulfonylamino, aralkylsulfonylamino, aralkenylsulfonylamino, arylsulfonylamino, heteroarylsulfonylamino, di(aralkylsulfonyl)amino, di(aralkenylsulfonyl)amino, di(arylsulfonyl)amino, or di-(heteroarylsulfonyl)amino, wherein any of the aryl or heteroaryl containing groups can be optionally substituted on the aromatic ring; or amino, monoalkylamino, dialkylamino, monoarylamino, diarylamino, monoalkylmonoarylamino, monoaralkylamino, diaralkylamino, monoalkylmonoaralkylamino, monoheterocycleamino, diheterocycleamino, monoalkylmonoheterocycleamino, wherein any of the aryl or heteroaryl containing groups can be optionally substituted on the aromatic ring and wherein any of the heterocycle containing groups can be optionally ring substituted; or alkanoylamino, alkenoylamino, alkynoylamino, aroylamino, aralkanoylamino, aralkenoylamino, heteroaroylamino, heteroarylalkanoylamino, any of which is optionally substituted on the aromatic ring; or alkoxy and alkylthio, either of which is optionally substituted, or aryloxy, aralkoxy, arylthio, aralkylthio, arylsulfonyl, aralkylsulfonyl, aralkenylsulfonyl, any of which is optionally substituted on the aromatic ring; or alkoxycarbonylamino, aralkoxycarbonylamino, aryloxycarbonylamino, wherein any of the aryl containing groups can be optionally substituted on the aromatic ring; or formylamino, H(S)CNH—, or thioacylamino.

Preferred optional substituents are halogen, $C_{1-6}$ alkyl, $C_{1-6}$ alkoxy, hydroxy, nitro, trifluoromethyl, $C_{6-10}$ aryl, $C_{6-10}$ aryloxy, $C_{6-10}$ arylmethoxy (wherein the aryl groups on these aryl-containing substituents are further optionally substituted by one or two of chloro, halogen, $C_{1-6}$ alkyl, $C_{1-6}$ alkoxy, phenyl, hydroxy, nitro, trifluoromethyl, carboxy, 3,4-methylenedioxy, 3,4-ethylenedioxy, 3,4-propylenedioxy, or amino), $C_{1-6}$ aminoalkyl, carboxy, alkyl, 3,4-methylenedioxy, 3,4-ethylenedioxy, 3,4-propylenedioxy, amino, mono- or di-$(C_{1,6})$alkylamino, mono- or di-$C_{6-10}$ arylamino, $C_{1-6}$ alkylsulfonylamino, $C_{6-10}$arylsulfonylamino, $C_{1-8}$ acylamino, $C_{1-8}$ alkoxycarbonyl, $C_{1-6}$ alkanoylamino, $C_{6-14}$aroylamino, $C_{1-6}$ hydroxyalkyl, methylsulfonyl, phenylsulfonyl, thienyl (further optionally substituted by one or two of chloro, amino, methyl, methoxy, or hydroxy) and tetrazolyl.

In one aspect of this embodiment, $R^2$ is preferably $C_{1-6}$ alkylsulfonylamino, $C_{6-10}$ ar($C_{1-6}$)alkylsulfonylamino, $C_{6-10}$ ar($C_{2-6}$)alkenylsulfonylamino, $C_{6-10}$ arylsulfonylamino, heteroarylsulfonylamino, di($C_{6-10}$ ar($C_{1-6}$)alkylsulfonyl)amino, di($C_{6-10}$ ar($C_{2-6}$)alkenylsulfonyl)amino, di($C_{6-10}$ arylsulfonyl)amino, or di-(heteroarylsulfonyl)amino, wherein any of the aryl or heteroaryl containing groups can be optionally substituted on the aromatic ring.

Especially preferred $R^2$ groups in this embodiment of the invention include $C_{6-10}$ arylsulfonylamino, di-($C_{6-10}$ arylsulfonyl)amino, $C_{6-10}$ ar($C_{1-3}$)alkylsulfonylamino, di-($C_{6-10}$ ar($C_{1-3}$)alkylsulfonyl)amino, thienylsulfonylamino, any of which is optionally substituted on the aromatic ring.

Useful values of $R^2$, when $R^2$ is a substituted sulfonylamino group include biphenylsulfonylamino, bis (biphenylsulfonyl)amino, naphth-2-ylsulfonylamino, di(naphth-2-ylsulfonyl)amino, 6-bromonaphth-2-ylsulfonylamino, di(6-bromonaphth-2-ylsulfonyl)amino, naphth-1-ylsulfonylamino, di(naphth-1-ylsulfonyl)amino, 2-methylphenylsulfonylamino, di-(2-methylphenylsulfonyl) amino, 3-methylphenylsulfonylamino, di-(3-methylphenylsulfonyl)amino, 4-methylphenylsulfonylamino, di-(4-methylphenylsulfonyl) amino, benzylsulfonylamino, 4-methoxyphenylsulfonylamino, di-(4-methoxyphenylsulfonyl)amino, 4-iodophenylsulfonylamino, di-(4-iodophenylsulfonyl) amino, 3,4-dimethoxyphenylsulfonylamino, bis-(3,4-dimethoxyphenylsulfonyl)amino, 2-chlorophenylsulfonylamino, di-(2-chlorophenylsulfonyl) amino, 3-chlorophenylsulfonylamino, di-(3-chlorophenylsulfonyl)amino, 4-chlorophenylsulfonylamino, di-(4-chlorophenylsulfonyl)amino, phenylsulfonylamino, di-(phenylsulfonyl)amino, 4-tert-butylphenylsulfonylamino, di-(4-tert-butylphenylsulfonyl) amino, 2-phenylethenylsulfonylamino, and 4-(phenylsulfonyl)thien-2-ylsulfonylamino.

In another aspect of this embodiment, $R^2$ is preferably amino, mono($C_{1-6}$)alkylamino, di($C_{1-6}$)alkylamino, mono ($C_{6-10}$)arylamino, di($C_{6-10}$)arylamino, mono($C_{1-6}$) alkylmono($C_{6-10}$)arylamino, monoar($C_{1-6}$)alkylamino, di($C_{6-10}$)ar($C_{1-6}$)alkylamino, mono($C_{1-6}$)alkylmono($C_{6-10}$) ar($C_{1-6}$)alkylamino, monoheteroarylamino, diheteroarylamino, mono($C_{1-6}$)alkylmonoheteroarylamino, wherein any of the aryl or heteroaryl containing groups can be optionally substituted on the aromatic ring.

Especially preferred $R^2$ groups in this embodiment of the invention include mono($C_{6-10}$)arylamino, mono($C_{1-6}$) alkylmono($C_{6-10}$)arylamino, mono($C_{6-10}$)ar($C_{1-3}$) alkylamino, mono($C_{1-6}$)alkylmono($C_{6-10}$)ar($C_{1-3}$) alkylamino, monoheteroarylamino, and mono($C_{1-6}$) alkylmonoheteroarylamino. Examples of suitable heteroarylamino groups include 1,3-thiazol-2-ylamino, imidazol-4-ylamino, quinolin-2-ylamino and quinolin-6-ylamino.

Useful values of $R^2$, when $R^2$ is a substituted amino group include anilino, naphth-2-ylamino, naphth-1-ylamino, 4-(biphenyl)thiazol-2-ylamino, 4-(phenyl)thiazol-2-ylamino, 4-phenyl-5-methylthiazol-2-ylamino, 4-hydroxy-4-trifluoromethylthiazol-2-ylamino, 3-phenylphenylamino, pyrimidin-2-ylamino, 4-isopropylphenylamino, 3-isopropylphenylamino, 4-phenylphenylamino, 3-fluoro-4-phenylphenylamino, 3,4-methylenedioxyphenylamino, n-butylphenylamino, N-methyl-N-(2-methylphenyl)amino, 3-nitrophenylamino, 4-methoxyphenylamino, 3-methoxyphenylamino, 2-methoxyphenylamino, 2-methylphenylamino, 3-methylphenylamino, 3,4-dimethylphenylamino, 3-chlorophenylamino, 4-chlorophenylamino, 4-(3-fluoro-4-methylphenyl)amino, 4-(indan-5-yl)amino, benzylamino, indanylmethylamino, 2,3-dihydrobenzofuranylmethyl, 2-phenylimidazol-5-yl, 3-hydroxybenzyl, 3-phenoxyphenylamino, 4-phenoxyphenylamino, 3-benzyloxyphenylamino, 4-benzyloxyphenylamino, quinolin-6-ylamino, quinolin-3-ylamino, 4-(phenylamino)phenylamino, 4-(4-ethylphenyl) phenylamino, 4-(dimethylamino)phenylamino, 4-cyclohexylphenylamino, 4-(9-ethylcarbazol-3-yl)amino, 4-(t-butyl)phenylamino, and 4-methylthiophenyl amino.

In another aspect of this embodiment, $R^2$ is preferably an acylamino group, such as alkanoylamino, alkenoylamino, aroylamino, aralkanoylamino, aralkenoylamino, heteroaroylamino, heteroarylalkanoylamino, any of which is optionally substituted on the aromatic ring.

Especially preferred $R^2$ groups in this embodiment of the invention include $(C_{6-10})$arylcarbonylamino, $C_{6-10}$ ar$(C_{1-3})$alkylcarbonylamino, $C_{6-10}$ ar$(C_{2-3})$alkenylcarbonylamino, $C_{6-10}$ aryloxy$(C_{1-3})$alkylcarbonylamino, $C_{3-8}$ cycloalkylcarbonylamino, $C_{1-6}$ alkylcarbonylamino, and heteroarylcarbonylamino, such as furanylcarbonylamino, and quinolinylcarbonylamino.

Useful values of $R^2$, when $R^2$ is an acylamino group include 3-hydroxyphenylcarbonylamino, 2-phenylethenylcarbonylamino, phenylcarbonylamino, cyclohexylcarbonylamino, 4-methyl-3-nitrophenylcarbonylamino, furan-2-ylcarbonylamino, tert-butylcarbonylamino, 5-(3,5-dichlorophenoxy)furan-2-ylcarbonylamino, naphth-1-ylcarbonylamino, quinolin-2-ylcarbonylamino, 4-ethoxyphenylcarbonylamino, phenoxymethylcarbonylamino, and 3-methylphenylcarbonylamino.

In another aspect of this embodiment, $R^2$ is preferably $C_{6-10}$ aryloxy, $C_{6-10}$ ar$(C_{1-6})$alkoxy, $C_{6-10}$ arylsulfonyl, $C_{6-10}$ ar$(C_{1-6})$alkylsulfonyl, or $C_{6-10}$ ar$(C_{2-6})$alkenylsulfonyl, any of which is optionally substituted on the aromatic ring. Especially preferred $R^2$ groups in this embodiment of the invention include $C_{6-10}$ aryloxy, and $C_{6-10}$ arylsulfonyl.

Useful values of $R^2$, when $R^2$ is an aryloxy or arylsulfonyl group include phenoxy, naphthyloxy, phenylsulfonyl, and naphthylsulfonyl.

Representative compounds within the scope of this seventh embodiment of the invention include:
5-methylthio-4-(6-quinolylamino)thiophene-2-carboxamindine
5-methylthio-4-[(3-phenylphenyl)amino]thiophene-2-carboxamidine
5-methylthio-4-(3-quinolylamino)thiophene-2-carboxamidine
5-methylthio-4-(pyrimidin-2-ylamino)thiophene-2-carboxamidine
4-[(4-cyclohexylphenyl)amino]-5-methylthiothiophene-2-carboxamidine
methyl 4-amino-5-methylthiothiophene-2-carboxylate
methyl 4-[(aminothioxomethyl)amino]-5-methylthiothiophene-2-carboxylate
5-methylthio-4-[(4-phenyl(1,3-thiazol-2-yl))amino]thiophene-2-carboxamidine
5-methylthio-4-{[4-(4-phenylphenyl)(1,3-thiazol-2-yl)]amino}thiophene-2-carboxamidine
4-[(5-methyl-4-phenyl(1,3-thiazol-2-yl))amino]-5-methylthiothiophene-2-carboxamidine
4-{[4-hydroxy-4-(trifluoromethyl)(1,3-thiazolin-2-yl)]amino}-5-methylthiothiophene-2-carboxamidine
5-methylthio-4-(2-naphthylamino)thiophene-2-carboxamidine
4-[(4-chlorophenyl)amino]-5-methylthiothiophene-2-carboxamidine
4-[(3-methylphenyl)amino]-5-methylthiothiophene-2-carboxamidine
4-[(3-methoxyphenyl)amino]-5-methylthiothiophene-2-carboxamidine
4-{[3-(methylethyl)phenyl]amino}-5-methylthiothiophene-2-carboxamidine
5-methylthio-4-[(3-nitrophenyl)amino]thiophene-2-carboxamidine
4-{[4-(methylethyl)phenyl]amino}-5-methylthiothiophene-2-carboxamidine
4-[(3,4-dimethylphenyl)amino]-5-methylthiothiophene-2-carboxamidine
5-methylthio-4-[(4-phenylphenyl)amino]thiophene-2-carboxamidine
4-[(3-fluoro-4-phenylphenyl)amino]-5-methylthiothiophene-2-carboxamidine
4-(2H-benzo[d]1,3-dioxolen-5-ylamino)-5-methylthiothiophene-2-carboxamidine
4-[(4-butylphenyl)amino]-5-methylthiothiophene-2-carboxamidine
5-methylthio-4-[benzylamino]thiophene-2-carboxamidine
4-(indan-5-ylamino)-5-methylthiothiophene-2-carboxamidine
4-(2,3-dihydrobenzo[b]furan-5-ylamino)-5-methylthiothiophene-2-carboxamidine
5-methylthio-4-[(2-phenylimidazol-4-yl)amino]thiophene-2-carboxamidine
5-methylthio-4-[(2-quinolylmethyl)amino]thiophene-2-carboxamidine
4-{[(3-hydroxyphenyl)methyl]amino}-5-methylthiothiophene-2-carboxamidine
5-methylthio-4-(phenylcarbonylamino)thiophene-2-carboxamidine
4-((2E)-3-phenylprop-2-enoylamino)-5-methylthiothiophene-2-carboxamidine
4-[(4-chlorophenyl)carbonylamino]-5-methylthiothiophene-2-carboxamidine
4-(cyclohexylcarbonylamino)-5-methylthiothiophene-2-carboxamidine
methyl 4-[(4-methyl-3-nitrophenyl)carbonylamino]-5-methylthiothiophene-2-carboxylate
4-(2-furylcarbonylamino)-5-methylthiothiophene-2-carboxamidine
4-(2,2-dimethylpropanoylamino)-5-methylthiothiophene-2-carboxamidine
4-{[5-(3,5-dichlorophenoxy)(2-furyl)]carbonylamino}-5-methylthiothiophene-2-carboxamidine
5-methylthio-4-(naphthylcarbonylamino)-thiophene-2-carboxamidine
5-methylthio-4-(2-quinolylcarbonyl-amino)thiophene-2-carboxamidine
4-[(3-methoxyphenyl)carbonylamino]-5-methylthiothiophene-2-carboxamidine
4-[2-(2-hydroxy-5-methoxyphenyl)acetylamino]-5-methylthiothiophene-2-carboxamidine
4-[(4-ethoxyphenyl)carbonylamino]-5-methylthiothiophene-2-carboxamidine
5-methylthio-4-(2-phenoxyacetylamino)-thiophene-2-carboxamidine
4-[(3-methylphenyl)carbonylamino]-5-methylthiothiophene-2-carboxamidine
5-methylthio-4-{[3-(phenylmethoxy)phenyl]amino}thiophene-2-carboxamidine
5-methylthio-4-[(3-phenoxyphenyl)amino]thiophene-2-carboxamidine
5-methylthio-4-[(4-phenoxyphenyl)amino]thiophene-2-carboxamidine
4-[(2-methoxyphenyl)amino]-5-methylthiothiophene-2-carboxamidine
4-[(2-methylphenyl)amino]-5-methylthiothiophene-2-carboxamidine
4-[(3-chlorophenyl)amino]-5-methylthiothiophene-2-carboxamidine
4-(methylphenylamino)-5-methylthiothiophene-2-carboxamidine
5-methyl-4-(phenylamino)thiophene-2-carboxamidine
4-{[4-(dimethylamino)phenyl]amino}-5-methylthiothiophene-2-carboxamidine 4-[(4-ethylphenyl)amino]-5-methylthiothiophene-2-carboxamidine
5-methylthio-4-{[4-(phenylaminomethoxy)phenyl]amino}thiophene-2-carboxamidine
5-methylthio-4-{[4-(phenylamino)phenyl]amino}thiophene-2-carboxamidine
4-[(4-methoxyphenyl)amino]-5-methylthiothiophene-2-carboxamidine
4-[(3-fluoro-4-methylphenyl)amino]-5-methylthiothiophene-2-carboxamidine
4-(indan-5-ylamino)-5-methylthiothiophene-2-carboxamidine
4-[(9-ethylcarbazol-3-yl)amino]-5-methylthiothiophene-2-carboxamidine
5-methylthio-4-{[(4-phenylphenyl)sulfonyl]amino}thiophene-2-carboxamidine
4-{bis[(4-phenylphenyl)sulfonyl]amino}-5-methylthiothiophene-2-carboxamidine
5-methylthio-4-[(2-naphthylsulfonyl)-amino]thiophene-2-carboxamidine
4-[bis(2-naphthylsulfonyl)amino]-5-methylthiothiophene-2-carboxamidine
4-{[(6-bromo(2-naphthyl))sulfonyl]amino}-5-methylthiothiophene-2-carboxamidine
4-{bis[(6-bromo(2-naphthyl))sulfonyl]amino}-5-methylthiothiophene-2-carboxamidine
5-methylthio-4-[(naphthylsulfonyl)-amino]thiophene-2-carboxamidine
4-[bis(naphthylsulfonyl)amino]-5-methylthiothiophene-2-carboxamidine
4-{[(2-methylphenyl)sulfonyl]amino}-5-methylthiothiophene-2-carboxamidine
4-{bis[(2-methylphenyl)sulfonyl]amino}-5-methylthiothiophene-2-carboxamidine
4-{[(3-methylphenyl)sulfonyl]amino}-5-methylthiothiophene-2-carboxamidine
4-{bis[(3-methylphenyl)sulfonyl]amino}-5-methylthiothiophene-2-carboxamidine
4-{[(4-methylphenyl)sulfonyl]amino}-5-methylthiothiophene-2-carboxamidine
4-{bis [(4-methylphenyl)sulfonyl]amino}-5-methylthiothiophene-2-carboxamidine
5-methylthio-4-{[benzylsulfonyl]amino}-thiophene-2-carboxamidine
5-methylthio-4-phenoxythiophene-2-carboxamidine
5-methylthio-4-(phenylsulfonyl)thiophene-2-carboxamidine
as well as salts thereof, such as hydrochloride or trifluoracetate salts and prodrugs thereof.

Methods of Use and Pharmaceutical Compositions

For medicinal use, the pharmaceutically acceptable acid addition salts, those salts in which the anion does not contribute significantly to toxicity or pharmacological activity of the organic cation, are preferred. The acid addition salts are obtained either by reaction of an organic base of Formula I with an organic or inorganic acid, preferably by contact in solution, or by any of the standard methods detailed in the literature available to any practitioner skilled in the art. Examples of useful organic acids are carboxylic acids such as maleic acid, acetic acid, tartaric acid, propionic acid, fumaric acid, isethionic acid, succinic acid, cyclamic acid, pivalic acid and the like; useful inorganic acids are hydrohalide acids such as HCl, HBr, HI; sulfuric acid; phosphoric acid and the like. Preferred acids for forming acid addition salts include HCl and acetic acid.

The compounds of the present invention represent a novel class of potent inhibitors of metallo, acid, thiol and serine proteases. Examples of the serine proteases inhibited by compounds within the scope of the invention include leukocyte neutrophil elastase, a proteolytic enzyme implicated in the pathogenesis of emphysema; chymotrypsin and trypsin, digestive enzymes; pancreatic elastase, and cathepsin G, a chymotrypsin-like protease also associated with leukocytes; thrombin and factor Xa, proteolytic enzymes in the blood coagulation pathway. Inhibition of thermolysin, a metalloprotease, and pepsin, an acid protease, are also contemplated uses of compounds of the present invention. The compounds of the present invention are preferably employed to inhibit trypsin-like proteases.

Compounds of the present invention that inhibit urokinase plasminogen activator are potentially useful in treating excessive cell growth disease state. Compounds of the present that inhibit urokinase are, therefore, useful as anti-angiogenic, anti-arthritic, anti-inflammatory, anti-invasive, anti-metastatic, anti-restenotic, anti-osteoporotic, anti-retinopathic (for angiogenesis-dependent retinopathies), contraceptive, and tumoristatic treatment agents. For example, such treatment agents are useful in the treatment of a variety of disease states, including but not limited to, benign prostatic hypertrophy, prostatic carcinoma, tumor metastasis, restenosis and psoriasis. Also provided are methods to inhibit extracellular proteolysis, methods to treat benign prostatic hypertrophy, prostatic carcinoma, tumor metastasis, restenosis and psoriasis by administering the compound of Formula I. For their end-use application, the potency and other biochemical parameters of the enzyme inhibiting characteristics of compounds of the present invention are readily ascertained by standard biochemical techniques well known in the art. Actual dose ranges for this application will depend upon the nature and severity of the disease state of the patient or animal to be treated as determined by the attending diagnostician. It is to be expected that a general dose range will be about 0.01 to 50 mg, preferably 0.1 to about 20 mg per kg per day for an effective therapeutic effect.

An end use application of the compounds that inhibit chymotrypsin and trypsin is in the treatment of pancreatitis. For their end-use application, the potency and other biochemical parameters of the enzyme-inhibiting characteristics of the compounds of the present invention is readily ascertained by standard biochemical techniques well known in the art. Actual dose ranges for their specific end-use application will, of course, depend upon the nature and severity of the disease state of the patient or animal to be treated, as determined by the attending diagnostician. It is expected that a useful dose range will be about 0.01 to about 50 mg, preferably about 0.1 to about 20 mg per kg per day for an effective therapeutic effect.

Compounds of the present invention that are distinguished by their ability to inhibit either factor Xa or thrombin may be employed for a number of therapeutic purposes. As factor Xa or thrombin inhibitors, compounds of the present invention inhibit thrombin production. Therefore, these compounds are useful for the treatment or prophylaxis of states characterized by abnormal venous or arterial thrombosis involving either thrombin production or action. These states include, but are not limited to, deep vein thrombosis; disseminated intravascular coagulopathy which occurs during septic shock, viral infections and cancer; myocardial infarction; stroke; coronary artery bypass; fibrin formation in the eye; hip replacement; and thrombus formation resulting from either thrombolytic therapy or percutaneous transluminal coronary angioplasty (PCTA).

By virtue of the effects of both factor Xa and thrombin on a host of cell types, such as smooth muscle cells, endothelial cells and neutrophils, the compounds of the present invention find additional use in the treatment or prophylaxis of adult respiratory distress syndrome; inflammatory responses; wound healing; reperfusion damage; atherosclerosis; and restenosis following an injury such as balloon angioplasty, atherectomy, and arterial stent placement. The compounds of the present invention may be useful in treating neoplasia and metastasis as well as neurodegenerative diseases, such as Alzheimer's disease and Parkinson's disease.

When employed as thrombin or factor Xa inhibitors, the compounds of the present invention may be administered in an effective amount within the dosage range of about 0.1 to about 500 mg/kg, preferably between 0.1 to 30 mg/kg body weight, on a regimen in single or 2–4 divided daily doses.

Human leucocyte elastase is released by polymorphonuclear leukocytes at sites of inflammation and thus is a contributing cause for a number of disease states. Compounds of the present invention are expected to have an anti-inflammatory effect useful in the treatment of gout, rheumatoid arthritis and other inflammatory diseases, and in the treatment of emphysema. The leucocyte elastase inhibitory properties of compounds of the present invention are determined by the method described below. Cathepsin G has also been implicated in the disease states of arthritis, gout and emphysema, and in addition, glomerulonephritis and lung infestations caused by infections in the lung. In their end-use application the enzyme inhibitory properties of the compounds of Formula I is readily ascertained by standard biochemical techniques that are well-known in the art.

The Cathepsin G inhibitory properties of compounds within the scope of the present invention are determined by the following method. A preparation of partially purified human Cathepsin G is obtained by the procedure of Baugh et al., *Biochemistry* 15: 836 (1979). Leukocyte granules are a major source for the preparation of leukocyte elastase and cathepsin G (chymotrypsin-like activity). Leukocytes are lysed and granules are isolated. The leukocyte granules are extracted with 0.20 M sodium acetate, pH 4.0, and extracts are dialyzed against 0.05 M Tris buffer, pH 8.0 containing 0.05 M NaCl overnight at 4° C. A protein fraction precipitates during dialysis and is isolated by centrifugation. This fraction contains most of the chymotrypsin-like activity of leukocyte granules. Specific substrates are prepared for each enzyme, namely N-Suc-Ala-Ala-Pro-Val-p-nitroanilide and Suc-Ala-Ala-Pro-Phe-p-nitroanilide. The latter is not hydrolyzed by leukocyte elastase. Enzyme preparations are assayed in 2.00 mL of 0.10 M Hepes buffer, pH 7.5, containing 0.50 M NaCl, 10% dimethylsulfoxide and 0.0020 M Suc-Ala-Ala-Pro-Phe-p-nitroanilide as a substrate. Hydrolysis of the p-nitroanilide substrate is monitored at 405 nm and at 25° C.

Useful dose range for the application of compounds of the present invention as neutrophil elastase inhibitors and as Cathepsin G inhibitors depend upon the nature and severity of the disease state, as determined by the attending diagnostician, with a range of 0.01 to 10 mg/kg body weight, per day, being useful for the aforementioned disease states.

Additional uses for compounds of the present invention include analysis of commercial reagent enzymes for active site concentration. For example, chymotrypsin is supplied as a standard reagent for use in clinical quantitation of chymotrypsin activity in pancreatic juices and feces. Such assays are diagnostic for gastrointestinal and pancreatic disorders. Pancreatic elastase is also supplied commercially as a reagent for quantitation of $\alpha_1$-antitrypsin in plasma. Plasma $\alpha_1$-antitrypsin increases in concentration during the course of several inflammatory diseases, and a,-antitrypsin deficiencies are associated with increased incidence of lung disease. Compounds of the present invention can be used to enhance the accuracy and reproducibility of these assays by titrametric standardization of the commercial elastase supplied as a reagent. See, U.S. Pat. No. 4,499,082.

Protease activity in certain protein extracts during purification of particular proteins is a recurring problem which can complicate and compromise the results of protein isolation procedures. Certain proteases present in such extracts can be inhibited during purification steps by compounds of the present invention, which bind tightly to various proteolytic enzymes.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions and cyclodextrin inclusion complexes. Especially preferred salts are hydrochloride and acetate salts. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

Methods of Making

Many synthetic methods used to form compounds of the present invention generally involve the formation of an amidine from a carboxylic acid derivative, such as an ester or a nitrile. In the process a Lewis acid, such as trimethylaluminum, is added to a source of ammonia, such as ammonium chloride in an aprotic solvent, such as a toluene, under an inert atmosphere (e.g., under an atmosphere of nitrogen or argon gas) at a temperature between −15° C. and 5° C., preferably at 0° C. An appropriate carboxylic acid derivative is added to the mixture and the mixture is heated at reflux for a predetermined period of time, preferably between 1 hr. and 24 hrs., and most preferably between 1 hr. and 4 hrs. The resulting solution is allowed to cool to room temperature and the amidine product isolated by known methods.

Description of Syntheses

The chemical schemes appear after the description of the schemes.

Scheme 1a

Scheme 1a illustrates a general approach to compounds of Formula I where X=O or S, $R^3$=alkylthio, aralkylthio, arylthio, alkyloxy, aralkyloxy or aryloxy, Y=bond and Z=$NR^5R^6$. When $R^{22}$ and $R^{21}$ of compounds 2 and 3 are retained in the final product, they correspond to $R^2$ and $R^3$ of Formula I, respectively. Otherwise $R^{22}$ and $R^{21}$ represent groups which, after further transformations, will become $R^2$ and $R^3$ of Formula I.

Starting with the heterocycle where X=O or S appropriately substituted by two leaving groups, the leaving groups can be sequentially displaced by appropriate nucleophiles (preferably the anion of the group $R^{21}$ or $R^{22}$ to be substituted) to produce the mono- or disubstituted heterocycles. Examples of leaving groups include halogens (chlorine, bromine or iodine), sulfonates (methanesulfonate, toluenesulfonate or trifluoromethanesulfonate) or sulfones (methylsulfonyl). Preferable nucleophiles include anions of thiols or alcohols having as the counterion an alkali or alkali earth metal such as sodium, lithium, potassium, magnesium or cesium, or in some cases, a transition group metal such as zinc, copper or nickel. In certain cases where the nucleophile used contains an anion on carbon, catalysis of the displacement may be useful for this transformation. Examples of catalysts would include compounds containing palladium, silver or Ni salts.

Scheme 1b

Scheme 1b illustrates approaches to providing the functionality of $Y(CNR^4)Z$ in compounds of Formula I where X=N, O or S, $R^{22}$ and $R^{21}$ are defined as in Scheme 1a. Depending on the nature of the group W in 3, several methods may be employed in the transformation of W to $Y(CNR^4)Z$.

When W in 3 is a cyano group (CN), primary amide ($CONH_2$) or ester ($CO_2R^{23}$), direct conversion to an unsubstituted amidine 5 (i.e. Formula I where Y=bond, Z=$NR^5R^6$ and $R^4$, $R^5$, $R^6$=H) can be effected by treatment with a reagent consisting of a Lewis acid complexed to ammonia. This complex is produced by treatment of ammonia or an ammonium salt, preferably an ammonium halide and most preferably ammonium chloride or bromide, with an appropriate Lewis acid, preferably a trialkylaluminum and most preferably trimethyl- or triethylaluminum in a solvent inert to the Lewis acid employed. For example, when a trialkylaluminum Lewis acid is employed with an ammonium halide, reaction occurs with loss of one equivalent of alkane to produce the dialkylhaloaluminum complex of ammonia (see for example Sidler, D. R., et al, *J. Org. Chem.*, 59:1231 (1994)). Examples of suitable solvents include unsaturated hydrocarbons such as benzene, toluene, xylenes, or mesitylene, preferably toluene, or halogenated hydrocarbons such as dichloroethane, chlorobenzene or dichlorobenzene. The amidination reaction is generally carried out at elevated temperatures, preferably 40–200° C., more preferably 80–140° C., and most preferably at the reflux temperature of a solvent in the range of 80–120° C.

When W is a cyano group (CN), direct conversion to a mono- or disubstituted amidine 5 ($R^4$, $R^5$, $R^6$=H) is also possible by treatment with a reagent consisting of a Lewis acid, preferably a trialkylaluminum, complexed to a mono- or disubstituted amine $H_2NR^5$ or $HNR^5R^6$ (Garigipati, R., *Tetrahedron Lett.* 31: 1969 (1990)). Alternatively the same addition of a mono- or disubstituted amine may catalyzed by a copper salt such as Cu(I) chloride (Rousselet, G., et al, *Tetrahedron Lett.* 34: 6395 (1993)).

When W in 3 is a carboxyl group ($CO_2H$), indirect conversion to an unsubstituted amidine 5 can be carried out by initial esterification to 4 by any of a number of well-known dehydrating agents (for example, dicyclohexylcarbodiimide) with an alcohol ($R^{23}OH$). More preferably 4 can be made by initial formation of an acid chloride by treatment of 3 with any of a number of anhydrides of HCl and another acid, such as thionyl chloride, $POCl_3$, $PCl_3$, $PCl_5$, or more preferably oxalyl chloride, with or without an added catalyst such as N,N-dimethylformamide (DMF), followed by the alcohol $R^{23}OH$. Conversion to the unsubstituted amidine 5 ($R^4$, $R^5$, $R^6$=H) can be carried out by treatment with a Lewis acid complexed to ammonia.

Amidines 5 also can be produced indirectly by conversion of 3 (W=CN) to iminoethers 6 by exposure to a strong acid such as a hydrogen halide, $HBF_4$ or other non-nucleophilic acid, preferably gaseous HCl in the presence of an alcohol $R^{23}OH$ ($R^{23}$=alkyl, branched alkyl or cycloalkyl, preferably Me or Et) and most preferably with the alcohol as solvent. Alternatively when W=$CONH_2$, conversion to an iminoether can be carried out by treatment with a trialkyloxonium salt (Meerwein's salts). In either case, treatment of the iminoether 6 with ammonia ($R^5$, $R^6$=H) or a mono- or disubstituted amine ($HNR^5R^6$) provides the corresponding unsubstituted or substituted amidines 5 (i.e. via classical Pinner synthesis: Pinner, A., Die Iminoaether und ihre Derivate, Verlag R. Oppenheim, Berlin (1892)).

When W=$NH_2$ in 3, treatment with a reagent Z($CNR^4$)L where Z=alkyl and L is a leaving group such as O-alkyl and preferably OMe, provides the subclass of amidines 135 (Z=alkyl) which are isomeric to 5 (Formula I, where Y=NH, Z=H or alkyl). Examples of reagents for this reaction include methyl or ethyl acetimidate hydrochloride. Alternatively treatment of 3 (W=$NH_2$) with a trialkyl orthoformate ester, preferably trimethyl- or triethyl orthoformate, followed by an amine $R^4NH_2$ affords the corresponding formidines 135 (Z=H) (Formula I, where Y=NH, Z=H).

Also, when W=$NH_2$, 3 can be treated with a reagent Z($CNR^4$)L where $R_4$=H and Z=$NR^5R^6$ and L is a leaving group such as pyrazole, methylpyrazole, $SO_3H$, S-alkyl, S-aryl, trifluoromethanesulfonate (OTf) or trifluoromethanesulfonamide (NHTf), preferably pyrazole, $SO_3H$ or trifluoromethanesulfonamide (NHTf). Examples of these reagents include aminoiminosulfonic acid (Miller, A. E. and Bischoff, J. J., *Synthesis*, 777 (1986) and 1H-pyrazole-1-carboxamidine hydrochloride (Bernatowicz, M. S., et al., *J. Org. Chem.* 57:2497 (1992)). Such treatment provides guanidines 136 directly (Formula I where Y=NH, Z=$NR^5R^6$). Alternatively a reagent Z($CNP^1$)L may be also used where Z=$NHP^2$ and L again a leaving group such as pyrazole, methylpyrazole, $SO_3H$, S-alkyl, S-aryl, trifluoromethanesulfonate (OTf) or trifluoromethanesulfonamide (NHTf), to provide protected guanidines ($P^1$, $P^2$=alkoxylcarbonyl, aralkoxycarbonyl or polymer-bound alkoxylcarbonyl similar to those described below in Scheme 4a) where the protecting groups $P^1$ and $P^2$ can then be removed to give unsubstituted 136 ($R^4$, $R^5$ and $R^6$=H). Protected guanidines are advantageous when further transformations are required after introduction of the guanidine functionality where an unprotected guanidine would not be stable. Examples of these protected reagents include reagents such as N,N'-bis(tert-butoxycarbonyl)-S-methylthiourea (Bergeron, R. J. and McManis, J. S, *J. Org. Chem.* 52:1700 (1987)), N,N'-bis(benzyloxycarbonyl)-1H-pyrazole-1-carboxamidine or N,N'-bis(tert-butoxycarbonyl)-1H-pyrazole-1-carboxamidine (Bernatowicz, M. S., et al., *Tetrahedron Letters*, 34: 3389 (1993)), N,N'-bis(benzyloxycarbonyl)-N"-trifluoromethanesulfonylguanidine, and N,N'-bis(tert-butoxycarbonyl)-N"-trifluoromethanesulfonylguanidine (Feichtinger, K., et al, *J. Org. Chem.* 63:3804 (1998)). Detailed descriptions and examples of these protecting groups and their use as protection for amidines are further outlined in Schemes 4a, 4b and 5.

When W in 3 is an ester ($CO_2R^{23}$) or carboxyl group ($CO_2H$), indirect conversion to an N-substituted or unsubstituted methylamidine (Formula I where Y=$CH_2$, Z=$NR^5R^6$) can be carried out by initial reduction of the ester or carboxyl by any of a number of well-known reducing agents. When W in 3 is an ester ($CO_2R^{23}$), examples of reducing agents include reducing agents such lithium aluminum hydride (LAH) and lithium borohydride. When W in 3 is a carboxyl group ($CO_2H$), examples of reducing agents include LAH and borane complexed to THF, dimethyl sulfide, dimethylamine or pyridine. The resulting hydroxymethyl derivative (W=$CH_2OH$) is converted to a cyanomethyl derivative (W=$CH_2CN$) by initial formation of a leaving group (W=$CH_2L$) where the leaving group L is a halogen (chlorine, bromine or iodine) or sulfonate ester (for example methanesulfonate, toluenesulfonate or trifluoromethanesulfonate). Displacement of L by cyanide can then be performed by treatment with a metal cyanide such as LiCN, NaCN, KCN or CuCN in a polar solvent such as DMF and with or without a catalyst such as a crown ether, to afford the cyanomethyl derivative (see for example Mizuno, Y., et al, *Synthesis*, 1008 (1980)). More preferably, the conversion of W=$CH_2OH$ to W=$CH_2CN$ may be effected by a Mitsunobu reaction (Mitsunobu, O., *Synthesis*, 1 (1981)) using an azodicarboxylate ester such as diethyl azodicarboxylate or diisopropyl azodicarboxylate, $Ph_3P$ and a source of cyanide such as HCN or more preferably acetone cyanohydrin (Wilk, B. *Synthetic Commun.* 23:2481 (1993)). Treatment of the resulting cyanomethyl intermediate (W=$CH_2CN$) under the conditions described for the conversion of 3 (W=CN) to 5 (either directly or indirectly via 6) provides the corresponding amidinomethyl products.

Scheme 1c

When not commercially available, alkylthiothiophenes (3, X=S, $R^1$=OH or $NH_2$, $R^{21}$=$SR^{54}$, W=CN, $CO_2R^{23}$, $CONH_2$) can be synthesized by the methods illustrated in Scheme 1c. Condensation of carbon disulfide and a malonic acid derivative ($R^{52}CH_2R^{22}$) in the presence of two alkylating agents $R^{54}L$ and $WCH_2L$ and a base in a suitable medium provide 3 (Dolman, H., European Patent Application No. 0 234 622 A1 (1987)). When $R^{22}$=$R^{52}$=CN, the resulting $R^1$ will be $NH_2$; when $R^{22}$=$R^{52}$=$CO_2R^{23}$, the resulting $R^1$ will be OH; and when $R^{22}$ and $R^{52}$=CN, $CO_2R^{23}$, the resulting $R^1$ can be selected to be OH or $NH_2$ (and $R^{22}$=CN or $CO_2R^{23}$) depending on the reaction conditions and order of reagent addition. Examples of malonic acid derivatives suitable for this transformation include but are not limited to malonate diesters such as dimethyl malonate or diethyl malonate ($R^{52}$, $R^{22}$=$CO_2R^{23}$, $R^{23}$=Me or Et), malononitrile ($R^{52}$, $R^{22}$=CN), or methyl or ethyl cyanoacetate ($R^{52}$=$CO_2R^{23}$, $R^{22}$=CN, $R^{23}$=Me or Et). Leaving groups L include halides such as chloride, bromide or iodide, preferably bromide or iodide, or sulfonates such as toluenesulfonate, benzenesulfonate, methanesulfonate or trifluoromethanesulfonate. Examples of alkylating agent $R^{54}L$ include primary or secondary alkyl, allyl or aralkyl halides or sulfonates, such as methyl iodide, isopropyl bromide, allyl bromide, benzyl chloride or methyl trifluoromethanesulfonate, or a 2-haloacetate ester such as tert-butyl 2-bromoacetate. Examples of alkylating agents $WCH_2L$ include 2-chloroacetonitrile, methyl 2-bromoacetate or 2-bromoacetamide. Suitable media are generally polar aprotic solvents, for example, N,N-dimethylformamide (DMF), N,N-dimethylacetamide (DMA), N-methylpyrrolidinone (NMP) or dimethylsulfoxide (DMSO), preferably DMF.

Alternatively compounds 3 ($R^{22}$=CN) can be synthesized from precursors 138 (derived from malononitrile, $R^{54}L$ and carbon disulfide), a thioglycolate WCHSH and a base in a suitable polar solvent, preferably methanol (Tominaga, Y., et al, *J. Heterocyclic Chem.* 31:771 (1994)).

When 3 contains an amino group at $R^1$, it can be diazotized with subsequent loss of nitrogen to give 3, $R^1$=H by treatment with a nitrosating agent in suitable solvent. Nitrosating agents include nitrosonium tetrafluoroborate, nitrous acid or, more preferably and alkyl nitrite ester such as tert-butyl nitrite. Suitable solvents are those which are stable to the nitrosating agents, preferably DMF, benzene or toluene.

Scheme 1d

When not commercially available, heterocyclic precursors 1 or 2 (X=O, S; W=$CO_2R^{23}$, COOH; L=halogen) used in Scheme 1a can be synthesized by the methods illustrated in Scheme 1d. Depending on the conditions used, treatment of compounds such as 139 with elemental halogen ($Cl_2$, $Br_2$ or $I_2$, preferably $Br_2$) or an N-halosuccinimide reagent, preferably N-bromosuccinimide (NBS), affords either 1 or 2 directly. Description of suitable solvents and conditions to selectively produce 1 or 2 are found in Karminski-Zamola, G. et al, *Heterocycles* 38:759 (1994); Divald, S., et al, *J. Org. Chem.* 41:2835 (1976); and Bury, P., et al, *Tetrahedron* 50:8793 (1994).

Scheme 2a

Scheme 2a illustrates the synthesis of compounds 12 representing the subclass of compounds for which $R^2$ is Formula II, where Ar=2-thiazolyl, Y=bond and Z=$NR^5R^6$. Starting with compound 1 (L=Br) and using the sequential displacement methodology discussed for Scheme 1a, $R^{21}$ can be first introduced to give 7. This is followed by a second displacement with a metal cyanide such as copper (I) cyanide, sodium cyanide or lithium cyanide and most preferably copper (I) cyanide at a temperature of 80–200° C. and preferably at 100–140° C., in a polar aprotic solvent, preferably DMF or DMSO, to give 8. After esterification by any of the means described for the conversion of 3 to 4, conversion to the thioamide is carried out by treatment of the nitrile with any of the methods well known in the art (see for example Ren, W., et al., *J. Heterocyclic Chem.* 23:1757 (1986) and Paventi, M. and Edward, J. T., *Can. J. Chem.* 65:282 (1987)). A preferable method is treatment of the nitrile with hydrogen sulfide in the presence of a base such as a trialkyl or heterocyclic amine, preferably triethylamine or pyridine, in a polar solvent such as acetone, methanol or DMF and preferably methanol. Conversion to the thiazole can be executed by classical Hantzsch thiazole synthesis followed by amidine formation as discussed in Scheme 1b.

Scheme 2b

Scheme 2b illustrates the synthesis of compounds representing the subclass of compounds for which $R^2$ is Formula II where, in addition to being an alternate route to Ar=2-thiazolyl (20) (see 12, Scheme 2a) also provide compounds of Formula II where Ar=2-oxazolyl (16) or 2-imidazolyl (18) (Y=bond and Z=$NR^5R^6$). Starting with compound 9, a selective hydrolysis of the nitrile with a tetrahalophthalic acid, preferably tetrafluoro- or tetrachlorophthalic acid, can be used to give 7 according to the method of Gribble, G. W. et al., *Tetrahedron Lett.* 29: 6557 (1988). Conversion to the acid chloride can be accomplished using the procedures discussed for conversion of 3 to 4, preferably with oxalyl chloride in dichloromethane in the presence of a catalytic amount of DMF. Coupling of the acid chloride to an aminoketone ($R^{26}$COCH($R^{27}$)$NH_2$) can be performed in the presence of an acid scavenger, preferably N,N-diisopropylethylamine (DIEA) or pyridine in a suitable solvent such as DMF, dichloromethane or tetrahydrofuran (THF) to afford the common intermediate 14. Alternatively coupling of the acid chloride to a less-substituted aminoketone ($R^{26}$COCH$_2$NH$_2$) can be used followed by optional alkylation with alkylating agent $R^{27}$L in the presence of a base, preferably NaH or t-BuOK. Transformation of 14 to the corresponding 2-oxazolyl (15), 2-imidazolyl (17) or 2-thiazolyl (19) esters can carried out by the methodology of Suzuki, M., et al., *Chem. Pharm. Bull.* 34:3111 (1986) followed by amidination according to Scheme 1b. In addition, direct conversion of ketoamide 14 to imidazolyl derivative 18 is possible under the same conditions for conversion of 17 to 18 when conducted for extended periods, preferably greater than 2 h.

Scheme 2c

Scheme 2c describes a general route to the synthesis of oxazoles, imidazoles and thiazoles of structure 27, 29 and 31 respectively. Acid 2 (see Scheme 1a) is converted to the ester by methods that are well known in the art (Theodora W. Greene and Peter G. M. Wuts, John Wiley and Sons, Inc. 1991). For example methyl ester 21 is formed by treating the acid in an appropriate solvent such as methanol with trimethylsilyldiazomethane. Alternatively the acid is treated with oxalyl chloride and catalytic amounts of dimethylformamide (DMF) in an appropriate solvent such as dichloromethane to form the acid chloride, which is then treated with methanol to give the methyl ester. Ester 21 is treated with a palladium (0) catalyst such as palladium tetrakistriphenylphosphine, and an alkylstannane such as hexa-n-butyldistannane or tri-n-butyltin chloride in an appropriate solvent such as DMF at elevated temperatures (50° C.–120° C.) to give the arylstannane of general structure 22 (Stille, J. K., *Angew. Chem. Int. Ed. Engl.* 25:508–524 (1986)). The stannane 22 is then treated with acid chlorides in the presence of a palladium(0) catalyst to give ketone 23. The ketone is treated with ammonia/ammonium chloride to give amine 24. Alternatively the ketone is reacted with an azide such as sodium azide in a suitable solvent such as DMF, and the resulting azidoketone is reduced to amine 23 with a suitable reducing agent such as catalytic hydrogenation in the presence of palladium on carbon and an acid such as HCl (*Chem. Pharm. Bull.* 33:509–514 (1985)). Ketoamides 25 are formed by coupling the ketoamine 24 with a variety of suitably flnctionalized acid chlorides. Alternatively amide coupling may be performed using any of a number of peptide coupling reagents such as 1,3-dicyclohexylcarbodiimide (Sheehan, J. C. et al., *J. Am. Chem. Soc.,* 77:1067 (1955)) or Castro's reagent (BOP, Castro, B., et al., *Synthesis* 413 (1976)). In another approach, amides 25 are formed directly from ketones 23 by reacting with various amide salts in an appropriate solvent such as DMF. The amide salts are generated by treating the amides with a suitable base such as sodium hydride (NaH). For example acetamide is treated with NaH in DMF at 0° C. to give sodium acetamide. Keto amide 25 is cyclized to the oxazole 26, imidazole 28 and thiazole 30 using procedures similar to that shown in scheme 2b. Oxazole 26, imidazole 28 and thiazole 30 are treated with trimethylaluminum and ammonium chloride in refluxing toluene to give the amidines 27, 29 and 31 respectively.

Scheme 2d

Scheme 2d illustrates to the preparation of compounds of Examples 42–43, where $R^{21}$ and $R^{43}$ correspond in Formula I to groups $R^3$ and $R^2$, respectively. The acids 2 can be converted to the stannane by treatment with base, such as n-butyl lithium or sec-butyl lithium, followed by trimethyltin chloride. The resulting acid can be then converted to the ester 22 by methods that are well known in the art (Theodora W. Greene and Peter G. M. Wuts, *Protective Groups in Organic Chemistry*, John Wiley and Sons, Inc. 1991). For example the methyl ester can be made by treating the acid 2 in a suitable solvent such as methanol with trimethylsilyldiazomethane. The stannane 22 can be reacted with suitable halides in the presence of catalytic amounts of a palladium catalyst, such as palladium tetrakistriphenylphosphine, to give the esters 32 (Stille, J. K., *Angew. Chem. Int. Ed. Engl.* 25:508–524 (1986)). These esters are then treated with trimethylaluminum and ammonium chloride in refluxing toluene to give the amidines 33. In the case where $R^{43}L$, (n=2), this can be cross-coupled to an aryl, heteroaryl or vinyl boronic acid or ester to give compounds 34 (Miyaura, N. and Suzuki, A., *Chem. Rev.* 95:2457–2483 (1995)). This can usually be done in the presence of catalytic amounts of a palladium (0) catalyst such as tetrakistriphenylphosphine palladium and a base such as potassium carbonate in DMF at 90° C. Similar cross-coupling reactions can also be achieved by using aryl, heteroaryl and vinyl stannanes instead of boronic acids or esters. These esters are converted to the amidines 35 in the manner previously described.

Scheme 2e

Scheme 2e represents a modification to the methodology outlined in Scheme 2b which allows synthesis of compounds of Formula II where Ar=2-thiazolyl, 2-oxazolyl or 2-imidazolyl (Y=bond and $Z=NR^5R^6$) but which are regioisomeric to 16, 18 or 20 in the relative positions of substituents $R^{26}$ and $R^{27}$. This is illustrated in Scheme 2b by the synthesis of 2-oxazolyl derivative 39. Thus, acid 13 can be coupled to an hydroxy-containing amine $R^{27}CH(NH_2)CH(R^{26})OH$ to give amide 36 by any of a number of amide coupling reagents well known in the art (see Bodanszky, M. and Bodanszky, A., *The Practice of Peptide Synthesis*, Springer-Verlag, New York (1984)). More preferably 13 can be converted to the corresponding acid chloride using any of the procedures mentioned for conversion of 3 to 4 followed by treatment with the $R^{27}CH(NH_2)CH(R^{26})OH$ in the presence of an acid scavenger, preferably N,N-diisopropylethylamine (DIEA) or pyridine in a suitable solvent such as DMF, dichloromethane or tetrahydrofuran (THF) to give 36. Oxidation of the alcohol 36 to the aldehyde 37 ($R^{26}$=H) or ketone 37 ($R^{26}$=alkyl, aryl, aralkyl, heterocycle) can be effected by any of a number of common methods known in the art (see for example F. Carey, F. A., Sundberg, R. J. *Advanced Organic Chemistry, Part B: Reactions and Synthesis*, 3rd Edition, Plenum Press, New York (1990)), preferably by a mild Moffatt-type oxidation such as a Swern oxidation (Mancuso, A. J., Huang, S. L. and Swern, D., *J. Org. Chem.* 3329 (1976)) or more preferably using Dess-Martin reagent (Dess, D. B. and Martin, J. C., *J. Org. Chem.* 48:4155 (1983)). Conversion to the heterocycle (in this case the oxazole) is effected with any of a number of reagents including phosphorus oxychloride, $P_2O_5$ or thionyl chloride (see Moriya, T., et al., *J. Med. Chem.* 31:1197 (1988) and references therein). Alternatively closure of 37 with either Burgess reagent or under Mitsunobu conditions affords the corresponding oxazolinyl derivatives (Wipf, P. and Miller, C. P., *Tetrahedron Lett.* 3: 907 (1992)). Final amidination to 39 as in Scheme 1b completes the synthesis.

Scheme 2f

Scheme 2f illustrates a general approach to the synthesis of thiazoles of structure 43 (Formula II, X=S, Ar=thiazolyl).

Nitriles of structure 40 can be treated with hydrogen sulfide ($H_2S$) in a suitable solvent such as methanol, or pyridine in the presence of a base such as triethylamine to give thioamides 41 (Ren, W. et al., *J. Heterocyclic Chem.* 23:1757–1763 (1986)). Thioamides 41 can be then treated with various haloketones 42 preferably bromoketones under suitable reaction conditions such as refluxing acetone or DMF heated to 50° C.–80° C. to form the thiazoles 43 (Hantzsch, A. R. et al., *Ber.* 20:3118 (1887)).

Scheme 2g

Scheme 2g illustrates one synthetic route to 2-haloketones of structure 42 which are employed in the synthesis of thiazolyl derivatives as in Schemes 2a and 2f. 2-Bromoketones 42 (L=Br) are prepared by treating the ketone 44 with a suitable brominating agent such as $Br_2$ or N-bromosuccinimide in a suitable solvent such as chloroform or acetic acid (EP 0393936 A1). Alternatively, the ketone 44 is treated with a polymer-supported brominating agent such as poly(4-vinyl)pyridinium bromide resin (Sket, B., et al., *Synthetic Communications* 19:2481–2487 (1989)) to give bromoketones 42. In a similar fashion 2-chloroketones are obtained by treating 44 with copper (II) chloride in a suitable solvent such as chloroform (Kosower, E. M., et al., *J. Org. Chem.* 28:630 (1963)).

Scheme 2h

Scheme 2h illustrates another synthetic route to 2-haloketones of structure 42 which is particularly useful in that it employs acids 45 or activated carbonyl compounds such as 46 as precursors which are more readily available than the ketones 44. The acid 45 is converted to the acid halide 46 (L=Cl, Br or $OCOR^{39}$) by treating with a suitable halogenating reagent. For example, an acid chloride is formed by treating 45 with oxalyl chloride and catalytic amounts of DMF in dichloromethane. The acid chloride is converted to a diazoketone by treatment with trimethysilyldiazomethane (Aoyama, T. et al., *Tetrahedron Lett.* 21:4461–4462 (1980)). The resulting diazoketone is converted to a 2-haloketone of structure 42 by treatment with a suitable mineral acid. For example a bromoketone is formed by treating the diazoketone in a suitable solvent such as acetonitrile ($CH_3CN$) with a solution of 30% hydrogen bromide (HBr) in acetic acid (Organic Synthesis Collective Vol III, 119, John Wiley and Sons, New York, Ed. Horning E. C.). In an alternative approach the acid 45 is converted to the mixed-anhydride 46 by treatment with a suitable chloroformate such as isobutyl chloroformate or tert-butyl chloroformate in a suitable solvent, such as tetrahydrofuran or dichloromethane, in the presence of a base such as N-methylmorpholine. The mixed anhydride 46 is converted to a diazoketone by treatment with trimethylsilyldiazomethane and the resulting diazoketone is converted to a haloketone in the manner described above.

Scheme 2i

When amide coupling as described in Scheme 2e is followed directly by amidination, compounds of Formula I where $R^2$ or $R^3$ is aminoacyl or aminoiminomethyl can be derived. Thus, coupling of acid 13 (or the corresponding acid chloride as previously described) with an amine $R^{51}R^{52}NH$ can afford 130 which can be carried on to the amidine 131. Upon either longer or more vigorous additional treatment (for example, higher temperatures) with a Lewis acid-ammonia reagent as described in Scheme 1b, the amide group can be converted to an aminoiminomethyl group to give a bisamidine compound 132.

Scheme 3a

Acid 13 can also be converted to an amine 47 from which sulfonamides, ureas and urethanes can be formed (Formula I where $R^2$ or $R^3 = NR^{32}SO_2R^{31}$, $NHCONR^{51}R^{52}$ or $NHCOR^{31}$, respectively). Scheme 3a illustrates this methodology for introduction of these three groups at $R^2$ of Formula I. Conversion of the acid 13 to an intermediate acyl azide can be followed by heating of such azide in the presence of an alcohol under Curtius rearrangement conditions to form the carbamate ester of the alcohol. Subsequent carbamate ester hydrolysis yields amine 47. The intermediate acyl azide may be synthesized by coupling the acid 13 to hydrazine through the acid chloride or by any of the amide coupling procedures discussed for Scheme 2e followed by nitrosation of the resulting hydrazide by any of the nitrosating agents discussed for conversion of 3 ($R^1 = NH_2$) to 3 ($R^1 = H$) in Scheme 1c. More preferably conversion of 13 to 47 is carried out through treatment of acid 13 with diphenylphosphoryl azide in the presence of an alcohol, preferably tert-butanol, and a base, preferably triethylamine or DIEA, as shown in Scheme 3a, to give a tert-butylcarbamate that is readily decomposed to the salt of amine 47 on exposure to an acid, preferably HCl or trifluoroacetic acid in a suitable solvent such as $CH_2Cl_2$. Further treatment with a base such as NaOH or preferably $K_2CO_3$ or $NaHCO_3$ provides the free base 47. Treatment of amine 47 with a sulfonyl chloride $R^3SO_2Cl$ in the presence of an acid scavenger, such as pyridine or DIEA, followed by optional alkylation on nitrogen with an alkylating agent $R^{32}L$ in the presence of a base such as $K_2CO_3$, DIEA or more preferably sodium hydride, in a solvent such as THF, MeCN or $CH_2Cl_2$ affords the sulfonylamine functionality at $R^2$ (48). When necessary, this transformation can be catalyzed by the presence of 4-dimethylaminopyridine for less reactive sulfonyl chlorides. Similar treatment of amine 47 with an isocyanate $R^{51}NCO$ or carbamyl chloride $R^{51}R^{52}COCl$ affords the aminocarbonylamine functionality at $R^2$ (50). Similar treatment of amine 47 with an acid chloride $R^{31}COCl$ affords the carbonylamine functionality at $R^2$ (52). Conversion of the esters in 48, 50 and 52 to amidines as previously mentioned gives the products 49, 51 and 53. Further conversion of the acylamino group of 53 as discussed for synthesis of 132 also provides access to the iminomethylamino group at $R^2$ (54).

Scheme 3b

Introduction of an aminosulfonyl group (including monoalkylaminosulfonyl and dialkylaminosulfonyl groups) for $R^2$ of Formula I can be carried out starting from amine such as 47 as well. Conversion to a sulfonyl chloride by the method of Gengnagel, et al. (U.S. Pat. No. 3,947,512 (1976)) and treatment with an amine $R^{34}NH_2$ followed by optional alkylation on nitrogen with $R^{35}L$ (under the sulfonylation and alkylation conditions described in Scheme 3a) provides 56 which is further converted to amidines 57 as previously described.

Scheme 3c

In addition to the synthesis outlined in Scheme 3a, amine 47 may also be produced as illustrated in Scheme 3c. A nitrothienyl ester 122 (Dell'Erba, C. and Spinelli, D., *Tetrahedron*, 21: 1061 (1965), Dell'Erba, C. et al., *J. Chem. Soc, Perkin Trans* 2, 1779 (1989)) with a suitable leaving group L may be substituted with an anion of $R^{21}$ to give intermediate 123. Amine 47 is then derived from reduction of the nitro group. Appropriate reagents to effect reduction of the nitro functionality include hydrogen gas in the presence of a catalyst such as palladium or platinum metal deposited on carbon or barium sulfate in any of a number of solvents such as methanol, ethanol, ethyl acetate, DMF or THF. More preferably, tin (II) chloride may be employed as a reductant in solvents such as DMF or THF, or in the presence of HCl in a solvent such as methanol or ethanol. Alternatively, metals such as zinc or iron (Stanetty, P. and Kremslehner, M., *Heterocycles* 48: 259 (1998)) may also be used.

Scheme 4a

Scheme 4a illustrates the preparation of the compounds of Formula III and Examples 48–59 and 61–77. The amidine moiety of compounds of structure 60 can be protected with a protecting group $P^1$ that can be readily removed from 62 and 64 using methods known to those skilled in the art (Theodora W. Greene and Peter G. M. Wuts, John Wiley and Sons, Inc. 1991). For example, a tert-butoxycarbonyl (BOC) protecting group can be removed by exposure to strongly acidic medium such as hydrogen chloride in a suitable solvent such as dioxane, or by trifluoroacetic acid in a suitable solvent such as methylene chloride. Benzyloxycarbonyl (Cbz) protecting groups can be removed by catalytic hydrogenation using palladium on carbon as a catalyst in solvents such as ethanol or tetrahydrofuran.

In some cases, $P^1$ can be a solid support such as polystyrene or polyethyleneglycol-grafted polystyrene which can be attached to the amidine moiety via a cleavable linker such as 4-(benzyloxy)benzyloxy-carbonyl (using carbonate Wang resin). Attaching an amidine to a solid support can be achieved by treating a solid support having a linker containing an appropriately activated functional group with the amidine under suitable conditions. For example, an amidine can be attached to Wang resin by treating para-nitrophenylcarbonate Wang resin with the amidine and a suitable base such as DBU in a suitable solvent such as DMF. When D is OH or SH the protected amidines 61 can be alkylated with carboxy-protected (protecting group is $R^{36}$) haloaliphatic acids, such as bromoacetic acid or bromopropionic acid in the presence of a suitable base such as cesium carbonate or DIEA, in a suitable solvent such as DMF with heating when necessary to give compounds of structure 62. When D is $NO_2$, the nitro group can be reduced prior to alkylation using an appropriate reducing agent, such as tin (II) chloride, in a suitable solvent such as DMF, or by catalytic hydrogenation using palladium on carbon as a catalyst in solvents such as ethanol or tetrahydrofuran. Other useful carboxy protecting groups are well known in the art (Theodora W. Greene and Peter G. M. Wuts, *Protective Groups in Organic Chemistry*, John Wiley and Sons, Inc. 1991). For example, tert-butyl ester can be removed by exposure to strongly acidic medium such as hydrogen chloride in a suitable solvent such as dioxane, or such as trifluoroacetic acid in a suitable solvent such as methylene chloride. Benzyl ester can be removed by catalytic hydrogenation using palladium on carbon as a catalyst in solvents such as ethanol or tetrahydrofuran or by base hydrolysis.

When protecting groups $P^1$ and $R^{36}$ in compounds 62 are orthogonal (as defined by the ability to remove one protecting group preferentially in the presence of the other), $R^{36}$ can be preferentially removed to give acids 63. For example when $P^1$ is BOC and $R^{36}$ is OMe, the methyl ester can be removed by treating with a base such as sodium hydroxide in a suitable solvent such as aqueous tetrahydrofuran leaving the BOC group intact. When protecting groups $P^1$ and $R^{36}$ in compounds 62 are not orthogonal, both protecting groups are removed, and the amidine can be protected with a suitable protecting group such as BOC or a suitably functionalized resin. The protected amidine 63 can be treated with various amines under suitable amide coupling conditions, such as in the presence 1-hydroxy-7-azabenzotriazole (HOAt), O-(7-azabenzotriazol-1-yl)-1,1,3,3-tetramethyluronium hexafluorophosphate (HATU) and DIEA to form amides of structure 64. The amidine protecting group can be then removed, for example by treating with an acid, such as trifluoroacetic acid in a suitable solvent such as methylene chloride, when a BOC protecting group is employed, to give amidines 65.

Scheme 4b

Scheme 4b illustrates a specific example which utilizes the method described in Scheme 4a. The amidine moiety of 66 can be monoprotected with a tert-butyloxycarbonyl group. The monoprotected phenoxyamidine 67 can be alkylated on the phenolic hydroxy group with an ester of 2-bromoacetic acid to give 68. In the case where the ester can be removed by base, it can be hydrolyzed with aqueous base, such as NaOH, to give the acid 69. This acid can be treated with various amines in the presence of 1-hydroxy-7-azabenzotriazole (HOAt), O-(7-azabenzotriazol-1-yl)-1,1,3,3-tetramethyluronium hexafluorophosphate (HATU) and DIEA to form amides of structure 70. The amines are unsubstituted, di- or mono-substituted aliphatic or aromatic amines. In some cases the amines are cyclic-amines such as piperazine and piperidine. The amides 70 are then treated with trifluoroacetic acid to give the amidines 71. In the case where the ester 68 is acid-labile, it can be treated with trifluoroacetic acid to give the amidino-acid 72. This amidine can be loaded on to an insoluble support, such as polystyrene or polyethyleneglycol-grafted polystyrene via a cleavable linker, such as Wang, which is functionalized as an activated carbonate such as p-nitrophenylcarbonate or succinimidyl carbonate. Generally this can be done by treating the activated carbonate resin with the amidine and a suitable base such as DBU in a suitable solvent such as DMF. The support-bound acid 73 can be treated with various amines in the presence of 1-hydroxy-7-azabenzotriazole (HOAt), O-(7-azabenzotriazol-1-yl)-1,1,3,3-tetramethyluronium hexafluorophosphate (HATU) and DIEA to form amides. These amides are then cleaved from the solid support by treating with trifluoroacetic acid to give compounds of structure 71.

Scheme 5

Scheme 5 illustrates a synthetic route to amidines containing di-substituted thiazoles represented by compounds for which $R^2$ is Formula II and both $R^8$ and $R^9$ are non-hydrogen substituents. The ketoamide 74 can be converted to the mono-bromoketoamide by treating with bromine in acetic acid. Thiazoles 76 are formed by reacting the bromoketoamide with 10 under suitable conditions, preferably by heating the mixture in DMF or acetone. Amidines 77 are formed by heating 76 in toluene with trimethylaluminum and ammonium chloride. The amidines 77 are treated with strong acid such as HCl to give the acids 78. The amidines 78 are in one route protected with a suitable protecting group such as BOC to give 79. The protected amidines 79 are treated with various amines under suitable coupling conditions, such as in the presence of HOAt, HATU, and DIEA to form various amides. The amidine protecting group can be then removed, for example by treating with trifluoroacetic acid in a suitable solvent such as methylene chloride, when a BOC protecting group is employed to give amidines 80. In a second route, the amidines 78 can be loaded onto an insoluble support, such as polystyrene or polyethyleneglycol-grafted polystyrene via a cleaveable linker, such as Wang resin, which is functionalized as an activated carbonate ester, such as p-nitrophenylcarbonate or succinimidyl carbonate, to give a resin-bound scaffold 81. The resin-bound acid 81 can be treated with various amines under suitable coupling conditions such as in the presence of HOAT, HATU and DIEA to form amides. These amides are then cleaved from the solid support by treating with trifluoroacetic acid to give amidines 80.

Scheme 6a

Scheme 6a illustrates the preparation of compounds of Examples 144, 145, 146, 147, 148, 149, 150 and 151. Compounds of this invention correspond to those of Formula I where $R^2$ is Formula II and where Ar is thiazole and $R^{37}$ and $R^{38}$ ($R^8$ and $R^9$ of Formula II) are phenyl, which can be additionally substituted. Starting from 2,5-dibromothiophene 90, treatment with lithium diisopropylamide followed by $R^{21}L$, where L is a leaving group, preferably a halogen, mesylate, tosylate, or methyl sulfate, and more preferably iodomethane or methyl sulfate, according to the procedure of Kano, et al., *Heterocycles* 20(10):2035 (1983), gives 91. Compound 91 can be treated with an appropriate base, preferably a lithium alkyl like n-butyllithium, sec-butyllithium, or t-butyllithium, and more preferably n-butyllithium, followed by carbon dioxide gas and conversion of the resulting carboxylate salt to the free acid with a mineral acid, preferably hydrochloric acid. Conversion to ester 21 can be carried out by preparation of the acid chloride using oxalyl chloride and treatment of this intermediate acid chloride with an alcohol $R^{23}$ in an appropriate solvent, preferably dichloromethane, with an appropriate base, preferably pyridine. Compound 21 can be treated with copper (I) cyanide in refluxing dimethylformamide to give compound 9. Compound 9 can be treated with hydrogen sulfide gas in an appropriate solvent, preferably methanol, containing an appropriate base, preferably triethylamine to give compound 10. Compound 10 can be treated with an appropriate ketone where L is a leaving group, preferably halogen, mesyl, or tosyl, and most preferably bromo, refluxing in a suitable solvent, preferably, acetone, dimethylformamide, dimethyl acetamide, methyl ethyl ketone, or other polar aprotic solvents, and most preferably acetone to give compound 92. Compound 92 is treated with an appropriate reagent, preferably the aluminum amide reagent to give amidine 93.

Scheme 6b

Scheme 6b illustrates the preparation of the compound of Example 144, which corresponds to a compound for which $R^2$ is Formula II, and where Ar is thiazole and $R^8$ and $R^9$ ($R^{37}$ and $R^{38}$ in Scheme 6b) are phenyl, which can be optionally substituted. Starting from 2,5-dibromothiophene 90, treatment with n-butyllithium produces an anion which undergoes a rearrangement (Kano, S., et al, *Heterocycles* 20:2035 (1983)). Quenching with carbon dioxide gas and conversion of the resulting carboxylate salt to the free acid with a mineral acid, preferably hydrochloric acid, gives acid 94. Conversion to ester 95 can be carried out by preparation of the acid chloride using oxalyl chloride and treatment of this intermediate acid chloride with an alcohol $R^{23}$—OH in an appropriate solvent, preferably dichloromethane, with an appropriate base, preferably pyridine. Compound 95 can be treated with copper (I) cyanide in refluxing dimethylformamide to give compound 96. Compound 96 can be treated with hydrogen sulfide gas in an appropriate solvent, preferably methanol, containing an appropriate base, preferably triethylamine to give compound 97. Compound 97 can be treated with an appropriate ketone where L is a leaving group, preferably halogen, mesyl, or tosyl, and most preferably bromo, refluxing in a suitable solvent, preferably, acetone, dimethylformamide, dimethyl acetamide, methyl ethyl ketone, or other polar aprotic solvents, and most preferably acetone to give compound 98. Compound 98 is treated with an appropriate reagent, preferably the aluminum amide reagent $(Al(CH_3)_3/NH_4Cl)$ to give amidine 99.

Scheme 7a

Scheme 7a illustrates the preparation of compounds for which $R^2$ is Formula II and Ar is thiazol-4-yl. As illustrated, the acids 13 can be converted to their acid chlorides by treatment with oxalyl chloride with dimethylformamide catalysis in methylene chloride, or by using thionyl chloride, either neat or in an organic solvent, at ambient or elevated temperature. Compounds are then homologated to the desired a-haloketones 100 by sequential treatment with trimethylsilyldiazomethane and hydrogen bromide. An alternative would be to substitute diazomethane (generated from Diazald®, Aldrich Chemical Co., Milwaukee, Wis.) for the trimethylsilyldiazomethane. Also, the conversion of 13 to 100 can be effected using the procedure derived for the synthesis of compound 42 from compound 46.

The alpha-haloketones 100 are then allowed to react with the appropriate thiourea (Scheme 7b) or thioamide derivative in an organic solvent, preferably acetone or dimethylformamide at 70° C. to give 2-aminothiazoles or thiazoles 101.

The thiazoles 101 can be treated with the aluminum amine reagent $(Al(CH_3)_3/NH_4Cl)$ formed at ambient temperature by the reaction of trimethylaluminum with ammonium chloride in an organic solvent, preferably toluene. The ester can then be converted to the amidines 102 at elevated temperatures, preferably higher than 80° C.

Scheme 7b

As shown in Scheme 7b, amines 110 (or their hydrochloride salts) can be converted to their respective monosubstituted thioureas (methan-1-thiones) 112 by treatment with thiophosgene to form the intermediate isothiocyanates 111. Preferred conditions include treating the amine with thiophosgene in a biphasic solvent system composed of a halogenated solvent such as chloroform and an aqueous phase of saturated sodium bicarbonate. Alternatively, the reaction may be effected by treatment of 110 with a hindered amine and thiophosgene such as triethylamine or diisopropylethylamine in an organic solvent such as tetrahydrofuran or methylene chloride. Another alternative to forming isothiocyanates 111 is the direct treatment of primary amines and carbon disulfide in pyridine with dicyclohexylcarbodiimide (Jochims, *Chem. Ber.* 101:1746 (1968)).

Isothiocyanates 111 can be converted to thioureas 112 by treatment with an ammonia-alcohol solution, preferably a 2M ammonia in methanol or ethanol solution, at room temperature or elevated temperatures (>70° C.). Alternatively, the thioureas 112 can be prepared directly form the appropriate urea (or thioamide from the appropriate amide when $R^8$=alkyl or aryl)) by treatment with Lawesson's reagent (Lawesson, S.-O., et. al. *Bull. Soc. Chim. Belg.* 87:223, 293 (1978)).

Scheme 8

Scheme 8 illustrates the preparation of compounds of this invention where $R^2$ is Formula II and Ar is thiazole and $R^{37}$ and $R^{38}$ are phenyl which is further substituted by a sulfonylamino or carbonylamino group. Starting from thioamide 10, treatment with a nitro substituted 2-halo-acetophenone, where the halogen is chloro, bromo, or iodo, preferably bromo, refluxing in a suitable solvent, preferably acetone, dimethylformamide, dimethyl acetamide, methyl ethyl ketone, or other polar aprotic solvents, and most preferably acetone. The reduction of nitroaryl compound 113 can be carried out with a suitable reducing agent, preferably tin (II) chloride, titanium (II) chloride, iron (III) chloride, lithium metal, sodium metal, catalytic hydrogenation over platinum or palladium catalyst, and most preferably 20% aqueous solution of titanium (III) chloride. The acylation of aniline 114 can be carried out with an appropriate acyl compound $R^{42}L$ where L is a halogen, preferably chloro, in an appropriate solvent, preferably dichloromethane, containing a base, preferably pyridine, N-methylmorpholine, or diisopropylethylamine. Alternatively, the acylation of aniline 114 is carried out with an activated carboxylic acid compound $R^{42}COL$ where L is hydroxy activated with dicyclohexylcarbodiimide, ethyl-3-(diethylamino) propylcarbodiimide (EDAC), O-(7-azabenzotriazol-1-yl)-N, N,N',N'-tetramethyluronium hexafluorophosphate (HATU), or pentafluorophenyl. The sulfonylation of aniline 114 can be carried out with and appropriate sulfonyl chloride compound $R^4SO_2L$ in an appropriate solvent, preferably dichloromethane, containing a base, preferably N-methyl morpholine, diisopropylethylamine, or pyridine, most preferably N-methyl morpholine, with or without a condensation catalyst, preferable dimethylaminopyridine (DMAP). The amidinylation of compounds 115 and 117 can be carried out with an appropriate reagent, preferably the aluminum amide reagent $(Al(CH_3)_3/NH_4Cl)$.

Scheme 9

Scheme 9 illustrates the preparation of compounds of Formula I, for which one of $R^5$ and $R^6$ is a non-hydrogen substituent. The amidines 5 are converted to the amidoximes 119 by heating with hydroxylamine in a suitable solvent such as ethanol. The cyanoamidines 120 are prepared by heating the amidines 5 with cyanamide in a suitable solvent such as ethanol. (Huffman, K. R. and Schaeffer, F., *J. Amer. Chem. Soc.* 28:1812 (1963). Alternatively 5 can be heated with an amine such as methylamine to give the N-alkylated amidines 121.

Scheme 10

Scheme 10 illustrates an approach to compounds of Formula I where X=S or O, $R^2$=arylamino, $R^3$=alkylthio, aralkylthio, arylthio, alkyloxy, aralkyloxy, aryloxy, alkylamino, dialkylamino, aralkylamino, diaralkylamino, arylamino or diarylamino, Y=bond and Z=$NR^5R^6$.

Aminothiophenes 47 (Formula I where X=S, or O; $R^2$=$NH_2$) can be reacted with an arylboronic acid ($R^{56}B(OR^{58})_2$, $R^{58}$=H) or arylboronic ester ($R^{56}B(OR^{58})_2$, $R^{58}$= alkyl) in the presence of a copper catalyst, preferably copper (II) acetate, and an amine base such as triethylamine or pyridine (Chan, D. M. T. et al., *Tetrahedron Lett* 39: 2933 (1998)) to give a thienylarylamine 124. Conversion of the ester to amidine 125 is carried out in the manner previously described in Scheme 1b.

Scheme 11

Another route to compounds of this invention, where $R^2$=arylamino or alkylarylamino and alkylamino and where $R^3$, Y and Z are as described in Scheme 10, is shown in Scheme 11 where intermediate 2 ($R^{21}=R^3$, L=leaving group) is aminated using conditions well known in the art. (See for example: Ahman, J. and Buchwald, S. L., *Tetrahedron Lett.* 38: 6363 (1997) and Wolfe, J. P. and Buchwald, S. L., *Tetrahedron Lett.* 38: 6359 (1997). For reviews see: Frost, C. G and Mendonca, P., *J. Chem. Soc, Perkin Trans* 1: 2615 (1998) and Wolfe, J. P. et al., *Acc. Chem. Res.* 31: 805 (1998).) Thus, 2 may be treated with an aniline $R^{56}R^{57}NH$ ($R^{56}$=aryl, $R^{57}$=H or alkyl) in the presence of a palladium catalyst, a suitable palladium ligand and a base to give 127. Suitable catalysts include any of a number of Pd(0) or Pd(II) salts, such as tetrakis(triphenylphosphino) palladium (0), dichlorobis(acetonitrile)palladium (II) or preferably palladium (II) acetate or tris(dibenzylideneacetone)dipalladium. The most appropriate ligands for any given reaction are often compound-dependent and are discussed in detail in the aforementioned references but may include 1,1'-bis(diphenylphosphino)ferrocene (DPPF), 1-[2-(diphenylphosphino)ferrocenyl]ethyl methyl ether (PPF-OMe), or preferably 2,2'-bis(diphenylphosphino)-1,1'-binaphthyl (BINAP). Appropriate bases include sodium t-butoxide or preferably cesium carbonate or potassium phoshate. Useful solvents include DMF, dioxane, dimethoxyethane or preferably toluene. Conversion of the ester to amidine 128 is carried out in the manner previously described in Scheme 1b.

Scheme 12

The corresponding compounds of Formula I where $R^2$=alkylamino and $R^3$, Y and Z are as described in Scheme 10 are produced as shown in Scheme 12 by initial reductive alkylation of amine 47 with an aldehyde $R^{59}CHO$ or ketone $R^{59}COR^{60}$ in the presence of any of a number of suitable reducing agents including sodium borohydride, sodium cyanoborohydride or, more preferably, sodium or tetraalkylammonium salts of triacetoxyborohydride to give 129. Depending on the reducing agent employed, suitable solvents may include an alcohol, such as methanol, ethanol or isopropanol, or solvents such as THF or dichloromethane. Conversion of the ester to the amidine 130 is again carried out in the manner previously described in Scheme 1b.

Scheme 13

Scheme 13 illustrates an approach to compounds of Formula I where $R^2$ is a 2-thiazolylamino and $R^3$, Y and Z are as described in Scheme 10. In this method, amine 47 can be first converted to a thiourea 131 using the various procedures outlined in Scheme 7b. Further reaction of the thiourea with a leaving group-substituted ketone $R^{37}COCH(L)R^{38}$, preferably a 2-haloketone as described in Schemes 2f, 2g or 2h, can provide thiazolylaminothiophenes 132 which are then converted to the corresponding amidines 133 by the previously described methodology of Scheme 1b.

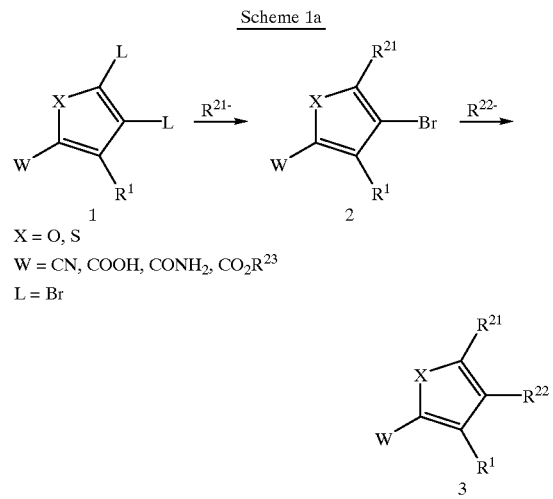

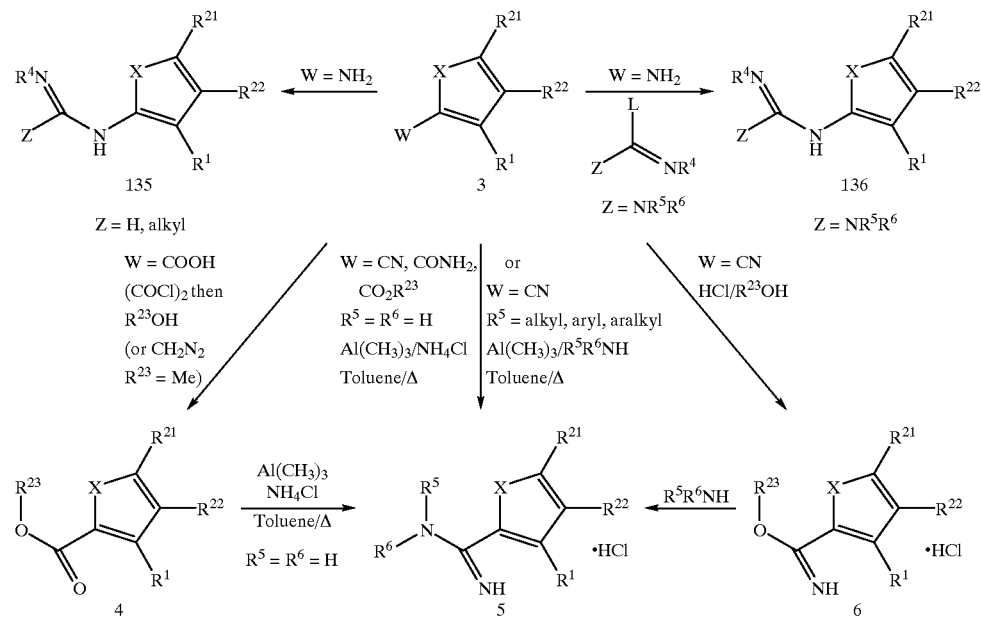

Scheme 1c
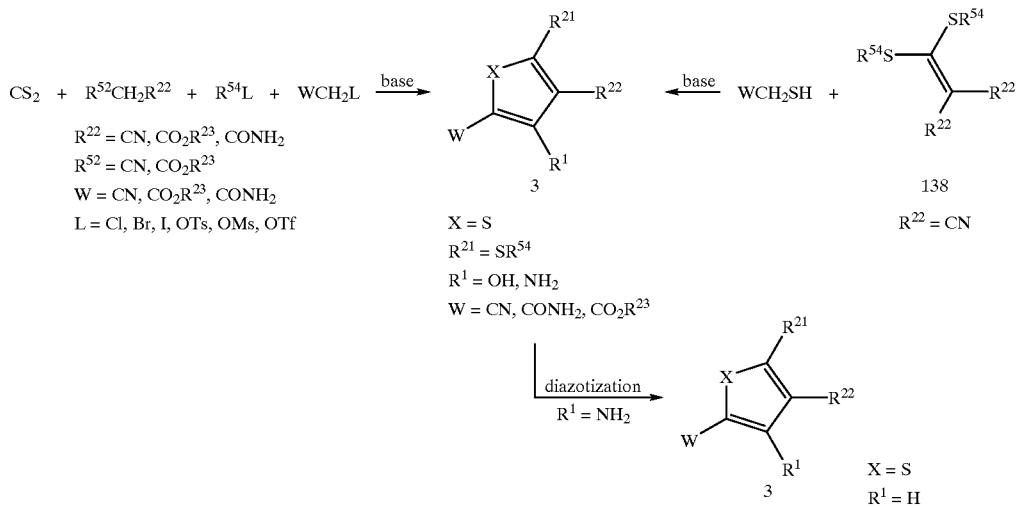
Scheme 1d
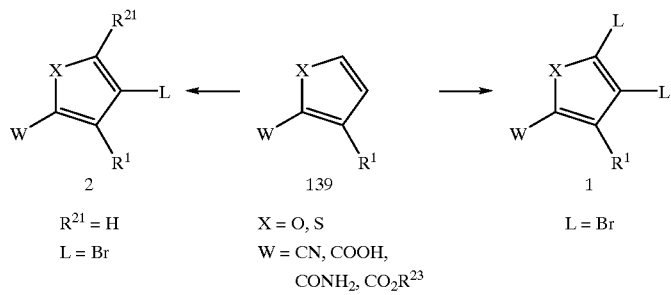
Scheme 2a
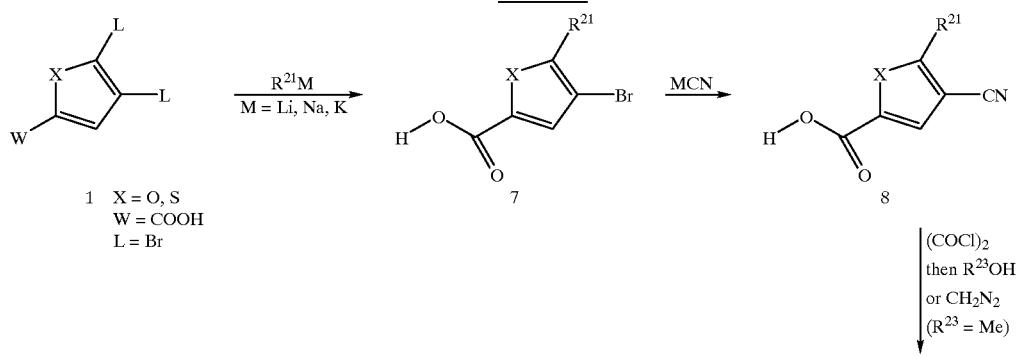

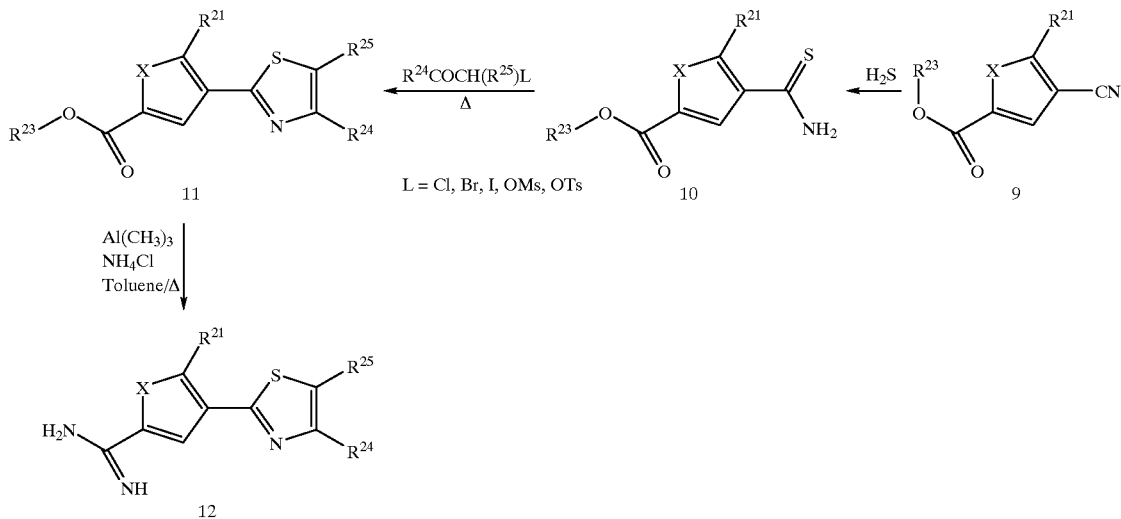
Scheme 2b
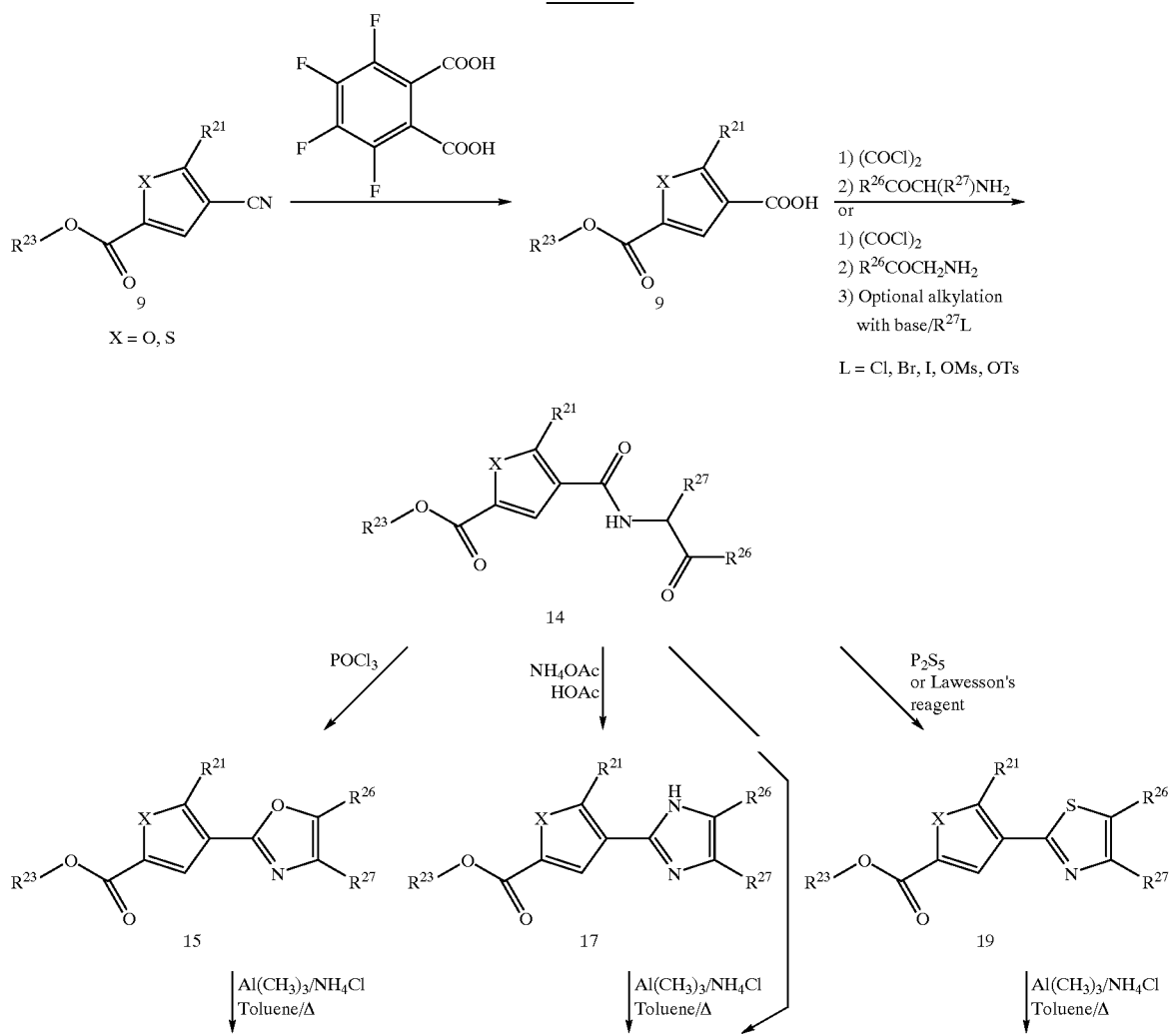

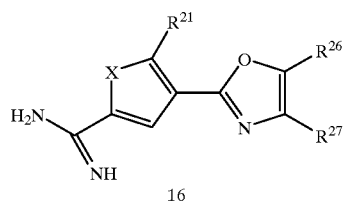
16
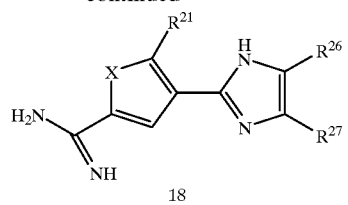
18
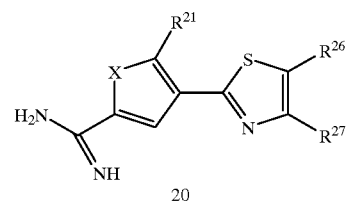
20
Scheme 2c
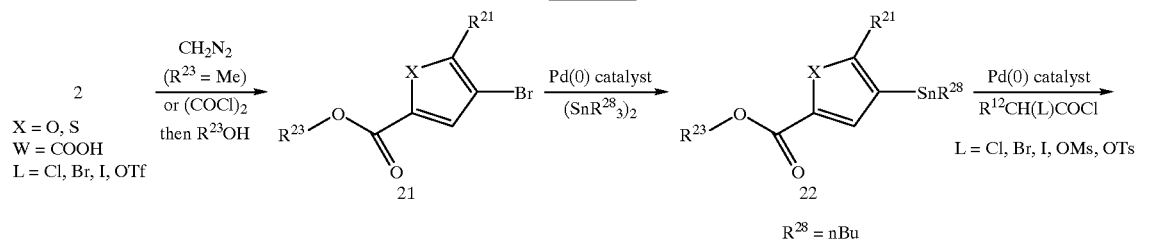
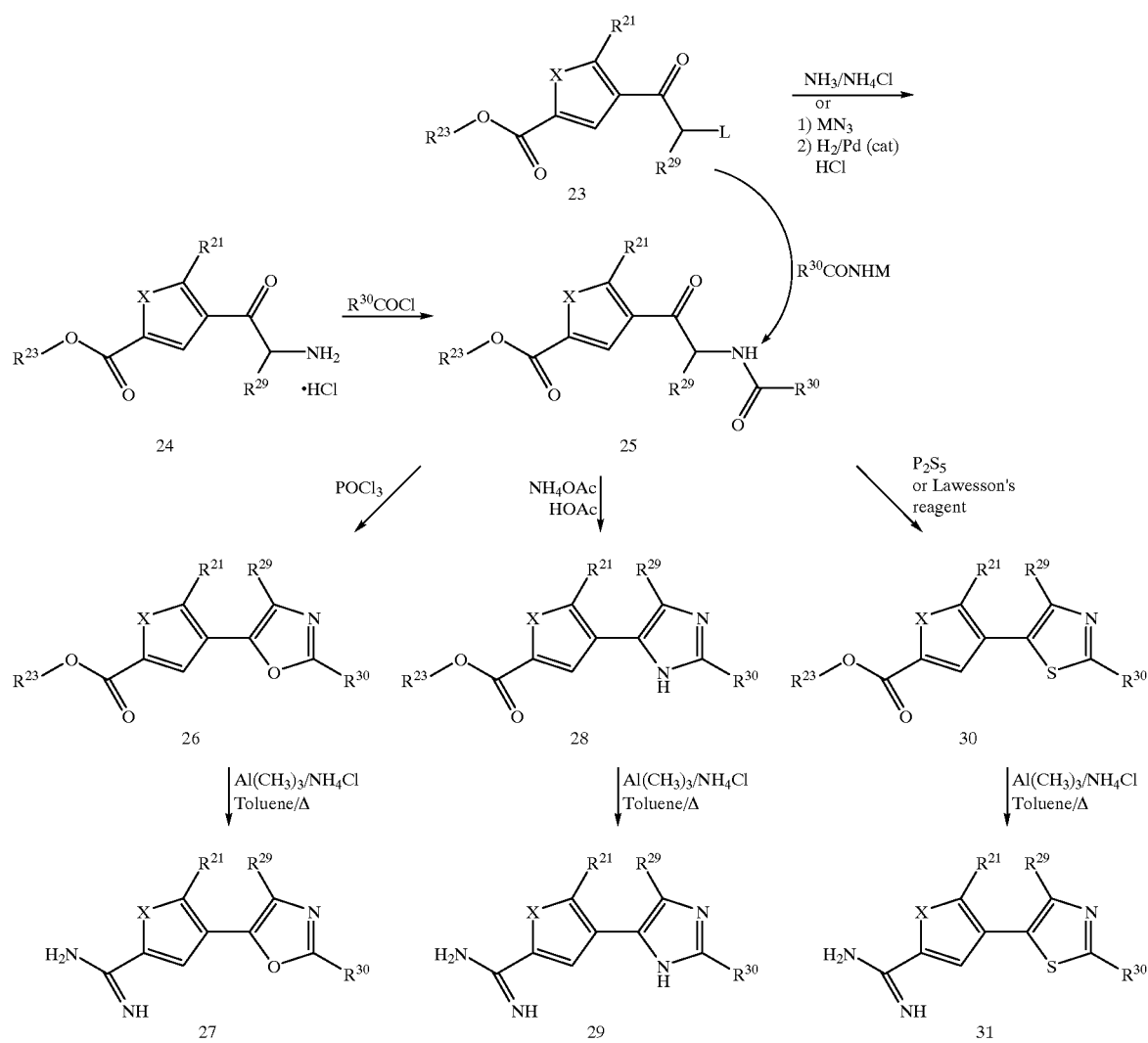

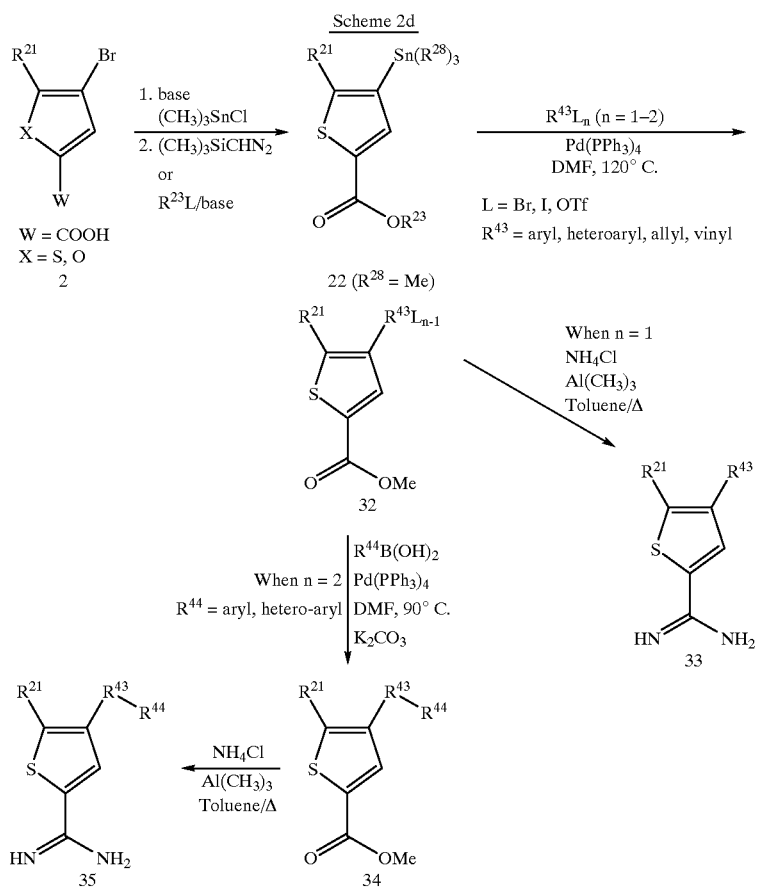
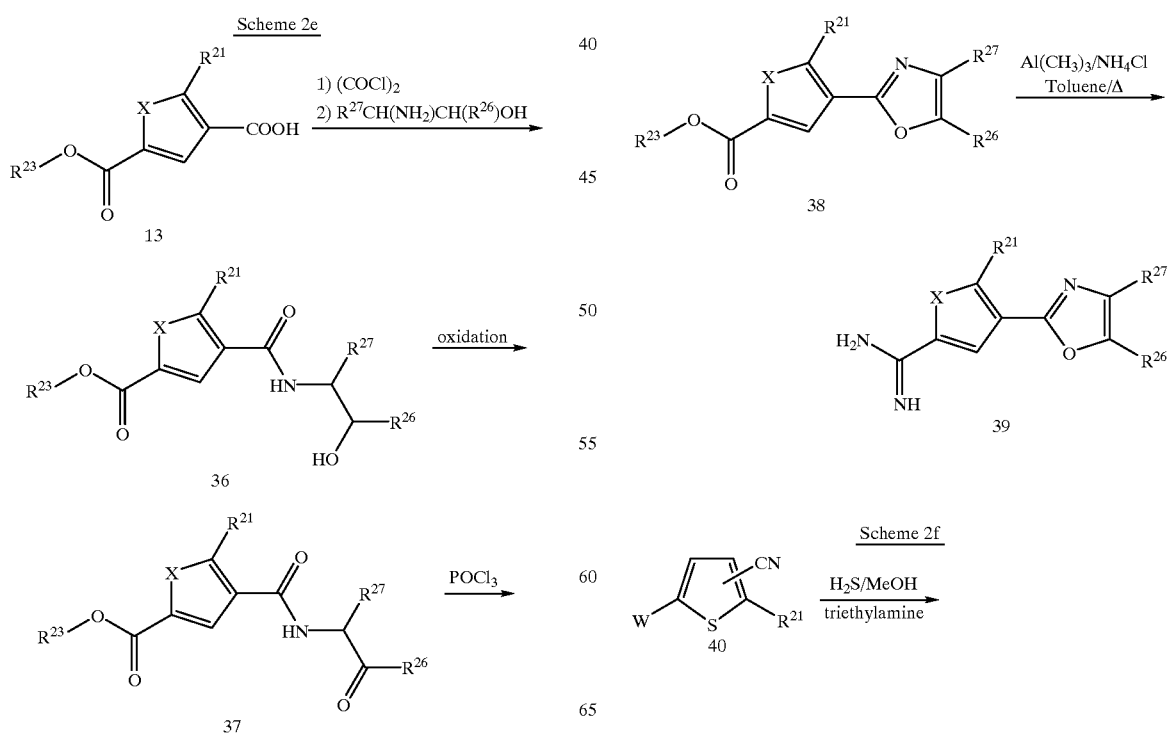

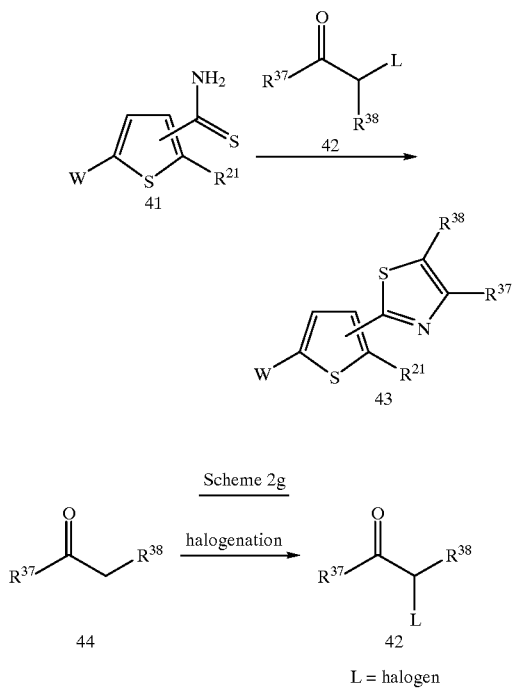
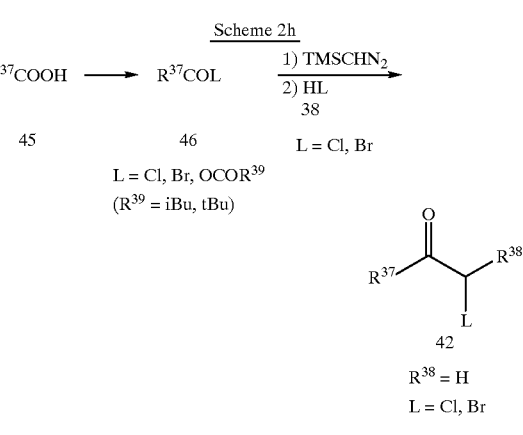
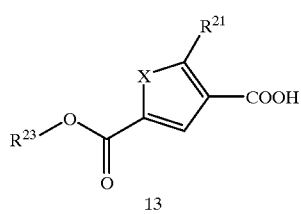
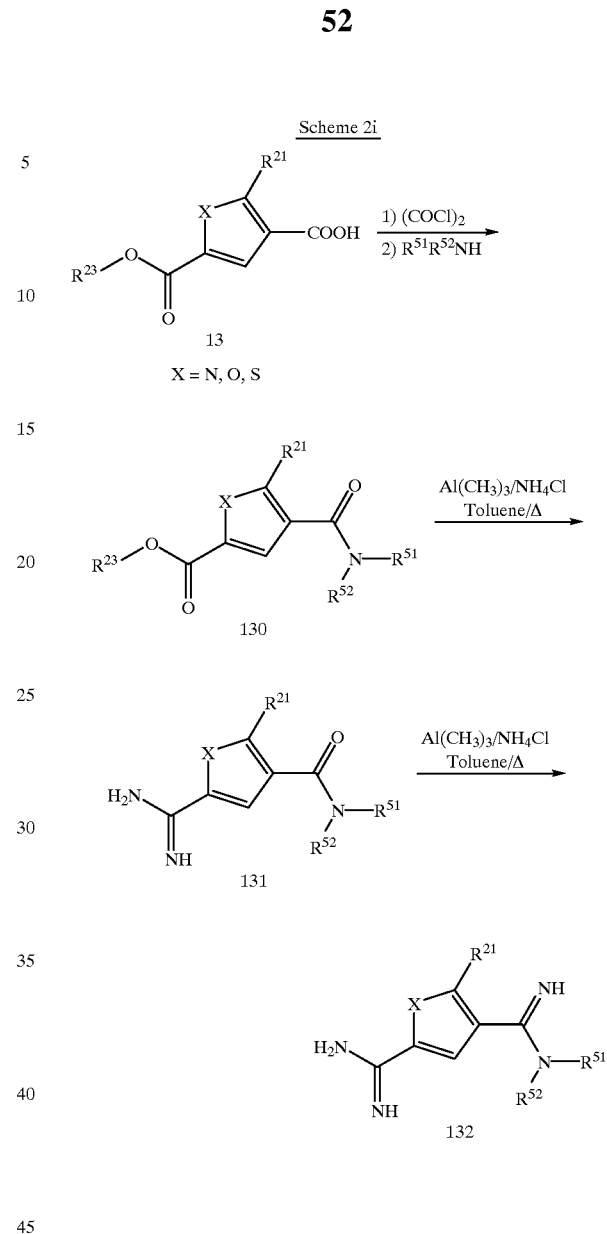
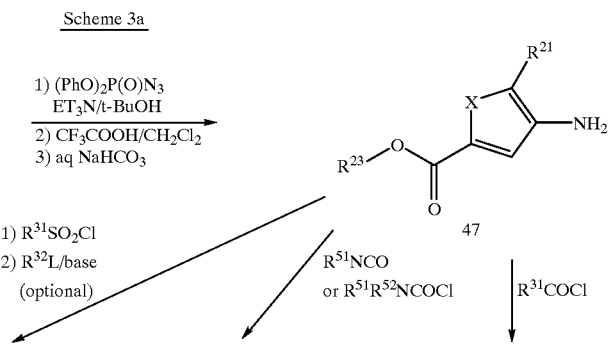

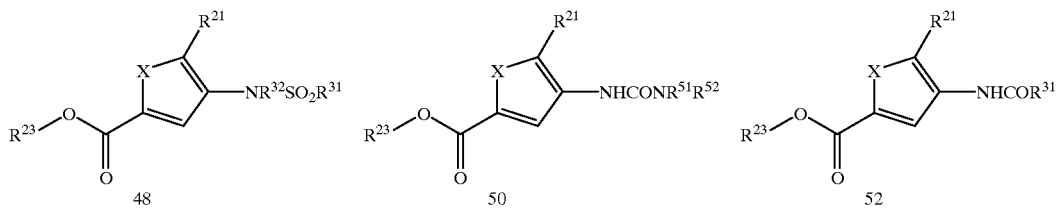
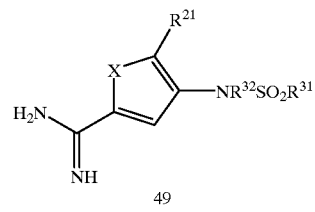
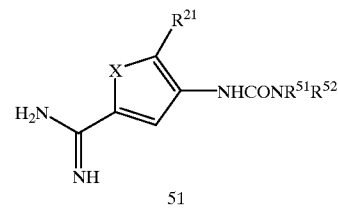
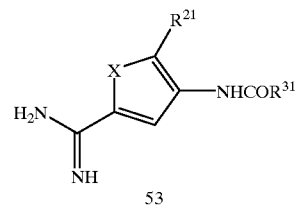
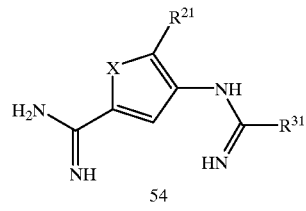
Scheme 3b
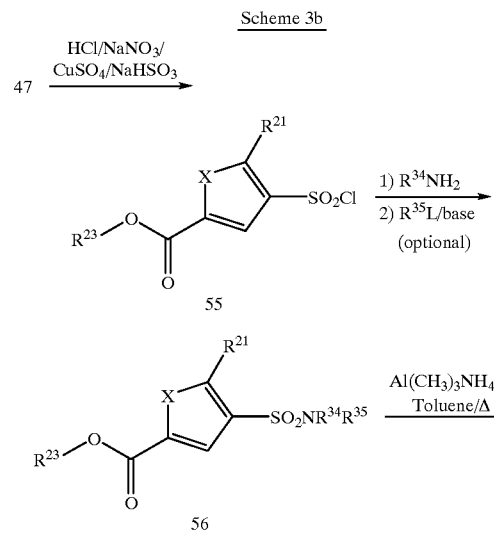
Scheme 3c
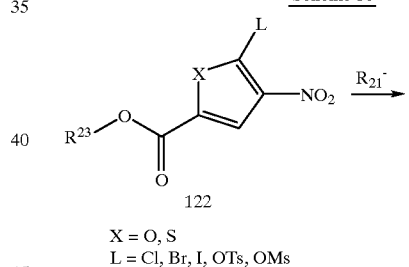
X = O, S
L = Cl, Br, I, OTs, OMs
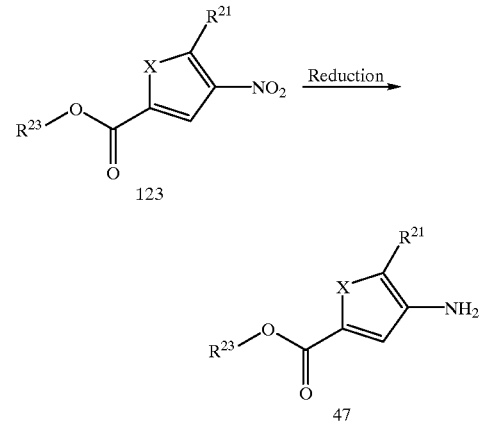
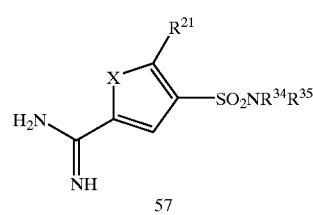

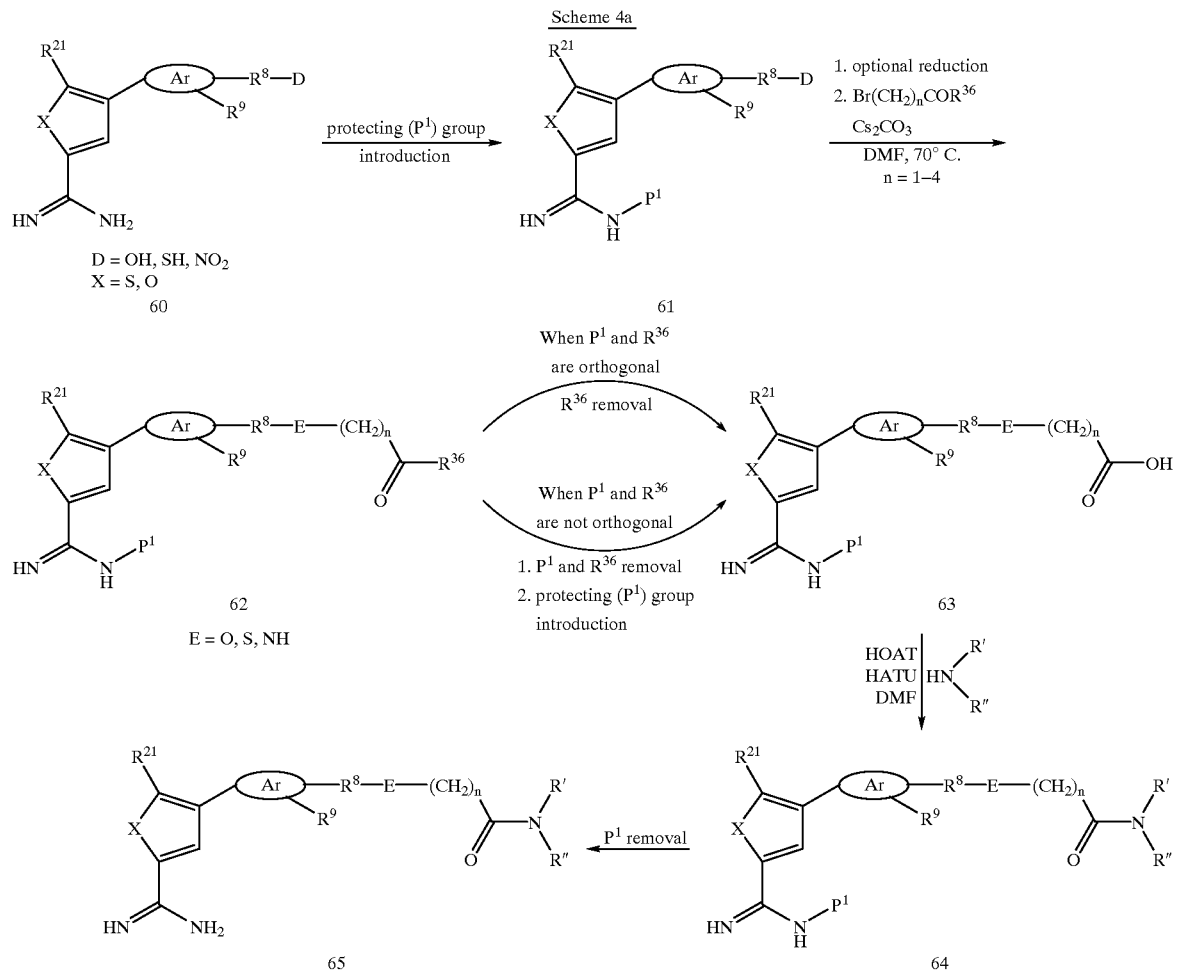
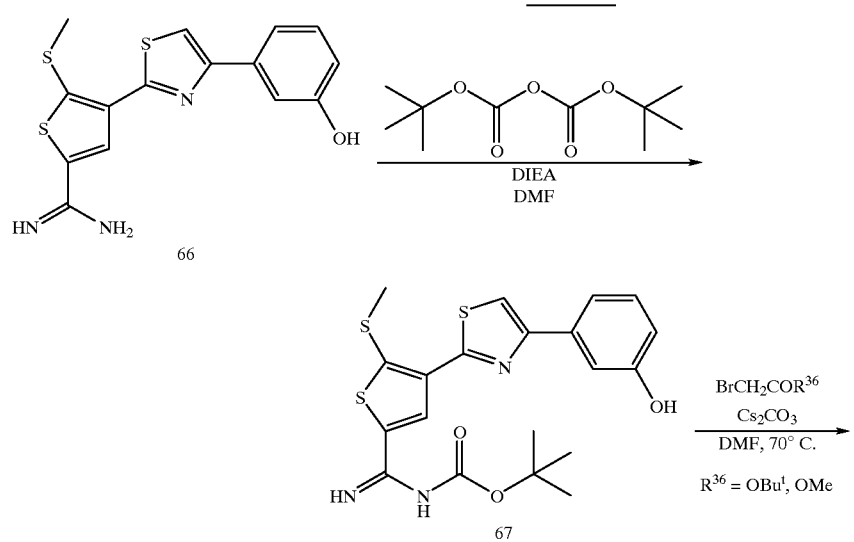

57 58
-continued
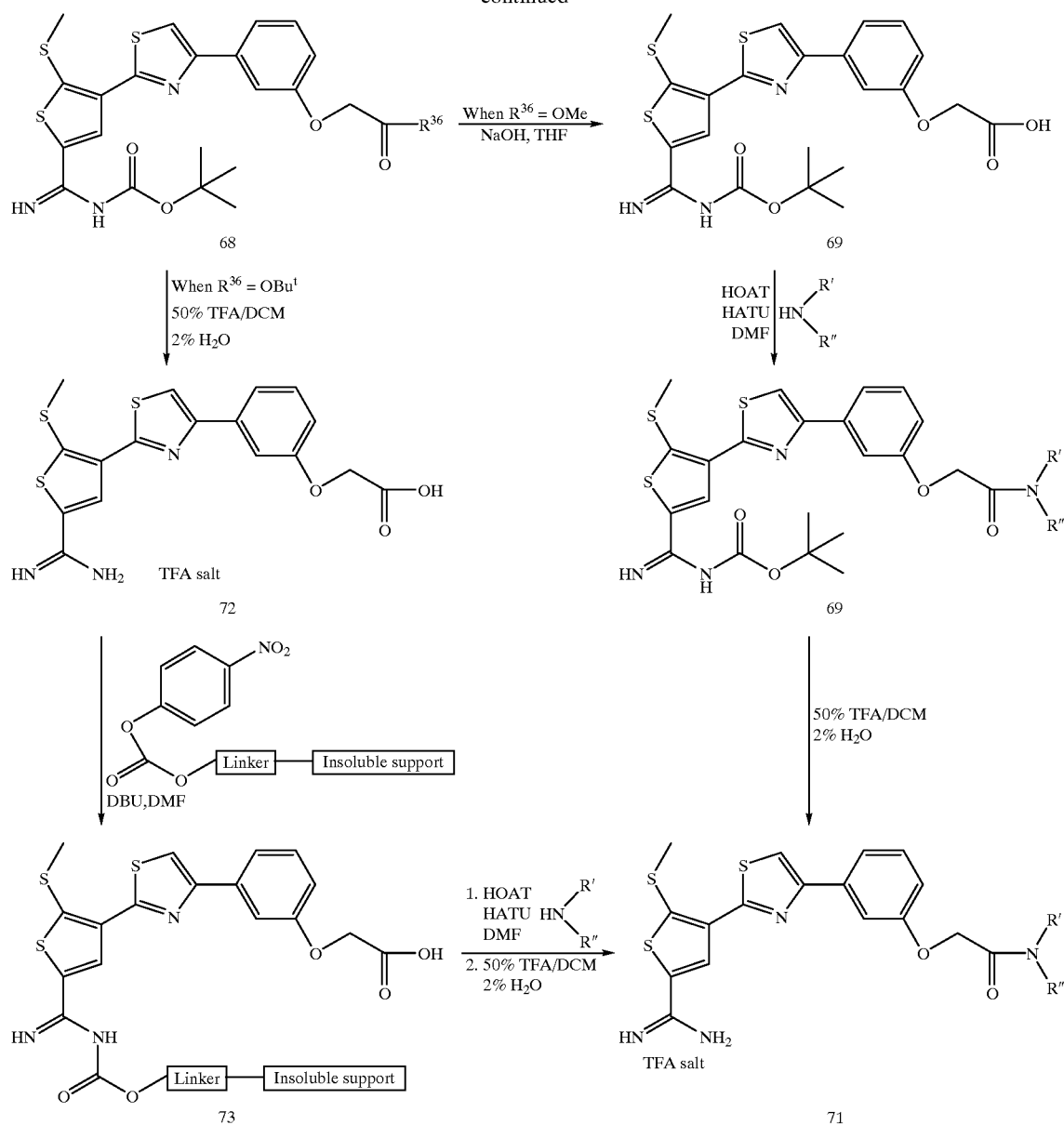
Scheme 5
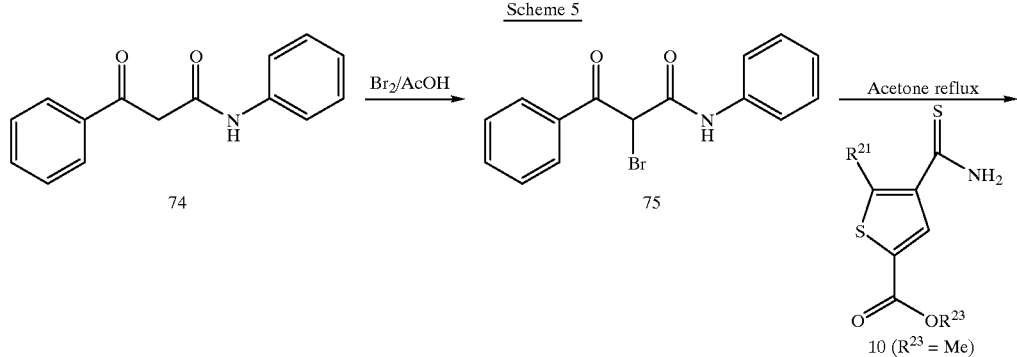

-continued
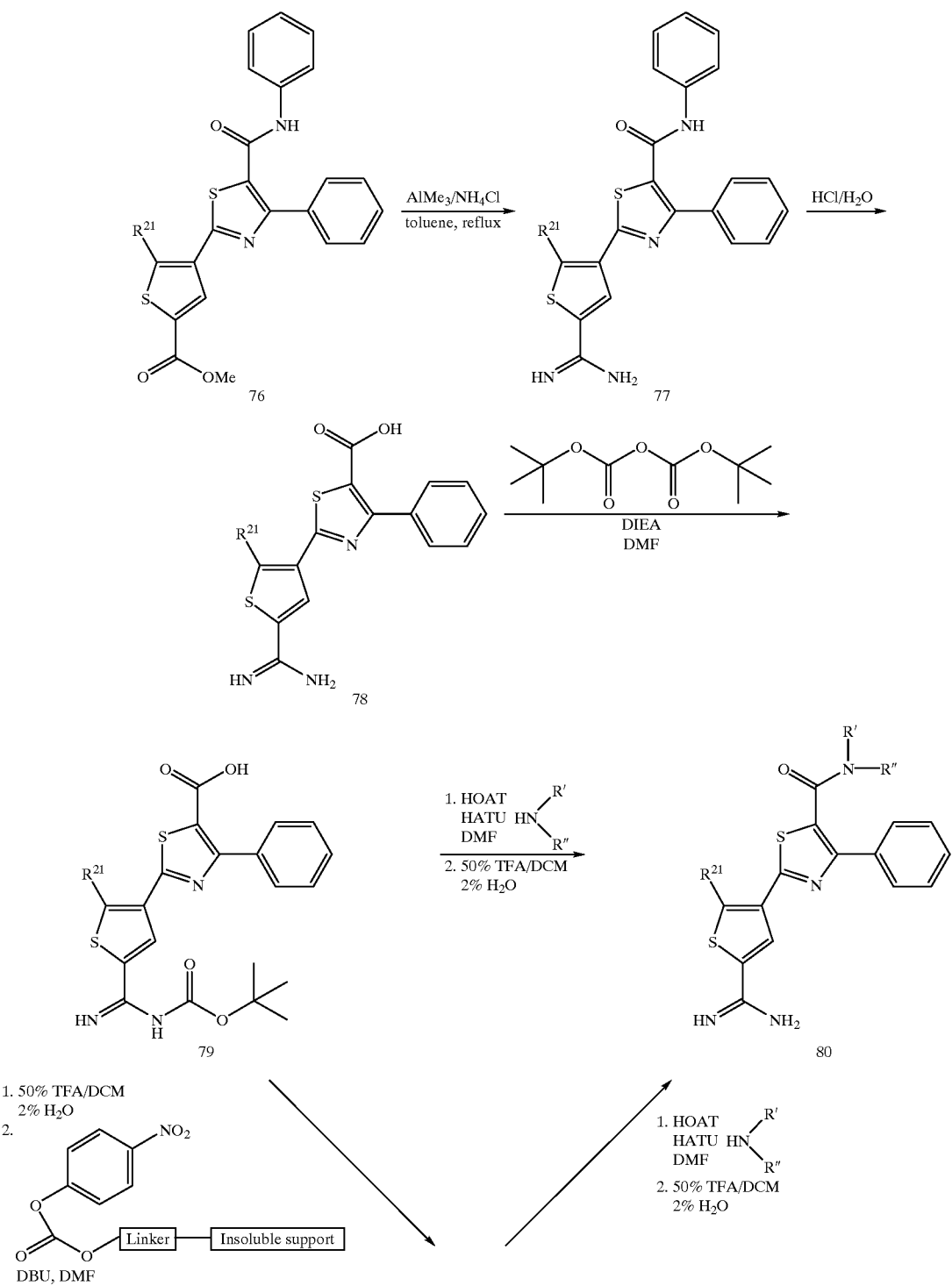

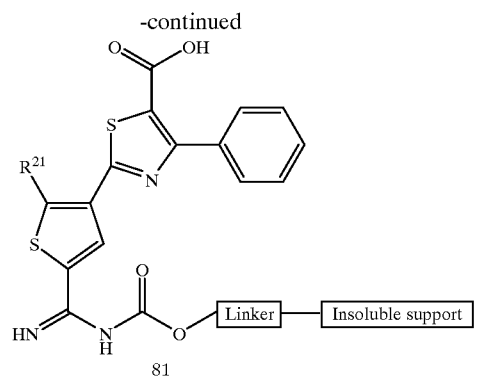
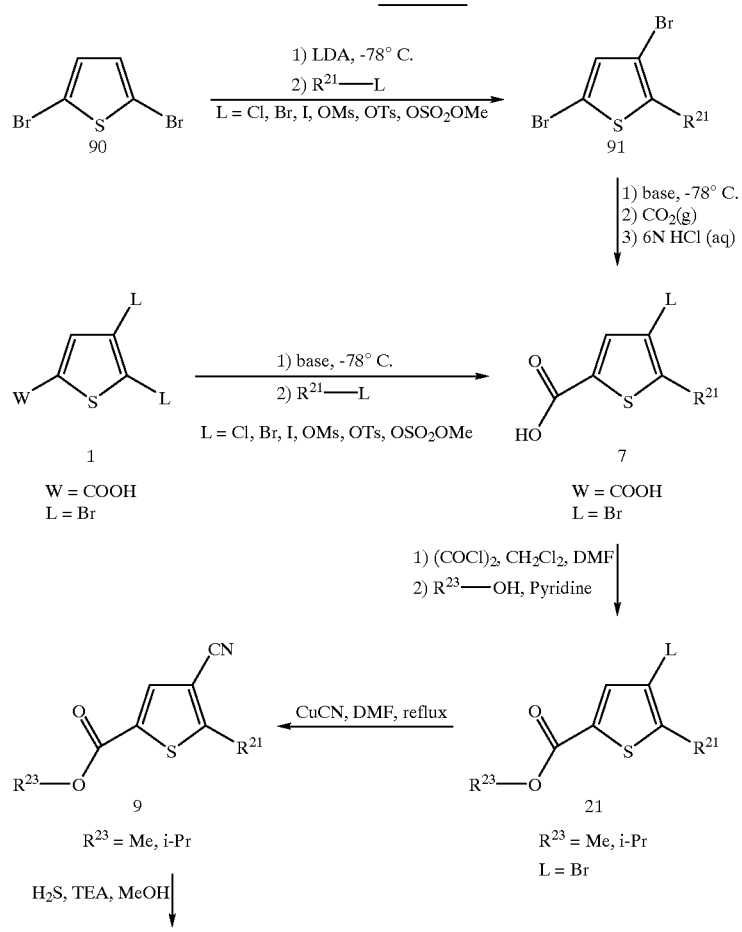

-continued
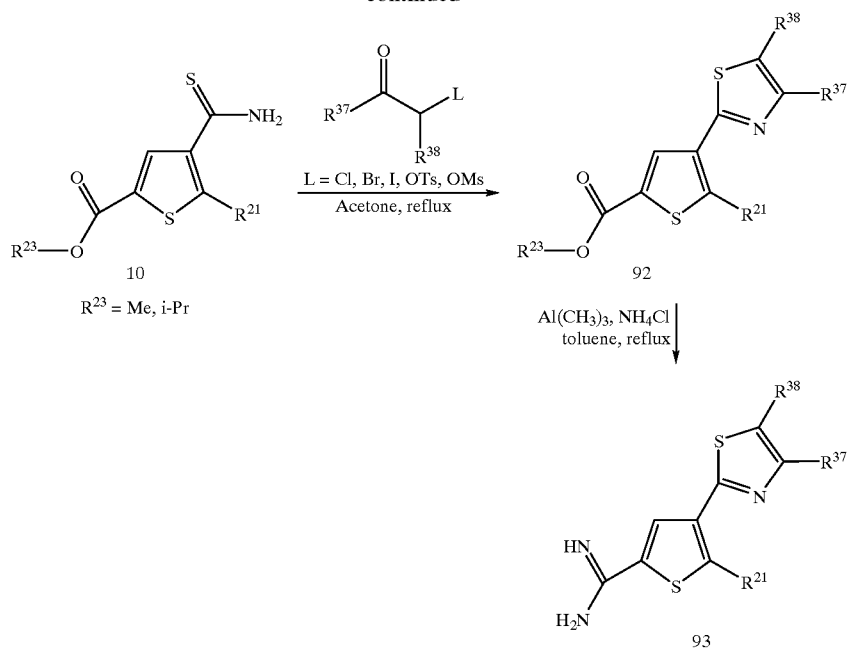
Scheme 6b
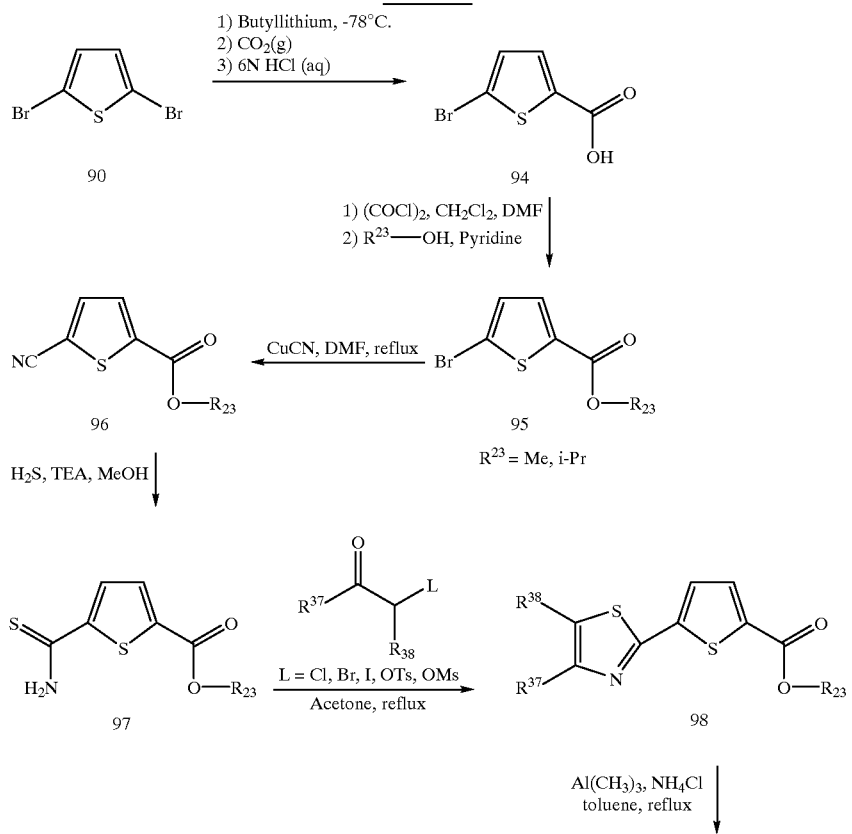

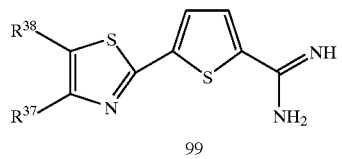
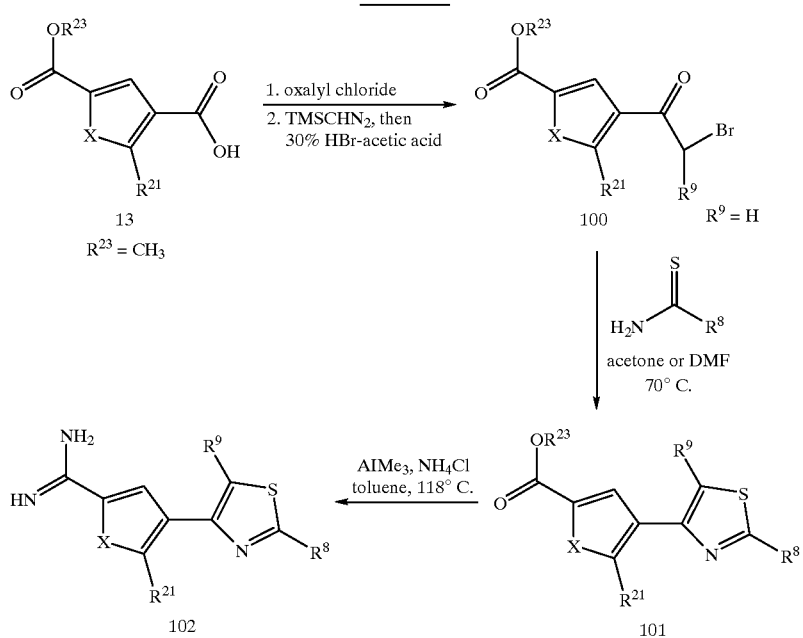
Scheme 7a
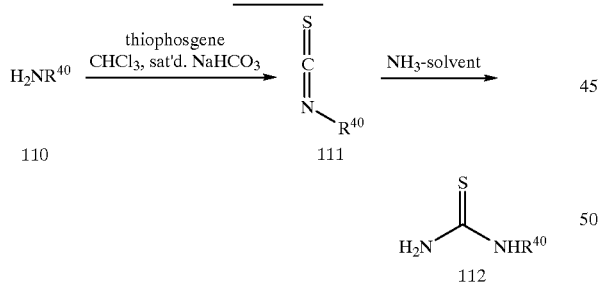
Scheme 7b

Scheme 8
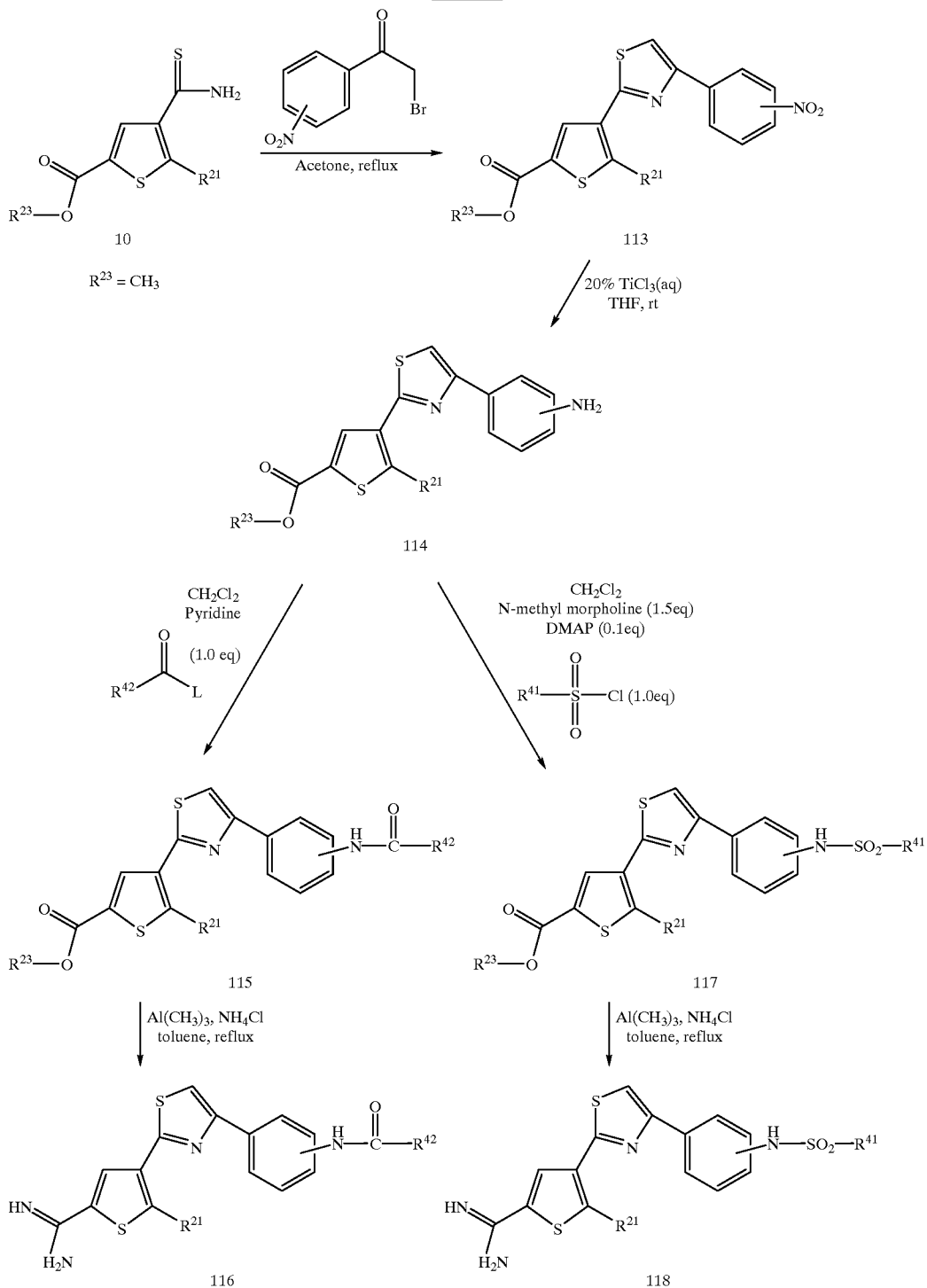

Scheme 9
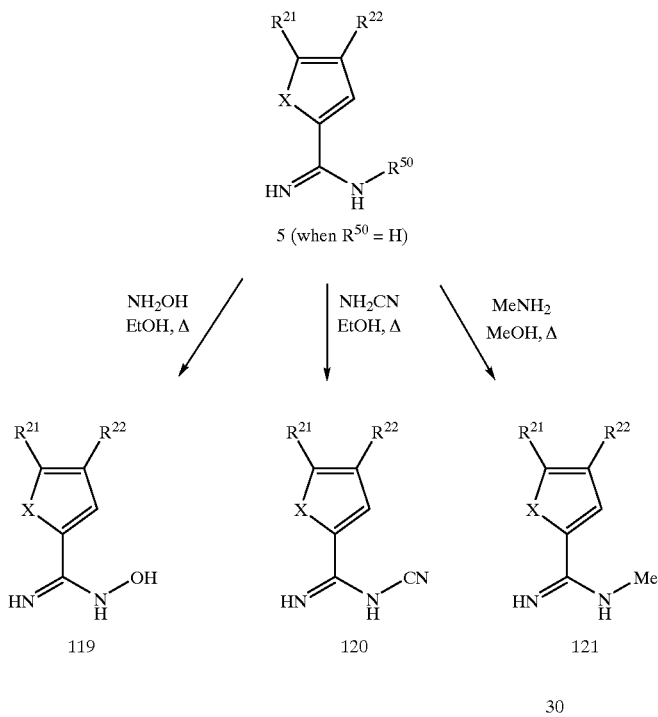
Scheme 10
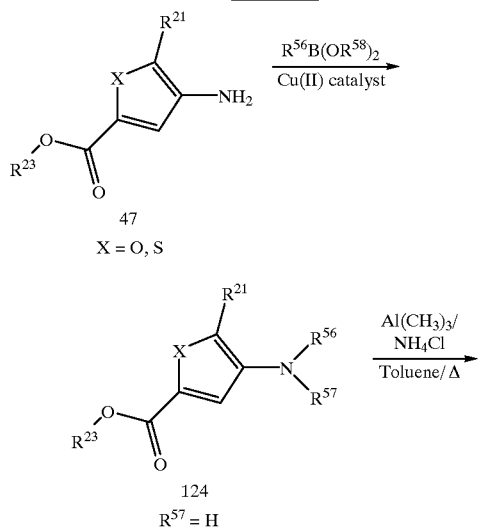
Scheme 11
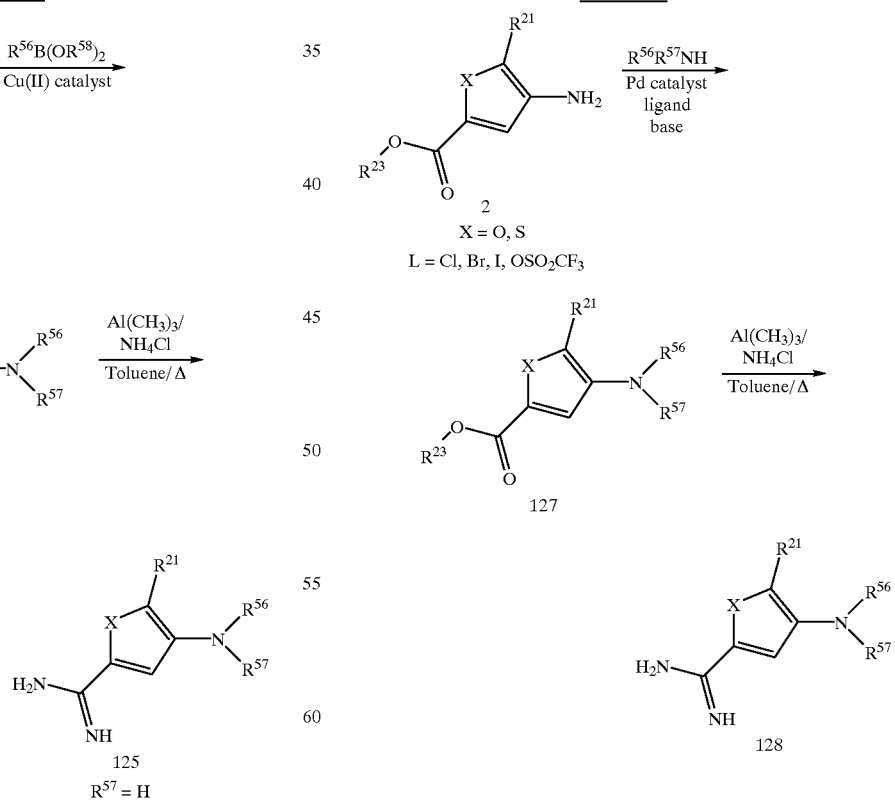

Scheme 12

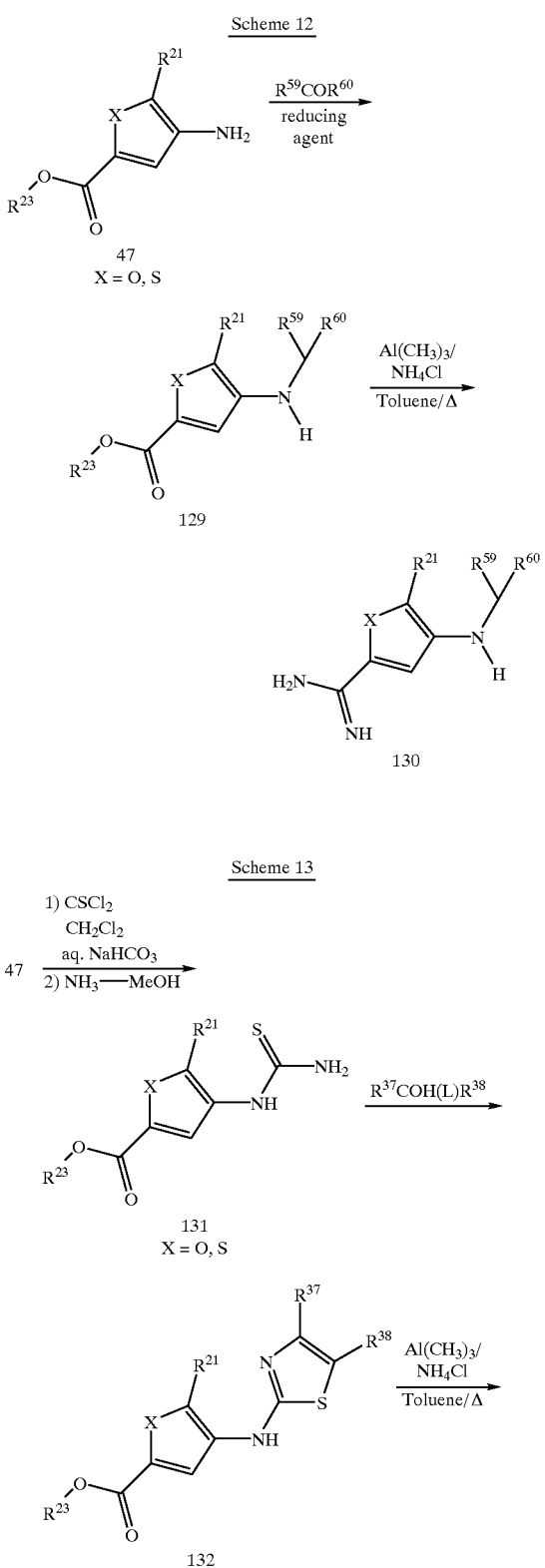

Scheme 13

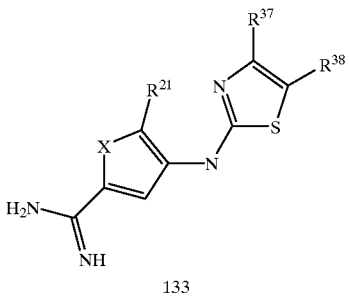

EXAMPLE 1

4-[4-(4-chlorophenyl)(1,3-thiazol-2-yl)]-5-methylthiothiophene-2-carboxamidine

Trimethylaluminum (2.0 M in toluene, 2 mL) was added dropwise over 10 min to a suspension of ammonium chloride (216 mg) in toluene (2 mL), stirred under $N_2$ at 0° C. When gas evolution moderated, the mixture was stirred at 25° C. for 30 min, when most of the solid had dissolved, methyl 4-[4-(4-chlorophenyl)(1,3-thiazol-2-yl)]-5-methylthiothiophene-2-carboxylate (100 mg, Maybridge Chemical Co., Cornwall, U.K.) was added in one portion. This solution was heated to reflux in stages over 1 h. After 2.5 h of reflux, the reaction mixture was allowed to cool to 25° C., and was poured on to a vigorously stirred slurry of silica gel (2 g) in $CHCl_3$ (20 mL). After 20 min the solids were collected by suction filtration, and washed with MeOH (3×10 mL). The combined filtrates were evaporated to dryness, and the residual yellow solid was subjected to preparative thin-layer chromatography to obtain 77 mg of 4-[(4-chlorophenyl)thiazol-2-yl]-5-methylthiothiophene-2-carboxamidine as a yellow solid. $^1$H-NMR (DMSO-$d_6$; 300 MHz) δ 2.80 (s, 3H), 7.55–7.59 (m, 1H), 8.04–8.13 (m, 1H), 8.31 (s, 1H), 8.69 (s, 1H), ), 9.2 (broad s, 4H). Mass spectrum (MALDI-TOF, m/z): Calcd. for $C_{15}H_{12}ClN_3S_3$, 365.9 (M+H), found 366.9.

EXAMPLE 2

5-Methylthiothiophene-2-carboxamidine 5-(Methylthio)thiophene-2-carbonitrile (100 mg, Maybridge Chemical Company, Cornwall, UK) was taken in a dry 2 dram vial. To this a solution of saturated HCl in anhydrous MeOH (4 mL) was added. The vial was tightly capped and the mixture was stirred for 24 h. The vial was cooled in an ice bath, uncapped and $N_2$ was bubbled through the solution to remove dissolved HCl. The solvent was removed under reduced pressure and the resulting residue was dried under high vacuum for 24 h. A solution of methanolic ammonia (2M $NH_3$ in MeOH) was added to the vial, and the mixture was stirred for 3 days. Methanol was removed under vacuum and the resulting residue was subjected to preparative thin-layer chromatography to obtain 5-(methylthio)thiophene-2-carboxamidine as a yellow solid. $^1$H-NMR (DMSO-$d_6$; 300 MHz) δ 2.64 (s, 3H), 7.22 (d, J=3.8 Hz, 1H), 7.95 (broad d, J=3.33 Hz, 1H), 9.4 (broad s, 4H). Mass spectrum (MALDI-TOF, m/z): Calcd. for $C_6H_8N_2S_2$, 172.3 (M+H), found 173.0.

EXAMPLE 3

5-Methylthio-4-phenylthiophene-2-carboxamidine

Methyl 5-methylthio-4-phenylthiophene-2-carboxylate (100 mg, Maybridge Chemical Company, Cornwall, UK) was treated in a manner similar to that for Example 1, to give 50 mg of 4-phenyl-5-methylthiothiophene-2-carboxamidine as an off-white solid. $^1$H-NMR (DMSO-$d_6$; 300 MHz) δ 2.65 (s, 3H), 7.39–7.60 (m, 5H), 8.27 (s, 1H), 9.2 (broad s, 4H). Mass spectrum (MALDI-TOF, m/z): Calcd. for $C_{12}H_{12}N_2S_2$, 248.4 (M+H), found 249.0.

EXAMPLE 4

4-[4-(2,4-Dichlorophenyl)(1,3-thiazol-2-yl)]-5-methylthiothiophene-2-carboxamidine Methyl 4-[4-(2,4-dichlorophenyl)(1,3-thiazol-2-yl)]-5-methylthiothiophene-2-carboxylate (100 mg, Maybridge Chemical Company, Cornwall, UK) was treated in a manner similar to that for Example 1, to give 60 mg of 4-[4-(2,4-dichlorophenyl)thiazol-2-yl]-5-methylthiothiophene-2-carboxamidine as a yellow solid. $^1$H-NMR (DMSO-$d_6$; 300 MHz) δ 2.77 (s, 3H), 7.6 (dd, J=2.2 and 8.5 Hz, 1H), 7.79 (d, J=2.2 Hz, 1H), 8.09 (d, J=8.5 Hz, 1H), 8.3 (s, 1H), 8.6 (s, 1H). Mas spectrum (MALDI-TOF, m/z): Calcd. for $C_{15}H, N_3S_3C_2$, 400.0 (M+H), found 400.1.

EXAMPLE 5

4-(4-Methyl(1,3-thiazol-2-yl))-5-methylthiothiophene-2-carboxamidine

Methyl 4-(4-methyl(1,3-thiazol-2-yl))-5-methylthiothiophene-2-carboxylate (100 mg, Maybridge Chemical Company, Cornwall, UK) was treated in a manner similar to that for Example 1, to give 40 mg of 4-(4-methylthiazol-2-yl)-5-methylthiothiophene-2-carboxamidine as a yellow solid. $^1$H-NMR (DMSO-$d_6$; 300 MHz) δ 2.43 (s, 3H), 2.7 (s, 3H), 7.38 (s, 1H), 8.28 (s, 1H). Mass spectrum (MALDI-TOF, m/z): Calcd. for $C_{10}H_{11}N_3S_3$, 270.0 (M+H), found 270.1.

EXAMPLE 6 a) Methyl 5-methylthio-4-(4-(2-naphthyl) (1,3-thiazol-2-yl))thiophene-2-carboxylate: Methyl 4-(aminothioxomethyl)-5-methylthiothiophene-2-carboxylate (40 mg, Maybridge Chemical Company, Cornwall, UK) was reacted with 2-bromo-2'-acetonaphthone (1.1 eq) in a manner similar to Example 13 step (a) to give 40 mg of methyl 5-methylthio-4-(4-(2-naphthyl)(1,3-thiazol-2-yl))thiophene-2-carboxylate. $^1$H-NMR (CDCl$_3$/CD$_3$OD; 300 MHz) δ 3.71 (s, 3H), 3.94 (s, 3H), 7.47–7.55 (m, 2H), 7.67 (s, 1H), 7.84–7.99 (m, 3H), 8.08 (dd, J=1.75 Hz and 8.6 Hz, 1H), 8.3 (s, 1H), 8.5 (s, 1H).

b) 5-Methylthio-4-(4-(2-naphthyl)(1,3-thiazol-2-yl))thiophene-2-carboxamidine: Methyl 5-methylthio-4-(4-(2-naphthyl)(1,3-thiazol-2-yl))thiophene-2-carboxylate, (40 mg) as prepared in the previous step was treated in a manner similar to that for Example 1, to give 30 mg of 4-[4-(naphth-2-yl)thiazol-2-yl]-5-methylthiothiophene-2-carboxamidine. $^1$H-NMR (DMSO-$d_6$; 300 MHz) δ 2.83 (s, 3H), 7.52–7.69 (m, 2H), 7.95–8.01 (m, 2H), 8.05 (d, J=8.6 Hz, 1H), 8.24 (dd, J=1.69 Hz and 8.6 Hz, 1H), 8.4 (s, 1H), 8.65 (s, 1H), 8.74 (s, 1H). Mass spectrum (MALDI-TOF, CHCA matrix, m/z): Calcd. for $C_{19}H_{15}N_3S_3$, 382.1 (M+H), found 382.0.

EXAMPLE 7

5-Methylthio-4-[4-(4-phenylphenyl)(1,3-thiazol-2-yl)]thiophene-2-carboxamidine hydrochloride a) Methyl 5-methylthio-4-[4-(4-phenylphenyl) (1,3-thiazol-2-yl)]thiophene-2-carboxylate: 27 mg (0.109 mmol) of methyl 4-(aminothioxomethyl)-5-methylthiothiophene-2-carboxylate (Maybridge Chemical Co. LTD., Cornwall, U.K.) was dissolved in 2 mL of reagent grade acetone. 4'-Phenyl-2-bromoacetophenone (33 mg; 0.120 mmol; Aldrich Chemical Co., Milwaukee, Wis.) was added and the solution was allowed to reflux for 2.5 h. The solution was allowed to cool and solid was filtered and washed with methanol and dried in vacuo to afford 30 mg (65% yield) of methyl 5-methylthio-4-[4-(4-phenylphenyl)(1,3-thiazol-2-yl)]thiophene-2-carboxylate. $^1$H-NMR (DMSO-$d_6$, 300 MHz) δ 8.28 (s, 1H), 8.24 (s, 1H), 8.17 (d, J=8.5 Hz, 2H), 7.8 (d, J=8.5Hz, 2H), 7.74–7.77 (m, 2H), 7.48–7.53 (m, 2H), 7.40 (m, 1H), 2.78 (s, 3H). Mass Spectrum (MALDI-TOF, CHCA matrix, m/z). Calcd. for $C_{22}H_{16}NO_2S_3$: 423.0 (M+H), found 424.4.

b) 5-Methylthio-4-[4-(4-phenylphenyl)(1,3-thiazol-2-yl)]thiophene-2-carboxamidine hydrochloride: To a stirred suspension of 0.473 mmol (25 mg) of ammonium chloride (Fisher Scientific Pittsburgh, Pa.) in 2 mL of anhydrous toluene (Aldrich Chemical Co.) placed under nitrogen atmosphere at 0° C., 237 μL (0.473 mmol) of 2M trimethylaluminum in toluene (Aldrich Chemical Co.) was added via syringe over 10 min and then let stir at 0° C. for 30 min after which 20 mg (0.0473 mmol) of methyl 5-methylthio-4-[4-(4-phenylphenyl)(1,3-thiazol-2-yl)]thiophene-2-carboxylate was added to solution and allowed to reflux for 2.5 h. The reaction mixture was quenched by pouring over a slurry of 500 mg of silica in 10 mL of chloroform. The silica was poured onto a sintered glass funnel and washed with a 10% methanol/CH$_2$Cl$_2$ solution and concentrated. The crude product was purified on a 1 mm silica prep plate eluting with 10% methanol/CH$_2$Cl$_2$ to afford 10 mg (53% yield) of 5-methylthio-4-[4-(4-phenylphenyl)(1,3-thiazol-2-yl)]thiophene-2-carboxamidine hydrochloride. Mass Spectrum (MALDI-TOF, CHCA matrix, m/z) Calcd. for $C_{21}H_{17}N_3S_3$: 408.1 (M+H), found 408.0.

EXAMPLES 8 & 9

4-[4-(3-Methoxyphenyl)(1,3-thiazol-2-yl)]-5-methylthiothiophene-2-carboxamidine hydrochloride and 4-[4-(3-hydroxyphenyl)(1,3-thiazol-2-yl)]-5-methylthiothiophene-2-carboxamidine hydrochloride a) Methyl 4-[4-(3-methoxyphenyl)(1,3-thiazol-2-yl)-5-methylthiothiophene-2-carboxylate: 32 mg (0.133 mmol) of methyl 4-(aminothioxomethyl)-5-methylthiothiophene-2-carboxylate (Maybridge Chemical Co. LTD., Cornwall, U.K.) was dissolved in 2 mL of reagent grade acetone. 3'-Methoxy-2-bromo acetophenone (0.155 mmol; 36 mg; Aldrich Chemical Co.) was added and the solution was allowed to reflux for 2.5 h. The solution was allowed to cool and a solid was filtered and washed with methanol and dried in vacuo. The solid was purified on 1 mm silica plate eluting with 25% ethyl acetate/hexane to afford 31 mg (63% yield) of methyl 4-[4-(3-methoxyphenyl)(1,3-thiazol-2-yl)]-5-methylthiothiophene-2-carboxylate.

b) 4-[4-(3-Methoxyphenyl)(1,3-thiazol-2-yl)]-5-methylthiothiophene-2-carboxamidine hydrochloride and 4-[4-(3-hydroxyphenyl)(1,3-thiazol-2-yl)]-5-methylthiothiophene-2-carboxamidine hydrochloride: To a stirred suspension of 0.821 mmol (44 mg) of ammonium chloride (Fisher Scientific) in 2 mL of anhydrous toluene (Aldrich Chemical Co.) placed under nitrogen atmosphere at 0° C., was added 411 µL (0.821 mmol) of 2M trimethtlaluminum in toluene (Aldrich Chemical Co.) via syringe over 10 min and then let stir at 0° C. for 30 min after which 31 mg (0.0821 mmol) of methyl 4-14-(3-methoxyphenyl)(1,3-thiazol-2-yl)]-5-methylthiothiophene-2-carboxylate was added to solution and allowed to reflux for 2.5 h. The reaction mixture was quenched by pouring over a slurry of 500 mg of silica in 10 mL of chloroform. The silica was poured onto a sintered glass funnel and washed with a 10% methanol/$CH_2Cl_2$ solution and concentrated. The crude product was purified on a 1 mm silica prep plate eluting with 10% methanol/$CH_2Cl_2$ to afford 4.4 mg (15% yield) of 4-[4-(3-methoxyphenyl)(1,3-thiazol-2-yl)]-5-methylthiothiophene-2-carboxamidine hydrochloride and 4.2 mg (15% yield) of 4-[4-(3-hydroxyphenyl)(1,3-thiazol-2-yl)]-5-methylthiothiophene-2-carboxamidine hydrochloride. 4-[4-(3-methoxyphenyl)(1,3-thiazol-2-yl)]-5-methylthiothiophene-2-carboxamidine hydrochloride: $^1$H-NMR ($CD_3OD$; 300 MHz) δ 8.5 (s, 1H), 7.9 (s, 1H), 7.59–7.65 (m, 2H), 7.33–7.38 (m, 1H), 6.91–6.95 (m, 1H), 3.87 (s, 1H), 2.8 (s, 3H) Mass Spectrum (MALDI-TOF, CHCA matrix, m/z) Calcd. for $C_{16}H_{15}N_3OS_3$: 361.5(M+H), found 362.2. 4-[4-(3-hydroxyphenyl)(1,3-thiazol-2-yl)]-5-methylthiothiophene-2-carboxamidine hydrochloride: $^1$H-NMR ($CD_3OD$; 300 MHz) δ 8.50 (s, 1H), 7.81 (s, 1H), 7.26–7.51 (m, 2H), 7.24 (m, 1H), 6.79 (m, 1H), 2.8 (s, 3H) Mass Spectrum (MALDI-TOF, CHCA matrix, m/z) Calcd. for $C_{15}H_{13}N_3OS_3$: 347.5(M+H), found 348.0.

EXAMPLE 10

5-Methylthio-4-(4-phenyl(1,3-thiazol-2-yl)) thiophene-2-carboxamidine hydrochloride a) Methyl 5-methylthio-4-(4-phenyl(1,3-thiazol-2-yl)) thiophene-2-carboxylate: 33 mg (0.33 mmol) methyl 4-(aminothioxomethyl)-5-methylthiothiophene-2-carboxylate (Maybridge Chemical Co., LTD., Cornwall U.K.) was dissolved in 2 mL of reagent grade acetone. 2-Bromoacetophenone (0.133 mmol; 27 mg; Aldrich Chemical Co.) was added and the solution was allowed to reflux for 2.5 h. The solution was allowed to cool and the solid silica plate eluting with 25% ethyl acetate/hexane mixture to afford 46 mg (90% yield) of methyl 5-methylthio-4-(4-phenyl(1,3-thiazol-2-yl))thiophene-2-carboxylate.

b) 5-Methylthio-4-(4-phenyl(1,3-thiazol-2-yl))thiophene-2-carboxamidine hydrochloride: To a stirred suspension of 1.32 mmol (71 mg) of ammonium chloride (Fisher Scientific) in 2 mL of anhydrous toluene (Aldrich Chemical Co.) placed under nitrogen atmosphere at 0° C., 662 µL (1.32 mmol) of 2M trimethylaluminum in toluene (Aldrich Chemical Co.) was added via syringe over 10 min and then let stir at 0° C. for 30 min after which 46 mg (0.133 mmol) of methyl 5-methylthio-4-(4-phenyl(1,3-thiazol-2-yl)) thiophene-2-carboxylate was added to solution and allowed to reflux for 2.5 h. The reaction mixture was quenched by pouring over a slurry of 500 mg of silica in 10 mL of chloroform. The silica was poured onto a sintered glass funnel and washed with a 10% methanol/$CH_2Cl_2$ solution and concentrated. The crude product was purified on a 2 g silica silica SPE column eluting with 10% methonol/$CH_2Cl_2$ to afford 32.5 mg (75% yield) of 5-methylthio-4-(4-phenyl (1,3-thiazol-2-yl))thiophene-2-carboxamidine hydrochloride. $^1$H-NMR (DMSO-$d_6$; 300 MHz) δ 8.70 (s, 1H), 8.25 (s, 1H), 8.07–8.11 (m, 2H), 7.37–7.53 (m, 3H), 2.8 (s, 3H). Mass Spectrum (MALDI-TOF, CHCA matrix, m/z) Calcd. for $C_{15}H_{13}N_3S_3$: 331.5(M+H), found 332.1.

EXAMPLE 11

5-Methylthio-4-[4-(4-nitrophenyl)(1,3-thiazol-2-yl)] thiophene-2-carboxamidine hydrochloride a) Methyl 5-methylthio-4-[4-(4-nitrophenyl)(1,3-thiazol-2-yl)]thiophene-2-carboxylate: 38 mg (0.141 mmol) of methyl 4-(aminothioxomethyl)-5-methylthiothiophene-2-carboxylate (Maybridge Chemical Co. LTD., Cornwall, U.K.) was dissolved in 2 mL of reagent grade acetone. 2-Bromo-4'-nitroacetophenone (0.155 mmol; 38 mg; Aldrich Chemical Co.) was added and the solution was allowed to reflux for 2.5 h. The solution was allowed to cool and a solid was filtered and washed with methanol and dried in vacuo. The crude product was dissolved in $CH_2Cl_2$ and 0.141 mmol of N-(2-mercapto)aminoethyl polystyrene resin (Calbiochem, San Diego, Calif.; 1.28 mmol/g; 110 mg) was added and allowed to stir overnight. The solution was filtered, concentrated and dried to afford 60 mg (90% yield) of crude methyl 5-methylthio-4-[4-(4-nitrophenyl)(1,3-thiazol-2-yl)]thiophene-2carboxylate.

b) 5-Methylthio-4-[4-(4-nitrophenyl)(1,3-thiazol-2-yl)] thiophene-2-carboxamidine hydrochloride: To a stirred suspension of 1.66 mmol (90 mg) of ammonium chloride (Fisher Scientific) in 2 mL of anhydrous toluene (Aldrich Chemical Co.) placed under nitrogen atmosphere at 0° C., 830 µL (1.66 mmol) of 2M trimethylaluminum in toluene (Aldrich Chemical Co.) was added via syringe over 10 min and then let stir at 0° C. for 30 min after which 60 mg (0.166 mmol) of 5-methylthio-4-[4-(4-nitrophenyl)(1,3-thiazol-2-yl)]thiophene-2-carboxylate was added to solution and allowed to reflux for 2.5 h. The reaction mixture was quenched by pouring over a slurry of 500 mg of silica in 10 mL of chloroform. The silica was poured onto a sintered-glass funnel and washed with a 10% methanol/$CH_2Cl_2$ solution and concentrated. The crude product was purified on a 1 mm silica prep plate eluting with 10% methanol/$CH_2Cl_2$ to afford 12 mg (19% yield) of 5-methylthio-4-[4-(4-nitrophenyl)(1,3-thiazol-2-yl)]thiophene-2-carboxamidine hydrochloride. $^1$H-NMR ($CD_3OD$, 300 MHz) δ 8.58 (s, 1H), 8.32–8.33 (m, 4H), 8.24 (s, 1H), 2.83 (s, 3H). Mass Spectrum (MALDI-TOF, CHCA matrix, m/z) Calcd. for $C_{15}H_{12}N_4O_2S_3$: 376.5(M+H), found 377.3.

EXAMPLE 12

4-[4-(3,4-Ethylenedioxyphenyl)thiazol-2-yl]-5-methylthiothiophene-2-carboxamidine hydrochloride a) Methyl 4-(4-(2H,3H-benzo[3,4-e]4-dioxin-6-yl)(1,3-thiazol-2-yl))-5-methylthiothiophene-2-carboxylate: 40 mg (0.162 mmol) of methyl 4-(aminothioxomethyl)-5-methylthiothiophene-2-carboxylate (Maybridge Chemical Co. LTD., Cornwall, U.K.) was dissolved in 2 mL of reagent grade acetone. 1-(2H,3H-benzo[e]1,4-dioxin-6-yl)-2-bromoethan-1-one (0.162 mmol; 42 mg; Maybridge Chemical Co. LTD., Cornwall, U.K.) was added and the solution was allowed to reflux for 3 h. The solution was allowed to cool and allowed to stir for 2 days after which the reaction solution was concentrated in vacuo. The crude product was dissolved in 50 mL of $CH_2Cl_2$ and partitioned between 50 mL of 1 N NaOH (aq.). The organic layer was obtained and dried over sodium sulfate and concentrated to afford 60 mg (90% yield) of methyl 4-[4-(3,4-ethylenedioxyphenyl) thiazol-2-yl]-5-methylthiothiophene-2-carboxylate.

b) 4-[4-(3,4-Ethylenedioxyphenyl)thiazol-2-yl]-5-methylthiothiophene-2-carboxamidine hydrochloride: To a stirred suspension of 1.62 mmol (86 mg) of ammonium chloride (Fisher Scientific) in 2 mL of anhydrous toleune (Aldrich Chemical Co.) placed under nitrogen atmosphere at 0° C., 810 µL (1.62 mmol) of 2M trimethylaluminum in toluene Aldrich Chemical Co.) was added via syringe over 10 min and then let stir at 0° C. for 30 min after which 60 mg (0.162 mmol) of methyl 4-[4-(3,4-ethylenedioxyphenyl) thiazol-2-yl]-5-methylthiothiophene-2-carboxylate was added to solution and allowed to reflux for 2.5 h. The reaction mixture was quenched by pouring over a slurry of 500 mg of silica in 10 mL of chloroform. The silica was poured onto a sintered glass funnel and washed with a 10% methanol/$CH_2Cl_2$ solution and concentrated. The crude product was purified on a 1 mm silica prep plate eluting with 10% methanol/$CH_2Cl_2$ to afford 47 mg (75% yield) of 4-[4-(3,4-ethylenedioxyphenyl)thiazol-2-yl]-5-methylthiothiophene-2-carboxamidine hydrochloride. $^1$H-NMR ($CD_3OD$; 300 MHz) δ 8.53 (s, 1H), 7.73 (s, 1H), 7.56 (d, J=2Hz, 1H), 7.50 (dd, J=2.1 Hz and 8.4 Hz, 1H), 6.89 (d, J=8.4 Hz, 1H), 4.28 (s, 4H), 2.8 (s, 3H). Mass Spectrum (MALDI-TOF, CHCA matrix, m/z) Calcd. for $C_{17}H_{15}N_3O_2S_3$: 389.5(M+H), found 390.1.

EXAMPLE 13

4-[4-(4-Methoxyphenyl)(1,3-thiazol-2-yl)]-5-methylthiothiophene-2-carboxamidine hydrochloride a) Methyl 4-[4-(4-methoxyphenyl)(1,3-thiazol-2-yl)]-5-methylthiothiophene-2-carboxylate: 30 mg (0.122 mmol) of methyl 4-(aminothioxomethyl)-5-methylthiothiophene-2-carboxylate (Maybridge Chemical Co. LTD., Cornwall, U.K.) was dissolved in 1.2 mL of reagent grade acetone. 2-bromo-4'-methoxy acetophenone (0.146 mmol; 28 mg; Aldrich Chemical Co.) was added and the solution was allowed to reflux for 3 h. The solution was allowed to cool and a solid was filtered and washed with methanol and dried in vacuo to afford 46 mg (90% yield) of methyl 4-[4-(4-methoxyphenyl)(1,3-thiazol-2-yl)]-5-methylthiothiophene-2-carboxylate.

b) 4-[4-(4-Methoxyphenyl)(1,3-thiazol-2-yl)J-5-methylthiothiophene-2-carboxamidine hydrochloride: To a stirred suspension of 1.22 mmol (66 mg) of ammonium chloride (Fisher Scientific) in 2 mL of anhydrous toleune (Aldrich Chemical Co.) placed under nitrogen atmosphere at 0° C., 612 µL (1.22 mmol) of 2M trimethylaluminum in toluene (Aldrich Chemical Co.) was added via syringe over 10 min and then let stir at 0° C. for 30 min after which 46 mg (0.122 mmol) of 4-[4-(4-methoxyphenyl)(1,3-thiazol-2-yl)]-5-methylthiothiophene-2-carboxylate was added to solution and allowed to reflux for 2.5 h. The reaction mixture was quenched by pouring over a slurry of 500 mg of silica in 10 mL of chloroform. The silica was poured onto a sintered glass funnel and washed with a 10% methanol/$CH_2Cl_2$ solution and concentrated. The crude product was purified on a 1 mm silica prep plate eluting with 10% methanol/$CH_2Cl_2$ to afford 32 mg (73% yield) of 4-[4-(4-methoxyphenyl)(1,3-thiazol-2-yl)]-5-methylthiothiophene-2-carboxamidine hydrochloride. $^1$H-NMR ($CD_3OD$; 300 MHz) δ 8.53 (s, 1H), 7.98 (d, J=7 Hz, 2H), 7.75 (s, 1H), 7.01 (d, J=5 Hz, 2H), 3.9 (s, 3H), 2.8 (s, 3H). Mass Spectrum (MALDI-TOF, CHCA matrix, m/z) Calcd. for $C_{16}H_{15}N_3OS_3$: 362.0 (M+H), found 362.2.

EXAMPLE 14

4-[4-(3,4-Propylenedioxyphenyl)thiazol-2-yl]-5-methylthiothiophene-2-carboxamidine hydrochloride a) Methyl 4-[4-(3,4-propylenedioxyphenyl)thiazol-2-yl]-5-methylthiothiophene-2-carboxylate: 42 mg (0.170 mmol) of methyl 4-(aminothioxomethyl)-5-methylthiothiophene-2-carboxylate (Maybridge Chemical Co. LTD., Cornwall, U.K.) was dissolved in 5 mL of reagent grade acetone. 3',4'-Propylenedioxy-2-bromoacetophenone (0.170 mmol; 28 mg; Maybridge Chemical Co. LTD., Cornwall, U.K.) was added and the solution was allowed to reflux for 3 h. The solution was allowed to cool and a solid was filtered and purified on a 1 mm silica prep plate eluting with 20% ethyl acetate/hexane and dried in vacuo to afford 42 mg (59% yield) of methyl 4-[4-(3,4-propylenedioxyphenyl)thiazol-2-yl]-5-methylthiothiophene-2-carboxylate.

b) 4-[4-(3,4-Propylenedioxyphenyl)thiazol-2-yl]-5-methylthiothiophene-2-carboxamidine hydrochloride: To a stirred suspension of 1.01 mmol (54 mg) of ammonium chloride (Fisher Scientific) in 2 mL of anhydrous toluene (Aldrich Chemical Co.) placed under nitrogen atmosphere at 0° C., 510 µL (101 mmol) of 2M trimethylaluminum in toluene (Aldrich Chemical Co.) was added via syringe over 10 min and then let stir at 0° C. for 30 min after which 42 mg (0.101 mmol) of methyl 4-[4-(3,4-propylenedioxyphenyl)thiazol-2-yl]-5-methylthiothiophene-2-carboxylate was added to solution and allowed to reflux for 3 h. The reaction mixture was quenched by pouring over a slurry of 500 mg of silica in 20 mL of chloroform. The silica was poured onto a sintered glass funnel and washed with a 10% methanol/$CH_2Cl_2$ solution and concentrated to afford 20 mg (50% yield) of 4-[4-(3,4-propylenedioxyphenyl)thiazol-2-yl]-5-methylthiothiophene-2-carboxamidine hydrochloride. $^1$H-NMR ($CD_3OD$; 300 MHz) δ 8.53 (s, 1H), 7.78 (s, 1H), 7.68 (d, J=2.2 Hz, 1H), 7.60 (dd, J=2.2 Hz and 8.4 Hz, 1H), 7.00 (d, J=8.3 Hz; 1H), 4.19–4.28 (m, 4H), 2.77 (s, 3H), 2.18–2.23 (m, 2H). Mass Spectrum (MALDI-TOF, CHCA matrix, m/z) Calcd. for $C_{18}H_{17}N_3O_2S_3$: 404.1 (M+H), found 404.1.

EXAMPLE 15

5-Methylthio-4-(4-(2-thienyl)(1,3-thiazol-2-yl))thiophene-2-carboxamidine acetate a) 2-Bromo-1-(2-thienyl)ethan-1-one: To a solution of 500 mg (3.96 mmol) of 2-acetyl thiophene (Aldrich Chemical Co.) dissolved in 20 mL of $CHCl_3$, was added 1 drop of 30% HBr/$CH_3COOH$ (Aldrich Chemical Co.) followed by 3.96 mmol (633 mg; 204 µL) of bromine (Aldrich Chemical Co.) added dropwise over 30 min. The reaction was allowed to stir for 1 h. The solution was concentrated to an oil and dried in vacuo. The crude product was purified on 1 mm silica prep plates eluting with neat $CH_2Cl_2$ to obtain 300 mg (37% yield) of 2-bromo-1-(2-thienyl)ethan-1-one. $^1$H-NMR ($CDCl_3$; 300 MHz) δ 7.80 (m, 2H), 7.18 (m, 1H), 4.37 (s, 2H).

b) Methyl 5-methylthio-4-(4-(2-thienyl)(1,3-thiazol-2-yl))thiophene-2-carboxylate: 44 mg (0.176 mmol) of methyl 4-(aminothioxomethyl)-5-methylthiothiophene-2-carboxylate (Maybridge Chemical Co. LTD., Cornwall, U.K.) was dissolved in 3 mL of reagent grade acetone. 2-Bromo-1-(2-thienyl)ethan-1-one (0.176 mmol; 36 mg) was added and the solution was allowed to reflux for 3 h. The solution was allowed to cool and was concentrated. The crude product was dissolved in 20 mL of $CH_2Cl_2$ and washed with 20 mL of 1 N HCl (aq.). The organic layer was obtained and dried over sodium sulfate to afford 115 mg (80% yield) of crude methyl 5-methylthio-4-(4-(2-thienyl) (1,3-thiazol-2-yl))thiophene-2-carboxylate.

c) 5-Methylthio-4-(4-(2-thienyl)(1,3-thiazol-2-yl))thiophene-2-carboxamidine acetate: To stirred suspension of 2.80 mmol (150 mg) of ammonium chloride (Fisher Scientific) in 5 mL of anhydrous toluene (Aldrich Chemical Co.) placed under nitrogen atmosphere at 0° C., 1.5 mL (2.8 mmol) was added 2M trimethylaluminum in toluene (Aldrich Chemical Co.) via syringe over 15 min and then let stir at 0° C. for 25 min. after which 115 mg (0.280 mmol) of methyl 5-methylthio-4-(4-(2-thienyl)(1,3-thiazol-2-yl)) thiophene-2-carboxylate in 5 mL of anhydrous toluene was added to solution and allowed to reflux for 1.5 h. The reaction mixture was quenched by pouring over a slurry of silica in $CH_2Cl_2$. The silica was poured onto a sintered glass funnel and washed with a 10% methanol/$CH_2Cl_2$ solution and concentrated. The crude product was purified on a 1 mm silica prep plate eluting with 10% methanol/$CH_2Cl_2$ with 1% $CH_3COOH$ to afford 40 mg (43% yield) of 5-methylthio-4-(4-(2-thienyl)(1,3-thiazol-2-yl))thiophene-2-carboxamidine acetate. $^1$H-NMR (CD$_3$OD; 300 MHz) δ 8.52 (s, 1H), 7.74 (s, 1H), 7.59 (dd, J=2 Hz and 5 Hz, 1H), 7.42 (dd, J=2 Hz and 5 Hz, 1H), 7.11 (m, 1H, 2.79 (s, 3H). Mass Spectrum (MALDI-TOF, CHCA matrix, m/z) Calcd. for $C_{13}H_{11}N_3S_4$: 338.0 (M+H), found 337.9.

EXAMPLE 16

4-[4-(3-Bromophenyl)(1,3-thiazol-2-yl)]-5-methylthiothiophene-2-carboxamidine hydrochloride a) Methyl 4-[4-(3-bromophenyl)(1,3-thiazol-2-yl)]-5-methylthiothiophene-2-carboxylate: 99 mg (0.400 mmol) of methyl 4-(aminothioxomethyl)-5-methylthiothiophene-2-carboxylate (Maybridge Chemical Co. LTD., Cornwall, U.K.) was dissolved in 25 mL of reagent grade acetone. 2-Bromo-3'-bromo acetophenone (0.4 mmol; 111 mg) was added and the solution was allowed to reflux for 3 h. The solution was allowed to cool and a solid was filtered and dissolved in 5 mL of hot tetrahydrofuran (THF), Aldrich Chemical Co.) and purified on a 1 mm silica prep plate eluting with 20% ethyl acetate/hexane and dried in vacuo to afford 66 mg (40% yield) of methyl 4-[4-(3-bromophenyl) (1,3-thiazol-2-yl)]-5-methylthiothiophene-2-carboxylate.

b) 4-[4-(3-Bromophenyl)(1,3-thiazol-2-yl)]-5-methylthiothiophene-2-carboxamidine hydrochloride: To a stirred suspension of 1.55 mmol (83 mg) of ammonium chloride (Fisher Scientific) in 10 mL of anhydrous toluene (Aldrich Chemical Co.) placed under nitrogen atmosphere at 0° C., 774 µL (1.55 mmol) of 2M trimethylaluminum in toluene (Aldrich Chemical Co.) was added via syringe over 10 min and then let stir at 25° C. for 20 min after which 66 mg (0.155 mmol) of 4-[4-(3-bromophenyl)(1,3-thiazol-2-yl)]-5-methylthiothiophene-2-carboxylate was added to solution and allowed to reflux for 3 h. The reaction mixture was quenched by pouring over a slurry of 5 g of silica in 25 mL of chloroform. The silica was poured onto a sintered glass funnel and washed with a 10% methanol/$CH_2Cl_2$ solution and concentrated. The crude product was purified on 1 mm silica plates eluting with 10% methanol/$CH_2Cl_2$ to afford 63 mg (90% yield) of 4-[4-(3-bromophenyl)(1,3-thiazol-2-yl)]-5-methylthiothiophene-2-carboxamidine hydrochloride. $^1$H-NMR (CD$_3$OD; 300 MHz) δ 8.49 (s, 1H), 8.21 (m, 1H), 7.96 (m, 2H), 7.50 (m, 1H), 7.5 (m, 1H), 7.34 (m, 1H), 2.8 (s, 3H). Mass Spectrum (MALDI-TOF, CHCA matrix, m/z) Calcd. for $C_{15}H_{12}BrN_3S_3$: 411.9 (M+H), found 411.9.

EXAMPLE 17

4-[4-(4-Chloro-3-nitrophenyl)(1,3-thiazol-2-yl)]-5-methylthiothiophene-2-carboxamidine hydrochloride a) Methyl 4-[4-(4-chloro-3-nitrophenyl)(1,3-thiazol-2-yl)]-5-methylthiothiophene-2-carboxylate: 50 mg (0.202 mmol) of methyl 4-(aminothioxomethyl-5-methylthiothiophene-2-carboxylate (Maybridge Chemical Co. LTD., Cornwall, U.K.) was dissolved in 10 mL of reagent grade acetone. 2-Bromo-4'-chloro-3'-nitroacetophenone (0.212 mmol; 59 mg) was added and the solution was allowed to reflux for 3 h. The solution was allowed to cool and a solid was filtered and dissolved in hot tetrahydrofuran (THF) and purified on a 1 mm silica prep plate eluting with 20% ethyl acetate/hexane and dried in vacuo to afford 60 mg (70% yield) of methyl 4-[4-(4-chloro-3-nitrophenyl)(1,3-thiazol-2-yl)]-5-methylthiothiophene-2-carboxylate.

b) 4-[4-(4-Chloro-3-nitrophenyl)(1,3-thiazol-2-yl)]-5-methylthiothiophene-2-carboxamidine hydrochloride: To a stirred suspension of 1.40 mmol (75 mg) of ammonium chloride (Fisher Scientific) in 10 mL of anhydrous toluene (Aldrich Chemical Co.) placed under nitrogen atmosphere at 0° C., 700 µL (1.40 mmol) of 2M trimethylaluminum in toluene (Aldrich Chemical Co.) was added via syringe over 10 min and then let stir for 20 min after which 60 mg (0.140 mmol) of 4-[4-(4-chloro-3-nitrophenyl)(1,3-thiazol-2-yl)]-5-methylthiothiophene-2-carboxylate was added to solution and allowed to reflux for 3 h. The reaction mixture was quenched by pouring over a slurry of 5 g of silica in 50 mL of chloroform. The silica was poured onto a sintered glass funnel and washed with a 10% methanol/$CH_2Cl_2$ solution and concentrated. The crude product was purified on 1 mm silica plates eluting with 10% methanol/$CH_2Cl_2$ to afford 17 mg (32% yield) of 4-[4-(4-chloro-3-nitrophenyl)(1,3-thiazol-2-yl)]-5-methylthiothiophene-2-carboxamidine hydrochloride. $^1$H-NMR (CD$_3$OD; 300 MHz) δ8.53–8.58 (m, 2H), 8.26 (dd, J=2.2 Hz and 8.5 Hz, 1H), 8.16 (s, 1H), 7.72 (d, J=8.5 Hz, 1H), 2.80 (s, 3H).

EXAMPLE 18

4-[4-(4-Chloro-3-methylphenyl)(1,3-thiazol-2-yl)]-5-methylthiothiophene-2-carboxamidine hydrochloride a) Methyl 4-[4-(4-chloro-3-methylphenyl)(1,3-thiazol-2-yl)]-5-methylthiothiophene-2-carboxylate: 155 mg (0.627 mmol) of methyl 4-(aminothioxomethyl)-5-methylthiothiophene-2-carboxylate (Maybridge Chemical Co. LTD., Cornwall, U.K.) was dissolved in 10 mL of reagent grade acetone. 2-Bromo-1-(4-chloro-3-methylphenyl)ethan-1-one (0.658 mmol; 163 mg) was added and the solution was allowed to reflux for 3 h. The solution was allowed to cool and the reaction mixture was concentrated and dissolved in 50 mL of $CH_2Cl_2$. The organic layer was washed with 50 mL of 1N HCl (aq.), dried over sodium sulfate and concentrated. The crude product was purified on a 1 mm silica plate eluting with 20% ethyl acetate/hexane to afford 168 mg (68% yield) of methyl 4-[4-(4-chloro-3-methylphenyl)(1,3-thiazol-2-yl)]-5-methylthiothiophene-2-carboxylate.

b) 4-[4-(4-Chloro-3-methylphenyl)(1,3-thiazol-2-yl)1-5-methylthiothiophene-2-carboxamidine hydrochloride: To a stirred suspension of 4.24 mmol (227 mg) of ammonium chloride (Fisher Scientific) in 15 mL of anhydrous toluene (Aldrich Chemical Co.) placed under nitrogen atmosphere at 0° C., 2.2 mL (4.24 mmol) of 2M trimethylaluminum in toluene (Aldrich Chemical Co.) was added via syringe over 10 min and then let stir for 20 min at 25° C. after which 168 mg (0.424 mmol) of methyl 4-[4-(4-chloro-3-methylphenyl) (1,3-thiazol-2-yl)]-5-methylthiothiophene-2-carboxylate was added to solution and allowed to reflux for 2.5 h. The reaction mixture was quenched by pouring over a slurry of 5 g silica in chloroform. The silica was poured onto a sintered glass funnel and washed with a 10% methanol/$CH_2Cl_2$ solution and concentrated to afford 117 mg (73% yield) of 4-[4-(4-chloro-3-methylphenyl)(1,3-thiazol-2-yl)]-5-methylthiothiophene-2-carboxamidine hydrochloride. $^1$H-NMR ($CD_3OD$; 300 MHz) δ 8.53 (s, 1H), 8.03 (dd, J=1.2 Hz and 2.7 Hz, 1H), 7.9 (s, 1H), 7.85 (dd, J=2 Hz and 8.5 Hz 1H), 7.38 (dd, J=8.3 Hz and 17.4 Hz, 1H), 2.8 (s, 3H) 2.45 (s, 3H). Mass Spectrum (MALDI-TOF, CHCA matrix, m/z) Calcd. for $C_{16}H_{14}ClN_3S_3$: 380.0 (M+H), found 380.3.

EXAMPLE 19

4(5-Methyl-4-phenyl(1,3-thiazol-2-yl)-5-methylthiothiophene-2-carboxamidine hydrochloride a) Methyl 4-(5-methyl-4-phenyl(1,3-thiazol-2-yl)-5-methylthiothiophene-2-carboxylate: 48 mg (0.194 mmol) of methyl 4-(aminothioxomentyl)-5-methylthiothiophene-2-carboxylate (Maybridge Chemical Co. LTD., Cornwall, U.K.) was dissolved in 5 mL of reagent grade acetone. 2-Bromo-1-phenylpropan-1-one (0.223 mmol; 48 mg) was added and the solution was allowed to reflux for 5 h. The solution was allowed to cool and the reaction mixture was concentrated and dissolved in 50 mL of $CH_2Cl_2$. The organic layer was washed with 50 mL of 1N HCl (aq.), dried over sodium sulfate and concentrated. The crude product was purified on a 1 mm silica plate eluting with 20% ethyl acetate/hexane to afford 53 mg (76% yield) of methyl 4-(5-methyl-4-phenyl(1,3-thiazol-2-yl))-5-methylthiothiophene-2-carboxylate.

b) 4-(5-Methyl-4-phenyl(1,3-thiazol-2-yl))-5-methylthiothiophene-2-carboxamidine hydrochloride: To a stirred suspension of 1.47 mmol (78 mg) of ammonium chloride (Fisher Scientific) in 5 mL of anhydrous toluene (Aldrich Chemical Co.) placed under nitrogen atmosphere at 0° C., 735 µL (1.47 mmol) of 2M trimethylaluminum in toluene (Aldrich Chemical Co.) was added via syringe over 10 min and then let stir for 20 min at 25° C. then, 53 mg (0.147 mmol) of methyl 4-(5-methyl-4-phenyl(1,3-thiazol-2-yl))-5-methylthiothiophene-2-carboxylate were added to solution and allowed to reflux for 2.5 h. The reaction mixture was quenched by pouring over a slurry of 5 g silica in chloroform. The silica was poured onto a sintered glass funnel and washed with a 10% methanol/$CH_2Cl_2$ solution and concentrated to afford 26 mg (51% yield) of 4-(5-methyl-4-phenyl(1,3-thiazol-2-yl))-5-methylthiothiophene-2-carboxamidine hydrochloride. $^1$H-NMR ($CD_3OD$; 300 MHz) δ 8.45 (s, 1H), 7.74–7.77 (m, 2H), 7.44–7.50 (m, 2H), 7.38–7.41 (m, 1H), 2.8 (s, 3H) 2.6 (s, 3H). Mass Spectrum (MALDI-TOF, CHCA matrix, m/z) Calcd. for $C_{16}H_{15}N_3S_3$: 346.0 (M+H), found 345.6.

EXAMPLE 20

4-[4-(4-Methylphenyl)(1,3-thiazol-2-yl)]-5-methylthiothiophene-2-carboxamidine trifluoroacetate a) Methyl 4-[4-(4-methylphenyl)(1,3-thiazol-2-yl)]-5-methylthiothiophene-2-carboxylate: 103 mg (0.416 mmol) of methyl 4-(aminothioxomethyl)-5-methylthiothiophene-2-carboxylate (Maybridge Chemical Co. LTD., Cornwall, U.K.) was dissolved in 5 mL of reagent grade acetone. 2-Bromo-4'-methyl acetophenone (0.416 mmol; 89 mg) was added and the solution was allowed to reflux for 3 h. The solution was allowed to cool and crude product was filtered and washed two times with acetone and purified on a 1 mm silica plate eluting with 20% ethyl acetate/hexane to afford 104 mg (69% yield) of methyl 4-[4-(4-methylphenyl)(1,3-thiazol-2-yl)]-5-methylthiothiophene-2-carboxylate.

b) 4-[4-(4-Methylphenyl)(1,3-thiazol-2-yl)]-5-methylthiothiophene-2-carboxamidine trifluoroacetate: To a stirred suspension of 2.87 mmol (154 mg) of ammonium chloride (Fisher Scientific) in 10 mL of anhydrous toluene (Aldrich Chemical Co.) placed under nitrogen atmosphere at 0° C., 144 µL (2.87 mmol) of 2M trimethylaluminum in toluene (Aldrich Chemical Co.) was added via syringe over 10 min and then let stirred for 20 min at 25° C. after which 104 mg (0.287 mmol) of 4-[4-(4-methylphenyl)(1,3-thiazol-2-yl)]-5-methylthiothiophene-2-carboxylate was added to solution and allowed to reflux for 3 h. The reaction mixture was quenched by pouring over a slurry of 5 g of silica in 50 mL of chloroform. The silica was poured onto a sintered glass funnel and washed with a 10% methanol/$CH_2Cl_2$ solution and concentrated. The crude product was then purified on a 1 mm silica prep plate eluting with 10% methanol/$CH_2Cl_2$ with 1% $CH_3COOH$. The product was then basified with aq. NaOH and extracted with $CHCl_3$ and concentrated. TFA was added and the product was crystallized from methanol as 4-[4-(4-methylphenyl)(1,3-thiazol-2-yl)]-5-methylthiothiophene-2-carboxamidine trifluoroacetate (20 mg; 30% yield). $^1$H-NMR (DMSO-$d_6$; 300 MHz) δ 8.62 (s, 1H), 8.12 (s, 1H), 7.98 (d, 1H, J=8.1 Hz) 7.31 (d, 1H, J=8.1 Hz), 2.8 (s, 3H) 2.5 (s, 3H). Mass Spectrum (MALDI-TOF, CHCA Matrix, m/z) Calcd. for $C_{16}H_{15}N_3S_3$: 346.0 (M+H), found 346.1.

EXAMPLE 21

4-[4-(2-methoxyphenyl)(1,3-thiazol-2-yl)]-5-methylthiothiophene-2-carboxamidine hydrochloride a) Methyl 4-[4-(2-methoxyphenyl)(1,3-thiazol-2-yl)-5-methylthiothiophene-2-carboxylate: 105 mg (0.424 mmol) of methyl 4-(aminothioxomethyl)-5-methylthiothiophene-2-carboxylate (Maybridge Chemical Co. LTD., Cornwall, U.K.) was dissolved in 5 mL of reagent grade acetone. 2-Bromo-2-methoxy acetophenone (0.467 mmol; 110 mg) was added and the solution was allowed to reflux for 3 h. The solution was allowed to cool and the solution concentrated. The crude product was dissolved in 100 mL of $CH_2Cl_2$ and washed one time with 50 mL of 1N NaOH. The organic layer was obtained, dried over sodium sulfate, concentrated and purified on a 1 mm silica plate eluting with 20% ethyl acetate/hexane to afford 160 mg (95% yield) of methyl 4-[4-(2-methoxyphenyl)(1,3-thiazol-2-yl)]-5-methylthiothiophene-2-carboxylate.

b) 4-[4-(2-Methoxyphenyl)(1,3-thiazol-2-yl)]-5-methylthiothiophene-2-carboxamidine hydrochloride: To a stirred suspension of 4.23 mmol (227 mg) of ammonium chloride (Fisher Scientific) in 10 mL of anhydrous toluene placed under nitrogen atmosphere at 0° C., 2.12 mL (4.23 mmol) of 2M trimethylaluminum in toluene (Aldrich Chemical Co.) was added via syringe over 10 min and then let stir for 20 min at 25° C. after which 160 mg (0.287 mmol) of methyl 4-[4-(2-methoxyphenyl)(1,3-thiazol-2-yl)]-5-methylthiothiophene-2-carboxylate in a solution of 5 mL of anhydrous toluene was added to solution and allowed to reflux for 3 h. The reaction mixture was quenched by pouring over a slurry of 5 g of silica in 30 mL of chloroform. The silica was poured onto a sintered glass funnel and washed with a 10% methanol/$CH_2Cl_2$ solution and concentrated. The crude product was then purified on a 2 mm silica prep plate eluting with 10% methanol/$CH_2Cl_2$ with 1% $NH_4OH$. The product was then dissolved in 2 mL of 4N HCl/dioxane and concentrated to afford 45 mg (29% yield) of 4-[4-(2-methoxyphenyl)(1,3-thiazol-2-yl)]-5-methylthiothiophene-2-carboxamidine hydrochloride. $^1$H-NMR (DMSO-d$_6$; 300 MHz) δ 8.68 (s, 1H), 8.36 (dd, J=1.6 Hz and 7.74 Hz, 1H), 8.21 (s, 1H), 7.36–7.42 (m, 1H), 7.05–7.22 (m, 3H), 3.97 (s, 3H), 2.8 (s, 3H). Mass Spectrum (MALDI-TOF, CHCA Matrix, m/z) Calcd. for C$_{16}$H$_{15}$N$_3$OS$_3$: 362.0 (M+H), found 361.7.

EXAMPLE 22

4-[4-(2,4-Dimethoxyphenyl)(1,3-thiazol-2-yl)]-5-methylthiothiophene-2-carboxamidine hydrochloride a) Methyl 4-[4-(2,4-dimethoxyphenyl)(1,3-thiazol-2-yl)]-5-methylthiothiophene-2-carboxylate: 99 mg (0.424 mmol) of methyl 4-(aminothioxomethyl)-5-methylthiothiophene-2-carboxylate (Maybridge Chemical Co. LTD., Cornwall, U.K.) was dissolved in 5 mL of reagent grade acetone. 2-Bromo-2',4'-dimethoxyacetophenone (0.440 mmol; 114 mg) was added and the solution was allowed to reflux for 2.5 h. The solution was allowed to cool and the crude product was collected as a solid and washed with methanol and dried yielding 91 mg (56% yield) of methyl 4-[4-(2,4-dimethoxyphenyl)(1,3-thiazol-2-yl)]-5-methylthiothiophene-2-carboxylate.

b) 4-[4-(2,4-Dimethoxyphenyl)(1,3-thiazol-2-yl)1-5-methylthiothiophene-2-carboxamidine hydrochloride: To a stirred suspension of 2.23 mmol (119 mg) of ammonium chloride (Fisher Scientific) in 10 mL of anhydrous toluene placed under nitrogen atmosphere at 0° C., 1.1 mL (2.23 mmol) of 2M trimethylaluminum in toluene was added via syringe over 10 min and then let stirred for 20 min at 25° C. after which 81 mg (0.223 mmol) of methyl 4-[4-(2,4-dimethoxyphenyl)(1,3-thiazol-2-yl)]-5-methylthiothiophene-2-carboxylate was added to solution and allowed to reflux for 2.5 h. The reaction mixture was quenched by pouring over a slurry of silica in chloroform. The silica was poured onto a sintered glass funnel and washed with a 10% methanol/CH$_2$Cl$_2$ solution and concentrated. The crude product was then purified on a 0.5 mm silica prep plate eluting with 10% methanol/CH$_2$Cl$_2$ to afford 32 mg (37% yield) of 4-[4-(2,4-dimethoxyphenyl)(1,3-thiazol-2-yl)]-5-methylthiothiophene-2-carboxamidine hydrochloride. $^1$H-NMR (CD$_3$OD; 300 MHz) δ 8.49 (s, 1H), 8.31 (d, J=8.5 Hz, 1H), 7.93 (s, 1H), 6.64 (m, 2H), 3.97 (s, 3H), 3.85 (s, 3H), 2.79 (s, 3H). Mass Spectrum (MALDI-TOF, CHCA Matrix, m/z) Calcd. for C$_{17}$H$_{17}$N$_3$O$_2$S$_3$: 392.1 (M+H), found 392.4.

EXAMPLE 23

4-[4-(3,4-Dichlorophenyl)(1,3-thiazol-2-yl)]-5-methylthiothiophene-2-carboxamidine hydrochloride a) Methyl 4-[4-(3,4-dichlorophenyl)(1,3-thiazol-2-yl)]-5-methylthiothiophene-2-carboxylate: 176 mg (0.712 mmol) of methyl 4-(aminothioxomethyl)-5-methylthiothiophene-2-carboxylate (Maybridge Chemical Co. LTD., Cornwall, U.K.) was reacted with 2-bromo-3',4'-dichloroacetophenone (0.854 mmol; 330 mg) in a manner similar to Example 22, step (a) to afford 270 mg (91% yield) of methyl 4-[4-(3,4-dichlorophenyl)(1,3-thiazol-2-yl)]-5-methylthiothiophene-2-carboxylate.

b) 4-[4-(3,4-Dichlorophenyl)(1,3-thiazol-2-yl)]-5-methylthiothiophene-2-carboxamidine hydrochloride: 270 mg (0.648 mmol) of methyl 4-[4-(3,4-dichlorophenyl)(1,3-thiazol-2-yl)]-5-methylthiothiophene-2-carboxylate was treated in a manner similar to Example 22, step (b) to afford 135 mg (52% yield) of 4-[4-(3,4-dichlorophenyl)(1,3-thiazol-2-yl)]-5-methylthiothiophene-2-carboxamidine hydrochloride. $^1$H-NMR (CD$_3$OD; 300 MHz) δ 8.54 (s, 1H), 8.22 (d, J=2 Hz, 1H), 8.02 (s, 1H), 7.94 (dd, J=2 Hz and 8.4 Hz, 1H), 7.58 (d, J=8.5 Hz, 1H), 2.79 (s, 3H). Mass Spectrum (MALDI-TOF, CHCA Matrix, m/z) Calcd. for C$_{15}$H$_{11}$Cl$_2$N$_3$S$_3$: 400.0 (M+H), found 400.6.

EXAMPLE 24

4-[4-(3-Methylphenyl)(1,3-thiazol-2-yl)]-5-methylthiothiophene-2-carboxamidine hydrochloride a) Methyl 4-[4-(3-methylphenyl)(1,3-thiazol-2-yl)]-5-methylthiothiophene-2-carboxylate: Methyl 4-(aminothioxomentyl)-5-methylthiothiophene-2-carboxylate, 106 mg (0.428 mmol) (Maybridge Chemical Co. LTD., Cornwall, U.K.) was reacted with 2-bromo-3'methylacetophenone (0.428 mmol, 91 mg) in a manner similar to Example 22, step (a) to afford 98 mg (63% yield) of methyl 4-[4-(3-methylphenyl)(1,3-thiazol-2-yl)]-5-methylthiothiophene-2-carboxylate.

b) 4-[4-(3-Methylphenyl)(1,3-thiazol-2-yl)]-5-methylthiothiophene-2-carboxamidine hydrochloride: 4-[4-(3-methylphenyl)(1,3-thiazol-2-yl)]-5-methylthiothiophene-2-carboxylate, (98 mg, 0.271 mmol) was treated in a similar manner to Example 22, step (b) to afford 75 mg (80% yield) of 4-[4-(3-methylphenyl)(1,3-thiazol-2-yl)]-5-methylthiothiophene-2-carboxamidine hydrochloride. $^1$H-NMR (CD$_3$OD; 300 MHz) δ 8.56 (s, 1H), 7.88 (s, 1H), 7.86 (d, J=14 Hz, 2H), 7.33 (m, 1H), 7.19 (m, 1H), 2.79 (s, 3H), 2.42 (s, 3H). Mass Spectrum (MALDI-TOF, CHCA Matrix, m/z) Calcd. for C$_{16}$H$_{15}$N$_3$S$_3$: 346.0 (M+H), found 346.7.

EXAMPLE 25

5-Methylthio-4-(4-(2-5,6,7,8-tetrahydronaphthyl)(1,3-thiazol-2-yl))thiophene-2-carboxamidine hydrochloride a) Methyl 5-methylthio-4-(4-(2-5,6,7,8-tetrahydronaphthyl)(1,3-thiazol-2-yl))thiophene-2-carboxylate: Methyl 4-(aminothioxomethyl)-5-methylthiothiophene-2-carboxylate, (160 mg, 0.647 mmol) (Maybridge Chemical Co. LTD., Cornwall, U.K.) was reacted with 2-bromo-1-(2-5,6,7,8-tetrahydronaphthyl)ethan-1-one (0.712 mmol; 180 mg) in a manner similar to Example 22, step (a) to afford 106 mg (41% yield) of methyl 5-methylthio-4-(4-(2-5,6,7,8-tetrahydronaphthyl)(1,3-thiazol-2-yl))thiophene-2-carboxylate.

b) 5-Methylthio-4-(4-(2-5,6,7,8-tetrahydronaphthyl)(1,3-thiazol-2-yl))thiophene-2-carboxamidine hydrochloride: 106 mg (0.264 mmol) of methyl 5-methylthio-4-(4-(2-5,6,7,8-tetrahydronaphthyl)(1,3-thiazol-2-yl))thiophene-2-carboxylate was treated in a similar manner to Example 22, step (b) to afford 88 mg (80% yield) of 5-methylthio-4-(4-(2-5,6,7,8-tetrahydronaphthyl)(1,3-thiazol-2-yl))thiophene-2-carboxamidine hydrochloride. $^1$H-NMR (CD$_3$OD; 300 MHz) δ 8.49 (s, 1H), 7.78 (s, 1H), 7.73 (m, 2H), 7.11 (m, 1H), 2.79 (m, 7H), 1.82–1.86 (m, 4H). Mass Spectrum (MALDI-TOF, CHCA Matrix, m/z) Calcd. for C$_{19}$H$_{19}$N$_3$S$_3$: 386.1 (M+H), found 386.2.

EXAMPLE 26

4-[4-(3,5-Dimethoxyphenyl)(1,3-thiazol-2-yl)]-5-methylthiothiophene-2-carboxamidine hydrochloride a) Methyl 4-[4-(3,5-dimethoxyphenyl)(1,3-thiazol-2-yl)]-5-methylthiothiophene-2-carboxylate: 100 mg (0.404 mmol) of methyl 4-(aminothioxomethyl)-5-methylthiothiophene-2-carboxylate (Maybridge Chemical Co. LTD., Cornwall, U.K.) was reacted with 2-bromo-3',5'-dimethoxy acetophenone (0.444 mmol) in a manner similar to Example 22, step (a) to afford 44 mg (27% yield) of methyl 4-[4-(3,5-dimethoxyphenyl)(1,3-thiazol-2-yl)]-5-methylthiothiophene-2-carboxylate.

b) 4-[4-(3,5-Dimethoxyphenyl)(1,3-thiazol-2-yl)]-5-methylthiothiophene-2-carboxamidine hydrochloride: 44 mg (0.108 mmol) of methyl 4-[4-(3,5-dimethoxyphenyl)(1,3-thiazol-2-yl)]-5-methylthiothiophene-2-carboxylate was treated in a manner similar to Example 22, step (b) to afford 25 mg (60% yield) of 4-[4-(3,5-dimethoxyphenyl)(1,3-thiazol-2-yl)]-5-methylthiothiophene-2-carboxamidine hydrochloride. $^1$H-NMR (CD$_3$OD; 300 MHz) δ 8.52 (s, 1H), 7.91 (s, 1H), 7.23 (d, J=2.2 Hz, 1H), 6.50 (t, 1H), 3.85 (s, 6H), 2.89 (s, 3H). Mass Spectrum (MALDI-TOF, CHCA Matrix, m/z) Calcd. for $C_{17}H_{17}N_3O_2S_3$: 392.11 (M+H), found 392.4.

EXAMPLE 27

4-[4-(2-Methylphenyl)(1,3-thiazol-2-yl)]-5-methylthiothiophene-2-carboxamidine hydrochloride a) Methyl 4-[4-(2-methylphenyl)(1,3-thiazol-2-yl)]-5-methylthiothiophene-2-carboxylate: 160 mg (0.647 mmol) of methyl 4-(aminothioxomethyl)-5-methylthiothiophene-2-carboxylate (Maybridge Chemical Co. LTD., Cornwall, U.K.) was reacted with 2-bromo-2'-methyl acetophenone (0.711 mmol, 152 mg) in a manner similar to Example 22, step (a) to afford 124 mg (53% yield) of methyl 4-[4-(2-methylphenyl)(1,3-thiazol-2-yl)]-5-methylthiothiophene-2-carboxylate.

b) 4-[4-(2-Methylphenyl)(1,3-thiazol-2-yl)]-5-methylthiothiophene-2-carboxamidine hydrochloride: 124 mg (0.343 mmol) of methyl 4-[4-(2-methylphenyl)(1,3-thiazol-2-yl)]-5-methylthiothiophene-2-carboxylate was treated in a manner similar to Example 22, step (b) to afford 60 mg (50% yield) of 4-[4-(2-methylphenyl)(1,3-thiazol-2-yl)]-5-methylthiothiophene-2-carboxamidine hydrochloride. $^1$H-NMR (CD$_3$OD; 300 MHz) δ 8.50 (s, 1H), 7.65 (m, 2H), 7.22–7.32 (m, 3H), 2.79 (s, 3H), 2.51 (s, 3H). Mass Spectrum (MALDI-TOF, CHCA Matrix, m/z) Calcd. for $C_{16}H_{15}N_3S_3$: 346.0 (M+H), found 346.2.

EXAMPLE 28

4-[4-(2,5-Dimethoxyphenyl)(1,3-thiazol-2-yl)]-5-methylthiothiophene-2-carboxamidine hydrochloride a) Methyl 4-[4-(2,5-dimethoxyphenyl)(1,3-thiazol-2-yl)]-5-methylthiothiophene-2-carboxylate: 132 mg (0.534 mmol) of methyl 4-(aminothioxomethyl)-5-methylthiothiophene-2-carboxylate (Maybridge Chemical Co. LTD., Cornwall, U.K.) was reacted with 2-bromo-2',5'-dimethoxy acetophenone (0.587 mmol; 152 mg) in a manner similar to Example 22, step (a) to afford 97 mg (45% yield) of methyl 4-[4-(2,5-dimethoxyphenyl)(1,3-thiazol-2-yl)]-5-methylthiothiophene-2-carboxylate.

b) 4-[4-(2,5-Dimethoxyphenyl)(1,3-thiazol-2-yl)]-5-methylthiothiophene-2-carboxamidine hydrochloride: 97 mg (0.238 mmol) of methyl 4-[4-(2,5-dimethoxyphenyl)(1,3-thiazol-2-yl)]-5-methylthiothiophene-2-carboxylate was treated in a manner similar to Example 22, step (b) to afford 30 mg (32% yield) of 4-[4-(2,5-dimethoxyphenyl)(1,3-thiazol-2-yl)]-5-methylthiothiophene-2-carboxamidine hydrochloride. $^1$H-NMR (CD$_3$OD; 300 MHz) δ 8.46 (s, 1H), 8.10 (s, 1H), 7.99 (d, J=3.2 Hz, 1H), 7.05 (d, J=9 Hz, 1H), 6.93 (d, J=3.2 Hz, 1H), 6.90 (d, J=3.2 Hz, 1H), 3.94 (s, 3H), 3.83 (s, 3H), 2.51 (s, 3H). Mass Spectrum (MALDI-TOF, CHCA Matrix, m/z) Calcd. for $C_{17}H_{17}N_3O_2S_3$: 392.1 (M+H), found 392.1.

EXAMPLE 29

4-[4-(4-Chloro(3-pyridyl)(1,3-thiazol-2-yl)]-5-methylthiothiophene-2-carboxamidine hydrochloride a) Methyl 4-[4-(4-chloro(3-pyridyl))(1,3-thiazol-2-yl)]-5-methylthiothiophene-2-carboxylate: 240 mg (0.970 mmol) of methyl 4-(aminothioxomethyl)-5-methylthiothiophene-2-carboxylate (Maybridge Chemical Co. LTD., Cornwall, U.K.) was reacted with 2-bromo-1-(4-chloro(3-pyridyl)) ethan-1-one (1.06 mmol; 250 mg) in a manner similar to Example 22, step (a) to afford 286 mg (77% yield) of methyl 4-[4-(4-chloro(3-pyridyl))(1,3-thiazol-2-yl)]-5-methylthiothiophene-2-carboxylate.

b) 4-[4-(4-Chloro(3-pyridyl))(1,3-thiazol-2-yl)]-5-methylthiothiophene-2-carboxamidine hydrochloride: 286 mg (0.747 mmol) of methyl 4-[4-(4-chloro(3-pyridyl))(1,3-thiazol-2-yl)]-5-methylthiothiophene-2-carboxylate was treated in a manner similar to Example 22, step (b) to afford 134 mg (49% yield) of 4-[4-(4-chloro(3-pyridyl))(1,3-thiazol-2-yl)]-5-methylthiothiophene-2-carboxamidine hydrochloride. Mass Spectrum (MALDI-TOF, CHCA Matrix, m/z) Calcd. for $C_{14}H_{11}N_4ClS_3$: 366.9 (M+H), found 366.6.

EXAMPLE 30

4-(4-(2H-Benzo[d]1,3-dioxolen-5-yly ( )(1,3-thiazol-2-yl))-5-methylthiothiophene-2-carboxamidine hydrochloride a) 1-(2H-Benzo[3,4-d]1,3-dioxolen-5-yl)-2-bromoethan-1-one: To a solution of 2.5 g (15.23 mmol) of 3,4-methylenedioxy acetophenone in 200 mL of anhydrous methanol was added 61 mmol (20 g) of poly(4-vinylpyridinium tribromide), Aldrich Chemical Co., and allowed to reflux for 2.5 h. The solution was filtered and concentrated. 1-(2H-benzo[3,4-d]1,3-dioxolen-5-yl)-2-bromoethan-1-one (1.4 g, 38% yield) was obtained methylene chloride/hexanes as off-white crystals. $^1$H-NMR (DMSO-d$_6$; 300 MHz) δ 8.20 (s, 1H), 8.07 (s, 1H), 7.63 (m, 2H), 7.03 (dd, J=1.2 Hz and 7.1 Hz, 1H), 6.09 (s, 2H), 3.86 (s, 3H), 2.75 (s, 3H).

b) Methyl 4-(4-(2H-benzo[d]1,3-dioxolen-5-yl)(1,3-thiazol-2-yl))-5-methylthiothiophene-2-carboxylate: 1.4 g (5.66 mmol) of methyl 4-(aminothioxomethyl)-5-methylthiothiophene-2-carboxylate (Maybridge Chemical Co. LTD., Cornwall, U.K.) was reacted 1-(2H-benzo[3,4-d]1,3-dioxolen-5-yl)-2-bromoethan-1-one (5.66 mmol, 1.37 g) in a manner similar to Example 22, step (a) to afford 1.55 g (70% yield) of methyl 4-(4-(2H-benzo[d]1,3-dioxolen-5-yl)(1,3-thiazol-2-yl))-5-methylthiothiophene-2-carboxylate.

c) 4-(4-(2H-Benzo[d]1,3-dioxolen-5-yl)(1,3-thiazol-2-yl))-5-methylthiothiophene-2-carboxamidine hydrochloride: 1.55 g (3.95 mmol) of methyl 4-(4-(2H-benzo[d]1,3-dioxolen-5-yl)(1,3-thiazol-2-yl))-5-methylthiothiophene-2-carboxylate was treated in a manner similar to Example 22, step (b) to afford 130 mg (9% yield) of 4-(4-(2H-benzo[d]1,3-dioxolen-5-yl)(1,3-thiazol-2-yl))-5-methylthiothiophene-2-carboxamidine hydrochloride. $^1$H-NMR (CD$_3$OD; 300 MHz) δ 8.51 (s, 1H), 7.73 (s, 1H), 7.58 (m, 2H), 6.89 (d, J=8 Hz, 1H), 6.00 (s, 2H), 2.79 (s, 3H). Mass Spectrum (MALDI-TOF, CHCA Matrix, m/z) Calcd. for $C_{16}H_{13}N_3O_2S_3$: 376.0 (M+H), found 376.1.

EXAMPLE 31

4-[4-(3,4-Dimethoxyphenyl)(1,3-thiazol-2-yl)]-5-methylthiothiophene-2-carboxamidine hydrochloride a) 1-(3,4-Dimethoxyphenyl)-2-bromoethan-1-one: 2 g of 1-(3,4-dimethoxyphenyl)ethan-1-one (11.1 mmol) was reacted in a manner similar to Example 15, step (a), to yield 1.2 g (42% yield) of 1-(3,4-dimethoxyphenyl)-2-bromoethan-1-one.

b) Methyl 4-[4-(3,4-dimethoxyphenyl)(1,3-thiazol-2-yl)]-5-methylthiothiophene-2-carboxylate: 105 mg (0.424 mmol) of methyl 4-(aminothioxomethyl)-5-methylthiothiophene-2-carboxylate (Maybridge Chemical Co. LTD., Cornwall, U.K.) was reacted with 1-(3,4-dimethoxyphenyl)-2-bromoethan-1-one (0.467 mmol; 120 mg) in a manner similar to Example 22, step (a) to afford 148 mg (85% yield) of methyl 4-[4-(3,4-dimethoxyphenyl)(1,3-thiazol-2-yl)]-5-methylthiothiophene-2-carboxylate.

c) 4-[4-(3,4-Dimethoxyphenyl)(1,3-thiazol-2-yl)]-5-methylthiothiophene-2-carboxamidine hydrochloride: 148 mg (0.363 mmol) of methyl 4-[4-(3,4-dimethoxyphenyl)(1, 3-thiazol-2-yl)]-5-methylthiothiophene-2-carboxylate was reacted in a manner similar to Example 22, step (b) to afford 70 mg (50% yield) of 4-[4-(3,4-dimethoxyphenyl)(1,3-thiazol-2-yl)]-5-methylthiothiophene-2-carboxamidine hydrochloride. $^1$H-NMR (CD$_3$OD; 300 MHz) δ 8.50 (s, 1H), 7.76 (s, 1H), 7.61 (m, 2H), 7.31 (m, 1H), 7.01 (d, J=8 Hz, 1H), 3.9 (s, 3H) 3.86 (s, 3H), 2.78 (s, 3H). Mass Spectrum (MALDI-TOF, CHCA Matrix, m/z) Calcd. for $C_{17}H_{17}N_3O_2S_3$: 392.1 (M+H), found 392.4.

EXAMPLE 32

4-[4(2-Chloro(3-pyridyl))(1,3-thiazol-2-yl)]-5-methylthiothiophene-2-carboxamidine a) Methyl 4-[4-(2-chloro(3-pyridyl))(1,3-thiazol-2-yl)]-5-methylthiothiophene-2-carboxylate: 2-Chloropyridine-3-carbonyl chloride (300 mg, 1.7 mmol) was dissolved in anhydrous CH$_3$CN (4 mL). While stirring well with a magnetic stirrer, trimethylsilyldiazomethane (4 mL, 2M solution in hexane, 8 mmol) was dripped into the reaction mixture. The resulting yellow solution was stirred for 2 h at room temperature, at which time the mixture was cooled in an ice bath. To the cold solution, 30% HBr in acetic acid (2 mL) was added dropwise with vigorous evolution of gas. This solution was stirred for 1 h during which time 2-bromo-1-(2-chloro(3-pyridyl))ethan-1-one precipitated. This solid was collected by filtration and dried under vacuum. The dry solid (142 mg, 0.6 mmol) was dissolved in acetone (10 ml). To this solution 5-(methoxycarbonyl)-2-(methylthio)-thiophene-3-thiocarboxamide (100 mg, 0.4 mmol, Maybridge Chemical Company, Cornwall, UK) was added and heated at reflux for 5 h. At this point the solid that precipitated was filtered off and washed with methanol and dried under vacuum to give 110 mg (71%) of methyl 4-[4-(2-chloro(3-pyridyl))(1,3-thiazol-2-yl)]-5-methylthiothiophene-2-carboxylate. $^1$H-NMR (CDCl$_3$; 300 MHz) δ 2.70 (s, 3H), 3.92 (s, 3H), 7.39 (dd, J=4.7 and 7.7 Hz, 1H), 8.11 (s, 1H), 8.22 (s, 1H), 8.38 (dd, J=1.9 and 4.7 Hz, 1H), 8.62 (dd, J=1.9 and 7.7 Hz, 1H).

b) 4-[4-(2-Chloro(3-pyridyl))(1,3-thiazol-2-yl)]-5-methylthiothiophene-2-carboxamidine: Methyl 4-[4-(2-chloro(3-pyridyl))(1,3-thiazol-2-yl)]-5-methylthiothiophene-2-carboxylate (100 mg, 0.26 mmol) as prepared in previous step was treated in a manner similar to that for Example 1, to give 50 mg (52%) of 4-[4-(2-chloro (3-pyridyl))(1,3-thiazol-2-yl)]-5-methylthiothiophene-2-carboxamidine as a solid. $^1$H-NMR (DMSO-d$_6$; 300 MHz) δ 2.79 (s, 3H), 7.62 (dd, J=4.9 and 7.4 Hz, 1H), 8.41 (s, 1H), 8.49 (m, 2H), 8.69 (s, 1H), 9.1 (broad s, 2H), 9.4 (broad s, 2H). Mass spectrum (ESI, m/z): Calcd. for $C_{14}H_{11}N_4S_3Cl$: 367.0 (M+H), found 369.0.

EXAMPLE 33

4-(4-Cyclohexyl(1,3-thiazol-2-yl))-5-methylthiothiophene-2-carboxamidine a) Methyl 4-(4-cyclohexyl(1,3-thiazol-2-yl))-5-methylthiothiophene-2-carboxylate: Cyclohexanecarbonyl chloride (300 mg, 2.0 mmol) was treated in a manner similar to that for Example 32 to give 2-bromo-1-cyclohexylethan-1-one. The dry solid (125 mg) was dissolved in acetone (10 ml). To this solution 5-(methoxycarbonyl)-2-(methylthio)-thiophene-3-thiocarboxamide (100 mg, 0.4 mmol, Maybridge Chemical Company, Cornwall, UK) was added and heated at reflux for 5 h. At this point the solid that precipitated was filtered off and washed with methanol and dried under vacuum to give 100 mg (70%) of methyl 4-(4-cyclohexyl(1,3-thiazol-2-yl))-5-methylthiothiophene-2-carboxylate which was used without further purification in the following step.

b) 4-(4-Cyclohexyl(1,3-thiazol-2-yl))-5-methylthiothiophene-2-carboxamidine: Methyl 4-(4-cyclohexyl(1,3-thiazol-2-yl))-5-methylthiothiophene-2-carboxylate (100 mg, 0.28 mmol) as prepared in previous step was treated in a manner similar to that for Example 1, to give 60 mg (63%) of 4-(4-cyclohexyl(1,3-thiazol-2-yl))-5-methylthiothiophene-2-carboxamidine as a solid. $^1$H-NMR (DMSO-d$_6$; 300 MHz) δ 1.21–1.53 (m, 5H), 1.61–1.78 (m, 3H), 2.05 (m, 2H), 2.7 (s, 3H), 2.74 (m, 1H), 7.33 (s, 1H), 8.32 (s, 1H). Mass spectrum (MALDI-TOF, m/z): Calcd. for $C_{15}H_{19}N_3S_3$, 338.1 (M+H), found 338.1.

EXAMPLE 34

4-Phenyl-5-(trifluoromethyl)thiophene-2-carboxamidine

Methyl 4-phenyl-5-(trifluoromethyl)thiophene-2-carboxylate (100 mg, 0.37 mmol, Maybridge Chemical Company, Cornwall, UK) was treated in a manner similar to that for Example 1 to give 80 mg (85%) of 4-phenyl-5-(trifluoromethyl)thiophene-2-carboxamidine as a solid. $^1$H-NMR (DMSO-d$_6$; 300 MHz) δ 7.45–7.52 (m, 5H), 7.79 (d, J=1.4 Hz, 1H). Mass spectrum (MALDI-TOF, m/z): Calcd. for $C_{12}H_9F_3N_2S$, 271.1 (M+H), found 271.2.

EXAMPLE 35

5-Methylthio-4-(2-phenyl(1,3-thiazol-4-yl)) thiophene-2-carboxamidine a) Methyl 4-(2-bromoacetyl)-5-methylthiothiophene-2-carboxylate: 5-(Methoxycarbonyl)-2-methylthiothiophene-3-carboxylic acid (200 mg, 0.86 mmol) as prepared in Example 95 was taken in a round bottomed flask and anhydrous CH$_2$Cl$_2$ (10 mL) was introduced to the flask. This solution was cooled in an ice bath under an argon atmosphere. To this mixture oxalyl chloride (328 mg, 2.6 mmol) was added followed by anhydrous DMF (500 μL). The resulting solution was stirred at 4° C. for 30 min and then allowed to warm up to room temperature, while monitoring for the disappearance of the acid by TLC. After 2 h solvents were removed under vacuum and the residual oxalyl chloride was removed azeotropically with toluene. The resulting residue was dried under high-vacuum to give the acid chloride as a gray solid. This solid was dissolved in anhydrous $CH_3CN$ (8 mL). While stirring well with a magnetic stirrer trimethylsilyldiazomethane (4 mL, 8 mmol, 2M solution in hexane) was dripped into the reaction mixture. The resulting yellow solution was stirred for 2 h at room temperature, at which time the mixture was cooled in an ice bath. To the cold solution 30% HBr in acetic acid (2 mL,) was added dropwise, with vigorous evolution of gas. This solution was stirred for 1 h, during which methyl 4-(2-bromoacetyl)-5-methylthiothiophene-2-carboxylate precipitates. This solid was collected by filtration and dried under vacuum to give 120 mg (45%). $^1$H-NMR ($CDCl_3$; 300 MHz) δ 2.64 (s, 3H), 3.91 (s, 3H), 4.27 (s, 2H), 8.10 (s, 1H).

b) Methyl 5-methylthio-4-(2-phenyl(1,3-thiazol-4-yl))thiophene-2-carboxylate: 5-(Methoxycarbonyl)-2-(methylthio)-thiophene-3-thiocarboxamide (100 mg, 0.4 mmol, Maybridge Chemical Company, Cornwall, UK) was dissolved in acetone (20 ml). To this solution, methyl 4-(2-bromoacetyl)-5-methylthiothiophene-2-carboxylate (112 mg) as prepared in previous step was added and heated at reflux for 3 h. At this point the solid that precipitated was filtered off and washed with acetone and dried under vacuum to give 82 mg (65%) of methyl 5-methylthio-4-(2-phenyl(1,3-thiazol-4-yl))thiophene-2-carboxylate. $^1$H-NMR ($CDCl_3$; 300 MHz) δ 2.67 (s, 3H), 3.91 (s, 3H), 7.44–7.49 (m, 3H), 7.61 (s, 1H), 8.03–8.06 (m, 2H), 8.28 (s, 1H).

c) 5-Methylthio-4-(2-phenyl(1,3-thiazol-4-yl))thiophene-2-carboxamidine: Methyl 5-methylthio-4-(2-phenyl(1,3-thiazol-4-yl))thiophene-2-carboxylate (80 mg) as prepared in previous step was treated in a manner similar to that for Example 1, to give 50 mg of 5-methylthio-4-(2-phenyl(1,3-thiazol-4-yl))thiophene-2-carboxamidine as a solid. $^1$H-NMR (DMSO-$d_6$; 300 MHz) δ 2.75 (s, 3H), 7.51–7.60 (m, 3H), 8.02 (s, 1H), 8.06 (m, 2H), 8.70 (s, 1H), 9.06 (broad s, 2H), 9.38 (broad s, 2H). Mass spectrum (MALDI-TOF, m/z): Calcd. for $C_{15}H_{13}N_3S_3$, 332.0 (M+H), found 332.1.

EXAMPLE 36

4-[4-(2-Chloro(4-pyridyl))(1,3-thiazol-2-yl)]-5-methylthiothiophene-2-carboxamidine a) Methyl 4-[4-(2-chloro(4-pyridyl))(1,3-thiazol-2-yl)]-5-methylthiothiophene-2-carboxylate: 2-Chloropyridine-4-carbonyl chloride (300 mg, 1.7 mmol) was dissolved in anhydrous $CH_3CN$ (4 mL). While stirring well with a magnetic stirrer trimethylsilyldiazomethane (4 mL, 8 mmol, 2M solution in hexane) was dripped into the reaction mixture. The resulting yellow solution was stirred for 2 h at room temperature, at which time the mixture was cooled in an ice bath. To the cold solution 30% HBr in acetic acid (2 mL) was added dropwise, with vigorous evolution of gas. This solution was stirred for 1 h, during which time 2-bromo-1-(2-chloro(4-pyridyl))ethan-1-one precipitates. This solid was collected by filtration and dried under vacuum. The dry solid (142 mg, 0.6 mmol) was dissolved in acetone (10 ml). To this solution 5-(methoxycarbonyl)-2-(methylthio)-thiophene-3-thiocarboxamide (100 mg, 0.4 mmol, Maybridge Chemical Company, Cornwall, UK) was added and heated at reflux for 5 h. At this point the solid that precipitated was filtered off and washed with methanol and dried under vacuum to give 100 mg of methyl 4-[4-(2-chloro(4-pyridyl))(1,3-thiazol-2-yl)]-5-methylthiothiophene-2-carboxylate. $^1$H-NMR ($CD_3OD$; 300 MHz) δ 2.73 (s, 3H), 3.94 (s, 3H, overlapping $H_2O$ peak), 7.92–7.99 (m, 2H), 8.05 (s, 1H), 8.24 (s, 2H), 8.48 (m, 1H).

b) 4-[4-(2-Chloro(4-pyridyl))(1,3-thiazol-2-yl)]-5-methylthiothiophene-2-carboxamidine: Methyl 4-[4-(2-chloro(4-pyridyl))(1,3-thiazol-2-yl)]-5-methylthiothiophene-2-carboxylate (100 mg, 0.26 mmol) as prepared in previous step was treated in a manner similar to that for Example 1, to give 50 mg of 4-[4-(2-chloro(4-pyridyl))(1,3-thiazol-2-yl)]-5-methylthiothiophene-2-carboxamidine as a solid. $^1$H-NMR ($CDCl_3$/$CD_3OD$; 300 MHz) δ 2.82 (s, 3H), 7.95 (dd, J=1.4 and 5.3 Hz, 1H), 8.08 (d, J=1.0 Hz, 1H), 8.23 (s, 1H), 8.42 (d, J=5.3 Hz, 1H), 8.56 (s, 1H). Mass spectrum (MALDI-TOF, m/z): Calcd. for $C_{14}H_{11}N_4S_3Cl$, 367.0 (M+H), found 367.1.

EXAMPLE 37

4-[4-(4-Chlorophenyl)(1,3-thiazol-2-yl)]-5-(methylsulfonyl)thiophene-2-carboxamidine 4-[4-(4-Chlorophenyl)(1,3-thiazol-2-yl)]-5-methylthiothiophene-2-carboxamidine (35 mg, 0.1 mmol) prepared according to Example 1 was dissolved in a mixture of MeOH and $CH_2Cl_2$ (1:1, 6 mL). While stirring well, m-chloroperoxybenzoic acid (100 mg) was added in portions to this solution over a 3 h period. The mixture was stirred for a further 2 h and the solvents were removed under vacuum. The resulting residue was dissolved in MeOH (8 mL). Strong anion exchange resin (AG 1-X8, 5 ml, 1.4 meq/mL) was packed into a disposable chromatography column and washed with $H_2O$ (5×5 mL) and MeOH (3×5 mL). The methanolic solution from the reaction was slowly introduced into this column, and the column effluent was collected. The column was washed with MeOH (2×5 mL) and these washings were also collected. The combined effluents were evaporated under vacuum and the residue was subjected to preparative thin layer chromatography (silica gel, 10% MeOH in $CH_2Cl_2$ with 2% acetic acid). The major band was isolated and suspended in $CH_2Cl_2$ and filtered. The filtrate was collected and the residue was washed with 10% MeOH in $CH_2Cl_2$ saturated with $NH_3$. The washings were combined with the original filtrate and the solvents were removed under vacuum. The resulting solid was dissolved in 10% MeOH in $CHCl_3$ and filtered through a 0.45 micron filter. The filtrate was collected and evaporated under vacuum to give 20 mg (53%) of an off-white solid. $^1$H-NMR ($CDCl_3$/$CD_3OD$; 300 MHz) δ 3.78 (s, 3H), 7.47 (d, J=8.7 Hz, 2H), 7.96 (d, J=8.7 Hz, 1H), 8.00 (s, 1H), 8.35 (s, 1H). Mass spectrum (MALDI-TOF, m/z): Calcd. for $C_{15}H_{12}O_2N_3S_3Cl$, 398.0 (M+H), found 398.0.

EXAMPLE 38

Hydrazino[5-methylthio-4-(4-phenyl(1,3-thiazol-2-yl))(2-thienyl)]methanimine a) 5-Methylthio-4-(4-phenyl(1,3-thiazol-2-yl))thiophene-2-carboxamide: Liquid ammonia (5 mL) was condensed into a cold (−78° C.) Teflon-lined steel bomb. Methyl 5-methylthio-4-(4-phenyl(1,3-thiazol-2-yl))thiophene-2-carboxylate (0.6 g, 1.7 mmol) as prepared in Example 10 step (a) was introduced in one portion and the bomb was sealed and heated in an oil bath at 80° C. for 48 h. The bomb was cooled to −78° C., opened and the ammonia was allowed to evaporate at room temperature. The residual solid was collected and dried under vacuum to give 0.5 g (88%) of 5-methylthio-4-(4-phenyl(1,3-thiazol-2-yl))thiophene-2- carboxamide. $^1$H-NMR (DMSO-$d_6$; 300 MHz) δ 2.75 (s, 3H), 7.38 (m, 1H), 7.40–7.51 (m, 2H), 8.04–8.18 (m, 2H), 8.19 (s, 1H), 8.20 (s, 1H).

b) 5-Methylthio-4-(4-phenyl(1,3-thiazol-2-yl))thiophene-2-carbonitrile: A slurry of $P_2O_5$ (2.7 g, 19 mmol) and hexamethyldisiloxane (6.7 mL) in dichloroethane (13 mL) was heated to 90° C., while stirring under a $N_2$ atmosphere. After stirring for 2 h, the resulting clear solution was allowed to cool to 40° C. 5-methylthio-4-(4-phenyl(1,3-thiazol-2-yl))thiophene-2-carboxamide (0.9 g, 2.7 mmol) as prepared in previous step was added to this solution and the mixture was heated at 75° C. for 5 h. This solution was cooled to room temperature and stirred with aqueous NaCl (6 M, 100 mL) for 10 min. As the aqueous solution is added a yellow solid precipitated. After 10 min this solid was separated by filtration, and dried under vacuum to give (0.5 g, 59%) of 5-methylthio-4-(4-phenyl(1,3-thiazol-2-yl)) thiophene-2-carbonitrile as a yellow solid. $^1$H-NMR (DMSO-$d_6$; 300 MHz) δ 2.76 (s, 3H), 7.38 (m, 1H), 7.48 (m, 2H), 8.07 (m, 2H), 8.22 (s, 1H), 8.51 (s, 1H).

c) Hydrazino[5-methylthio-4-(4-phenyl(1,3-thiazol-2-yl)) (2-thienyl)]methanimine: 5-Methylthio-4-(4-phenyl(1,3-thiazol-2-yl))thiophene-2-carbonitrile (100 mg, 0.32 mmol) as prepared in previous step was dissolved in EtOH (10 mL). To this solution hydrazine monohydrate (10 eq) was added and the mixture was heated at reflux for 3 h. The EtOH solution was concentrated down to 1 mL and water (2 mL) was added to this solution. This resulted in the formation of a white solid. The solid was collected by filtration washed with a small amount of water and dried under vacuum to give 50 mg (45%) of hydrazino[5-methylthio-4-(4-phenyl (1,3-thiazol-2-yl))(2-thienyl)]methanimine. $^1$H-NMR (CD$_3$OD/CDCl$_3$; 300 MHz) δ 2.69 (s, 3H), 7.39 (m, 1H), 7.47 (m, 2H), 7.52 (s, 1H), 7.98 (m, 2H), 8.10 (s, 1H). Mass spectrum (ESI, m/z): Calcd. for $C_{15}H_{14}N_4S_3$, 347.04 (M+H), found 347.1.

EXAMPLE 39

{Imino[5-methylthio-4-(4-phenyl(1,3-thiazol-2-yl)) (2-thienyl)]methyl}methylamine 5-Methylthio-4-(4-phenyl(1,3-thiazol-2-yl))thiophene-2-carboxamidine (20 mg, 0.06 mmol) as prepared in Example 10 step (b) was dissolved in MeOH, and to this solution methylamine (0.6 mL, 2M solution in tetrahydrofuran) was added. This solution was refluxed for 6 h, at which time the solvents were removed under vacuum to give a solid. This solid was dissolved in a small amount of MeOH. $H_2O$ was added dropwise to the methanolic solution until a precipitate was formed. This solid was isolated, washed with a small amount of water and dried under vacuum to give 15 mg (72%) of {imino[5-methylthio-4-(4-phenyl(1,3-thiazol-2-yl))(2-thienyl)]methyl}methylamine. $^1$H-NMR (DMSO-$d_6$; 300 MHz) δ 2.77 (s, 3H), 3.00 (s, 3H), 7.36–7.42 (m, 1H), 7.47–7.52 (m, 2H), 8.07–8.10 (m, 2H), 8.23 (s, 1H), 8.55 (s, 1H). Mass spectrum (ESI, m/z): Calcd. for $C_{16}H_{15}N_3S_3$, 346.5 (M+H), found 346.2.

EXAMPLE 40

2-{3-[2-(5-Amidino-2-methylthio-3-thienyl)-13-thiazol-4-yl]phenoxy}acetic acid a) 2-Bromo-1-(3-hydroxyphenyl)ethan-1-one: 2-Bromo-1-(3-methoxyphenyl)ethan-1-one (2 g, 8.7 mmol) was taken in a round bottomed flask equipped with magnetic stir bar. The flask was put under a $N_2$ atmosphere and $CH_2Cl_2$ was introduced into the flask. The resulting solution was cooled in a dry ice-acetone bath and BBr$_3$ (27 mL, 1M in $CH_2Cl_2$) was introduced dropwise. The resulting solution was allowed to warm up to room temperature overnight. The solvents were removed under vacuum and the residue was purified by passing through a short pad of silica gel (50 g) to give 1.3 g (69%) of 2-bromo-1-(3-hydroxyphenyl)ethan-1-one as an oil. $^1$H-NMR (CDCl$_3$; 300 MHz) δ 4.47 (s, 2H), 6.21 (s, 1H), 7.14 (m, 1H), 7.35 (m, 1H), 7.52–7.82 (m, 2H).

b) Methyl 4-[4-(3-hydroxyphenyl)(1,3-thiazol-2-yl)]-5-methylthiothiophene-2-carboxylate: 2-Bromo-1-(3-hydroxyphenyl)ethan-1-one (229 mg, 1.1 mmol) as prepared in previous step was treated in a manner similar to that of Example 13, step (a) to give 225 mg (61%) of methyl 4-[4-(3-hydroxyphenyl)(1,3-thiazol-2-yl)]-5-methylthiothiophene-2-carboxylate as a solid. $^1$H-NMR (DMSO-$d_6$; 300 MHz) δ 2.76 (s, 3H), 3.86 (s, 3H), 6.87 (m, 1H), 7.27 (t, J=7.8 Hz, 1H), 7.49 (m, 2H), 8.12 (s, 1H), 8.20 (s, 1H).

c) (tert-Butoxy)-N-({4-[4-(3-hydroxyphenyl)(1,3-thiazol-2-yl)]-5-methylthio(2-thienyl)}iminomethyl)carboxamide: 4-[4-(3-Hydroxyphenyl)(1,3-thiazol-2-yl)]-5-methylthiothiophene-2-carboxamidine (2 g, 5.8 mmol), prepared by treating methyl 4-[4-(3-hydroxyphenyl)(1,3-thiazol-2-yl)]-5-methylthiothiophene-2-carboxylate in a manner similar to that for Example 1, was dissolved in anhydrous DMF (10 mL). To this solution di-tert-butyl dicarbonate (1.38 g, 6.3 mmol) and DIEA (2 mL, 11.5 mmol) was added, and the mixture was stirred at room temperature for 18 h. DMF was removed under vacuum and the residue was purified by silica gel column chromatography to give 1.8 g (70%) of (tert-butoxy)-N-({4-[4-(3-hydroxyphenyl)(1,3-thiazol-2-yl)]-5-methylthio(2-thienyl) }iminomethyl)carboxamide as an oil. $^1$H-NMR (DMSO-$d_6$; 300 MHz) δ 1.58 (s, 9H), 2.81 (s, 3H), 6.81 (m, 1H), 7.28 (t, J=8.0 Hz, 1H), 7.49–7.52 (m, 2H), 8.09 (s, 1H), 8.71 (s, 1H).

d) tert-Butyl 2-{3-[2-(5-{[(tert-butoxy)carbonylamino] iminomethyl}-2-methylthio-3-thienyl)-1,3-thiazol-4-yl] phenoxy}acetate: (tert-Butoxy)-N-({4-[4-(3-hydroxyphenyl)(1,3-thiazol-2-yl)]-5-methylthio(2-thienyl) }iminomethyl)carboxamide (23 mg, 0.05 mmol) as prepared in previous step was dissolved in anhydrous DMF (1 mL). To this solution tert-butyl 2-bromoacetate (20 mg, 0.1 mmol), $Cs_2CO_3$ (33.5 mg, 0.1 mmol) and KI (5 mg) was added and the mixture was heated at 70° C. for 18 h. The solvents were removed under vacuum and the residue was purified by preparative silica gel thin-layer chromatography to give 12 mg (42%) of tert-butyl 2-{3-[2-(5-{[(tert-butoxy) carbonylamino]iminomethyl}-2-methylthio-3-thienyl)-1,3-thiazol-4-yl]phenoxy}acetate which was used in the following step.

e) 2-{3-[2-(5-Amidino-2-methylthio-3-thienyl)-1,3-thiazol-4-yl]phenoxy}acetic acid: tert-Butyl 2-{3-[2-(5-{ [(tert-butoxy)carbonylamino]iminomethyl}-2-methylthio-3-thienyl)-1,3-thiazol-4-yl]phenoxy}acetate which was used in the following step. 1 ml 50% TFA in $CH_2Cl_2$ containing 2% $H_2O$ and stirred for 4 h. The solvents were removed under vacuum. The residual TFA was removed by azeotroping with toluene to give 8.7 mg (100%) of 2-{3-[2-(5-amidino-2-methylthio-3-thienyl)-1,3-thiazol-4-yl] phenoxy}acetic acid as a buff colored solid. $^1$H-NMR (CD$_3$OD/CDCl$_3$; 300 MHz) δ 2.77 (s, 3H), 4.74 (S, 2H), 6.93 (m, 1H), 7.35 (t, J=7.9 Hz, 1H), 7.62 (m, 1H), 7.68 (M, 1H), 7.84 (s, 1H), 8.46 (s, 1H). Mass spectrum (ESI, m/z): Calcd. for $C_{17}H_{15}N_3O_3S_3$, 406.5 (M+H), found 406.3.

EXAMPLE 41

2-{2-[2-(5-Amidino-2-methylthio-3-thienyl)-1,3-thiazol-4-yl]phenoxy}acetic acid a) tert-Butyl 2-{2-[2-(5-{[(tert-butoxy)carbonylamino] iminomethyl}-2-methylthio-3-thienyl)-1,3-thiazol-4-yl]

phenoxy}acetate: 4-[4-(2-Hydroxyphenyl)(1,3-thiazol-2-yl)]-5-methylthiothiophene-2-carboxamidine (100 mg, 0.29 mmol) as prepared in Example 196 step (b) was treated in a manner similar to that shown in Example 40 step (c) to give 100 mg (0.22 mmol, 77%) of (tert-butoxy)-N-({4-[4-(2-hydroxyphenyl)(1,3-thiazol-2-yl)]-5-methylthio(2-thienyl)}iminomethyl)carboxamide. This compound was treated in a manner similar to that shown in Example 40, step (d) to give 63 mg (50%) of tert-butyl 2-{2-[2-(5 -{[(tert-butoxy)carbonylamino]iminomethyl}-2-methylthio-3-thienyl)-1,3-thiazol-4-yl]phenoxy}acetate. $^1$H-NMR (CDCl$_3$; 300 MHz) δ 1.55 (s, 9H), 1.56 (s, 9H), 2.69 (s, 3H), 4.66 (s, 2H), 6.88 (dd, J=0.8 and 8.3 Hz, 1H), 7.14 (dt, J=1.0 and 7.6 Hz, 1H), 7.30 (m, 1H), 8.08 (s, 1H), 8.48 (dd, J=1.8 and 7.8 Hz, 1H), 8.51 (s, 1H).

b) 2-{2-[2-(5-Amidino-2-methylthio-3-thienyl)-1,3-thiazol-4-yl]phenoxy}acetic acid: tert-Butyl 2-{2-[2-(5-{[(tert-butoxy)carbonylamino]iminomethyl}-2-methylthio-3-thienyl)-1,3-thiazol-4-yl]phenoxy}acetate (60 mg, 0.12 mmol) as prepared in previous step was treated in a manner similar to that shown in Example 40, step (e) to give 22 mg (50%) of 2-{2-[2-(5-amidino-2-methylthio-3-thienyl)-1,3-thiazol-4-yl]phenoxy}acetic acid. $^1$H-NMR (DMSO-d$_6$; 300 MHz) δ 2.80 (s, 3H), 4.90 (s, 2H), 7.17 (m, 2H), 7.36 (m, 1H), 8.41 (d, J=6.3 Hz, 1H), 8.60 (s, 1H), 8.62 (s, 1H), 9.00 (broad s, 2H), 9.37 (broad s, 2H). Mass spectrum (ESI, m/z): Calcd. for C$_{17}$H$_{15}$N$_3$O$_3$S$_3$, 406.5 (M+H), Found 406.1.

EXAMPLE 42

5-Methylthio-4-(6-phenyl(2-pyridyl))thiophene-2-carboxamidine a) Methyl 4-(1,1-dimethyl-1-stannaethyl)-5-methylthiothiophene-2-carboxylate: 4-Bromo-5-methylthiothiophene-2-carboxylic acid (EP 0676395 A2) (4.67 g, 18.4 mmol) was dissolved in anhydrous THF (30 mL), taken in a round bottomed flask and cooled to −78° C. under a N$_2$ atmosphere. To this solution n-butyllithium (20.3 mL, 40.6 mmol, 2M in cyclohexane) was introduced in a dropwise manner. The resulting solution was stirred at −78° C. for 45 min and then allowed to warm up to −60° C. To this solution trimethyltin chloride (40.6 mL, 40.6 mmol, 1M in THF) was added dropwise. This solution was stirred at −60° C. for 30 min and then allowed to warm up to room temperature. The THF was removed under vacuum and the residue was treated with H$_2$O and extracted with hexane. The hexane layer was evaporated and the residue was dissolved in Et$_2$O. The Et$_2$O solution was washed with 10% HCl, saturated NaCl and dried over anhydrous MgSO$_4$. Et$_2$O was removed under vacuum and the residue was taken in MeOH. The MeOH solution was treated with trimethylsilyldiazomethane (18.5 mL, 2M in hexane) and stirred at room temperature for 1 h. The solvents were removed under vacuum to give 2 g (31%) of methyl 4-(1,1 -dimethyl-1-stannaethyl)-5-methylthiothiophene-2-carboxylate as an oil. $^1$H-NMR (CDCl$_3$; 300 MHz) δ 0.31 (s, 9H), 2.57 (s, 3H), 3.86 (s, 3H), 6.98 (s, 1H).

b) Methyl 4-(6-bromo(2-pyridyl))-5-methylthiothiophene-2-carboxylate: Methyl 4-(1,1-dimethyl-1-stannaethyl)-5-methylthiothiophene-2-carboxylate (195 mg, 0.56 mmol) as prepared in previous step, and 2,6-dibromopyridine (398 mg, 1.7 mmol) were taken in anhydrous DMF (2 mL). To this mixture tetrakistriphenylphosphine-palladium (20 mg) was added and heated at 120° C. for 24 h. DMF was removed under vacuum and the residue was purified by preparative silica gel thin-layer chromatography to give 78 mg (41%) of methyl 4-(6-bromo(2-pyridyl))-5-methylthiothiophene-2-carboxylate as a solid. $^1$H-NMR (CDCl$_3$; 300 MHz) δ 2.60 (s, 3H), 3.78 (s, 3H), 7.19 (s, 1H), 7.47 (dd, J=1.1 and 7.7 Hz, 1H), 7.58 (t, J=7.7, 1H), 7.65 (dd, J=1.1 and 7.4 Hz, 1H).

c) Methyl 5-methylthio-4-(6-phenyl(2-pyridyl))thiophene-2-carboxylate: Methyl 4-(6-bromo(2-pyridyl))-5-methylthiothiophene-2-carboxylate (78 mg, 0.23 mmol) as prepared in previous step, phenylboronic acid (33 mg, 0.27 mmol) and tetrakistriphenylphosphine-palladium (10 mg) were taken in DMF (1 mL). To this solution K$_2$CO$_3$ (75 mg, 0.54 mmol) and H$_2$O (0.3 mL) were added and the mixture was stirred and heated at 90° C. for 18 h. Solvents were removed under vacuum and the residue was dissolved in EtOAc and extracted with H$_2$O, washed with saturated NaCl and dried over anhydrous Na$_2$SO$_4$. Thin-layer chromatography of the aqueous layer indicated the presence of some hydrolyzed product. Therefore the aqueous layer was separated acidified with 10% HCl and extracted with EtOAc. The EtOAc layer was washed with saturated NaCl and dried over anhydrous Na$_2$SO$_4$. This second EtOAc fraction was evaporated and the residue was dissolved in MeOH and treated with trimethylsilyldiazomethane (1.2 eq). This methanolic solution and the first EtOAc fraction were combined and evaporated. The residue was subjected to preparative thin-layer chromatography (10% EtOAc in Hexane) to give 40 mg (51%) of methyl 5-methylthio-4-(6-phenyl(2-pyridyl))thiophene-2-carboxylate which was used directly in the next step.

d) 5-Methylthio-4-(6-phenyl(2-pyridyl))thiophene-2-carboxamidine: Methyl 5-methylthio-4-(6-phenyl(2-pyridyl))thiophene-2-carboxylate (40 mg, 0.12 mmol) as prepared in previous step was treated in a manner similar to that for Example 1, to give 10 mg of 5-methylthio-4-(6-phenyl(2-pyridyl))thiophene-2-carboxamidine as a solid. $^1$H-NMR (CD$_3$OD; 300 MHz) δ 2.69 (s, 3H), 7.45–7.60 (m, 3H), 7.62 (s, 1H), 7.79 (dd, J=0.9 and 7.8 Hz, 1H), 7.96 (dd, J=0.9 and 8.0 Hz, 1H), 8.03–8.12 (m, 3H). Mass spectrum (ESI, m/z): Calcd. for C$_{17}$H$_{15}$N$_3$S$_2$, 326.1 (M+H), found 326.1.

EXAMPLE 43

5-Methylthio-4-(3-phenylphenyl)thiophene-2-carboxamidine a) Methyl 5-methylthio-4-(3-phenylphenyl)thiophene-2-carboxylate: Methyl 4-(1,1-dimethyl-1-stannaethyl)-5-methylthiothiophene-2-carboxylate (200 mg, 0.57 mmol, as prepared in Example 42, step a) and 1-bromo-3-phenylbenzene (266 mg, 1.14 mmol) were taken in anhydrous DMF (2 mL). To this mixture tetrakistriphenylphosphine-palladium (20 mg) was added and heated at 120° C. for 24 h. DMF was removed under vacuum and the residue was purified by preparative silica gel thin-layer chromatography to give 39 mg (20%) methyl 5-methylthio-4-(3-phenylphenyl)thiophene-2-carboxylate as a solid. $^1$H-NMR (CD$_3$OD; 300 MHz) δ 2.60 (s, 3H), 3.75 (s, 3H), 7.3–7.5 (m, 6H), 7.60–7.66 (m, 4H).

b) 5-Methylthio-4-(3-phenylphenyl)thiophene-2-carboxamidine: Methyl 5-methylthio-4-(3-phenylphenyl)thiophene-2-carboxylate (35 mg, 0.1 mmol) as prepared in previous step was treated in a manner similar to that for Example 1, to give 17 mg of 5-methylthio-4-(3-phenylphenyl)thiophene-2-carboxamidine as a solid. $^1$H-NMR (CD$_3$OD; 300 MHz) δ 2.60 (s, 3H), 7.3–7.6 (m, 10H). Mass spectrum (ESI, m/z): Calcd. for C$_{18}$H$_{16}$N$_2$S$_2$, 325.4 (M+H), found 325.2.

EXAMPLE 44

5-Methylthio-4-[4-(phenylthiomethyl)(1,3-thiazol-2-yl)]thiophene-2-carboxamidine a) Methyl 5-methylthio-4-[4-(phenylthiomethyl)(1,3-thiazol-2-yl)]thiophene-2-carboxylate: 2-Phenylthioacetyl chloride (1.0 g, 5.4 mmol) was treated in a manner similar to that for Example 32 step (a) to give 2-bromo-1-phenylthiomethylethan-1-one. The dry solid (1.3 g, 5.3 mmol) was dissolved in acetone (25 ml). To this solution 5-(methoxycarbonyl)-2-(methylthio)-thiophene-3-thiocarboxamide (1.32 g, 5.3 mmol, Maybridge Chemical Co.) was added and heated at reflux for 5 h. At this point the solid that precipitated was filtered off and washed with acetone and dried under vacuum to give 1.5 g (71%) of methyl 5-methylthio-4-[4-(phenylthiomethyl)(1,3-thiazol-2-yl)]thiophene-2-carboxylate which was used without further purification in the following step.

b) 5-Methylthio-4-[4-(phenylthiomethyl)(1,3-thiazol-2-yl)]thiophene-2-carboxamidine: Methyl 5-methylthio-4-[4-(phenylthiomethyl)(1,3-thiazol-2-yl)]thiophene-2-carboxylate (1.5 g, 3.8 mmol) as prepared in previous step was treated in a manner similar to that for Example 1, however the product was purified by crystallizing from methanol to give 0.86 g (60%) 5-methylthio-4-[4-(phenylthiomethyl)(1,3-thiazol-2-yl)]thiophene-2-carboxamidine as a solid. $^1$H-NMR (DMSO-d$_6$; 300 MHz) δ 2.72 (s, 3H), 4.38 (s, 2H), 7.18–7.39 (m, 5H), 7.57 (s, 1H), 8.46 (s, 1H). Mass spectrum (MALDI-TOF, m/z): Calcd. for $C_{16}H_{15}N_3S_4$, 378.0 (M+H), found 378.1.

EXAMPLE 45

4-[4-(2-Chloro-4,5-dimethoxyphenyl)(1,3-thiazol-2-yl)]-5-methylthiothiophene-2-carboxamidine a) Methyl 4-[4-(2-chloro-4,5-dimethoxyphenyl)(1,3-thiazol-2-yl)]-5-methylthiothiophene-2-carboxylate: 2-Chloro-4,5-dimethoxybenzoic acid (0.5 g, 2.3 mmol) and PCl$_5$ (0.54 g, 2.6 mmol) were placed in a round bottomed flask fitted with a reflux condenser. The mixture was heated in an oil bath at 120° C. for 70 min. The mixture was allowed to cool and the formed phosphorus oxychloride was removed under vacuum to give 0.52 g (96%) of 2-chloro-4,5-dimethoxybenzoyl chloride as a solid. 2-Chloro-4,5-dimethoxybenzoyl chloride (0.52 g, 2.2 mmol) was treated in a manner similar to that for Example 32 step (a) to give 2-bromo-1-(2-chloro-4,5-dimethoxyphenyl)ethan-1-one. The dry solid (0.65 g, 2.2 mmol) was dissolved in acetone (25 ml). To this solution 5-(methoxycarbonyl)-2-(methylthio)-thiophene-3-thiocarboxamide (0.55 g, 2.2 mmol) was added and heated at reflux for 5 h. At this point the solid that precipitated was filtered off and washed with acetone and dried under vacuum to give 0.53 g (54%) of methyl 4-[4-(2-chloro-4,5-dimethoxyphenyl)(1,3-thiazol-2-yl)]-5-methylthiothiophene-2-carboxylate. $^1$H-NMR (DMSO-d$_6$; 300 MHz) δ 2.73 (s, 3H), 3.83 (s, 3H), 3.84 (s, 3H), 3.85 (s, 3H), 7.13 (s, 1H), 7.69 (s, 1H), 8.13 (s, 1H), 8.17 (s, 1H).

b) 4-[4-(2-Chloro-4,5-dimethoxyphenyl)(1,3-thiazol-2-yl)]-5-methylthiothiophene-2-carboxamidine: Methyl 4-[4-(2-chloro-4,5-dimethoxyphenyl)(1,3-thiazol-2-yl)]-5-methylthiothiophene-2-carboxylate (0.53 g, 1.2 mmol) as prepared in previous step was treated in a manner similar to that for Example 1, however the product was purified by crystallizing from methanol to give to give 0.3 g (60%) 4-[4-(2-chloro-4,5-dimethoxyphenyl)(1,3-thiazol-2-yl)]-5-methylthiothiophene-2-carboxamidine as a solid. $^1$H-NMR (DMSO-d$_6$; 300 MHz) δ 2.77 (s, 3H), 3.84 (s, 6H), 7.13 (s, 1H), 7.71 (s, 1H), 8.17 (s, 1H), 8.69 (s, 1H), 9.16 (broad s, 2H), 9.48 (broad s, 2H). Mass spectrum (MALDI-TOF, m/z): Calcd. for $C_{17}H_{16}N_3O_2S_3Cl$, 426.0 (M+H), found 426.6.

EXAMPLE 46

4-[(Methylethyl)sulfonyl]-5-methylthiothiophene-2-carboxamidine

Methyl 4-[(methylethyl)sulfonyl]-5-methylthiothiophene-2-carboxylate (100 mg, Maybridge Chemical Company, Cornwall, UK) was treated in a manner similar to that for Example 1, to give 50 mg of 4-[(methylethyl)sulfonyl]-5-methylthiothiophene-2-carboxamidine. $^1$H-NMR (DMSO-d$_6$; 300 MHz) δ 1.21 (d, J=6.77 Hz, 6H), 2.66 (s, 3H), 3.55 (m, 1H), 7.85 (s, 1H). Mass spectrum (MALDI-TOF, CHCA matrix, m/z): Calcd. for $C_9H_{14}N_2O_2S_3$, 279.0 (M+H), found 279.3.

EXAMPLE 47

Methyl 2-{3-[2-(5-amidino-2-methylthio-3-thienyl)-1,3-thiazol-4-yl]phenoxy}acetate trifluoroacetate To a solution of 42 mg (0.094 mmol) of (tert-butoxy)-N-({4-[4-(3-hydroxyphenyl)(1,3-thiazol-2-yl)]-5-methylthio(2-thienyl)}iminomethyl)carboxamide, prepared in a manner similar to Example 40, step (c), in 2 mL of anhydrous N'N'-dimethylformamide (DMF) was added potassium iodide (0.006 mmol, 1 mg, Aldrich Chemical Co.), cesium carbonate (0.187 mmol, 61 mg, Aldrich Chemical Co.), and methyl bromoacetate (0.187 mmol, 18 μL, Aldrich Chemical Co.) and heated to 60° C. overnight. The reaction solution was concentrated and purified on a 1 mm silica prep plate eluting with 3% methanol/CH$_2$Cl$_2$ to afford 11 mg (23% yield) of methyl 2-{3-[2-(5-{[(tert-butoxy)carbonylamino]iminomethyl}-2-methylthio-3-thienyl)-1,3-thiazol-4 -yl]phenoxy}acetate which was then subjected to a solution of 50% trifluoracetic acid/CH$_2$Cl$_2$ for 1 h then concentrated and triturated with diethyl ether and dried to afford 7 mg (77% yield) of methyl 2-{3-[2-(5-amidino-2-methylthio-3-thienyl)-1,3-thiazol-4-yl]phenoxy}acetate trifluoroacetate. $^1$H-NMR (CD$_3$OD; 300 MHz) δ 8.51 (s, 1H), 7.92 (s, 1H), 7.66 (m, 2H), 7.34–7.39 (t, 1H), 6.93 (m, 1H), 4.8 (s, 2H) 3.80 (s, 3H), 2.78 (s, 3H). Mass Spectrum (LC-Q ESI, m/z) Calcd. for $C_{18}H_{17}N_3O_3S_3$: 419.5 (M+H), found 420.3.

EXAMPLE 48

5-Methylthio-4-[4(3-{[N-benzylcarbamoyl]methoxy}phenyl)(1,3-thiazol-2-yl)]thiophene-2-carboxamidine trifluoroacetate 100 mg (0.197 mmol) of 2-{3-[2-(5-{[(tert-butoxy)carbonylamino]iminomethyl}-2-methylthio-3-thienyl)-1,3-thiazol-4-yl]phenoxy}acetic acid, as prepared in the previous step, were dissolved in 1 mL of anhydrous DMF and PyBOP (0.396 mmol, 206 mg), benzylamine (0.396 mmol, 42 mg), and diisopropylethylamine (0.494 mmol; 86 μL) were added to the solution and stirred for 18 hrs after which the solution was concentrated and purified on a 2 g silica SPE column and deprotected with 50% trifluoroacetic acid/methylene chloride to afford 60 mg (67% yield) of 5-methylthio-4-[4-(3-{[N-benzylcarbamoyl]methoxy}phenyl)(1,3-thiazol-2-yl)]thiophene-2-carboxamidine trifluoroacetate. $^1$H-NMR (CDCl$_3$/TFA-d;

300 MHz) δ 8.97 (s, 1H), 7.86 (s, 1H), 7.53 (t, 1H), 7.33 (m, 7H), 7.17 (d, 1H), 4.79 (s, 2H) 4.59 (s, 2H), 2.95 (s, 3H). Mass Spectrum (ESI, m/z) Calcd. for $C_{24}H_{22}N_4O_2S_3$: 494.6 (M+H), found 495.2.

EXAMPLE 49

4-{4-[3-({N-[(3,4-Dimethoxyphenyl)methyl]carbamoyl}methoxy)phenyl](1,3-thiazol-2-yl)}-5-methylthiothiophene-2-carboxamidine trifluoroacetate Dissolved 100 mg (0.197 mmol) of 2-{3-[2-(5-{[(tert-butoxy)carbonylamino]iminomethyl}-2-methylthio-3-thienyl-1,3-thiazol-4-yl]phenoxy}acetic acid, prepared in a manner similar to Example 48, step (c), in 1 mL of anhydrous DMF and added PyBOP (0.396 mmol, 206 mg), 3,4-dimethoxybenzylamine (0.396 mmol,66 mg), and diisopropylethylamine (0.494 mmol; 86 μL) and let stir for 18 hrs after which solution was concentrated and purified on a 2 g silica SPE column and deprotected with 50% trifluoroacetic acid/methylene chloride to afford 45 mg (41% yield) 4-{4-[3-({N-[(3,4-dimethoxyphenyl)methyl]carbamoyl}methoxy)phenyl](1,3-thiazol-2-yl)}-5-methylthiothiophene-2-carboxamidine trifluoroacetate. $^1$H-NMR (CDCl$_3$/TFA-d; 300 MHz) δ 8.48 (s, 1H), 7.78 (s, 1H), 7.72 (m, 1H), 7.66 (d, 1H), 7.39 (t, 1H), 7.02 (d, 1H), 4.68 (s, 2H), 4.43 (s, 2H), 3.75 (s, 3H), 3.56 (s, 3H), 2.78 (s, 3H). Mass Spectrum (LC-Q ESI, m/z) Calcd. for $C_{26}H_{26}N_4O_4S_3$: 554.6 (M+H), found 555.2

EXAMPLE 50

5-Methylthio-4-{4-[3-({N-[2-(phenylamino)ethyl]carbamoyl}methoxy)phenyl](1,3-thiazol-2-yl)}thiophene-2-carboxamidine trifluoroacetate Dissolved 100 mg (0.197 mmol) of 2-{3-[2-(5-{[(tert-butoxy)carbonylamino]iminomethyl}-2-methylthio-3-thienyl)-1,3-thiazol-4-yl]phenoxy}acetic acid, prepared in a manner similar to Example 48, step (c), in 1 mL of anhydrous DMF and added PyBOP (0.396 mmol, 206 mg), N-phenylethylenediamine (0.396 mmol, 54 mg), and diisopropylethylamine (0.494 mmol; 86 μL) and let stir for 18 hrs after which solution was concentrated and purified on a 2 g silica SPE column and deprotected with 50% trifluoroacetic acid/methylene chloride to afford 65 mg (63% yield) 5-methylthio-4-{4-[3-({N-[2-(phenylamino)ethyl]carbamoyl}methoxy)phenyl](1,3-thiazol-2-yl)}thiophene-2-carboxamidine trifluoroacetate $^1$H-NMR (CDCl$_3$/TFA-d; 300 MHz) δ 8.50 (s, 1H), 7.82 (s, 1H), 7.77 (s, 1H), 7.66 (d, 1H), 7.39 (t,1H), 7.02 (d, 1H) 4.68 (s, 2H), 4.43 (s, 2H), 3.75 (s, 3H), 3.56 (s, 3H), 2.78 (s, 3H). Mass Spectrum (LC-Q ESI, m/z) Calcd. for $C_{25}H_{25}N_5O_2S_3$: 523.6 (M+H), found 524.1

EXAMPLE 51

5-Methylthio-4-[4-(3-{[N-(2-morpholin-4-ylethyl)carbamoyl]methoxy}phenyl)(1,3-thiazol-2-yl)]thiophene-2-carboxamidine trifluoroacetate 83 mg (0.164 mmol) of 2-{3-[2-(5-{[(tert-butoxy)carbonylamino]iminomethyl]-2-methylthio-3-thienyl)-1,3-thiazol-4-yl]phenoxy}acetic acid, prepared in a manner similar to Example 40, step (c), was reacted with 2-morpholin-4-ylethylamine (0.328 mmol, 43 μL) in a manner similar to Example 48 to afford 46 mg (54% yield) of 5-methylthio-4-[4-(3-{[N-(2-morpholin-4-ylethyl)carbamoyl]methoxy}phenyl)(1,3-thiazol-2-yl)]thiophene-2carboxamidine trifluoroacetate. $^1$H-NMR (DMSO-d$_6$, 300 MHz) δ 9.38 (bs, 2H), 9.08 (bs, 2H), 8.61 (s, 1H), 8.45 (t, 1H), 8.27 (s, 1H), 7.72 (m, 2H) 7.45 (t, 1H), 7.02 (d, J=8 Hz, 1H), 4.62 (s, 2H), 3.53–3.64 (m, 5H), 3.24–3.38 (m, 5H), 2.80 (s, 3H), 1.1 (t, 2H). Mass Spectrum (ESI, m/z) Calcd. for $C_{23}H_{27}N_5O_3S_3$: 517.6 (M+H), found 518.2.

EXAMPLE 52

5-Methylthio-4-{4-[3-(2-morpholin-4-yl-2-oxoethoxy)phenyl](1,3-thiazol-2-yl)}thiophene-2-carboxamidine trifluoroacetate 73 mg (0.144 mmol) of 2-{3-[2-(5-{[(tert-butoxy)carbonylamino]iminomethyl}-2-methylthio-3-thienyl)-1,3-thiazol-4-yl]phenoxy}acetic acid, prepared in a manner similar to Example 48, step (c), was reacted with morpholine (0.288 mmol; 25 μL) in a manner similar to Example 48 step (b) to afford 50 mg (75% yield) 5-methylthio-4-{4-[3-(2-morpholin-4-yl-2-oxoethoxy)phenyl](1,3-thiazol-2-yl)}thiophene-2-carboxamidine trifluoroacetate. $^1$H-NMR (DMSO-d$_6$/TFA-d; 300 MHz) δ 9.38 (bs, 1H), 9.08 (bs, 2H), 8.66 (s, 1H), 8.22 (s, 1H), 7.72 (m, 2H) 7.42 (t, 1H), 6.98–7.00 (dd, J=2.3 Hz and 8.2 Hz, 1H), 4.95 (s, 2H), 3.53–3.67 (m, 8H), 2.82 (s, 3H). Mass Spectrum (ESI, m/z) Calcd. for $C_{21}H_{22}N_4O_3S_3$: 474.6 (M+H), found 475.2.

EXAMPLE 53

5-Methylthio-4-{4-[3-(2-oxo-2-piperazinylethoxy)phenyl](1,3-thiazol-2-yl)}thiophene-2-carboxamidine trifluoroacetate 100 mg (0.198 mmol) of 2-{3-[2-(5-{[(tert-butoxy)carbonylamino]iminomethyl}-2-methylthio-3-thienyl)-1,3-thiazol-4-yl]phenoxy}acetic acid, prepared in a manner similar to Example 48, step (c), was reacted with tert-butyl piperazinecarboxylate (0.396 mmol; 74 mg) in a manner similar to Example 48, step (b) to afford 40 mg (43% yield) of 5-methylthio-4-{4-[3-(2-oxo-2-piperazinylethoxy)phenyl](1,3-thiazol-2-yl)}thiophene-2-carboxamidine trifluoroacetate. $^1$H-NMR (DMSO-d$_6$/TFA-d; 300 MHz) δ 8.68 (s, 1H), 8.20(s, 1H), 7.75 (m, 2H) 7.43 (t, 1H), 7.01 (dd, J=2.3 Hz and 8.1 Hz, 1H), 5.02 (s, 2H), 3.76 (bs, 4H), 3.17–3.26 (m, 4H), 2.82 (s, 3H). Mass Spectrum (LC-Q ESI, m/z) Calcd. for $C_{21}H_{23}N_5O_2S_3$: 473.6 (M+H), found 474.2.

EXAMPLE 54

4-[4-(3-{[N-(2-Aminoethyl)carbamoyl]methoxy}phenyl)(1,3-thiazol-2-yl)}-5-methylthiothiophene-2-carboxamidine hydrochloride 51 mg (0.101 mmol) of 2-{3-[2-(5-{[(tert-butoxy)carbonylamino]iminomethyl}-2-methylthio-3-thienyl)-1,3-thiazol-4-yl]phenoxy}acetic acid, prepared in a manner similar to Example 48, step (c), was reacted with N-(2-aminoethyl)(tert-butoxy)carboxamide (0.202 mmol; 32 mg) in a manner similar to Example 48, step (b) to afford 80 mg (80% yield) of 4-(4-{3-[(N-{2-[(tert-butoxy)carbonylamino]ethyl}carbamoyl)methoxy]phenyl}(1,3-thiazol-2-yl))-5-methylthiothiophene-2-carboxamidine which was then deprotected with 4N HCl in dioxane to afford 36 mg (68% yield) of 4-[4-(3-{[N-(2-aminoethyl)carbamoyl]methoxy}phenyl)(1,3-thiazol-2-yl)]-5-methylthiothiophene-2-carboxamidine hydrochloride. $^1$H-NMR (CD$_3$OD; 300 MHz) δ 8.55 (s, 1H), 7.95 (s, 1H), 7.73 (m, 2H) 7.41 (t, 1H), 7.05 (m, 1H), 4.80 (s, 2H), 3.51

(m, 2H), 3.13–3.31 (m, 2H), 2.83 (s, 3H). Mass Spectrum (ESI, m/z) Calcd. for $C_{19}H_{21}N_5O_2S_3$: 447.5 (M+H), found 448.2.

EXAMPLE 55

4-(4-{3-[2-(4-Acetylpiperazinyl)-2-oxoethoxy]phenyl}(1,3-thiazol-2-yl))-5-methylthiothiophene-2-carboxamidine trifluoroacetate 52 mg (0.103 mmol) of 2-{3-[2-(5-{[(tert-butoxy)carbonylamino]iminomethyl}-2-methylthio-3-thienyl)-1,3-thiazol-4-yl]phenoxy}acetic acid, prepared in a manner similar to Example 48, step (c), was reacted with 1-acetyl piperazine (0.154 mmol, 20 mg), 1-hydroxy-7-azabenzotriazole (HOAt)) (0.154 mmol, 21 mg), O-(7-azabenzotriazol-1-yl)-1,1,3,3-tetramethyluronium hexafluorophosphate) HATU (0.154 mmol, 58 mg) and diisopropylethylamine (0.258 mmol, 44 µL) in DMF to afford crude product which was then purified on 1 mm silica prep plates eluting with 3% methanol/methylene chloride to afford 28 mg (53% yield) of N-{[4-(4-{3-[2-(4-acetylpiperazinyl)-2-oxoethoxy]phenyl}(1,3-thiazol-2-yl))-5-methylthio(2-thienyl)]iminomethyl}(tert-butoxy)carboxamide. This was subsequently reacted with a solution of trifluoroacetic acid:methylene chloride:water (47.5%:47.5%:2.5%) for 1 hour, concentrated and purified on a silica SPE column eluting with 15% methanol/methylene chloride to afford 20 mg (80% yield) of 4-(4-{3-[2-(4-acetylpiperazinyl)-2-oxoethoxy]phenyl}(1,3-thiazol-2-yl))-5-methylthiothiophene-2-carboxamidine trifluoroacetate. $^1$H-NMR (CD$_3$OD; 300 MHz) δ 8.48 (s, 1H), 7.91 (s, 1H), 7.69 (m, 2H) 7.38 (t, 1H), 6.99 (dd, J=2 Hz and 8.1 Hz, 1H), 4.93 (s, 2H), 3.52–3.67 (m, 8H), 2.78 (s, 3H), 2.12 (s, 3H). Mass Spectrum (ESI, m/z) Calcd. for $C_{23}H_{25}N_5O_3S_3$: 515.6 (M+H), found 516.2.

EXAMPLE 56

4-(4-{3-[2-(4-Methylpiperazinyl)-2-oxoethoxy]phenyl}(1,3-thiazol-2-yl)-5-methylthiothiophene-2-carboxamidine trifluoroacetate 54 mg (0.107 mmol) of 2-{3-[2-(5-{[(tert-butoxy)carbonylamino]iminomethyl}-2-methylthio-3-thienyl)-1,3-thiazol-4-yl]phenoxy}acetic acid, prepared in a manner similar to Example 48, step (c), was reacted with N-methyl piperazine (0.128 mmol, 14 µL), 1-hydroxy-7-azabenzotriazole (HOAt) (0.128 mmol, 17 mg), O-(7-azabenzotriazol-1-yl)-1,1,3,3-tetramethyluronium hexafluorophosphate) HATU (0.128 mmol, 49 mg) and diisopropylethylamine (0.268 mmol, 56 µL) in DMF to afford crude product which was then partitioned between methylene chloride and 1N NaOH and washed. The organic layer was obtained and similarly washed with 10% citric acid and saturated aq. sodium chloride, dried over sodium sulfate and concentrated to a yellow oil. The oil was then purified on 1 mm silica prep plates eluting with 5% methanol/methylene chloride to afford (tert-butoxy)-N-{imino[4-(4-{3-[2-(4-methylpiperazinyl)-2-oxoethoxy]phenyl}(1,3-thiazol-2-yl))-5-methylthio(2-thienyl)]methyl}carboxamide. This was subsequently reacted with a solution of trifluoroacetic acid:methylene chloride:water (47.5%:47.5%:2.5%) for 1 hour, concentrated and purified on a silica SPE column eluting with 10–15% methanol/methylene chloride to afford 17 mg (33% yield) of 4-(4-{3-[2-(4-methylpiperazinyl)-2-oxoethoxy]phenyl}(1,3-thiazol-2-yl))-5-methylthiothiophene-2-carboxamidine trifluoroacetate. $^1$H-NMR (CD$_3$OD; 300 MHz) δ 8.52 (s, 1H), 7.91 (s, 1H), 7.69 (m, 2H), 7.38 (t, 1H), 6.98 (dd, J=2.0 Hz and 8.1 Hz, 1H), 4.90 (s, 2H), 3.66 (t, 4H), 2.78 (s, 3H), 2.49–2.57 (m, 4H), 2.35 (s, 3H). Mass Spectrum (ESI, m/z) Calcd. for $C_{22}H_{25}N_5O_2S_3$: 487.6 (M+H), found 488.2

EXAMPLE 57

5-Methylthio-4-[4-(3-{2-oxo-2-[4-benzylpiperzinyl]ethoxy}phenyl)(1,3-thiazol-2-yl)]thiophene-2-carboxamidine trifluoroacetate 54 mg (0.107 mmol) of 2-{3-[2-(5-{[(tert-butoxy)carbonylamino]iminomethyl}-2-methylthio-3-thienyl-1,3-thiazol-4-yl]phenoxy}acetic acid, prepared in a manner similar to Example 48, step (c), was reacted with N-benzylpiperazine (0.128 mmol, 22 µL), 1-hydroxy-7-azabenzotriazole (HOAt) (0.128 mmol, 17 mg), O-(7-azabenzotriazol-1-yl)-1,1,3,3-tetramethyluronium hexafluorophosphate) HATU (0.128 mmol, 48 mg) and diisopropylethylamine (0.267 mmol, 50 µL) in DMF to afford crude product which was then partitioned between methylene chloride and 1N NaOH and washed. The organic layer was obtained and similarly washed with 10% citric acid and saturated aq. sodium chloride, dried over sodium sulfate and concentrated to a yellow oil. The oil was then purified on 1 mm silica prep plates eluting with 5% methanol/methylene chloride to afford (tert-butoxy)-N-(imino{5-methylthio-4-[4-(3-{2-oxo-2-[4-benzylpiperazinyl]ethoxy}phenyl)(1,3-thizol-2-yl)](2-thienyl)}methyl)carboxamide. This was subsequently reacted with a solution of trifluoroacetic acid:methylene chloride:water (47.5%:47.5%:2.5%) for 1 hour, concentrated and purified on a 5 g silica SPE column eluting with 10–15% methanol/methylene chloride to afford 36 mg (60% yield) of 5-methylthio-4-[4-(3-{2-oxo-2-[4-benzylpiperazinyl]ethoxy}phenyl)(1,3-thiazol-2-yl)]thiophene-2-carboxamidine trifluoroacetate. $^1$H-NMR (CD$_3$OD; 300 MHz) δ 8.54 (s, 1H), 7.93 (s, 1H), 7.71 (m, 2H), 7.50 (s, 5H) 7.39 (t, 1H), 6.99 (dd, J=2 Hz and 8.1 Hz, 1H), 4.94 (s, 2H), 4.37 (s, 2H), 3.3 (m, 4H), 2.81 (s, 3H), 2.49–2.57 (m, 4H), 2.35 (s, 3H). Mass (ESI, m/z) Calcd. for $C_{28}H_{29}N_5O_2S_3$: 563.7 (M+H), found 564.3.

EXAMPLE 58

(D,L)-4-(4-{3-[2-(3-Aminopyrrolidinyl)-2-oxoethoxy]phenyl}(1,3-thiazol-2-yl))-5-methylthiothiophene-2-carboxamidine trifluoroacetate 41 mg (0.081 mmol) of 2-{3-[2-(5-{[(tert-butoxy)carbonylamino]iminomethyl}-2-methylthio-3thienyl)-1,3-thiazol-4-yl]phenoxy}acetic acid, prepared in a manner similar to Example 48, step (c), was reacted with (D,L)(tert-butoxy)-N-pyrrolidin-3-ylcarboxamide (0.122 mmol, 23 mg), O-(7-azabenzotriazol-1-yl)-1,1,3,3-tetramethyluronium hexafluorophosphate) HATU (0.122 mmol, 46 mg), 1-hydroxy-7-azabenzotriazole (HOAt) (0.122 mmol, 17 mg) and diisopropylethylamine (0.203 mmol, 35 µL) in a manner similar to Example 56 to afford 20 mg (53% yield) of (D,L)-4-(4-{3-[2-(3-aminopyrrolidinyl)-2-oxoethoxy]phenyl}(1,3-thiazol-2-yl))-5-methylthiothiophene-2-carboxamidine trifluoroacetate. $^1$H-NMR (CD$_3$OD; 300 MHz) δ 8.54 (s, 1H), 7.94 (s, 1H), 7.71 (m, 2H), 7.39 (t, 1H), 6.99 (dd, J=2.0 Hz and 8.1 Hz, 1H), 4.85 (s, 2H), 4.37 (s, 2H), 360–4.01 (m, 5H), 2.81 (s, 3H), 2.15–2.71 (m, 2H). Mass Spectrum (ESI, m/z) Calcd. for $C_{21}H_{23}N_5O_2S_3$: 473.6 (M+H), found 474.3.

EXAMPLE 59

5-Methylthio-4-{4-[3-(2-oxo-2-piperidylethoxy)phenyl](1,3-thiazol-2-yl)}thiophene-2-carboxamidine trifluoroacetate 33 mg (0.065 mmol) of 2-{3-[2-(5-{[(tert-butoxy)carbonylamino]iminomethyl}-2-methylthio-3-thienyl)-1,3- thiazol-4-yl]phenoxy}acetic acid, prepared in a manner similar to Example 40, step (c), was reacted with piperidine (0.078 mmol, 8 μL), O-(7-azabenzotriazol-1-yl)-1,1,3,3-tetramethyluronium hexafluorophosphate) HATU (0.078 mmol, 30 mg), 1-hydroxy-7-azabenzotriazole (HOAt) (0.078 mmol, 11 mg) and diisopropylethylamine (0.163 mmol, 56 μL) in a manner similar to Example 57 to afford 15 mg (41% yield) of 5-methylthio-4-{4-[3-(2-oxo-2-piperidylethoxy)phenyl](1,3-thiazol-2-yl)}thiophene-2-carboxamidine trifluoroacetate. $^1$H-NMR (CD$_3$OD; 300 MHz) δ 8.54 (s, 1H), 7.92 (s, 1H), 7.69 (m, 2H), 7.35–7.40 (t, 1H), 6.98 (dd, J=2 Hz and 8.1 Hz, 1H), 4.95 (s, 2H), 3.52–3.60 (m, 4H), 2.80 (s, 3H), 1.57–1.70 (m, 6H). Mass Spectrum (ESI, m/z) Calcd. for C$_{22}$H$_{24}$N$_4$O$_2$S$_3$: 472.6 (M+H), found 473.2.

EXAMPLE 60

2-(3-{2-[5-Imino{[(4-polystyryloxyphenyl)methoxy]carbonylamino}methyl)-2-methylthio-3-thienyl]-1,3-thiazol-4-yl}phenoxy)acetic acid 2 g (1.86 mmol) of p-nitrophenyl carbonate Wang resin (0.93 mmol/g) (Calbiochem-Novabiochem, San Diego, Calif.) was suspended in 9 mL of a 2:1 mixture of anhydrous DMSO:DMF. 2 g (4.93 mmol) of 2-{3-[2-(5-amidino-2-methylthio-3-thienyl)-1,3-thiazol-4-yl]phenoxy}acetic acid was added to suspension followed by the addition of 1 mL of 1,8-diazabicyclo[5.4.0]undec-7-ene, (DBU, 6.69 mmol) and let shake vigorously for 5 days after which resin was washed thoroughly with DMF, MeOH, and diethyl ether and dried in vacuo to afford 2 g of resin-bound 2-{3-[2-(5-amidino-2-methylthio-3-thienyl)-1,3-thiazol-4-yl]phenoxy}acetic acid.

EXAMPLE 61

(D,L)-Ethyl 1-(2-{3-[2-(5-amidino-2-methylthio-3-thienyl)-1,3-thiazol-4-yl]phenoxy}acetyl)piperidine-2-carboxylate trifluoroacetate 100 mg (0.093 mmol) of resin-bound 2-{3-[2-(5-amidino-2-methylthio-3-thienyl)-1,3-thiazol-4-yl]phenoxy}acetic acid (0.93 mmol/g), as prepared in a manner similar to Example 60, was suspended 1 mL of anhydrous DMF. O-(7-azabenzotriazol-1-yl)-1,1,3,3-tetramethyluronium hexafluorophosphate) HATU (0.5 M, 190 mg), 1-hydroxy-7-azabenzotriazole (HOAt) (0.5 M; 68 mg), ethyl piperidine-2-carboxylate (0.5 M; 78 μL) and diisopropylethylamine (0.233 mmol, 40 μL) were added and allowed to shake vigorously for 18 hrs, after which the resin was washed thoroughly with DMF, methanol, methylene chloride, and diethyl ether. After drying, crude product was removed from resin by reaction with a solution of trifluoroacetic acid:methylene chloride:water (47.5%:47.5%:2.5%) for 1 hour. The solution was filtered and concentrated to a yellow oil. After purification on a 2 g silica SPE column, eluting with a gradient of 3%–10% MeOH/methylene chloride, 15 mg (30% yield) of (D,L)-ethyl 1-(2-{3-[2-(5-amidino-2-methylthio-3-thienyl)-1,3-thiazol-4-yl]phenoxy}acetyl)piperidine-2-carboxylate trifluoroacetate was obtained. Mass Spectrum (ESI, m/z) Calcd. for C$_{25}$H$_{28}$N$_4$O$_4$S$_3$: 544.70 (M+H), found 545.2

EXAMPLE 62

5-Methylthio-4-{4-[3-(2-oxo-2-pyrrolidinylethoxy)phenyl](1,3-thiazol-2-yl)}thiophene-2-carboxamidine trifluoroacetate 100 mg (0.093 mmol) of resin-bound 2-{3-[2-(5-amidino-2-methylthio-3-thienyl)-1,3-thiazol-4-yl]phenoxy}acetic acid (0.93 mmol/g), as prepared in a manner similar to Example 60, was suspended 1 mL of anhydrous DMF. O-(7-azabenzotriazol-1-yl)-1,1,3,3-tetramethyluronium hexafluorophosphate) HATU (0.5 M, 190 mg), 1-hydroxy-7-azabenzotriazole (HOAt) (0.5 M; 68 mg), pyrrolidine (0.5 M; 42 μL) and diisopropylethylamnine (0.233 mmol, 40 μL) were added and allowed to shake vigorously for 18 hours, after which the resin was washed thoroughly with DMF, methanol, methylene chloride, and diethyl ether. After drying, crude product was removed from resin by reaction with a solution of trifluoroacetic acid:methylene chloride:water (47.5%:47.5%:2.5%) for 1 hour. After trituration with diethyl ether and drying, 18 mg (42% yield) of 5-methylthio-4-{4-[3-(2-oxo-2-pyrrolidinylethoxy)phenyl](1,3-thiazol-2-yl)}thiophene-2-carboxamidine trifluoroacetate was obtained. Mass Spectrum (ESI, m/z) Calcd. for C$_{21}$H$_{22}$N$_4$O$_2$S$_3$: 458.6 (M+H), found 459.2

EXAMPLE 63

5-Methylthio-4-[4-(3-{2-oxo-2-[4-benzylpiperidyl]ethoxy}phenyl)(1,3-thiazol-2-yl)]thiophene-2-carboxamidine trifluoroacetate 80 mg (0.074 mmol) of resin-bound 2-{3-[2-(5-amidino-2-methylthio-3-thienyl)-1,3-thiazol-4-yl]phenoxy}acetic acid (0.93 mmol/g), as prepared in a manner similar to Example 60, was suspended in 1 mL of anhydrous DMF. O-(7-azabenzotriazol-1-yl)-1,1,3,3-tetramethyluronium hexafluorophosphate) HATU (0.5 M, 190 mg), 1-hydroxy-7-azabenzotriazole (HOAt) (0.5 M; 68 mg), 4-benzyl piperidine (0.5 M; 88 μL) and diisopropylethylamnine (0.185 mmol, 32 μL) were added and allowed to shake vigorously for 18 hrs, after which the resin was washed thoroughly with DMF, methanol, methylene chloride, and diethyl ether. After drying, crude product was removed from resin by reaction with a solution of trifluoroacetic acid:methylene chloride:water (47.5%:47.5%:2.5%) for 1 hour. After trituration with diethyl ether and drying, 17 mg (40% yield) of 5-methylthio-4-[4-(3-{2-oxo-2-[4-benzylpiperidyl]ethoxy}phenyl)(1,3-thiazol-2-yl)]thiophene-2-carboxamidine trifluoroacetate was obtained. Mass Spectrum (ESI, m/z) Calcd. for C$_{29}$H$_{30}$N$_4$O$_2$S$_3$: 562.7 (M+H), found 563.3.

EXAMPLE 64

(D,L)-4-(4-{3-[2-(3-Methylpiperidyl)-2-oxoethoxy]phenyl}(1,3-thiazol-2-yl))-5-methylthiothiophene-2-carboxamidine trifluoroacetate 80 mg (0.074 mmol) of resin-bound 2-{3-[2-(5-amidino-2-methylthio-3-thienyl)-1,3-thiazol-4-yl]phenoxy}acetic acid (0.93 mmol/g), as prepared in a manner similar to Example 60, was reacted with (+/−)-3-methyl piperidine (0.5 M, 59 μL) and O-(7-azabenzotriazol-1-yl)-1,1,3,3-tetramethyluronium hexafluorophosphate) HATU (0.5 M, 190 mg), 1-hydroxy-7-azabenzotriazole (HOAt) (0.5 M; 68 mg) and diisopropylethylamine (0.185 mmol, 32 μL) in 1 mL of anhydrous DMF in a manner similar to Example 63 to afford 10 mg (28% yield) of 4-(4-{3-[2-(3-methylpiperidyl)-2-oxoethoxy]phenyl}(1,3-thiazol-2-yl))-5-methylthiothiophene-2-carboxamidine trifluoroacetate. Mass Spectrum (ESI, m/z) Calcd. for C$_{23}$H$_{26}$N$_4$O$_2$S$_3$: 486.6 (M+H), found 487.3.

EXAMPLE 65

4-(4-{3-[2-(3-methylpiperidyl)-2-oxoethoxy]phenyl}(1,3-thiazol-2-yl))-5-methylthiothiophene-2-carboxamidine trifluoroacetate 80 mg (0.074 mmol) of resin-bound 2-{3-[2-(5-amidino-2-methylthio-3-thienyl)-1,3-thiazol-4-yl]phenoxy}acetic acid (0.93 mmol/g), as prepared in a manner similar to Example 60, was reacted with 4-methyl piperidine (0.5 M, 59 μL) and O-(7-azabenzotriazol-1-yl)-1,1,3,3-tetramethyluronium hexafluorophosphate) HATU (0.5 M, 190 mg), 1-hydroxy-7-azabenzotriazole (HOAt) (0.5 M; 68 mg) and diisopropylethylamine (0.185 mmol, 32 μL) in 1 mL of anhydrous DMF in a manner similar to Example 63 to afford 12 mg (33% yield) of 4-(4-{3-[2-(4-methylpiperidyl)-2-oxoethoxy]phenyl}(1,3-thiazol-2-yl))-5-methylthiothiophene-2-carboxamidine trifluoroacetate. Mass Spectrum (ESI, m/z) Calcd. for $C_{23}H_{26}N_4O_2S_3$ 486.6 (M+H), found 487.3.

EXAMPLE 66

4-(4-{3-[2-(2azabicyclo[4,4,0]dec-2-yl)-2-oxoethoxy]phenyl}(1,3-thiazol-2-yl))-5-methylthiothiophene-2-carboxamidine trifluoroacetate 80 mg (0.074 mmol) of resin-bound 2-{3-[2-(5-amidino-2-methylthio-3-thienyl)-1,3-thiazol-4-yl]phenoxy}acetic acid (0.93 mmol/g), as prepared in a manner similar to Example 60, was reacted with decahydroquinoline (0.5 M, 75 μL) and O-(7-azabenzotriazol-1-yl)-1,1,3,3-tetramethyluronium hexafluorophosphate) HATU (0.5 M, 190 mg), 1-hydroxy-7-azabenzotriazole (HOAt) (0.5 M; 68 mg) and diisopropylethylamine (0.185 mmol, 32 μL) in 1 mL of anhydrous DMF in a manner similar to Example 63 to afford 16 mg (41% yield) of 4-(4-{3-[2-(2-azabicyclo[4.4.0]dec-2-yl)-2-oxoethoxy]phenyl}(1,3-thiazol-2-yl))-5-methylthiothiophene-2-carboxamidine trifluoroacetate. Mass Spectrum (ESI, m/z) Calcd. for $C_{26}H_{30}N_4O_2S_3$: 526.7 (M+H), found 527.2.

EXAMPLE 67

(D,L)-Ethyl 1-(2-{3-[2-(5-amidino-2-methylthio-3-thienyl)-1,3-thiazol-4-yl]phenoxy}acetyl)piperidine-3-carboxylate trifluoroacetate 80 mg (0.074 mmol) of resin-bound 2-{3-[2-(5-amidino-2-methylthio-3-thienyl)-1,3-thiazol-4-yl]phenoxy}acetic acid (0.93 mmol/g), as prepared in a manner similar to Example 60, was reacted with ethyl nipecotate (0.5 M, 78 μL) and O-(7-azabenzotriazol-1-yl)-1,1,3,3-tetramethyluronium hexafluorophosphate) HATU (0.5 M, 190 mg), 1-hydroxy-7-azabenzotriazole (HOAt) (0.5 M, 68 mg) and diisopropylethylamine (0.185 mmol, 32 μL) in 1 mL of anhydrous DMF in a manner similar to Example 63 to afford 18 mg (45% yield) of ethyl 1-(2-{3-[2-(5-amidino-2-methylthio-3-thienyl)-1,3-thiazol-4-yl]phenoxy}acetyl)piperidine-3-carboxylate trifluoroacetate. Mass Spectrum (ESI, m/z) Calcd. for $C_{25}H_{28}N_4O_4S_3$: 545.7 (M+H), found 545.2.

EXAMPLE 68

5-Methylthio-4-{4-[3-(2-oxo-2-(1,2,3,4-tetrahydroquinolyl)ethoxy)phenyl](1,3-thiazol-2-yl)}thiophene-2-carboxamidine trifluoroacetate 100 mg (0.093 mmol) of resin-bound 2-{3-[2-(5-amidino-2-methylthio-3-thienyl)-1,3-thiazol-4-yl]phenoxy}acetic acid (0.93 mmol/g), as prepared in a manner similar to Example 60, was reacted with 1,2,3,4-tetrahydroisoquinoline (0.5M) and O-(7-azabenzotriazol-1-yl)-1,1,3,3-tetramethyluronium hexafluorophosphate) HATU (0.5 M, 190 mg), 1-hydroxy-7-azabenzotriazole (HOAt) (0.5 M; 68 mg) and diisopropylethylamine (0.233 mmol, 40 μL) in 1 mL of anhydrous DMF in a manner similar to Example 63 to afford 20 mg (42% yield) of 5-methylthio-4-{4-[3-(2-oxo-2-(1,2,3,4-tetrahydroquinolyl)ethoxy)phenyl](1,3-thiazol-2-yl)}thiophene-2-carboxamidine trifluoroacetate. Mass Spectrum (ESI, m/z) Calcd. for $C_{26}H_{24}N_4O_2S_3$: 520.7 (M+H), found 521.2.

EXAMPLE 69

Ethyl 1-(2-{3-[2-(5-amidino-2-methylthio-3-thienyl)-1,3-thiazol-4-yl]phenoxy}acetyl)piperidine-4-carboxylate trifluoroacetate 100 mg (0.093 mmol) of resin-bound 2-{3-[2-(5-amidino-2-methylthio-3-thienyl)-1,3-thiazol-4-yl]phenoxy}acetic acid (0.93 mmol/g), as prepared in a manner similar to Example 60, was reacted with ethyl isonipecotate (0.5 M, 77 mg) and O-(7-azabenzotriazol-1-yl)-1,1,3,3-tetramethyluronium hexafluorophosphate) HATU (0.5 M, 190 mg), 1-hydroxy-7-azabenzotriazole (HOAt) (0.5 M; 68 mg) and diisopropylethylamine (0.233 mmol, 40 μL) in 1 mL of anhydrous DMF in a manner similar to Example 63 to afford 21 mg (42% yield) of ethyl 1-(2-{3-[2-(5-amidino-2-methylthio-3-thienyl)-1,3-thiazol-4-yl]phenoxy}acetyl)piperidine-4-carboxylate trifluoroacetate. Mass Spectrum (ESI, m/z) Calcd. for $C_{25}H_{28}N_4O_4S_3$: 545.7 (M+H), found 545.3.

EXAMPLE 70

4-(4-{3-[2-((3R)-3-Hydroxypiperidyl)-2-oxoethoxy]phenyl}(1,3-thiazol-2-yl))-5-methylthiothiophene-2-carboxamidine trifluoroacetate 100 mg (0.093 mmol) of resin-bound 2-{3-[2-(5-amidino-2-methylthio-3-thienyl)-1,3-thiazol-4-yl]phenoxy}acetic acid (0.93 mmol/g), as prepared in a manner similar to Example 60, was reacted with R-(+)-3-hydroxy piperidine (0.5 M, 69 mg) and O-(7-azabenzotriazol-1-yl)-1,1,3,3-tetramethyluronium hexafluorophosphate) HATU (0.5 M, 190 mg), 1-hydroxy-7-azabenzotriazole (HOAt) (0.5M; 68 mg) and diisopropylethylamine (0.233 mmol, 40 μL) in 1 mL of anhydrous DMF in a manner similar to Example 63 to afford 16 mg (36% yield) of 4-(4-{3-[2-((3R)-3-hydroxypiperidyl)-2-oxoethoxy]phenyl}(1,3-thiazol-2-yl))-5-methylthiothiophene-2-carboxamidine trifluoroacetate. Mass Spectrum (ESI, m/z) Calcd. for $C_{22}H_{23}N_4O_3S_3$: 489.7 (M+H), found 489.2.

EXAMPLE 71

D,L-4-(4-{3-[2-(2-Ethylpiperidyl)-2-oxoethoxy]phenyl}(1,3-thiazol-2-yl))-5-methylthiothiophene-2-carboxamidine trifluoroacetate 100 mg (0.093 mmol) of resin-bound 2-{3-[2-(5-amidino-2-methylthio-3-thienyl)-1,3-thiazol-4-yl]phenoxy}acetic acid (0.93 mmol/g), as prepared in a manner similar to Example 60, was reacted with 2-ethyl piperidine (0.5M) and O-(7-azabenzotriazol-1-yl)-1,1,3,3-tetramethyluronium hexafluorophosphate) HATU (0.5 M, 190 mg), 1-hydroxy-7-azabenzotriazole (HOAt) (0.5M; 68 mg) and diisopropylethylamine (0.233 mmol, 40 μL) in 1 mL of anhydrous DMF in a manner similar to Example 63 to afford 11 mg (23% yield) of D,L-4-(4-{3-[2-(2-ethylpiperidyl)-2-oxoethoxy]phenyl}(1,3-thiazol-2-yl))-5-methylthiothiophene-2-carboxamidine trifluoroacetate. Mass Spectrum (ESI, m/z) Calcd. for $C_{24}H_{27}N_4O_2S_3$: 501.4 (M+H), found 501.4.

EXAMPLE 72

4-(4-{3-[2-((3S)-3-Hydroxypyrrolidinyl)-2-oxoethoxy]phenyl}(1,3-thiazol-2-yl))-5-methylthiothiophene-2-carboxamidine trifluoroacetate 100 mg (0.093 mmol) of resin-bound 2-{3-[2-(5-amidino-2-methylthio-3-thienyl)-1,3-thiazol-4-yl]phenoxy}acetic acid (0.93 mmol/g), as prepared in a manner similar to Example 60, was reacted with R-(−)-3-pyrrolidinol (0.5 M, 62 mg) and O-(7-azabenzotriazol-1-yl)-1,1,3,3-tetramethyluronium hexafluorophosphate) (HATU, 0.5 M, 190 mg), 1-hydroxy-7-azabenzotriazole (HOAt) (0.5M; 68 mg) and diisopropylethylamnine (0.233 mmol, 40 μL) in 1 mL of anhydrous DMF in a manner similar to Example 63 to afford 10 mg (23% yield) of 4-(4-{3-[2-((3S)-3-hydroxypyrrolidinyl)-2-oxoethoxy]phenyl}(1,3-thiazol-2-yl))-5-methylthiothiophene-2-carboxamidine trifluoroacetate. Mass Spectrum (ESI, m/z) Calcd. for $C_{21}H_{22}N_4O_3S_3$: 475.2 (M+H), found 475.2.

EXAMPLE 73

5-Methylthio-4-(4-{3-[(N-(5,6,7,8-tetrahydronaphthyl)carbamoyl)methoxy]phenyl}(1,3-thiazol-2-yl))thiophene-2-carboxamidine trifluoroacetate 100 mg (0.093 mmol) of resin-bound 2-{3-[2-(5-amidino-2-methylthio-3-thienyl-1,3-thiazol-4-yl]phenoxy}acetic acid (0.93 mmol/g), as prepared in a manner similar to Example 60, was reacted with 5,6,7,8-tetrahydro-1-naphthylamine (0.5 M, 73 mg) and O-(7-azabenzotriazol-1-yl)-1,1,3,3-tetramethyluronium hexafluorophosphate) (HATU, 0.5 M, 190 mg), 1-hydroxy-7-azabenzotriazole (HOAt) (0.5 M; 68 mg) and diisopropylethylamine (0.233 mmol, 40 μL) in 1 mL of anhydrous DMF in a manner similar to Example 63 to afford 15 mg (30% yield) of 5-methylthio-4-(4-{3-[(N-(5,6,7,8-tetrahydronaphthyl)carbamoyl)methoxy]phenyl}(1,3-thiazol-2-yl))thiophene-2-carboxamidine trifluoroacetate. Mass Spectrum (ESI, m/z) Calcd. for $C_{27}H_{26}N_4O_2S_3$: 535.2 (M+H), found 535.3.

EXAMPLE 74

D,L-4-[4-(3-{2-[3-(Hydroxymethyl)piperidyl]-2-oxoethoxy}phenyl)(1,3-thiazol-2-yl)]-5-methylthiothiophene-2-carboxamidine trifluoroacetate 100 mg (0.093 mmol) of resin-bound 2-{3-[2-(5-amidino-2-methylthio-3-thienyl)-1,3-thiazol-4-yl]phenoxy}acetic acid (0.93 mmol/g), as prepared in a manner similar to Example 60, was reacted with 3-piperidine methanol (0.5 M, 58 mg) and O-(7-azabenzotriazol-1-yl)-1,1,3,3-tetramethyluronium hexafluorophosphate) (HATU, 0.5 M, 190 mg), 1-hydroxy-7-azabenzotriazole (HOAt) (0.5M; 68 mg) and diisopropylethylamine (0.233 mmol, 40 μL in 1 mL of anhydrous DMF in a manner similar to Example 40 to afford to 19 mg (40% yield) of D,L-4-[4-(3-{2-[3-(hydroxymethyl)piperidyl]-2-oxoethoxy}phenyl)(1,3-thiazol-2-yl)]-5-methylthiothiophene-2-carboxamidine trifluoroacetate. Mass Spectrum (ESI, m/z) Calcd. for $C_{23}H_{25}N_4O_3S_3$: 503.2 (M+H), found 503.2.

EXAMPLE 75

4-{4-[3-(2-{(2R)-2-[(Phenylamino)methyl]pyrrolidinyl}-2-oxoethoxy)phenyl](1,3-thiazol-2-yl)}-5-methylthiothiophene-2-carboxamidine trifluoroacetate 100 mg (0.093 mmol) of resin-bound 2-{3-[2-(5-amidino-2-methylthio-3-thienyl)-1,3-thiazol-4-yl]phenoxy}acetic acid (0.93 mmol/g), as prepared in a manner similar to Example 60, was reacted with (S)-(+)-2-anilino methyl pyrrolidine (0.5 M, 88 mg) and O-(7-azabenzotriazol-1-yl)-1,1,3,3-tetramethyluronium hexafluorophosphate) (HATU, 0.5 M, 190 mg), 1-hydroxy-7-azabenzotriazole (HOAt) (0.5M; 68 mg) and diisopropylethylamine (0.233 mmol, 40 μL) in 1 mL of anhydrous DMF in a manner similar to Example 63 to afford 13 mg (25% yield) of 4-{4-[3-(2-{(2R)-2-[(phenylamino)methyl]pyrrolidinyl}-2-oxoethoxy)phenyl](1,3-thiazol-2-yl)}-5-methylthiothiophene-2-carboxamidine trifluoroacetate. Mass Spectrum (ESI, m/z) Calcd. for $C_{28}H_{28}N_5O_2S_3$: 563.8 (M+H), found 564.2.

EXAMPLE 76

4-[4-(3-{2-[(3R)-3-(Methoxymethyl)pyrrolidinyl]-2-oxoethoxy}phenyl)(1,3-thiazol-2-yl)]-5-methylthiothiophene-2-carboxamidine trifluoroacetate 100 mg (0.093 mmol) of resin-bound 2-{3-[2-(5-amidino-2-methylthio-3-thienyl)-1,3-thiazol-4-yl]phenoxy}acetic acid (0.93 mmol/g), as prepared in a manner similar to Example 60, was reacted with (S)-(+)-2-methoxymethyl pyrrolidine (0.5 M, 58 mg) and O-(7-azabenzotriazol-1-yl)-1,1,3,3-tetramethyluronium hexafluorophosphate) (HATU, 0.5 M, 190 mg), 1-hydroxy-7-azabenzotriazole (HOAt) (0.5M; 68 mg) and diisopropylethylamine (0.233 mmol, 40 μL) in 1 mL of anhydrous DMF in a manner similar to Example 63 to afford 16 mg (35% yield) of 4-[4-(3-{2-[(3R)-3-(methoxymethyl)pyrrolidinyl]-2-oxoethoxy}phenyl)(1,3-thiazol-2-yl)]-5-methylthiothiophene-2-carboxamidine trifluoroacetate. Mass Spectrum (ESI, m/z) Calcd. for $C_{23}H_{26}N_4O_3S_3$: 503.2 (M+H), found 503.3.

EXAMPLE 77

1-(2-{3-[2-(5-Amidino-2-methylthio-3-thienyl)-1,3-thiazol-4-yl]phenoxy}acetyl)piperidine-3-carboxamide trifluoroacetate 100 mg (0.093 mmol) of resin-bound 2-{3-[2-(5-amidino-2-methylthio-3-thienyl)-1,3-thiazol-4-yl]phenoxy}acetic acid (0.93 mmol/g), as prepared in a manner similar to Example 60, was reacted with nipecotamide (0.5 M, 64 mg) and 0-(7-azabenzotriazol-1-yl)-1,1,3,3-tetramethyluronium hexafluorophosphate) (HATU, 0.5 M, 190 mg), 1-hydroxy-7-azabenzotriazole (HOAt) (0.5M; 68 mg) and diisopropylethylamine (0.233 mmol, 40 μL) in 1 mL of anhydrous DMF in a manner similar to Example 63 to afford 11 mg (23% yield) 1-(2-{3-[2-(5-amidino-2-methylthio-3-thienyl)-1,3-thiazol-4-yl]phenoxy}acetyl)piperidine-3-carboxamide trifluoroacetate. Mass Spectrum (ESI, m/z) Calcd. for $C_{23}H_{25}N_4O_3S_3$: 516.2 (M+H), found 516.3.

EXAMPLE 78

5-Methylthio-4-{4-[3-(trifluoromethoxy)phenyl](1,3-thiazol-2-yl)}thiophene-2-carboxamidine hydrochloride a) Methyl 5-methylthio-4-{4-[3-(trifluoromethoxy)phenyl](1,3-thiazol-2-yl)}thiophene-2-carboxylate: 435 mg (1.76 mmol) of methyl 4-(aminothioxomethyl)-5-methylthiothiophene-2-carboxylate was dissolved in 10 mL of reagent grade acetone. 2-bromo-3'-trifluoromethoxy acetophenone, prepared in a manner similar to Example 95, step (a), (1.76 mmol; 497 mg) was added and the solution was allowed to reflux for 3 h. The solution was allowed to cool and concentrated to an oil which was then dissolved in 150 mL of methylene chloride and washed with 50 mL of 10% HCl (aq.) and 50 mL of 2N NaOH (aq.). The organic layer was obtained and dried over magnesium sulfate and concentrated affording 877 mg (90% yield) of a methyl-5-methylthio-4-{4-[3-(trifluoromethoxy)phenyl](1,3-thiazol-2-yl)}thiophene-2-carboxylate.

b) 5-Methylthio-4-{4-[3-(trifluoromethoxy)phenyl](1,3-thiazol-2-yl)}thiophene-2-carboxamidine hydrochloride: To a stirred suspension of 19.4 mmol (1.04 g) of ammonium chloride (Fisher Scientific) in 20 mL of anhydrous toluene (Aldrich Chemical Co.) placed under nitrogen atmosphere at 0° C., 9.7 mL (19.4 mmol) of 2M trimethylaluminum in toluene (Aldrich Chemical Co.) was added via syringe over 15 min and then let stir at 0° C. for 30 min after which 837 mg (1.94 mmol) of methyl-5-methylthio-4-{4-[3-(trifluoromethoxy)phenyl](1,3-thiazol-2-yl)}thiophene-2-carboxylate was added to solution and allowed to reflux for 3 h. The reaction mixture was quenched by pouring over a slurry of 10 g of silica in 50 mL of chloroform. The silica was poured onto a sintered glass funnel and washed with ethyl acetate and eluting with a 15% methanol/$CH_2Cl_2$ solution and concentrated. The crude product was purified on 1 mm silica prep plates eluting with 15% methanol/$CH_2Cl_2$ and treated with 4N HCl/dioxane to afford 37 mg (5% yield) of 5-methylthio-4-{4-[3-(trifluoromethoxy)phenyl](1,3-thiazol-2-yl)}thiophene-2-carboxamidine hydrochloride. $^1$H-NMR (DMSO-$d_6$; 300 MHz) δ 9.43 (bs, 1.9H), 9.05 (bs, 1.9H), 8.67 (s, 1H), 8.43 (s, 1H), 8.10 (m, 2H), 7.65 (t, 1H), 7.40 (m, 1H), 2.8 (s, 3H). Mass Spectrum (LCQ-ESI, m/z) Calcd. for $C_{16}H_{12}F_3N_3OS_3$: 415.5(M+H), found 416.2.

EXAMPLE 79

5-Methylthio-4-(5-phenyl(1,3-oxazol-2-yl))thiophene-2-carboxamidine hydrochloride a) Methyl 5-methylthio-4-[N-(2-oxo-2-phenylethyl)carbamoyl]thiophene-2-carboxylate: To a stirred suspension of 300 mg (1.29 mmol) of 5-(methoxycarbonyl)-2-methylthiothiophene-3-carboxylic acid (as prepared in Example 95) in 10 mL of anhyd $CH_2Cl_2$ (under a $CaSO_4$ drying tube) was added 135 mL (1.55 mmol) of oxalyl chloride followed by 30 mL of anhyd DMF. After stirring for 2 h at room temperature, the mixture was concentrated in vacuo. The resulting yellow solid was dissolved in 10 mL of anhyd $CH_2Cl_2$, cooled (0° C.) and 266 mg (1.55 mmol) of 2-aminoacetophenone was added. N,N-diisopropylethylamine (DIEA) (756 mL, 4.34 mmol) was added dropwise over 3 min and the mixture stirred for 1 h at room temperature. The mixture was concentrated to an oil and partitioned between 125 mL of EtOAc and 80 mL of 1 M HCl. The aqueous layer was extracted with ethyl acetate (2×30 mL) and the combined organic phases were washed with 1 M HCl (60 mL), saturated $NaHCO_3$ (120 mL), and brine (120 mL) and dried over $Na_2SO_4$. After removing the solvent in vacuo, the residue was recrystallized from MeOH to afford the title compound as a cream-colored powder (314 mg, 70%). $^1$H-NMR (300 MHz, DMSO-$d_6$) δ 8.82 (t, 1H, J=6 Hz), 8.43 (s, 1H), 8.02 (d, 2H, J=7 Hz), 7.69 (t, 1H, J=7 Hz), 7.57 (t, 2H, J=7 Hz), 4.72 (d, 2H, J=6 Hz), 3.84 (s, 3H) and 2.57 (s, 3H). Mass spectrum (MALDI-TOF, a-cyano-4-hydroxycinnamic acid matrix) calcd. for $C_{16}H_{15}NO_4S_2$: 372.0(M+Na). Found: 372.1.

b) Methyl 5-Methylthio-4-(5-phenyl(1,3-oxazol-2-yl))thiophene-2-carboxylate: To a cooled (0° C.) solution of 80.1 mg (0.229 mmol) of methyl 5-methylthio-4-[N-(2-oxo-2-phenylethyl)carbamoyl]thiophene-2-carboxylate (as prepared in the previous step) in 2 mL of anhyd DMF was added 26.7 mL (0.286 mmol) of phosphorus oxychloride. After stirring for 20 h at room temperature, the mixture was concentrated in vacuo. The resulting yellow solid was recrystallized twice from MeOH to afford the title compound as a beige powder (48.8 mg, 64%). $^1$H-NMR (300 MHz, DMSO-$d_6$) δ 8.26 (s, 1H), 7.88 (s, 1H), 7.86 (d, 2H, J=7 Hz), 7.51 (m, 2H), 7.40 (m, 1H), 3.86 (s, 3H), and 2.79 (s, 3H). Mass spectrum (MALDI-TOF, a-cyano-4-hydroxycinnamic acid matrix) calcd. for $C_{16}H_{13}NO_3S_2$: 332.0 (M+H). Found: 331.9.

c) 5-Methylthio-4-(5-phenyl(1,3-oxazol-2-yl))thiophene-2-carboxamidine hydrochloride: Methyl 5-methylthio-4-(5-phenyl(1,3-oxazol-2-yl))thiophene-2-carboxylate (37.0 mg, 0.112 mmol, as prepared in the previous step) was treated according to the procedure in Example 10, step (b) using 59.9 mg (1.12 mmol) of ammonium chloride in 0.50 mL of toluene and 0.560 mL (1.12 mmol) of 2 M trimethylaluminum in toluene. The resulting residue was chromatographed on a 5 g silica SPE column (Waters Sep-Pak) with 10% MeOH-$CH_2Cl_2$ to elute an impurity followed by 20% MeOH-$CH_2Cl_2$ to give 39 mg of a light yellow glass. Crystallization from MeOH-MeCN afforded the title compound as a cream-colored solid (33.4 mg, 85%). $^1$H-NMR (300 MHz, DMSO-$d_6$) δ 9.45 (broad s, 2H), 9.13 (broad s, 2H), 8.72 (s, 1H), 7.93 (s, 1H), 7.84 (d, 2H, J=7 Hz), 7.53 (t, 2H, J=7 Hz), 7.42 (t, 1H, J=7 Hz), and 2.80 (s, 3H). Mass spectrum (MALDI-TOF, a-cyano-4-hydroxycinnamic acid matrix) calcd. for $C_{15}H_{13}N_3OS_2$: 316.1 (M+H). Found: 316.5.

EXAMPLES 80 AND 81

5-Methylthio-4-(4-phenylimidazol-2-yl)thiophene-2-carboxamidine trifluoroacetate and 5-Methylthio-4-[N-(2-oxo-2-phenylethyl)carbamoyl]thiophene-2-carboxamidine trifluoroacetate Methyl 5-methylthio-4-[N-(2-oxo-2-phenylethyl)carbamoyl]thiophene-2-carboxylate (39.4 mg, 0.100 mmol, as prepared in Example 79, step (a)) was treated according to the procedure in Example 10, step (b) using 64.2 mg (1.20 mmol) of ammonium chloride in 0.2 mL of toluene and 0.600 mL (1.20 mmol) of 2 M trimethylaluminum in toluene. The resulting residue was chromatographed on a 5-g silica SPE column (Waters Sep-Pak) with a gradient of 5–20% MeOH-$CH_2Cl_2$ to elute an impurity followed by 20% MeOH-$CH_2Cl_2$ to give a yellow resin. Crystallization from MeOH-$Et_2$O-MeCN afforded 16 mg of a yellow solid consisting of two products by $^1$H-NMR spectra. A portion of the mixture (11 mg) was purified by reverse-phase HPLC (5 m $C_8$ column, 4.6×100 mm, gradient 5–100% solvent B over 15 min, solvent A=0.1% TFA/$H_2O$, solvent B=0.1%TFA/MeCN, detection at 215 nm) to afford 6 mg of 5-methylthio-4-(4-phenylimidazol-2-yl)thiophene-2-carboxamidine trifluoroacetate as a colorless glass. $^1$H-NMR (300 MHz, $CD_3OD$) δ 8.23 (s, 1H), 7.80 (s, 1H), 7.79 (d, 2H, J=7 Hz), 7.48 (m, 2H), 7.39 (m, 1H), and 2.78 (s, 3H). Mass spectrum (electrospray ionization) calcd. for $C_{15}H_{14}N_4S_2$: 315.1 (M+H). Found: 315.3. Also isolated was 4 mg of 5-methylthio-4-[N-(2-oxo-2-phenylethyl)carbamoyl]-thiophene-2-carboxamidine trifluoroacetate as a colorless glass. $^1$H-NMR (300 MHz, DMSO-$d_6$) δ 9.30 (broad s, 2H), 8.86 (broad s, 2H), 8.68 (t, 1H. J=5.4 Hz), 8.43 (s, 1H), 8.04 (d, 2H, J=7 Hz), 7.70 (t, 1H, J=7 Hz), 7.58 (t, 2H, J=7 Hz), 4.78 (d, 2H, J=5.4 Hz), and 2.63 (s, 3H). Mass spectrum (electrospray ionization) calcd. for $C_{15}H_{13}N_3O_2S_2$: 334.1 (M+H). Found: 334.3.

EXAMPLE 82

4-(4-Phenyl-1,3-thiazol-2-yl)thiophene-2-carboxamidine hydrochloride a) 4-Bromothiophene-2-carboxylic acid: To a cooled (0° C.) solution of 10.0 g (47.1 mmol based on 90% purity) of 4-bromothiophene-2-carbaldehyde (Aldrich Chemical Company, Milwaukee, Wis.) in 200 mL of t-butanol was added 100 mL of 20% (w/v) $NaH_2PO_4$ followed by 60 mL (0.566 mol) of 2-methyl-2-butene. Sodium chlorite (70.8 mmol based on 80% purity) in 60 mL of water was added with stirring. After stirring the two-phase mixture vigorously for 16 h at room temperature, the pH of the aqueous layer was adjusted to 1–2 with 20% HCl. The layers were separated and the aqueous layer extracted with EtOAc (2×120 mL). The combined organic layers were dried ($Na_2SO_4$) and concentrated in vacuo to afford 9.8 g of an off-white solid. Recrystallization from a minimum of MeCN (three crops) gave the title compound as a white solid (9.02 g, 93%). $^1$H-NMR (300 MHz, $CDCl_3$) δ 7.79 (d, 1H, J=1.5 Hz), and 7.55 (d, 1H, J=1.5 Hz).

b) Methyl 4-bromothiophene-2-carboxylate: To a cooled (−20° C.) solution of 6.02 g (29.1 mmol) of 4-bromothiophene-2-carboxylic acid (as prepared in the previous step) in 100 mL of anhyd MeOH under nitrogen was added 2.55 mL (34.9 mmol) of thionyl chloride dropwise at a rate to keep the temperature below −5° C. (ca. 8–10 min). After stirring for 1 h at room temperature, the mixture was refluxed for 8 h, cooled, and concentrated in vacuo. The resulting 6.7 g of pale amber oil was passed through a 150 g pad of silica gel with ca. 600 mL of $CH_2Cl_2$ (discarding the first 120 mL which contained a minor impurity) to afford, after concentration in vacuo the title compound as a colorless oil (6.11 g, 95%). $^1$H-NMR (300 MHz, $CDCl_3$) δ 7.69 (d, 1H, J=1.5 Hz), 7.45 (d, 1H, J=1.5 Hz), and 3.90 (s, 3H).

c) Methyl 4-cyanothiophene-2-carboxylate: To a solution of 3.82 g (17.3 mmol) methyl 4-bromothiophene-2-carboxylate (as prepared in the previous step) in 10 mL of anhyd DMF was added 3.10 g (34.6 mmol) of copper (I) cyanide. The mixture was heated to reflux with stirring for 18 h, cooled and poured into 100 mL of 10% (w/v) KCN. The mixture was extracted with EtOAc (3×60 mL) and the combined extracts were washed with 150 mL each of water and brine. The dark solution was dried over $Na_2SO_4$, treated with decolorizing carbon, filtered and the resulting colorless solution concentrated in vacuo. The resulting light yellow solid was recrystallized from MeOH to afford the title compound as a cream-colored solid (1.67 g, 58%). $^1$H-NMR (300 MHz, $CDCl_3$) δ 8.09 (d, 1H, J=1.4 Hz), 7.93 (d, 1H, J=1.4 Hz), and 3.93 (s, 3H). IR (film): 2235 and 1712 $cm^{-1}$.

d) Methyl 4-(aminothioxomethyl)thiophene-2-carboxylate: A solution of 1.32 g (7.89 mmol) of methyl 4-cyanothiophene-2-carboxylate (as prepared in the previous step) in 200 mL of reagent grade MeOH was degassed with nitrogen through a fritted gas dispersion tube for 10 min. Triethylamine (5.50 mL, 39.5 mmol) was added and hydrogen sulfide gas was bubbled into the solution at a vigorous rate for 5 min and then at a minimal rate (as measured through an outlet oil bubbler) for 5 h with stirring. The gas introduction was stopped and the mixture was capped and stirred for 19 h at room temperature. The mixture was concentrated in vacuo to a yellow solid which was suspended in 10 mL of EtOH, cooled to −20° C., and filtered washing with 5 mL of cold (−20° C.) EtOH. The resulting solid was dried under suction followed by high vacuum to afford the title compound as a beige solid (1.31 g, 82%). $^1$H-NMR (300 MHz, DMSO-$d_6$) δ 9.85 (broad s, 1H), 9.51 (broad s, 1H), 8.50 (d, 1H, J=1.5 Hz), 8.28 (d, 1H, J=1.5 Hz), and 3.84 (s, 3H).

e) Methyl 4-(4-phenyl-1,3-thiazol-2-yl)thiophene-2-carboxylate: To a solution of 150 mg (0.745 mmol) of methyl 4-(aminothioxomethyl)-thiophene-2-carboxylate (as prepared in the previous step) in 6 mL of acetone was added 148 mg (0.745 mmol) of 2-bromoacetophenone. After refluxing for 2 h, the mixture was concentrated by boiling to a volume of ca. 2 mL. The resulting mixture was cooled (−10° C.) and filtered washing with cold acetone (2×0.5 mL). A second crop was obtained from the mother liquors and the combined crops dried to afford the title compound as a beige solid (202 mg, 90%). $^1$H-NMR (300 MHz, DMSO-$d_6$) δ 8.56 (d, 1H, J=1.5 Hz), 8.25 (d, 1H, J=1.5 Hz), 8.18 (s, 1H), 8.04 (d, 2H, J=7 Hz), 7.48 (t, 2H, J=7 Hz), 7.38 (t, 1H, J=7 Hz), and 3.89 (s, 3H). Mass spectrum (MALDI-TOF, a-cyano-4-hydroxycinnamic acid matrix) calcd. for $C_{15}H_{11}NO_2S_2$: 302.0 (M+H). Found 301.8.

f) 4-(4-Phenyl-1,3-thiazol-2-yl)thiophene-2-carboxamidine hydrochloride: Methyl 4-(4-phenyl-1,3-thiazol-2-yl)thiophene-2-carboxylate (160 mg, 0.531 mmol, as prepared in the previous step) was treated according to the procedure in Example 10, step (b) using 284 mg (5.31 mmol) of ammonium chloride in 2.6 mL of toluene and 2.65 mL (5.30 mmol) of 2 M trimethylaluminum in toluene. The resulting light yellow solid was chromatographed on a 10 g silica SPE column (Waters Sep-Pak) with a gradient of 5–20% MeOH-$CH_2Cl_2$. The resulting pale amber glass was triturated with $CH_2Cl_2$-MeCN and concentrated in vacuo to afford the title compound as a beige solid (68 mg, 45%). $^1$H-NMR (300 MHz, DMSO-$d_6$) δ 9.51 (broad s, 2H), 9.09 (broad s, 2H), 8.71 (d, 1H, J=1.5 Hz), 8.61 (d, 1H, J=1.5 Hz), 8.21 (s, 1H), 8.05 (d, 2H, J=7 Hz), 7.50 (t, 2H, J=7 Hz), and 7.40 (t, 1H, J=7 Hz). Mass spectrum (MALDI-TOF, a-cyano-4-hydroxycinnamic acid matrix) calcd. for $C_{14}H_{11}N_3S_2$: 286.0 (M+H). Found: 286.3.

EXAMPLE 83

5-Methylthio-4-[4-benzyl(1,3-thiazol-2-yl)]thiophene-2-carboxamidine hydrochloride a) Bromo-3-phenylacetone: To a solution of 132 mL (1.00 mmol) of phenylacetyl chloride in 1.0 mL of anhyd MeCN was added 1.05 mL (2.10 mmol) of a 2 M solution of trimethylsilyldiazomethane in hexane. After stirring 1 h at room temperature, the mixture was cooled (0° C.) and 300 mL (1.50 mmol) of 30 wt % HBr in acetic acid was added dropwise (gas evolution). After stirring 15 min, the mixture was concentrated in vacuo and rapidly chromatographed on a 2 g silica SPE column (Waters Sep-Pak) with 50% $CH_2Cl_2$-hexane to afford the title compound as a pale yellow oil (201 mg, 94%). $^1$H-NMR (300 MHz, $CDCl_3$) δ 7.2–7.4 (m, 5H), 3.95 (s, 2H), 3.92 (s, 2H).

b) Methyl 5-methylthio-4-[4-benzyl(1,3-thiazol-2-yl)]thiophene-2-carboxylate: Using a procedure similar to that of Example 10 with 171 mg (0.690 mmol) of methyl 4-(aminothioxomethyl)-5-methylthiothiophene-2-carboxylate (as prepared in Example 82, step (e)) in 4 mL of acetone and 147 mg (0.690 mmol) of 1-bromo-3-phenylacetone (as prepared in the previous step) afforded the title compound as a light tan powder (236 mg, 95%). $^1$H-NMR (300 MHz, DMSO -$d_6$) δ 8.11 (s, 1H), 7.2–7.4 (m, 5H), 4.11 (s, 2H), 3.84 (s, 3H), and 2.72 (s, 3H). Mass spectrum (MALDI-TOF, a-cyano-4-hydroxycinnamic acid matrix) calcd. for $C_{17}H_{15}NO_2S_3$: 362.0 (M+H). Found: 362.3.

c) 5-Methylthio-4-[4-benzyl(1,3-thiazol-2-yl)]thiophene-2-carboxamidine hydrochloride: Methyl 5-methylthio-4-[4-benzyl(1,3-thiazol-2-yl)]thiophene-2-carboxylate (60 mg, 0.166 mmol, as prepared in the previous step) was treated according to the procedure in Example 10, step (b) using 88.8 mg (1.66 mmol) of ammonium chloride in 0.5 mL of toluene and 0.830 mL (5.30 mmol) of 2 M trimethylaluminum in toluene to afford, after trituration from MeOH with $Et_2O$, the title compound as a yellow solid (38.2 mg, 60%). $^1$H-NMR (300 MHz, $CD_3OD$) δ 8.43 (s, 1H), 7.16–7.33 (m, 5H), 4.15 (s, 2H), and 2.75 (s, 3H). Mass spectrum (MALDI-TOF, a-cyano-4-hydroxycinnamic acid matrix) calcd. for $C_{16}H_{15}N_3S_3$: 346.0 (M+H), Found: 346.0.

EXAMPLE 84

5-Methylthio-4-(4-phenyl(1,3-oxazol-2-yl)) thiophene-2-carboxamidine hydrochloride a) Methyl 4-[N-(2-hydroxy-1-phenylethyl)carbamoyl]-5-methylthiothiophene-2-carboxylate: To a stirred suspension of 1.23 g (5.29 mmol) of 5-(methoxycarbonyl)-2-methylthiothiophene-3-carboxylic acid (as prepared in Example 79, step (a)) in 20 mL of anhyd $CH_2Cl_2$ (under a $CaSO_4$ drying tube) was added 1.85 mL (21.2 mmol) of oxalyl chloride followed by 30 mL of anhyd DMF. After stirring for 2 h at room temperature, the mixture was concentrated in vacuo. The resulting yellow solid was dissolved in 20 mL of anhyd $CH_2Cl_2$, cooled (0° C.) and 1.85 mL of N,N-diisopropylethylamine (10.6 mmol) and 1.02 g (7.41 mmol) of phenylglycinol was added and the mixture stirred for 1 h at room temperature. The mixture was concentrated to an oil and partitioned between 200 mL of EtOAc and 200 mL of saturated $NaHCO_3$. The organic phase was washed with saturated $NaHCO_3$ (200 mL), 10% (w/v) citric acid, and brine (200 mL), and dried over $Na_2SO_4$. After removing the solvent in vacuo, the residue was chromatographed on a 10 g silica SPE column (Waters Sep-Pak) with a gradient of 0–20% EtOAc-$CH_2Cl_2$ to afford the title compound as a light yellow solid (1.26 g, 68%). $^1$H-NMR (300 MHz, $CDCl_3$) δ 8.00 (s, 1H), 7.30–7.42 (m, 5H), 7.08 (d, 1H, J=7.2 Hz), 5.26 (m, 1H), 3.99 (t, 2H, J=5.4 Hz), 3.89 (s, 3H), 2.60 (s, 3H), and 2.33 (t, 1H, J=6.1 Hz). Mass spectrum (electrospray ionization) calcd. for $C_{16}H_{17}NO_4S_2$: 352.1 (M+H). Found: 352.0.

b) Methyl 5-methylthio-4-[N-(2-oxo-1-phenylethyl) carbamoyl]thiophene-2-carboxylate: To a solution of 505 mg (1.44 mmol) methyl 4-[N-(2-hydroxy-1-phenylethyl) carbamoyl]-5-methylthiothiophene-2-carboxylate (as prepared in the previous step) in 20 mL of anhydrous $CH_2Cl_2$ was added 856 mg (2.02 mmol) of Dess Martin reagent (Omega Chemical Company, Inc., Levis (Qc) Canada). After stirring in an open flask for 1.5 h at room temperature, the mixture was concentrated in vacuo. to ca. 10% volume and partitioned between 50 mL of EtOAc and 50 mL of saturated $NaHCO_3$-brine (1:1). The organic phase were washed with brine (200 mL), dried over $Na_2SO_4$ and concentrated in vacuo. Concentrated again from $CH_2Cl_2$ followed by high vacuum afforded the title compound as a light yellow foam (495 mg, 98%) which was used in the next step without further purification. $^1$H-NMR (300 MHz, $CDCl_3$) δ 9.64 (s, 1H), 8.04 (s, 1H), 7.59 (d, 1H, J=5 Hz), 7.36–7.46 (m, 5H), 5.76 (d, 1H, J=5 Hz), 3.90 (s, 3H), and 2.62 (s, 3H).

c) Methyl 5-methylthio-4-(4-phenyl(1,3-oxazol-2-yl)) thiophene-2-carboxylate: To a cooled (0° C.) solution of 465 mg (1.33 mmol) methyl 5-methylthio-4-[N-(2-oxo-1-phenylethyl)carbamoyl]thiophene-2-carboxylate (as prepared in the previous step) in 6 mL of anhyd DMF was added 186 mL (2.00 mmol) of phosphorus oxychloride. After stirring for 14 h at room temperature, the mixture was treated with 10 mL of saturated $NaHCO_3$ and concentrated to dryness under high vacuum. The resulting residue was partitioned between 80 mL of EtOAc and 60 mL of water. The aqueous layer was extracted with EtOAc (2×10 mL) and the combined organic phases washed with brine (60 mL), and dried over $Na_2SO_4$. The resulting 406 mg of amber-colored solid was recrystallized from $CH_2Cl_2$-$Et_2O$ to remove the majority of a polar impurity as a cream-colored solid. The remaining mother liquors were chromatographed on a 10 g silica SPE column (Waters Sep-Pak) with a gradient of 40–100% $CH_2Cl_2$-hexane and the resulting residue triturated with $Et_2O$-hexane (2:1)) to afford the title compound as a light beige solid (114 mg, 26%). $^1$H-NMR (300 MHz, $CDCl_3$) δ 8.24 (s, 1H), 7.93 (s, 1H), 7.83 (m, 2H), 7.43 (m, 2H), 7.33 (m, 1H), 3.91 (s, 3H), and 2.72 (s, 3H). Mass spectrum (ESI) calcd. for $C_{16}H_{13}NO_3S_2$: 332.0 (M+H). Found: 332.2.

d) 5-Methylthio-4-(4-phenyl(1,3-oxazol-2-yl))thiophene-2-carboxamidine hydrochloride: Methyl 5-methylthio-4-(4-phenyl(1,3-oxazol-2-yl))thiophene-2-carboxylate (80.3 mg, 0.242 mmol, as prepared in the previous step) was treated according to the procedure in Example 10, step (b) using 155 mg (2.90 mmol) of ammonium chloride in 1.45 mL of toluene and 1.45 mL (2.90 mmol) of 2 M trimethylaluminum in toluene. The resulting light yellow solid was chromatographed on a 5 g silica SPE column (Waters Sep-Pak) with 10% MeOH-$CH_2Cl_2$ to give a light yellow resin. Crystallization from MeOH-$Et_2O$ (ca. 1:3) afforded the title compound as a yellow solid (62.2 mg, 82%). $^1$H-NMR (300 MHz, DMSO-$d_6$) δ 9.39 (broad s, 2H), 8.97 (broad s, 2H), 8.78 (s, 1H), 8.60 (s, 1H), 7.89 (d, 2H, J=7 Hz), 7.49 (t, 2H, J=7 Hz), 7.38 (t, 1H, J=7 Hz), and 2.80 (s, 3H). Mass spectrum (ESI) calcd. for $C_{15}H_{13}N_3OS_2$: 316.1 (M+H). Found: 316.2.

EXAMPLE 85

4-[4-(4-hydroxy-3-methoxyphenyl)(1,3-thiazol-2-yl)]-5-methylthiothiophene-2-carboxamidine hydrochloride a) 4-(Chlorocarbonyl)-2-methoxyphenyl acetate: To a stirred suspension of 1.00 g (4.76 mmol) of 4-acetoxy-3-methoxybenzoic acid (Pfaltz and Bauer, Inc.) in 4 mL of anhyd $CH_2Cl_2$ (under a $CaSO_4$ drying tube) was added 4.15 mL (47.6 mmol) of oxalyl chloride followed by 25 mL of anhyd DMF. After stirring for 4 h at room temperature, the mixture was concentrated in vacuo to afford the title compound as light yellow crystals (1.12 g, 103%). $^1$H-NMR (300 MHz, $CDCl_3$) δ 7.81 (dd, 1H, J=8.4, 2.1 Hz), 7.66 (d, 1H, 2.1 Hz), 7.19 (d, 1H, 8.4 Hz), 3.91 (s, 3H), and 2.35 (s, 3H).

b) 4-(2-Bromoacetyl)-2-methoxyphenyl acetate: To a solution of 1.09 g (4.6 mmol) of 4-(chlorocarbonyl)-2-methoxyphenyl acetate (as prepared in the previous step) in 10 mL of anhyd $CH_2Cl_2$ was added 10.0 mL (20.0 mmol) of a 2 M solution of trimethylsilyldiazomethane in hexane. After stirring 2 h at room temperature, the mixture was cooled (0° C.) and 3.20 mL (16.0 mmol) of 30 wt % HBr in acetic acid was added dropwise (gas evolution). After stirring 5 min, the mixture was concentrated in vacuo and rapidly chromatographed on a 10-g silica SPE column (Waters Sep-Pak) with $CH_2Cl_2$ to afford the title compound as a light yellow crystalline solid (1.28 g, 97%). $^1$H-NMR (300 MHz, CDCl$_3$) δ 7.63 (d, 1H, 1.9 Hz), 7.59 (dd, 1H, J=8.2, 1.9 Hz), 7.16 (d, 1H, 8.2 Hz), 4.43 (s, 2H), 3.91 (s, 3H), and 2.35 (s, 3H).

c) 2-Methoxy-4-{2-[5-(methoxycarbonyl)-2-methylthio(3-thienyl)](1,3-thiazol-4-yl)}phenyl acetate. Using a procedure similar to that of Example 82, step (e) with 1.00 g (4.04 mmol) of methyl 4-(aminothioxomethyl)-5-methylthiothiophene-2-carboxylate (Maybridge Chemical Company, Cornwall, UK) in 15 mL of reagent acetone and 1.16 g (4.04 mmol) of 4-(2-bromoacetyl)-2-methoxyphenyl acetate (as prepared in the previous step) afforded the title compound as 1.42 g of a yellow solid which, according to the $^1$H-NMR spectrum, consisted of a ca. 1:1 mixture of the title compound and the corresponding compound resulting from partial loss of the acetate. $^1$H-NMR (300 MHz, DMSO-d$_6$) δ 8.27 (s, 1H), 8.22 (s, 1H), 8.19 (s, 1H), 8.00 (s, 1H), 7.78 (d, 1H, 1.9 Hz), 7.67 (dd, 1H, J=8.2, 1.9 Hz), 7.61 (d, 1H, 1.9 Hz), 7.51 (dd, 1H, J=8.2, 1.9 Hz), 7.19 (d, 1H, 8.2 Hz), 6.86 (d, 1H, 8.2 Hz), 8.87 (m, 12H), 2.76 (s, 3H), 2.75 (s, 3H), and 2.28 (s, 3H). Mass spectrum (ESI) calcd. for C$_{19}$H$_{17}$NO$_5$S$_3$ and C$_{17}$H$_{15}$NO$_3$S$_3$ 436.0 (M+H) and 394.1 (M+H). Found: 436.1 and 394.2. The mixture was used without further purification in the following step where formation of the amidine involves concomitant removal of the acetate.

d) 4-[4-(4-hydroxy-3-methoxyphenyl)(1,3-thiazol-2-yl)]-5-methylthiothiophene-2-carboxamidine hydrochloride: A portion of the mixture (500 mg, ca. 1.21 mmol as based on the $^1$H-NMR integration) containing the 2-methoxy-4-{2-[5-(methoxycarbonyl)-2-methylthio(3-thienyl)](1,3-thiazol-4-yl)}phenyl acetate (as prepared in the previous step) was treated according to the procedure in Example 10, step (b) using 610 mg (11.4 mmol) of ammonium chloride in 5.7 mL of toluene and 5.70 mL (11.4 mmol) of 2 M trimethylaluminum in toluene. After chromatography of the resulting residue on a 10 g silica SPE column (Waters Sep-Pak) with a gradient of 5–20% MeOH-CH$_2$Cl$_2$ to obtain a yellow glass which was recrystallized from MeOH-CH$_2$Cl$_2$ to afford the title compound as a pale yellow solid (192 mg, 42%). $^1$H-NMR (300 MHz, DMSO-d$_6$) δ 9.35 (broad s, 2H), 9.27 (s, 1H), 8.97 (broad s, 2H), 8.62 (s, 1H), 8.04 (s, 1H), 7.62 (s, 1H), 7.54 (d, 1H J=8.2 Hz), 6.88 (d, 1H, J=8.2 Hz), 3.87 (s, 3H), and 2.79 (s, 3H). Mass spectrum (ESI) calcd. for C$_{16}$H$_{15}$N$_3$O$_2$S$_3$: 378.0(M+H). Found: 378.1.

EXAMPLE 86

4-[4-(3-Hydroxy-4-methoxyphenyl)(1,3-thiazol-2-yl)]-5-methylthiothiophene-2-carboxamidine hydrochloride a) 3-Acetyloxy-4-methoxybenzoic acid: To a suspension of 600 mg (3.57 mmol) of 3-hydroxy-4-methoxybenzoic acid (Aldrich Chemical Company, Milwaukee, Wis.) in 5 mL of anhyd CH$_2$Cl$_2$ was added 1.31 mL (7.50 mmol) of N,N-diisopropylethylamine and the mixture stirred until homogeneous (ca. 5 min). Acetyl chloride (305 mL, 4.28 mmol) was added dropwise over 2 min followed by 2.0 mg ((0.016 mmol) of 4-dimethylaminopyridine. After stirring at room temperature for 1 h, the mixture was poured into 50 mL of EtOAc and washed with 1 M HCl (3×25 mL). The organic phase was extracted with saturated NaHCO$_3$ (6×15 mL) and the combined extracts saturated with solid NaCl and acidified to pH 2 with conc HCl. The resulting suspension was extracted with EtOAc (3×20 mL) and the combined extracts were dried over Na$_2$SO$_4$ and concentrated in vacuo to afford the title compound as a light beige powder (463 mg, 62%). $^1$H-NMR (300 MHz, CDCl$_3$) δ 8.00 (dd, 1H, J=8.7, 2.0 Hz), 7.79 (d, 1H, 2.0 Hz), 7.00 (d, 1H, 8.7 Hz), 3.91 (s, 3H), and 2.34 (s, 3H).

b) 3-(Chlorocarbonyl)-6-methoxyphenyl acetate: Using the procedure in Example 85, step (a), 400 mg (1.90 mmol) of 3-acetyloxy-4-methoxybenzoic acid (as prepared in the previous step) was treated with 663 mL (7.60 mmol) of oxalyl chloride and 25 mL of anhyd DMF for 2 h to afford, after workup, the title compound as a beige crystalline solid which was used in the following step without further purification.

c) 5-(2-Bromoacetyl)-2-methoxyphenyl acetate: Using the procedure in Example 85, step (b), the entire sample of 3-(chlorocarbonyl)-6-methoxyphenyl acetate (as prepared in the previous step) in 5 mL of anhyd CH$_2$Cl$_2$ was treated with 2.09 mL (4.18 mmol) of a 2 M solution of trimethylsilyldiazomethane in hexane and 456 mL (2.28 mmol) of 30 wt % HBr in acetic acid. Chromatography as in Example 85, step (b) followed by recrystallization from CH$_2$Cl$_2$-hexane afforded the title compound as a faintly yellow solid (366 mg, 67%). $^1$H-NMR (300 MHz, CDCl$_3$) δ 7.79 (dd, 1H, J=8.6, 2.2 Hz), 7.70 (d, 1H, 2.2 Hz), 7.03 (d, 1H, 8.6 Hz), 4.38 (s, 2H), 3.92 (s, 3H), and 2.34 (s, 3H).

d) 2-Methoxy-5-{2-[5-(methoxycarbonyl)-2-methylthio(3-thienyl)](1,3-thiazol-4-yl)}phenyl acetate: Using a procedure similar to that of Example 82, step (e) with 282 mg (1.14 mmol) of methyl 4-(aminothioxomethyl)-5-methylthiothiophene-2-carboxylate (Maybridge Chemical Company, Cornwall, UK) in 4 mL of acetone and 3.27 mg (1.14 mmol) of 5-(2-bromoacetyl)-2-methoxyphenyl acetate (as prepared in the previous step) afforded a yellow solid (374 mg) which, according to the $^1$H-NMR spectrum, consisted of a 3:7 mixture of the title compound and the corresponding compound resulting from partial loss of the acetate. Mass spectrum (ESI) calcd. for C$_{19}$H$_{17}$NO$_5$S$_3$ and C$_{17}$H$_{15}$NO$_3$S$_3$ 436.0 (M+H) and 394.1 (M+H). Found: 436.0 and 394.0. The mixture was used without further purification in the following step where formation of the amidine involves concomitant removal of the acetate.

e) 4-[4-(3-Hydroxy-4-methoxyphenyl)(1,3-thiazol-2-yl)]-5-methylthiothiophene-2-carboxamidine hydrochloride: A portion of the mixture (320 mg, ca. 0.788 mmol as based on the $^1$H-NMR spectrum) containing the 2-methoxy-5-{2-[5-(methoxycarbonyl)-2-methylthio(3-thienyl)](1,3-thiazol-4-yl)}phenyl acetate (as prepared in the previous step) was treated according to the procedure in Example 10, step (b), using 415 mg (7.76 mmol) of ammonium chloride in 3.5 mL of toluene and 3.88 mL (7.66 mmol) of 2 M trimethylaluminum in toluene. After chromatography of the resulting residue on a 10 g silica SPE column (Waters Sep-Pak) with 10–40% MeOH-CH$_2$Cl$_2$, a light yellow solid was obtained which was dissolved in 45 mL of DMF and filtered to remove silica gel. Concentration under high vacuum and recrystallization from MeOH-Et$_2$O afforded the title compound as a light tan solid (132 mg, 44%). $^1$H-NMR (300 MHz, DMSO-d$_6$) δ 9.49 (broad s, 2H), 9.16 (broad s, 2H), 8.67 (s, 1H), 7.98 (s, 1H), 7.5 (obscured m, 3H), 7.00 (obscured d, 1H, J=8.3 Hz), 3.82 (s, 3H), and 2.79 (s, 3H). Mass spectrum (ESI) calcd. for C$_{16}$H$_{15}$N$_3$O$_2$S$_3$: 378.0(M+H). Found: 378.1.

EXAMPLE 87

5-Methylthio-4-(N-phenylcarbamoyl)thiophene-2-carboxamidine hydrochloride a) Methyl 5-methylthio-4-(N-phenylcarbamoyl)thiophene-2-carboxylate: To 182 mg (0.785 mmol) of 5-(methoxycarbonyl)-2-methylthiothiophene-3-carboxylic acid (as prepared in Example 95) in 4 mL of anhyd $CH_2Cl_2$ was treated with 275 mL (3.15 mmol) of oxalyl chloride and 6 mL of anhyd DMF for 2 h similar to Example 79, step (a); followed by 206 mL (1.18 mmol) of N,N-diisopropylethylamine and 85.9 mL (0.942 mmol) of aniline in 3 mL of anhyd $CH_2Cl_2$ for 20 min. The mixture was poured into 25 mL of EtOAc and washed with 1 M HCl (2×25 mL), saturated $NaHCO_3$ (2×25 mL), and brine (25 mL), and dried over $Na_2SO_4$. Removal of the solvent in vacuo, afforded the pure title compound as a light yellow solid (163 mg, 68%). $^1$H-NMR (300 MHz, $CDCl_3$) δ 8.23 (broad s, 1H), 8.10 (s, 1H), 7.63 (d, 2H, J=7 Hz), 7.36 (t, 2H, J=7 Hz), 7.15 (t, 2H, J=7 Hz), 3.90 (s, 3H), and 2.64 (s, 3H).

b) 5-Methylthio-4-(N-phenylcarbamoyl)thiophene-2-carboxamidine hydrochloride: Methyl 5-methylthio-4-(N-phenylcarbamoyl)thiophene-2-carboxylate (60.0 mg, 0.195 mmol, as prepared in the previous step) was treated similarly to the procedure in Example 10, step (b) using 310 mg (5.80 mmol) of ammonium chloride in 2 mL of toluene and 2.90 mL (5.80 mmol) of 2 M trimethylaluminum in toluene for 6 h. Chromatography of the resulting residue on a 2 g silica SPE column (Waters Sep-Pak) with a gradient of 5–20% MeOH-$CH_2Cl_2$, followed by crystallization from MeOH-$Et_2O$ afforded the title compound as a beige solid (40.3 mg, 71%). $^1$H-NMR (300 MHz, DMSO-$d_6$) δ 10.24 (s, 1H), 9.34 (broad s, 2H), 9.05 (broad s, 2H), 8.75 (s, 1H), 7.73 (d, 2H, J=8 Hz), 7.36 (t, 2H, J=8 Hz), 7.11 (m, 1H), and 2.67 (s, 3H). Mass spectrum (ESI) calcd. for $C_{13}H_{13}N_3OS_2$: 292.1 (M+H). Found: 292.4.

EXAMPLE 88 AND 89

5-Methylthio-4-[N-benzylcarbamoyl]thiophene-2-carboxamidinehydrochloride and 4-{Imino [benzylamino]methyl}-5-methylthiothiophene-2-carboxamidine hydrochloride a) Methyl 5-methylthio-4-[N-benzylcarbamoyl] thiophene-2-carboxylate: The identical procedure of Example 87, step (a) was used with 103 mL (0.942 mmol) of benzylamine and the same amounts of all other reagents to afford the title compound as a light yellow solid (167 mg, 66%). $^1$H-NMR (300 MHz, $CDCl_3$) δ 7.93 (s, 1H), 7.28–7.38 (m, 5H), 6.58 (broad s, 1H), 4.62 (s, 2H, J=5.7 Hz), 3.87 (s, 3H), and 2.60 (s, 3H).

b) 5-Methylthio-4-[N-benzylcarbamoyl]thiophene-2-carboxamidinehydrochloride and 4-{Imino[benzylamino] methyl}-5-methylthiothiophene-2-carboxamidinehydrochloride: Methyl 5-methylthio-4-[N-benzylcarbamoyl]thiophene-2-carboxylate (62.7 mg, 0.195 mmol, as prepared in the previous step) was treated similarly to the procedure in Example 10, step (b) using 310 mg (5.80 mmol) of ammonium chloride in 2 mL of toluene and 2.90 mL (5.80 mmol) of 2 M trimethylaluminum in toluene for 6 h.

Chromatography of the resulting residue on a 2 g silica SPE column (Waters Sep-Pak) with a gradient of 5–20% MeOH-$CH_2Cl_2$, followed by crystallization from MeOH-$Et_2O$ afforded 5-methylthio-4-[N-benzylcarbamoyl] thiophene-2-carboxamidinehydrochloride as a beige solid (21.1 mg, 35%). $^1$H-NMR (300 MHz, DMSO-$d_6$) δ 7.93 (s, 1H), 7.28–7.38 (m, 5H), 6.58 (broad s, 1H), 4.62 (s, 2H, J=5.7 Hz), 3.87 (s, 3H), and 2.60 (s, 3H). Mass spectrum (ESI) calcd. for $C_{14}H_{15}N_3OS_2$: 306.1 (M+H). Found: 306.6.

Also isolated and crystallized from MeOH-$Et_2O$ was the more polar 4-{imino[benzylamino]methyl}-5-methylthiothiophene-2-carboxamidinehydrochloride as a beige solid (32.0 mg, 54%). $^1$H-NMR (300 MHz, DMSO-$d_6$) consistent with desired product as broad mixture of rotomers. Mass spectrum (ESI) calcd. for $C_{14}H_{16}N_4S_2$: 305.1 (M+H). Found: 305.8.

EXAMPLE 90 AND 91

4-[N-Methyl-N-benzylcarbamoyl]-5-methylthiothiophene-2-carboxamidine hydrochloride and 4{Imino[methylbenzylamino]methyl}-5-methylthiothiophene-2-carboxamidinehydrochloride a) Methyl 4-[N-methyl-N-benzylcarbamoyl]-5-methylthiothiophene-2-carboxylate: The identical procedure of Example 87, step (a) was used with 122 mL (0.942 mmol) of N-benzylmethylamine and the same amounts of all other reagents to afford the title compound as a light yellow solid (169 mg, 64%). $^1$H-NMR (300 MHz, $CDCl_3$) δ 7.68 (s, 1H), 7.34 (m, 5H), 4.6 (broad m, 2H), 3.86 (s, 3H), 2.91 (m, 3H), and 2.60 (s, 3H).

b) 4-[N-Methyl-N-benzylcarbamoyl]-5-methylthiothiophene-2-carboxamidine hydrochloride and 4-{Imino[methylbenzylamino]methyl}-5-methylthiothiophene-2-carboxamidine hydrochloride: Methyl 4-[N-methyl-N-benzylcarbamoyl]-5-methylthiothiophene-2-carboxylate (65.4 mg, 0.195 mmol, as prepared in the previous step) was treated similarly to the procedure in Example 10, step (a) using 310 mg (5.80 mmol) of ammonium chloride in 2 mL of toluene and 2.90 mL (5.80 mmol) of 2 M trimethylaluminum in toluene for 6 h.

Chromatography of the resulting residue on a 2 g silica SPE column (Waters Sep-Pak) with a gradient of 5–20% MeOH-$CH_2Cl_2$ afforded 4-[N-methyl-N-benzylcarbamoyl]-5-methylthiothiophene-2-carboxamidine hydrochloride as a amber-colored glass (34.3 mg, 55%). $^1$H-NMR (300 MHz, DMSO-$d_6$) δ 9.32 (broad s, 2H), 9.06 (broad s, 2H), 8.11 (s, 1H), 7.36 (m, 5H), 4.66 (m, 2H), 2.88 (s, 3H) and 2.66 (s, 3H). Mass spectrum (ESI) calcd. for $C_{15}H_{17}N_3OS_2$: 320.1 (M+H). Found: 320.4.

Also isolated and then crystallized from MeOH-$Et_2O$ was the more polar 4-{imino[methylbenzylamino]methyl}-5-methylthiothiophene-2-carboxamidine hydrochloride as a beige solid (19.8 mg, 32%). $^1$H-NMR (300 MHz, DMSO-$d_6$) consistent with desired product as broad mixture of rotomers. Mass spectrum (ESI) calcd. for $C_{15}H_{18}N_4S_2$: 319.1 (M+H). Found: 319.6.

EXAMPLE 92 AND 93

5-Methylthio-4-[N-(2-phenylethyl)carbamoyl] thiophene-2-carboxamidine hydrochloride and 4-{Imino[(2-phenylethyl)amino]methyl}-5-methylthiothiophene-2-carboxamidine hydrochloride a) Methyl 5-methylthio-4-[N-(2-phenylethyl)carbamoyl] thiophene-2-carboxylate: The identical procedure of Example 87, step (a) was used with 118 mL (0.942 mmol) of phenethylamine and the same amounts of all other reagents to afford the title compound as a light yellow solid (165 mg, 63%). $^1$H-NMR (300 MHz, $CDCl_3$) δ 7.86 (s, 1H), 7.30–7.35 (m, 5H), 6.44 (m, 1H), 3.87 (s, 3H), 3.70 (q, 2H, J=7 Hz), 2.93 (t, 2H, J=7 Hz), and 2.53 (s, 3H).

b) 5-Methylthio-4-[N-(2-phenylethyl)carbamoyl] thiophene-2-carboxamidine hydrochloride and 4-{Imino[(2-phenylethyl)amino]methyl}-5-methylthiothiophene-2-carboxamidine hydrochloride: Methyl 5-methylthio-4-[N-(2-phenylethyl)carbamoyl]thiophene-2-carboxylate (65.4 mg, 0.195 mmol, as prepared in the previous step) was treated similarly to the procedure in Example 10, step (a) using 310 mg (5.80 mmol) of ammonium chloride in 2 mL of toluene and 2.90 mL (5.80 mmol) of 2 M trimethylaluminum in toluene for 6 h.

Chromatography of the resulting residue on a 2 g silica SPE column (Waters Sep-Pak) with a gradient of 5–20% MeOH-CH$_2$Cl$_2$, followed by crystallization from MeOH-Et$_2$O afforded 5-methylthio-4-[N-(2-phenylethyl)carbamoyl]thiophene-2-carboxamidine hydrochloride as a beige solid (17.4 mg, 28%). $^1$H-NMR (300 MHz, DMSO-d$_6$) δ 8.8–9.3 (broad m, 4H), 8.48 (m, 1H), 8.35 (s, 1H), 7.26 (m, 5H), 3.44 (m, 2H), 2.82 (t, 3H, J=7.5 Hz), and 2.61 (s, 3H). Mass spectrum (ESI) calcd. for C$_{15}$H$_{17}$N$_3$OS$_2$: 320.1 (M+H). Found: 320.4.

Also isolated and crystallized from MeOH-Et$_2$O was the more polar 4-{imino[(2-phenylethyl)amino]methyl}-5-methylthiothiophene-2-carboxamidine hydrochloride as a beige solid (19.1 mg, 31%). $^1$H-NMR (300 MHz, DMSO-d$_6$) δ 8.37 (s, 1H), 7.2–7.4 (m, 5H), 3.70 (t, 2H, J=7.6 Hz), 2.96 (t, 2H, J=7.6 Hz), and 2.71 (s, 3H). Mass spectrum (ESI) calcd. for C$_{15}$H$_{18}$N$_4$S$_2$: 319.1 M+H). Found 319.5.

EXAMPLE 94

3-Amino-2-aza-3-[5-methylthio-4-(4-phenyl(1,3-thiazol-2-yl))(2-thienyl)]prop-2-enenitrile To 100 mg (0.302 mmol) of 5-methylthio-4-(4-phenyl(1,3-thiazol-2-yl))thiophene-2-carboxamidine (as prepared in Example 10, step b) in 3 mL of EtOH was added 29.6 mg (0.604 mmol) of cyanamide as a solution in 0.3 mL of water. The mixture was heated to reflux and 0.302 mL (0.302 mmol) of 1 M aqueous KOH was added. After 3 h, the mixture was cooled (0° C.) and filtered washing with ice-cold EtOH. The resulting solid was dried in vacuo to afford the title compound as a light yellow powder (78.4 mg, 73%). $^1$H-NMR (300 MHz, DMSO-d$_6$) δ 9.31 (broad s, 1H), 8.70 (broad s, 1H), 8.63 (s, 1H), 8.19 (s, 1H), 8.09 (d, 2H, J=7 Hz), 7.49 (t, 2H, J=7 Hz), 7.39 (t, 1H, J=7 Hz), and 2.75 (s, 3H). Mass spectrum (MALDI-TOF, a-cyano-4-hydroxycinnamic acid matrix) calcd. for C$_{16}$H$_{12}$N$_4$S$_3$: 357.0 (M+H). Found: 357.1.

EXAMPLE 95

5-(Methoxycarbonyl)-2-methylthiothiophene-3-carboxylic acid

Methyl 4-cyano-5-methylthiothiophene-2-carboxylate (2.20 g, 10.3 mmol, Maybridge Chemical Company, Cornwall, UK) and tetrafluorophthalic acid (2.45 g, 10.3 mmol) in an 8-mL sealable pressure tube (Ace Glass Company) with stir bar was heated to 160° C. The molten mixture was stirred for 4 days, cooled and the resulting residue broken up and extracted by refluxing with 80 mL chloroform. The mixture was cooled, decolorizing carbon (ca. 0.5 g) was added and the mixture filtered (Celite). The resulting solution was extracted with saturated NaHCO$_3$ (4×30 mL) and the combined aqueous extracts acidified to pH 1–2 with conc HCl and filtered to provide a light tan solid. After dissolving the solid in a minimum of 1 M K$_2$CO$_3$ (35–40 mL) and filtering (washing with 10–20 mL of water) to clarify the solution, it was slowly acidified to pH 6.5–7.0 with stirring and filtered (Celite) to remove a brown precipitate. The pH adjustment and filtration was repeated and the resulting solution was saturated with solid NaCl and acidified to pH 1–2 with conc HCl. The precipitate was filtered, washed with water (3×10 mL) and dried over P$_2$O$_5$ under high vacuum to afford the title compound as a cream-colored powder (1.24 g, 52%). $^1$H-NMR (300 MHz, DMSO-d$_6$) δ 13.14 (broad s, 1H), 7.89 (s, 1H), 3.82 (s, 3H) and 2.64 (s, 3H). Mass spectrum (ESI, negative mode) calcd. for C$_8$H$_8$O$_4$S$_2$: 232.0 (M–). Found: 231.7.

EXAMPLE 96

5-Ethylthio-4-(4-phenyl(1,3-thiazol-2-yl))thiophene-2-carboxamidine hydrochloride 5 a) Methyl 4-(4-phenyl(1,3-thiazol-2-yl))-5-(methylsulfonyl)thiophene-2-carboxylate: Using the procedure of Example 141, step (a) with 600 mg (1.73 mmol) of methyl 5-methylthio-4-(4-phenyl(1,3-thiazol-2-yl))thiophene-2-carboxylate as prepared in Example 10, step (a) afforded 642 mg (98%) of the title compound as a light yellow powder. $^1$H-NMR (300 MHz, CDCl$_3$) δ 7.93 (s, 1H), 7.90 (m, 2H), 7.63 (s, 1H), 7.47 (m, 2H), 7.39 (m, 1H), 3.98 (s, 3H) and 3.73 (s, 3H). Mass spectrum (ESI, m/z): calcd. for C$_{16}$H$_{13}$NO$_4$S$_3$380.0 (M+H), found 380.2.

b) 4-(4-Phenyl)(1,3-thiazol-2-yl))-5-(methylsulfonyl)thiophene-2-carboxamidine hydrochloride: Using the procedure of Example 141, step (b) with 560 mg (1.48 mmol) methyl 4-[4-(4-chlorophenyl)(1,3-thiazol-2-yl)]-5-(methylsulfonyl)thiophene-2-carboxylate as prepared in the previous step afforded 392 mg (66%) of the title compound as a off-white solid. $^1$H-NMR (300 MHz, DMSO-d$_6$) δ 9.7 (broad s, 2H), 9.4 (broad s, 2H), 8.58 (s, 1H), 8.43 (s, 1H), 8.02 (d, 2H, J=7 Hz), 7.52 (t, 2H, J=7 Hz), 7.43 (t, 1H, J=7 Hz), and 3.90 (s, 3H). Mass spectrum (ESI, m/z): calcd. for C$_{15}$H$_{13}$N$_3$O$_2$S$_3$364.0 (M+H), found 364.1.

c) 5-Ethylthio-4-(4-phenyl(1,3-thiazol-2-yl))thiophene-2-carboxamidine hydrochloride: Using the procedure of Example 141, step (c) with 23.1 mg (0.0578 mmol) of the 4-(4-phenyl)(1,3-thiazol-2-yl))-5-(methylsulfonyl)thiophene-2-carboxamidine hydrochloride (as prepared in the previous step), 64.1 mL (0.867 mmol) of ethanethiol (in 2 portions over 2 h) and 40.3 mL (0.231 mmol) of DIEA in 3 mL of methanol gave a yellow resin which was chromatographed on a 2 g silica SPE column (Waters Sep-Pak) with a gradient of 0–15% MeOH-CH$_2$Cl$_2$, followed by trituration with CH$_2$Cl$_2$ to afford the title compound as an off-white solid (21.7 mg, 98%). $^1$H-NMR (300 MHz, DMSO-d$_6$) δ 9.45 (broad s, 2H), 9.07 (broad s, 2H), 8.68 (s, 1H), 8.28 (s, 1H), 8.09 (d, 2H, J=7 Hz), 7.51 (t, 2H, J=7 Hz), 7.40 (t, 1H, J=7 Hz), 3.23 (q, 2H, J=7 Hz) and 1.42 (t, 3H, J=7 Hz). Mass spectrum (ESI) calcd. for C$_{16}$H$_{15}$N$_3$S$_3$: 346.1 (M+H). Found: 346.2.

EXAMPLE 97

5-Methylthio-4-[4-(phenoxymethyl)(1,3-thiazol-2-yl)]thiophene-2-carboxamidine hydrochloride a) 3-Bromo-1-phenoxyacetone: To a solution of 6.c (0.050 mmol) of phenoxyacetyl chloride in 250 mL of anhyd MeCN in a 1-dram short vial (Wheaton Glass) was added 50 mL (0.100 mmol) of a 2 M solution of trimethylsilyldiazomethane in hexane and the vial capped with a PTFE-lined cap. After stirring 1 h at room temperature on a vortex shaker, the mixture was cooled (0° C.) and 21 mL (0.105 mmol) of 30 wt % HBr in acetic acid was added dropwise (gas evolution). After vortexing for 10 min, the mixture was concentrated in vacuo on a vacuum centrifuge concentrator (Speed-Vac, Savant Instruments, Inc.) to provide an amber-colored oil which was used directly in the following step.

b) Methyl 5-methylthio-4-[4-(phenoxymethyl)(1,3-thiazol-2-yl)]thiophene-2-carboxylate: To the 3-bromo-1-phenoxyacetone (as prepared in the previous step in a 1-dram vial) was added 14.8 mg (0.060 mmol) of methyl 4-(aminothioxomethyl)-5-methylthiothiophene-2-carboxylate (Maybridge Chemical Company, Cornwall, UK) as 1.48 mL of a 10 mg/mL solution in acetone. The vial was tightly capped and placed on a heated platform shaker (Innova model 4080, New Brunswick Scientific Co., Inc.) and vortexed at 55° C. and 250 rpm for 4 h. To the resulting mixture was added 50 mg (0.150 mmol) of diethylaminomethyl-polystyrene resin (Fluka Chemika-Biochemika, 3.0 mmol/g) as 0.50 mL of a 100 mg/mL suspension in acetone and the mixture vortexed briefly. Chloroacetylpolystyrene resin (30 mg, 0.150 mmol, Advanced Chem Tech Inc., 5.0 mmol/g) was then added followed by (0.750 mg, 0.005 mmol) NaI as 100 mL of a 7.5 mg/mL solution in acetone. The mixture was again capped tightly and placed on a heated platform shaker and vortexed at 55° C. and 250 rpm for 22 h. The mixture was filtered through a 2 mL fritted column (BioRad Biospin minicolumn) washing with acetone (2×0.5 mL) and MeOH (2×0.5 mL) into a 2 dram vial and concentrated on a vacuum centrifuge concentrator to afford 21.0 mg of the title compound as an off-white solid. $^1$H-NMR (300 MHz, DMSO-$d_6$) δ 8.17 (s, 1H), 7.82 (s, 1H), 7.13 (m, 2H), 7.07 (m, 2H), 6.96 (m, 1H), 5.22 (s, 2H), 3.85 (s, 3H), and 2.74 (s, 3H). Mass spectrum (MALDI-TOF, a-cyano-4-hydroxycinnamic acid matrix) calcd. for $C_{17}H_{15}NO_3S_3$: 378.0 (M+H). Found: 378.3.

b) 5-Methylthio-4-[4-(phenoxymethyl)(1,3-thiazol-2-yl)]thiophene-2-carboxamidine hydrochloride: The methyl 5-methylthio-4-[4-(phenoxymethyl)(1,3-thiazol-2-yl)]thiophene-2-carboxylate (as prepared in the previous step) under nitrogen in a 2 dram vial with a micro magnetic stir bar) was capped with an open-top phenolic cap containing a PTFE-backed silicone septum. A 1 M solution of the reagent freshly prepared from trimethylaluminum and ammonium chloride in toluene according to the procedure in Example 10, step b (0.750 mL, 0.750 mmol) was added by syringe by puncturing the septum once with the needle to allow venting of gas followed by a second puncture to inject the reagent. The vial was placed in an aluminum heating block under nitrogen (Fisher Scientific Dry Bath Incubator fitted with a custom-made nitrogen manifold cover). The manifold was flushed with nitrogen and the reaction stirred by means of a large magnetic stir motor placed inverted on top of the manifold. The reaction was heated to 100° C. for 4 h, and cooled to room temperature over ca. 2 h. The contents of the vial were quenched carefully into 0.5 g of silica gel in 2 mL of $CH_2Cl_2$, capped and shaken to homogeneity. The slurry was filtered through a 4-mL fritted column (Isolab microcolumn) into a 2-dram vial washing with $CH_2Cl_2$ (2×1 mL), $CH_2Cl_2$-MeOH (1:1, 1×1 mL) and MeOH(2×1 mL) and the filtrate concentrated on a vacuum centrifuge concentrator to a yellow solid. Filtration through a 500 mg silica SPE column (Supelco LC—Si) with 10% MeOH-$CH_2Cl_2$ afforded the title compound as a yellow solid (14.8 mg). $^1$H-NMR (300 MHz, DMSO-$d_6$) δ 9.45 (d, 2H, J=8.2 Hz), 9.11 (d, 2H, J=8.2 Hz), 8.97 (broad s, 2H), 8.65 (s, 1H), 7.90 (s, 1H), 7.0–7.5 (m, 5H), 5.25 (s, 2H), and 2.79 (s, 3H). Mass spectrum (MALDI-TOF, gentisic acid matrix) calcd. for $C_{17}H_{15}NO_3S_3$: 362.0 (M+H). Found: 361.7.

EXAMPLES 98–126

Examples 98–104 were carried out using the procedure of Example 97, steps (b) and (c) using 0.050 mmol of the reagent specified in the table. Examples 105–126 were carried out using the procedure of Example 97, steps (a), (b) and (c) using 0.05 mmol of reagent.

| | | | | Mass Spectrum (ESI) | |
| --- | --- | --- | --- | --- | --- |
| Example | Reagent | Compound | Formula | Calcd (M + H) | Found |
| 98 | 1-bromo-pinacolone | 4-[4-(tert-butyl)(1,3-thiazol-2-yl)]-5-methylthiothiophene-2-carboxamidine hydrochloride | C13 H17 N3 S3 | 312.1 | 312.2 |
| 99 | 4-fluoro-phenacyl bromide | 4-[4-(4-fluorophenyl)(1,3-thiazol-2-yl)]-5-methylthiothiophene-2-carboxamidine hydrochloride | C15 H12 F N3 S3 | 350.0 | 350.2 |
| 100 | 4-cyano-phenacyl bromide | 4-[4-(4-amidinophenyl)(1,3-thiazol-2-yl)]-5-methylthiothiophene-2-carboxamidine hydrochloride | C16 H15 N5 S3 | 374.1 | 374.2 |
| 101 | 3-fluoro-phenacyl bromide | 4-[4-(3-fluorophenyl)(1,3-thiazol-2-yl)]-5-methylthiothiophene-2-carboxamidine hydrochloride | C15 H12 F N3 S3 | 350.0 | 350.2 |
| 102 | 4-(diethylamino)-phenacyl bromide | 4-{4-[4-(diethylamino)-phenyl](1,3-thiazol-2-yl)}-5-methylthiothiophene-2-carboxamidine hydrochloride | C19 H22 N4 S3 | 403.1 | 403.2 |

-continued

| Example | Reagent | Compound | Formula | Mass Spectrum (ESI) Calcd (M + H) | Found |
|---|---|---|---|---|---|
| 103 | 3-chloro-phenacyl bromide | 4-[4-(3-chlorophenyl)(1,3-thiazol-2-yl)]-5-methylthiothiophene-2-carboxamidine hydrochloride | C15 H12 Cl N3 S3 | 366.0 | 366.1 |
| 104 | 3,4-difluoro-phenacyl bromide | 4-[4-(3,4-difluorophenyl)(1,3-thiazol-2-yl)]-5-methylthiothiophene-2-carboxamidine hydrochloride | C15 H11 F2 N3 S3 | 368.0 | 368.2 |
| 105 | 2,6-difluoro-benzoyl chloride | 4-[4-(2,6-difluorophenyl)(1,3-thiazol-2-yl)]-5-methylthiothiophene-2-carboxamidine hydrochloride | C15 H11 F2 N3 S3 | 368.0 | 368.2 |
| 106 | 4-ethoxy-benzoyl chloride | 4-[4-(4-ethoxyphenyl)(1,3-thiazol-2-yl)]-5-methylthiothiophene-2-carboxamidine hydrochloride | C17 H17 N3 O S3 | 376.1 | 376.2 |
| 107 | 4-chloro-phenoxyacetyl chloride | 4-{4-[(4-chlorophenoxy)-methyl](1,3-thiazol-2-yl)}-5-methylthiothiophene-2-carboxamidine hydrochloride | C16 H14 Cl N3 O S3 | 396.0 | 396.1 |
| 108 | cyclopentane-carbonyl chloride | 4-(4-cyclopentyl(1,3-thiazol-2-yl))-5-methylthiothiophene-2-carboxamidine hydrochloride | C14 H17 N3 S3 | 324.1 | 324.2 |
| 109 | 1-naphthoyl chloride | 5-methylthio-4-(4-naphthyl(1,3-thiazol-2-yl))thiophene-2-carboxamidine hydrochloride | C19 H15 N3 S3 | 382.1 | 382.2 |
| 110 | 3,5-dichloro-benzoyl chloride | 4-[4-(3,5-dichlorophenyl)(1,3-thiazol-2-yl)]-5-methylthiothiophene-2-carboxamidine hydrochloride | C15 H11 Cl2 N3 S3 | 400.0 | 400.1 |
| 111 | 2,5-difluorobenzoyl chloride | 4-[4-(2,5-difluorophenyl)(1,3-thiazol-2-yl)]-5-methylthiothiophene-2-carboxamidine hydrochloride | C15 H11 F2 N3 S3 | 368.0 | 368.2 |
| 112 | 9-fluorenone-4-carbonyl chloride | 5-methylthio-4-[4-(9-oxofluoren-4-yl)(1,3-thiazol-2-yl)]thiophene-2-carboxamidine hydrochloride | C22 H15 N3 O S3 | 434.1 | 434.2 |
| 113 | 3-methoxyphenyl-acetyl chloride | 4-{4-[(3 methoxyphenyl)methyl](1,3-thiazol-2-yl)}-5-methylthiothiophene-2-carboxamidine hydrochloride | C17 H17 N3 O S3 | 376.1 | 376.2 |
| 114 | 4-methyl valeroyl chloride | 4-[4-(3-methylbutyl)(1,3-thiazol-2-yl)]-5-methylthiothiophene-2 carboxamidine hydrochloride | C14 H19 N3 S3 | 326.1 | 326.2 |

-continued

| Example | Reagent | Compound | Formula | Mass Spectrum (ESI) Calcd (M + H) | Found |
|---|---|---|---|---|---|
| 115 | 3-(2-chlorophenyl)-5-methylisoxazole-4-carbonyl chloride | 4-{4-[3-(2-chlorophenyl)-5-methylisoxazol-4-yl](1,3-thiazol-2-yl)}-5-methylthiothiophene-2-carboxamidine hydrochloride | C19 H15 Cl N4 O S3 | 447.0 | 447.1 |
| 116 | 4-n-amyloxy-benzoyl chloride | 5-methylthio-4-[4-(4-pentyloxyphenyl)(1,3-thiazol-2-yl)]thiophene-2-carboxamidine hydrochloride | C20 H23 N3 O S3 | 418.1 | 418.2 |
| 117 | 1-(4-chlorophenyl)-1-cyclopentanecarbonyl-chloride | 4-{4-[(4-chlorophenyl)-cyclopentyl](1,3-thiazol-2-yl)}-5-methylthiothiophene-2-carboxamidine hydrochloride | C20 H20 Cl N3 S3 | 434.1 | 434.3 |
| 118 | 4-(trifluoro-methoxy)benzoyl chloride | 5-methylthio-4-{4-[4-(trifluoromethoxy)phenyl](1,3-thiazol-2-yl)}thiophene-2-carboxamidine hydrochloride | C16 H12 F3 N3 O S3 | 416.0 | 416.1 |
| 119 | 3-chloro-benzo[b]thiophene-2-carbonyl chloride | 4-[4-(3-chlorobenzo[b]thiophen-2-yl)(1,3-thiazol-2-yl)]-5-methylthiothiophene-2-carboxamidine hydrochloride | C17 H12 Cl N3 S4 | 422.0 | 422.1 |
| 120 | 3-(2-chloro-6-fluorophenyl)-5-methylisoxazole-4-carbonyl chloride | 4-{4-[3-(6-chloro-2-fluorophenyl)-5-methylisoxazol-4-yl](1,3-thiazol-2-yl)}-5-methylthiothiophene-2-carboxamidine hydrochloride | C19 H14 Cl F N4 O S3 | 465.0 | 465.1 |
| 121 | 3-cyanobenzoyl chloride | 4-[4-(3-amidinophenyl)(1,3-thiazol-2-yl)]-5-methylthiothiophene-2-carboxamidine hydrochloride | C16 H15 N5 S3 | 374.1 | 374.7 |
| 122 | 4-methoxyphenyl-acetyl chloride | 4-{4-[(4-methoxyphenyl)-methyl](1,3-thiazol-2-yl)}-5-methylthiothiophene-2-carboxamidine hydrochloride | C17 H17 N3 O S3 | 376.1 | 376.2 |
| 123 | 3-(t-butyl)-1-benzylpyrazole-5-carbonyl chloride | 4-{4-[3-(tert-butyl)pyrazol-5-yl](1,3-thiazol-2-yl)}-5-methylthiothiophene-2-carboxamidine hydrochloride | C16 H19 N5 S3 | 378.1 | 378.2 |
| 124 | 3-(4-chlorophenyl)-2,2-dimethyl-propanoyl chloride | 5-methylthio-4-[4-(1-methylvinyl)(1,3-thiazol-2-yl)]thiophene-2-carboxamidine hydrochloride | C12 H13 N3 S3 | 296.0 | 296.2 |
| 125 | n-(1-naphthalene-sulfonyl)-1-phenylalanyl chloride | 5-methylthio-4-(4-{1-[(naphthylsulfonyl)amino]-2-phenylethyl}(1,3-thiazol-2-yl))thiophene-2-carboxamidine hydrochloride | C27 H24 N4 O2 S4 | 565.1 | 565.1 |
| 126 | 2-bromo-5-methoxybenzoyl chloride | 4-[4-(2-bromo-5-methoxyphenyl)(1,3-thiazol-2-yl)]-5-methylthiothiophene-2-carboxamidine hydrochloride | C16 H14 Br N3 O S3 | 440.0 | 440.2 |

EXAMPLE 127 a) 1-[3,5-Bis(trifluoromethyl)phenyl]-2-bromoethan-1-one: A stirred suspension of 1 g (3.9 mmol) of 3,5-bis(trifluoromethyl)acetophenone (Lancaster, Windham, N.H., U.S.A.) in dry methanol (20 mL) and 1 g (15 mmol, 2.6 eq) of poly(4-vinyl pyridinium tribromide) (Aldrich, Milwaukee, Wis., U.S.A.) was protected from moisture with dry nitrogen, and heated at reflux for 70 min. The polymer was filtered from the cooled solution and washed with methanol and twice with dichloromethane. The solvents were removed in vacuo to give 1-[3,5-bis(trifluoromethyl)phenyl]-2-bromoethan-1-one (1.2 g, 92%). $^1$H-NMR (DMSO-$d_6$; 300 MHz) δ 8.43 (m, 2H), 8.12 (m, 1H), 4.46 (s, 3H).

b) Methyl 4-{4-[3,5-bis(trifluoromethyl)phenyl]1,3-thiazol-2-yl)}-5-methylthiothiophene-2-carboxylate: A solution of 75 mg (0.3 mmol) of methyl 4-(aminothioxomethyl)-5-methylthiothiophene-2-carboxylate (Maybridge, Cornwall, UK) was reacted with 101 mg (0.3 mmol) of 1-[3,5-bis(trifluoromethyl)phenyl]-2-bromoethane-1-one in a manner similar Example 8, step (a) to give methyl 4-{4-[3,5-bis(trifluoromethyl)phenyl](1,3-thiazol-2-yl)}-5-methylthiothiophene-2-carboxylate (7 mg, 5%) as a solid. $^1$H-NMR (DMSO-$d_6$; 300 MHz) δ 8.75 (s, 1H), 8.73 (m, 2H), 8.29 (s, 1H), 8.13 (m, 1H), 3.87 (s, 3H), 2.79 (s, 3H). Mass spectrum (MALDI-TOF, CHCA matrix, m/z): Calcd. for $C_{18}H_{11}NO_2S_3F_6$, 484.0 (M+H), found 484.0.

c) 4-{4-[3,5-Bis(trifluoromethyl)phenyl](1,3-thiazol-2-yl)}-5-methylthiothiophene-2-carboxamidine: Methyl 4-[4-3,5-bis(trifluoromethyl)phenyl](1,3-thiazol-2-yl)}-5-methylthiothiophene-2-carboxylate (7 mg, 14.5 mmol) was treated in a manner similar to that for Example 10, step (b), to give 4-{4-[3,5-bis(trifluoromethyl)phenyl](1,3-thiazol-2-yl)}-5-methylthiothiophene-2-carboxamidine (6 mg, 89%) as a yellow solid. $^1$H-NMR (DMSO-$d_6$; 300 MHz) 8.78 (s, 1H), 8.74 (s, 2H), 8.62 (s, 1H), 8.15 (s, 1H), 2.82 (s, 3H). Mass spectrum (MALDI-TOF, CHCA matrix, m/z): Calcd. for $C_{17}H_{11}N_3S_3F_6$, 468.0 (M+H), found 468.0.

EXAMPLE 128 a) 2-Bromo-1-[3-fluoro-5-(trifluoromethyl)phenyl]ethan-1-one: A stirred suspension of 1 g (4.5 mmol) of 3-fluoro-5-(trifluoromethyl)acetophenone (Lancaster, Windham, N.H., U.S.A.) was treated in a manner similar to that for Example 127, step (a) to give of a 1:1 mixture of 2-bromo-1-[3-fluoro-5-(trifluoromethyl)phenyl]ethan-1-one and dibrominated product (1.6 g, 100%). $^1$H-NMR (DMSO-$d_6$; 300 MHz) δ 8.25–7.52 (m, 6H), 6.54 (s, 1H), 4.42 (s, 2H).

b) Methyl 4-{4-[3-fluoro-5-(trifluoromethyl)phenyl](1,3-thiazol-2-yl))-5-methylthiothiophene-2-carboxylate: A solution of 75 mg (0.3 mmol) of methyl 4-(aminothioxomethyl)-5-methylthiothiophene-2-carboxylate (Maybridge, Cornwall, UK) was reacted with of 86 mg (0.3 mmol) 2-bromo-1-[3-fluoro-5-(trifluoromethyl)phenyl]ethan-1-one in a manner similar to Example 8, step (a) to give, methyl 4-{4-[3-fluoro-5-(trifluoromethyl)phenyl](1,3-thiazol-2-yl)}-5 -methylthiothiophene-2-carboxylate (41 mg, 31%) as a solid. $^1$H-NMR (DMSO-$d_6$; 300 MHz) δ 8.59 (s, 1H), 8.29 (m, 1H), 8.27 (s, 1H), 8.25 and 8.21 (m, 1H, 1:1 ratio conformers), 7.73 and 7.70 (m, 1 H, 1:1 ratio conformers). Mass spectrum (MALDI-TOF, CHCA matrix, m/z): Calcd. for $C_{17}H_{11}NO_2S_3F_4$, 434.0 (M+H), found 434.0.

c) 4-{4-[3-Fluoro-5-(trifluoromethyl)phenyl](1,3-thiazol-2-yl)}-5-methylthiothiophene-2-carboxamidine: Methyl 4-{4-[3-fluoro-5-(trifluoromethyl)phenyl](1,3-thiazol-2-yl)}-5-methylthiothiophene-2-carboxylate (40 mg, 0.92 mmol) was treated in a manner similar to that for Example 10, step (b), to give 4-{4-[3-fluoro-5-(trifluoromethyl)phenyl](1,3-thiazol-2-yl)}-5-methylthiothiophene-2-carboxamidine (31 mg, 81%) as a yellow solid. $^1$H-NMR (DMSO-$d_6$; 300 MHz) δ 9.36 (br s, 2H), 9.01 (br s, 2H), 8.68 (s, 1H), 8.63 (s, 1H), 8.30 (m, 1H), 8.25 and 8.22 (m, 1H, 1:1 ratio conformers), 7.75 and 7.73 (m, 1H, 1:1 ratio conformers), 2.82 (s, 3H). Mass spectrum (MALDI-TOF, CHCA matrix, m/z): Calcd. for $C_{16}H_{11}N_3S_3F_4$, 418.5 (M+H), found 418.0.

EXAMPLE 129 a) 2-Bromo-1-[3-fluoro-5-(trifluoromethyl)phenyl]propan-1-one: A stirred suspension of 1 g (4.5 mmol) of 1-[3-fluoro-5-(trifluoromethyl)phenyl]propan-1-one (Lancaster, Windham, N.H., U.S.A.) was treated in a manner similar to that for Example 127, step (a) to give 2-bromo-1-[3-fluoro-5-(trifluoromethyl)phenyl]propan-1-one (1.33 g, 99%). $^1$H-NMR (DMSO-$d_6$; 300 MHz) δ 8.07 (m, 1H), 7.92 and 7.89 (m, 1H, 1:1 ratio conformers), 7.57 and 7.55 (m, 1H, 1:1 ratio conformers), 5.20 (q, 1H, J=6.6 Hz), 1.93 (d, 3H, J=6.6 Hz).

b) Methyl 4-{4-[3-fluoro-5-(trifluoromethyl)phenyl]-5-methyl(1,3-thiazol-2-yl)}-5-methylthiothiophene-2-carboxylate: A solution of 75 mg (0.3 mmol) of methyl 4-(aminothioxomethyl)-5-methylthiothiophene-2-carboxylate (Maybridge, Cornwall, UK) was reacted with 90 mg (0.3 mmol) of 2-bromo-1-[3-fluoro-5-(trifluoromethyl)phenyl]propan-1-one in a manner similar to Example 8, step (a) to give, methyl 4-{4-[3-fluoro-5-(trifluoromethyl)phenyl]-5-methyl(1,3-thiazol-2-yl)}-5-methylthiothiophene-2-carboxylate (31.9 mg, 24%) as a solid. $^1$H-NMR (DMSO-$d_6$; 300 MHz) δ 8.17 (s, 1H), 7.98 (m, 1H), 7.95 and 7.92 (m, 1H, 1:1 ratio conformers), 7.77 and 7.74 (m, 1H, 1:1 ratio conformers), 3.87 (s, 3H), 2.75 (s, 3H), 2.70 (s, 3H). Mass spectrum (MALDI-TOF, CHCA matrix, m/z): Calcd. for $C_{18}H_{13}NO_2S_3F_4$, 448.0 (M+H), found 448.0.

c) 4-{4-[3-Fluoro-5-(trifluoromethyl)phenyl]-5-methyl(1,3-thiazol-2-yl)}-5-methylthiothiophene-2-carboxamidine: Methyl 4-{4-[3-fluoro-5-(trifluoromethyl)phenyl]-5-methyl(1,3-thiazol-2-yl)}-5-methylthiothiophene-2-carboxylate (30 mg, 0.067 mmol) was treated in a manner similar to that for Example 10, step (b), to give 4-{4-[3-fluoro-5-(trifluoromethyl)phenyl]-5-methyl(1,3-thiazol-2-yl)}-5-methylthiothiophene-2-carboxamidine (32 mg, quantitive yield) as a yellow solid. $^1$H-NMR (DMSO-$d_6$; 300 MHz) δ 9.42 (br s, 2H), 9.03 (br s, 2H), 8.60 (s, 1H), 7.98 (m, 1H), 7.95 and 7.92 (m, 1H, 1:1 ratio conformers), 7.79 and 7.76 (m, 1H, 1:1 ratio conformers), 2.78 (s, 3H), 2.71 (s, 3H). Mass spectrum (MALDI-TOF, CHCA matrix, m/z): Calcd. for $C_{17}H_{13}N_3S_3F_4$, 432.0 (M+H), found 432.6.

EXAMPLE 130 a) 1-[3,5-Bis(trifluoromethyl)phenyl]-2-bromopropan-1-one: A stirred suspension of 1 g (3.7 mmol) of 1-[3,5-bis(trifluoromethyl)phenyl]-propan-1-one (Lancaster, Windham, N.J., U.S.A.) treated in a manner similar to that for Example 127, step (a) to give 2-bromo-1-[3-fluoro-5-(trifluoromethyl)phenyl]propan-1-one (1.1 g, 86%). $^1$H-NMR (DMSO-$d_6$; 300 MHz) δ 8.46 (m, 2H), 8.09 (m, 1), 5.26 (q, 1H, J=6.6Hz), 1.96 (d, 3H, J=6.5 Hz). Mass spectrum (MALIDI-TOF, CHCA matrix, m/z): Calcd. for $C_{11}H_7OBrF_6$, 349.0 (M+H), found 348.9.

b) Methyl 4-{4-[3,5-bis(trifluoromethyl)phenyl]-5-methyl(1,3-thiazol-2-yl)}-5-methylthiothiophene-2- carboxylate: A solution of 75 mg (0.3 mmol) of methyl 4-(aminothioxomethyl)-5-methylthiothiophene-2-carboxylate (Maybridge, Cornwall, UK) was reacted with 105 mg 1-[3,5-Bis(trifluoromethyl)phenyl]-2-bromopropan-1-one in a manner similar to Example 8, step (a) to give, after preparative thin-layer chromatrography purification, methyl 4-{4-[3,5-bis(trifluoromethyl)phenyl]-5-methyl(1,3-thiazol-2-yl)}-5-methylthiothiophene-2-carboxylate (16.2 mg, 11%) as a solid. $^1$H-NMR (DMSO-$d_6$; 300 MHz) δ 8.41 (m, 2H), 8.18 (m, 2H), 3.86 (s, 3H), 2.75 (s, 3H), 2.71 (s, 3H). Mass spectrum (MALDI-TOF, CHCA matrix, m/z): Calcd. for $C_{19}H_{13}NO_2S_3F_6$, 498.0 (M+H), found 497.6.

c) 4-{4-[3,5-Bis(trifluoromethyl)phenyl]-5-methyl(1,3-thiazol-2-yl)}-5-methylthiothiophene-2-carboxamidine: Methyl 4-{4-[3,5-bis(trifluoromethyl)phenyl]-5-methyl(1,3-thiazol-2-yl)}-5-methylthiothiophene-2-carboxylate (15 mg, 0.031 mmol) was treated in a manner similar to that for Example 10, step (b), to give 4-{4-[3,5-bis(trifluoromethyl)phenyl]-5-methyl(1,3-thiazol-2-yl)}-5-methylthiothiophene-2-carboxamidine (13 mg, 88%) as a yellow solid. $^1$H-NMR (DMSO-$d_6$; 300 MHz) δ 9.39 (br s, 2H), 8.94 (br s, 2H), 8.58 (s, 1H), 8.40 (m, 2H), 8.19 (m, 1H), 2.79 (s, 3H), 2.73 (s, 3H). Mass spectrum (MALDI-TOF, CHCA matrix, m/z): Calcd. for $C_{18}H_{13}N_3S_3F_6$, 482.0 (M+H), found 482.5.

EXAMPLE 131 a) 2-Bromo-1,2-diphenylethan-1-one: A stirred suspension of 0.2 g (1 mmol) of deoxybenzoin was treated in a manner similar to that for Example 127, step (a) to give 2-bromo-1,2-diphenylethan-1-one (270 mg, 98%). $^1$H-NMR (DMSO-$d_6$; 300 MHz) δ 8.10–8.06 (m, 2H), 7.95–7.31 (m, 8H), 7.21 (s, 1H).

b) Methyl 4-(4,5-diphenyl(1,3-thiazol-2-yl))-5-methylthiothiophene-2-carboxylate: A solution of 75 mg (0.3 mmol) of methyl 4-(aminothioxomethyl)-5-methylthiothiophene-2-carboxylate (Maybridge, Cornwall, UK) was reacted with 92 mg, 0.3 mmol of 2-bromo-1,2-diphenylethan-1-one in a manner similar to Example 8, step (a) to give, after preparative thin-layer chromatography purification, methyl 4-(4,5-diphenyl(1,3-thiazol-2-yl))-5-methylthiothiophene-2-carboxylate (9 mg, 7%) as a solid. $^1$H-NMR (DMSO-$d_6$; 300 MHz) δ 8.94 (br s, 0.4H), 8.66 (s, 1H), 8.60 (br s, 0.3H), 8.08 (s, 1H), 7.93 and 7.20 (AB quartet, 2H, J=8.7 Hz), 7.68 and 7.35 (AB quartet, 2H, J=8.2 Hz), 2.77 (s, 3H), ), 2.33 (s, 3H). Mass spectrum (MALDI-TOF, CHCA matrix, m/z): Calcd. for $C_{22}H_{17}NO_2S_3$, 424.0 (M+H), found 424.3.

c) 4-(4,5-Diphenyl(1,3-thiazol-2-yl))-5-methylthiothiophene-2-carboxamidine: Methyl 4-(4,5-diphenyl(1,3-thiazol-2-yl))-5-methylthiothiophene-2-carboxylate (9 mg, 0.021 mmol) was treated in a manner similar to that for Example 10, step (b), to give 4-(4,5-diphenyl(1,3-thiazol-2-yl))-5-methylthiothiophene-2-carboxamidine (3 mg, 35%) as a brown oil. Mass spectrum (MALDI-TOF, CHCA matrix, m/z): Calcd. for $C_{21}H_{17}N_3S_3$, 408.1 (M+H), found 408.0.

EXAMPLE 132 a) Methyl 4-(4-benzo[b]thiophen-2-yl(1,3-thiazol-2-yl))-5-methylthiothiophene-2-carboxylate: A solution of 75 mg (0.3 mmol) of methyl 4-(aminothioxomethyl)-5-methylthiothiophene-2-carboxylate was reacted with 77 mg (0.3 mmol) of 3-bromoacetylbenzo[b]thiophene (Maybridge, Cornwall, UK) in a manner similar to Example 8, step (a) to give, after preparative thin-layer chromatrography purification, methyl 4-(4-benzo[b]thiophen-2-yl(1,3-thiazol-2-yl))-5-methylthiothiophene-2-carboxylate (28 mg, 23%) as a solid. $^1$H-NMR (DMSO-$d_6$; 300 MHz) δ 8.63 (d, 1H, J=7.4 Hz), 8.30 (s, 1H), 8.25 (s, 1H), 8.22 (s, 1H), 7.53–7.46 (m, 2H), 3.87 (s, 3H), 2.78 (s, 3H).

b) 4-(4-Benzo[b]thiophen-2-yl(1,3-thiazol-2-yl))-5-methylthiothiophene-2-carboxamidine: Methyl 4-(4-benzo[b]thiophen-2-yl(1,3-thiazol-2-yl))-5-methylthiothiophene-2-carboxylate (28 mg, 0.69 mmol) was treated in a manner similar to that for Example 10, step (b), to give 4-(4-benzo[b]thiophen-2-yl(1,3-thiazol-2-yl))-5-methylthiothiophene-2-carboxamidine (17 mg, 64%) as a brown solid. $^1$H-NMR (DMSO-$d_6$; 300 MHz) δ 9.22 (br s, 4H), 8.68 (s, 1H), 8.66 (d, 1H, J=7.6 Hz), 8.30 (s, 1H), 8.25 (s, 1H), 8.10 (d, 1H, J=7.3 Hz), 7.55–7.45 (m, 2H), 2.81 (s, 3H). Mass spectrum (MALDI-TOF, GA matrix, m/z): Calcd. for $C_{17}H_{13}N_3S_4$, 388.0 (M+H), found 388.2.

EXAMPLE 133 a) Methyl 4-(4-benzo[d]benzo[3,4-b]furan-3-yl(1,3-thiazol-2-yl))-5-methylthiothiophene-2-carboxylate: A solution of 75 mg (0.3 mmol) of methyl 4-(aminothioxomethyl)-5-methylthiothiophene-2-carboxylate (Maybridge, Cornwall, UK) was reacted with 86 mg (0.3 mmol) of 2-(bromoacetyl)-dibenzofuran (Aldrich, Milwaukee, Wis., U.S.A.) in a manner similar to Example 8, step (a) to give, after preparative thin-layer chromatography purification, methyl 4-(4,5-diphenyl(1,3-thiazol-2-yl))-5-methylthiothiophene-2-carboxylate (45 mg, 36%) as a solid. $^1$H-NMR (DMSO-$d_6$; 300 MHz) δ 8.83–7.44 (m, 7H), 8.29 (s, 1H), 8.27 (s, 1H), 3.88 (s, 3H), 2.80 (s, 3H). Mass spectrum (MALDI-TOF, CHCA matrix, m/z): Calcd. for $C_{22}H_{15}NO_3S_3$, 438.0 (M+H), found 438.5.

b) 4-4-Benzo[d]benzo[3,4-b]furan-3-yl(1,3-thiazol-2-yl))-5-methylthiothiophene-2-carboxamidine: Methyl 4-(4-benzo[d]benzo[3,4-b]furan-3-yl(1,3-thiazol-2-yl))-5-methylthiothiophene-2-carboxylate (45 mg, 0.11 mmol) was treated in a manner similar to that for Example 10, step (b), to give 4-4-benzo[d]benzo[3,4-b]furan-3-yl(1,3-thiazol-2-yl))-5-methylthiothiophene-2-carboxamidine (16.8 mg, 36%) as a yellow solid. $^1$H-NMR (DMSO-$d_6$; 300 MHz) δ 9.72–9.10 (m, 3H), 8.84–7.31 (m, 9H), 2.84 (s, 3H). Mass spectrum (MALDI-TOF, CHCA matrix, m/z): Calcd. for $C_{21}H_{15}N_3OS_3$, 422.0 (M+H), found 421.9.

EXAMPLE 134 a) Methyl 4-(4-(4-nitrophenyl)(1,3-thiazol-2-yl))-5-methylthiothiophene-2-carboxylate: A solution of 1 g (4 mmol) of methyl 4-(aminothioxomethyl)-5-methylthiothiophene-2-carboxylate (Maybridge, Cornwall, UK) was reacted with 987 mg (4 mmol) of 2-bromo-4'-nitroacetophenone in a manner similar to Example 8, step (a) to give methyl 4-(4-(4-nitrophenyl)(1,3-thiazol-2-yl))-5-methylthiothiophene-2-carboxylate (1.7 g, quantitive yield) as a brown solid. $^1$H-NMR (DMSO-$d_6$; 300 MHz) δ 8.57 (s, 1H), 8.34 (s, 4H), 8.25 (s, 1H), 3.94 (s, 3H), 3.81 (s, 3H). Mass spectrum (MALDI-TOF, CHCA matrix, m/z): Calcd. for $C_{16}H_{12}N_2O_4S_3$ 393.0 (M+H), found 392.8.

b) Methyl 4-(4-(4-aminophenyl)(1,3-thiazol-2-yl))-5-methylthiothiophene-2-carboxylate: Methyl 4-(4-(4-nitrophenyl)(1,3-thiazol-2-yl))-5-methylthiothiophene-2-carboxylate (800 mg, 2 mmol) was dissolved in 150 mL tetrahydrofuran and treated with 20% titanium chloride solution (Fisher Scientific, Pittsburgh, Pa., U.S.A.) for 1 h. The mixture was poured into 2 M sodium hydroxide solution (100 mL), extracted with dichloromethane (4×50 mL). The combined organic layers were washed with saturated brine solution and dried over anhydrous sodium sulfate. The solid was filtered off, and the solvent removed in vacuo. This material was purified by column chromatography on silica gel (30 g) eluting with dichloromethane:methanol 98/2 (v:v) to give methyl 4-(4-(4-aminophenyl)(1,3-thiazol-2-yl))-5-methylthiothiophene-2-carboxylate (500 mg, 69%) as a solid. $^1$H-NMR (DMSO-d$_6$; 300 MHz) δ 8.17 (s, 1H), 7.77 (s, 1H), 7.74 and 6.62 (AB quartet, 2H, J=8.6 Hz), 5.35 (s, 2H), 3.86 (s, 3H), 2.74 (s, 3H). ). Mass spectrum (MALDI-TOF, CHCA matrix, m/z): Calcd. for $C_{16}H_{14}N_2O_2S_3$ 363.0 (M+H), found 362.4.

c) Methyl 4-(4-{4-[(methylsulfonyl)amino]phenyl}(1,3-thiazol-2-yl))-5-methylthiothiophene-2-carboxylate: Methyl 4-(4-(4-aminophenyl)(1,3-thiazol-2-yl))-5-methylthiothiophene-2-carboxylate (200 mg, 0.55 mmol) was dissolved in dry dichloromethane (20 mL). To this, N-methyl morpholine (150 μL, 1.38 mmol) and dimethylaminopyridine (6.1 mg, 0.055 mmol) were added, the mixture was cooled on an ice bath, and methanesulfonyl chloride (43 μL, 0.55 mmol) was added dropwise. The mixture was then stirred for 8 days at room temperature. The mixture was partitioned between saturated sodium bicarbonate (50 mL) and dichloromethane (20 mL). The aqueous layer was extracted with dichloromethane (3×20 mL), and the combined organic layers were washed with saturated sodium bicarbonate (20 mL), brine (2×20 mL), and dried over anhydrous sodium sulfate. The solvent was removed in vacuo. Column chromatrography on silica gel (100 g) eluting with dichloromethane:methanol 99/1 (v:v), gave methyl 4-(4-{4-[(methylsulfonyl)amino]phenyl}(1,3-thiazol-2-yl))-5-methylthiothiophene-2-carboxylate (155 mg, 64%) as a solid. $^1$H-NMR (DMSO-d$_6$; 300 MHz) δ 9.92 (s, 1H), 8.22 (s, 1H), 8.11 (s, 1H), 8.40 and 6.90 (AB quartet, 2H, J=8.7 Hz), 3.87 (s, 3H), 3.05 (s, 3H), 2.76 (s, 3H). Mass spectrum (MALDI-TOF, CHCA matrix m/z): Calcd. for $C_{17}H_{16}N_2O_4S_4$ 441.0 (M+H), found 441.2.

d) 4-(4-{4-[(Methylsulfonyl)amino]phenyl(1,3-thiazol-2-yl))-5-methylthiothiophene-2-carboxamidine: Methyl 4-(4-{4-[(methylsulfonyl)amino]phenyl}(1,3-thiazol-2-yl))-5-methylthiothiophene-2-carboxylate (81 mg, 0.184 mmol) was treated in a manner similar to that for Example 10, step (b), to give 4-(4-{4-[(methylsulfonyl)amino]phenyl}(1,3-thiazol-2-yl))-5-methylthiothiophene-2-carboxamidine (24.9 mg, 32%) as a light brown solid. $^1$H-NMR (DMSO-d$_6$; 300 MHz) δ 10.0 (br s, 1H), 9.3 (br s, 2H), 8.98 (s, 1H), 8.65 (s, 1H), 8.21 (s, 1H), 7.98 and 7.5 (AB quartet, 2H, J=8.6 Hz), 3.05 (s, 3H), 2.79 (s, 3H). Mass spectrum (MALDI-TOF, CHCA matrix, m/z): Calcd. for $C_{16}H_{16}N_4O_2S_4$ 425.0 (M+H), found 425.1.

EXAMPLE 135 a) Methyl 4-(4-{4-[(phenylsulfonyl)amino]phenyl}(1,3-thiazol-2-yl))-5-methylthiothiophene-2-carboxylate: Methyl 4-(4-(4-aminophenyl)(1,3-thiazol-2-yl))-5-methylthiothiophene-2-carboxylate (100 mg, 0.28 mmol) was dissolved in dry dichloromethane (10 mL). To this, N-methyl morpholine (46 μL, 0.42 mmol) and dimethylaminopyridine (3.4 mg, 0.028 mmol) were added, the mixture was cooled on an ice bath, and benzenesulfonyl chloride (35 μL, 0.28 mmol) was added dropwise. The mixture was then stirred for 24 h at room temperature. Workup was carried out as in Example 134, step (c). Trituration with dichloromethane and methanol gave methyl 4-(4-{4-[(phenylsulfonyl)amino]phenyl}(1,3-thiazol-2-yl))-5-methylthiothiophene-2-carboxylate (44 mg, 31%) as a crystalline solid. $^1$H-NMR (DMSO-d$_6$; 300 MHz) δ 10.46 (s, 1H), 8.19 (s, 1H), 8.05 (s, 1H), 7.91 and 7.19 (AB quartet, 2H, J=8.7 Hz), 7.81 (m, 2H), 7.64–7.54 (m, 3H) 3.85 (s, 3H), 2.74 (s, 3H). Mass spectrum (MALDI-TOF, CHCA matrix, m/z): Calcd. for $C_{22}H_{18}N_2O_4S_4$ 504.2 (M+H), found 504.1 b) 4-(4-{4-[(Phenylsulfonyl)amino]phenyl}(1,3-thiazol-2-yl))-5-methylthiothiophene-2-carboxamidine: Methyl 4-(4-{4-[(phenylsulfonyl)amino]phenyl}(1,3-thiazol-2-yl))-5-methylthiothiophene-2-carboxylate (30 mg, 0.060 mmol) was treated in a manner similar to that for Example 10, step (b), to give 4-(4-{4-[(phenylsulfonyl)amino]phenyl}(1,3-thiazol-2-yl))-5-methylthiothiophene-2-carboxamidine (12.6 mg, 43%) as a yellow solid. $^1$H-NMR DMSO-d$_6$; 300 MHz) δ 9.13 (br s, 3H), 8.60 (s, 1H), 8.08 (s, 1H) 7.93 and 7.20 (AB quartet, 2H, J=8.7 Hz), 7.82–7.79 (m, 2H), 7.65–7.53 (m, 3H) 3.85 (s, 3H), 2.74 (s, 3H). Mass spectrum (MALDI-TOF, CHCA matrix, m/z): Calcd. for $C_{21}H_{18}N_4O_2S_4$, 87.0 (M+H), found 487.7.

EXAMPLE 136 a) Methyl 4-(4-{4-[(trifluoromethylsulfonyl)amino]phenyl}(1,3-thiazol-2-yl))-5-methylthiothiophene-2-carboxylate: Methyl 4-(4-(4-aminophenyl)(1,3-thiazol-2-yl))-5-methylthiothiophene-2-carboxylate (200 mg, 0.55 mmol) was dissolved in dry pyridine (20 mL). The mixture was cooled on an ice bath, and trifluoromethanesulfonic anhydride (0.5 mL, 3 mmol) was added. The mixture was then stirred for 1.5 h at room temperature. Workup was carried out as in Example 134, step (c). Column chromatrography on silica gel (30 g) eluting with hexanes:ethyl acetate 7/3 (v:v), followed by preparative thin layer chromatography eluting with dichloromethane:methanol 99/1 (v:v) gave methyl 4-(4-{4-[(trifluoromethylsulfonyl)amino]phenyl}(1,3-thiazol-2-yl))-5-methylthiothiophene-2-carboxylate (160 mg, 59%) as a solid. $^1$H-NMR (DMSO-d$_6$; 300 MHz) δ 8.48 and 7.87(s, 3/2 ratio conformers, 1H), 8.23 (s, 1H), 8.21 (s, 1H), 8.29 and 7.84 (AB quartet, 2H, 2/3 ratio conformers, J=8.7 Hz), 8.10 and 7.37 (AB quartet, 2H, J=8.7 Hz), 3.87 and 3.86 (s, 2/3 ratio conformers, 3H), 2.77 and 2.76 (s, 2/3 ratio conformers, 3H). Mass spectrum (MALDI-TOF, CHCA matrix, m/z): Calcd. for $C_{17}H_{13}N_2O_4S_4F_4$ 495.0 (M+H), found 495.6 b) 4-(4-{4-[(Trifluoromethylsulfonyl)amino]phenyl}(1,3-thiazol-2-yl))-5-methylthiothiophene-2-carboxamidine: Methyl 4-(4-{4-[(trifluoromethylsulfonyl)amino]phenyl}(1,3-thiazol-2-yl))-5-methylthiothiophene-2-carboxylate (30 mg, 0.061 mmol) was treated in a manner similar to that for Example 10, step (b), to give of 4-(4-{4-[(trifluoromethylsulfonyl)amino]phenyl}(1,3-thiazol-2-yl))-5-methylthiothiophene-2-carboxamidine (21.6 mg, 74%) as a light brown solid. $^1$H-NMR (DMSO-d$_6$; 300 MHz) δ 9.39 (br s, 2H), 8.97 (br s, 2H), 8.64 (s, 1H), 8.24 (s, 1H), 8.12 and 7.39 (AB quartet, 2H, J=8.7 Hz), 4.78 (br s, 1H), 2.79 (s, 3H). Mass spectrum (MALDI-TOF, CHCA matrix, m/z): Calcd. for $C_{16}H_{13}N_4O_2S_4F_3$, 479.0 (M+H), found 479.5.

EXAMPLE 137 a) Methyl 4-(4-{4-[(toluenesulfonyl)amino]phenyl}(1,3-thiazol-2-yl))-5-methylthiothiophene-2-carboxylate: Methyl 4-(4-(4-aminophenyl)(1,3-thiazol-2-yl))-5-methylthiothiophene-2-carboxylate (33 mg, 0.09 mmol) was dissolved in dry dichloromethane (5 mL). To this, N-methyl morpholine (10 μL, 0.09 mmol) and p-toluenesulfonyl chloride (17 mg, 0.09 mmol) was added and the mixture was stirred at room temperature for 5 days. Workup was carried out as in Example 134, step (c). Trituration with dichloromethane and methanol gave methyl 4-(4-{4-

[(toluenesulfonyl)amino]phenyl}(1,3-thiazol-2-yl))-5-methylthiothiophene-2-carboxylate (20 mg, 43%) as a brown solid. $^1$H-NMR (DMSO-d$_6$; 300 MHz) δ 10.39 (s, 1H), 8.19 (s, 1H), 8.05 (s, 1H), 7.91 and 7.18 (AB quartet, 2H, J=8.7 Hz), 7.68 and 7.35 (AB quartet, 2H, J=8.2 Hz), 3.85 (s, 3H), 2.74 (s, 3H), 2.27 (s, 3H). Mass spectrum (MALDI-TOF, CHCA matrix, m/z): Calcd. for C$_{23}$H$_{20}$N$_2$O$_4$S$_4$, 517.2 (M+H), found 517.0.

b) 4-(4-{4-[(Toluenesulfonyl)amino]phenyl}(1,3-thiazol-2-yl))-5-methylthiothiophene-2-carboxamidine: Methyl 4-(4-{4-[(toluenesulfonyl)amino]phenyl}(1,3-thiazol-2-yl))-5-methylthiothiophene-2-carboxylate (15 mg, 0.029 mmol) was treated in a manner similar to that for Example 10, step (b), to give 4-(4-{4-[(toluenesulfonyl)amino]phenyl}(1,3-thiazol-2-yl))-5-methylthiothiophene-2-carboxamidine (17.9 mg, 81%) as a light brown solid. $^1$H-NMR (DMSO-d$_6$; 300 MHz) δ 8.94 (br s, 0.4H), 8.66 (s, 1H), 8.60 (br s, 0.3H), 8.08 (s, 1H), 7.93 and 7.20 (AB quartet, 2H, J=8.7 Hz), 7.68 and 7.35 (AB quartet, 2H, J=8.2 Hz), 2.77 (s, 3H), 2.33 (s, 3H). Mass spectrum (MALDI-TOF, CHCA matrix, m/z): Calcd. for C$_{22}$H$_{20}$N$_4$O$_2$S$_4$: 501.1 (M+H), found 501.1.

EXAMPLE 138 a) Methyl 4-[4-(4-chlorophenyl)(1,3-thiazol-2-yl)]-5-(methylsulfinyl)thiophene-2-carboxylate: To a stirred solution of 764 mg (2 mmol) of methyl 4-[4-(4-chlorophenyl)(1,3-thiazol-2-yl)]-5-methylthiothiophene-2-carboxylate (Maybridge, Cornwall, UK) dissolved in 1,1,1,3,3,3-hexafluoroisopropanol (2.5 mL) was added 30% hydrogen peroxide (0.45 mL, 4 mmol). This solution was stirred for 45 h at room temperature. Dichloromethane (10 mL) was added after 2 hours. Additional hydrogen peroxide (2×0.45 mL portions) was added after 4 hours and 24 hours. The mixture was quenched with 10% sodium sulfite in brine (4 mL). The organic layer was separated, dried over anhydrous sodium sulfate, and the solvents removed in vacuum. Column chromatography on silica gel (45 g), eluting with dichloromethane:methanol 99/1 (v:v) gave methyl 4-[4-(4-chlorophenyl)(1,3-thiazol-2-yl)]-5-(methylsulfinyl)thiophene-2-carboxylate (720 mg, 90%) as a solid. $^1$H-NMR (DMSO-d$_6$; 300 MHz) δ 8.37 (s, 1H), 8.30 (s, 1H), 8.05 and 7.52 (AB quartet, 2H, J=8.6 Hz), 3.91 (s, 3H), 3.16 (s, 3H). Mass spectrum (MALDI-TOF, GA matrix, m/z): Calcd. for C$_{16}$H$_{12}$NO$_3$S$_3$Cl:398.0 (M+H), found 397.8.

b) 4-[4-(4-Chlorophenyl)(1,3-thiazol-2-yl)]-5-(methylsulfinyl)thiophene-2-carboxamidine: Methyl 4-[4-(4-chlorophenyl)(1,3-thiazol-2-yl)]-5-(methylsulfinyl)thiophene-2-carboxylate (100 mg, 0.25 mmol) was treated in a manner similar to that for Example 10, step (b), to give, after preparative thin layer chromatography purification eluting with dichloromethane:methanol:acetic acid 9/1/0.5 (v:v:v), 4-[4-(4-chlorophenyl)(1,3-thiazol-2-yl)]-5-(methylsulfinyl)thiophene-2-carboxamidine (18.2 mg, 19%) as a solid. $^1$H-NMR (DMSO-d$_6$; 300 MHz) δ 8.33 (s, 1H), 8.22 (s, 1H), 8.05 and 7.57 (AB quartet, 2H, J=8.6 Hz), 3.12 (s, 3H). Mass spectrum (MALDI-TOF, CHCA matrix m/z): Calcd. for C$_{15}$H$_{12}$N$_3$OS$_3$Cl382.0 (M+H), found 382.1.

EXAMPLE 139 a) Methyl 4-cyano-5-(methylsulfonyl)thiophene-2-carboxylate: To a stirred solution of (4.5 g, 21 mmol) of methyl 4-cyano-5-methylthiothiophene-2-carboxylate (Maybridge, Cornwall, UK) was dissolved in dichloromethane (250 mL) and treated with m-chloroperbenzoic acid (15.3 g, 90 mmol) at room temperature for 2.25 h. The mixture was filtered and the solid washed with dichloromethane (2×50 mL). The filtrate was washed with sodium bicarbonate (2×100 mL), sodium thiosulfate (100 mL), sodium bicarbonate (100 mL), water (100 mL), brine (100 mL), and dried over anhydrous sodium sulfate. The solvent was removed in vacuo to give methyl 4-cyano-5-(methylsulfonyl)thiophene-2-carboxylate (4.91 g, 95%) as a solid. $^1$H-NMR (DMSO-d$_6$; 300 MHz) δ 8.44 (s, 1H), 3.91 (s, 3H), 3.58 (s, 3H).

b) Methyl 4-cyano-5-methoxythiophene-2-carboxylate: Methyl 4-cyano-5-(methylsulfonyl)thiophene-2-carboxylate (2 g, 8 mmol) was refluxed with 0.5 M sodium methoxide in methanol (16 mL) for 15 minutes. The solution was cooled, the crystallized solid collected on a Büchner funnel and washed with methanol (50 mL) to give methyl 4-cyano-5-methoxythiophene-2-carboxylate (1.145 g, 73%) as a solid. $^1$H-NMR (DMSO-d$_6$; 300 MHz) δ 8.87 (s, 1H) 4.19 (s, 3H), 3.82 (s, 3H).

c) Methyl 4-(aminothioxomethyl)-5-methoxythiophene-2-carboxylate: Methyl 4-cyano-5-methoxythiophene-2-carboxylate (1 g, 5 mmol) was dissolved in dry methanol (150 mL) and triethylamine (3.5 mL, 25.4 mmol) was added. After degassing the solution with argon for 10 minutes, hydrogen sulfide gas was bubbled through the solution for 5 h. After stirring 18 h at room temperature, the solution was degassed by bubbling argon (6 h), concentrated to 20 mL and acetone (20 mL) was added. The dark solid was collected on a Büchner funnel and washed with acetone. Recrystallize solid from hot ethanol (15 mL) to give methyl 4-(aminothioxomethyl)-5-methoxythiophene-2-carboxylate (683 mg, 59%) as a brown oil. Mass spectrum (MALDI-TOF, CHCA matrix, m/z): Calcd. for C$_8$H$_9$NO$_3$S$_2$ 232.0 (M+H), found 232.4 d) Methyl 5-methoxy-4-(4-phenyl(1,3-thiazol-2-yl))thiophene-2-carboxylate: A solution of 400 mg (1.73 mmol) of methyl 4-(aminothioxomethyl)-5-methoxythiophene-2-carboxylate was reacted with 345 mg (1.73 mmol) of 2-bromoacetophenone (Aldrich, Milwaukee, Wis., U.S.A.) in a manner similar to Example 8, step (a) to give methyl 5-methoxy-4-(4-phenyl(1,3-thiazol-2-yl))thiophene-2-carboxylate (56 mg, 10%) as a solid. $^1$H-NMR (DMSO-d$_6$; 300 MHz) δ 8.22 (s, 1H), 8.14 (s, 1H), 8.05 (m, 2H), 7.47 (m, 2H), 7.36 (m, 1H), 4.26 (s, 3H), 3.85 (s, 3H).

e) 5-Methoxy-4-(4-phenyl(1,3-thiazol-2-yl))thiophene-2-carboxamidine: Methyl 5-methoxy-4-(4-phenyl(1,3-thiazol-2-yl))thiophene-2-carboxylate (55 mg, 0.16 mmol) was treated in a manner similar to that for Example 10, step (b), to give 5-methoxy-4-(4-phenyl(1,3-thiazol-2-yl))thiophene-2-carboxamidine (36 mg, 69%) as a yellow solid. $^1$H-NMR (DMSO-d$_6$; 300 MHz) δ 9.34 (br s, 2H), 8.94 (br s, 2H), 8.70 (s, 1H), 8.20 (s, 1H), 8.07 (m, 2H), 7.49 (m, 2H), 7.38 (m, 1H), 4.32 (s, 3H). Mass spectrum (MALDI-TOF, CHCA matrix, m/z): Calcd. for C$_{15}$H$_{13}$N$_3$OS$_2$ 316.5 (M+H), found 316.1

EXAMPLE 140 a) Methyl 4-cyano-5-[(4-methoxyphenyl)methylthio]thiophene-2-carboxylate: To a stirred solution of 2.5 g (10 mmol) of methyl 4-cyano-5-(methylsulfonyl)thiophene-2-carboxylate (Example 139, step (a)) in dry methanol (15 mL) was added p-methoxybenzylmercaptan (3.8 mL, 28 mmol) and triethylamine (1.4 mL, 10 mmol). This solution was refluxed for 15 min and cooled. The resulting solid was collected on a büichner funnel and washed with methanol (2×25 mL) to methyl 4-cyano-5-[(4-methoxyphenyl)methylthio]thiophene-2-carboxylate (2.84 g, 89%) as a solid.

b) Methyl 4-(aminothioxomethyl)-5-[(4-methoxyphenyl) methylthio]thiophene-2-carboxylate: Methyl 4-cyano-5-[(4-methoxyphenyl)methylthio]thiophene-2-carboxylate (2.5 g, 7.8 mmol) was treated as in Example 139, step (c) to give methyl 4-(aminothioxomethyl)-5-[(4-methoxyphenyl) methylthio]thiophene-2-carboxylate (1.32 g, 48%) as a solid. $^1$H-NMR (DMSO-d$_6$; 300 MHz) δ 9.64 (s, 1H), 9.28 (s, 1H), 8.08 (s, 1H), 7.35 and 6.92 (AB quartet, 2H, J=8.7 Hz), 4.27 (s, 2H), 3.82 (s, 3H), 3.75 (s, 3H).

c) Methyl 5-(methoxyphenylthio)-4-(4-phenyl(1,3-thiazol-2-yl))thiophene-2-carboxylate: A solution of 1.2 g (3.4 mmol) of methyl 4-(aminothioxomethyl)-5-[(4-methoxyphenyl)methylthio]thiophene-2-carboxylate was reacted with 676 mg (3.4 mmol) of 2-bromoacetophenone (Aldrich, Milwaukee, Wis., U.S.A.) in a manner similar to Example 8, step (a) to give methyl 5-(methoxyphenylthio)-4-(4-phenyl(1,3-thiazol-2-yl))thiophene-2-carboxylate (755 mg, 49%) as a solid. $^1$H-NMR (DMSO-d$_6$; 300 MHz) δ 8.26 (s, 1H), 8.22 (s, 1H), 8.04 (m, 2H), 7.48 (m, 2H), 7.38 (m, 1H), 7.33 and 6.89 (AB quartet, 2H, J=8.7 Hz), 4.40 (s, 2H), 3.86 (s, 3H), 3.72 (s, 3H).

d) 5-(Methoxyphenylthio)-4-(4-phenyl(1,3-thiazol-2-yl)) thiophene-2-carboxamidine: Methyl 5-(methoxyphenylthio)-4-(4-phenyl(1,3-thiazol-2-yl)) thiophene-2-carboxylate (100 mg, 0.22 mmol) was treated in a manner similar to that for Example 10, step (b), to give 5-methoxy-4-(4-phenyl(1,3-thiazol-2-yl))thiophene-2-carboxamidine (94 mg, 91%) as an orange solid. $^1$H-NMR (DMSO-d$_6$; 300 MHz) δ 9.49 (br s, 2H), 9.15 (br s, 2H), 8.70 (s, 1H), 8.26 (s, 1H), 8.07 (m, 2H), 7.49 (m, 2H), 7.40 (m, 1H), 7.35 and 6.90 (AB quartet, 2H, J=8.7 Hz), 4.41 (s, 2H), 3.73 (s, 3H). Mass spectrum (MALDI-TOF, CHCA matrix, m/z): Calcd. for $C_{22}H_{19}N_3OS_3$ 438.5 (M+H), found 438.1.

EXAMPLE 141 a) Methyl 4-[4-(4-chlorophenyl)(1,3-thiazol-2-yl)]-5-(methylsulfonyl)thiophene-2-carboxylate: To a stirred solution of 1 g (2.6 mmol) of methyl 4-[4-(4-chlorophenyl)(1,3-thiazol-2-yl)]-5-methylthiothiophene-2-carboxylate (Maybridge, Cornwall, UK) was dissolved in dry dichloromethane (50 mL) and treated with m-chloroperbenzoic acid (1.94 g, 11.3 mmol) at room temperature for 1.5 h. The solution was filtered and the solid washed with dichloromethane. The filtrate was washed with sodium bicarbonate solution (2×20 mL), sodium thiosulfate solution (20 mL), sodium bicarbonate solution (20 mL), brine (20 mL), and dried over anhydrous sodium sulfate. The solvent was removed in vacuo to give methyl 4-[4-(4-chlorophenyl)(1,3-thiazol-2-yl)]-5-(methylsulfonyl)thiophene-2-carboxylate (826 mg, 77%) as a tan solid. Mass spectrum (MALDI-TOF, CHCA matrix, m/z): Calcd. for $C_{16}H_{12}NO_4S_3Cl$ 414.0 (M+H), found 414.8.

b) 4-[4-(4-Chlorophenyl)(1,3-thiazol-2-yl)]-5-(methylsulfonyl)thiophene-2-carboxamidine: Methyl 4-[4-(4-chlorophenyl)(1,3-thiazol-2-yl)]-5-(methylsulfonyl) thiophene-2-carboxylate (200 mg, 0.4 mmol) was treated in a manner similar to that for Example 10, step (b), to give 4-[4-(4-chlorophenyl)(1,3-thiazol-2-yl)]-5-(methylsulfonyl) thiophene-2-carboxamidine (85 mg, 53%) as a yellow solid.

c) 4-[4-(4-Chlorophenyl)(1,3-thiazol-2-yl)]-5-(phenylmethylthio)thiophene-2-carboxamidine: A stirred solution of 80 mg (0.2 mmol) of 4-[4-(4-chlorophenyl)(1,3-thiazol-2-yl)]-5-(methylsulfonyl)thiophene-2-carboxamidine benzyl mercaptan (115 μL, 0.980 μmol) was treated in a manner similar to that for Example 140, step (a) to give, after silica gel column chromatography (20 g) eluting with dichloromethane:methanol:acetic acid 9/1/0.5 (v:v:v), 4-[4-(4-chlorophenyl)(1,3-thiazol-2-yl)]-5-(phenylmethylthio)thiophene-2-carboxamidine (75 mg, 85%) as a pale orange solid. $^1$H-NMR (DMSO-d$_6$; 300 MHz) δ 9.44 (br s, 2H), 9.03 (br s, 2H), 8.67 (s, 1H), 8.33 (s, 1H), 8.08 and 7.56 (AB quartet, 2H, J=8.7 Hz), 7.54–7.17 (m, 5H), 4.45 (s, 2H). Mass spectrum (MALDI-TOF, CHCA matrix, m/z): Calcd. for $C_{21}H_{16}N_3S_3Cl$ 442.0 (M+H), found 442.7.

EXAMPLE 142 a) 1-[5-(tert-Butyl)-2-methyl(3-furyl)]-2-bromoethan-1-one: A solution of 1 g (5 mmol) of 5-(tert-butyl)-2-methylfuran-3-carbonyl chloride (Maybridge, Cornwall, UK) dissolved in dry acetonitrile (4 mL) and 6.25 mL (12.5 mmol) of 2 M trimethylsilyldiazomethane in hexanes (Aldrich, Milwaukee, Wis.) was stirred 1.75 h at room temperature and the mixture was cooled on an ice bath for 5 min. To this, 30% hydrogen bromide in acetic acid (2 mL, 10 mmol) was added dropwise over 10 min. This was stirred an additional 20 minutes on an ice bath. Evaporation of the solvents gave 1-[5-(tert-butyl)-2-methyl(3-furyl)]-2-bromoethan-1-one (1 g, 77%) as a brown oil. $^1$H-NMR (DMSO-d$_6$; 300 MHz) δ 6.50 (s, 1H), 4.57(s, 2H), 2.52 (s, 1H), 1.24 (s, 9H). Mass spectrum (LCA, m/z): Calcd. for $C_{11}H_{15}O_2Br$, 259.1 and 261.1 (M+H), found 259.1 and 261.1.

b) Methyl 4-{4-[5-(tert-butyl)-2-methyl(3-furyl)](1,3-thiazol-2-yl)}-5-methylthiothiophene-2-carboxylate: A solution of 955 mg (3.86 mmol) of methyl 4-(aminothioxomethyl)-5-methylthiothiophene-2-carboxylate (Maybridge, Cornwall, UK) was reacted with 1 g (3.86 mmol) of 1-[5-(tert-butyl)-2-methyl(3-furyl)]-2-bromoethan-1-one (1 g) in a manner similar to Example 8, step (a) to give methyl 4-{4-[5-(tert-butyl)-2-methyl(3-furyl)](1,3-thiazol-2-yl)}-5-methylthiothiophene-2-carboxylate (999 mg, 64%) as a red-brown solid. $^1$H-NMR (DMSO-d$_6$; 300 MHz) 67 8.14 (s, 1H), 7.74 (s, 1H), 6.46 (s, 1H), 3.86 (s, 3H), 2.74 (s, 3H), 2.66 (s, 3H), 1.27 (s, 9H). Mass spectrum (MALDI-TOF, CHCA matrix, m/z): Calcd. for $C_{19}H_{21}NO_3S_3$, 408.1 (M+H), found 408.0.

c) 4-{4-[5-(tert-Butyl)-2-methyl(3-furyl)](1,3-thiazol-2-yl)}-5-methylthiothiophene-2-carboxamidine: Methyl 4-{4-[5-(tert-butyl)-2-methyl(3-furyl)](1,3-thiazol-2-yl)}-5-methylthiothiophene-2-carboxylate (940 mg, 2.3 mmol) was treated in a manner similar to that for Example 10, step (b) to give 4-{4-[5-(tert-butyl)-2-methyl(3-furyl)](1,3-thiazol-2-yl)}-5-methylthiothiophene-2-carboxamidine (930 mg, quantitive yield) as a yellow solid. $^1$H-NMR (DMSO-d$_6$; 300 MHz) δ 9.42 (br s, 2H), 9.03 (br s, 2H), 8.59 (s, 1H), 7.77 (s, 1H), 6.47 (s, 1H), 2.78 (s, 3H), 2.68 (s, 3H), 1.27 (s, 9H). Mass spectrum (MALDI-TOF, CHCA matrix, m/z): Calcd. for $C_{18}H_{21}N_3OS_3$, 392.1 (M+H), found 392.1.

EXAMPLE 143 a) 1-[3-(tert-Butyl)-1-benzylpyrazol-5-yl]-2-bromoethan-1-one: A solution of 1 g (3.6 mmol) of 3-(tert-butyl)-1-benzylpyrazole-5-carbonyl chloride (Maybridge, Cornwall, UK) was dissolved in dry acetonitrile (4 mL) and 4.5 mL (9 mmol) of 2 M trimethylsilyldiazomethane in hexanes (Aldrich, Milwaukee, Wis., U.S.A.) was added. After stirring 1 h 20 min at room temperature, the mixture was cooled on an ice bath for 5 min. To this, 30% hydrogen bromide in acetic acid (2 mL, 10 mmol) was added dropwise over 15 min. This was stirred an additional 15 minutes on an ice bath. Filtration of the precipitated solid and evaporation of the solvents gave 1-[3-(tert-butyl)-1-benzylpyrazol-5-yl]-2-bromoethan-1-one (1.47 g, quantitive yield) as an orange solid. $^1$H-NMR (DMSO-d$_6$; 300 MHz) δ 7.33–7.06 (m, 5H), 7.08 (s, 1H), 5.64 (s, 2H), 4.57 (s, 2H), 1.28 (s, 9H). Mass spectrum (MALDI-TOF, CHCA matrix, m/z): Calcd. for C$_{16}$H$_{19}$N$_2$OBr, 335.1 and 337.1 (M+H), found 335.6 and 337.6.

b) Methyl 4-{4-[3-(tert-Butyl)-1-benzylpyrazol-5-yl](1,3-thiazol-2-yl)}-5-methylthiothiophene-2-carboxylate: A solution of 823 mg (3.3 mmol of methyl 4-(aminothioxomethyl)-5-methylthiothiophene-2-carboxylate (Maybridge, Cornwall, UK) was reacted with 1.36 g (3.3 mmol) of 1-[3-(tert-butyl)-1-benzylpyrazol-5-yl]-2-bromoethan-1-one in a manner similar to Example 8, step (a) to give methyl 4-{4-[3-(tert-butyl)-1-benzylpyrazol-5-yl](1,3-thiazol-2-yl)}-5-methylthiothiophene-2-carboxylate (1.25 g, 79%) as a crystalline solid. $^1$H-NMR (DMSO-d$_6$; 300 MHz) δ 8.11 (s, 1H), 8.05 (s, 1H), 7.28–6.99 (m, 5H), 6.70 (s, 1H), 5.88 (s, 2H), 3.86 (s, 3H), 2.70 (s, 3H), 1.30 (s, 9H). Mass spectrum (MALDI-TOF, CHCA matrix, m/z): Calcd. for C$_{24}$H$_{25}$N$_3$O$_2$S$_3$, 484.1 (M+H), found 483.9.

c) 4-{4-[3-(tert-Butyl)-1-benzylpyrazol-5-yl](1,3-thiazol-2-yl)}-5-methylthiothiophene-2-carboxamidine: Methyl 4-{4-[3-(tert-butyl)-1-benzylpyrazol-5-yl](1,3-thiazol-2-yl)}-5-methylthiothiophene-2-carboxylate (1.2 mg, 2.6 mmol) was treated in a manner similar to that for Example 10, step (b) to give 4-{4-[3-(tert-butyl)-1-benzylpyrazol-5-yl](1,3-thiazol-2-yl)}-5-methylthiothiophene-2-carboxamidine (1.21 g, quantitive yield) as a yellow solid. $^1$H-NMR (DMSO-d$_6$; 300 MHz) δ 9.43 (br s, 1H), 9.07 (br s, 1H), 8.60 (s, 1H), 8.04 (s, 1H), 7.37–6.97 (m, 5H), 6.70 (s, 1H), 5.92 (s, 2H), 2.73 (s, 3H), 1.30 (s, 9H). Mass spectrum (MALDI-TOF, CHCA matrix, m/z): Calcd. for C$_{23}$H$_{25}$N$_5$S$_3$, 468.1 (M+H), found 468.1.

EXAMPLE 144 a) 4-Bromo-5-methylthiophene-2-carboxylic acid: A stirred solution of 1 g (3.9 mmol) of 2-methyl-3,5-dibromothiophene (prepared by the method of Kano, S. et al., *Heterocycles* 20(10):2035, 1983) in dry tetrahydrofuran (10 mL) was cooled to −78° C. and 2 M n-butyllithium in cyclohexane (1.93 mL, 3.87 mmol) was added over 3 min. After stirring 3 min at −78° C., the mixture was added to tetrahydrofuran (100 mL) with dry ice suspended. This mixture was allowed to stir and warm to room temperature. To this, 6 N hydrochloric acid (50 mL) was added carefully. Then, water (50 mL) was added and the layers were separated. The aqueous layer was extracted with diethyl ether (4×30 mL). The combined organic layers were washed with water, brine, and dried over anhydrous sodium sulfate. The solvents were removed in vacuo to give an 85/15 mixture of 4-bromo-5-methylthiophene-2-carboxylic acid and 5-bromothiophene-2-carboxylic acid (780 mg, 90%) as a tan solid. $^1$H-NMR (DMSO-d$_6$; 300 MHz) δ 13.33 (br s, 1H), 7.62 (s, 1H), 7.56 and 7.34 (AB quartet, 0.35H, J=3.9 Hz), 2.41 (s, 3H). Gas Chromatography/Mass spectroscopy (m/z): Calcd. for C$_6$H$_5$O$_2$SBr, 220.9 and 222.9 (M+H), found 221.3 and 223.3. Calcd. for C$_5$H$_3$O$_2$SBr, 206.9 and 208.9 (M+H), found 207.3 and 209.3.

b) Methyl 4-bromo-5-methylthiophene-2-carboxylate: A solution of 780 mg (3.5 mmol) of an 85/15 mixture of 4-bromo-5-methylthiophene-2-carboxylic acid and 5-bromothiophene-2-carboxylic acid was dissolved in methanol (50 mL) and treated with 9 ml (18 mmol) 2 M trimethylsilyldiazomethane in hexanes (Aldrich, Milwaukee, Wis., U.S.A.). Evaporation of the solvents gave an 8/2 mixture of methyl 4-bromo-5-methylthiophene-2-carboxylate and methyl 5-bromothiophene-2-carboxylate (858 mg, quantitive yield) as a brown oil. Gas Chromatography/Mass spectroscopy (m/z): Calcd. for C$_7$H$_7$O$_2$SBr, 234.9 and 236.9 (M+H), found 235.3 and 237.3. Calcd. for C$_6$H$_4$O$_2$SBr, 220.9 and 222.9 (M+H), found 221.3 and 223.3.

c) Methyl 4-cyano-5-methylthiophene-2-carboxylate: A solution of an 8/2 mixture of 823 mg (3.5 mmol) of methyl 4-bromo-5-methylthiophene-2-carboxylate and methyl 5-bromothiophene-2-carboxylate was dissolved in dry dimethylformamide (5 mL) and refluxed with copper cyanide (345 mg, 3.9 mmol) for 7 hours. The cooled solution was poured into 0.1 M aqueous sodium cyanide solution (200 mL) and extracted with diethyl ether (5×30 mL). The organic layers were washed with brine (2×30 mL), dried over anhydrous sodium sulfate, and the solvents removed in vacuo. The resulting brown solid was purified by column chromatography on silica gel eluting with hexanes:ethyl acetate 9/1 (v:v) to give a 95/5 mixture of methyl 4-cyano-5-methylthiophene-2-carboxylate and methyl 5-methylthiophene-2-carboxylate (369 mg, 68%) as a yellow solid. $^1$H-NMR (DMSO-d$_6$; 300 MHz) δ 8.06 (s, 1H), 8.05 and 7.90 (2H, 0.1H, J=4.0 Hz, minor component), 3.87 (s, 3H, minor component), 3.84 (s, 3H) 2.68 (s, 3H).

d) Methyl 4-(aminothioxomethyl)-5-methylthiophene-2-carboxylate: A stirred solution of 804 mg (4.4 mmol) of methyl 4-cyano-5-methylthiophene-2-carboxylate was treated in a manner similar to Example 139, step (c) to give, after fractional crystallization ethanol of the unreacted starting nitrile, a 2:3 ratio of methyl 4-(aminothioxomethyl)-5-methylthiophene-2-carboxylate and methyl 4-cyano-5-methylthiophene-2-carboxylate (457 mg, 48%) as a light brown solid. $^1$H-NMR (DMSO-d$_6$; 300 MHz) δ 9.93 (br s, 1H, minor), 9.34 (br s, 1H, minor), 8.06 (s, 1H, major), 7.77 (s, 1H, minor component), 3.84 (s, 3H, minor), 3.81 (s, 3H, major), 2.68 (s, 3H, major), 2.61 (s, 2H, minor). Mass spectrum (MALDI-TOF, CHCA matrix, m/z): Calcd. for C$_8$H$_9$NO$_2$S$_2$ 216.0 (M+H), found 216.4.

e) Methyl 5-methyl-4-(4-phenyl(1,3-thiazol-2-yl))thiophene-2-carboxylate: A solution of 200 mg (0.93 mmol) of methyl 4-(aminothioxomethyl)-5-methylthiophene-2-carboxylate was reacted with 185 mg (0.93 mmol) of 2-bromoacetophenone in a manner similar to Example 8, step (a) to give, after purification by preparative thin layer chromatography eluting with hexanes:ethyl acetate 7/3 (v:v), a mixture of methyl 5-methyl-4-(4-phenyl(1,3-thiazol-2-yl))thiophene-2-carboxylate and methyl 4-cyano-5-methylthiophene-2-carboxylate (96 mg, 36%) as a solid.

f) 5-Methyl-4-(4-phenyl(1,3-thiazol-2-yl))thiophene-2-carboxamidine: Methyl-4-(4-phenyl(1,3-thiazol-2-yl))thiophene-2-carboxylate (64 mg, 0.23 mmol) was treated in a manner similar to Example 10, step (b) to give, after preparative high pressure liquid chromatography (Dynamax C18 column, 300 Å pore size, 10 μm particle size, 40% to 100% acetonitrile over 30 minutes in 0.1% aqueous trifluoroacetic acid) 5-methyl-4-(4-phenyl(1,3-thiazol-2-yl))thiophene-2-carboxamidine (0.6 mg, 0.9%) as an an off-white solid. $^1$H-NMR (CD$_3$OD, 300 MHz) δ 8.44 (s, 1H), 8.02 (m, 2H), 7.92 (s, 1H), 7.45 (m, 2H), 7.36 (m, 1H), 2.96 (s, 3H). Mass spectrum (MALDI-TOF, CHCA matrix, m/z): Calcd. for C$_{15}$H$_{13}$N$_3$S$_2$ 300.1 (M+H), found 300.6.

g) 5-(4-Phenyl-1,3-thiazol-2-yl)thiophene-2-carboxamide: From the HPLC purified mixture in the previous step was isolated 5-(4-phenyl-1,3-thiazol-2-yl)

thiophene-2-carboxamide as an off-white solid (2 mg). $^1$H-NMR (Methanol-d$_4$; 300 MHz) δ 7.99 (m, 2H), 7.97 (s, 1H), 7.95 and 7.78 (AB quartet, 2H, J=4.2 Hz), 7.48–7.35 (m, 3H). Mass spectrum (MALDI-TOF, CHCA matrix, m/z): Calcd. for C$_{14}$H$_{11}$N$_3$S$_2$ 286.0 (M+H), found 286.2.

EXAMPLE 145 a) Methyl 4-[4-(3,4-dimethoxyphenyl)(1,3-thiazol-2-yl)]-5-methylthiophene-2-carboxylate: A solution of 257 mg (0.48 mmol, based on a mixture containing 60% nitrile) of methyl 4-(aminothioxomethyl)-5-methylthiophene-2-carboxylate was reacted with 124 mg (0.48 mmol) of 2-bromo-(3',4'-dimethoxy)-acetophenone (Example 31, step (a)) was reacted in a manner similar to Example 8, step (a) to give methyl 4-[4-(3,4-dimethoxyphenyl)(1,3-thiazol-2-yl)]-5-methylthiophene-2-carboxylate (95 mg, 53%) as a solid. Mass spectrum (MALDI-TOF, CHCA matrix, m/z): Calcd. for C$_{18}$H$_{17}$NO$_4$S$_2$ 376.1 (M+H), found 376.3.

b) 4-[4-(3,4-Dimethoxyphenyl)(1,3-thiazol-2-yl)]-5-methylthiophene-2-carboxamide: Methyl 4-[4-(3,4-dimethoxyphenyl)(1,3-thiazol-2-yl)]-5-methylthiophene-2-carboxylate (95 mg, 0.25 mmol) was treated in a manner similar to Example 10, step (b) to give 4-[4-(3,4-dimethoxyphenyl)(1,3-thiazol-2-yl)]-5-methylthiophene-2-carboxamide (8 mg, 9%) as a yellow solid. $^1$H-NMR (Methanol-d$_4$; 300 MHz) δ 8.42 (s, 1H), 7.81 (s, 1H), 7.61 (m, 2H), 7.03 (m, 1H), 3.92 (s, 3H), 3.88 (s, 3H), 2.95 (s, 3H). Mass spectrum (MALDI-TOF, CHCA matrix, m/z): Calcd. for C$_{17}$H$_{17}$N$_3$O$_2$S$_2$ 360.1 (M+H), found 360.2.

EXAMPLE 146 a) 4-Bromo-5-methylthiophene-2-carboxylic acid: A solution of 27.65 g (108 mmol) of 2-methyl-3,5-dibromothiophene (prepared by the method of Kano, S. et al., *Heterocycles* 20(10):2035, 1983) was dissolved in dry tetrahydrofuran (280 mL), cooled to −78° C. and 2 M n-butyl lithium in cyclohexane (54 mL, 108 mmol) was added over 10 min. After stirring 20 min at −78° C., dry carbon dioxide gas was bubbled through the solution for 1.5 h as the mixture was allowed to warm to room temperature. To this 6 N hydrochloric acid (100 mL) was added carefully. The layers were separated and the aqueous layer was extracted with diethyl ether (4×50 mL). The combined organic layers were washed with brine, and dried over anhydrous sodium sulfate. The solvents were removed in vacuo to give 4-bromo-5 -methylthiophene-2-carboxylic acid (22.4 g, 94%) as an off-white solid. $^1$H-NMR (DMSO-d$_6$; 300 MHz) δ 13.34 (br s, 1H), 7.61 (s, 1H), 2.41 (s, 3H).

b) Isopropyl 4-bromo-5-methylthiophene-2-carboxylate: A solution of 5 g (22.6 mmol) of 4-bromo-5-methylthiophene-2-carboxylic acid was dissolved in dry dichloromethane (200 mL) and reacted with oxalyl chloride (2 mL, 22.6 mmol) and dimethylformamide (100 μL) stirring on an ice bath for 30 min and then at room temperature for 2.5 h. The solvents were removed in vacuo and the residue was passed through silica gel, eluting off with hexanes:ethyl acetate 7/3 (v:v), ethyl acetate, and dichloromethane. The solvents were removed in vacuo and the resulting oil dissolved in dry dichloromethane (100 mL). This solution was reacted with dry pyridine (9 mL, 113 mmol) and dry isopropanol (40 mL, 522 mmol) for 88 h. The solvents were removed in vacuo and the residue partitioned between sodium bicarbonate (150 mL) and dichloromethane (75 mL). The aqueous layers were extracted with dichloromethane (2×20 mL), and the combined organic layers were washed with sodium bicarbonate (30 mL), brine (30 mL), and dried over anhydrous sodium sulfate. The solvents were removed in vacuo. The residue was purified by column chromatography eluting with hexanes:ethyl acetate 9/1 (v:v) to give isopropyl 4-bromo-5-methylthiophene-2-carboxylate (1.91 g, 32%) as a pale yellow oil. $^1$H-NMR (DMSO-d$_6$; 300 MHz) δ 7.66 (s, 1H), 5.07 (septet, 1H, J=6.2 Hz), 2.42 (s, 3H), 1.29 (d, 6H, J=6.2 Hz). Mass spectrum (ESI, m/z): Calcd. for C$_9$H$_{11}$O$_2$SBr 264.2 (M+H), found 264.8.

c) Isopropyl 4-cyano-5-methylthiophene-2-carboxylate: A stirred solution of 1.9 g (7.3 mmol) of isopropyl 4-bromo-5-methylthiophene-2-carboxylate was dissolved in dry dimethylformamide (30 mL) and refluxed with copper cyanide (785 mg, 8.8 mmol) for 16 hours. The cooled solution was poured into 0.1 M aqueous sodium cyanide solution (300 mL) and extracted with diethyl ether (4×40 mL). The organic layers were washed with brine (2×40 mL), dried over anhydrous sodium sulfate, and the solvents removed in vacuo. Column chromatography on silica gel eluting with hexanes:ethyl acetate 9/1 (v:v), gave isopropyl 4-cyano-5-methylthiophene-2-carboxylate (960 mg, 63%) as a yellow crystalline solid $^1$H-NMR (DMSO-d$_6$; 300 MHz) δ 8.01 (s, 1H), 5.09 (septet, 1H, J=6.2 Hz), 2.67 (s, 3H), 1.29 (d, 6H, J=6.2 Hz).

d) Isopropyl 4-(aminothioxomethyl)-5-methylthiophene-2-carboxylate: A stirred solution of 960 mg (4.59 mmol) of isopropyl 4-cyano-5-methylthiophene-2-carboxylate was treated in a manner similar to Example 139, step (c) to give, after crystallization from diethyl ether, isopropyl 4-(aminothioxomethyl)-5-methylthiophene-2-carboxylate (623 mg, 56%) as a solid. $^1$H-NMR (DMSO-d$_6$; 300 MHz) δ 9.93 (br s, 1H), 9.34 (br s, 1H), 7.54 (s, 1H), 5.07 (septet, 1H, J=6.2 Hz), 2.60 (s, 3H), 1.29 (d, 6H, J=6.2 Hz). Mass spectrum (MALDI-TOF, GA matrix, m/z): Calcd. for C$_{10}$H$_{13}$NO$_2$S$_2$ 244.0 (M+H), found 243.8.

e) Isopropyl 5-methyl-4-(4-phenyl(1,3-thiazol-2-yl))thiophene-2-carboxylate: A solution of 375 mg (1.54 mmol) of isopropyl 4-(aminothioxomethyl)-5-methylthiophene-2-carboxylate was reacted with 307 mg (1.54 mmol) of 2-bromoacetophenone (Aldrich, Milwaukee, Wis., U.S.A.) in a manner similar to Example 8, step (a) to give, after crystallization from methanol, isopropyl 5-methyl-4-(4-phenyl(1,3-thiazol-2-yl))thiophene-2-carboxylate (347 mg, 66%) as light brown needles. $^1$H-NMR (DMSO-d$_6$; 300 MHz) δ 8.23 (s, 1H), 8.09 (s, 1H), 8.05 (m, 2H), 7.49 (m, 2H), 7.38 (m, 1H), 5.13 (septet, 1H, J=6.2 Hz), 2.86 (s, 3H), 1.33 (d, 6H, J=6.2 Hz). Mass spectrum (ESI, m/z): Calcd. for C$_{18}$H$_{17}$NO$_2$S$_2$ 344.1 (M+H), found 344.1.

f) 5-Methyl-4-(4-phenyl(1,3-thiazol-2-yl))thiophene-2-carboxamidine: Isopropyl 5-methyl-4-(4-phenyl(1,3-thiazol-2-yl))thiophene-2-carboxylate (340 mg, 0.99 mmol) was treated in a manner similar to Example 10, step (b) to give 5-methyl-4-(4-phenyl(1,3-thiazol-2-yl))thiophene-2-carboxamidine (360 mg, quantitive yield) as a yellow solid. This material was dissolved in dry methanol (20 mL) and treated with 1 M HCl (g) in diethyl ether. Evaporation of the solvents in vacuo and recrystallization from methanol gave the hydrochloride salt of 5-methyl-4-(4-phenyl(1,3-thiazol-2-yl))thiophene-2-carboxamidine (252 mg, 76%) as a light brown crystalline solid. $^1$H-NMR (DMSO-d$_6$; 300 MHz) δ 9.45 (br s, 2H), 9.10 (br s, 2H), 8.56 (s, 1H), 8.27 (s, 1H), 8.06 (m, 2H), 7.50 (m, 2H), 7.40 (m, 1H), 2.93 (s, 3H), Mass spectrum (ESI, m/z): Calcd. for C$_{15}$H$_{13}$N$_3$S$_2$ 300.1 (M+H), found 300.2.

EXAMPLE 147 a) 2-Methyl-5-[(methylethyl)oxycarbonyl]thiophene-3-carboxylic acid: A stirred mixture of 500 mg (2.39 mmol) of isopropyl 2-methyl-3-cyanothiophene-5-carboxylate and tetrafluorophthalic acid (570 mg, 2.39 mmol) was heated in a glass bomb at 160° C. for 66 hours. The cooled residue was digested in hot chloroform (30 mL), treated with norite, and filtered through celite. The celite was washed with hot chloroform (30 mL). The cooled chloroform extracts were filtered and extracted with saturated sodium bicarbonate (4×10 mL). The basic extracts were washed with chloroform, filtered through celite, and acidified to pH 1 with concentrated hydrochloric acid. The solid was collected by filtration and washed with water (3×10 mL) to give 2-methyl-5-[(methylethyl)oxycarbonyl]thiophene-3-carboxylic acid (288 mg, 53%) as a light brown solid. $^1$H-NMR (DMSO-d$_6$; 300 MHz) δ 13.03 (br s, 1H), 7.85 (s, 1H), 5.08 (septet, 1H, J=6.2 Hz), 2.71 (s, 3H), 1.29 (d, 6H, J=6.2 Hz). Mass spectrum (ESI, m/z): Calcd. for $C_{10}H_{12}O_4S$ 229.1 (M+H), found 228.8 b) Isopropyl 4-(2-bromoacetyl)-5-methylthiophene-2-carboxylate: A stirred solution of 300 mg (1.3 mmol) of 2-methyl-5-[(methylethyl)oxycarbonyl]thiophene-3-carboxylic acid was dissolved in dry dichloromethane (10 mL) and treated with oxalyl chloride (174 μL, 2 mmol) and dimethylformamide (50 μL). The mixture was stirred at room temperature for 1.25 h, the solvents removed in vacuo, and the residue passed through silica gel (1 inch in a 60 mL sintered-glass Büchner funnel) and eluted off with dichloromethane (150 mL). This material was treated in a manner similar to Example 142, step (a) to give isopropyl 4-(2-bromoacetyl)-5-methylthiophene-2-carboxylate (266 mg, 67%) as a solid.

c) Isopropyl 4-(2-amino(1,3-thiazol-4-yl))-5-methylthiophene-2-carboxylate: A solution of 260 mg (0.85 mmol) of isopropyl 4-(2-bromoacetyl)-5-methylthiophene-2-carboxylate was reacted with 65 mg (0.85 mmol) of thiourea in a manner similar to Example 8, step (a) to give isopropyl 4-(2-amino(1,3-thiazol-4-yl))-5-methylthiophene-2-carboxylate (257 mg, quantitive yield) as a white solid. $^1$H-NMR (DMSO-d$_6$; 300 MHz) δ 7.90 (s, 1H), 6.93 (s, 1H), 5.09 (septet, 1H, J=6.2 Hz), 2.61 (s, 3H), 1.29 (d, 6H, J=6.2 Hz). Mass spectrum (ESI, m/z): Calcd. for $C_{12}H_{14}N_2O_2S_2$ 283.1 (M+H), found 283.1 d) 4-(2-Amino(1,3-thiazol-4-yl))-5-methylthiophene-2-carboxamidine: Isopropyl 4-(2-amino(1,3-thiazol-4-yl))-5-methylthiophene-2-carboxylate (240 mg, 0.85 mmol) was treated in a manner similar to Example 10, step (b) to give 4-(2-amino(1,3-thiazol-4-yl))-5-methylthiophene-2-carboxamidine (20 mg, 10%) as a solid. $^1$H NMR (DMSO-d$_6$, 300 MHz): δ 9.30 (br s, 2H), 8.99 (bs, 2H), 8.28 (s, 1H), 6.78 (s, 1H), 2.71 (s, 3H); Mass Spectrum (ESI, m/z) calcd. for $C_9H_{10}N_4S_2$, 238.8 (M+H), found 239.2.

EXAMPLE 148 a) 4-Bromo-5-ethylthiophene-2-carboxylic acid: A stirred solution of 10 g (35 mmol) of 4,5-dibromothiophene-2-carboxylic acid (Lancaster, Windham, N.H., U.S.A.) in dry THF (100 mL) was cooled to −78° C. To this, 35 mL (70 mmol) of 2.0 M n-butyllithium in cyclohexane (Aldrich, Milwaukee, Wis., U.S.A.) was added dropwise over 15 min, and the reaction was allowed to stir for 15 min at −78° C. The mixture was quenched with ethyl iodide (2.8 mL, 35 mmol) and allowed to warm to room temperature. The mixture was carefully poured into 6N hydrochloric acid (100 mL) and extracted with diethyl ether (4×50 mL). The organic layers were washed with water (2×50 mL), brine (50 mL), and dried over anhydrous sodium sulfate. The solvents were removed in vacuo to give 2-ethyl-3-bromo-thiophene-5-carboxylate (7 g, 85%) as a dark solid. $^1$H-NMR (DMSO-d$_6$; 300 MHz) δ 13.25 (br s, 1H), 7.62 (s, 1H), 2.80 (q, 2H, J=7.5 Hz), 1.23 (t, 3H, J=7.5 Hz).

b) Isopropyl 4-bromo-5-ethylthiophene-2-carboxylate: A solution of 7 g (30 mmol) of 4-bromo-5-ethylthiophene-2-carboxylic acid was dissolved in dry dichloromethane (200 mL) and treated with oxalyl chloride (3.2 mL, 36 mmol) and dimethylformamide (0.5 mL) for 18.5 h. The solvents were removed in vacuo and the residual brown oil was passed through silica gel (2 inches in a 350 mL scintered-glass Büchner funnel) and eluted with 700 mL of hexanes:ethyl acetate 9/1 (v:v). The elutate was concentrated in vacuo and the oil dissolved in dry dichloromethane (200 mL). This solution was treated with pyridine (12 mL, 150 mmol) and dry isopropanol (60 mL, 750 mmol) for 4 h at room temperature. The solvents were removed in vacuo and the residue partioned between dichloromethane (100 mL) and water (200 mL). The aqueous layers were extracted with dichloromethane (2×30 mL). The combined organic layers were extracted with sodium bicarbonate (2×30 mL), brine (30 mL), and dried over anhydrous sodium sulfate. The solvent was removed in vacuo. Purification by column chromatography on silica gel (250 g) eluting with hexanes:ethyl acetate 95/5 (v:v) gave isopropyl 2-ethyl-3-bromo-thiophene-5-carboxylate (4 g, 48%) as a yellow oil. $^1$H-NMR (DMSO-d$_6$; 300 MHz) δ 7.66 (s, 1H), 5.89 (septet, 1H, J=6.2 Hz), 2.80 (q, 2H, J=7.5 Hz), 1.29 (d, 6H, J=6.0 Hz), 1.24 (t, 3H, J=7.5 Hz).

c) Isopropyl 4-cyano-5-ethylthiophene-2-carboxylate: A stirred solution of 4 g (14.4 mmol) of isopropyl 4-bromo-5-ethylthiophene-2-carboxylate was refluxed in dry dimethylformamide (50 mL) with copper cyanide (1.94 g, 22 mmol) for 8 hours. The cooled mixture was poured into 0.1 M sodium cyanide (500 mL) and extracted with diethyl ether (4×50 mL). The organic layers were washed twice with brine (50 mL) and dried over anhydrous sodium sulfate. The solvents were removed in vacuo. Column chromatography on silica gel (400 g), eluting with hexanes:ethyl acetate 9/1 (v:v) gave isopropyl 2-ethyl-3-cyano-thiophene-5-carboxylate (1.7 g, 53%) as a pale yellow oil. $^1$H-NMR (DMSO-d$_6$; 300 MHz) δ 8.03 (s, 1H), 5.10 (septet, 1H, J=6.2 Hz), 3.04 (q, 2H, J=7.5 Hz), 1.31 (t, 3H, J=7.5 Hz), 1.30 (d, 6H, J=6.2 Hz). Mass spectrum (ESI m/z): Calcd. for $C_{11}H_{13}NO_2S$ 224.1 (M+H), found 224.0.

d) Isopropyl 4-(aminothioxomethyl)-5-ethylthiophene-2-carboxylate: A stirred solution of 1.7 g (7.6 mmol) of isopropyl 4-cyano-5-ethylthiophene-2-carboxylate was treated as in Example 139, step (c) to give isopropyl 5-ethyl-4-(aminothioxomethyl)-5-ethylthiophene-2-carboxylate (1.45 g, 74%) as a yellow solid. $^1$H-NMR (DMSO-d$_6$; 300 MHz) δ 9.93 (br s, 1H), 9.39 (br s, 1H), 8.04 (s, 1H), 5.08 (septet, 1H, J=6.2 Hz), 3.08 (q, 2H, J=7.5 Hz), 1.29 (d, 6H, J=6.2 Hz), 1.24 (t, 3H, J=7.5 Hz).

e) Isopropyl 5-ethyl-4-(4-phenyl(1,3-thiazol-2-yl))thiophene-2-carboxylate: A solution of 450 mg (1.75 mmol) of isopropyl 5-ethyl-4-(aminothioxomethyl)-5-ethylthiophene-2-carboxylate was reacted with 348 mg (1.75 mmol) of 2-bromoacetophenone (Aldrich, Milaukee, Wis., U.S.A.) in a manner similar to Example 8, step (a) to give isopropyl 5-ethyl-4-(4-phenyl(1,3-thiazol-2-yl)) thiophene-2-carboxylate (303 mg, 49%) as an off-white solid. $^1$H-NMR (DMSO-d$_6$; 300 MHz) δ 8.22 (s, 1H), 8.07 (s, 1H), 8.03 (m, 2H), 7.49 (m, 2H), 7.38 (m, 1H), 5.13 (septet, 1H, J=6.2 Hz), 3.34 (q, 2H, J=7.4 Hz), 1.39 (t, 3H, J=7.4 Hz), 1.33 (d, 6H, J=6.2 Hz). Mass spectrum (ESI, m/z): Calcd. for $C_{19}H_{19}NO_2S_2$ 358.1 (M+H), found 358.1.

f) 5-Ethyl-4-(4-phenyl(1,3-thiazol-2-yl))thiophene-2-carboxamidine: Isopropyl 5-ethyl-4-(4-phenyl(1,3-thiazol- 2-yl))thiophene-2-carboxylate (250 mg, 0.70 mmol) was treated in a manner similar to that for Example 10, step (b), to give 5-ethyl-4-(4-phenyl(1,3-thiazol-2-yl))thiophene-2-carboxamidine (148 mg, 67%) as a yellow solid. $^1$H-NMR (DMSO-$d_6$; 300 MHz) δ 9.44 (br s, 2H), 9.07 (br s, 2H), 8.54 (s, 1H), 8.26 (s, 1H), 8.05 (m, 2H), 7.50 (m, 2H), 8.70 (s, 1H), 7.40 (m, 1H), 3.44 (q, 2H, J=7.4 Hz), 1.42 (t, 3H, J=7.4 Hz). Mass spectrum (ESI, m/z): Calcd. for $C_{16}H_{15}N_3S_2$ 314.1 (M+H), found 314.2.

EXAMPLE 149 a) Isopropyl 4-[4-(3-hydroxyphenyl)(1,3-thiazol-2-yl)]-5-methylthiophene-2-carboxylate: A solution of 1.97 g (8.1 mmol) of isopropyl 4-(aminothioxomethyl)-5-methylthiophene-2-carboxylate was reacted with 1.74 g (8.1 mmol) of 3'-hydroxy-2-bromoacetophenone (Example 40, step (a)) were reacted in a manner similar to Example 8, step (a) to give, after column chromatography on silica gel eluting with hexane:ethyl acetate 7/3 (v:v), crystallization from acetonitrile, and recrystallization from hexanes, isopropyl 4-[4-(3-hydroxyphenyl)(1,3-thiazol-2-yl)]-5-methylthiophene-2-carboxylate (1.4 g, 48%) as brown solid. $^1$H-NMR (DMSO-$d_6$; 300 MHz) δ 9.57 (br s, 1H), 8.14 (s, 1H), 8.08 (s, 1H), 7.46 (m, 2H), 7.26 (m, 1H),), 6.78 (m, 1H), 5.12 (septet, 1H, J=6.2 Hz), 2.85 (s, 3H), 1.33 (d, 6H, J=6.2 Hz). Mass spectrum (ESI, m/z): Calcd. for $C_{18}H_{17}NO_3S_2$ 360.1 (M+H), found 360.1.

b) 4-[4-(3-Hydroxyphenyl)(1,3-thiazol-2-yl)]-5-methylthiophene-2-carboxamide: Isopropyl 4-[4-(3-hydroxyphenyl)(1,3-thiazol-2-yl)]-5-methylthiophene-2-carboxylate (1.4 g, 3.89 mmol) was treated in a manner similar to Example 10, step (b) to give 4-[4-(3-hydroxyphenyl)(1,3-thiazol-2-yl)]-5-methylthiophene-2-carboxamide (360 mg, 31%) as a brown solid. $^1$H-NMR (DMSO-$d_6$; 300 MHz) δ 9.62 (br s, 1H), 9.45 (br s, 2H), 9.09 (br s, 2H), 8.53 (s, 1H), 8.16 (s, 1H), 7.47 (m, 2H), 7.27 (m, 1H), 6.80 (m, 1H), 2.93 (s, 3H). Mass spectrum (ESI, m/z): Calcd. for $C_{15}H_{13}N_3OS_2$ 316.1 (M+H), found 316.2.

EXAMPLE 150 a) (tert-Butoxy)-N-({4-[4-(3-hydroxyphenyl)(1,3-thiazol-2-yl)]-5-methyl(2-thienyl)}iminomethyl)carboxamide: A stirred solution of 320 mg (1 mmol) of 4-[4-(3-hydroxyphenyl)(1,3-thiazol-2-yl)]-5-methylthiophene-2-carboxamide was dissolved in dry dimethylformamide (50 mL) and treated with 262 mg (1.2 mmol) of di-tert-butyl-dicarbonate (Acros, Pittsburgh, Pa., U.S.A.) and diisopropylethylamine (261 μL, 1.5 mmol) for 64 hours at room temperature. The mixture was poured into sodium bicarbonate solution (200 mL) and extracted with dichloromethane (6×30 mL). The organic extracts were washed twice with brine (50 mL) and dried over anhydrous sodium sulfate. The solvents were in vacuo and column chromatography on silica gel (100 g) eluting with dichloromethane:methanol 95/5 (v:v) gave (tert-butoxy)-N-({4-[4-(3-hydroxyphenyl)(1,3-thiazol-2-yl)]-5-methyl(2-thienyl)}iminomethyl)carboxamide (247 mg, 59%) as a yellow oil. $^1$H-NMR (DMSO-$d_6$; 300 MHz) δ 9.56 (s, 1H), 9.12 (br s, 2H), 8.47 (s, 1H), 8.09 (s, 1H), 7.46 (m, 2H), 7.26 (m, 1H), 6.78 (m, 1H), 2.83 (s, 3H), 1.45 (s, 9H). Mass spectrum (ESI, m/z): Calcd. for $C_{20}H_{21}N_3O_3S_2$ 416.1 (M+H), found 415.7 b) Methyl 2-{3-[2-(5-{[(tert-butoxy)carbonylamino]iminomethyl}-2-methyl-3-thienyl)-1,3-thiazol-4-yl]phenoxy}acetate: A stirred solution of 247 mg (0.595 mmol) of (tert-butoxy)-N-({4-[4-(3-hydroxyphenyl)(1,3-thiazol-2-yl)]-5-methyl(2-thienyl)}iminomethyl)carboxamide was dissolved in dry dimethylformamide (4 mL) and treated with cesium carbonate (291 mg, 0.89 mmol) and methyl bromoacetate (136 mg, 0.89 mmol) for 3 h at 60° C. The mixture was poured into water (50 mL) and extracted with dichloromethane (9×10 mL). The organic extracts were washed with brine (10 mL) and dried over anhydrous sodium sulfate. The solvents were removed in vacuo and column chromatography on silica gel (50 g) eluting with dichloromethane:methanol 98/2 (v:v) gave methyl 2-{3-[2-(5-{[(tert-butoxy)carbonylamino]iminomethyl}-2-methyl-3-thienyl)-1,3-thiazol-4-yl]phenoxy}acetate (178 mg, 61%) as an oil. Mass spectrum (ESI, m/z): Calcd. for $C_{23}H_{25}N_3O_5S_2$ 488.1 (M+H), 388.1 ((M-BOC)+H), found 487.8, 388.2.

c) Methyl 2-{3-[2-(5-amidino-2-methyl-3-thienyl)-1,3-thiazol-4-yl]phenoxy}acetate: Methyl 2-{3-[2-(5-{[(tert-butoxy)carbonylamino]iminomethyl}-2-methyl-3-thienyl)-1,3-thiazol-4-yl]phenoxy}acetate (15 mg, 0.031 mmol) treated with dichloromethane:trifluoroacetic acid 1/1 (v:v) with 2.5% water added at room temperature for 1.5 h. Removal of the solvents in vacuo gave methyl 2-{3-[2-(5-amidino-2-methyl-3-thienyl)-1,3-thiazol-4-yl]phenoxy}acetate (8.1 mg, 52%) as a brown solid. $^1$H-NMR (DMSO-$d_6$; 300 MHz) δ 9.38 (br s, 2H), 8.94 (br s, 2H), 8.51 (s, 1H), 8.31 (s, 1H), 7.62 (m, 2H), 7.41 (m, 1H), 6.96 (m, 1H), 4.89 (s, 2H), 3.72 (s, 3H), 2.92 (s, 3H). Mass spectrum (ESI, m/z): Calcd. for $C_{18}H_{17}N_3O_3S_2$ 388.1 (M+H), found 388.3.

EXAMPLE 151 a) 2-{3-[2-(5-{[(tert-Butoxy)carbonylamino]iminomethyl}-2-methyl-3-thienyl)-1,3-thiazol-4-y]phenoxy}acetic acid: A stirred solution of 50 mg (0.11 mmol) of methyl 2-{3-[2-(5-{[(tert-butoxy)carbonylamino]iminomethyl}-2-methyl-3-thienyl)-1,3-thiazol-4-yl]phenoxy}acetate was dissolved in tetrahydrofuran (10 mL) and treated 2M aqueous sodium hydroxide solution (2 mL) at room temperature for 1 h 10 min. The solvents were removed in vacuo. Purification by passing the solid through silica gel (1 inch in a 60 mL sintered-glass Büchner funnel) eluting with dichloromethane:methanol 8/2 (v:v) gave 2-{3-[2-(5-{[(tert-butoxy)carbonylamino]iminomethyl}-2-methyl-3-thienyl)-1,3-thiazol-4-yl]phenoxy}acetic acid (44 mg, 88%) as a yellow solid. $^1$H-NMR (DMSO-$d_6$; 300 MHz) δ 9.38 (br s, 2H), 8.94 (br s, 2H), 8.51 (s, 1H), 8.31 (s, 1H), 7.62 (m, 2H), 7.41 (m, 1H), 6.96 (m, 1H), 4.89 (s, 2H), 3.72 (s, 3H), 2.92 (s, 3H). Mass spectrum (ESI, m/z): Calcd. for $C_{22}H_{23}N_3O_5S_2$ 474.1 (M+H), 374.1 ((M-BOC)+H) found 374.2, 473.7.

b) 2-{3-[2-(5-Amidino-2-methyl-3-thienyl)-1,3-thiazol-4-yl]phenoxy}acetic acid: Methyl 2-{3-[2-(5-{[(tert-butoxy)carbonylamino]iminomethyl}-2-methyl-3-thienyl)-1,3-thiazol-4-yl]phenoxy}acetate (4 mg, 0.0084 mmol) was treated with dichloromethane:trifluoroacetic acid 1/1 (v:v) with 2.5% water added at room temperature for 2 h 35 min. Removal of the solvents in vacuo gave 2-{3-[2-(5-amidino-2-methyl-3-thienyl)-1,3-thiazol-4-yl]phenoxy}acetic acid (2.9 mg, 71%) as a solid. Mass spectrum (ESI, m/z): Calcd. for $C_{17}H_{15}N_3O_3S_2$ 373.1 (M+H), found 374.2.

c) tert-Butyl 4-(2-{3-[2-(5-{[(tert-butoxy)carbonylamino]iminomethyl}-2-methyl-3-thienyl)-1,3-thiazol-4-yl]phenoxy}acetyl)piperazinecarboxylate: A stirred solution of 40 mg (0.084 mmol) of 2-{3-[2-(5-{[(tert-butoxy)carbonylamino]iminomethyl}-2-methyl-3-thienyl)-1,3-thiazol-4-yl]phenoxy}acetic acid dissolved in dry dimethylformamide (5 mL) was treated with hydroxybenzotriazole (23 mg, 0.17 mmol), 32 mg (0.17 mmol) of N-tert-butoxycarbonyl-piperazine (Lancaster, Windham, N.H., U.S.A.), 65 mg (0.17 mmol) of O-(7-azabenzotriazol-1-yl)-N,N,N',N'-tetramethyluronium hexafluorophosphate (HATU) at room temperature for 20 h. The mixture was partitioned between dichloromethane (50 mL) and brine (50 mL). The aqueous layers were extracted twice with dichloromethane (50 mL) and the combined organic layers were washed with brine (50 mL) and dried over anhydrous sodium sulfate. The solvents were removed in vacuo. Purification preparative thin layer chromatography eluting with dichloromethane:methanol 95/5 (v:v) gave tert-butyl 4-(2-{3-[2-(5-{[(tert-butoxy)carbonylamino]iminomethyl}-2-methyl-3-thienyl)-1,3-thiazol-4-yl]phenoxy}acetyl) piperazinecarboxylate (25 mg, 46%) as a white solid. $^1$H-NMR (DMSO-$d_6$; 300 MHz) δ 9.13 (br s, 2H), 8.50 (s, 1H), 8.20 (s, 1H), 7.63 (m, 2H), 7.39 (m, 1H), 6.95 (m, 1H), 4.93 (s, 2H), 3.47–3.34 (m, 8H), 2.82 (s, 3H), 1.45 (s, 9H), 1.42 (s, 9H). Mass spectrum (ESI, m/z): Calcd. for $C_{31}H_{39}N_5O_6S_2$ 642.3 (M+H), 542.3 ((M-BOC)+H), 442.3 ((M-2 BOC)+H), found 642.0, 542.2, 442.3.

d) 5-Methyl-4-{4-[3-(2-oxo-2-piperazinylethoxy)phenyl] (1,3-thiazol-2-yl)}thiophene-2-carboxamidine: tert-Butyl 4-(2-{3-[2-(5-{[(tert-butoxy)carbonylamino]iminomethyl}-2-methyl-3-thienyl)-1,3-thiazol-4-yl]phenoxy}acetyl) piperazinecarboxylate (25 mg, 0.039 mmol) treated with dichloromethane:trifluoroacetic acid 1/1 (v:v) with 2.5% water added at room temperature for 2 h. Removal of the solvents in vacuo gave 5-methyl-4-{4-[3-(2-oxo-2-piperazinylethoxy)phenyl](1,3-thiazol-2-yl)}thiophene-2-carboxamidine (27.4 mg, quantitive yield) as an off-white solid. $^1$H-NMR (Methanol-$d_4$; 300 MHz) δ 8.41 (s, 1H), 7.94 (s, 1H), 7.67 (m, 2H), 7.39 (m, 1H), 7.00 (m, 1H), 4.96 (s, 2H), 3.88 (m, 4H), 3.25 (m, 4H), 2.95 (s, 3H). Mass spectrum (ESI, m/z): Calcd. for $C_{21}H_{23}N_5O_2S_2$ 442.1 (M+H), found 442.4.

EXAMPLE 152

Methyl 4-(2-bromoacetyl)-5-methylthiothiophene-2-carboxylate

To a stirring slurry of 2-methylthio-(5-carbomethoxy)-thiophene-3-carboxylic acid (2.0 g, 8.61 mmol) in 28 mL of $CH_2Cl_2$ under $N_2$ containing 0.8 mL DMF at 0° C. was added oxalyl chloride (1.9 equiv, 16.3 mmol) slowly via syringe. The reaction was allowed to warm to ambient temperature after 1 h, and then stirred an additional 1 h. The reaction mixture was filtered through a 20 cm pad of silica gel in a 30 mL sintered glass funnel wetted with 50% ethyl acetate-hexanes and further eluted with the same solvent system until the eluent showed no product by UV visualization. The solvent was concentrated in vacuo, azeotroped with toluene (1×), and dried under vacuum to afford the acid chloride (1.52 g) as a light yellow solid. The acid chloride was dissolved in 20 mL of $CH_3CN$, cooled to 0° C., and treated with $TMSCHN_2$ (2.1 equiv, 6.3 mL, 2 M in hexanes) dropwise via syringe. The reaction was allowed to warm to ambient temperature (0.5 h), cooled back to 5° C. and immediately treated with 30% HBr-acetic acid (0.66 mL) dropwise via an addition funnel. After 15 min. at 0° C., the reaction diluted with 20 mL of ether, filtered and thoroughly washed with ether (3×20 mL). The yellow solids were dried under vacuum to afford methyl 4-(2-bromoacetyl)-5-methylthiothiophene-2-carboxylate (1.0 g, 37% yield) as a yellow powder. $^1$H NMR (DMSO-$d_6$, 300 MHz) δ 2.66 (s, 3H), 3.84 (s, 3H), 5.03 (s, 2H), 8.29 (s, 1H).

EXAMPLE 153

Isopropyl-4-(2-bromoacetyl)-5-methylthiophene-2-carboxylate

To a stirring slurry of 2-methyl-(5-carboisopropoxy)-thiophene-3-carboxylic acid (0.40 g, 1.75 mmol) in 15 mL of $CH_2Cl_2$ under $N_2$ containing 0.8 mL DMF at 0° C. was added oxalyl chloride (1.9 equiv, 3.32 mmol,) slowly via syringe. The reaction was allowed to warm to ambient temperature after 1 h, and then stirred an additional 1 h. The solvent was concentrated in vacuo, azeotroped with toluene (1×), and dried under vacuum to afford the acid chloride (0.397 g, 1.60 mmol) as a light yellow solid. The acid chloride was dissolved in 7 mL of $CH_3CN$, cooled to 0° C., and treated with $TMSCHN_2$ (2.1 equiv, 1.68 mL, 2 M in hexanes) dropwise via syringe. The reaction was allowed to warm to ambient temperature (0.5 h), cooled back to 5° C. and immediately treated with 30% HBr-acetic acid (0.5 mL) dropwise via an addition funnel. After 15 min. at 0° C., the reaction mixture was filtered through a 10 cm pad of silica gel in a 15 mL sintered glass funnel wetted with 50% ethyl acetate-hexanes and further eluted with the same solvent system until the eluent showed no product by UV visualization. The solvent was concentrated in vacuo dried under vacuum to afford isopropyl-4-(2-bromoacetyl)-5-methylthiophene-2-carboxylate (0.329 g, 61% yield) as an oil which solidified upon standing to a tan solid. $^1$H NMR (DMSO-$d_6$, 300 MHz) δ 1.31 (d, 6H, J=6.3 Hz), 2.71 (s, 3H), 4.60 (s, 2H), 5.09 (m, 1H), 8.08 (s, 1H).

EXAMPLE 154 a) Methyl 5-methylthio-4-[2-(phenylamino)-(1,3-thiazol-4-yl)]-thiophene-2-carboxylate hydrobromide: Methyl 4-(2-bromoacetyl)-5-methylthiothiophene-2-carboxylate (60.5 mg, 0.19 mmol) was slurried in 4 mL of acetone with phenyl thiourea (1 equiv, 30 mg) and heated to 70° C. After 3 h the reaction was allowed to cool to room temperature, filtered, and dried in vacuo to give 62.5 mg (69% yield) of methyl 5-methylthio-4-[2-(phenylamino)-(1,3-thiazol-4-yl)]-thiophene-2-carboxylate hydrobromide. $^1$H NMR (DMSO-$d_6$, 300 MHz) δ 2.65 (s, 3H), 3.83 (s, 3H), 6.95–6.99 (m, 1H), 7.28–7.35 (m, 4H), 7.67 (d, 1H, J=1.4, 7.7 Hz), 8.06 (s, 1H), 10.54 (s, 1H); Mass Spectrum (ESI) m/z calcd. for $C_{16}H_{14}N_2O_2S_3$, 362.49 (M+H), found 363.7.

b) 5-Methylthio-4-[2-(phenylamino)(1,3-thiazol-4-yl)] thiophene-2-carboxamidine hydrochloride: To a flame-dried flask containing 57.8 mg (8 equiv, 1.08 mmol) of $NH_4Cl$ under $N_2$ was charged 1.3 mL of toluene. $AlMe_3$ (8 equiv, 2M/hexanes, 0.54 mL) was added dropwise to the stirred slurry over a 3 min. period, and allowed to stir another 5 min. At this time methyl 5-methylthio-4-[2-(phenylamino)-(1,3-thiazol-4-yl)]-thiophene-2-carboxylate hydrobromide (1 equiv, 60 mg, 0.135 mmol) was quickly added in one portion and the resultant mixture was immersed in a 120° C. oil bath. After 2 h 10 min. at this temperature, TLC (silica gel 60 $F_{254}$, Merck KGaA, Darmstadt, Germany, 9:1:0.5 $CH_2Cl_2$-MeOH-AcOH eluent) indicated the reaction to be complete by disappearance of the starting material. The reaction was allowed to cool to ambient temperature, then added via pipette to a stirred slurry of 1.3 g of $SiO_2$ in 20 mL of $CHCl_3$. The residual residue in the flask was rinsed with 4 mL of MeOH, briefly sonicated and added to the $SiO_2$ slurry. The slurry was stirred for 10 min. and then filtered through a 15-mL sintered glass funnel containing 20 cm of $SiO_2$ with 50% $CHCl_3$-MeOH. The yellow fraction was collected, discarding the forerun. TLC indicated the product was essentially pure. The solvent was removed in vacuo, and the residue triturated with 10% MeOH-$CH_2Cl_2$. The solids were removed by filtration. The solvent was concentrated in vacuo to give 30.1 mg (66% yield) of 5-methylthio-4-[2-(phenylamino)-(1,3-thiazol-4-yl)]thiophene-2-carboxamidine hydrochloride as a red-brown powder. $^1$H NMR (DMSO-$d_6$, 300 MHz) δ 2.73 (s, 3H), 6.94–7.00 (m, 1H), 7.15 (s, 1H), 7.30–7.35 (m, 1H), 7.78 (d, 1H, J=8.7 Hz), 8.49 (s, 1H), 8.87 (bs, 2H), 9.31 (bs, 2H), 10.38 (s, 1H); Mass Spectrum (ESI) m/z calcd. for $C_{15}H_{14}N_4S_3$, 346.50 (M+H), found 347.2.

EXAMPLE 155 a) Methyl 4-{2-[(2-chlorophenyl)amino](1,3-thiazol-4-yl)}-5-methylthiothiophene-2-carboxylate hydrobromide: Methyl 4-(2-bromoacetyl)-5-methylthiothiophene-2-carboxylate (50 mg) was allowed to react with 2-chlorophenyl thiourea (26.7 mg) as described in Example 154, step (a), to give 58 mg (75%) of methyl 4-{2-[(2-chlorophenyl)amino]-(1,3-thiazol-4-yl)}-5-methylthiothiophene-2-carboxylate hydrobromide. $^1$H NMR (DMSO-$d_6$, 300 MHz) δ 2.66 (s, 3H), 3.82 (s, 3H), 7.04 (m, 1H), 7.32–7.38 (m, 2H), 7.47 (dd, 1H, J=1.4, 8.7 Hz), 8.12 (s, 1H), 8.56 (dd, 1H, J=1.4, 8.3 Hz), 9.75 (s, 1H); Mass Spectrum (ESI) m/z calcd. for $C_{16}H_{13}ClN_2O_2S_3$, 396.94 (M+H), found 397.1.

b) 4-{2-[(2-Chlorophenyl)amino](1,3-thiazol-4-yl)}-5-methylthiothiophene-2-carboxamidine hydrochloride: Methyl 4-{2-[(2-chlorophenyl)amino]-1,3-thiazol-4-yl)}-5-methylthiothiophene-2-carboxylate hydrobromide (40 mg, 0.08 mmol) was treated as described in Example 154, step (b) to give 24 mg (71.8%)of 4-{2-[(2-chlorophenyl)amino]-(1,3-thiazol-4-yl)}-5-methylthiothiophene-2-carboxamidine hydrochloride. $^1$H NMR (DMSO-$d_6$, 300 MHz) δ 2.71 (s, 3H), 7.04 (td, 1H, J=1.4, 7.8 Hz), 7.21 (s, 1H), 7.35 (t, 1H, J=8.5 Hz), 8.42 (s, 1H), 8.57 (dd, 1H, J=1.3, 8.3 Hz), 8.80 (bs, 2H), 9.26 (bs, 2H), 9.79 (s, 1H); Mass Spectrum (ESI) m/z calcd. for $C_{15}H_{14}N_4S_3Cl$, 380.94 (M+H), found 381.1.

EXAMPLE 156 a) Methyl 4-(2-amino(1,3-thiazol-4-yl))-5-methylthiothiophene-2-carboxylate hydrobromide: Methyl 4-(2-bromoacetyl)-5-methylthiothiophene-2-carboxylate (50 mg, 0.16 mmol) was allowed to react with thiourea (12 mg) as described in Example 154, step (a), to give 54 mg (70% yield) of methyl 4-(2-amino-(1,3-thiazol-4-yl))-5-methylthiothiophene-2-carboxylate hydrobromide. $^1$H NMR (DMSO-$d_6$, 300 MHz) δ 2.69 (s, 3H), 3.83 (s, 3H), 7.00 (s, 1H), 8.05 (s, 1H); Mass Spectrum (ESI) m/z calcd. for $C_{10}H_{10}O_2S_3N_2$, 286.41 (M+H), found 287.1;

b) 4-(2-Amino-(1,3-thiazol-4-yl))-5-methylthiothiophene-2carboxamidine hydrochloride: Methyl 4-(2-amino-(1,3-thiazol-4-yl))-5-methylthiothiophene-2-carboxylate hydrobromide (110 mg, 0.29 mmol) was treated as described in Example 154, step (b). The resultant amidine (74 mg) was stirred in 3 mL of dry methanol under $N_2$ and treated with ca. 1 mL of ether saturated with dry HCl gas. Dry ether (1.5 mL) was then added and the result was allowed to sit for 2 h at ambient temperature and then filtered to give 40 mg (45% yield) of 4-(2-amino-(1,3-thiazol-4-yl))-5-methylthiothiophene-2-carboxamidine hydrochloride. $^1$H NMR (DMSO-$d_6$, 300 MHz) δ 2.69 (s, 3H), 6.90 (s, 1H), 8.44 (s, 1H), 9.20, 9.42 (s, 4H, NH); Mass Spectrum (ESI) m/z calcd.$C_9H_{10}N_4S_3$, 270.4 (M+H), found 271.2.

EXAMPLE 157 a) Methyl 4-{2-[(2,5-dimethoxyphenyl)amino](1,3-thiazol-4-yl)}-5-methylthiothiophene-2-carboxylate hydrobromide: Methyl 4-(2-bromoacetyl)-5-methylthiothiophene-2-carboxylate (49.4 mg, 0.15 mmol) was allowed to react with 2,5-dimethoxy phenyl thiourea (37.2 mg) as described in Example 154, step (a), to give 65.5 mg (87% yield) of methyl 4-{2-[(2,5-dimethoxyphenyl)amino](1,3-thiazol-4-yl)}-5-methylthiothiophene-2-carboxylate hydrobromide. $^1$H NMR (DMSO-$d_6$, 300 MHz) δ 2.66 (s, 3H), 3.76 (s, 3H), 3.81 (s, 3H), 3.83 (s, 3H), 6.49 (dd, 1H, J=3.0, 8.8 Hz), 6.92 (d, 1H, J=8.9 Hz), 7.26 (s, 1H), 8.17 (s, 1H), 8.37 (d, 1H, J=3.1 Hz), 9.70 (s, 1H); Mass Spectrum (ESI) m/z calcd. for $C_{18}H_{18}N_2O_4S_3$, 422.54 (M+H), found 423.1.

b) 4-{2-[(2,5-Dimethoxyphenyl)amino](1,3-thiazol-4-yl)}-5-methylthiothiophene-2-carboxamidine: Methyl 4-{2-[(2,5-dimethoxyphenyl)amino]-(1,3-thiazol-4-yl)}-5-methylthiothiophene-2-carboxylate hydrobromide (45.5 mg, 0.09 mmol) was treated as described in Example 154, step (b), followed by preparative thin layer chromatography (500 mm silica gel plate, J.T. Baker, Phillipsburg, N.J., 10%-methanol-$CH_2Cl_2$-sat'd. $NH_3$ eluent) to give 9.9 mg (27% yield of 4-{2-[(2,5-dimethoxyphenyl)amino](1,3-thiazol-4-yl)}-5-methylthiothiophene-2-carboxamidine. $^1$H NMR (DMSO-$d_6$, 300 MHz) δ 2.60 (s, 3H), 3.73 (s, 3H), 3.81 (s, 3H), 6.48 (dd, 1H, J=3.1, 8.8 Hz), 6.92 (d, 1H, J=7.9 Hz), 7.05 (s, 1H), 7.5 (bs, 2H), 8.04 (s, 1H), 8.34 (d, 1H, J=1.0 Hz), 9.6 (bs, 1H); Mass Spectrum (ESI) m/z calcd. for $C_{17}H_{18}N_4O_2S_3$, 406.55 (M+H), found 407.1.

EXAMPLE 158 a) Methyl 4-{2-[(3-methoxyphenyl)amino](1,3-thiazol-4-yl)}-5-methylthiothiophene-2-carboxylate hydrobromide: Methyl 4-(2-bromoacetyl)-5-methylthiothiophene-2-carboxylate (53.3 mg, 0.17 mmol) was allowed to react with 2-methoxy phenyl thiourea (34.5 mg) as described in Example 154, step (a), to give 61 mg (76% yield) of methyl 4-{2-[(3-methoxyphenyl)amino](1,3-thiazol-4-yl)}-5-methylthiothiophene-2-carboxylate hydrobromide. $^1$H NMR (DMSO-$d_6$, 300 MHz) δ 2.67 (s, 3H), 3.78 (s, 3H), 3.83 (s, 3H), 6.53 (d, 1H, J=6.8 Hz), 7.13–7.24 (m, 2H), 7.29 (s, 3H), 7.59 (m, 1H), 8.16 (s, 3H), 10.32 (s, 1H); Mass Spectrum (ESI) m/z calcd. for $C_{17}H_{16}N_2O_3S_3$, 392.52 (M+H), found 393.2.

b) 4-{2-[(3-Methoxyphenyl)amino](1,3-thiazol4-yl)}-5-methylthiothiophene-2-carboxamidine hydrochloride: Methyl 4-{2-[(3-methoxyphenyl)amino]-(1,3-thiazol-4-yl)}-5-methylthiothiophene-2-carboxylate hydrobromide (54.6 mg, 0.11 mmol) was treated as described in Example 154, step (b) to give 25.2 mg (56%) of 4-{2-[(3-methoxyphenyl)amino](1,3-thiazol-4-yl)}-5-methylthiothiophene-2-carboxamidine hydrochloride. $^1$H NMR (DMSO-$d_6$, 300 MHz) δ 2.71 (s, 3H), 3.77 (s, 3H), 6.54 (m, 1H), 7.15 (s, 3H), 7.19–7.28 (m, 2H), 7.47 (m, 1H), 8.46 (s, 1H), 8.86 (bs, 2H), 9.28 (bs, 2H), 10.36 (s, 1H); Mass Spectrum (ESI) m/z calcd. for $C_{16}H_{16}N_4OS_3$, 376.52 (M+H), found 377.2.

EXAMPLE 159 a) Methyl 4-{2-[(4-methoxyphenyl)amino](1,3-thiazol-4-yl)}-5-methylthiothiophene-2-carboxylate hydrobromide: Methyl 4-(2-bromoacetyl)-5 -methylthiothiophene-2-carboxylate (41.3 mg, 0.13 mmol) was allowed to react with 5-methoxy phenyl thiourea (26.8 mg) as described in Example 154, step (a) to give 25 mg (41% yield) of methyl 4-{2-[(4-methoxyphenyl)amino](1,3-thiazol-4-yl)}-5-methylthiothiophene-2-carboxylate hydrobromide. $^1$H NMR (DMSO-$d_6$, 300 MHz) δ 2.64, 2.68 (s, 3H rotomer) ), 3.72, 3.73 (s, 3H rotomer), 3.83 (s, 3H), 6.91 (dd, 2H, J=6.7, 8.8 Hz), 7.21 (s, 1H), 7.59 (d, 1H, J=9.0 Hz), 7.67 (d, 1H, J=9.0 Hz), 8.05, 8.13 (s, 1H rotomer), 10.16, 10.34 (bs, 1H, rotomer); Mass Spectrum (ESI) m/z calcd. for $C_{17}H_{16}N_2O_2S_3$, 392.52 (M+H), found 393.1.

b) 4-{2-[(4-Methoxyphenyl)amino](1,3-thiazol-4-yl)}-5-methylthiothiophene-2-carboxamidine hydrochloride:

Methyl 4-{2-[(4-methoxyphenyl)amino]-(1,3-thiazol-4-yl)}-5-methylthiothiophene-2-carboxylate hydrobromide (22 mg, 0.046 mmol) was treated as described in Example 154, step (b) to give 11.5 mg (61% yield) of 4-{2-[(4-methoxyphenyl)amino](1,3-thiazol-4-yl)}-5-methylthiothiophene-2-carboxamidine hydrochloride. $^1$H NMR (DMSO-d$_6$, 300 MHz) δ 2.72 (s, 3H), 3.73 (s, 3H), 6.91 (d, 2H, J=9.0 Hz), 7.08 (s, 1H), 7.69 (d, 2H, J=9.1 Hz), 8.44 (s, 1H), 8.83 (bs, 2H), 9.28 (bs, 2H), 10.15 (s, 1H); Mass Spectrum (ESI) m/z calcd. for C$_{16}$H$_{16}$N$_4$OS$_3$, 376.52 (M+H), found 377.1.

EXAMPLE 160 a) Methyl 4-(2-{[4-(dimethylamino)phenyl]amino}(1,3-thiazol-4-yl))-5-methylthiothiophene-2-carboxylate hydrobromide: Methyl 4-(2-bromoacetyl)-5-methylthiothiophene-2-carboxylate (50 mg, 0.16 mmol) was allowed to react with 4-N,N-dimethylaminophenyl thiourea (31.5 mg) as described in Example 154, step (a), to give 53.2 mg (75% yield) of methyl 4-(2-{[4-(dimethylamino)phenyl]amino}(1,3-thiazol-4-yl))-5-methylthiothiophene-2-carboxylate hydrobromide. $^1$H NMR (DMSO-d$_6$, 300 MHz) δ 2.69 (s, 3H), 3.15 (s, 6H), 3.83 (s, 3H), 7.36 (s, 1H), 7.55 (bs, 2H), 7.88 (d, 2H, J=8.3 Hz), 8.16 (s, 1H), 10.56 (bs, 1H); Mass Spectrum (ESI) m/z calcd. for C$_{18}$H$_{19}$N$_3$O$_2$S$_3$, 405.56 (M+H), found 406.1.

b) 4-(2-{[4-(Dimethylamino)phenyl]amino}(1,3-thiazol-4-yl))-5-methylthiothiophene-2-carboxamidine hydrochloride: Methyl 4-(2-{[4-(dimethylamino)phenyl]amino}(1,3-thiazol-4-yl))-5-methylthiothiophene-2-carboxylate hydrobromide (50 mg, 0.10 mmol) was treated as described in Example 154, step (b) to give 9.4 mg (22% yield) of 4-{2-[(4-methoxyphenyl)amino](1,3-thiazol-4-yl)}-5-methylthiothiophene-2-carboxamidine hydrochloride. $^1$H NMR (DMSO-d$_6$, 300 MHz) 2.70 (s, 3H), 2.84 (s, 6H), 6.75 (d, 2H, J=9.2 Hz), 7.00 (s, 1H), 7.56 (d, 2H, J=9.1 Hz), 8.31 (s, 1H), 8.68 (bs, 3H), 9.92 (bs, 1H).

EXAMPLE 161 a) Methyl 4-{2-[(4-chloro-2-methylphenyl)amino](1,3-thiazol-4-yl)}-5-methylthiothiophene-2-carboxylate hydrobromide: Methyl 4-(2-bromoacetyl)-5-methylthiothiophene-2-carboxylate (50 mg, 0.16 mmol) was allowed to react with 2-methyl-4-chlorophenyl thiourea (32.1 mg) as described in Example 154, step (a), to give 62.2 mg (79% yield) of methyl 4-{2-[(4-chloro-2-methylphenyl)amino](1,3-thiazol-4-yl)}-5-methylthiothiophene-2-carboxylate hydrobromide. $^1$H NMR (DMSO-d$_6$, 300 MHz) δ 2.28, 2.29 (s, 3H rotamer), 2.62, 2.66 (s, 3H rotamer), 3.82 (s, 3H), 7.21–7.29 (m, 3H), 8.04, 8.11 (s, 1H rotamer), 8.17 (d, 1H, J=8.8 Hz), 8.30 (d, 1H), J=8.4 Hz), 9.44 (s, 1H), 9.59 (s, 1H); Mass Spectrum (ESI) m/z calcd. for C$_{17}$H$_{15}$ClN$_2$O$_2$S$_3$, 410.96 (M+H), found 411.1.

b) 4-{2-[(4-Chloro-2-methylphenyl)amino](1,3-thiazol-4-yl)}-5-methylthiothiophene-2-carboxamidine hydrochloride: Methyl 4-{2-[(4-chloro-2-methylphenyl)amino]-(1,3-thiazol-4-yl)}-5-methylthiothiophene-2-carboxylate hydrobromide (55 mg, 0.17 mmol) was treated as described in Example 154, step (b) to give 16 mg (22% yield) of 4-{2-[(4-chloro-2-methylphenyl)amino](1,3-thiazol-4-yl)}-5-methylthiothiophene-2-carboxamidine hydrochloride. $^1$H NMR (DMSO-d$_6$, 300 MHz) δ 2.30 (s, 3H), 2.70 (s, 3H), 7.15 (s, 1H), 7.23–7.29 (m, 2H), 8.34 (d, 1H, J=8.6 Hz), 8.44 (s, 1H), 8.86 (bs, 2H), 9.29 (bs, 2H), 9.47 (s, 1H); Mass Spectrum (ESI) m/z calcd. for C$_{16}$H$_{15}$ClN$_4$S$_3$, 394.97 (M+H), found 395.1.

EXAMPLE 162 a) Methyl 4-{2-[(diphenylmethyl)amino](1,3-thiazol-4-yl)}-5-methylthiothiophene-2-carboxylate hydrobromide: Methyl 4-(2-bromoacetyl)-5-methylthiothiophene-2-carboxylate (50 mg, 0.16 mmol) was allowed to react with diphenylmethane thiourea (38 mg) as described in Example 154, step (a), to give 145 mg (100% yield) of methyl 4-{2-[(diphenylmethyl)amino](1,3-thiazol-4-yl)}-5-methylthiothiophene-2-carboxylate hydrobromide after removal of solvent in vacuo. $^1$H NMR (DMSO-d$_6$, 300 MHz) δ 2.50 (s, 3H), 2.80 (s, 3H), 6.13, 6.18 (d, 1H rotomer, J=7.9 Hz), 7.23–7.41 (m, 1H), 8.00, 8.02 (s, 1H rotomer), 8.73, 8.86 (d, 1H, rotomer, J=8.0 Hz); Mass Spectrum (ESI) m/z calcd. for C$_{23}$H$_{20}$N$_2$O$_2$S$_3$, 452.62 (M+H), found 453.0.

b) 4-{2-[(Diphenylmethyl)amino](1,3-thiazol-4-yl)}-5-methylthiothiophene-2-carboxamidine: Methyl 4-{2-[(diphenylmethyl)amino](1,3-thiazol-4-yl)}-5-methylthiothiophene-2-carboxylate hydrobromide. (96.3 mg. 0.18 mmol) was treated as described in Example 154, step (b) to give 16 mg (20% yield) of 4-{2-[(diphenylmethyl)amino](1,3-thiazol-4-yl)}-5-methylthiothiophene-2-carboxamidine hydrochloride. $^1$H NMR (DMSO-d$_6$, 300 MHz) 2.59 (s, 3H), 6.23 (d, 1H, J=7.9 Hz), 6.84 (s, 1H), 7.22–7.40 (m, 10H), 8.09 (bs, 3H), 8.12 (s, 1H), 8.68 (d, 1H, J=8.4 Hz); Mass Spectrum (ESI) m/z calcd. for C$_{22}$H$_{20}$N$_4$S$_3$, 436.62 (M+H), found 437.1.

EXAMPLE 163 a) Methyl 5-methylthio-4-{2-[(3-phenylpropyl)amino](1,3-thiazol-4-yl)}thiophene-2-carboxylate hydrobromide: Methyl 4-(2-bromoacetyl)-5-methylthiothiophene-2-carboxylate (131 mg, 0.42 mmol) was allowed to react with propylphenyl thiourea (82.3 mg) in DMF as described in Example 154, step (a), then filtered through a 5 cm pad of silica gel in a 15 mL glass fritted funnel with 10% methanol-CHCl$_3$. Concentration of the solvent in vacuo gave 203 mg (100% yield) of methyl 5-methylthio-4-{2-[(3-phenylpropyl)amino](1,3-thiazol-4-yl)}thiophene-2-carboxylate hydrobromide. $^1$H NMR (DMSO-d$_6$, 300 MHz) δ 1.89 (m, 2H), 2.62 (s, 3H), 2.63–2.71 (m, 2H), 3.27–3.39 (m, 2H), 3.82 (s, 3H), 6.97 (s, 1H), 7.15–7.31 (m, 5H), 8.06 (s, 1H); Mass Spectrum (ESI) m/z calcd. for C$_{19}$H$_{20}$N$_2$O$_2$S$_3$, 404.57 (M+H), found 405.1.

b) 5-Methylthio-4-{2-[(3-phenylpropyl)amino](1,3-thiazol4-yl)}thiophene-2-carboxamidine hydrochloride: Methyl -5-methylthio-4-{2-[(3-phenylpropyl)amino](1,3-thiazol-4-yl)}thiophene-2-carboxylate hydrobromide (112 mg, 0.23 mmol) was treated as described in Example 154, step (b) to give 16 mg (16% yield) of 4-{2-[(diphenylmethyl)amino](1,3-thiazol-4-yl)}-5-methylthiothiophene-2-carboxamidine hydrochloride, which was further purified by preparative thin layer chromatography using 20%-methanol-CH$_2$Cl$_2$-sat'd. NH$_3$ as eluent. $^1$H NMR (DMSO-d$_6$, 300 MHz) δ 1.89 (m, 2H), 2.54 (s, 1H), 2.66 (at, 2H, J=7.3 Hz), 3.31 (m, 2H), 6.69 (bs, 3H), 6.76 (s, 1H), 7.15–7.31 (m, 5H), 7.69 (m, 1H), 7.84 (s, 1H); Mass Spectrum (ESI) m/z calcd. for C$_{18}$H$_{20}$N$_4$S$_3$, 388.58 (M+H), found 389.2.

EXAMPLE 164 a) Methyl 5-methylthio-4-{2-[(2,4,5-trimethylphenyl)amino](1,3-thiazol-4-yl)}thiophene-2-carboxylate hydrobromide: Methyl 4-(2-bromoacetyl)-5-methylthiothiophene-2-carboxylate (60 mg, 0.21 mmol) was allowed to react with 2,4,5-trimethylphenyl thiourea as described in Example 154, step (a) to give 42.3 mg (41% yield) of methyl 5-methylthio-4-{2-[(2,4,5-trimethylphenyl)amino](1,3-thiazol-4-yl)}thiophene-2-carboxylate hydrobromide. $^1$H NMR (DMSO-$d_6$, 300 MHz) δ 2.16 (s, 3H), 2.18 (s, 3H), 2.19 (s, 3H), 2.64 (s, 3H), 3.82 (s, 3H), 6.97 (s, 1H), 7.18 (s, 1H), 7.86 (s, 1H), 8.12 (s, 1H), 9.29 (s, 1H); Mass Spectrum (ESI) m/z calcd. for $C_{19}H_{20}N_2O_2S_3$, 404.57 (M+H), found 405.1.

b) 5-Methylthio-4-{2-[(2,4,5-trimethylphenyl)amino](1,3-thiazol-4-yl)}thiophene-2-carboxamidine hydrochloride: Methyl -5-methylthio-4-{2-[(2,4,5-trimethylphenyl)amino](1,3-thiazol-4-yl)}thiophene-2-carboxylate hydrobromide (37.3 mg, 0.07 mmol) was treated as described in Example 154, step (b) to give 28.3 mg (95% yield) of 5-methylthio-4-{2-[(2,4,5-trimethylphenyl)amino](1,3-thiazol-4-yl)}thiophene-2-carboxamidine hydrochloride. $^1$H NMR (DMSO-$d_6$, 300 MHz) δ 2.16 (s, 3H), 2.19 (s, 3H), 2.20 (s, 3H), 2.68 (s, 3H), 6.97 (s, 1H), 7.03 (s, 1H), 7.84 (s, 1H), 8.41 (s, 1H), 8.84 (bs, 2H), 9.26 (bs, 3H); Mass Spectrum (ESI) m/z calcd. for $C_{18}H_{20}N_4S_3$, 388.58 (M+H), found 389.2.

EXAMPLE 165 a) Methyl 4-{2-[(2-fluorophenyl)amino](1,3-thiazol-4-yl)}-5-methylthiothiophene-2-carboxylate hydrobromide: Methyl 4-(2-bromoacetyl)-5-methylthiothiophene-2-carboxylate (60 mg, 0.19 mmol) was allowed to react with 2-fluorophenyl thiourea as described in Example 154, step (a) to give 55.6 mg (70% yield) of methyl 4-{2-[(2-fluorophenyl)amino](1,3-thiazol-4-yl)}-5-methylthiothiophene-2-carboxylate hydrobromide. $^1$H NMR (DMSO-$d_6$, 300 MHz) δ 2.68 (s, 3H), 3.83 (s, 3H), 6.96–7.04 (m, 1H), 7.14–7.29 (m, 3H), 7.35 (s, 1H), 8.06, 8.14 (s, 1H rotomer), 8.61 (td, 1H rotomer, J=1.5, 8.5 Hz), 10.14, 10.30 (s, 1H rotomer); Mass Spectrum (ESI) m/z calcd. for $C_{16}H_{13}FN_2O_2S_3$, 380.48 (M+H), found 381.1.

b) 4-{2-[(2-Fluorophenyl)amino](1,3-thiazol-4-yl)}-5-methylthiothiophene-2-carboxamidine hydrochloride: Methyl 4-{2-[(2-fluorophenyl)amino](1,3-thiazol-4-yl)}-5-methylthiothiophene-2-carboxylate hydrobromide (55.6 mg, 0.13 mmol)) was treated as described in Example 154, step (b) to give 12.4 mg (24%) of 4-{2-[(2-fluorophenyl)amino](1,3-thiazol-4-yl)}-5-methylthiothiophene-2-carboxamidine hydrochloride. $^1$H NMR (DMSO-$d_6$, 300 MHz); δ 2.72 (s, 3H), 3.16 (s, 3H), 6.97–7.08 (m, 1H), 7.18–7.36 (m, 4H), 8.49 (s, 1H), 8.70 (td, 1H, 1.4, 8.4 Hz), 8.92 (bs, 2H), 9.32 (bs, 2H), 10.18 (d, 1H, J=1.6 Hz); Mass Spectrum (ESI) m/z calcd. for $C_{15}H_{13}FN_4S_3$, 364.49 (M+H), found 365.1.

EXAMPLE 166 a) Methyl 4-{2-[(3-chloro-2-methylphenyl)amino](1,3-thiazol-4-yl)}-5-methylthiothiophene-2-carboxylate hydrobromide: Methyl 4-(2-bromoacetyl)-5-methylthiothiophene-2-carboxylate (60 mg, 0.19 mmol) was allowed to react with 2-methyl-3-chlorophenyl thiourea (39 mg) as described in Example 154, step (a) to give 61.8 mg (66% yield) of methyl 4-{2-[(3-chloro-2-methylphenyl)amino](1,3-thiazol-4-yl)}-5-methylthiothiophene-2-carboxylate hydrobromide. Mass Spectrum (ESI) m/z calcd. for $C_{17}H_{15}ClN_2O_2S_3$, 410.96 (M+H), found 411.1.

b) 4-{2-[(3-Chloro-2-methylphenyl)amino](1,3-thiazol-4-yl)}-5-methylthiothiophene-2-carboxamidine hydrochloride: Methyl 4-{2-[(3-chloro-2-methylphenyl)amino](1,3-thiazol-4-yl)}-5-methylthiothiophene-2-carboxylate hydrobromide (61.8 mg, 0.12 mmol) was treated as described in Example 154, step (b) to give 46.7 mg (90% yield) of 4-{2-[(3-chloro-2-methylphenyl)amino](1,3-thiazol-4-yl)}-5-methylthiothiophene-2-carboxamidine hydrochloride. $^1$H NMR (DMSO-$d_6$, 300 MHz) δ 2.34 (s, 3H), 2.69 (s, 3H), 7.15 (s, 1H), 7.18–7.26 (m, 2H), 8.12 (d, 1H, J=7.9 Hz), 8.41 (s, 1H), 8.84 (bs, 2H), 9.27 (bs, 2H), 9.61 (s, 1H); Mass Spectrum (ESI) m/z calcd. for $C_{16}H_{15}ClN_4S_3$, 394.97 (M+H), found 395.1.

EXAMPLE 167 a) Methyl 4-(2-{[2-(methylethyl)phenyl]amino}(1,3-thiazol-4-yl))-5-methylthiothiophene-2-carboxylate hydrobromide: Methyl 4-(2-bromoacetyl)-5-methylthiothiophene-2-carboxylate (60 mg, 0.19 mmol) was allowed to react with 2-isopropyl phenyl thiourea (40 mg) as described in Example 154, step (a) to give 33.1 mg (36% yield) of methyl 4-(2-{[2-(methylethyl)phenyl]amino}(1,3-thiazol-4-yl))-5-methylthiothiophene-2-carboxylate hydrobromide. $^1$H NMR (DMSO-$d_6$, 300 MHz) δ 1.17 (d, 6H, J=6.7 Hz), 2.60, 2.65 (s, 3H rotomer), 3.27 (s, 1H), 3.82 (s, 3H), 7.13 (s, 1H), 7.14–7.25 (m, 2H), 7.34–7.37 (m, 1H), 7.78 (m, 1H), 7.99, 8.08 (s, 1H rotomer), 9.52, 9.61 (bs, 1H rotomer); Mass Spectrum (ESI) m/z calcd. for $C_{19}H_{20}N_2O_2S_3$, 404.57 (M+H), found 405.1.

b) 4-(2-{[2-(Methylethyl)phenyl]amino{(1,3-thiazol-4-yl))-5-methylthiothiophene-2-carboxamidine hydrochloride: Methyl 4-(2-{[2-(methylethyl)phenyl]amino}(1,3-thiazol-4-yl))-5-methylthiothiophene-2-carboxylate hydrobromide (33.1 mg, 0.06 mmol) was treated as described in Example 154, step (b) to give 22.4 mg (88%) of 4-(2-{[2-(methylethyl)phenyl]amino}(1,3-thiazol-4-yl))-5-methylthiothiophene-2-carboxamidine hydrochloride. $^1$H NMR (DMSO-$d_6$, 300 MHz) δ 1.19 (d, 6H, J=6.8 Hz), 2.70 (s, 3H), 3.32 (m, 1H), 7.04 (s, 1H), 7.14–7.25 (m, 2H), 7.35 (dd, 1H, J=1.4, 7.5 Hz), 7.86 (dd, 1H, J=1.4, 7.9 Hz), 8.37 (s, 1H); Mass Spectrum (ESI) m/z calcd. for $C_{18}H_{20}N_4S_3$, 388.58 (M+H), found 389.2.

EXAMPLE 168 a) Methyl 5-methylthio-4-(2-{[4-(phenylmethoxy)phenyl]amino}(1,3-thiazol-4-yl))thiophene-2-carboxylate: Methyl 4-(2-bromoacetyl)-5-methylthiothiophene-2-carboxylate (336.3 mg, 1.08 mmol) was allowed to react with 4-benzyloxyphenyl thiourea (279 mg) as described in Example 154, step (a) to give 450 mg (76% yield) of methyl 4-(2-{[4-phenylmethoxyphenyl]amino}(1,3-thiazol-4-yl))-5-methylthiothiophene-2-carboxylate hydrobromide. Mass Spectrum (ESI) m/z calcd. for $C_{23}H_{20}N_2O_3S_3$, 468.61 (M+H), found 469.2.

b) 5-Methylthio-4-(2-{[4-(phenylmethoxy)phenyl]amino}(1,3-thiazol-4yl)thiophene-2-carboxamidine hydrochloride: Methyl 4(2-{[4 -phenylmethoxyphenyl]amino}(1,3-thiazol-4-yl))-5-methylthiothiophene-2-carboxylate hydrobromide (100 mg, 0.18 mmol) was treated as described in Example 154, step (b) to give 23.9 mg (27% yield) 5-methylthio-4-(2-{[4-(phenylmethoxy)phenyl]amino}(1,3-thiazol-4-yl))thiophene-2-carboxamidine hydrochloride. $^1$H NMR (DMSO-$d_6$, 300 MHz) δ 2.73 (s, 3H), 5.08 (s, 2H), 7.00 (d, 2H, J=8.2 Hz), 7.09 (s, 1H), 7.31–7.47 (m, 5H), 7.70 (d, 2H, J=8.0 Hz), 8.47 (s, 1H), 8.88 (bs, 2H), 9.30 (bs, 2H), 10.20 (s, 1H); Mass Spectrum (ESI) m/z calcd. for $C_{22}H_{20}N_4OS_3$, 452.62 (M+H), found 453.1.

EXAMPLE 169 a) Methyl 4-{2-[(2-bromophenyl)amino](1,3-thiazol-4-yl)}-5-methylthiothiophene-2-carboxylate hydrobromide: Methyl 4-(2-bromoacetyl)-5-methylthiothiophene-2-carboxylate (60 mg, 0.19 mmol) was allowed to react with 2-bromophenyl thiourea (44 mg) as described in Example 154, step (a) to give 63.1 mg (64% yield) of methyl 4-{2-[(2-bromophenyl)amino](1,3-thiazol-4-yl)}-5-methylthiothiophene-2-carboxylate hydrobromide. $^1$H NMR (DMSO-d$_6$, 300 MHz) δ 2.65 (s, 3H), 3.82 (s, 3H), 7.00 (m, 1H), 7.33 (s, 1H), 7.40 (m, 1H), 7.64 (dd, 1H, J=1.4, 7.9 Hz), 8.04, 8.11 (s, 1H rotomer), 8.27, 8.37 (dd, 1H 9.60, 9.80 (bs, 1H rotomer, J=1.5, 8.2 Hz), Mass Spectrum (ESI) m/z calcd. for $C_{16}H_{13}BrN_2O_2S_3$, 441.39 (M+H), found 441.1.

b) 4-{2-[(2-Bromophenyl)amino](1,3-thiazol-4-yl)}-5-methylthiothiophene-2-carboxamidine hydrochloride: Methyl 4-{2-[(2-bromophenyl)amino](1,3-thiazol-4-yl)}-5-methylthiothiophene-2-carboxylate hydrobromide (63.1 mg, 0.12 mmol) was treated as described in Example 154, step (b) to give 47.9 mg (86% yield) of 4-{2-[(2-bromophenyl) amino](1,3-thiazol-4-yl)}-5-methylthiothiophene-2-carboxamidine hydrochloride. $^1$H NMR (DMSO-d$_6$, 300 MHz) δ 2.70 (s, 3H), 7.01 (m 1H), 7.20 (s, 1H), 7.40 (m, 1H), 7.65 (dd, 1H, J=1.5, 8.0), 8.38 (dd, 1H, J=1.5, 8.3 Hz), 8.44 (s, 1H), 8.89 (bs, 2H), 9.30 (bs, 2H), 9.62 (s, 1H); Mass Spectrum (ESI) m/z calcd. for $C_{15}H_{13}BrN_4S_3$, 425.39 (M+H), found 425.1.

EXAMPLE 170 a) Methyl 4-{2-[(2,6-dichlorophenyl)amino](1,3-thiazol-4-yl)}-5-methylthiothiophene-2-carboxylate hydrobromide: Methyl 4-(2-bromoacetyl)-5-methylthiothiophene-2-carboxylate (60 mg, 0.19 mmol) was allowed to react with 2,6-dichlorophenyl thiourea (42 mg) as described in Example 154, step (a) to give 63.1 mg (65% yield) of methyl 4-{2-[(2,6-dichlorophenyl)amino](1,3-thiazol-4-yl)}-5-methylthiothiophene-2-carboxylate hydrobromide. $^1$H NMR (DMSO-d$_6$, 300 MHz) δ 2.59 (s, 3H), 3.8 (s, 3H), 7.15 (s, 1H), 7.36 (m, 1H), 7.61 (m, 2H), 7.97 (s, 1H); Mass Spectrum (ESI) m/z calcd. for $C_{16}H_{12}Cl_2N_2O_2S_3$, 431.38 (M+H), found 431.0.

b) 4-{2-[(2,6-Dichlorophenyl)amino](1,3-thiazol-4-yl)}-5-methylthiothiophene-2-carboxamidine hydrochloride: Methyl 4-{2-[(2,6-dichlorophenyl)amino](1,3-thiazol-4-yl)}-5-methylthiothiophene-2-carboxylate hydrobromide (43 mg, 0.08 mmol) was treated as described in Example 154, step (b) to give 14.5 mg (40% yield) of 4-{2-[(2,6-dichlorophenyl)amino](1,3-thiazol-4-yl)}-5-methylthiothiophene-2-carboxamidine hydrochloride. $^1$H NMR (DMSO-d, 300 MHz) δ 2.69 (s, 3H), 7.15 (s, 1H), 7.18–7.26 (m, 2H), 8.13 (d, 1H, J=7.5 Hz), 8.41 (s, 1H), 8.84 (bs, 2H), 9.27 (bs, 2H), 9.61 (bs, 1H); Mass Spectrum (ESI) m/z calcd. for $C_{15}H_{12}Cl_2N_4S_3$, 415.39 (M+H), found 415.1.

EXAMPLE 171 a) Methyl 4-{2-[(2-bromo-4-methylphenyl)amino](1,3-thiazol-4-yl)}-5-methylthiothiophene-2-carboxylate hydrobromide: Methyl 4-(2-bromoacetyl)-5-methylthiothiophene-2-carboxylate (60 mg, 0.19 mmol) was allowed to react with 2-bromo-4-methylphenyl thiourea (47 mg) as described in Example 154, step (a) to give 62 mg (61% yield) of methyl 4-{2-[(2-bromo-4-methylphenyl)amino](1,3-thiazol-4-yl)}-5-methylthiothiophene-2-carboxylate hydrobromide. $^1$H NMR (DMSO-d$_6$, 300 MHz) δ 2.28 (s, 3H), 3.82 (s, 3H), 7.21 (m, 1H), 7.27 (s, 1H), 7.48 (m, 1H), 8.14, 8.17 (s, 1H rotomer), 9.52, 9.72 (bs, 1H rotomer); Mass Spectrum (ESI) m/z calcd. for $C_{17}H_{15}BrN_2O_2S_3$, 455.42 (M+H), found 455.0.

b) 4-{2-[(2-Bromo-4-methylphenyl)amino](1,3-thiazol-4-yl)}-5-methylthiothiophene-2-carboxamidine hydrochloride: Methyl 4-{2-[(2-bromo-4-methylpheny)amino](1,3-thiazol-4-yl)}-5-methylthiothiophene-2-carboxylate hydrobromide (62 mg, 0.11 mmol) was treated as described in Example 154, step (b) to give 26 mg (50% yield) of 4-{2-[(2-bromo-4-methylphenyl)amino](1,3-thiazol-4-yl)}-5-methylthiothiophene-2-carboxamidine hydrochloride. $^1$H NMR (DMSO-d$_6$, 300 MHz) δ 2.28 (s, 3H), 2.70 (s, 3H), 7.14 (s, 1H), 7.21 (dd, 1H, J=1.6, 8.5 Hz), 7.49 (d, 1H, J=1.5 Hz), 8.16 (d, 1H, 8.3 Hz), 8.41 (s, 1H), 8.85 (bs, 2H), 9.28 (bs, 2H), 9.53 (s, 1H); Mass Spectrum (ESI) m/z calcd. for $C_{16}H_{15}BrN_4S_3$, 439.42 (M+H), found 439.1.

EXAMPLE 172 a) Methyl 5-methylthio-4-{2-[(2-morpholin-4-ylethyl) amino](1,3-thiazol-4-yl)}thiophene-2-carboxylate hydrobromide: Methyl 4-(2-bromoacetyl)-5-methylthiothiophene-2-carboxylate (100 mg, 0.32 mmol), was allowed to react with 1-ethylmorpholinothiourea (61.2 mg) as described in Example 154, step (a) to give 120.8 mg (79% yield) methyl 5-methylthio-4-{2-[(2-morpholin-4-ylethyl)amino](1,3-thiazol-4-yl)}thiophene-2-carboxylate hydrobromide. $^1$H NMR (CD$_3$OD, 300 MHz) δ 2.64 (s, 3H), 3.43–3.52 (m, 5H), 3.83–3.86 (m, 10H), 6.95 (s, 1H), 8.04 (s, 1H); Mass Spectrum (ESI) m/z calcd. for $C_{16}H_{21}N_3O_3S_3$, 399.55 (M+H), found 400.1.

b) 5-Methylthio-4-{2-[(2-morpholin-4-ylethyl)amino](1,3-thiazol-4-yl)}thiophene-2-carboxylate hydrochloride: Methyl-5-methylthio-4-{2-[(2-morpholin-4-ylethyl)amino] (1,3-thiazol-4-yl)}thiophene-2-carboxylate hydrobromide (62 mg, 0.12 mmol) was treated as described in Example 154, step (b) to give 26 mg (52% yield) of 5-methylthio-4-{2-[(2-morpholin-4-ylethyl)amino](1,3-thiazol-4-yl)} thiophene-2-carboxylate hydrochloride. $^1$H NMR (DMSO-d$_6$, 300 MHz) δ 2.69 (s, 3H), 3.16–3.95 (m, 15H), 6.96 (s, 1H), 8.01 (bs, 1H), 8.49 (s, 1H), 8.84 (bs, 2H), 9.28 (bs, 2H), 10.49 (bs, 1H); Mass Spectrum (ESI) m/z calcd. for $C_{15}H_{21}N_5OS_3$, 383.56 (M+H), found 384.2.

EXAMPLE 173 a) Methyl 4-{2-[(2,3-dichlorophenyl)amino](1,3-thiazol-4-yl)}-5-methylthiothiophene-2-carboxylate hydrobromide: Methyl 4-(2-bromoacetyl)-5-methylthiothiophene-2-carboxylate (60 mg, 0.19 mmol) was allowed to react with 2,3-dichlorophenylthiourea (42 mg) as described in Example 154, step (a) to give 60.5 mg (62% yield) methyl 4-{2-[(2,3-dichlorophenyl)amino](1,3-thiazol-4-yl)}-5-methylthiothiophene-2-carboxylate hydrobromide. $^1$H NMR (DMSO-d$_6$, 300 MHz) δ 2.66 (s, 3H), 3.82 (s, 3H), 7.27 (dd, 1H, J=1.5, 6.5 Hz), 7.36 (d, 1H, J=8.2 Hz), 7.43 (s, 1H), 8.14 (s, 1H), 8.62 (dd, 1H, J=1.5, 8.4 Hz), 9.95 (bs, 1H); Mass Spectrum (ESI) m/z calcd. for $C_{16}H_{12}Cl_2N_2O_2S_3$, 431.38 (M+H), found 431.1.

b) 4-{2-[(2,3-Dichlorophenyl)amino](1,3-thiazol-4-yl)}-5-methylthiothiophene-2-carboxamidine hydrochloride: Methyl 4-{2-[(2,3-dichlorophenyl)amino](1,3-thiazol-4-yl)}-5-methylthiothiophene-2-carboxylate hydrobromide (60.5 mg, 0.11 mmol) was treated as described in Example 154, step (b) to give 15 mg (30% yield) of 4-{2-[(2,3-dichlorophenyl)amino](1,3-thiazol-4-yl)}-5-methylthiothiophene-2-carboxamidine hydrochloride. $^1$H NMR (DMSO-d$_6$, 300 MHz) δ 2.71 (s, 3H), 7.27–7.28–7.41 (m, 2H), 8.45 (s, 1H), 8.63 (dd, 1H, J=1.5, 8.4 Hz), 8.84 (bs, 2H), 9.29 (bs, 2H), 9.99 (s, 1H); Mass Spectrum (ESI) m/z calcd. for $C_{15}H_{12}Cl_2N_4S_3$, 415.34 (M+H), found 415.1.

EXAMPLE 174 a) Methyl 5-methylthio-4-{2-[(3,4,5-trimethoxyphenyl) amino](1,3-thiazol-4-yl)}thiophene-2-carboxylate hydrobromide: Methyl 4-(2-bromoacetyl)-5-methylthiothiophene-2-carboxylate (60 mg, 0.19 mmol) was allowed to react with 2,3,4-trimethoxyphenylthiourea (46 mg) as described in Example 154, step (a) to give 61.8 mg (63% yield) of methyl 5-methylthio-4-{2-[(3,4,5-trimethoxyphenyl)amino](1,3-thiazol-4-yl)}thiophene-2-carboxylate hydrobromide. $^1$H NMR (DMSO-$d_6$, 300 MHz) δ 2.67 (s, 3H), 3.81 (s, 6H), 3.82 (s, 3H), 7.11 (s, 2H), 7.25 (s, 1H), 8.19 (s, 1H), 10.25 (s, 1H); Mass Spectrum (ESI) m/z calcd. for $C_{18}H_{20}N_4O_3S_3$, 436.56 (M+H), found 437.1.

b) 5-Methylthio-4-{2-[(3,4,5-trimethoxyphenyl)amino](1,3-thiazol-4-yl)}thiophene-2-carboxamidine hydrochloride: Methyl 5-methylthio-4-{2-[(3,4,5-trimethoxyphenyl)amino](1,3-thiazol-4-yl)}thiophene-2-carboxylate hydrobromide (61.8 mg, 0.11 mmol) was treated as described in Example 154, step (b) to give 14 mg (27% yield) of 5-methylthio-4-{2-[(3,4,5-trimethoxyphenyl)amino](1,3-thiazol-4-yl)}thiophene-2-carboxamidine hydrochloride. $^1$H NMR (DMSO-$d_6$, 300 MHz) δ 2.70 (s, 3H), 3.61 (s, 3H), 3.80 (s, 6H), 7.08 (s, 2H), 7.14 (s, 1H), 8.44 (s, 1H), 8.84 (bs, 2H), 9.26 (bs, 2H), 10.29 (s, 1H); Mass Spectrum (ESI) m/z calcd. for $C_{18}H_{20}N_4O_3S_3$, 436.56 (M+H), found 437.1.

EXAMPLE 175 a) Methyl 5-methylthio-4-{2-[(2-piperidylethyl)amino](1,3-thiazol-4-yl)}thiophene-2-carboxylate hydrobromide: Methyl 4-(2-bromoacetyl)-5-methylthiothiophene-2-carboxylate (100 mg, 0.32 mmol) was allowed to react with N-ethylpiperidylthiourea (60.6 mg) as described in Example 154, step (a) to give 90 mg (59% yield) of methyl 5-methylthio-4-{(2-[(2-piperidylethyl)amino](1,3-thiazol-4-yl)}thiophene-2-carboxylate hydrobromide. $^1$H NMR (DMSO-$d_6$, 300 MHz) δ 1.41 (m, 2H), 1.70–1.79 (m, 6H), 2.65 (s, 3H), 2.95 (m, 2H), 3.52 (m, 2H), 3.73 (m, 2H), 3.82 (s, 3H), 7.08 (s, 1H), 7.96 (at, 1H, J=5.3 Hz), 8.09 (s, 1H), 9.40 (bs, 1H); Mass Spectrum (ESI) m/z calcd. for $C_{17}H_{23}N_3O_2S_3$, 397.6 (M+H), found 398.1.

b) 5-Methylthio-4-{2-[(2-piperidylethyl)amino](1,3-thiazol4-yl)}thiophene-2-carboxamidine hydrochloride: Methyl 5-methylthio-4-{2-[(2-piperidylethyl)amino](1,3-thiazol-4-yl)}thiophene-2-carboxylate hydrobromide (72 mg, 0.15 mmol) was treated as described in Example 154, step (b) to give 26.8 mg (43% yield) of 5-methylthio-4-{2-[(2-piperidylethyl)amino](1,3-thiazol-4-yl)}thiophene-2-carboxamidine hydrochloride. $^1$H NMR (DMSO-$d_6$, 300 MHz) δ 1.40 (m, 2H), 1.72–1.79 (m, 6H), 2.69 (s, 3H), 2.69 (m, 2H), 3.51 (m, 2H), 3.76 (m, 2H), 6.97 (s, 1H), 8.08 (t, 1H, J=5.5 Hz), 8.60 (s, 1H), 8.95 (bs, 1H), 9.35 (bs, 2H), 10.25 (s, 1H); Mass Spectrum (ESI) m/z calcd. for $C_{16}H_{23}N_5S_3$, 381.1 (M+H), found 382.2.

EXAMPLE 176 a) Methyl 4-(2-{[(4-methylphenyl)methyl]amino}(1,3-thiazol-4-yl))-5-methylthiothiophene-2-carboxylate hydrobromide: Methyl 4-(2-bromoacetyl)-5-methylthiothiophene-2-carboxylate (111 mg, 0.35 mmol) was allowed to react with 4-methylphenylmethylthiourea as described in Example 154, step (a) to give 125 mg (81% yield) of methyl 4-(2-{[(4-methylphenyl)methyl]amino}(1,3-thiazol-4-yl))-5-methylthiothiophene-2-carboxylate hydrobromide. Mass Spectrum (ESI) m/z calcd. for $C_{18}H_{18}N_2O_2S_2$, 358.5 (M+H), found 359.1.

b) 4-(2-{[(4-Methylphenyl)methyl]amino}(1,3-thiazol-4-yl))-5-methylthiothiophene-2-carboxamidine hydrochloride: Methyl 4-(2-{[(4-methylphenyl)methyl]amino}(1,3-thiazol-4-yl))-5-methylthiothiophene-2-carboxylate hydrobromide (118 mg, 0.26 mmol) was treated as described in Example 154, step (b) to give 58.2 mg (54% yield) of 4-(2-{[(4-methylphenyl)methyl]amino}(1,3-thiazol-4-yl))-5-methylthiothiophene-2-carboxamidine hydrochloride. $^1$H NMR (DMSO-$d_6$, 300 Mhz) δ 2.27 (s, 3H), 2.66 (s, 3H), 4.49 (d, 2H, J=5.7 Hz), 6.88 (s, 1H), 7.13 (d, 2H, J=7.8 Hz), 7.27 (d, 2H, J=8.0 Hz), 8.20 (t, 1H, J=5.8 Hz), 8.42 (s, 1H), 8.90 (bs, 2H), 9.27 (bs, 2H); Mass Spectrum (ESI) m/z calcd. for $C_{17}H_{18}N_4S_3$, 374.55 (M+H), found 375.2.

EXAMPLE 177 a) Amino{[4-(4-chlorophenoxy)phenyl]amino}methane-1-thione: Unless otherwise indicated, all thioureas, isothiocyanates, thioamides and amines were purchased from Maybridge Chemical Co. Ltd.(Cornwall, U.K.), Transworld Chemical Co. (Rockville, Md.), or Aldrich Chemical Co., (Milwaukee, Wis.). (i) 4-Amino-4'-chlorodiphenylether (TCI America, Portland Oreg., 520 mg, 2.03 mmol) was slurried in 10 mL of ether and treated with ca. 1 mL of ether saturated with HCl gas. After 5 min. the solvent was removed in vacuo. To a stirring biphasic solution amine-HCl salt in 20 mL CHCl$_3$-sat'd NaHCO$_3$ (1:1, v/v) at ambient temperature was added thiophosgene (1.2 equiv, 2.4 mmol) in 5 mL of CHCl$_3$ dropwise via an addition funnel. The reaction was vigorously stirred for 1 h (TLC, 50% ethyl acetate-hexanes indicates clean conversion to a higher Rf spot), at which time the layers were separated, the aqueous layer extracted with CHCl$_3$ (1×20 mL), and the combined organic layers washed with brine (1×20 mL) and dried (Na$_2$SO$_4$). Concentration of the solvent in vacuo yielded the crude 4-(4-chlorophenoxy)-phenylisothiocyanate (414 mg). (ii) The 4-(4-chlorophenoxy)-phenylisothiocyanate was transferred to an Ace Glass pressure tube equipped with a Teflon coated stir bar and treated with a 2.0 M solution of NH$_3$ in 5 ml methanol (Aldrich Chemical Co., Milwaukee, Wis.)). The tube was sealed and immersed in a 80° C. oil bath. After 2 h, the reaction was cooled to 0° C. in an ice bath. The precipitates were filtered and dried under vacuum to yield amino{[4-(4-chlorophenoxy)phenyl]amino}methane-1-thione (328 mg, 79%). $^1$H NMR (DMSO-$d_6$, 300 MHz) δ 7.02 (m, 4H), 7.41 (m, 4H), 9.65 (s, 1H); Mass Spectrum (ESI) m/z calcd. for $C_{13}H_{11}ClN_2OS$, 278.8 (M+H), found 279.4.

b) Methyl 4-(2-{[4-(4-chlorophenoxy)phenyl]amino}(1,3-thiazol-4-yl))-5-methylthiothiophene-2-carboxylate hydrobromide: Methyl 4-(2-bromoacetyl)-5-methylthiothiophene-2-carboxylate (309 mg, 1.0 mmol) was allowed to react with amino{[4-(4-chlorophenoxy)phenyl]amino}methane-1-thione (297 mg) as described in Example 154, step (a) to give 410 mg (72% yield) of methyl 4-(2-{[4-(4-chlorophenoxy)phenyl]amino}(1,3-thiazol-4-yl))-5-methylthiothiophene-2-carboxylate hydrobromide. Mass Spectrum (ESI) m/z calcd. for $C_{22}H_{17}ClN_2O_3S_3$, 489.1 (M+H), found 489.1.

c) 4-(2-{[4-(4-Chlorophenoxy)phenyl]amino}(1,3-thiazol-4-yl))-5-methylthiothiophene-2-carboxamidine hydrochloride: Methyl 4-(2-{[4-(4-chlorophenoxy)phenyl]amino}(1,3-thiazol-4-yl))-5-methylthiothiophene-2-chlorophenoxy)phenyl]aamino}(1,3-thiazol-4-yl))-5-methylthiothiophene-2-carboxylate hydrobromide (300 mg, 0.52 mmol) was treated as described in Example 154, step (b) to give 129.9 mg (49% yield) of 4-(2-{[4-(4-chlorophenoxy)phenyl]amino}(1,3-thiazol-4-yl))-5-methylthiothiophene-2-carboxamidine hydrochloride. $^1$H NMR (DMSO-$d_6$, 300 MHz) δ 2.72 (s, 3H), 6.97 (m, 2H), 7.07 (m, 2H), 7.15 (s, 1H), 7.40 (m, 2H), 7.85 (m, 2H), 8.46

(s, 1H), 8.82 (bs, 2H), 9.27 (bs, 2H), 10.43 (bss, 1H); Mass Spectrum (ESI) m/z calcd. for $C_{21}H_{17}ClN_4OS_3$, 473.1 (M+H), found 473.2, 475.1.

EXAMPLE 178 a) Methyl 5-methylthio-4-[2-({4-[5-(trifluoromethyl)(2-pyridyloxy)]phenyl}amino)(1,3-thiazol-4-yl)]thiophene-2-carboxylate: Methyl 4-(2-bromoacetyl)-5-methylthiothiophene-2-carboxylate (70 mg, 0.23 mmol) was allowed to react with 4-[5-(trifluoromethyl)pyrid-2-yloxy] thiobenzamide (50 mg) as described in Example 154, step (a) to give 115 mg (98% yield) of methyl 5-methylthio-4-[2-({4-[5-(trifluoromethyl)(2-pyridyloxy)]phenyl}amino)(1,3-thiazol-4-yl)]thiophene-2-carboxylate. $^1$H NMR (DMSO-$d_6$, 300 MHz) δ 2.70 (s, 3H), 3.85 (s, 3H), 7.38 (m, 3H), 8.10 (m, 1H), 8.18 (s, 1H), 8.28 (dd, 1H, J=2.7, 8.8 Hz), 8.32 (s, 1H), 8.60 (m, 1H); Mass Spectrum (ESI) m/z calcd. for $C_{22}H_{15}F_3N_2O_3S_3$, 508.56 (M+H), found 509.2.

b) 5-Methylthio-4-[2-({4-[5-(trifluoromethyl)(2-pyridyloxy)]phenyl}amino)(1,3-thiazol-4-yl)]thiophene-2-carboxamidine hydrochloride: Methyl 5-methylthio-4-[2-({4-[5-(trifluoromethyl)(2-pyridyloxy)]phenyl}amino)(1,3-thiazol-4-yl)]thiophene-2-carboxylate (95 mg, 0.18 mmol) was treated as described in Example 154, step (b) to give 30.3 mg (32% yield) of 5-methylthio-4-[2-({4-[5-(trifluoromethyl)(2-pyridyloxy)]phenyl}amino)(1,3-thiazol-4-yl)]thiophene-2-carboxamidine hydrochloride. $^1$H NMR (DMSO-$d_6$, 300 MHz) δ 2.75 (s, 3H), 7.34 (d, 1H, J=8.7 Hz), 7.41 (m, 2H), 8.01 (s, 1H), 8.10–8.14 (m, 2H), 8.29 (dd, 1H, J=2.5, 8.4 Hz), 8.60 (m, 1H), 8.63 (s, 1H), 8.91 (bs, 2H), 9.31 (bs, 2H); Mass spectrum (ESI) m/z calcd. for $C_{21}H_{15}F_3N_4OS_3$, 492.6 (M+H), found 493.1.

EXAMPLE 179 a) Methyl 4-(2-{[4-phenoxyphenyl]amino}(1,3-thiazol-4-yl))-5-methylthiothiophene-2-carboxylate hydrobromide: Methyl 4-(2-bromoacetyl)-5-methylthiothiophene-2-carboxylate (200 mg, 0.64 mmol) was allowed to react with 4-phenoxyphenylthiourea (158 mg) as described in Example 154, step (a) to give 300 mg (88% yield) of methyl 4-(2-{[4-(phenoxy)phenyl]amino}(1,3-thiazol-4-yl))-5-methylthiothiophene-2-carboxylate hydrobromide. Mass Spectrum (ESI) m/z calcd. for $C_{22}H_{18}N_2O_3S_3$, 454.6 (M+H), found 455.2.

b) 4-(2-{[4-Phenoxyphenyl]amino}(1,3-thiazol-4-yl))-5-methylthiothiophene-2-carboxamidine hydrochloride: Methyl 4-(2-{[4-(phenoxy)phenyl]amino}(1,3-thiazol-4-yl))-5-methylthiothiophene-2-carboxylate hydrobromide (230 mg, 0.42 mmol) was treated as described in Example 154, step (b) and purified by preparative thin layer chromatography (20% methanol-$CH_2Cl_2$-sat'd. $NH_3$, 500 mm silica gel plate, J.T. Baker, Phillipsburg, N.J.) to give 86 mg (47% yield) of the product. A 46 mg aliquot was dissolved in 1 mL of methanol, treated with 3 drops of ether saturated with HCl gas, and concentrated in vacuo with toluene (2×5 mL) to give 42.3 mg (21% yield) of 4-(2-{[4-phenoxyphenyl]amino}(1,3-thiazol-4-yl))-5-methylthiothiophene-2-carboxamidine hydrochloride. $^1$H NMR (DMSO-$d_6$, 300 MHz) 67 2.71 (s, 3H), 6.97–7.11 (m, 4H), 7.15 (s, 1H), 7.36 (m, 2H), 7.72, 7.85 (d, 2H rotomer, J=8.7 Hz), 8.36, 8.55 (s, 1H rotomer), 9.00 (bs, 2H), 9.35 (bs, 2H), 10.49 (s, 1H); Mass Spectrum (ESI) m/z calcd. for $C_{21}H_{18}N_4OS_3$, 438.6 (M+H), found 439.2.

EXAMPLE 180 a) Amino{[4-(phenylamino)phenyl]amino}methane-1-thione: 4-Aminodiphenylamine (500 mg, 2.71 mmol) was treated as described in Example 177, step (a) and recrystallized from toluene to give 350 mg (53% yield) of amino{[4-(phenylamino)phenyl]amino}methane-1-thione. $^1$H NMR (DMSO-$d_6$, 300 MHz) δ 6.80 (m, 1H), 7.01–7.24 (m, 8H), 8.15 (s, 1H), 9.45 (s, 1H); Mass Spectrum (ESI) m/z calcd. for $C_{13}H_{13}N_3S$, 243.33 (M+H), found 244.2.

b) Methyl 5-methylthio-4-(2-{[4-(phenylamino)phenyl]amino}(1,3-thiazol-4-yl))thiophene-2-carboxylate hydrobromide: Methyl 4-(2-bromoacetyl)-5-methylthiothiophene-2-carboxylate (90 mg, 0.28 mmol) was allowed to react with amino{[4-(phenylamino)phenyl]amino}methane-1-thione (70.8 mg) as described in Example 154, step (a) to give 71 mg (47% yield) of methyl 5-methylthio-4-(2-{[4-(phenylamino)phenyl]amino}(1,3-thiazol-4-yl))thiophene-2-carboxylate hydrobromide. $^1$H NMR (DMSO-$d_6$, 300 MHz) δ 2.66 (s, 3H), 3.82 (s, 3H), 6.73 (m, 1H), 6.96–7.24 (m, 9H), 7.63 (d, 1H, J=8.6 Hz), 8.12 (s, 1H), 10.13 (bs, 1H); Mass Spectrum (ESI) m/z calcd. for $C_{22}H_{19}N_3O_2S_3$, 453.60 (M+H), found 454.2.

c) 5-Methylthio-4-(2-{[4-(phenylamino)phenyl]amino}(1,3-thiazol-4-yl))thiophene-2-carboxamidine hydrochloride: Methyl 5-methylthio-4-(2-{[4-(phenylamino)phenyl]amino}(1,3-thiazol-4-yl))thiophene-2-carboxylate hydrobromide (71 mg, 0.13 mmol) was treated as described in Example 154, step (b) to give 23.3 mg (38% yield) of 5-methylthio-4-(2-{[4-(phenylamino)phenyl]amino}(1,3-thiazol-4-yl))thiophene-2-carboxamidine hydrochloride. $^1$H NMR (DMSO-$d_6$, 300 MHz) δ 2.72 (s, 3H), 6.74 (t, 1H, J=7.3 Hz), 6.98 (d, 1H, J=7.6 Hz), 7.08 (m, 2H), 7.18 (m, 2H), 7.66 (d, 2H, J=8.9 Hz), 7.99 (s, 1H), 8.45 (s, 1H), 9.03 (bs, 4H), 10.17 (s, 1H); Mass Spectrum (ESI) m/z calcd. for $C_{21}H_{19}N_5S_3$, 437.59 (M+H), found 438.2.

EXAMPLE 181 a) Amino{[4-benzylphenyl]amino}methane-1-thione: 4-Benzylphenylamine (500 mg, 2.73 mmol) was treated as described in Example 177, step (a) to give 410 mg (62% yield) of amino {[4-benzylphenyl]amino}methane-1-thione. $^1$H NMR (DMSO-$d_6$, 300 MHz) δ 3.89 (s, 2H), 7.14–7.28 (m, 9H), 9.59 (s, 1H); Mass Spectrum (ESI) m/z calcd. for $C_{14}H_{14}N_2S_3$, 242.1 (M+H), found 243.2.

b) Methyl 5-methylthio-4-(2-{[4-benzylphenyl]amino}(1,3-thiazol-4-yl))thiophene-2-carboxylate hydrobromide: Methyl 4-(2-bromoacetyl)-5-methylthiothiophene-2-carboxylate (90 mg, 0.28 mmol) was allowed to react with amino {[4-benzylphenyl]amino}methane-1-thione (70.5 mg) as described in Example 154, step (a) to give 70.1 (47% yield) of methyl 5-methylthio-4-(2-{[4-benzylphenyl]amino}(1,3-thiazol-4-yl))thiophene-2-carboxylate hydrobromide. $^1$H NMR (DMSO-$d_6$, 300 MHz) δ 2.66 (s, 3H), 3.82 (s, 3H), 3.87 (s, 2H), 7.14–7.30 (m, 8H), 7.66 (d, 2H, J=8.5 Hz), 8.12 (s, 1H), 10.23 (s, 1H); (Mass Spectrum (ESI) m/z calcd. for $C_{22}H_{19}N_3O_2S_3$, 453.6 (M+H), found 454.2.

c) 5-Methylthio-4-(2-{[4-benzylphenyl]amino}(1,3-thiazol-4-yl))thiophene-2-carboxamidine hydrochloride: Methyl 5-methylthio-4-(2-{[4-benzylphenyl]amino}(1,3-thiazol-4-yl))thiophene-2-carboxylate hydrobromide (82.2 mg, 0.15 mmol) was treated as described in Example 154, step (b) to give 33.4 mg (47% yield) of 5-methylthio-4-(2-{[4-benzylphenyl]amino}(1,3-thiazol-4-yl))thiophene-2-carboxamidine hydrochloride. $^1$H NMR (DMSO-$d_6$, 300 MHz) δ 2.72 (s, 3H), 3.89 (s, 2H), 7.12 (s, 1H), 7.16–7.29 (m, 7H), 7.69 (d, 2H, J=8.6 Hz), 8.43 (s, 1H), 9.02 (bs, 4H), 10.28 (s, 1H); Mass Spectrum (ESI) m/z calcd. for $C_{22}H_{20}N_4S_3$, 436.6 (M+H), found 437.2.

EXAMPLE 182 a) ({4-[(Aminothioxomethyl)amino]phenyl}sulfonyl)piperidine: 4-Aminophenylsulphonylpiperidine (500 mg, 2.08 mol) was treated as described in Example 177, step (a) to give 382 mg (61% yield) of ({4-[(aminothioxomethyl)amino]phenyl}sulfonyl)piperidine. $^1$H NMR (DMSO-d6, 300 MHz) δ 1.34 (m, 2H), 1.53 (m, 4H), 2.85 (m, 4H), 7.62 (m, 2H), 7.78 (m, 2H), 10.10 (bs, 1H); Mass Spectrum (ESI) m/z calcd. for $C_{12}H_{17}N_3O_2S_2$, 299.4 (M+H), found 300.2.

b) Methyl 5-methylthio-4-(2-{[4-(piperidylsulfonyl)phenyl]amino}(1,3-thiazol-4-yl))thiophene-2-carboxylate hydrobromide: Methyl 4-(2-bromoacetyl)-5-methylthiothiophene-2-carboxylate (90 mg, 0.28 mmol) was allowed to react with ({4-[(aminothioxomethyl)amino]phenyl}sulfonyl)piperidine (87.1 mg) as described in Example 154, step (a) to give 105 mg (63% yield) of methyl 5-methylthio-4-(2-{[4-(piperidylsulfonyl)phenyl]amino}(1,3-thiazol-4-yl))thiophene-2-carboxylate hydrobromide. $^1$H NMR (DMSO-d$_6$, 300 MHz) δ 1.33 (m, 2H), 1.52 (m, 4H), 2.69 (s, 3H), 2.84 (m, 4H), 3.82 (s, 3H), 7.43 (s, 1H), 7.66 (m, 2H), 7.98 (m, 2H), 8.16 (s, 1H), 10.85 (s, 1H); (Mass Spectrum (ESI) m/z calcd. for $C_{21}H_{23}N_3O_4S_4$, 509.69 (M+H), found 510.2.

c) 5-Methylthio-4-(2-{[4-piperidylsulfonyl)phenyl]amino}(1,3-thiazol4-yl))thiophene-2-carboxamidine hydrochloride: Methyl 5-methylthio-4-(2-{[4-(piperidylsulfonyl)phenyl]amino}(1,3-thiazol-4-yl))thiophene-2-carboxylate hydrobromide (105 mg, 0.17 mmol) was treated as described in Example 154, step (b) to give 30.3 mg (34% yield) of 5-methylthio-4-(2-{[4-(piperidylsulfonyl)phenyl]amino}(1,3-thiazol-4-yl))thiophene-2-carboxamidine hydrochloride. $^1$H NMR (DMSO-d$_6$, 300 MHz) δ 1.36 (m, 2H), 1.54 (m, 4H), 2.76 (s, 3H), 2.86 (m, 4H), 7.30 (s, 1H), 7.68 (d, 2H, J=8.8 Hz), 8.03 (d, 2H, J=8.8 Hz), 8.51 (s, 1H), 8.84 (bs, 2H), 9.28 (bs, 2H), 10.94 (s, 1H); Mass Spectrum (ESI) m/z calcd. for $C_{20}H_{23}N_5O_2S_5$, 493.69 (M+H), found 494.2.

EXAMPLE 183 a) Amino(3-quinolylamino)methane-1-thione: 3-Aminoquinoline (500 mg, 3.46 mmol) was treated as described in Example 177, step (a) to give 285 mg (41% yield) of amino(3-quinolylamino)methane-1-thione. $^1$H NMR (DMSO-d$_6$, 300 MHz) δ 7.57 (m, 1H), 7.67 (m, 1H), 7.94 (m, 2H), 8.41 (d, 1H, J=2.4 Hz), 8.85 (d, 1H, J=2.5 Hz), 10.03 (s, 1H); Mass Spectrum (ESI) m/z calcd. for $C_{10}H_9N_3S$, 203.3 (M+H), found 204.1.

b) Methyl 5-methylthio-4-[2-(3-quinolylamino)(1,3-thiazol-4-yl)]thiophene-2-carboxylate: Methyl 4-(2-bromoacetyl)-5-methylthiothiophene-2-carboxylate (90 mg, 0.28 mmol) was allowed to react with amino(3-quinolylamino)methane-1-thione (59.1 mg) as described in Example 154, step (a) to give 107.5 mg (78% yield) of methyl 5-methylthio-4-[2-(3-quinolylamino)(1,3-thiazol-4-yl)]thiophene-2-carboxylate hydrobromide. $^1$H NMR (DMSO-d$_6$, 300 MHz) δ 2.75 (s, 3H), 3.84 (s, 3H), 7.52 (s, 1H), 7.92–8.05 (m, 2H), 8.22 (s, 1H), 9.22 (m, 2H); Mass Spectrum (ESI) m/z calcd. for $C_{19}H_{15}N_3O_2S_3$, 413.54 (M+H), found 414.1.

c) 5-Methylthio-4-[2-(3-quinolylamino)(1,3-thiazol-4-yl)]thiophene-2-carboxamidine hydrochloride: Methyl 5-methylthio-4-[2-(3-quinolylamino)(1,3-thiazol-4-yl)]thiophene-2-carboxylate hydrobromide (107.5 mg, 0.21 mmol) was treated as described in Example 154, step (b) to give 4.5 mg (4.9% yield) of 5-methylthio-4-[2-(3-quinolylamino)(1,3-thiazol-4-yl)]thiophene-2-carboxamidine hydrochloride. 1H NMR (DMSO-d$_6$, 300 MHz) δ 2.80 (s, 3H), 7.29 (s, 1H), 7.59 (m, 2H), 7.93 (m, 2H), 8.54 (s, 1H), 8.89 (bs, 2H), 8.91 (m, 1H), 9.16 (m, 1H), 9.29 (bs, 2H), 10.97 (s, 1H); Mass Spectrum (ESI) m/z calcd. for $C_{18}H_{15}N_5S_3$, 397.5 (M+H), found 398.1.

EXAMPLE 184 a) Methyl 5-methylthio-4-[2-(2-naphthylamino)(1,3-thiazol-4-yl)]thiophene-2-carboxylate hydrobromide: Methyl 4-(2-bromoacetyl)-5-methylthiothiophene-2-carboxylate (65 mg, 0.21 mmol) was allowed react with 2-napthylthiourea (42.4 mg) as described in Example 154, step (a) to give 82.5 mg (80% yield)of methyl 5-methylthio-4-[2-(2-naphthylamino)(1,3-thiazol-4-yl)]thiophene-2-carboxylate hydrobromide. $^1$H NMR (DMSO-d$_6$, 300 MHz) δ 2.67 (s, 3H), 3.83 (s, 3H), 7.31 (s, 1H), 7.50–7.67 (m, 4H), 7.93 (m, 1H), 8.15 (s, 1H), 8.31–8.35 (m, 1H), 8.46 (d, 1H, J=7.6), 10.22 (s, 1H)); Mass Spectrum (ESI) m/z calcd. for $C_{20}H_{16}N_2O_2S_3$, 412.6 (M+H), found 413.1.

c) 5-Methylthio-4-[2-(2-naphthylamino)(1,3-thiazol-4-yl)]thiophene-2-carboxamidine hydrochloride: Methyl 5-methylthio-4-[2-(2-naphthylamino)(1,3-thiazol-4-yl)]thiophene-2-carboxylate hydrobromide (42.7 mg, 0.086 mmol) was treated as described in Example 154, step (b) to give 5.8 mg (16% yield) of 5-methylthio-4-[2-(2-naphthylamino)(1,3-thiazol-4-yl)]thiophene-2-carboxamidine hydrochloride. $^1$H NMR (DMSO-d$_6$, 300 MHz) δ 2.72 (s, 3H), 7.12–7.27 (m, 3H), 7.50–7.68 (m, 3H), 7.94 (m, 1H), 8.32–8.35 (m, m, 1H), 8.51 (s, 1H), 8.97 (bs, 2H), 9.34 (bs, 2H), 10.26 (s, 1H); Mass Spectrum (ESI) m/z calcd. for $C_{19}H_{16}N_4S_3$, 396.6 (M+H), found 397.2.

EXAMPLE 185 a) Methyl 4-[2-(2H-benzo[3,4-d]1,3-dioxolan-5-ylamino)(1,3-thiazol-4-yl)]-5-methylthiothiophene-2-carboxylate hydrobromide: Methyl 4-(2-bromoacetyl)-5-methylthiothiophene-2-carboxylate (65 mg, 0.21 mmol) was allowed to react with 2,3-methylenedioxyphenylthiourea (41.2 mg) as described in Example 154, step (a) to give 51 mg (50% yield) of methyl 4-[2-(2H-benzo[3,4-d]1,3-dioxolan-5-ylamino)(1,3-thiazol-4-yl)]-5-methylthiothiophene-2-carboxylate hydrobromide. $^1$H NMR (DMSO-d$_6$, 300 MHz) δ 2.66 (s, 3H), 3.83 (s, 3H), 5.98 (s, 2H), 6.84–6.89 (m, 1H), 6.96, 7.04 (dd, 1H rotomer, J=2.2, 8.5 Hz), 7.25 (s, 1H), 7.46, 7.60 (d, 1H rotomer, J=2.1 Hz), 8.05, 8.13 (s, 1H rotomer), 10.19, 10.34 (s, 1H, rotomer); Mass Spectrum (ESI) m/z calcd. for $C_{17}H_{14}N_2O_4S_3$, 406.5 (M+H), found 407.1.

b) 4-[2-(2H-Benzo[3,4-d]1,3-dioxolan-5-ylamino)(1,3-thiazol4-yl)]-5-methylthiothiophene-2-carboxamidine hydrochloride: Methyl 4-[2-(2H-benzo[3,4-d]1,3-dioxolan-5-ylamino)(1,3-thiazol-4-yl)]-5-methylthiothiophene-2-carboxylate hydrobromide (51 mg, 0.10 mmol) was treated as described in Example 154, step (b) to give 16.6 mg (39% yield) of 4-[2-(2H-benzo[3,4-d]1,3-dioxolan-5-ylamino)(1,3-thiazol-4-yl)]-5-methylthiothiophene-2-carboxamidine hydrochloride. $^1$H NMR (DMSO-d$_6$, 300 MHz) δ 2.71(s, 3H), 5.98 (s, 2H), 6.87 (d, 1H, J=8.2 Hz), 7.09–7.13 (m, 2H), 7.67 (d, 1H, J=2.4 Hz), 8.50 (s, 1H), 8.95 (bs, 2H), 9.33 (bs, 2H), 10.30 (s, 1H); Mass Spectrum (ESI) m/z calcd. for $C_{16}H_{14}N_4O_2S3$, 390.51 (M+H), found 391.2;

EXAMPLE 186 a) Amino[(7-bromofluoren-2-yl)amino]methane-1-thione: 2-Amino-7-bromofluorene (500 mg, 1.90 mmol) was treated as described in Example 177, step (a) to give 128 mg (21% yield) of amino[(7-bromofluoren-2-yl)amino]methane-1-thione. $^1$H NMR (DMSO-d$_6$, 300 MHz) δ 3.35 (s, 2H), 7.35 (d, 1H, J=8.3 Hz), 7.54 (d, 1H, J=8.0 Hz), 7.66 (s, 1H), 7.77–7.87 (m, 3H), 9.80 (s, 1H); Mass Spectrum (ESI) m/z calcd. for $C_{14}H_{11}BrN_2S$, 319.2 (M+H), found 320.1, 321.1.

b) Methyl 4-{2-[(7-bromofluoren-2-yl)amino](1,3-thiazol-4-yl)}-5-methylthiothiophene-2-carboxylate hydrobromide: Methyl 4-(2-bromoacetyl)-5-methylthiothiophene-2-carboxylate (90 mg, 0.28 mmol) was allowed to react with amino[(7-bromofluoren-2-yl)amino]methane-1-thione (92.8 mg) as described in Example 154, step (a) to give 141 mg (82% yield) of methyl 4-{2-[(7-bromofluoren-2-yl)amino](1,3-thiazol-4-yl)}-5-methylthiothiophene-2-carboxylate hydrobromide. $^1$H NMR (DMSO-$d_6$, 300 MHz) δ 2.70 (s, 3H), 3.83 (s, 3H), 3.93 (s, 2H), 7.33 (s, 1H), 7.51 (dd, 1H, J=1.9, 8.0 Hz), 7.65 (dd, 1H, J=2.0, 8.4 Hz), 7.74 (ad, 2H, J=8.3 Hz), 7.83 (ad, 1H, J=8.4 Hz), 8.18 (s, 1H), 8.23 (d, 1H, J=1.4 Hz), 10.47 (s, 1H).

c) 4-{2-[(7-Bromofluoren-2-yl)amino](1,3-thiazol-4-yl)}-5-methylthiothiophene-2-carboxamidine hydrochloride: Methyl 4-{2-[(7-bromofluoren-2-yl)amino](1,3-thiazol-4-yl)}-5-methylthiothiophene-2-carboxylate hydrobromide (100 mg, 0.15 mmol) was treated as described in Example 154, step (b) to give 3.3 mg (4% yield) of 4-{2-[(7-bromofluoren-2-yl)amino](1,3-thiazol-4-yl)}-5-methylthiothiophene-2-carboxamidine hydrochloride. $^1$H NMR (DMSO-$d_6$, 300 MHz) δ 2.76 (s, 3H), 3.95 (s, 2H), 7.18 (s, 1H), 7.54 (dd, 1H, J=1.8, 10.0 Hz), 7.67–7.76 (m, 3H), 7.85 (d, 1H, J=8.2 Hz), 8.23 (s, 1H), 8.50 (s, 1H), 10.53 (s, 1H); Mass Spectrum (ESI) m/z calcd. for $C_{22}H_{17}BrN_4S_3$, 513.5 (M+H), found 513.1, 515.1.

EXAMPLE 187 a) Methyl 4-{2-[(4-cyclohexylphenyl)amino](1,3-thiazol-4-yl)}-5-methylthiothiophene-2-carboxylate hydrobromide: Methyl 4-(2-bromoacetyl)-5-methylthiothiophene-2-carboxylate (65 mg, 0.21 mmol) was allowed to react with 4-cyclohexylphenylthiourea (49.2 mg) as described in Example 154, step (a) to give 45 mg (41% yield) of methyl 4-{2-[(4-cyclohexylphenyl)amino](1,3-thiazol-4-yl)}-5-methylthiothiophene-2-carboxylate hydrobromide. $^1$H NMR (DMSO-$d_6$, 300 MHz) δ 1.23–1.39 (m, 5H), 1.71–1.79 (m, 5H), 2.68 (s, 3H), 3.83 (s, 3H), 7.16 (d, 2H, J=8.6 Hz), 7.26 (s, 1H), 7.65 (d, 2H, J=8.7 Hz), 8.14 (s, 1H), 10.19 (s, 1H); Mass Spectrum (ESI) m/z calcd. for $C_{22}H_{24}N_2O_2S_3$, 444.64 (M+H), found 445.2.

b) 4-{2-[(4-Cyclohexylphenyl)amino](1,3-thiazol-4-yl)}-5-methylthiothiophene-2-carboxamidine hydrochloride: Methyl 4-{2-[(4-cyclohexylphenyl)amino](1,3-thiazol-4-yl)}-5-methylthiothiophene-2-carboxylate hydrobromide (31.1 mg, 0.059 mmol) was treated as described in Example 154, step (b) to give 12.8 mg (47% yield) of 4-{2-[(4-cyclohexylphenyl)amino](1,3-thiazol-4-yl)}-5-methylthiothiophene-2-carboxamidine hydrochloride. $^1$H NMR (DMSO-$d_6$, 300 MHz) δ 1.33–1.40 (m, 5H), 1.68–1.79 (m, 5H), 2.44 (m, 1H), 2.73 (s, 3H), 7.12 (s, 1H), 7.18 (d, 2H, J=8.7 Hz), 7.68 (d, 2H, J=8.7 Hz), 8.47 (s, 1H), 8.85 (bs, 2H), 9.32 (bs, 2H), 10.28 (s, 1H); Mass Spectrum (ESI) m/z calcd. for $C_{21}H_{24}N_4S_3$, 428.64 (M+H), found 429.2.

EXAMPLE 188 a) Amino{[4-(phenyldiazenyl)phenyl]amino}methane-1-thione: 4-Phenylazophenylisothiocyanate (314 mg, 1.30 mmol) was treated as described in Example 177, step (a), part (ii), to give 295 mg (88% yield) of amino{[4-(phenyldiazenyl)phenyl]amino}methane-1-thione. $^1$H NMR (DMSO-$d_6$, 300 MHz) δ 6.84 (m, 1H), 7.57 (m, 2H), 7.73 (m, 2H), 7.85–7.89 (m, 4H), 10.04 (s, 1H); Mass Spectrum (ESI) m/z calcd. for $C_{13}H_{12}N_4S$, 256.3 (M+H), found 257.2.

b) Methyl 5-methylthio-4-(2-{[4-(phenyldiazenyl)phenyl]amino}(1,3-thiazol-4-yl))thiophene-2-carboxylate hydrobromide: Methyl 4-(2-bromoacetyl)-5-methylthiothiophene-2-carboxylate (65 mg, 0.21 mmol) was allowed to react with amino{[4-(phenyldiazenyl)phenyl]amino}methane-1-thione (53.8 mg) as described in Example 154, step (a) to give 80.6 mg (70% yield) of methyl 5-methylthio-4-(2-{[4-(phenyldiazenyl)phenyl]amino}(1,3-thiazol-4-yl))thiophene-2-carboxylate hydrobromide. $^1$H NMR (DMSO-$d_6$, 300 MHz) δ 2.72 (s, 3H), 3.84 (s, 3H), 7.46 (s, 1H), 7.49–7.61 (m, 3H), 7.84 (m, 2H), 7.91–8.02 (m, 4H), 8.20 (s, 1H), 10.83 (s, 1H); Mass Spectrum (ESI) m/z calcd. for $C_{22}H_{18}N_4O_2S_3$, 466.6 (M+H), found 467.1.

c) 5-Methylthio-4-(2-{[4-phenyldiazenyl)phenyl]amino}(1,3-thiazol-4-yl))thiophene-2-carboxamidine hydrochloride: Methyl 5-methylthio-4-(2-{[4-(phenyldiazenyl)phenyl]amino}(1,3-thiazol-4-yl))thiophene-2-carboxylate hydrobromide (47.7 mg, 0.087 mmol) was treated as described in Example 154, step (b) to give 32.8 mg (77% yield) of 5-methylthio-4-(2-{[4-(phenyldiazenyl)phenyl]amino}(1,3-thiazol-4-yl))thiophene-2-carboxamidine hydrochloride. $^1$H NMR (DMSO-$d_6$, 300 MHz) δ 2.78 (s, 3H), 7.26 (s, 1H), 7.49–7.63 (m, 3H), 7.66–7.74 (m, 3H), 7.84–8.08 (m, 3H), 8.60 (s, 1H), 11.02 (bs, 1H); Mass Spectrum (ESI) m/z calcd. for $C_{21}H_{18}N_6S_3$, 450.6 (M+H), found 451.1.

EXAMPLE 189 a) {3-[(Aminothioxomethyl)amino]phenyl}methan-1-ol; 3-Aminobenzyl alcohol (550 mg, 4.46 mmol) was treated as described in Example 177, step (a) to give 618 mg (76% yield) of {3-[(aminothioxomethyl)amino]phenyl}methan-1-ol. $^1$H NMR (DMSO-$d_6$, 300 MHz) δ 4.47 (d, 2H, J=5.6 Hz), 5.19 (t, 1H, J=5.7 Hz), 7.06 (d, 1H, J=6.2 Hz), 7.18–7.30 (m, 3H), 9.73 (s, 1H).

b) Methyl-5-methylthio4-(2-{[3-(hydroxymethyl)phenyl]amino}(1,3-thiazol-4-yl))-thiophene-2-carboxylate hydrobromide: Methyl 4-(2-bromoacetyl)-5-methylthiothiophene-2-carboxylate (1.01 g, 3.26 mmol) was allowed to react with of {3-[(aminothioxomethyl)amino]phenyl}methan-1-ol as described in Example 154, step (a) to give 1.42 g (92% yield) of methyl-5-methylthio4-(2-{[3-(hydroxymethyl)phenyl]amino}(1,3-thiazol-4-yl))-thiophene-2-carboxylate hydrobromide. $^1$H NMR (DMSO-$d_6$, 300 MHz) δ 2.67 (s, 3H), 3.83 (s, 3H), 4.49 (s, 2H), 6.92 (m, 1H), 7.23–7.31 (m, 2H), 7.60 (m, 1H), 7.81 (bs, 1H), 8.17 (s, 1H), 10.29 (bs, 1H).

c) 5-Methylthio 4-(2-{[3-(hydroxymethyl)phenyl]amino}(1,3-thiazol-4-yl))-thiophene-2-carboxamidine hydrochloride: Methyl-5-methylthio4-(2-{[3-(hydroxymethyl)phenyl]amino}(1,3-thiazol-4-yl))-thiophene-2-carboxylate hydrobromide (700 mg, 1.47 mmol) was treated as described in Example 154, step (b) using 1:9:1 methanol-$CH_2Cl_2$-DMF as eluent to give 195 mg (32% yield) of 5-methylthio 4-(2-{[3-(hydroxymethyl)phenyl]amino}(1,3-thiazol-4-yl))-thiophene-2carboxamidine hydrochloride. $^1$H NMR (DMSO-$d_6$, 300 MHz) δ 2.71 (s, 3H), 4.50 (s, 2H), 6.93 (d, 1H, J=7.6 Hz), 7.15 (s, 1H), 7.21–7.27 (m, 1H), 7.38 (bs, 1H), 7.65 (d, 1H, J=8.1 Hz), 7.80 (s, 1H), 8.53 (s, 1H), 8.94 (bs, 2H), 9.32 (bs, 2H), 10.37 (s, 1H); Mass Spectrum (ESI) m/z calcd. for $C_{16}H_{16}N_4OS_3$, 376.5 (M+H), found 377.2.

EXAMPLE 190 a) (tert-Butoxy)-N-[(4-{2-[(3-hydroxymethylphenyl)amino](1,3-thiazol-4-yl)}-5-methylthio(2-thienyl))iminomethyl]-carboxamide: 5-Methylthio 4-(2-{[3-(hydroxymethyl)phenyl]amino}(1,3-thiazol-4-yl))-thiophene-2-carboxamidine (103 mg, 0.27 mmol) was slurried in THF (4 mL) and treated with 0.5 mL of 0.5 N NaOH. tert-Butyldicarbonate (0.40 mmol) was added in one portion and the resulting mixture was stirred overnight. The reaction was partitioned in $CH_2Cl_2$ and water. The organic layer was separated and washed with brine (1×20 mL) and dried ($Na_2SO_4$). Removal of the solvent in vacuo, followed by purification on preparative thin layer chromatography (500 mm silica gel plate, J.T.Baker, Phillipsburg, N.J., 1% methanol-$CH_2Cl_2$), gave 45 mg (35% yield) of ((tert-Butoxy)-N-[(4-{2-[(3-hydroxymethylphenyl)amino](1,3-thiazol-4-yl)}-5-methylthio(2-thienyl))iminomethyl]-carboxamide. $^1$H NMR (DMSO-$d_6$, 300 MHz) δ 1.44 (s, 9H), 2.66 (s, 3H), 4.49 (d, 2H, J=5.7 Hz), 5.15 (t, 1H, J=5.5 Hz), 6.92 (d, 1H, J=7.5 Hz), 6.96 (s, 1H), 7.26 (m, 1H), 7.66–7.75 (m, 2H), 8.38 (s, 1H), 8.98 (bs, 2H), 10.24 (s, 1H).

b) (tert-Butoxy)-N-(imino{4-[2-({3-[(3-methylpiperidyl)methyl]phenyl}amino)(1,3-thiazol-4-yl)]-5-methylthio(2-thienyl)}methyl)carboxamide: To a stirring solution of ((tert-butoxy)-N-[(4-{2-[(3-hydroxymethylphenyl)amino](1,3-thiazol-4-yl)}-5-methylthio(2-thienyl))iminomethyl]-carboxamide (45 mg, 0.094 mmol) under $N_2$ was added triethylamine (2 equiv, 26.3 µl), followed by methansulfonyl chloride (Aldrich Chemical Co., Milwaukee, Wis., 0.13 mmol, 10.2 µl). The reaction was stirred for 1 h, at which time the reaction was partitioned in $CH_2Cl_2$-water. The organic layer was washed with brine (20 mL), filtered through a 5-cm pad of silica gel in a 15-mL fritted glass funnel and dried ($Na_2SO_4$). Removal of the solvent in vacuo afforded the crude mesylate (44 mg) which was used immediately without further purification. To 25.3 mg (0.045 mmol) of the mesylate in 0.5 mL of DMF was added 3-methyl piperidine (0.18 mmol, 21.4 µL) and the result was heated to 65° C. in an oil bath for 4 h. The reaction was concentrated in vacuo and purified by preparative thin layer chromatography (250 mm silica gel plate, 10% methanol-$CH_2Cl_2$, J.T.Baker, Phillipsburg, N.J.) to give 8.2 mg (32% yield) of (tert-butoxy)-N-(imino{4-[2-({3-[(3-methylpiperidyl)methyl]phenyl}amino)(1,3-thiazol-4-yl)]-5-methylthio(2-thienyl)}methyl)carboxamide. Mass Spectrum (ESI) m/z calcd. for $C_{27}H_{35}N_5O_2S_3$, 557.8 (M+H), found 557.9, 458.2 (—C(O)OC(CH$_3$)$_3$.

c) 4-[2-({3-[(3-Methylpiperidyl)methyl]phenyl}amino)(1,3-thiazol-4-yl)]-5-methylthiothiophene-2-carboxamidine hydrochloride: (tert-Butoxy-N-(imino{4-[2-({3-[(3-methylpiperidyl)methyl]phenyl}amino)(1,3-thiazol-4-yl)]-5-methylthio(2 -thienyl)}methyl)carboxamide (8.2 mg, 0.014 mmol) was stirred 2 mL of a 10% 3N HCl-ethyl acetate solution at 0° C. for 30 min., at which time the solvent was removed in vacuo to give 8 mg (100% yield) of the 4-[2-({3-[(3-methylpiperidyl)methyl]phenyl}amino)(1,3-thiazol-4-yl)]-5-methylthiothiophene-2-carboxamidine hydrochloride. $^1$H NMR (DMSO-$d_6$, 300 MHz) δ 0.83 (d, 3H, J=5.6 Hz), 1.54–2.48 (m, 5H), 2.52–2.63 (m, 4H), 2.66 (s, 3H), 4.23 (d, 2H, J=4.8 Hz), 7.15–7.23 (m, 2H), 7.41 (t, 1H, J=7.8 Hz), 7.86–7.92 (m, 2H), 8.63 (s, 1H), 9.01 (bs, 2H), 9.42 (bs, 2H), 10.63 (s, 1H); (Mass Spectrum (ESI) m/z calcd. for $C_{22}H_{27}N_5S_3$, 457.7. (M+H), found 458.2.

EXAMPLE 191 a) Methyl-5-methylthio-4-{2-[(3-hydroxyphenyl)amino](1,3-thiazol-4-yl)}-thiophene-2-carboxylate hydrobromide: Methyl 4-(2-bromoacetyl)-5-methylthiothiophene-2-carboxylate (60 mg, 0.19 mmol) was allowed to react with 3-hydroxyphenylthiourea (32.6 mg) as described in Example 154, step (a) to give 80.2 mg (92% yield) of methyl-5-methylthio-4-{2-[(3-hydroxyphenyl)amino](1,3-thiazol-4-yl)}-thiophene-2-carboxylate hydrobromide. $^1$H NMR (DMSO-$d_6$, 300 MHz) δ 2.67 (s, 3H), 3.83 (s, 3H), 6.38 (d, 1H, J=7.6 Hz), 7.06–7.12 (m, 2H), 7.20–7.29 (m, 2H), 8.14 (s, 1H), 10.17 (s, 1H).

b) 4-{2-[(3-Hydroxyphenyl)amino](1,3-thiazol-4-yl)}-5-methylthiothiophene-2-carboxamidine hydrochloride: Methyl-5-methylthio-4-{2-[(3-hydroxyphenyl)amino](1,3-thiazol-4-yl)}-thiophene-2-carboxylate hydrobromide (460 mg, 1.0 mmol) was treated as described in Example 154, step (b) to give 215 mg (54% yield) of 4-{2-[(3-hydroxyphenyl)amino](1,3-thiazol-4-yl)}-5-methylthiothiophene-2-carboxamidine hydrochloride. (Mass Spectrum (ESI) m/z calcd. for $C_{15}H_{14}N_4OS_3$, 362.5 (M+H), found 363.2.

c) (tert-Butoxy)-N-[(4-{2-[(4-hydroxyphenyl)amino](1,3-thiazol-4-yl)}-5-methylthio(2-thienyl))iminomethyl]carboxamide: To a stirring solution of 4-{2-[(3-hydroxyphenyl)amino](1,3-thiazol-4-yl)}-5-methylthiothiophene-2-carboxamidine hydrochloride (215 mg, 0.48 mmol) in 4 mL of $CH_2Cl_2$-DMF (3:1, v/v) was added di-isopropylethylamine (1.2 equiv). Di-tert-butyl dicarbonate (1.2 equiv, 127 mg, Aldrich Chemicals, Milwaukee, Wis.) was then added dropwise in 1 mL $CH_2Cl_2$ via an addition funnel. The reaction was allowed to stir overnight, partitioned in $CH_2Cl_2$—$H_2O$, and the layers separated. The organic layer was dried ($Na_2SO_4$) and concentrated in vacuo. The residue was purified by flash chromatography (1% methanol-$CH_2Cl_2$) to give 60 mg (27% yield) of (tert-butoxy)-N-[(4-{2-[(4-hydroxyphenyl)amino](1,3-thiazol-4-yl)}-5-methylthio(2-thienyl))iminomethyl]carboxamide. $^1$H NMR (DMSO-$d_6$, 300 MHz) δ 1.44 (s, 9H), 2.72 (s, 3H), 6.38 (m, 1H), 6.96 (s, 1H), 7.06–7.12 (m, 2H), 7.28 (m, 1H), 8.35 (s, 1H), 9.00 (bs, 2H), 9.28 (s, 1H), 10.11 (s, 1H); Mass Spectrum (ESI) m/z calcd. for $C_{20}H_{22}N_4O_3S_3$, 462.6 (M+H), found 462.7, 363.2 [—C(O)OC(CH$_3$)$_3$].

d) (tert-Butoxy)-N-{[4-(2-{[3-(carbamoylmethoxy)phenyl]amino}(1,3-thiazol-4-yl))-5-methylthio(2-thienyl)]iminomethyl}carboxamide: To stirring solution of (tert-butoxy)-N-[(4-{2-[(4-hydroxyphenyl)amino](1,3-thiazol-4-yl)}-5-methylthio(2-thienyl))iminomethyl]carboxamide (65 mg, 0.14 mmol) in 1.5 mL of DMF was added sequentially $Cs_2CO_3$ (1.5 equiv, 60.1 mg, Aldrich Chemicals, Milwaukee, Wis.), bromoacetamide (1.2 equiv, 20.4 mg, Aldrich Chemicals, Milwaukee, Wis.), and a catalytic amount of KI. The reaction was warmed to 58° C. in an oil bath, stirred for 48 h, at which time another 0.6 equiv of bromoacetamide was added. Stirring was continued for another 24 h, at which time the reaction was filtered and concentrated in vacuo. The residue was purified by preparative thin layer chromatography (50% ethyl acetate-hexanes) to give 9 mg (12% yield) of (tert-butoxy)-N-{[4-(2-{[3-(carbamoylmethoxy)phenyl]amino}(1,3-thiazol-4-yl))-5-methylthio(2-thienyl)]iminomethyl}carboxamide. Mass Spectrum (ESI) m/z calcd. for $C_{22}H_{25}N_5O_4S_3$, 519.7 (M+H), found 519.7, 420.7 [—C(O)OC(CH$_3$)$_3$].

e) 4-(2-{[4-(Carbamoylmethoxy)phenyl]amino}(1,3-thiazol4-yl))-5-methylthiothiophene-2-carboxamidine trifluoroacetate: To a stirring suspension -butoxy)-N-{[4-(2-{[3-(carbamoylmethoxy)phenyl]amino}(1,3-thiazol-4-yl))-5of(tert-butoxy)-N-{[4-(2-{[3-(carbamoylmethoxy)phenyl]amino}(1,3-thiazol-4-yl))-5-methylthio(2-thienyl)]iminomethyl}carboxamide (ca. 4 mg, 0.007 mmol) in $CH_2Cl_2$—DMF (4 mL, 3:1 v/v) at 0° C. was added 1 mL of trifluoroacetic acid. The homogeneous solution was stirred an additional 40 min. at this temperature, warmed to ambient temperature over a 30 min. period and concentrated in vacuo to give 4 mg (100% yield) of 4-(2-{[4-(carbamoylmethoxy)

phenyl]amino}(1,3-thiazol-4-yl))-5-methylthiothiophene-2-carboxamidine trifluoroacetate. $^1$H NMR (DMSO-d$_6$, 300 MHz) δ 2.75 (s, 3H), 4.21(d, 2H, J=5.7 Hz), 6.64 (dd, 1H, J=2.4, 8.2 Hz), 6.97 (dd, 1H, J=1.1, 8.2 Hz), 7.16 (s, 1H), 7.22 (m, 1H), 7.60–7.63 (m, 1H), 7.69–7.72 (m, 1H), 7.88 (t, 1H, J=2.1 Hz), 8.42 (s, 1H); Mass Spectrum (ESI) m/z calcd. for C$_{17}$H$_{17}$N$_5$O$_2$S$_3$, 419.6 (M+H), found 420.1.

EXAMPLE 192 a) Isopropyl 5-methyl-4-{2-[(3,4,5-trimethoxyphenyl)amino](1,3-thiazol-4-yl)}thiophene-2-carboxylate hydrobromide: Isopropyl-4-(2-bromoacetyl)-5-methylthiophene-2-carboxylate (84 mg, 0.27 mmol) was allowed to react with 3,4,5-trimethoxyphenylthiourea (66.5 mg) as described in Example 154, step (a) to give 68 mg (48% yield) of isopropyl 5-methyl-4-{2-[(3,4,5-trimethoxyphenyl)amino](1,3-thiazol-4-yl)}thiophene-2-carboxylate hydrobromide. Mass Spectrum (ESI) m/z calcd. For C$_{21}$H$_{24}$N$_2$O$_5$S$_2$, 448.56 (M+H), found 449.0.

b) 5-Methyl-4-{2-[(3,4,5-trimethoxyphenyl)amino](1,3-thiazol-4-yl)}thiophene-2-carboxamidine hydrochloride: Isopropyl 5-methyl-4-{2-[(3,4,5-trimethoxyphenyl)amino](1,3-thiazol-4-yl)}thiophene-2-carboxylate hydrobromide (59 mg, 0.11 mmol) was treated as described in Example 154, step (b) to give 24.4 mg (50% yield) of 5-methyl-4-{2-[(3,4,5-trimethoxyphenyl)amino](1,3-thiazol-4-yl)}thiophene-2-carboxamidine hydrochloride. $^1$H NMR (DMSO-d$_6$, 300 MHz) δ 2.81 (s, 3H), 3.61 (s, 3H), 3.77 (s, 6H), 7.04 (s, 2H), 7.09 (s, 1H), 8.40 (s, 1H); Mass Spectrum (ESI) m/z calcd. for C$_{18}$H$_{20}$N$_4$O$_3$S$_2$, 404.5 (M+H), found 405.2.

EXAMPLE 193 a) Isopropyl 5-methyl-4-{2-[(4-phenoxyphenyl)amino](1,3-thiazol-4-yl)}thiophene-2-carboxylate hydrobromide: Isopropyl-4-(2-bromoacetyl)-5-methylthiophene-2-carboxylate (91 mg, 0.29 mmol) was allowed to react with 4-phenoxyphenylthiourea (72.6 mg) as described in Example 154, step (a) to give 115 mg (75% yield) of isopropyl 5-methyl-4-{2-[(4-phenoxyphenyl)amino](1,3-thiazol-4-yl)}thiophene-2-carboxylate hydrobromide. $^1$H NMR (DMSO-d$_6$, 300 MHz) δ 1.28 (d, 6H, J=6.2 Hz), 2.70 (s, 3H), 6.06 (quintet, 1H, J=6.2 Hz), 6.92–7.09 (m, 5H), 7.15 (s, 1H), 7.30–7.37 (m, 2H), 7.56–7.70 (m, 2H), 7.98 (s, 1H); Mass Spectrum (ESI) m/z calcd. for C$_{24}$H$_{22}$N$_2$O$_3$S$_2$, 450.6 (M+H), found 451.2, 409.2 [—CH(CH$_3$)$_2$].

b) 5-Methyl-4-{2-[(4-phenoxyphenyl)amino](1,3-thiazol-4-yl)}thiophene-2-carboxamidinehydrochloride: Isopropyl 5-methyl-4-{2-[(4-phenoxyphenyl)amino](1,3-thiazol-4-yl)}thiophene-2-carboxylate hydrobromide (95.5 mg, 0.17 mmol) was treated as described in Example 154, step (b) to give 23.8 mg (32% yield) of 5-methyl-4-{2-[(4-phenoxyphenyl)amino](1,3-thiazol-4-yl)}thiophene-2-carboxamidine hydrochloride. $^1$H NMR (DMSO-d$_6$, 300 MHz) δ 2.76 (s, 3H), 6.95–7.12 (m, 6H), 7.34–7.39 (m, 2H), 7.72–7.78 (m, 2H), 8.33 (s, 1H), 8.98 (bs, 3H), 10.29 (bs, 1H); Mass Spectrum (ESI) m/z calcd. for C$_{21}$H$_{18}$N$_4$O$_2$S$_3$, 406.5 (M+H), found 407.2.

EXAMPLE 194 a) Isopropyl 5-methyl-4-[2-(phenylamino)(1,3-thiazol-4-yl)]-thiophene-2-carboxylate hydrobromide: Isopropyl 4-(2-bromoacetyl)-5-methylthiophene-2-carboxylate (64 mg, 0.21 mmol) was allowed to react with phenylthiourea (32.1 mg) as described in Example 154, step (a) to give 80 mg (87% yield) of isopropyl 5-methyl-4-[2-(phenylamino)(1,3-thiazol-4-yl)]-thiophene-2-carboxylate hydrobromide. Mass Spectrum (ESI) m/z calcd. for C$_{18}$H$_{18}$N$_2$O$_2$S$_2$, 358.5 (M+H), found 359.2.

b) 5-Methyl-4-[2-phenylamino)(1,3-thiazol-4-yl)]thiophene-2-carboxamidine hydrochloride: Isopropyl 5-methyl-4-[2-(phenylamino)(1,3-thiazol-4-yl)]-thiophene-2-carboxylate hydrobromide (74 mg, 0.16 mmol) was treated with phenylthiourea (24.3 mg) as described in Example 154, step (b) to give 15 mg (28% yield) (of 5-methyl-4-[2-(phenylamino)(1,3-thiazol-4-yl)]thiophene-2-carboxamidine hydrochloride, which was further purified by recrystallization from methanol-water. $^1$H NMR (DMSO-d$_6$, 300 MHz) δ 2.79 (s, 3H), 6.96 (t, 1H, J=7.2 Hz), 7.09 (s, 1H), 7.33 (t, 2H, J=7.5 Hz), 7.71 (d, 2H, J=7.7 Hz), 8.39 (s, 1H), 8.95 (bs, 2H), 9.33 (bs, 2H), 10.37 (s, 1H); Mass Spectrum (ESI) m/z calcd. for C$_{15}$H$_{14}$N$_4$S$_3$, 314.4 (M+H), found 315.2.

EXAMPLE 195 a) Methyl 4-(4-isoxazol-5-yl(1,3-thiazol-2-yl))-5-methylthiothiophene-2-carboxylate: Methyl 4-(aminothioxomethyl)-5-methylthiothiophene-2-carboxylate (872 mg, 2.51 mmol) was allowed to react with 2-bromo-1-isoxazol-5-ylethan-1-one (737 mg, prepared from from isoxazole-5-carbonyl chloride [Maybridge Chemicals, Cornwall, UK] as described in Example 177, step (a) as described in Example 154, step (a) to give 704 mg (83% yield) of methyl 4-(4-isoxazol-5-yl(1,3-thiazol-2-yl))-5-methylthiothiophene-2-carboxylate. $^1$H NMR (DMSO-d$_6$, 300 MHz) δ 2.75 (s, 3H), 3.85 (s, 3H), 6.93 (d, 1H, J=1.8 Hz), 8.22 (s, 1H), 8.38 (s, 1H), 8.70 (d, 1H, J=1.8 Hz).

b) 4-(4-Isoxazol-5-yl(1,3-thiazol-2-yl))-5-methylthiothiophene-2-carboxamidine hydrochloride: Methyl 4-(4-isoxazol-5-yl(1,3-thiazol-2-yl))-5-methylthiothiophene-2-carboxylate (350 mg, 1.03 mmol) was treated as described in Example 154, step (b) to give 290 mg (78% yield) of 4-(4-isoxazol-5-yl(1,3-thiazol-2-yl))-5-methylthiothiophene-2-carboxamidine hydrochloride, of which an aliquot was further purified by recrystallization from methanol-isopropanol-water (3:1:0.2, v/v/v). $^1$H NMR (DMSO-d$_6$, 300 MHz) δ 2.79 (s, 3H), 6.93 (d, 1H, J=1.9 Hz), 8.45 (s, 1H), 8.74 (m, 2H), 9.23 (bs, 2H), 9.53 (bs, 2H); Mass Spectrum (MALDI-TOF, CHCA matrix) m/z calcd. for C$_{12}$H$_{10}$N$_4$OS$_3$, 322.4 (M+H), found 323.3.

EXAMPLE 196 a) Methyl 4-[4-(2-hydroxyphenyl)(1,3-thiazol-2-yl)]-5-methylthiothiophene-2-carboxylate: Methyl 4-(aminothioxomethyl)-5-methylthiothiophene-2-carboxylate (808 mg, 3.26 mmol) was allowed to react with 2-(2-bromoacetyl)hydroxybenzene (925 mg, prepared from 2-(chlorocarbonyl)phenyl acetate [Aldrich Chemicals, Milwaukee, Wis.] as described in Example 177, step (a)) as described in Example 154, step (a) to give 433 mg (37% yield) of methyl 4-[4-(2-hydroxyphenyl)(1,3-thiazol-2-yl)]-5-methylthiothiophene-2-carboxylate. $^1$H NMR(DMSO-d$_6$, 300 MHz) δ 2.77 (s, 3H), 3.86 (s, 3H), 6.91–7.00 (m, 2H), 7.23 (m, 1H), 8.14–8.19 (m, 2H), 8.24 (s, 1H); Mass Spectrum (ESI) m/z calcd. for C$_{16}$H$_{13}$NO$_3$S$_3$, 363.48 (M+H), found 364.2.

b) 4-[4-(2-Hydroxyphenyl)(1,3-thiazol-2-yl)]-5-methylthiothiophene-2-carboxamidine hydrochloride: Methyl 4-[4-(2-hydroxyphenyl)(1,3-thiazol-2-yl)]-5-methylthiothiophene-2-carboxylate (400 mg, 1.1 mmol) was treated as described in Example 154, step (b) to give 173 mg (41% yield) of 4-[4-(2-hydroxyphenyl)(1,3-thiazol-2-yl)]-5- methylthiothiophene-2-carboxamidine hydrochloride. $^1$H NMR (DMSO-d$_6$, 300 MHz) δ 2.81 (s, 3H), 6.92–7.02 (m, 2H), 7.22 (m, 1H), 8.20 (dd, 1H, J=1.7, 7.8 Hz), 8.27 (s, 1H), 8.65 (s, 1H), 9.00 (bs, 2H), 9.41 (bs, 2H), 10.58 (s, 1H); Mass Spectrum (ESI) m/z calcd. for C$_{15}$H$_{13}$N$_3$OS$_3$, 347.48 (M+H), found 348.2.

EXAMPLE 197

5-Methylthio-4-(6-quinolylamino)thiophene-2-carboxamidine hydrochloride a) Methyl 5-methylthio-4-(6-quinolylamino)thiophene-2-carboxylate: To an oven-dried glass vial with stir bar was added a mixture of 65.2 mg (0.244 mmol) of methyl 4-bromo-5-methylthiothiophene-2-carboxylate (as prepared in Example 241, step (a)), 5.2 mg (9.5 mol %) of palladium (II) acetate, 22.2 mg (14.6 mol %) of racemic-2,2'-bis (diphenylphosphino)-1,1'-binaphthyl (BINAP), 125 mg (0.384 mmol) of cesium carbonate and 50.3 mg (0.349 mmol) of 6-aminoquinoline. The vial was transferred to a glove bag, flushed with dry argon and anhydrous toluene (488 μL) was added. The vial was capped with a Teflon-lined screw cap and heated at 100° C. for 48 h. To the cooled suspension was added ethyl acetate (4 mL), the mixture filtered (Celite), washing with ethyl acetate (2×2 mL), and the solvents removed in vacuo. The resulting residue was purified by chromatography on a 10-g silica SPE column with a gradient of 5–12% ethyl acetate-CH$_2$Cl$_2$ to afford 53.3 mg (66%) of the title compound as a pale yellow resin. $^1$H-NMR (CDCl3, 400 MHz) δ 8.77 (dd, 1H, J =4.2, 1.6 Hz), 8.04 (d, 1H, J=9.4 Hz), 8.02 (d, 1H, J=8.4 Hz), 7.90 (s, 1H), 7.41 (dd, 1H, J=9.0, 2.6 Hz), 7.36 (dd, 1H, J=8.3, 4.2 Hz), 7.27 (d, 1H, J=2.6 Hz), 3.92 (s, 3H) and 2.45 (s, 3H). Mass spectrum (ESI, m/z): Calcd. For C$_{16}$H$_{15}$N$_2$O$_2$S$_2$, 331.1 (M+H), found 331.2.

b) 5-Methylthio-4-(6-quinolylamino)thiophene-2-carboxamidine hydrochloride: Trimethylaluminum (2.0 M in toluene, 0.76 mL, 1.52 mmol) was added dropwise to a suspension of ammonium chloride (85.6 mg, 1.60 mmol) in anhydrous toluene (0.76 mL) under Ar at 0° C. The mixture was stirred at 25° C. for 30 min and then 50.2 mg (0.152 mmol) of methyl 5-methylthio-4-(6-quinolylamino) thiophene-2-carboxylate (as prepared in previous step) was added. The reaction mixture was heated slowly to 100° C. and stirred for 4 h. The cooled mixture was added to a vigorously stirred slurry of silica gel (3 g) in chloroform (15 mL). The suspension was filtered (Celite) washing with 25% MeOH-CH$_2$Cl$_2$ (2×5 mL), 50% MeOH-CH$_2$Cl$_2$ (2×5 mL) and 75% MeOH-CH$_2$Cl$_2$ (2×5 mL). The combined washings were concentrated and the resulting residue was purified on a 5-g silica SPE column with a gradient of 10–15% MeOH-CH$_2$Cl$_2$ to afford 42.2 mg (79%) of the title compound as a yellow solid. $^1$H-NMR (DMSO-d$_6$, 400 MHz) δ 9.39 (br s, 2H), 9.12 (br s, 2H), 8.63 (dd, 1H, J=4.2, 1.6 Hz), 8.44 (s, 1H), 8.16 (m, 2H), 7.89 (d, 1H, J=8.5 Hz), 7.54 (dd, 1H, J=9.1, 2.6 Hz), 7.39 (dd, 1H, J=8.3, 4.2 Hz), 7.20 (d, 1H, J=2.5 Hz) and 2.55 (s, 3H). Mass Spectrum (ESI, m/z): Calcd. For C$_{15}$H$_{14}$N$_4$S$_2$, 315.1 (M+H), found 315.2.

EXAMPLE 198

5-Methylthio-4-[(3-phenylphenyl)amino]thiphene-2-carboxamidine hydrochloride a) Methyl 5-methylthio-4-[(3-phenylphenyl)amino] thiophene-2-carboxylate: The same procedure as in Example 197, step (a), was followed using 62.2 mg (0.233 mmol) of methyl 4-bromo-5-methylthiothiophene-2-carboxylate (as prepared in Example 241, step (a)), 4.7 mg (9.0 mol %) of palladium (II) acetate, 20.0 mg (13.8 mol %) of racemic-BINAP, 140 mg (0.430 mmol) of cesium carbonate, 48.2 mg (0.285 mmol) of 3-aminobiphenyl and 466 μL of toluene, and chromatographed as before using 20–40% CH$_2$Cl$_2$-hexane to afford 52.3 mg (63%) of the title compound as a yellow resin. $^1$H-NMR (CDCl$_3$, 400 MHz) δ 7.81 (s, 1H), 7.61 (m, 2H), 7.46 (m, 2H), 7.38 (m, 2H), 7.21 (m, 2H), 7.03 (m, 1H), 6.22 (s, 1H), 3.90 (s, 3H), 2.43 (s, 3H). Mass spectrum (ESI, m/z): Calcd. For C$_{19}$H$_{17}$NO$_2$S$_2$, 356.1 (M+H), found 356.2.

b) 5-Methylthio-4-[(3-phenylphenyl)amino]thiophene-2-carboxamidine hydrochloride: The same procedure as in Example 197, step (b) was followed using 46.4 mg (0.131 mmol) of methyl 5-methylthio-4-[(3-phenylphenyl)amino] thiophene-2-carboxylate (as prepared in previous step), 0.76 mL of trimethylaluminum (2.0 M in toluene, 1.57 mmol), 87.7 mg of ammonium chloride (1.64 mmol) and 0.79 mL of toluene, and purified on a 5-g silica SPE column with 5–10% MeOH-CH$_2$Cl$_2$ to afford 46.8 mg (95%) of the title compound as a yellow foam. $^1$H-NMR (DMSO-d$_6$, 400 MHz) δ 9.04 (br s, 4H), 8.10 (s, 1H), 8.06 (s, 1H), 7.62 (m, 2H), 7.46 (m, 2H), 7.35 (m, 2H), 7.19 (t, 1H, J=1.9 Hz), 7.12 (d, 1H, J=8.2 Hz), 6.95 (dd, 1H, J=7.8, 1.9 Hz), 2.53 (s, 3H). Mass spectrum (ESI, m/z): Calcd. For C$_{18}$H$_{17}$N$_3$S$_2$, 340.1 (M+H), found 340.2.

EXAMPLE 199

5-Methylthio-4-(3-quinolylamino)thiophene-2-carboxamidine hydrochloride a) Methyl 5-methylthio-4-(3-quinolylamino)thiophene-2-carboxylate: The same procedure as in Example 197, step (a) was followed using 104 mg (0.389 mmol) of methyl 4-bromo-5-methylthiothiophene-2-carboxylate (as prepared in Example 241, step (a)), 7.1 mg (8.1 mol %) of palladium (II) acetate, 29.3 mg (12.1 mol%) of racemic-BINAP, 192 mg (0.589 mmol) of cesium carbonate, 70.5 mg (0.489 mmol) of 3-aminoquinoline and 778 μL of toluene, and chromatographed as before using 3–8% ethyl acetate-CH$_2$Cl$_2$ to afford 34.4 mg (27%) of the title compound as a yellow resin. $^1$H-NMR (CDCl$_3$, 400 MHz) δ 8.73 (d, 1H, J=2.5 Hz), 8.04 (d, 1H, J=8.2 Hz), 7.85 (d, 1H, J=4.0 Hz), 7.71 (d, 1H, J=7.9 Hz), 7.62 (m, 1H), 7.56 (m, 2H), 6.34 (s, 1H), 3.93 (s, 3H) and 2.46 (s, 3H). Mass spectrum (ESI, m/z): Calcd. For C$_{16}$H$_{14}$N$_2$O$_2$S$_2$, 331.1 (M+H), found 331.3.

b) 5-Methylthio-4-(3-quinolylamino)thiophene-2-carboxamidine hydrochloride: The same procedures as in Example 197, step (b) was followed using 32.3 mg (0.0977 mmol) of methyl 5-methylthio-4-(3-quinolylamino) thiophene-2-carboxylate (as prepared in previous step), 0.586 mL of trimethylaluminum (2.0 M in toluene, 1.17 mmol) and 65.8 mg of ammonium chloride (1.26 mmol) and 0.59 mL of toluene and purified on a 5-g silica SPE column with 5–12% MeOH-CH$_2$Cl$_2$ to afford, after concentration once from MeOH-MeCN (1:1), 17.3 mg (51%) of the title compound as a light tan crystalline solid. $^1$H-NMR (DMSO-d$_6$, 400 MHz) δ 9.09 (br s, 4H), 8.79 (s, 1H), 8.56 (s, 1H), 8.12 (s, 1H), 7.89 (m, 1H), 7.79 (m, 1H), 7.56 (s, 1H), 7.50 (m, 2H) and 2.55 (s, 3H). Mass spectrum (ESI, m/z): Calcd. for C$_{15}$H$_{14}$N$_4$S$_2$, 315.1 (M+H), found 315.4.

EXAMPLE 200

5-Methylthio-4-(pyrimidin-2-ylamino)thiophene-2-carboxamidine hydrochloride a) Methyl 5-methylthio-4-(pyrimidin-2-ylamino) thiophene-2-carboxylate: The same procedure as in Example 197, step (a) was followed using 50.9 mg (0.191 mmol) of methyl 4-bromo-5-methylthiothiophene-2 -carboxylate (as prepared in Example 241, step (a)), 2.7 mg (6.3 mol %) of palladium (II) acetate, 11.3 mg (9.5 mol %) of racemic-BINAP, 101 mg (0.310 mmol) of cesium carbonate, 25.9 mg (0.270 mmol) of 2-aminopyrimidine and 381 µL of dioxane, and chromatographed as before using 5–10% ethyl acetate-hexane to afford 16.7 mg (31%) of the title compound as a yellow crystalline solid: 1H-NMR (CDCl$_3$, 400 MHz) δ 8.72 (s, 1H), 8.49 (d, 1H, J=4.8 Hz), 6.80 (t, 1H, J=4.8 Hz), 3.92 (s, 3H), 2.42 (s, 3H) and 1.28 (br s, 2H). Mass spectrum (ESI, m/z): Calcd. for $C_{11}H_{11}N_3O_2S_2$, 282.0 (M+H), found 282.3.

b) 5-Methylthio-4-(pyrimidin-2-ylamino)thiophene-2-carboxamidine hydrochloride: The same procedure as in Example 197, step (b) was followed using 15.2 mg (0.0540 mmol) of methyl 5-methylthio-4-(pyrimidin-2-ylamino) thiophene-2-carboxylate (as prepared in previous step), 0.324 mL or trimethylaluminum (2.0 M in toluene, 0.648 mmol) and 36.4 mg of ammonium chloride (0.680 mmol) and 0.32 mL of toluene, and purified on a 2-g silica SPE column with 5–15% MeOH-CH$_2$Cl$_2$ to afford, after concentration once from MeOH-MeCN (1:10), 11.4 mg (70%) of the title compound as a light yellow crystalline solid. $^1$H-NMR (DMSO-d$_6$, 300 MHz) δ 9.24 (br s, 2H), 8.85 (br s, 2H), 8.45 (d, 1H, J=4.8 Hz), 8.25 (s, 1H), 6.87 (t, 1H, J=4.8 Hz) and 2.53 (s, 3H). Mass spectrum (ESI, m/z): Calcd. for $C_{10}H_{11}N_5S_2$, 266.1 (M+H), found 266.2.

EXAMPLE 201

4-[(4-Cyclohexylphenyl)amino]-5-methylthiothiophene-2-carboxamidine hydrochloride a) Methyl 4-[(4-cyclohexylphenyl)amino]-5-methylthiothiophene-2-carboxylate: The same procedure as in Example 197, step (a) was followed using 122 mg (0.457 mmol) of methyl 4-bromo-5-methylthiothiophene-2-carboxylate (as prepared in Example 241, step (a)), 9.9 mg (9.7 mol %) of palladium (II) acetate, 42.3 mg (14.9 mol %) of racemic-BINAP, 206 mg (0.632 mmol) of cesium carbonate, 102 mg (0.582 mmol) of 4-cyclohexylaniline and 913 µL of toluene, and chromatographed as before using 20–40% CH$_2$Cl$_2$-hexane to afford 73.8 mg (45%) of the title compound as a light green resin: $^1$H-NMR (CDCl$_3$, 400 MHz) δ 7.74 (s, 1H), 7.15 (d, 2H, J=8.4 Hz), 6.98 (d, 2H, J=8.4 Hz), 6.12 (s, 1H), 3.88 (s, 3H), 2.48 (m, 1H), 2.39 (s, 3H), 1.87 (m, 4H), 1.76 (br d, 1H, J=12.5 Hz), 1.41 (m, 4H) and 1.28 (m, 1H). Mass spectrum (ESI, m/z): Calcd. for $C_{19}H_{23}NO_2S_2$, 362.1 (M+H), found 362.4.

b) 4-[(4-Cyclohexylphenyl)amino]-5-methylthiothiophene-2-carboxamidine hydrochloride: The same procedure as in Example 197, step (b) was followed using 70.2 mg (0.194 mmol) of methyl 4-[(4-cyclohexylphenyl)amino]-5-methylthiothiophene-2-carboxylate (as prepared in previous step), 0.970 mL or trimethylaluminum (2.0 M in toluene, 1.94 mmol), 109 mg of ammonium chloride (2.04 mmol) and 0.97 mL of toluene, and purified on a 10-g silica SPE column with 4–8% MeOH-CH$_2$Cl$_2$ to afford 57.7 mg (78%) of the title compound as a yellow foam. $^1$H-NMR (DMSO-d$_6$, 400 MHz) δ 8.45 (br s, 4H), 7.97 (s, 1H), 7.86 (s, 1H), 7.08 (d, 2H, J=8.5 Hz), 6.92 (d, 2H, J=8.5 Hz), 2.48 (s, 3H), 1.65–1.85 (m, 5H) and 1.35 (m, 5H). Mass spectrum (ESI, m/z): Calcd. for $C_{18}H_{23}N_3S_2$, 346.1 (M+H), found 346.4.

EXAMPLE 202

Methyl 4-amino-5-methylthiothiophene-2-carboxylate

To a pressure tube (Ace Glass, Vineland, N.J.) containing 1.0 g (4.30 mmol) of 5-(methoxycarbonyl)-2-methylthiothiophene-3-carboxylic acid (as prepared in Example 95), 1.01 mL (1.1 equiv, 4.73 mmol) of diphenylphosphoryl azide, and 1.57 mL (2.1 equiv, 9.03 mmol) of N,N-diisopropylethylamine was charged 7 mL of t-butanol. The resultant mixture was sealed and heated to 80° C. in an oil bath for 6 h. The dark reaction mixture was cooled to ambient temperature and concentrated in vacuo. The crude oil was dissolved in 3 mL of CH$_2$Cl$_2$ and then treated with 2 mL of 1:1 CH$_2$Cl$_2$-trifluoroacetic acid followed by 0.5 mL H$_2$O. After 6 h, the mixture was concentrated in vacuo, dissolved in 50 mL of CH$_2$Cl$_2$, washed with sat'd. NaHCO$_3$, dried (Na$_2$SO$_4$), and eluted through a pad of silica gel with 50% ethyl acetate-hexanes. The solvent was concentrated in vacuo and the crude amine was purified by preparative thin layer chromatography (20% ethyl acetate-hexanes, 2000 µm SiO$_2$ gel) to yield 210 mg (24%) of methyl 4 -amino-5-methylthiothiophene-2-carboxylate as a honey-colored oil. $^1$H NMR (DMSO-d$_6$, 300 MHz) δ 2.28 (s, 3H), 3.77 (s, 3H), 5.36 (bs, 2H), 7.24 (s, 1H). Mass spectrum (ESI, m/z): Calcd. for $C_7H_9NO_2S_2$, 204.02 (M+H), found 204.0.

EXAMPLE 203

Methyl 4-[(aminothioxomethyl)amino]-5-methylthiothiophene-2-carboxylate

To a stirring 5 mL biphasic CH$_2$Cl$_2$—NaHCO$_3$ (1:1, v/v) mixture of 98 mg (0.48 mmol) of methyl 4-amino-5-methylthiothiophene-2-carboxylate was added 43 µL (1.2 equiv, 0.57 mmol) of thiophosgene (Aldrich Chemical, Milwaukee, Wis.). The reaction was stirred vigorously overnight, diluted with CH$_2$Cl$_2$ (50 mL), and the layers separated. The organic layer was washed with NaHCO$_3$ (1×15 mL), brine (1×15 mL), and dried (Na$_2$SO$_4$). Concentration of the solvent in vacuo yielded the crude isothiocyanate, which was dissolved in 5 mL of 2M NH$_3$ in MeOH and stirred overnight. The reaction was concentrated to ½ volume and filtered. The filtered solids were washed with acetone and dried, yielding 79.8 mg (63.4%) of methyl 4-[(aminothioxomethyl)amino]-5-methylthiothiophene-2-carboxlyate as a light tan solid. $^1$H NMR (DMSO-d$_6$, 300 MHz) δ 2.51 (s, 3H), 3.81 (s, 3H), 7.41 (bs, 2H), 8.03 (s, 1H) and 9.27 (bs, 1H). Mass spectrum (ESI, m/z): Calcd. for $C_8H_{10}N_2O_2S_3$, 263.00 (M+H), found 263.2.

EXAMPLE 204

5-Methylthio-4-[(4-phenyl(1,3-thiazol-2-yl))amino]thiophene-2-carboxamidine a) Methyl 5-methylthio-4-[(4-phenyl(1,3-thiazol-2-yl)amino]thiophene-2-carboxylate: To a 25-mL round bottom flask containing 40 mg (0.15 mmol) of methyl 4-[(aminothioxomethyl)amino]-5-methylthiothiophene-2-carboxylate and 30.3 mg (1 equiv, 0.15 mmol) of bromoacetophenone was added 2 mL of acetone, and the resultant mixture was heated to reflux for 18 h. The reaction was cooled to room temperature and filtered to give 50 mg (92%) of methyl 5-methylthio-4-[(4-phenyl(1,3-thiazol-2-yl))amino]thiophene-2-carboxylate, which was used without further purification. $^1$H NMR (DMSO-d$_6$, 300 MHz) δ 2.49 (s, 3H), 3.84 (s, 3H), 7.09 (s, 1H), 7.26–7.48 (m, 3H), 7.85 (m, 2H), 8.63 (s, 1H), 10.06 (bs, 1H). Mass spectrum (ESI, m/z): Calcd. for $C_{16}H_{14}N_2O_2S_3$, 363.03 (M+H), found 363.4.

b) 5-Methylthio-4-[(4-phenyl(1,3-thiazol-2-yl)amino]thiophene-2-carboxamidine: Using a procedure similar to that of Example 154, step (b), 47 mg (0.13 mmol) of methyl 5-methylthio-4-[(4-phenyl(1,3-thiazol-2-yl))amino] thiophene-2-carboxylate was allowed to react with 0.5 mL (8 equiv, 1.04 mmol) of the AlMe$_3$/NH$_4$Cl reagent and purified by preparative thin layer chromatography (20% MeOH-CHCl$_3$-sat'd. NH$_3$, 500 μm SiO$_2$ gel plate) to give 19 mg (42%) of 5-mehtylthio-4-[(4-phenyl(1,3-thiazol-2-yl)) amino]thiophene-2-carboxamidine as a yellow solid. $^1$H NMR (DMSO-d$_6$, 300 MHz) δ 2.43 (s, 3H), 7.27–7.42 (m, 4H), 7.90 (d, 2H, J=7.1 Hz), 8.41 (s, 1H). Mass spectrum (ESI, m/z): Calcd. for C$_{15}$H$_{14}$N$_4$S$_3$, 347.05 (M+H), found 347.1.

EXAMPLE 205

5-Methylthio-4-{[4-(4-phenylphenyl)(1,3-thiazol-2-yl)]amino}thiophene-2-carboxamidine a) Methyl 5-methylthio-4-}[4-(4-phenylphenyl)(1,3-thiazol-2-yl)]amino}thiophene-2-carboxylate: Using a procedure similar to Example 204, step (a) 53 mg (0.2 mmol) of methyl 4-[(aminothioxomethyl)amino]-5-methylthiothiophene-2-carboxylate was allowed to react with 55.6 mg (0.2 mmol) of 4-phenyl-bromoacetophenone for 3 h to afford 57 mg (65%) of methyl 5-methylthio-4-{[4-(4-phenylphenyl)(1,3-thiazol-2-yl)]amino}thiophene-2-carboxylate. $^1$H NMR (DMSO-d$_6$, 300 MHz) δ 2.51 (s, 3H), 3.86 (s, 3H), 6.93 (s, 1H rotomer), 7.10 (s, 1H rotomer), 7.27 (s, 1H rotomer), 7.37–7.50 (m, 3H rotomer), 7.72–7.76 (m, 4H rotomer), 8.4 (d, 2H, 8.4 Hz), 8.66 (s, 1H rotomer), 10.10 (bs, 1H). Mass spectrum (ESI, m/z): Calcd. for C$_{22}$H$_{18}$N$_2$O$_2$S$_3$, 439.06 (M+H), found 439.2.

b) 5-Methylthio-4-{[4-(4-phenylphenyl(1,3-thiazol-2-yl)]amino}thiophene-2-carboxamidine: Using a procedure similar to that of Example 154, step (b), 57 mg (0.12 mmol) of methyl 5-methylthio-4-{[4-(4-phenylphenyl)(1,3-thiazol-2-yl)]amino}thiophene-2-carboxylate was allowed to react with 6.7 equiv (0.87 mmol) of the AlMe$_3$/NH$_4$Cl reagent and purified by preparative thin layer chromatography (20% MeOH-CHCl$_3$-sat'd. NH$_3$, 500 μm SiO$_2$ plate) to give 20.7 mg (40.7%) of 5-methylthio-4-{[4-(4-phenylphenyl)(1,3-thiazol-2-yl)]amino}thiophene-2-carboxamidine. $^1$H NMR (DMSO-d$_6$, 400 MHz) δ 2.51 (s, 3H), 6.93 (s, 1H), 7.10 (s, 1H), 7.27 (s, 1H), 7.35–7.50 (m, 4H), 7.72–7.76 (m, 4H), 7.94–7.96 (m, 2H), 8.66 (s, 1H), 10.11 (bs, 1H). Mass spectrum (ESI, m/z): Calcd. for C$_{21}$H$_{18}$N$_4$S$_3$, 423.08 (M+H), found 423.2.

EXAMPLE 206

4-[(5-Methyl-4-phenyl(1,3-thiazol-2-yl))amino]-5-methylthiothiophene-2-carboxamidine a) Methyl-4-[(5-methyl-4-phenyl(1,3-thiazol-2-yl)amino]-5-methylthiothiophene-2-carboxylate: Using a procedure similar to Example 204, step (a), 51 mg (0.19 mmol) of methyl 4-[(aminothioxomethyl)amino]-5-methylthiothiophene-2-carboxylate was allowed to react with 41.4 mg (0.38 mmol) of 2-bromopropiophenone (Aldrich Chemical Co., Milwaukee, Wis.) in 2 mL of DMF for 4 h. Concentration in vacuo of the reaction mixture afforded 73 mg (100%) of methyl-4-[(5-methyl-4-phenyl(1,3-thiazol-2-yl))amino]-5-methylthiothiophene-2-carboxylate. Mass spectrum (ESI, m/z): Calcd. for C$_{17}$H$_{16}$N$_2$O$_2$S$_3$, 377.05 (M+H), found 377.2.

b) 4-[(5-Methyl-4-phenyl(1,3-thiazol-2-yl))amino]-5-methylthiothiophene-2-carboxamidine: Using a procedure similar to Example 154, step (b), 73 mg (0.19 mmol) of methyl-4-[(5-methyl-4-phenyl(1,3-thiazol-2-yl))amino]-5-methylthiothiophene-2-carboxylate was allowed to react with 8 equiv (1.5 mmol) of the AlMe$_3$/NH$_4$Cl reagent and purified by preparative thin layer chromatography (20%-MeOH-CHCl$_3$-sat'd. NH$_3$, 500 μm SiO$_2$ plate) to afford 17.9 mg (26%) of 4-[(5-methyl-4-phenyl(1,3-thiazol-2-yl)) amino]-5-methylthiothiophene-2-carboxamidine. $^1$H NMR (DMSO-d$_6$, 300 MHz): δ 2.40 (s, 3H), 2.51 (s, 3H rotomer), 2.73 (s, 3H rotomer), 7.29–7.44 (m, 2H rotomer), 7.64–7.73 (m, 3H rotomer), 7.95 (s, 1H rotomer), 8.06 (s, 1H rotomer). Mass spectrum (ESI, m/z): Calcd. for C$_{16}$H$_{16}$N$_4$S$_3$, 361.06 (M+H), found 361.2.

EXAMPLE 207

4-{[4-Hydroxy-4-(trifluoromethyl)(1,3-thiazolin-2-yl)]amino}-5-methylthiothiophene-2-carboxamidine a) Methyl 4-{[4-hydroxy-4-(trifluoromethyl) (1,3-thiazolin-2-yl)]amino}-5-methylthiothiophene-2-carboxylate: Using a procedure similar to Example 204, step (a), 56 mg (0.21 mmol) of methyl 4-[(aminothioxomethyl) amino]-5-methylthiothiophene-2-carboxylate was allowed to react with 40 mg (0.21 mmol) of bromotrifluoroacetone (Aldrich Chemical Co., Milwaukee, Wis.) to afford 40.3 mg (54%) of methyl 4-{[4-hydroxy-4-(trifluoromethyl)(1,3-thiazolin-2-yl)]amino}-5-methylthiothiophene-2-carboxylate. Mass spectrum (ESI, m/z): Calcd. for C$_{11}$H$_{11}$F$_3$N$_2$O$_3$S$_3$, 373.00 (M+H), found 373.0.

b) 4-{[4-Hydroxy-4-(trifluoromethyl)(1,3-thiazolin-2-yl)]amino}-5-methylthiothiophene-2-carboxamidine: Using a procedure similar to Example 154, step (b), 40 mg (0.11 mmol) of methyl 4-{[4-hydroxy-4-(trifluoromethyl)(1,3-thiazolin-2-yl)]amino}-5-methylthiothiophene-2-carboxylate was allowed to react with 8 equiv (0.89 mmol) of the AlMe$_3$/NH$_4$Cl reagent and purified by preparative thin layer chromatography (20%-MeOH-CHCl$_3$-sat'd. NH$_3$, 500 μm SiO$_2$ plate) to afford 11 mg (28%) of 4-{[4-hydroxy-4-(trifluoromethyl)(1,3-thiazolin-2-yl)]amino}-5-methylthiothiophene-2-carboxamidine as a ca. 1:1 mixture of cyclized aminal and open imine tautomers. $^1$H NMR (DMSO-d$_6$, 300 MHz) δ 2.73 (s, 3H tautomer), 2.89 (s, 3H tautomer), 3.36 (d, 2H, J=6.5 Hz), 3.62 (d, 2H, J=7.2 Hz), 7.95 (s, 1H), 8.36 (bs, 2H), 9.79 (bs, 1H). Mass spectrum (ESI, m/z): Calcd. for C$_{10}$H$_{11}$F$_3$N$_4$OS$_3$, 357.01 (M+H), found 357.2.

EXAMPLE 208

5-Methylthio-4-(2-naphthylamino)thiophene-2-carboxamidine a) Methyl 5-methylthio-4-(2-naphthylamino)thiophene-2-carboxylate: To an oven-dried round bottom flask equipped with Teflon-coated stir bar and rubber septum was added 190 mg (0.93 mmol) of methyl 4-amino-5-methylthiothiophene-2-carboxylate, 320 mg (2 equiv, 1.86 mmol) of 2-napthalene boronic acid (Lancaster Synthesis, Windham, N.H.), and 168 mg (1 equiv, 0.93 mmol) of Cu(OAc)$_2$ (Aldrich Chemical Co., Milwaukee, Wis.). The flask was flushed with Ar, then charged with 4 mL CH$_2$Cl$_2$ followed by 259 μL (2 equiv, 1.86 mmol) of NEt$_3$. The mixture was stirred vigorously for 48 h and then filtered through a small pad of SiO$_2$, eluting with 50% ethyl acetate-hexanes. Concentration of the solvent in vacuo, and purification of the residue by preparative thin layer chromatography (25% ethyl acetate-hexanes, 1000 μM SiO$_2$ plate) afforded 170 mg (55%) of methyl 5-methylthio-4-(2-naphthylamino)thiophene-2-carboxylate and 54 mg (28%) of recovered methyl 4-amino- 5-methylthiothiophene-2-carboxylate. $^1$H NMR (CDCl$_3$, 400 MHz) δ 2.43 (s, 3H), 3.92 (s, 3H), 6.29 (s, 1H), 7.21 (dd, 1H, J=2.35, 8.7 Hz), 7.33–7.37 (m, 2H), 7.45 (m, 1H), 7.71 (d, 1H, J=8.2 Hz), 7.78 (m, 2H), 7.88 (s, 1H). Mass spectrum (ESI, m/z): Calcd. for C$_{17}$H$_{15}$NO$_2$S$_2$, 330.06 (M+H), found 330.1.

b) 5-Methylthio-4-(2-naphthylamino)thiophene-2-carboxamidine hydrochloride: Using a procedure similar to Example 154, step(b),730 mg (2.21 mmol) of methyl 5-methylthio-4-(2-naphthylamino)thiophene-2-carboxylate was allowed to react with 8 equiv (17.7 mmol) of the AlMe$_3$/NH$_4$Cl reagent and purified by preparative thin layer chromatography (20%-MeOH-CHCl$_3$-sat'd. NH$_3$, 1000 μm SiO$_2$ plate) to afford 5-methylthio-4-(2-naphthylamino)thiophene-2-carboxamidine, which was dissolved in 4 mL of dry MeOH, cooled to 0° C. and carefully treated with 1.6 mL(1.5 equiv, 3.31 mmol) of 2M HCl in ether. The reaction was stored at 5° C. overnight, then concentrated in vacuo with toluene (3×10 mL) and then hexanes (2×10 mL). The yellow solid was dried under vacuum to afford 415 mg (53.6%) of 5-methylthio-4-(2-naphthylamino)thiophene-2-carboxamidine hydrochloride. $^1$H NMR (DMSO-d$_6$, 400 MHz) δ 2.53 (s, 3H), 7.20 (d, 1H, J=2.2 Hz), 7.24–7.31 (m, 2H), 7.38 (m, 1H), 7.69 (d, 1H, 8.1 Hz), 7.75–7.79 (m, 2H), 8.13 (s, 1H), 8.24 (s, 1H), 9.06 (bs, 2H), 9.33 (bs, 2H). Mass spectrum (ESI, m/z): Calcd. for C$_{16}$H$_{15}$N$_3$S$_2$, 314.08 (M+H), found 314.5.

EXAMPLE 209

4-[(4-Chlorophenyl)amino]-5-methylthiothiophene-2-carboxamidine a) Methyl 4-[(4-chlorophenyl)amino]-5-methylthiothiophene-2-carboxylate: Using a procedure similar to Example 208, step (a), 66.6 mg (0.32 mmol) of methyl 4-amino-5-methylthiothiophene-2-carboxylate was allowed to react with 100 mg (2 equiv, 0.64 mmol) of 4-chlorophenyl boronic acid to give 11.8 mg (11.7%) of methyl 4-[(4-chlorophenyl)amino]-5-methylthiothiophene-2-carboxylate and 21 mg (31.5%) of unreacted starting material. $^1$H NMR (CDCl$_3$, 400 MHz) δ 2.41 (s, 3H), 3.89 (s, 3H), 6.09 (bs, 1H), 6.94 (d, 2H, J=8.6 Hz), 7.25 (d, 2H, J=8.6 Hz), 7.70 (s, 1H).

b) 4-[(4-chlorophenyl)amino]-5-methylthiothiophene-2-carboxamidine hydrochloride: Using a procedure similar to Example 154, step (b), 11.8 mg (0.037 mmol) of methyl 4-[(4-chlorophenyl)amino]-5-methylthiothiophene-2-carboxylate was allowed to react with 8 equiv (2.96 mmol) of the AlMe$_3$/NH$_4$Cl reagent to afford 13 mg (100%) of 4-[(4-chlorophenyl)amino]-5-methylthiothiophene-2-carboxamidine. $^1$H NMR (DMSO-d$_6$, 400 MHz) δ 2.41 (s, 3H), 6.91–6.95 (m, 2H), 7.10–7.13 (m, 2H), 7.64 (s, 1H), 7.93 (s, 1H), 8.67 (bs, 2H), 9.11 (bs, 2H). Mass spectrum (ESI, m/z): Calcd. for C$_{12}$H$_{12}$ClN$_3$S$_2$, 298.02 (M+H), found 298.1.

EXAMPLE 210

4-[(3-Methylphenyl)amino]-5-methylthiothiophene-2-carboxamidine a) Methyl 4-[(3-methylphenyl)amino]-5-methylthiothiophene-2-carboxylate: Using a procedure similar to Example 208, step (a), 55.7 mg (0.27 mmol) of methyl 4-amino-5-methylthiothiophene-2-carboxylate was allowed to react with 73.4 mg (2 equiv, 0.54 mmol) of 3-methylphenyl boronic acid to give 29.2 mg (36.8%) of methyl 4-[(3-methyl)amino]-5-methylthiothiophene-2-carboxylate. $^1$H NMR (CDCl$_3$, 400 MHz) δ 2.35 (s, 3H), 2.40 (s, 3H), 3.89 (s, 3H), 6.11 (bs, 1H), 6.80–6.86 (m, 3H), 7.20 (m, 1H), 7.77 (s, 1H). Mass spectrum (ESI, m/z): Calcd. for C$_{14}$H$_{15}$NO$_2$S$_2$, 294.06 (M+H), found 294.1.

b) 4-[(3-Methylphenyl)amino]-5-methylthiothiophene-2-carboxamidine: Using a procedure similar to Example 154, step (b), 29.2 mg (0.098 mmol) of methyl 4-[(3-methyl)amino]-5-methylthiothiophene-2-carboxylate was allowed to react with 8 equiv (0.78 mmol) of the AlMe$_3$/NH$_4$Cl reagent and purified by preparative thin layer chromatography (20%-MeOH-CHCl$_3$-sat'd. NH$_3$, 500 μm SiO$_2$ plate) to afford 27 mg (100%) of 4-[(3-methylphenyl)amino]-5-methylthiothiophene-2-carboxamidine. $^1$H NMR (CDCl$_3$, 400 MHz) δ 2.24 (s, 3H), 2.50 (s, 3H), 6.65 (d, 1H, J=7.3 Hz), 6.74–6.76 (m, 2H), 7.10 (m, 1H), 7.88 (s, 1H), 7.97 (s, 1H), 9.07 (bs, 3H). Mass spectrum (ESI, m/z): Calcd. for C$_{13}$H$_{15}$N$_3$S$_2$, 278.08 (M+H), found 278.2.

EXAMPLE 211

4-[(3-Methoxyphenyl)amino]-5-methylthiothiophene-2-carboxamidine a) Methyl-4-[(3-methoxyphenyl)amino]-5-methylthiothiophene-2-carboxylate: Using a procedure similar to Example 208, step (a), 73.2 mg (0.35 mmol) of methyl 4-amino-5-methylthiothiophene-2-carboxylate was allowed to react with 109 mg (2 equiv, 0.70 mmol) of 3-methoxyphenyl boronic acid to give 25.2 mg (23%) of methyl 4-[(3-methoxyphenyl)amino]-5-methylthiothiophene-2-carboxylate. $^1$H NMR (CDCl$_3$, 400 MHz) δ 2.40 (s, 3H), 3.81 (s, 3H), 3.89 (s, 3H), 6.12 (s, 1H), 6.43–6.63 (m, 2H), 7.20 (m, 1H), 7.78 (s, 1H). Mass spectrum (ESI, m/z): Calcd. for C$_{14}$H$_{15}$NO$_3$S$_2$, 310.06 (M+H), found 310.1.

b) 4-[(3-Methylphenyl)amino]-5-methylthiothiophene-2-carboxamidine hydrochloride: Using a procedure similar to Example 154, step (b), 25.2 mg (0.081 mmol) of methyl 4-[(3-methyl)amino]-5-methylthiothiophene-2-carboxylate was allowed to react with 8 equiv (0.64 mmol) of the AlMe$_3$/NH$_4$Cl reagent to afford 27 mg (100%) of 4-[(3-methoxyphenyl)amino]-5-methylthiothiophene-2-carboxamidine. $^1$H NMR (DMSO, 400 MHz) δ 2.49 (s, 3H), 3.71 (s, 3H), 6.41 (dd, 1H, J=2.1, 8.0 Hz), 6.49 (m, 1H), 6.50–6.54 (m, 1H), 7.12 (m, 1H), 7.97 (s, 1H), 8.01 (s, 1H), 8.88 (bs, 2H), 9.23 (bs, 2H). Mass spectrum (ESI, m/z): Calcd. for C$_{13}$H$_{15}$N$_3$OS$_2$, 294.07 (M+H), found 294.1.

EXAMPLE 212

4-{[3-(Methylethyl)phenyl]amino}-5-methylthiothiophene-2-carboxamidine a) Methyl 4-{[3-(methylethyl)phenyl]amino}-5-methylthiothiophene-2-carboxylate: Using a procedure similar to Example 208, step (a), 74.4 mg (0.36 mmol) of methyl 4-amino-5-methylthiothiophene-2-carboxylate was allowed to react with 118 mg (2 equiv, 0.72 mmol) of 3-isopropylphenyl boronic acid to give 22.6 mg (19.5%) of methyl 4-[(3-methylethylphenyl)amino]-5-methylthiothiophene-2-carboxylate. $^1$H NMR (CDCl$_3$, 400 MHz) δ 1.27 (d, 6H, J=6.9 Hz), 2.40 (s, 3H), 2.89 (m, 1H), 3.88 (s, 3H), 6.15 (s, 1H), 6.86–6.89 (m, 3H), 7.24 (m, 1H), 7.77 (s, 1H).

b) 4-{[3-(Methylethyl)phenyl]amino}-5-methylthiothiophene-2-carboxamidine: Using a procedure similar to Example 154, step (b), 22.6 mg (0.07 mmol) of methyl 4-{[3-(methylethyl)phenyl]amino}-5-methylthiothiophene-2-carboxylate was allowed to react with 8 equiv (0.56 mmol) of the AlMe$_3$/NH$_4$Cl reagent to afford 18.9 mg (78.8%) of) 4-{[3-(methylethyl)phenyl]amino}-5-methylthiothiophene-2-carboxamidine. $^1$H NMR (DMSO-d$_6$, 400 MHz) δ 1.18 (d, 6H, J=9.2 Hz), 2.51 (s, 3H), 2.81 (m, 1H), 6.71–6.77 (m, 2H), 6.85 (s, 1H), 7.14 (m, 1H), 7.98 (s, 1H), 8.32 (s, 1H), 8.88 (bs, 2H), 9.23 (bs, 2H). Mass spectrum (ESI, m/z): Calcd. for C$_{15}$H$_{19}$N$_3$S$_2$, 306.11 (M+H), found 306.2.

EXAMPLE 213

5-Methylthio-4-[(3-nitrophenyl)amino]thiophene-2-carboxamidine a) Methyl 5-methylthio-4-[(3-nitrophenyl)amino]thiophene-2-carboxylate: Using a procedure similar to Example 208, step (a), 74.4 mg (0.36 mmol) of methyl 4-amino-5-methylthiothiophene-2-carboxylate was allowed to react with 120 mg (2 equiv, 0.72 mmol) of 3-nitrophenyl boronic acid to give 14.5 mg (12.4%) of methyl 5-methylthio-4-[(3-nitrophenyl) amino]thiophene-2-carboxylate. $^1$H NMR (CDCl$_3$, 400 MHz) δ 2.45 (s, 3H), 3.93 (s, 3H), 6.21 (s, 1H), 7.41–7.47 (m, 2H), 7.73–7.78 (m, 3H).

b) 5-Methylthio-4-[(3-nitrophenyl)amino]thiophene-2-carboxamidine: Using a procedure similar to Example 154, step (b), 14.5 mg (0.04 mmol) of methyl 5-methylthio-4-[(3-nitrophenyl)amino]thiophene-2-carboxylate was allowed to react with 8 equiv (0.35 mmol) of the AlMe$_3$/NH$_4$Cl reagent to afford 4.3 mg (34.8%) of 5-methylthio-4-[(3-nitrophenyl)amino]thiophene-2-carboxamidine. Mass spectrum (ESI, m/z): Calcd. for C$_{12}$H$_{12}$N$_4$O$_2$S$_2$, 309.05 (M+H), found 309.2.

EXAMPLE 214

4-{[4-(Methylethyl)phenyl]amino}-5-methylthiothiophene-2-carboxamidine a) Methyl 4-{[4-(methylethyl)phenyl]amino}-5-methylthiothiophene-2-carboxylate: Using a procedure similar to Example 208, step (a), 74.4 mg (0.36 mmol) of methyl 4-amino-5-methylthiothiophene-2-carboxylate was allowed to react with 118 mg (2 equiv, 0.72 mmol) of 4-isopropylphenyl boronic acid to give 14.5 mg (12.5%) of methyl 4-[(4-methylethylphenyl)amino]-5-methylthiothiophene-2-carboxylate. $^1$H NMR (CDCl$_3$, 400 MHz) δ 1.26 (d, 6H, J=6.2 Hz), 2.39 (s, 3H), 2.89 (m, 1H), 3.89 (s, 3H), 6.98–7.01 (m, 2H), 7.17–7.19 (m, 2H), 7.73 (s, 1H).

b) 4-{[4-(Methylethyl)phenyl]amino}-5-methylthiothiophene-2-carboxamidine: Using a procedure similar to Example 154, step (b), 14.5 mg (0.045 mmol) of methyl 4-{[4-(methylethyl)phenyl]amino}-5-methylthiothiophene-2-carboxylate was allowed to react with 8 equiv (0.36 mmol) of the AlMe$_3$/NH$_4$Cl reagent to afford 11.4 mg (74%) of 4-{[4-(methylethyl)phenyl]amino}-5-methylthiothiophene-2-carboxamidine. $^1$H NMR (DMSO-d$_6$, 400 MHz) δ 1.17 (d, 6H, J=9.2 Hz), 2.51 (s, 3H), 2.81 (m, 1H), 6.92 (d, 2H, J=11.4 Hz), 7.10 (d, 2H,J=11.2 Hz), 7.88 (s, 1H), 7.96 (s, 1H), 8.89 (bs, 2H), 9.22 (bs, 2H). Mass spectrum (ESI, m/z): Calcd. for C$_{15}$H$_{19}$N$_3$S$_2$, 306.11 (M+H), found 306.2.

EXAMPLE 215

4-[(3,4-Dimethylphenyl)amino]-5-methylthiothiophene-2-carboxamidine a) Methyl 4-[(3,4-dimethylphenyl)amino]-5-methylthiothiophene-2-carboxylate: Using a procedure similar to Example 208, step (a), 74.4 mg (0.36 mmol) of methyl 4-amino-5-methylthiothiophene- 2-carboxylate was allowed to react with 108 mg (2 equiv, 0.72 mmol) of 3,4-dimethylphenyl boronic acid to give 135.9 mg (32.4%) of methyl 4-[(3,4-dimethylphenyl)amino]-5-methylthiothiophene-2-carboxylate. $^1$H NMR (CDCl$_3$, 400 MHz) δ 2.24 (s, 3H), 2.26 (s, 3H), 2.38 (s, 3H), 3.88 (s, 3H), 6.11 (bs, 1H), 6.80–6.84 (m, 2H), 7.07 (d, 1H, J=7.9 Hz), 7.71 (s, 1H).

b) 4-[(3,4-Dimethylphenyl)amino]-5-methylthiothiophene-2-carboxamidine: Using a procedure similar to Example 154, step (b), 35.6 mg (0.116 mmol) of methyl 4-[(3,4-dimethylphenyl)amino]-5-methylthiothiophene-2-carboxylate was allowed to react with 8 equiv (0.93 mmol) of the AlMe$_3$/NH$_4$Cl reagent to afford 26.1 mg (68.5%) of 4-[(3,4-dimethylphenyl)amino]-5-methylthiothiophene-2-carboxamidine. $^1$H NMR (DMSO-d$_6$, 400 MHz) δ 2.13 (s, 3H), 2.16 (s, 3H), 2.51 (s, 3H), 6.69–6.78 (m, 2H), 6.99 (d, 1H, J=10.8 Hz), 7.76 (s, 1H), 7.91 (s, 1H), 8.82 (bs, 2H), 9.17 (bs, 2H). Mass spectrum (ESI, m/z): Calcd. for C$_{14}$H$_{17}$N$_3$S$_2$, 292.09 (M+H), found 292.2.

EXAMPLE 216

5-Methylthio-4-[(4-phenylphenyl)amino]thiophene-2-carboxamidine a) Methyl 5-methylthio-4-[(4-phenylphenyl)amino]thiophene-2-carboxylate: Using a procedure similar to Example 208, step (a), 74.4 mg (0.36 mmol) of methyl 4-amino-5-methylthiothiophene-2-carboxylate was allowed to react with 142.5 mg (2 equiv, 0.72 mmol) of 4-phenylphenyl boronic acid to give 24.5 mg (19.1%) of methyl 4-[(4-phenylphenyl)amino]-5-methylthiothiophene-2-carboxylate. $^1$H NMR (CDCl$_3$, 400 MHz) δ 2.45 (s, 3H), 3.92 (s, 3H), 6.38 (bs, 1H), 7.08–7.14 (m, 2H), 7.33 (m, 1H), 7.43–7.46 (m, 2H), 7.54–7.60 (m, 4H), 7.82 (s, 1H).

b) 5-Methylthio-4-[(4-phenylphenyl)amino]thiophene-2-carboxamidine: Using a procedure similar to Example 154, step (b), 24.5 mg (0.07 mmol) of methyl 4-[(4-phenylphenyl)amino]-5-methylthiothiophene-2-carboxylate was allowed to react with 8 equiv (0.56 mmol) of the AlMe$_3$/NH$_4$Cl reagent to afford 16.9 mg (64.1%) of 5-methylthio-4-[(4-phenylphenyl)amino]thiophene-2-carboxamidine. $^1$H NMR (DMSO-d$_6$, 400 MHz) δ 2.51 (s, 3H), 7.03 (d, 2H, J=8.6 Hz), 7.26–7.61 (m, 7H), 8.04 (s, 1H), 8.15 (s, 1H), 8.88 (bs, 2H), 9.25 (bs, 2H). Mass spectrum (ESI, m/z): Calcd. for C$_{18}$H$_{17}$N$_3$S$_2$, 340.09 (M+H), found 340.2.

EXAMPLE 217

4-[(3-Fluoro-4-phenylphenyl)amino]-5-methylthiothiophene-2-carboxamidine a) Methyl 4-[(3-fluoro-4-phenylphenyl)amino]-5-methylthiothiophene-2-carboxylate: Using a procedure similar to Example 208, step (a), 74.4 mg (0.36 mmol) of methyl 4-amino-5-methylthiothiophene-2-carboxylate was allowed to react with 155.5 mg (2 equiv, 0.72 mmol) of 3-fluoro-4-phenylphenyl boronic acid to give 50.6 mg (41.6%) of methyl 4-[(3-fluoro-4-phenylphenyl)amino]-5-methylthiothiophene-2-carboxylate. $^1$H NMR (CDCl$_3$, 400 MHz) δ 2.44 (s, 3H), 3.91 (s, 3H), 6.19 (s, 1H), 6.78–6.86 (m, 2H), 7.32–7.39 (m, 2H), 7.73–7.47 (m, 2H), 7.55 (d, 1H, J=6.9 Hz), 7.82 (s, 1H).

b) 4-[(3-Fluoro-4-phenylphenyl)amino]-5-methylthiothiophene-2-carboxamidine: Using a procedure similar to Example 154, step (b), 50.6 mg (0.13 mmol) of methyl 4-[(3-fluoro-4-phenylphenyl)amino]-5-methylthiothiophene-2-carboxylate was allowed to react with 8 equiv (1.08 mmol) of the AlMe$_3$/NH$_4$Cl reagent to afford 39 mg (76.1%) of 4-[(3-fluoro-4-phenylphenyl) amino]-5-methylthiothiophene-2-carboxamidine. $^1$H NMR (DMSO-d$_6$, 400 MHz) δ 2.51 (s, 3H), 6.75–6.87 (m, 2H), 7.30–7.50 (m, 6H), 8.06 (s, 1H), 8.37 (s, 1H), 8.90 (bs, 2H), 9.27 (bs, 2H). Mass spectrum (ESI, m/z): Calcd. for C$_{18}$H$_{16}$FN$_3$S$_2$, 358.08 (M+H), found 358.2.

EXAMPLE 218

4-(2H-Benzo[d]1,3-dioxolen-5-ylamino)-5-methylthiothiophene-2-carboxamidine a) Methyl 4-(2H-benzo[d]1,3-dioxolen-5-ylamino)-5-methylthiothiophene-2-carboxylate: Using a procedure similar to Example 208, step (a), 74.4 mg (0.36 mmol) of methyl 4-amino-5-methylthiothiophene-2-carboxylate was allowed to react with 119.4 mg (2 equiv, 0.72 mmol) of 3,4-methylenedioxyphenyl boronic acid to give 24.4 mg (20.9%) of methyl 4-(2H-benzo[d]1,3-dioxolen-5-ylamino)-5-methylthiothiophene-2-carboxylate. $^1$H NMR (CDCl$_3$, 400 MHz) δ 2.39 (s, 3H), 3.87 (s, 3H), 5.96 (s, 2H), 6.00 (bs, 1H), 6.52 (dd, 1H, J=2.3, 8.3 Hz), 6.63 (d, 1H, J=2.2 Hz), 6.76 (d, 1H, J=8.3 Hz), 7.59 (s, 1H).

b) 4-(2H-Benzo[d]1,3-dioxolen-5-ylamino)-5-methylthiothiophene-2-carboxamidine: Using a procedure similar to Example 154, step (b), 24.4 mg (0.075 mmol) of methyl 4-(2H-benzo[d]1,3-dioxolen-5-ylamino)-5-methylthiothiophene-2-carboxylate was allowed to react with 8 equiv (0.6 mmol) of the AlMe$_3$/NH$_4$Cl reagent to afford 7.7 mg (29.7%) 4-(2H-benzo[d]1,3-dioxolen-5-ylamino)-5-methylthiothiophene-2-carboxamidine. $^1$H NMR (DMSO-d$_6$, 400 MHz) δ 2.51 (s, 3H), 5.95 (s, 2H), 6.46 (dd, 1H, J=3.0, 11.2 Hz), 6.65 (d, 1H, J=2.8 Hz), 6.79 (d, 1H, J=11.0 Hz), 7.80 (s, 1H), 7.87 (s, 1H), 8.91 (bs, 2H), 9.24 (bs, 2H). Mass spectrum (ESI, m/z): Calcd. for C$_{13}$H$_{13}$N$_3$O$_2$S$_2$, 308.05 (M+H), found 308.2.

EXAMPLE 219

4-[(4-Butylphenyl)amino]-5-methylthiothiophene-2-carboxamidine a) Methyl 4-[(4-butylphenyl)amino]-5-methylthiothiophene-2-carboxylate: Using a procedure similar to Example 208, step (a), 74.4 mg (0.36 mmol) of methyl 4-amino-5-methylthiothiophene-2-carboxylate was allowed to react with 128 mg (2 equiv, 0.72 mmol) of 4-butylphenyl boronic acid to give 22.2 mg (18.3%) of methyl 4-[(4-butylphenyl)amino]-5-methylthiothiophene-2-carboxylate. $^1$H NMR (CDCl$_3$, 400 MHz) δ 0.97 (t, 2H, J=7.4 Hz), 1.38 (m, 2H), 1.59 (m, 2H obscured by water), 2.39 (s, 3H), 2.58 (t, 2H, J=7.6 Hz), 3.90 (s, 3H), 6.12 (bs, 1H), 6.97 (d, 2H, J=8.2 Hz), 7.12 (d, 2H, J=8.4 Hz), 7.73 (s, 1H).

b) 4-[(4-Butylphenyl)amino]-5-methylthiothiophene-2-carboxamidine: Using a procedure similar to Example 154, step (b), 22.2 mg (0.06 mmol) of methyl 4-[(4-butylphenyl) amino]-5-methylthiothiophene-2-carboxylate was allowed to react with 8 equiv (0.52 mmol) of the AlMe$_3$/NH$_4$Cl reagent to afford 18.9 mg (88%) of 4-[(4-butylphenyl) amino]-5-methylthiothiophene-2-carboxamidine. $^1$H NMR (DMSO-d$_6$, 400 MHz) δ 0.89 (t, 2H, J=9.7 Hz), 1.23–1.33 (m, 2H), 1.51 (m, 2H), 2.47–2.50 (m, 2H obscured by DMSO-d$_6$), 2.51 (s, 3H), 6.90 (d, 2H, J=1 1.3 Hz), 7.05 (d, 2H, J=11.2 Hz), 7.86 (s, 1H), 7.94 (s, 1H), 8.78 (bs, 2H), 9.21 (bs, 2H). Mass spectrum (ESI, m/z): Calcd. for C$_{16}$H$_{21}$N$_3$S$_2$, 320.13 (M+H), found 320.2.

EXAMPLE 220

5-Methylthio-4-[benzylamino]thiophene-2-carboxamidine a) Methyl-5-methylthio-4-[benzylamino]thiophene-2-carboxylate: To a 2-dram vial equipped with a stir bar and septum cap was weighed 60 mg (0.29 mmol) of methyl 4-amino-5-methylthiothiophene-2-carboxylate and 30.7 mg (0.29 mmol) of benzaldehyde. The vial was charged with 1 mL CH$_2$Cl$_2$-DMF (2:1, v/v) and 135 mg (2.2 equiv, 0.63 mmol) of NaHB(OAc)$_3$ was added. The reaction was flushed with Ar and allowed to stir for 48 h. At this time 2 mL of CH$_3$OH was added, the reaction stirred an additional 15 min then diluted with 20 ml of CH$_2$Cl$_2$. The organic layer was washed with water (2×20 mL), dried (Na$_2$SO$_4$), and concentrated in vacuo into an oven-dried 2 dram vial to give the crude methyl-5-methylthio-4-[benzylamino]thiophene-2-carboxylate together with unreduced imine. The crude reaction mixture was converted to the amidine without further purification. Mass spectrum (ESI, m/z): Calcd. for C$_{14}$H$_{15}$NO$_2$S$_2$, 294.06 (M+H), found 292.2 (imine), 294.2.

b) 5-Methylthio-4-[benzylamino]thiophene-2-carboxamidine: To a 2-dram vial containing a stir bar and methyl-5-methylthio-4-[benzylamino]thiophene-2-carboxylate (assume 0.29 mmol) was added 2 mL of toluene, followed by 8 equiv (2.32 mmol) of the AlMe$_3$/NH$_4$Cl reagent. The resultant yellow mixture was heated to 110° C. for 3 h, cooled to ambient temperature, and then added to a slurry of 1 g of SiO$_2$ gel in 10 mL of CHCl$_3$. After stirring for 15 min, the slurry was eluted through a 15-mL sintered glass funnel containing a pad of silica gel with 50% CHCl$_3$—CH$_3$OH. The solvent was removed in vacuo and the residue was triturated with 10% CH$_3$OH—CHCl$_3$ and filtered. Removal of the solvent in vacuo gave the crude product which was purified by preparative thin layer chromatography (500 μm SiO$_2$, 20% CH$_3$OH—CHCl$_3$-sat'd. NH$_3$) 14.8 mg (18.3% from methyl 4-amino-5-methylthiothiophene-2-carboxylate) of 5-methylthio-4-[benzylamino]thiophene-2-carboxamidine. $^1$H NMR (DMSO-d$_6$, 400 MHz) δ 2.49 (s, 3H), 4.35 (d, 2H, J=6.7 Hz), 5.91 (t, 1H, J=6.8 Hz), 7.20–7.38 (m, 6H). Mass spectrum (ESI, m/z): Calcd. for C$_{13}$H$_{15}$N$_3$S$_2$, 278.08 (M+H), found 278.3.

EXAMPLE 221

4-(Indan-5-ylamino)-5-methylthiothiophene-2-carboxamidine a) Methyl 4-(indan-5-ylamino)-5-methylthiothiophene-2-carboxylate: Using the procedure described in Example 220, step (a), 60 mg (0.29 mmol) of methyl 4-amino-5-methylthiothiophene-2-carboxylate, 42.3 mg (0.29 mmol) of 5-indancarboxaldehyde, and 135 mg (2.2 equiv, 0.63 mmol) of NaHB(OAc)$_3$ were allowed to react to give methyl 4-(indan-5-ylamino)-5-methylthiothiophene-2-carboxylate. Mass spectrum (ESI, m/z): Calcd. for C$_{17}$H$_{19}$NO$_2$S$_2$, 334.09 (M+H), found 332.3 (imine), 333.4.

b) 4-(Indan-5-ylamino)-5-methylthiothiophene-2-carboxamidine: Using the procedure described in Example 220, step (b), 22.0 mg (27.3% from methyl 4-amino-5-methylthiothiophene-2-carboxylate) of 4-(indan-5-ylamino)-5-methylthiothiophene-2-carboxamidine was obtained. ¹H NMR (DMSO-d₆, 400 MHz) δ 1.94–2.01 (m, 2H), 2.49 (s, 3H), 2.77–2.82 (m, 4H), 4.29 (d, 2H, J=5.6 Hz), 5.78 (t, 1H, J=8.1 Hz), 7.08 (d, 1H, J=7.8 Hz), 7.14 (d, 1H, J=7.5 Hz), 7.20 (s, 1H), 7.23 (s, 1H). Mass spectrum (ESI, m/z): Calcd. for $C_{16}H_{19}N_3S_2$, 318.11 (M+H), found 318.3.

EXAMPLE 222

4-(2,3-Dihydrobenzo[b]furan-5-ylamino)-5-methylthiothiophene-2-carboxamidine a) Methyl 4-(2,3-dihydrobenzo[b]furan-5-ylamino)-5-methylthiothiophene-2-carboxylate: Using the procedure described in Example 220, step (a), 60 mg (0.29 mmol) of methyl 4-amino-5-methylthiothiophene-2-carboxylate, 42.9 mg (0.29 mmol) of 2,3-dihydrobenzo[b]furan-5-carboxaldehyde, and 135 mg (2.2 equiv, 0.63 mmol) of NaHB(OAc)₃ were allowed to react to give methyl 4-(2,3-dihydrobenzo[b]furan-5-ylamino)-5-methylthiothiophene-2-carboxylate. Mass spectrum (ESI, m/z): Calcd. for $C_{16}H_{17}NO_3S_2$, 336.07 (M+H), found 334.3 (imine), 335.3.

b) 4-(2,3-Dihydrobenzo[b]furan-5-ylamino)-5-methylthiothiophene-2-carboxamidine: Using the procedure described in Example 220, step (b), 21.8 mg (23.5% from methyl 4-amino-5-methylthiothiophene-2-carboxylate) of 4-(2,3-dihydrobenzo[b]furan-5-ylamino)-5-methylthiothiophene-2-carboxamidine was obtained. ¹H NMR (DMSO-d₆, 400 MHz) δ 2.49 (s, 3H), 3.13 (t, 2H, J=8.7 Hz), 4.24 (d, 2H, J=6.6 Hz), 4.48 (t, 2H, J=8.7Hz), 5.69 (t, 1H, J=6.7 Hz), 6.68 (d, 1H, J=12.4 Hz), 7.06 (d, 1H, J=7.4 Hz), 7.21 (s, 1H), 7.26 (s, 1H). Mass spectrum (ESI, m/z): Calcd. for $C_{15}H_{17}N_3OS_2$, 320.09 (M+H), found 320.3.

EXAMPLE 223

5-Methylthio4-[(2-phenylimidazol-4-yl)amino]thiophene-2-carboxamidine a) Methyl 5-methylthio-4-[(2-phenylimidazol-4-yl)amino]thiophene-2-carboxylate: Using the procedure described in Example 220, step (a), 60 mg (0.29 mmol) of methyl 4-amino-5-methylthiothiophene-2-carboxylate, 49.9 mg (0.29 mmol) of 4-formyl-2-phenylimidazole, and 135 mg (2.2 equiv, 0.63 mmol) of NaHB(OAc)₃ were allowed to react to give) methyl 5-methylthio-4-[(2-phenylimidazol-4-yl)amino]thiophene-2-carboxylate. Mass spectrum (ESI, m/z): Calcd. for $C_{17}H_{17}N_3O_2S_2$, 360.08 (M+H), found 360.0.

b) 5-Methylthio-4-[(2-phenylimidazol-4-yl)amino]thiophene-2-carboxamidine: Using the procedure described in Example 220, step (b), 30.9 mg (30% from methyl 4-amino-5-methylthiothiophene-2-carboxylate) of 5-methylthio-4-[(2-phenylimidazol-4-yl)amino]thiophene-2-carboxamidine was obtained. ¹H NMR (DMSO-d₆, 400 MHz) δ 2.49 (s, 3H), 4.30–4.38 (m, 3H), 7.09 (bs, 1H), 7.32 (m, 1H), 7.40–7.44 (m, 3H), 7.90–7.95 (m, 3H), 8.43 (bs, 3H). Mass spectrum (ESI, m/z): Calcd. for $C_{16}H_{17}N_5S_2$, 344.10 (M+H), found 344.2.

EXAMPLE 224

5-Methylthio-4-[(2-quinolylmethyl)amino]thiophene-2-carboxamidine a) Methyl 5-methylthio-4-[(2-quinolylmethyl)amino]thiophene-2-carboxylate: Using the procedure described in Example 220, step (a), 60 mg (0.29 mmol) of methyl 4-amino-5-methylthiothiophene-2-carboxylate, 45.5 mg (0.29 mmol) of 2-quinolinecarboxaldehyde, and 135 mg (2.2 equiv, 0.63 mmol) of NaHB(OAc)₃ were allowed to react to give methyl 5-methylthio-4-[(2-quinolylmethyl)amino]thiophene-2-carboxylate. Mass spectrum (ESI, m/z): Calcd. for $C_{17}H_{16}N_2O_2S_2$, 345.07 (M+H), found 343.3 (imine), 345.2.

b) 5-Methylthio-4-[(2-quinolylmethyl)amino]thiophene-2-carboxamidine: Using the procedure described in Example 220, step (b), 2.5 mg (2.6% from methyl 4-amino-5-methylthiothiophene-2-carboxylate) of 5-methylthio-4-[(2-quinolylmethyl)amino]thiophene-2-carboxamidine was obtained. Mass spectrum (ESI, m/z): Calcd. for $C_{16}H_{16}N_4S_2$, 329.09 (M+H), found 329.3.

EXAMPLE 225

4-{[(3-Hydroxyphenyl)methyl]amino}-5-methylthiothiophene-2-carboxamidine a) Methyl 4-{[(3-hydroxyphenyl)methyl]amino}-5-methylthiothiophene-2-carboxylate: Using the procedure described in Example 220, step (a), 61.6 mg (0.30 mmol) of methyl 4-amino-5-methylthiothiophene-2-carboxylate, 49.5 mg (0.30 mmol) of 3-acetoxybenzaldehyde, and 135 mg (2.2 equiv, 0.63 mmol) of NaHB(OAc)₃ were allowed to react to give methyl 4-{[(3-hydroxyphenyl)methyl]amino}-5-methylthiothiophene-2-carboxylate. Mass spectrum (ESI, m/z): Calcd. for $C_{14}H_{16}NO3S_2$, 352.07 (M+H), found, 350.2 (imine), 352.1.

b) Methyl 4-{[(3-hydroxyphenyl)methyl]amino}-5-methylthiothiophene-2-carboxylate: Using the procedure described in Example 220, step (b), 7.9 mg (8.9% from methyl 4-amino-5-methylthiothiophene-2-carboxylate) of methyl 4-{[(3-hydroxyphenyl)methyl]amino}-5-methylthiothiophene-2-carboxylate; Mass spectrum (ESI, m/z): Calcd. for $C_{13}H_{15}N_3OS_2$, 294.07 (M+H), found 294.3.

EXAMPLE 226

5-Methylthio-4-(phenylcarbonylamino)thiophene-2-carboxamidine a) Methyl 5-methylthio-4-(phenylcarbonylamino)thiophene-2-carboxylate: To a stirring solution of 114 mg (0.55 mmol) of methyl 4-amino-5-methylthiothiophene-2-carboxylate in 4 mL of $CH_2Cl_2$ at 0° C. was added 142 μL (1.5 equiv, 0.82 mmol) of N,N-diisopropylethylamine via syringe, followed by 71.3 μL (1.1 equiv, 0.61 mmol) of benzoyl chloride. The reaction was allowed to warm to room temperature, and stirred an additional 4 h. At this time the reaction was partitioned in 40 mL of 1:1 $CH_2Cl_2$-sat'd. $NaHCO_3$ (v/v) and the organic layer was separated, washed with 20 mL of brine, dried ($Na_2SO_4$), and concentrated in vacuo to afford 113 mg (66.8%) of methyl 5-methylthio-4-(phenylcarbonylamino)thiophene-2-carboxylate which was used without further purification. ¹H NMR (DMSO-d₆, 400 MHz) δ 2.55 (s, 3H), 3.83 (s, 3H), 7.47–7.56 (m, 2H), 7.64 (m, 1H), 7.88 (s, 1H), 7.93–7.99 (m, 2H), 10.12 (s, 1H). Mass spectrum (ESI, m/z): Calcd. for $C_{14}H_{13}NO_3S_2$, 308.04 (M+H), found 308.2.

b) 5-Methylthio-4-(phenycarbonylamino)thiophene-2-carboxamidine: Using a procedure similar to Example 154, step (b), 100 mg (0.32 mmol) of methyl 4-{[4-(methylethyl)phenyl]amino}-5-methylthiophene-2-carboxylate was allowed to react with 8 equiv (2.58 mmol) of the AlMe$_3$/NH$_4$Cl reagent to afford 95.4 mg (100%) of 5-methylthio-4-(phenylcarbonylamino)thiophene-2-carboxamidine. $^1$H NMR (DMSO-d$_6$, 400 MHz) δ 2.59 (s, 3H), 7.30–7.64 (m, 3H), 7.98–8.00 (m, 2H), 8.23 (s, 1H), 9.19 (bs, 2H), 9.41 (bs, 2H), 10.35 (s, 1H). Mass spectrum (ESI, m/z): Calcd. for C$_{13}$H$_{14}$N$_3$OS$_2$, 292.06 (M+H), found 292.2.

EXAMPLE 227–240

To each of a series of 2-dram vials equipped a with a stir bar and Teflon septum was added between 0.3 and 0.6 mmol an acid chloride (1 equiv), followed by 1 equiv of methyl 4-amino-5-methylthiothiophene-2-carboxylate as a 1M CH$_2$Cl$_2$ solution. An additional 2 mL of CH$_2$Cl$_2$ was charged into each vial, followed by 1.5 equiv of N,N-diisopropylethylamine. Each vial was swept with Ar and allowed to stir for 3 h. At this time 4 mL of sat'd. NaHCO$_3$ was added to each vial and stirring was continued for 5 min. The aqueous layers were removed by pipette and Na$_2$SO$_4$ was added to each vial. The vials were allowed to stand overnight, and the contents then eluted through 5-g silica gel (SPE column) cartridges with 0.5% MeOH-CH$_2$Cl$_2$. The amides were concentrated in vacuo into pre-weighed 2-dram vials equipped with a stir bar and Teflon septum for the subsequent amidination reactions. The vials were purged with Ar and charged with 2 mL of toluene, followed by 8 equiv of the AlMe$_3$/NH$_4$Cl reagent as a 1M solution in toluene. The reactions were heated to 110° C. in a heating block for 3 h. They were then cooled to ambient temperature and each was added by pipette to a slurry of 1.5 g silica gel in 15 mL of CH$_2$Cl$_2$. Each slurry was vigorously stirred for 15 min, at which time they were filtered through a 15 mL sintered glass funnel containing 20 cm of silica gel with 50% CHCl$_3$-MeOH. The yellow fractions were collected and concentrated in vacuo. The solids were triturated with 10% MeOH-CHCl$_3$ and filtered. Concentration in vacuo yielded the crude amidines, which were purified by preparative thin layer chromatography (20% MeOH-CHCl$_3$-sat'd. NH$_3$, 500 μm SiO$_2$) to afford the amidines as their respective free bases.

| Example | Acid Chloride | Amidine Product | % Yield[a] |
|---|---|---|---|
| 227 | cinnamoyl chloride | 4-((2E)-3-phenylprop-2-enoylamino)-5-methylthiothiophene-2-carboxamidine | 15.3% |
| 228 | 4-chlorobenzoyl chloride | 4-[(4-chlorophenyl)carbonylamino]-5-methylthiothiophene-2-carboxamidine | 44.6% |
| 229 | cyclohexoyl chloride | 4-(cyclohexylcarbonylamino)-5-methylthiothiophene-2-carboxamidine | 17.8% |
| 230 | 3-nitro-4-methylbenzoyl chloride | methyl 4-[(4-methyl-3-nitrophenyl)carbonylamino]-5-methylthiothiophene-2-carboxylate | 8.8% |
| 231 | 2-furoyl chloride | 4-(2-furylcarbonylamino)-5-methylthiothiophene-2-carboxamidine | 13.3% |
| 232 | 2,2-dimethyl-propanoyl chloride | 4-(2,2-dimethylpropanoylamino)-5-methylthiothiophene-2-carboxamidine | 8.5% |
| 233 | 5-(3,5-dichloro-phenoxy)furan-2-carbonyl chloride | 4-{[5-(3,5-dichlorophenoxy)(2-furyl)]carbonylamino}-5-methylthiothiophene-2-carboxamidine | 22.9% |
| 234 | 1-napthoyl chloride | 5-methylthio-4-(naphthylcarbonylamino)-thiophene-2-carboxamidine | 3.1% |
| 235 | 2-quinolinyl chloride | 5-methylthio-4-(2-quinolyicarbonyl-amino)thiophene-2-carboxamidine | 6.8% |
| 236 | 3-methoxybenzoyl chloride | 4-[(3-methoxyphenyl)carbonylamino]-5-methylthiothiophene-2-carboxamidine | 6.8% |
| 237 | 2-(2,5-dimethoxyphenyl)acetyl chloride | 4-[2-(2-hydroxy-5-methoxyphenyl)acetylamino]-5-methylthiothiophene-2-carboxamidine | 18.3% |
| 238 | 4-ethoxybenzoyl chloride | 4-[(4-ethoxyphenyl)carbonylamino]-5-methylthiothiophene-2-carboxamidine | 34% |
| 239 | 2-phenoxyacetyl chloride | 5-methylthio-4-(2-phenoxyacetylamino)-thiophene-2-carboxamidine | 10% |
| 240 | 3-methylbenzoyl chloride | 4-[(3-methylphenyl)carbonylamino]-5-methylthiothiophene-2-carboxamidine | 21.1% |

[a]Yield calculated from starting methyl 4-amino-5-methylthiothiophene-2-carboxylate.

EXAMPLE 227

4-((2E)-3-Phenylprop-2-enoylamino)-5-methylthiothiophene-2-carboxamidine a) Methyl 4-((2E)-3-phenylprop-2-enoylamino)-5-methylthiothiophene-2-carboxylate: yield: 100%. $^1$H NMR (DMSO-d$_6$, 400 MHz) δ 2.49 (s, 3H), 3.83 (s, 3H), 7.12 (d, 1H, J=15.7 Hz), 7.41–7.66 (m, 6H), 8.24 (s, 1H), 9.92 (s, 1H). Mass spectrum (ESI, m/z): Calcd. for C$_{16}$H$_{15}$NO$_3$S$_2$, 334.06 (M+H), 334.1.

b) 4-((2E)-3-Phenylprop-2-enoylamino)-5-methylthiothiophene-2-carboxamidine: $^1$H NMR (DMSO-d$_6$, 400 MHz) δ 2.54 (s, 3H), 7.13 (d, 1H, J=15.7 Hz), 7.41–7.51 (m, 3H), 7.59–7.66 (m, 2H), 8.40 (s, 1H), 8.81

(bs, 3H), 10.02 (bs, 1H). Mass spectrum (ESI, m/z): Calcd. for $C_{15}H_{15}N_3OS_2$, 318.07 (M+H), 318.2.

EXAMPLE 228

4-[(4-Chlorophenyl)carbonylamino]-5-methylthiothiophene-2-carboxamidine a) Methyl 4-[(4-chlorophenyl)carbonylamino]-5-methylthiothiophene-2-carboxylate: yield: 53%. $^1$H NMR (DMSO-d$_6$, 400 MHz) δ 2.55 (s, 3H), 3.83 (s, 3H), 7.62 (d, 2H, J=8.5 Hz), 7.87 (s, 1H), 7.97 (d, 2H, J=8.5 Hz), 10.21 (s, 1H).

b) 4-[(4-Chlorophenyl)carbonylamino]-5-methylthiothiophene-2-carboxamidine: $^1$H NMR (DMSO-d$_6$, 400 MHz) δ 2.59 (s, 3H), 7.63–7.66 (m, 2H), 7.98–8.01 (m, 2H), 8.99 (bs, 2H), 9.33 (bs, 2H), 10.39 (s, 1H). Mass spectrum (ESI, m/z): Calcd. for $C_{13}H_{12}ClN_3OS_2$, 326.02 (M+H), found 326.2.

EXAMPLE 229

4-(Cyclohexylcarbonylamino)-5-methylthiothiophene-2-carboxamidine a) Methyl 4-(cyclohexylcarbonylamino)-5-methylthiothiophene-2-carboxylate: yield: 69.9%. $^1$H NMR (DMSO-d$_6$, 400 MHz) δ 1.22–1.81 (m, 11H), 2.51 (s, 3H), 3.82 (s, 3H), 7.97 (s, 1H), 9.55 (s, 1H). Mass spectrum (ESI, m/z): Calcd. for $C_{14}H_{19}NO_3S_2$, 314.09 (M+H), found 314.2.

b) 4-(Cyclohexylcarbonylamino)-5-methylthiothiophene-2-carboxamidine: $^1$H NMR (DMSO-d$_6$, 400 MHz) δ 2.59 (s, 3H), 7.63–7.66 (m, 2H), 7.98–8.01 (m, 2H), 8.99 (bs, 2H), 9.33 (bs, 2H), 10.39 (s, 1H). Mass spectrum (ESI, m/z): Calcd. for $C_{13}H_{20}N_3OS_2$, 298.10 (M+H), found 298.2.

EXAMPLE 230

Methyl 4-[(4-methyl-3-nitrophenyl)carbonylamino]-5-methylthiothiophene-2-carboxylate a) Methyl 4-[(4-methyl-3-nitrophenyl)carbonylamino]-5-methylthiothiophene-2-carboxylate: yield: 80%. $^1$H NMR (DMSO-d$_6$, 400 MHz) δ 2.56 (s, 3H), 2.61 (s, 3H), 3.82 (s, 3H), 7.70 (d, 1H, J=8.1 Hz), 7.86 (s, 1H), 8.19 (dd, 1H, J=1.7, 8.0 Hz), 8.56 (d, 1H, J=1.7 Hz), 10.41 (s, 1H). Mass spectrum (ESI, m/z): Calcd. for $C_{15}H_{14}N_2O_5S_2$, 367.42 (M+H), found 367.2.

b) Methyl 4-[(4-methyl-3-nitrophenyl)carbonylamino]-5-methylthiothiophene-2-carboxylate: $^1$H NMR (DMSO-d$_6$, 400 MHz) δ 2.47 (s, 3H), 2.61 (s, 3H), 7.12 (bs, 3H), 7.69–7.73 (m, 2H), 8.20 (dd, 1H, J=1.6, 7.9 Hz), 8.57 (d, 1H, J=1.6 Hz). Mass spectrum (ESI, m/z): Calcd. for $C_{14}H_{14}N_4O_3S_2$, 351.06 (M+H), found 351.2.

EXAMPLE 231

4-(2-Furylcarbonylamino)-5-methylthiothiophene-2-carboxamidine a) Methyl 4-(2-furylcarbonylamino)-5-methylthiothiophene-2-carboxylate: yield: 100%; $^1$H NMR (DMSO-d$_6$, 400 MHz) δ 2.54 (s, 3H), 3.83 (s, 3H), 6.71 (dd, 1H, J=1.8, 3.4 Hz), 7.33 (d, 1H, J=3.5 Hz), 7.87 (s, 1H), 7.95 (m, 1H), 9.93 (s, 1H). Mass spectrum (ESI, m/z): Calcd. for $C_{12}H_{11}NO_4S_2$, 298.02 (M+H), found 298.3.

b) 4-(2-Furylcarbonylamino)-5-methylthiothiophene-2-carboxamidine: $^1$H NMR (DMSO-d$_6$, 400 MHz) δ 2.51 (s, 3H), 6.71 (dd, 1H, J=1.8, 3.5 Hz), 7.18 (bs, 3H), 7.32 (d, 1H, J=3.4 Hz), 7.79 (s, 1H), 7.96 (m, 1H). Mass spectrum (ESI, m/z): Calcd. for $C_{11}H_{11}N_3O_2S_2$, 282.04 (M+H), found 282.2.

EXAMPLE 232

4-(2,2-Dimethylpropanoylamino)-5-methylthiothiophene-2-carboxamidine a) Methyl 4-(2,2-dimethylpropanoylamino)-5-methylthiothiophene-2-carboxylate: yield: 93.4%. $^1$H NMR (DMSO-d6, 400 MHz) δ 1.23 (s, 9H), 2.51 (s, 3H), 3.81 (s, 3H), 7.74 (s, 1H), 9.04 (s, 1H). Mass spectrum (ESI, m/z): Calcd. for $C_{12}H_{17}NO_3S_2$, 288.07 (M+H), found 288.1.

b) 4-(2,2-Dimethylpropanoylamino)-5-methylthiothiophene-2-carboxamidine: $^1$H NMR (DMSO-d$_6$, 400 MHz) δ 1.24 (s, 9H), 2.55 (s, 3H), 8.05 (s, 1H), 9.0 (bs, 3H), 9.1 (s, 1H). Mass spectrum (ESI, m/z): Calcd. for $C_{11}H_{17}N_3OS_2$, 272.09 (M+H), found 272.2.

EXAMPLE 233

4-{[5-(3,5-Dichlorophenoxy)(2-furyl)]carbonylamino}-5-methylthiothiophene-2-carboxamidine a) Methyl 4-{[5-(3,5-dichlorophenoxy)(2-furyl)]carbonylamino}-5-methylthiothiophene-2-carboxylate: yield: 96.9%. Mass spectrum (ESI, m/z): Calcd. for $C_{18}H_{13}Cl_2NO_5S_2$, 457.97 (M+H), found 457.9.

b) 4-{[5-(3,5-Dichlorophenoxy)(2-furyl)]carbonylamino}-5-methylthiothiophene-2-carboxamidine: $^1$H NMR (DMSO-d$_6$, 400 MHz) δ 2.53 (s, 3H), 6.12–6.17 (m, 1H), 6.79 (d, 1H, J=1.8 Hz), 7.40–7.43 (m, 2H), 7.70 (m, 1H), 8.13 (s, 1H), 8.92 (bs, 2H), 9.21 (bs, 1H), 10.06 (s, 1H). Mass spectrum (ESI, m/z): Calcd. for $C_{17}H_{14}Cl_2N_3O_3S_2$, 441.99 (M+H), found 442.2.

EXAMPLE 234

5-Methylthio-4-(naphthylcarbonylamino)thiophene-2-carboxamidine a) Methyl 5-methylthio-4-(naphthylcarbonylamino)thiophene-2-carboxylate: yield: 80.8%. $^1$H NMR (DMSO-d$_6$, 400 MHz) δ 7.59–7.67 (m, 3H), 7.80 (d, 1H, J=6.8 Hz), 8.02–8.34 (m, 4H), 10.38 (s, 1H).

b) 5-Methylthio-4-(naphthylcarbonylamino)thiophene-2-carboxamidine: $^1$H NMR (DMSO-d$_6$, 400 MHz) δ 2.50 (s, 3H), 7.60 (m, 3H), 7.76 (d, 1H, J=6.7 Hz), 7.94 (s, 1H), 8.03 (d, 1H, J=6.8 Hz), 8.09 (d, 1H, 8.3 Hz), 8.30 (d, 1H, J=8.8 Hz). Mass spectrum (ESI, m/z): Calcd. for $C_{17}H_{15}N_3OS_2$, 342.07 (M+H), found 342.2.

EXAMPLE 235

5-Methylthio-4-(2-quinolylcarbonylamino)thiophene-2-carboxamidine a) Methyl 5-methylthio-4-(2-quinolylcarbonylamino)thiophene-2-carboxylate: yield: 80.9%. $^1$H NMR (DMSO-d$_6$, 400 MHz) δ 2.59 (s, 3H), 3.86 (s, 3H), 8.03–8.06 (m, 3H), 8.24–8.29 (m, 3H), 9.58 (s, 1H), 10.63 (s, 1H).

b) 5-Methylthio-4-(2-quinolylcarbonylamino)thiophene-2-carboxamidine: $^1$H NMR (DMSO-d$_6$, 400 MHz) δ 2.53 (s, 3H), 7.21 (bs, 3H), 7.74 (s, 1H), 7.96–7.98 (m, 2H), 8.19–8.22 (m, 4H), 9.77 (s, 1H). Mass spectrum (ESI, m/z): Calcd. for $C_{16}H_{14}N_4OS_2$, 343.45 (M+H), found 343.1.

EXAMPLE 236

4-[(3-Methoxyphenyl)carbonylamino]-5-methylthiothiophene-2-carboxamidine a) Methyl 4-[(3-methoxyphenyl)carbonylamino]-5-methylthiothiophene-2-carboxylate: yield: 90.3%. $^1$H NMR (DMSO-d$_6$, 400 MHz) δ 2.55 (s, 3H), 3.83 (s, 3H), 3.85 (s, 3H), 7.19 (m, 1H), 7.39–7.59 (m, 3H), 7.85 (s, 1H), 10.09 (s, 1H). Mass spectrum (ESI, m/z): Calcd. for C$_{15}$H$_{15}$NO$_4$S$_2$, 338.05 (M+H), found 338.3.

b) 4-[(3-Methoxyphenyl)carbonylamino]-5-methylthiothiophene-2-carboxamidine: $^1$H NMR (DMSO-d$_6$, 400 MHz) δ 2.58 (s, 3H), 3.84 (s, 3H), 7.19 (dd, 1H, J=2.1, 8.1 Hz), 7.45–7.57 (m, 3H), 8.15 (s, 1H), 9.11 (bs, 4H), 10.32 (bs, 1H). Mass spectrum (ESI, m/z): Calcd. for C$_{14}$H$_{15}$N$_3$O$_2$S$_2$, 322.07 (M+H), found 322.2.

EXAMPLE 237

4-[2-(2, 5-Dimethoxyphenyl)acetylamino]-5-methylthiothiophene-2-carboxamidine a) Methyl 4-[2-(2,5-dimethoxyphenyl)acetylamino]-5-methylthiothiophene-2-carboxylate: $^1$H NMR (DMSO-d$_6$, 400 MHz) δ 2.47 (s, 3H), 3.67 (s, 2H), 3.70 (s, 3H), 3.75 (s, 3H), 3.80 (s, 3H), 6.81 (dd, 1H, J=3.0, 8.8 Hz), 6.87 (d, 1H, J=3.0 Hz), 6.93 (d, 1H, J=8.9 Hz), 8.04 (s, 1H), 9.62 (s, 1H);

b) 4-[2-(2,5-Dimethoxyphenyl)acetylamino]-5-methylthiothiophene-2-carboxamidine: $^1$H NMR (DMSO-d$_6$, 400 MHz) δ 2.38 (s, 3H), 3.66 (s, 2H), 3.70 (s, 3H), 3.76 (s, 3H), 6.81 (dd, 1H, J=3.3, 8.0 Hz), 6.88–6.94 (m, 2H), 7.91 (s, 1H), 9.42 (bs, 1H).

EXAMPLE 238

4-[(4-Ethoxyphenyl)carbonylamino]-5-methylthiothiophene-2-carboxamidine a) Methyl 4-[(4-ethoxyphenyl)carbonylamino]-5-methylthiothiophene-2-carboxylate: $^1$H NMR (DMSO-d$_6$, 400 MHz) δ 1.36 (t, 3H, J=7.0 Hz), 2.54 (s, 3H), 3.83 (s, 3H), 4.13 (q, 2H, J=7.0 Hz), 7.05 (d, 2H, J=8.8 Hz), 7.87 (s, 1H), 7.93 (d, 2H, J=8.8 Hz), 9.93 (s, 1H). Mass spectrum (ESI, m/z): Calcd. for C$_{16}$H$_{17}$NO$_4$S$_2$, 352.07 (M+H), found 352.2.

b) 4-[(4-Ethoxyphenyl)carbonylamino]-5-methylthiothiophene-2-carboxamidine: $^1$H NMR (DMSO-d$_6$, 400 MHz) δ 1.36 (t, 3H, J=7.0 Hz), 2.55 (s, 3H), 4.13 (q, 2H, J=7.0 Hz), 7.04–7.08 (m, 2H), 7.94–7.97 (m, 2H), 8.09 (s, 1H);8.73 (bs, 3H), 10.01 (bs, 1H). Mass spectrum (ESI, m/z): Calcd. for C$_{15}$H$_{17}$N$_3$O$_2$S$_2$, 336.08 (M+H), found 336.2.

EXAMPLE 239

5-Methylthio-4-(2-phenoxyacetylamino)thiophene-2-carboxamidine a) Methyl 5-methylthio-4-(2-phenoxyacetylamino)thiophene-2-carboxylate: yield: 79%. $^1$H NMR (DMSO-d$_6$, 400 MHz) δ 2.48 (s, 3H), 3.82 (s, 3H), 4.78 (s, 2H), 6.97–7.02 (m, 2H), 7.31–7.35 (m, 2H), 8.05 (s, 1H), 9.80 (s, 1H).

b) 5-Methylthio-4-(2-phenoxyacetylamino)thiophene-2-carboxamidine: $^1$H NMR (DMSO-d$_6$, 400 MHz): δ 2.52 (s, 3H), 4.81 (s, 2H), 6.97–7.04 (m, 3H), 7.31–7.35 (m, 2H), 8.26 (s, 1H), 8.84 (bs, 4H). Mass spectrum (ESI, m/z): Calcd. for C$_{14}$H$_{15}$N$_3$O$_2$S$_2$, 322.43 (M+H), found 322.2.

EXAMPLE 240

4-[(3-Methylphenyl)carbonylamino]-5-methylthiothiophene-2-carboxamidine a) Methyl 4-[(3-methylphenyl)carbonylamino]-5-methylthiothiophene-2-carboxylate: yield: 79%. $^1$H NMR (DMSO-d$_6$, 400 MHz) δ 2.40 (s, 3H), 2.55 (s, 3H), 3.83 (s, 3H), 4.78 (s, 2H), 7.42–7.43 (m, 2H), 7.47–7.77 (m, 2H), 7.86 (s, 1H), 10.06 (s, 1H). Mass spectrum (ESI, m/z): Calcd. for C$_{15}$H$_{15}$NO$_3$S$_2$, 322.06 (M+H), found 322.2.

b) 4-[(3-Methylphenyl)carbonylamino]-5-methylthiothiophene-2-carboxamidine: $^1$H NMR (DMSO-d$_6$, 400 MHz) 2 2.40 (s, 3H), 2.55 (s, 3H), 7.43–7.44 (m, 2H), 7.75–7.78 (m, 2H), 8.05 (s, 1H), 8.52 (bs, 3H), 10.12 (bs, 1H). Mass spectrum (ESI, m/z): Calcd. for C$_{14}$H$_{15}$N$_3$OS$_2$, 306.07 (M+H), found 306.2.

EXAMPLE 241 a) Methyl 4-bromo-5-methylthiothiophene-2-carboxylate: To a stirred solution of 4-bromo-5-methylthiothiophene-2-carboxylic acid (87 mmol), prepared according to the procedure of Kleemann, et al., EP 0676395A2, in dry methanol (750 mL) was added thionyl chloride (7 mL, 96 mmol) dropwise. After stirring for 10 min at room temperature, the solution was heated to reflux and stirred 7.5 h. The solution was cooled and the solvents were removed in vacuo. The resulting solid was dissolved in dichloromethane (1500 mL) and washed with saturated sodium bicarbonate (2×300 mL), water (300 mL), saturated brine (300 mL), and dried over anhydrous sodium sulfate. The solvents were removed in vacuo. The resulting solid was recrystallized twice from hexane/ethyl acetate to give methyl 4-bromo-5-methylthiothiophene-2-carboxylate (4.4 g, 19%). $^1$H-NMR (CDCl$_3$, 400 MHz) δ 7.66 (s, 1H), 3.90 (s, 3H), 2.60 (s, 3H).

b) Methyl 5-methylthio-4-{[3-(phenylmethoxy)phenyl]amino}thiophene-2-carboxylate: A dry mixture of 60 mg (0.225 mmol) of methyl 4-bromo-5-methylthiothiophene-2-carboxylic acid, as prepared in the previous step, 3.0 mg (6 mole %) of palladium (II) acetate (Aldrich Chemical Co., Milwaukee, Wis.), 12.6 mg (9 mole %) of racemic-2,2'-bis (diphenylphosphino)-1,1'-binaphthyl (Strem, Newburyport, Mass.), 110 mg (0.34 mmol, 1.5 eq) of cesium carbonate (Aldrich Chemical Co., Milwaukee, Wis.), and 54 mg (0.29 mmol, 1.3 eq) of 3-benzyloxyaniline (Aldrich Chemical Co., Milwaukee, Wis.) was added to an oven-dried 1-dram glass vial. This vial was flushed with dry argon in a glove bag, dry toluene (450 μL, 0.5 M) was added, and the assembly was heated at 100° C. for 36 h. To the cooled suspension ethyl acetate (4 mL) was added, the mixture passed through 1 inch of Celite, washed with ethyl acetate (2×4 mL) and the solvents removed in vacuo. Purification by preparative thin-layer chromatography (1:1 dichloromethane/hexanes) gave 13 mg of the title compound (15%) as a pale yellow solid. $^1$H-NMR (CDCl$_3$, 400 MHz) δ 7.77 (s, 1H), 7.47–6.59 (m, 9H), 6.11 (s, 1H), 5.07 (s, 2H), 3.89 (s, 3H), 2.47 (s, 3H). Mass spectrum (ESI, m/z): Calcd. for C$_{20}$H$_{19}$NO$_3$S$_2$, 386.1 (M+H), found 386.3.

c) 5-Methylthio-4-{[3-(phenylmethoxy)phenyl]amino}thiophene-2-carboxamidine: Trimethylaluminum (2.0 M in toluene, 2 mL) was added dropwise over 10 min to a suspension of ammonium chloride (216 mg) in toluene (2 mL), stirred under dry nitrogen at 0° C. After the mixture was stirred at 25° C. for 30 min, when most of the solid had dissolved, this mixture was taken up in a syringe and added to 13 mg (0.03 mmol) of methyl 5-methylthio-4-{[3-(phenylmethoxy)phenyl]amino}thiophene-2-carboxylate. The reaction mixture was heated to reflux in stages and stirred for 2 h 10 min. The cooled mixture was poured in to a vigorously stirred slurry of silica gel (2 g) in chloroform (20 mL). To this suspension methanol (50 mL) was added, the mixture was passed through 1 inch of silica gel in a sintered glass Büchner funnel, washed with methanol (50 mL), and the solvents removed in vacuo. The crude product was purified on a 5 g silica gel SPE column washing first with dichloromethane and then eluting the product off with 10% methanol in dichloromethane. The product was further purified by preparative High Pressure Liquid Chromatography (HPLC) on a Dynamax C18 column, 60 Å pore size, 10 µM particle size, 40 to 100% methanol over 30 min in 0.1% trifluoroacetic acid to give 5.4 mg of the title compound (45%) as a yellow solid. $^1$H-NMR (CD$_3$OD, 400 MHz) δ 7.84 (s, 1H), 7.44–6.60 (m, 9H), 5.08 (s, 2H), 2.48 (s, 3H). Mass spectrum (ESI, m/z): Calcd. for C$_{19}$H$_{19}$N$_3$OS$_2$, 370.1 (M+H), found 370.2.

EXAMPLE 242 a) Methyl 5-methylthio-4-[(3-phenoxyphenyl)amino]thiophene-2-carboxylate: A stirred suspension of 80 mg (0.299 mmol) of methyl 4-bromo-5-methylthiothiophene-2-carboxylate and 72 mg (0.389 mmol, 1.3 eq) of 3-phenoxyaniline (Aldrich, Milwaukee, Wis.) was treated as in Example 241, step (b). Further purification of the product by preparative thin layer chromatography eluting with 10% ethyl acetate in hexane gave 36 mg of the title compound (32%) as a yellow oil. $^1$H-NMR (CDCl$_3$, 400 MHz) δ 7.76 (s, 1H), 7.40–6.65 (m, 9H), 6.26 (s, 1H), 3.89 (s, 3H), 2.40 (s, 3H). Mass spectrum (ESI, m/z): Calcd. for C$_{19}$H$_{17}$NO$_3$S$_2$, 372.1 (M+H), found 372.2.

b) 5-Methylthio-4-[(3-phenoxyphenyl)amino]thiophene-2-carboxamidine: Methyl 5-methylthio-4-[(3-phenoxyphenyl)amino]thiophene-2-carboxylate (36 mg, 0.097 mmol) was treated as in Example 241, step (c), but without HPLC purification to give 30 mg of the title compound (86%) as an orange glass. $^1$H-NMR (CDCl$_3$, 400 MHz) δ 9.28 (s, 2H), 8.11 (s, 2H), 7.99 (s, 1H), 7.34–6.50 (m, 9H), 6.29 (s, 1H), 2.35 (s, 3H). Mass spectrum (ESI, m/z): Calcd. for C$_{18}$H$_{17}$N$_3$OS$_2$, 356.1 (M+H), found 356.2.

EXAMPLE 243 a) 5-Methylthio-4-[(4-phenoxyphenyl)amino]thiophene-2-carboxamidine: A stirred suspension of 80 mg (0.299 mmol) of methyl 4-bromo-5-methylthiothiophene-2-carboxylate and 72 mg (0.389 mmol, 1.3 eq) of 4-phenoxyaniline (Aldrich, Milwaukee, Wis.) was treated as in Example 241, step (b). Further purification of the product by preparative thin layer chromatography eluting with 10% ethyl acetate in hexane gave 53 mg of the title compound (48%) as a yellow oil. $^1$H-NMR (CDCl$_3$, 400 MHz) δ 7.70 (s, 1H), 7.34–7.00 (m, 9H), 6.11 (s, 1H), 3.89 (s, 3H), 2.42 (s, 3H). Mass spectrum (ESI, m/z): Calcd. for C$_{19}$H$_{17}$NO$_3$S$_2$, 372.1 (M+H), found 372.1.

b) 5-Methylthio-4-[(4-phenoxyphenyl)amino]thiophene-2-carboxamidine: Methyl 5-methylthio-4-[(4-phenoxyphenyl)amino]thiophene-2-carboxylate (53 mg, 0.14 mmol) was treated as in Example 241, step (c), but without HPLC purification to give 58 mg of the title compound (quantitative yield) as an orange glass. $^1$H-NMR (CDCl$_3$, 400 MHz) δ 8.89 (s, 2H), 8.59 (s, 2H), 8.00 (s, 1H), 7.25–6.87 (m, 9H), 6.20 (s, 1H), 2.27 (s, 3H). Mass spectrum (ESI, m/z): Calcd. for C$_{18}$H$_{17}$N$_3$OS$_2$, 356.1 (M+H), found 356.2.

EXAMPLE 244 a) Methyl 4-[(2-methoxyphenyl)amino]-5-methylthiothiophene-2-carboxylate: A stirred suspension of 103 mg (0.386 mmol) of methyl 4-bromo-5-methylthiothiophene-2-carboxylate and 57 mg (0.46 mmol, 1.2 eq) of 2-methoxyaniline (Aldrich, Milwaukee, Wis.) was treated in a manner similar to Example 241, step (b) to give 78 mg the title compound (65%) as a yellow oil. $^1$H-NMR (CDCl$_3$, 400 MHz) δ 7.82 (s, 1H), 7.12–6.52 (m, 4H), 6.52 (s, 1H), 3.92 (s, 3H), 3.87 (s, 3H), 2.40 (s, 3H). Mass spectrum (ESI, m/z): Calcd. for C$_{14}$H$_{15}$NO$_3$S$_2$, 310.1 (M+H), found 310.2.

b) 4-[(2-Methoxyphenyl)amino]-5-methylthiothiophene-2-carboxamidine: Methyl 4-[(2-methoxyphenyl)amino]-5-methylthiothiophene-2-carboxylate (78 mg, 0.25 mmol) was treated as in Example 241, step (c), but without HPLC purification to give 75 mg of the title compound (quantitative yield) as an orange glass. $^1$H-NMR (CD$_3$OD, 400 MHz) δ 7.91 (s, 1H), 7.15–6.93 (m, 4H), 3.93 (s, 3H), 2.48 (s, 3H). Mass spectrum (ESI, m/z): Calcd. for C$_{13}$H$_{15}$N$_3$OS$_2$, 294.1 (M+H), found 294.2.

EXAMPLE 245 a) Methyl 4-[(2-methylphenyl)amino]-5-methylthiothiophene-2-carboxylate: A dry mixture of 100 mg (0.374 mmol) of methyl 4-bromo-5-methylthiothiophene-2-carboxylate, 51 mg (14.9 mole %) of tris(dibenzylideneacetone)dipalladium (Lancaster, Pelham, N.H.), 52 mg (22.3 mole %) of racemic-2,2'-bis(diphenylphosphino)-1,1'-binaphthyl (Strem, Newburyport, Mass.), 183 mg of (0.56 mmol, 1.5 eq) cesium carbonate (Aldrich Chemical Co., Milwaukee, Wis.), and 71 µL (0.49 mmol, 1.3 eq) of 2-methylaniline (Aldrich Chemical Co., Milwaukee, Wis.) was added to an oven-dried 1-dram glass vial. This vial was flushed with dry argon in a glove bag, dry toluene (750 µL, 0.5 M) was added, and the assembly was heated at 100° C. for 40 h. To the cooled suspension ethyl acetate (4 mL) was added, the mixture passed through 1 inch of Celite, washed with ethyl acetate (2×4 mL) and the solvents removed in vacuo. Purification by preparative thin-layer chromatography (1:1 dichloromethane/hexanes) gave 67 mg of the title compound (61%) as a yellow oil. $^1$H-NMR (CDCl$_3$, 400 MHz) δ 7.64 (s, 1H), 7.23–6.94 (m, 4H), 5.91 (br s, 1H), 3.88 (s, 3H), 2.41 (s, 3H), 2.31 (s, 3H). Mass spectrum (ESI, m/z): Calcd. for C$_{14}$H$_{15}$NO$_2$S$_2$, 294.1 (M+H), found 294.2.

b) 4-[(2-Methylphenyl)amino]-5-methylthiothiophene-2-carboxamidine: Methyl 4-[(2-methylphenyl)amino]-5-methylthiothiophene-2-carboxylate (67 mg, 0.23 mmol) was treated as in Example 241, step (c), but without HPLC purification to give 20 mg of the title compound (30%) as a yellow glass. $^1$H-NMR (CD$_3$OD; 400 MHz) δ 7.56 (s, 1H), 7.24–6.99 (m, 4H), 2.49 (s, 3H), 2.29 (s, 3H). Mass spectrum (ESI, m/z): Calcd. for C$_{13}$H$_{15}$N$_3$S$_2$, 278.1 (M+H), found 278.2.

EXAMPLE 246 a) Methyl 4-[(3-chlorophenyl)amino]-5-methylthiothiophene-2-carboxylate: A stirred suspension of 80 mg (0.299 mmol) of methyl 4-bromo-5-methylthiothiophene-2-carboxylate and 41 µL (0.389 mol, 1.3 eq) of 3-chloroaniline (Aldrich, Milwaukee, Wis.) was treated in a manner similar to Example 241, step (b) to give 47 mg of the title compound (50%) as a yellow oil. $^1$H-NMR (CDCl$_3$, 400 MHz) δ 7.75 (s, 1H), 7.23–6.89 (m, 4H), 6.10 (s, 1H), 3.89 (s, 3H), 2.42 (s, 3H). Mass spectrum (ESI, m/z): Calcd. for C$_{13}$H$_{12}$NO$_2$S$_2$Cl, 314.0 (M+H), found 314.1.

b) 4-[(3-Chlorophenyl)amino]-5-methylthiothiophene-2-carboxamidine: Methyl 4-[(3-chlorophenyl)amino]-5-methylthiothiophene-2-carboxylate (47 mg, 0.15 mmol) was treated as in Example 241, step (c) to give 33 mg of the title compound (75%) as a light yellow solid. $^1$H-NMR (DMSO-$d_6$, 400 MHz) δ 9.22 (s, 2H), 8.81 (s, 2H), 8.22 (s, 1H), 7.99 (s, 1H), 7.24–6.82 (m, 4H), 2.53 (s, 3H). Mass spectrum (ESI, m/z): Calcd. for $C_{12}H_{12}N_3S_2Cl$, 298.0 (M+H), found 298.3.

EXAMPLE 247 a) Methyl 4-(methylphenylamino)-5-methylthiothiophene-2-carboxylate: A stirred suspension of 100 mg (0.374 mmol) of methyl 4-bromo-5-methylthiothiophene-2-carboxylate and 72 μL (0.487 mmol, 1.3 eq) of N-methylaniline (Aldrich Chemical Co., Milwaukee, Wis.) was treated in a manner similar to Example 245, step (a) to give 23 mg of the title compound (21%) as a yellow oil. $^1$H-NMR (CDCl$_3$, 400 MHz) δ 7.61 (s, 1H), 7.26–6.68 (m, 5H), 3.89 (s, 3H), 3.25 (s, 3H), 2.50 (s, 3H). Mass spectrum (ESI, m/z): Calcd. for $C_{14}H_{15}NO_2S_2$, 294.1 (M+H), found 294.3.

b) 4-(Methylphenylamino)-5-methylthiothiophene-2-carboxamidine: Methyl 4-[(2-methylphenyl)amino]-5-methylthiothiophene-2-carboxylate (23 mg, 0.078 mmol) was treated as in Example 241, step (c), but without HPLC purification to give 5.6 mg of the title compound (26%) as a yellow glass. $^1$H-NMR (CD$_3$OD, 400 MHz) δ 7.83 (s, 1H), 7.24–6.71 (m, 4H), 3.27 (s, 3H), 2.57 (s, 3H). Mass spectrum (ESI, m/z): Calcd. for $C_{13}H_{15}N_3S_2$, 278.1 (M+H), found 278.3.

EXAMPLE 248 a) Methyl 5-methyl-4-(phenylamino)thiophene-2-carboxylate: A stirred suspension of 400 mg (1.7 mmol) methyl 5-methyl-4-bromo-thiophene-2-carboxylate and 192 μL (2.1 mmol, 1.25 eq) of aniline (Aldrich, Milwaukee, Wis.) was treated in a manner similar to Example 241, step (b) to give 66 mg of the title compound (16%) as a brown glass. $^1$H-NMR (DMSO-$d_6$, 400 MHz) δ 7.70 (s, 1H), 7.56 (s, 1H), 7.17 (m, 2H), 6.72 (m, 3H), 3.79 (s, 3H), 2.31 (s, 3H). Mass spectrum (MALDI, gentisic acid matrix, m/z): Calcd. for $C_{13}H_{13}NO_2S$, 248.1 (M+H), found 247.5.

b) 5-Methyl-4-(phenylamino)thiophene-2-carboxamidine: Methyl 4-(methylphenylamino)-5-methylthiothiophene-2-carboxylate (66 mg, 0.27 mmol) was treated as in Example 241, step (c), but without HPLC purification to give 57 mg of the title compound (91%) as a brown glass. $^1$H-NMR (DMSO-$d_6$, 400 MHz) δ 9.17 (s, 2H), 8.85 (s, 2H), 7.98 (s, 1H), 7.85 (s, 1H), 7.21–6.73 (m, 5H), 2.39 (s, 3H). Mass spectrum (ESI, m/z): Calcd. for $C_{12}H_{13}N_3S$, 232.1 (M+H), found 232.2.

EXAMPLE 249 a) Methyl 4-{[4-(dimethylamino)phenyl]amino}-5-methylthiothiophene-2-carboxylate: A stirred suspension of 100 mg (0.267 mmol) methyl 5-methyl-4-bromo-thiophene-2-carboxylate and 66 mg (0.35 mmol, 1.3 eq) of 4-amino-N,N-dimethylaniline (Fluka, Milwaukee, Wis.) was treated in a manner similar to Example 241, step (b), but eluting with 1:1 ethyl acetate/hexane for preparative thin-layer chromatrography purification, to give 86 mg of the title compound (quantitative yield) as an orange glass. $^1$H-NMR (CDCl$_3$, 400 MHz) δ 7.53 (s, 1H), 7.16 and 6.62 (AB quartet, 4H, J=8.9 Hz), 5.99 (s, 1H), 3.86 (s, 3H), 2.94 (s, 6H), 2.39 (s, 3H). Mass spectrum (ESI, m/z): Calcd. for $C_{15}H_{18}N_2O_2S_2$, 323.1 (M+H), found 323.3.

b) 4-{[4-(Dimethylamino)phenyl]amino}-5-methylthiothiophene-2-carboxamidine: Methyl 4-(methylphenylamino)-5-methylthiothiophene-2-carboxylate (86 mg, 0.267 mmol) was treated as in Example 241, step (c), but without HPLC purification. This material was further purified by passing through 1 inch of basic alumina and eluting with 10% methanol in dichloromethane (15 mL) to give 62 mg of the title compound (76%) as a brown glass. $^1$H-NMR (DMSO-$d_6$, 400 MHz) δ 8.95 (s, 4H), 7.75 (s, 1H), 7.56 (s, 1H), 6.97 and 6.72 (AB quartet, 4H, J=8.9 Hz), 2.83 (s, 6H), 2.44 (s, 3H). Mass spectrum (ESI, m/z): Calcd. for $C_{14}H_{18}N_4S_2$, 307.1 (M+H), found 307.3.

EXAMPLE 250

4-[(4-Ethylphenyl)amino]-5-methylthiothiophene-2-carboxamidine hydrochloride a) Methyl 4-[(4-ethylphenyl)amino]-5-methylthiothiophene-2-carboxylate: To an oven-dried glass vial with stir bar was added a mixture of 100 mg (0.374 mmol) of methyl 4-bromo-5-methylthiothiophene-2-carboxylate (as prepared in Example 241, step (a)), 5.8 mg (6.9 mol %) of palladium (II) acetate, 21.7 mg (9.3 mol %) of racemic-2,2'-bis(diphenylphosphino)-1,1'-binaphthyl, 171.5 mg (0.526 mmol) of cesium carbonate and 59 mg (0.487 mmol) of 4-ethylaniline. The vial was transferred to a glove bag, flushed with dry argon and anhydrous toluene (749 μL) was added. The vial was capped with a Teflon-lined screw cap and heated at 100° C. for 48 h. The cooled suspension was filtered (Celite) washing with ethyl acetate (2×2 mL), and the solvents removed in vacuo. The resulting residue was purified on 1 mm silica prep plates eluting with 40% methylene chloride-hexanes to afford 14 mg (12%) of methyl 4-[(4-ethylphenyl)amino]-5 -methylthiothiophene-2-carboxylate as a pale yellow resin which was used directly in the following step.

b) 4-[(4-Ethylphenyl)amino]-5-methylthiothiophene-2-carboxamidine hydrochloride: Trimethylaluminum (2.0 M in toluene, 0.182 mL, 0.363 mmol) was added dropwise to a suspension of ammonium chloride (19 mg, 0.363 mmol) in anhydrous toluene (1 mL) under Ar at 0° C. The mixture was stirred at 25° C. for 30 min and then 14 mg (0.036 mmol) of methyl 4-[(4-ethylphenyl)amino]-5-methylthiothiophene-2-carboxylate (as prepared in previous step) was added. The reaction mixture was heated slowly to 100 C. and stirred for 4 h. The cooled mixture was added to a vigorously stirred slurry of silica gel (1.3 g) in chloroform (20 mL). The suspension was filtered (silica) washing with 50% MeOH-CH$_2$Cl$_2$ (2×50 mL). The washings were concentrated and the resulting residue was purified on a 0.5 mm silica prep plate eluting with a 10% MeOH-CH$_2$Cl$_2$ to afford 8 mg (67%) of 4-[(4-ethylphenyl)amino]-5-methylthiothiophene-2-carboxamidine hydrochloride as a yellow oil. $^1$H-NMR (CD$_3$OD, 400 MHz) δ 7.84 (s, 1H), 7.14 (d, 2H, 8 Hz), 7.01 (d, 2H, 8 Hz), 2.55 (q, 2H, 65.5 Hz), 2.48 (s, 3H), 1.23 (t, 3H, 15.2 Hz). Mass spectrum (ESI, m/z): Calcd. for $C_{14}H_{17}N_3S_2$, 292.1 (M+H), found 292.5.

EXAMPLE 251

5-Methylthio-4-{[4-(phenylmethoxy)phenyl]amino}thiophene-2-carboxamidine hydrochloride a) Methyl 5-methylthio-4-{[4-(phenylmethoxy)phenyl]amino}thiophene-2-carboxylate: The same procedure as in Example 250, step a was followed using 100 mg (0.374 mmol) of methyl 4-bromo-5-methylthiothiophene-2-carboxylate (as prepared in Example 241, step (a)), 5.5 mg (6.5 mol %) of palladium (II) acetate, 23.6 mg (10.1 mol %)

of racemic-2,2'-bis(diphenylphosphino)-1,1'-binaphthyl, 194 mg (0.595 mmol) of cesium carbonate, 97.3 mg (0.488 mmol) of 4-benzyloxyaniline and 749 μL of toluene, and chromatographed as before using 40% $CH_2Cl_2$-hexane to afford 7 mg (5%) of methyl 5-methylthio-4-{[4-(phenylmethoxy)phenyl]amino}thiophene-2-carboxylate as a yellow resin which was used directly in the following step.

b) 5-Methylthio-4-{[4-(phenylmethoxy)phenyl]amino}thiophene-2-carboxamidine hydrochloride: The same procedure as in Example 250, step (b) was followed using 7 mg (0.018 mmol) of methyl 5-methylthio-4-{[4-(phenylmethoxy)phenyl]amino}thiophene-2-carboxylate (as prepared in previous step), 0.091 mL of trimethylaluminum (2.0 M in toluene, 0.182 mmol), 10 mg of ammonium chloride (0.182 mmol) and 1 mL of toluene, and purified on a 0.5 mm silica prep plate eluting with 10% MeOH-$CH_2Cl_2$ to afford 3 mg (41%) of 5-methylthio-4-{[4-(phenylmethoxy)phenyl]amino}thiophene-2-carboxamidine hydrochloride as a yellow oil. $^1$H-NMR ($CD_3OD$, 400 MHz) δ 7.72 (s, 1H), 7.45 (d, 2H, 7 Hz), 7.39 (t, 2H, 9 Hz), 7.37 (d, 1H, 12 Hz), 7.06 (d, 2H, 12Hz), 6.97 (d, 2H, 12Hz), 5.08 (s, 2H), 2.46 (s, 3H). Mass spectrum (ESI, m/z): Calcd. for $C_{19}H_{19}N_3OS_2$, 370.1 (M+H), found 370.3.

EXAMPLE 252

5-Methylthio-4-{[4-(phenylamino)phenyl]amino}thiophene-2-carboxamidine hydrochloride a) Methyl 5-methylthio-4-{[4-(phenylamino)phenyl]amino}thiophene-2-carboxylate: The same procedure as in Example 250, step (a) was followed using 100 mg (0.374 mmol) of methyl 4-bromo-5-methylthiothiophene-2-carboxylate (as prepared in Example 241, step a), 5.5 mg (6.5 mol %) of palladium (II) acetate, 21.6 mg (9.3 mol %) of racemic-2,2'-bis(diphenylphosphino)-1,1'-binaphthyl, 173.7 mg (0.533 mmol) of cesium carbonate, 92.3 mg (0.500 mmol) of N-phenyl-1,4-phenylenediamine, and 749 μL of toluene, and chromatographed as before using 40% $CH_2Cl_2$-hexane to afford 58 mg (42%) of methyl 5-methylthio-4-{[4-(phenylamino)phenyl]amino}thiophene-2-carboxylate as a brown solid. $^1$H-NMR (DMSO-d6, 400 MHz) δ 7.85 (s, 1H), 7.61 (s, 1H), 7.48 (s, 1H), 7.14 (t, 2H, 16 Hz), 6.99 (d, 2H, 16 Hz), 6.90 (q, 4H, 44 Hz), 6.70 (t, 2H, 4 Hz), 3.77 (s, 3H), 2.43 (s, 3H).

b) 5-Methylthio-4-{[4-(phenylamino)phenyl]amino}thiophene-2-carboxamidine hydrochloride: The same procedure as in Example 250, step (b) was followed using 58 mg (0.156 mmol) of methyl 5-methylthio-4-{[4-(phenylamino)phenyl]amino}thiophene-2-carboxylate (as prepared in previous step), 0.783 mL of trimethylaluminum (2.0 M in toluene, 1.56 mmol), 84 mg of ammonium chloride (1.56 mmol) and 10 mL of toluene, and purified by passing through a pad of silica eluting with 50% MeOH-$CH_2Cl_2$ to afford 50 mg (75%) of the 5-methylthio-4-{[4-(phenylamino)phenyl]amino}thiophene-2-carboxamidine hydrochloride as a brown solid. $^1$H-NMR (DMSO-$d_6$, 400 MHz) δ 7.91 (d, 2H, 12 Hz), 7.78 (s, 1H), 7.20 (t, 3H, 12 Hz), 7.04–6.94 (m, 5H), 6.71 (m, 1H), 2.47 (s, 3H). Mass spectrum (ESI, m/z): Calcd. for $C_{18}H_{18}N_4S_2$, 355.1 (M+H), found 355.4.

EXAMPLE 253

4-[(4-Methoxyphenyl)amino]-5-methylthiothiophene-2-carboxamidine hydrochloride a) Methyl 4-[(4-methoxyphenyl)amino]-5-methylthiothiophene-2-carboxylate: To an oven-dried glass vial with stir bar was added a mixture of 120 mg (0.449 mmol) of methyl 4-bromo-5-methylthiothiophene-2-carboxylate (as prepared in Example 241, step (a)), 7.1 mg (7 mol %) of palladium (II) acetate, 29.4 mg (10.5 mol %) of racemic-2,2'-bis(diphenylphosphino)-1,1'-binaphthyl, 205 mg (0.629 mmol) of cesium carbonate and 69.1 mg (0.561 mmol) of p-anisidine. The vial was transferred to a glove bag, flushed with dry argon and anhydrous toluene (0.9 mL) was added. The vial was capped with a Teflon-lined screw cap and heated at 100° C. for 48 h. To the cooled suspension was added ethyl acetate (4 mL), the mixture filtered (Celite) washing with ethyl acetate (2×2 mL), and the solvents removed in vacuo. The resulting residue was purified by silica gel preparative thin layer chromatography (40% $CH_2Cl_2$ in hexane) to afford 83 mg (60%) of the title compound as a yellow oil. $^1$H-NMR ($CDCl_3$, 400 MHz) δ 2.39 (s, 3H), 3.82 (s, 3H), 3.87 (s, 3H), 6.03 (s, 1H), 6.89 (m, 2H), 7.03 (m, 2H), 7.58 (s, 1H).

b) 4-[(4-Methoxyphenyl)amino]-5-methylthiothiophene-2-carboxamidine hydrochloride: Trimethylaluminum (2.0 M in toluene, 2 mL, 4 mmol) was added dropwise to a suspension of ammonium chloride (216 mg, 4 mmol) in anhydrous toluene (1 mL) under Ar at room temperature. The mixture was stirred at 25° C. for 30 min and then 80 mg (0.259 mmol) of methyl 4-[(4-methoxyphenyl)amino]-5-methylthiothiophene-2-carboxylate (as prepared in previous step) in anhydrous toluene (1 mL) was added. The reaction mixture was heated slowly to 100° C. and stirred for 2.5 h. The cooled mixture was added to a vigorously stirred slurry of silica gel (3 g) in chloroform (20 mL). The suspension was filtered washing with MeOH (4×5 mL) and 50% MeOH-$CH_2Cl_2$ (4×5 mL). The combined washings were concentrated and the resulting residue was purified on a 2-g silica SPE column with 5% MeOH-$CH_2Cl_2$ to afford 50 mg (59%) of the title compound as an orange solid. $^1$H-NMR (DMSO-$d_6$; 400 MHz) δ 2.44 (s, 3H), 3.69 (s, 3H), 6.84 (m, 2H), 6.98 (m, 2H), 7.73 (s, 1H), 7.84 (s, 1H), 9.01 (br s, 2H), 9.24 (br s, 2H). Mass spectrum (ESI, m/z): Calcd. for $C_{13}H_{15}N_3OS_2$, 294.1 (M+H), found 294.2.

EXAMPLE 254

4-[(3-Fluoro-4-methylphenyl)amino]-5-methylthiothiophene-2-carboxamidine a) Methyl 4-[(3-fluoro-4-methylphenyl)amino]-5-methylthiothiophene-2-carboxylate: To an oven-dried glass vial with stir bar was added a mixture of 120 mg (0.449 mmol) of methyl 4-bromo-5-methylthiothiophene-2-carboxylate (as prepared in Example 241, step (a), 41 mg (10 mol %) of tris-(dibenzylidineacetone)dipalladium, 42 mg (15 mol %) of racemic-2,2'-bis(diphenylphosphino)-1,1'-binaphthyl, 205 mg (0.629 mmol) of cesium carbonate and 70 mg (0.56 mmol) of 3-fluoro-4-methylaniline. The vial was transferred to a glove bag, flushed with dry argon and anhydrous toluene (0.9 mL) was added. The vial was capped with a Teflon-lined screw cap and heated at 100° C. for 48 h. To the cooled suspension was added ethyl acetate (4 mL), the mixture filtered (Celite) washing with ethyl acetate (2×2 mL), and the solvents removed in vacuo. The resulting residue was purified by silica gel preparative thin layer chromatography (10% $Et_2O$ in hexane) to afford 103 mg (78%) of the title compound as a yellow oil. $^1$H-NMR ($CDCl_3$, 400 MHz) δ 2.22 (d, 3H, J=1.6 Hz), 2.40 (s, 3H), 3.89 (s, 3H), 6.09 (s, 1H), 6.68 (m, 1H), 6.71 (s, 1H), 7.08 (m, 1H), 7.72 (s, 1H).

b) 4-[(3-Fluoro-4-methylphenyl)amino]-5-methylthiothiophene-2-carboxamidine: The same procedure as in Example 253, step (b) was followed using 103 mg (0.349 mmol) of methyl 4-[(3-fluoro-4-methylphenyl) amino]-5-methylthiothiophene-2-carboxylate (as prepared in previous step), 2 mL of trimethylaluminum (2.0 M in toluene, 4 mmol), 216 mg of ammonium chloride (4 mmol) and 2 mL of toluene, and purified on a 2-g silica SPE column with 5% MeOH-CH$_2$Cl$_2$ to afford 45 mg (44%) of the title compound as a yellow foam $^1$H-NMR (DMSO-d$_6$; 400 MHz) δ 2.13 (s, 3H), 2.50 (s, 3H ), 6.70 (m, 2H), 7.10 (m, 1H), 7.98 (s, 1H), 8.09 (s, 1H), 9.16 (br s, 4H). Mass spectrum (ESI, m/z): Calcd. for C$_{13}$H$_{14}$FN$_3$S$_2$, 296.1 (M+H), found 296.2.

EXAMPLE 255

4-(Indan-5-ylamino)-5-methylthiothiophene-2-carboxamidine a) Methyl 4-(indan-5-ylamino)-5-methylthiothiophene-2-carboxylate: The same procedure as in Example 254, step (a) was followed using 120 mg (0.449 mmol) of methyl 4-bromo-5-methylthiothiophene-2-carboxylate (as prepared in Example 241, step (a), 41 mg (10 mol %) of tris (dibenzylidineacetone)dipalladium, 42 mg (15 mol %) of racemic-2,2'-bis(diphenylphosphino)-1,1'-binaphthyl, 205 mg (0.629 mmol) of cesium carbonate and 74.8 mg (0.56 mmol) of 5-aminoindan in 900 μL of toluene, and chromatographed as before using 40% CH$_2$Cl$_2$-hexane to afford 100 mg (73%) of the title compound as a yellow resin. $^1$H-NMR (CDCl$_3$, 400 MHz) δ 2.05–2.12 (m, 2H), 2.85–2.90 (m, 4H), 3.86 (s, 3H), 6.09 (s, 1H), 6.82 (d, 1H, J=8.0 Hz), 6.93 (s, 1H), 7.14 (d, 1H, J=8.0 Hz), 7.70 (s, 1H).

b) 4-(Indan-5-ylamino)-5-methylthiothiophene-2-carboxamidine: The same procedure as in Example 253, step (b) was followed using 100 mg (0.33 mmol) of methyl 4-(indan-5-ylamino)-5-methylthiothiophene-2-carboxylate (as prepared in previous step), 2 mL of trimethylaluminum (2.0 M in toluene, 4 mmol), 216 mg of ammonium chloride (4 mmol) and 2 mL of toluene, and purified on a 2-g silica SPE column with 5% MeOH-CH$_2$Cl$_2$ to afford 65 mg (65%) of the title compound as a yellow foam. $^1$H-NMR (DMSO-d$_6$, 400 MHz) δ 1.99 (m, 2H), 2.48 (s, 3H), 2.78 (m, 4H), 6.77 (dd, 1H, J=8.0, 1.78 Hz), 6.86 (s, 1H), 7.08 (d, 1H, J=8.1 Hz), 7.80 (s, 1H), 7.94 (s, 1H), 9.13 (br s, 4H). Mass spectrum (ESI, m/z): Calcd. for C$_{15}$H$_{17}$N$_3$S$_2$, 304.1 (M+H), found 304.3.

EXAMPLE 256

4-[(9-Ethylcarbazol-3-yl)amino]-5-methylthiothiophene-2-carboxamidine a) Methyl 4-[(9-ethylcarbazol-3-yl)amino]-5-methylthiothiophene-2-carboxylate: The same procedure as in Example 254, step (a) was followed using 120 mg (0.449 mmol) of methyl 4-bromo-5-methylthiothiophene-2-carboxylate (as prepared in Example 241, step (a), 41 mg (10 mol %) of tris-(dibenzylidineacetone)dipalladium, 42 mg (15 mol %) of racemic-2,2'-bis(diphenylphosphino)-1,1'-binaphthyl, 205 mg (0.629 mmol) of cesium carbonate and 118 mg (0.56 mmol) of 3-amino-9-ethylcarbazole in 900 μL of toluene, and chromatographed as before using 40% CH$_2$Cl$_2$-hexane to afford 80 mg (47%) of the title compound as a yellow resin. $^1$H-NMR (CDCl$_3$, 400 MHz) δ 1.46 (t, 3H, J=7.2 Hz), 2.44 (s, 3H), 3.85 (s, 3H), 4.39 (q, 2H, J=7.2 Hz), 6.25 (s, 1H), 7.24 (m, 1H), 7.28 (s, 1H), 7.40 (m, 2H), 7.49 (m, 1H), 7.61 (s, 1H), 7.83 (d, 1H, J=2.1 Hz), 8.06 (d, 1H, J=7.8Hz).

b) 4-[(9-Ethylcarbazol-3-yl)amino]-5-methylthiothiophene-2-carboxamidine: The same procedure as in Example 253, step (b) was followed using 80 mg (0.21 mmol) of methyl 4-[(9-ethylcarbazol-3-yl)amino]-5-methylthiothiophene-2-carboxylate (as prepared in previous step), 2 mL of trimethylaluminum (2.0 M in toluene, 4 mmol), 216 mg of ammonium chloride (4 mmol) and 2 mL of toluene, and purified on a 2-g silica SPE column with 5% MeOH-CH$_2$Cl$_2$ to afford 56 mg (70%) of the title compound as a yellow foam. $^1$H-NMR (DMSO-d$_6$, 400 MHz) δ 1.31 (t, 3H, J=7.0 Hz), 2.50 (s, 3H), 4.42 (q, 2H, J=7.0 Hz), 7.14 (m, 1H), 7.27 (dd, 1H, J=8.7, 2.1 Hz), 7.43 (m, 1H), 7.56 (m, 2H), 7.82 (d, 1H, J=2.0 Hz), 7.87 (s, 1H), 7.92 (s, 1H), 8.10 (d, 1H, J=7.7 Hz), 9.11 (br s, 4H). Mass spectrum (ESI, m/z): Calcd. for C$_{20}$H$_{20}$N$_4$S$_2$, 381.1 (M+H), found 381.3.

EXAMPLES 257 AND 258

5-Methylthio-4-{[(4-phenylphenyl)sulfonyl] amino}thiophene-2-carboxamidine trifluoroacetate 4-{Bis[(4-phenylphenyl)sulfonyl]amino}-5-methylthiothiophene-2-carboxamidine trifluoroacetate a) Methyl 5-methylthio-4-[(phenylsulfonyl)amino] thiophene-2-carboxylate and methyl 4-{bis[(4-phenylphenyl)sulfonyl]amino}-5-methylthio-thiophene-2-carboxylate: To an oven-dried round bottom flask with stir bar was added a mixture of 50 mg (0.24 mmol) of methyl 4-amino-5-methylthiothiophene-2-carboxylate (as prepared in Example 202), 68 mg (0.27 mmol) of 4-biphenylsulfonyl chloride and 50 mg (0.49 mmol) of 4-dimethylaminopyridine. The flask was flushed with dry argon and anhydrous acetonitrile (3 mL) was added. The reaction was refluxed for 3 hours and then the solvent was removed in vacuo. The crude of the reaction was extracted with ethyl acetate (2×25 mL) and 1N HCl (50 mL). The organic layer was collected, dried (Na$_2$SO$_4$), filtered and concentrated under vacuum to yield a foam that was chromatographed on silica with 30% ethyl ether-hexane to obtain 143 mg of a mixture of methyl 5-methylthio-4-[(phenylsulfonyl)amino]thiophene-2-carboxylate and methyl 4-{bis[(4-phenylphenyl)-sulfonyl]aamino}-5-methylthiothiophene-2-carboxylate. This mixture was used in the next reaction without further purification. Mass spectrum (ESI, m/z): Calcd. for C$_{19}$H$_{17}$NO$_4$S$_3$, 420.0 (M+H), found 419.7.

b) 5-Methylthio-4-{[(4-phenylphenyl)sulfonyl] amino}thiophene-2-carboxamidine trifluoroacetate and 4-{bis[(4-phenylphenyl)sulfonyl]amino}-5-methylthiothiophene-2-carboxamidine trifluoroacetate: Trimethylaluminum (2.0 M in toluene, 1.36 mL, 2.72 mmol) was added dropwise to a suspension of ammonium chloride (155 mg, 2.89 mmol) in anhydrous toluene (2.0 mL) under Ar at 0° C. The mixture was stirred at 25° C. for 30 min and then 143 mg of a mixture of methyl 5-methylthio-4-[(phenylsulfonyl)amino]thiophene-2-carboxylate and methyl 4-{bis[(4-phenylphenyl)sulfonyl]amino}-5-methylthiothiophene-2-carboxylate (as prepared in previous step) in anhydrous toluene (2.0 mL) was added. The reaction mixture was heated slowly to 100° C. and stirred for 4 h. The cooled mixture was added to a vigorously stirred slurry of silica gel (3 g) in chloroform (15 mL). The suspension was filtered (Celite) washing with 25% MeOH-CH$_2$Cl$_2$ (2×5 mL), 50% MeOH-CH$_2$Cl$_2$ (2×5 mL) and 75% MeOH-CH$_2$Cl$_2$ (2×5 mL). The combined washings were concentrated and the resulting residue was purified on a 10-g silica SPE column with a gradient of 10–15% MeOH-CH$_2$Cl$_2$ saturated with ammonia to afford 66 mg of a mixture of the title compounds as a yellow solid. This mixture was chromatographed by preparative reverse phase HPLC performed with a Rainin SD-1 Dynamax system and a 2-in. C18 reverse phase Dynamax 60A column using a gradient of 30% MeOH/0.1% TFA in water to 100% MeOH and a flow rate of 50 mL/min. to yield 15 mg 5-methylthio-4-{[(4-phenylphenyl)sulfonyl]amino}thiophene-2-carboxamidine trifluoroacetate; mass spectrum (ESI, m/z): Calcd. for C$_{18}$H$_{17}$N$_3$O$_2$S$_3$, 404.0 (M+H), found 404.1; and 11 mg of 4-{bis[(4-phenylphenyl)sulfonyl]amino}-5-methylthiothiophene-2-carboxamidine trifluoroacetate. Mass spectrum (ESI, m/z): Calcd. for C$_{30}$H$_{25}$N$_3$O$_4$S$_4$, 619.8 (M+H), found 620.2.

EXAMPLES 259 TO 282

The same methods as for Examples 257 and 258 were used to synthesize the following compounds:

| Examp | Reagent | Compound | Formula | Mass spec, ESI, m/z Calc, M + H | Found |
|---|---|---|---|---|---|
| 259 | 1-Naphthalenesulfonyl chloride | 5-Methylthio-4-[(2-naphthylsulfonyl)-amino]thiophene-2-carboxamidine | C16H15N3O2S3 | 378.0 | 378.1 |
| 260 | 1-Naphthalenesulfonyl chloride | 4-[Bis(2-naphthylsulfonyl)amino]-5-methylthiothiophene-2-carboxamidine | C26H21N3O4S4 | 568.0 | 568.1 |
| 261 | 7-Bromonaphthalene sulfonyl chloride | 4-{[(6-Bromo(2-naphthyl))sulfonyl]amino}-5-methylthiothiophene-2-carboxamidine | C16H14BrN3O2S3 | 455.9 | * |
| 262 | 7-Bromonaphthalene sulfonyl chloride | 4-{Bis[(6-bromo(2-naphthyl))sulfonyl]amino}-5-methylthiothiophene-2-carboxamidine | C26H19Br2N3O4S4 | 723.9 | * |
| 263 | 2-Naphthalenesulfonyl chloride | 5-Methylthio-4-[(naphthylsulfonyl)-amino]thiophene-2-carboxamidine | C16H15N3O2S3 | 378.0 | 378.1 |
| 264 | 2-Naphthalenesulfonyl chloride | 4-[Bis(naphthylsulfonyl)amino-5-methylthiothiophene-2-carboxamidine | C26H21N3O4S4 | 568.7 | 568.3 |
| 265 | o-Toluenesulfonyl chloride | 4-{[(2-Methylphenyl)sulfonyl]amino}-5-methylthiothiophene-2-carboxamidine | C13H15N3O2S3 | 342.4 | 342.1 |
| 266 | o-Toluenesulfonyl chloride | 4-{Bis[(2-methylphenyl)sulfonyl]amino}-5-methylthiothiophene-2-carboxamidine | C20H21N3O4S4 | 496.6 | 496.1 |
| 267 | m-Toluenesulfonyl chloride | 4-{[(3-Methylphenyl)sulfonyl]amino}-5-methylthiothiophene-2-carboxamidine | C13H15N3O2S3 | 342.0 | 342.1 |
| 268 | m-Toluenesulfonyl chloride | 4-{Bis[(3-methylphenyl)sulfonyl]amino}-5-methylthiothiophene-2-carboxamidine | C20H21N3O4S4 | 496.6 | 496.0 |
| 269 | p-Toluenesulfonyl chloride | 4-{[(4-Methylphenyl)sulfonyl]amino}-5-methylthiothiophene-2-carboxamidine | C13H15N3O2S3 | 342.0 | 342.1 |
| 270 | p-Toluenesulfonyl chloride | 4-{Bis[(4-methylphenyl)sulfonyl]amino}-5-methylthiothiophene-2-carboxamidine | C20H21N3O4S4 | 496.6 | 496.1 |
| 271 | α-Toluenesulfonyl chloride | 5-Methylthio-4-{[benzylsulfonyl]amino}-thiophene-2-carboxamidine | C13H15N3O2S3 | 342.0 | 342.1 |
| 272 | 4-Methoxybenzene-sulfonyl chloride | 4-{[(4-Methoxyphenyl)sulfonyl]amino}-5-methylthiothiophene-2-carboxamidine | C13H15N3O3S3 | 358.0 | 358.1 |
| 273 | 4-Methoxybenzene-sulfonyl chloride | 4-{Bis[(4-methoxyphenyl)sulfonyl]amino}-5-methylthiothiophene-2-carboxamidine | C20H21N3O6S4 | 528.0 | 528.0 |
| 274 | 4-Iodobenzenesulfonyl chloride | 4-{[(4-Iodophenyl)sulfonyl]amino}-5-methylthiothiophene-2-carboxamidine | C12H12IN3O2S3 | 453.9 | 454.0 |
| 275 | 3,4-Dimethoxybenzene sulfonyl chloride | 4-{[(3,4-Dimethoxyphenyl)sulfonyl]amino}-5-methylthiothiophene-2-carboxamidine | C14H17N3O4S3 | 388.0 | 388.1 |
| 276 | 3,4-Dimethoxybenzene sulfonyl chloride | 4-{bis[(3,4-Dimethoxyphenyl)sulfonyl]amino}-5-methylthiothiophene-2-carboxamidine | C22H25N3O8S4 | 588.0 | 588.1 |
| 277 | 2-Chlorobenzenesulfonyl chloride | 4-{[(2-Chlorophenyl)sulfonyl]amino}-5-methylthiothiophene-2-carboxamidine | C12H12ClN3O2S3 | 361.9 | 362.1 |
| 278 | 3-Chlorobenzene-sulfonyl chloride | 4-{[(3-Chlorophenyl)sulfonyl]amino}-5-methylthiothiophene-2-carboxamidine | C12H12ClN3O2S3 | 361.9 | 362.1 |
| 279 | 3-Chlorobenzene-sulfonyl chloride | 4-{Bis[(3-chlorophenyl)sulfonyl]amino}-5-methylthiothiophene-2-carboxamidine | C18H15Cl2N3O4S4 | 535.9 | 537.9 |
| 280 | 4-Chlorobenzene-sulfonyl chloride | 4-{[(4-Chlorophenyl)sulfonyl]amino}-5-methylthiothiophene-2-carboxamidine | C12H12ClN3O2S3 | 361.9 | 362.1 |
| 281 | 4-Chlorobenzene-sulfonyl chloride | 4-{Bis[(4-chlorophenyl)sulfonyl]amino}-5-methylthiothiophene-2-carboxamidine | C18H15Cl2N3O4S4 | 535.9 | * |

-continued

| Examp | Reagent | Compound | Formula | Calc, M + H | Found |
|---|---|---|---|---|---|
| 282 | Benzenesulfonyl chloride | 5-Methylthio-4-[(phenylsulfonyl)amino]-thiophene-2-carboxaimidine | C12H13N3O2S3 | 328.0 | 328.1 |
| 283 | Benzenesulfonyl chloride | 4-[Bis(phenylsulfonyl)amino]-5-methylthiothiophene-2-carboxamidine | C18H17N3O4S4 | 468.0 | 467.9 |
| 284 | 4-tert-Butylbenzene-sulfonyl chloride | 4-({[4-(Tert-butyl)phenyl]sulfonyl}amino)-5-methylthiothiophene-2-carboxamidine | C16H21N3O2S3 | 384.0 | 384.2 |
| 285 | 4-tert-Butylbenzene-sulfonyl chloride | 4-(Bis{[4-(tert-butyl)phenyl]sulfonyl}amino)-5-methylthiothiophene-2-carboxamidine | C26H33N3O4S4 | 580.1 | 580.2 |
| 286 | Trans-β-styrene sulfonyl chloride | 4-{[((1E)-2-Phenylvinyl)sulfonyl]amino}-5-methyithiothiophene-2-carboxamidine | C14H15N3O2S3 | 354.0 | * |
| 287 | 4-benzensulfonyl-thiophene-2-sulfonyl chloride | 5-Methylthio-4-({[4-(phenylsulfonyl)(2-thienyl)]sulfonyl}amino)thiophene-2-carboxamidine | C16H15N3O4S5 | 473.9 | 474.1 |

* Mass spectral data inconclusive.

EXAMPLE 288

5-Methylthio-4-phenoxythiophene-2-carboxamidine trifluoroacetate a) Methyl 5-methylthio-4-phenoxythiophene-2-carboxylate: To an oven-dried round bottom flask with stir bar was added a mixture of 100 mg (0.37 mmol) of methyl 4-bromo-5-methylthiothiophene-2-carboxylate (as prepared in Example 241), 20 mg of Cu (0) (Brewster, R. Q. and Groening T., Organic Syntheses, Vol. II, Note 1, pp 445–446) and 42 mg (0.46 mmol) of phenol. The flask was flushed with dry argon and anhydrous tetrahydrofuran (5 mL) was added. The reaction was refluxed for 48 hours and then the solvent was removed in vacuo. The resulting residue was purified on a 10-g silica SPE column with a gradient of 50–100% $CH_2Cl_2$-hexane to yield 48 mg of methyl 5-methylthio-4-phenoxythiophene-2-carboxylate (37%). $^1$H-NMR (CDCl$_3$, 400 MHz) δ 7.39 (s, 1H), 7.32 (m, 2H), 7.09 (m, 2H), 6.97 (d, 1H, J=8.4 Hz), 3.86 (s, 3H) and 2.49 (s, 3H).

b) 5-Methylthio-4-phenoxythiophene-2-carboxamidine trifluoroacetate: The same procedure as in Example 257, step (b) was followed using 48.0 mg (0.17 mmol) of methyl 5-methylthio-4-phenoxythiophene-2-carboxylate (as prepared in the step before), 78 mg of ammonium chloride (1.5 mmol), 0.68 ml of trimethylaluminum (2.0 M in toluene, 1.3 mmol) and 3 ml of anhydrous toluene and chromatographed as before using preparative reverse phase HPLC performed with a Rainin SD-1 Dynamax system and a 2-in. C18 reverse phase Dynamax 60A column using a gradient of 30% MeOH/0.1% TFA in water to 100% MeOH and a flow rate of 50 mL/min. $^1$H-NMR (CD$_3$OD, 400 MHz) δ 7.66 (s, 1H), 7.39 (t, 2H, J=7.5 Hz), 7.17 (t, 2H, J=7.4Hz), 7.02 (d, 1H, J=7.7 Hz) and 2.58 (s, 3H). Mass spectrum (ESI, m/z): Calcd. $C_{12}H_{12}N_2OS_2$, 265.0 (M+H), found 262.2.

EXAMPLE 289

5-Methylthio-4-(phenylsulfonyl)thiophene-2-carboxamidine trifluoroacetate a) 4-Bromo-5-methylthiothiophene-2-carboxylic acid: To 1.0 g (3.7 mmol) of methyl 4-bromo-5-methylthiothiophene-2-carboxylate (as prepared in Example 241, step (a) dissolved in 25 ml of MeOH was added 450 mg of NaOH dissolved in 10 ml of H$_2$O. The reaction was stirred for 5 hours at room temperature, and then the solvents were removed under vacuum. The residue of the reaction was extracted with ethyl acetate (2×50 mL) and 1N HCl. The organic layer was collected, dried (Na$_2$SO$_4$), filtered and concentrated under vacuum to yield 833 mg (89%) of 4-bromo-5-methylthiothiophene-2-carboxylic acid as a white solid.

b) 5-Methylthio-4-(phenylsulfonyl)thiophene-2-carboxylic acid: To an oven-dried round bottom flask with stir bar was added 100 mg (0.39 mmol) 4-bromo-5-methylthiothiophene-2-carboxylic acid (as prepared in Example before). The flask was flushed with dry argon and anhydrous tetrahydrofuran (3 mL) was added. Then the solution was cooled at −78° C. before adding 511 μL of tert-butyl lithium (0.87 mmol, 1.7 M in tetrahydrofuran). The mixture was stirred for a period of 45 minutes and 77 mg of benzenesulfonyl flouride (0.39 mmol) was added and the reaction was allowed to rise to room temperature. The reaction was stirred for 12 hours and then quenched carefully with H$_2$O. The solvents were removed under vacuum and the residue of the reaction was extracted with ethyl acetate (2×50 ml) and 1N HCl. The organic layer was collected, dried (Na$_2$SO$_4$), filtered and concentrated under vacuum to yield 130 mg of a solid. This solid was used in the next step without further purification.

c) Methyl 5-methylthio-4-(phenylsulfonyl)thiophene-2-carboxylate: To a solution of 25 mg of the mixture from the previous step dissolved in 3 mL of MeOH was added dropwise 397 μL of trimethylsilyldiazomethane (0.79 mmol, 2 M solution in hexanes) and the reaction was stirred for a period of 1 hour. The solvents were removed under vacuum. The resulting residue was purified on a 10-g silica SPE column with a gradient of 50–100% ethyl acetate-hexane to yield 13.8 mg of methyl 5-methylthio-4-(phenylsulfonyl)thiophene-2-carboxylate. Mass spectrum (ESI, m/z): Calcd. $C_{13}H_{12}O_4S_3$, 329.0 (M+H), found 329.0.

d) 5-Methylthio-4-(phenylsulfonyl)thiophene-2-carboxamidine trifluoroacetate: The same procedure as in Example 257, step (b) was followed using 13.8 mg (0.044 mmol) of methyl 5-methylthio-4-(phenylsulfonyl)

thiophene-2-carboxylate (as prepared in the step before), 20 mg of ammonium chloride (0.376 mmol), 0.176 ml of trimethylaluminum (2.0 M in toluene, 0.353 mmol) and 3 ml of anhydrous toluene and chromatographed as before by preparative reverse phase HPLC performed with a Rainin SD-1 Dynamax system and a 2-in. C18 reverse phase Dynamax 60A column using a gradient of 30% MeOH/0.1% TFA in water to 100% MeOH and a flow rate of 50 mL/min to yield 2.3 mg of 5-methylthio-4-(phenylsulfonyl) thiophene-2-carboxamidine. $^1$H-NMR (CD$_3$OD, 400 MHz) δ 8.42 (s, 1H), 8.04 (m, 2H), 7.70 (m, 2H), 7.62 (m, 1H) and 2.70 (s, 3H). Mass spectrum (ESI, m/z): Calcd. $C_{12}H_{12}N_2O_2S_3$, 313.0 (M+H), found 313.2.

EXAMPLE 290

Tablet Preparation

Tablets containing 25.0, 50.0, and 100.0 mg, respectively, of the following active compounds are prepared as illustrated below:

a. 4-(4-methylthiazol-2-yl)-5-methylthiothiophene-2-carboxamidine;
b. 4-[4-(4-phenylphenyl)thiazol-2-yl]-5-methylthiothiophene-2-carboxamidine.

| TABLET FOR DOSES CONTAINING FROM 25–100 MG OF THE ACTIVE COMPOUND | | | |
|---|---|---|---|
| | Amount-mg | | |
| Active Compound | 25.0 | 50.0 | 100.00 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the cornstarch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 291

Intravenous Solution Preparation

An intravenous dosage form of the above-indicated active compounds is prepared as follows:

| Active Compound | 0.5–10.0 mg |
|---|---|
| Sodium Citrate | 5–50 mg |
| Citric Acid | 1–15 mg |
| Sodium Chloride | 1–8 mg |
| Water for Injection (USP) | q.s. to 1 ml |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md. (1994).

EXAMPLE 292

In vitro Inhibition of Purified Enzymes

Reagents: All buffer salts were obtained from Sigma Chemical Company (St. Louis, Mo.), and were of the highest purity available. The enzyme substrates, N-benzoyl-Phe-Val-Arg-p-nitroanilide (Sigma B7632), N-benzoyl-Ile-Glu-Gly- Arg-p-nitroanilide hydrochloride (Sigma B2291), N-p-tosyl-Gly-Pro-Lys-p-nitroanilide (Sigma T6140), N-succinyl-Ala-Ala-Pro-Phe-p-nitroanilide (Sigma S7388) and N-CBZ-Val-Gly-Arg-p-nitroanilide (Sigma C7271) were obtained from Sigma. N-Succinyl-Ala-Ala-Pro-Arg-p-nitroanilide (BACHEM L-1720) and N-succinyl-Ala-Ala-Pro-Val-p-nitroanilide (BACHEM L-1770) were obtained from BACHEM (King of Prussia, Pa.).

Human α-thrombin, human factor Xa and human plasmin were obtained from Enzyme Research Laboratories (South Bend, Ind.). Bovine α-chymotrypsin (Sigma C4129), bovine trypsin (Sigma T8642) and human kidney cell urokinase (Sigma U5004) were obtained from Sigma. Human leukocyte elastase was obtained from Elastin Products (Pacific, Mo.).

$K_i$ Determinations: All assays are based on the ability of the test compound to inhibit the enzyme catalyzed hydrolysis of a peptide p-nitroanilide substrate. In a typical $K_i$ determination, substrate is prepared in DMSO, and diluted into an assay buffer consisting of 50 mM HEPES, 200 mM NaCl, pH 7.5. The final concentrations for each of the substrates is listed below. In general, substrate concentrations are lower than the experimentally determined value for $K_m$. Test compounds are prepared as a 1.0 mg/mL solution in DMSO. Dilutions are prepared in DMSO yielding 8 final concentrations encompassing a 200 fold concentration range. Enzyme solutions are prepared at the concentrations listed below in assay buffer.

In a typical $K_i$ determination, into each well of a 96 well plate is pipetted 280 μL of substrate solution, 10 μL of test compound solution, and the plate allowed to thermally equilibrate at 37° C. in a Molecular Devices plate reader for >15 minutes. Reactions were initiated by the addition of a 10 μL aliquot of enzyme and the absorbance increase at 405 nm is recorded for 15 minutes. Data corresponding to less than 10% of the total substrate hydrolysis were used in the calculations. The ratio of the velocity (rate of change in absorbance as a function of time) for a sample containing no test compound is divided by the velocity of a sample containing test compound, and is plotted as a function of test compound concentration. The data are fit to a linear regression, and the value of the slope of the line calculated. The inverse of the slope is the experimentally determined $K_i$ value.

Thrombin: Thrombin activity was assessed as the ability to hydrolyze the substrate N-succinyl-Ala-Ala-Pro-Arg-p-nitroanilide. Substrate solutions were prepared at a concentration of 32 μM (32 μM<<Km=180 μM) in assay buffer. Final DMSO concentration was 4.3%. Purified human α-thrombin was diluted into assay buffer to a concentration of 15 nM. Final reagent concentrations were: [thrombin]= 0.5 nM, [substrate N-succinyl-Ala-Ala-Pro-Arg-p-nitroanilide]=32 μM.

Factor X [FXa]: FXa activity was assessed as the ability to hydrolyze the substrate N-benzoyl-Ile-Glu-Gly-Arg-p-nitroanilide hydrochloride. Substrate solutions were prepared at a concentration of 51 μM (51<<$K_m$=1.3 mM) in assay buffer. Final DMSO concentration was 4.3%. Purified activated human Factor X was diluted into assay buffer to a concentration of 300 nM. Final reagent concentrations were: [FXa]=10 nM, [N-benzoyl-Ile-Glu-Gly-Arg-p-nitroanilide hydrochloride]=51 μM.

Plasmin: Plasmin activity was assessed as the ability to hydrolyze the N-p-Tosyl-Gly-Pro-Lys-p-nitroanilide. Substrate solutions were prepared at a concentration of 37 μM (37 μM<<$K_m$=243 μM) in assay buffer. Final DMSO concentration was 4.3%. Purified human plasmin was diluted into assay buffer to a concentration of 240 nM. Final reagent concentrations were: [Plasmin]=8 nM, [N-p-Tosyl-Gly-Pro-Lys-p-nitroanilide]=37 μM.

Chymotrypsin: Chymotrypsin activity was assessed as the ability to hydrolyze N-succinyl-Ala-Ala-Pro-Phe-p-nitroanilide. Substrate solutions were prepared at a concentration of 14 μM (14 μM<<$K_m$=62 μM) in assay buffer. Final DMSO concentration was 4.3%. Purified bovine chymotrypsin was diluted into assay buffer to a concentration of 81 nM. Final reagent concentrations were: [Chymotrypsin]=2.7 nM, [N-succinyl-Ala-Ala-Pro-Phe-p-nitroanilide]=14 μM.

Trypsin: Trypsin activity was assessed as the ability to hydrolyze N-benzoyl-Phe-Val-Arg-p-nitroanilide. Substrate solutions were prepared at a concentration of 13 μM (13 μM<<$K_m$=291 μM) in assay buffer. Final DMSO concentration was 4.3%. Purified bovine trypsin was diluted into assay buffer to a concentration of 120 nM. Final reagent concentrations were: [Trypsin]=4 nM, [N-benzoyl-Phe-Val-Arg-p-nitroanilide]=13 μM.

Elastase: Elastase activity was assessed as the ability to hydrolyze N-succinyl-Ala-Ala-Pro-Val-p-nitroanilide. Substrate solutions were prepared at a concentration of 19 μM (19 μM<<$K_m$=89 μM) in assay buffer. Final DMSO concentration was 4.3%. Purified human leukocyte elastase was diluted into assay buffer to a concentration of 750 nM. Final reagent concentrations were: [Elastase]=25 nM, [N-succinyl-Ala-Ala-Pro-Val-p-nitroanilide]=19 μM.

Urokinase: Urokinase activity was assessed as the ability to hydrolyze N-CBZ-Val-Gly-Arg-p-nitroanilide. Substrate solutions were prepared at a concentration of 100 μM (100 μM<$K_m$=1.2 mM) in assay buffer. Final DMSO concentration was 4.3%. Purified human kidney urokinase was diluted into assay buffer to a concentration of 1.2 μM. Final reagent concentrations were: [Urokinase]=40 nM, and N-CBZ-Val-Gly-Arg-p-nitroanilide]=100 mM.

The results of exemplary assays are shown in the following table.

Protease Inhibition Data

| Protease | Ki micromolar | Example# |
|---|---|---|
| Trypsin | 0.858 | 8 |
| Trypsin | 0.474 | 52 |
| Factor Xa | 2.73 | 94 |
| Factor Xa | 3.00 | 119 |
| Chymotrypsin | 4.90 | 11 |
| tPA | 9.49 | 1 |
| Plasmin | 7.31 | 12 |
| C1S | 0.940 | 283 |

Additionally, the following compounds have Ki values in the range of 0.016 to 3.5 micromolar for uPA:

Ex. #28, 40, 53, 79, 84, 89, 131, 138, 139, 140, 143, 145, 172, 187, 200, 204, 206, 208, 213, 220, 222, 223, 227, 233, 235, 239, 260, 281 and 288.

The results indicate that the compounds of the present invention are inhibitors of proteases, including urokinase.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A compound of Formula I:

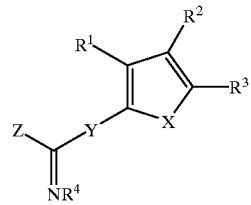

or a solvate, hydrate or pharmaceutically-acceptable salt thereof, wherein:

X is sulfur;

Y is a covalent bond or NH;

Z is $NR^5R^6$;

$R^1$ is a hydrogen, amino, hydroxy or halogen;

$R^2$ is alkylsulfonylamino, aralkylsulfonylamino, aralkenylsulfonylamino, arylsulfonylamino, heteroarylsulfonylamino, di(aralkylsulfonyl)amino, di(aralkenylsulfonyl)amino, di(arylsulfonyl)amino, or di(heteroarylsulfonyl)amino, wherein any of the aryl or heteroaryl containing groups are optionally substituted on the aromatic ring; or amino, monoalkylamino, dialkylamino, monoarylamino, diarylamino, monoalkylmonoarylamino, monoaralkylamino, diaralkylamino, monoalkylmonoaralkylamino, monoheterocycleamino, diheterocycleamino, monoalkylmonoheterocycleamino, wherein any of the aryl or heterocycle containing groups is optionally substituted; or alkanoylamino, alkenoylamino, alkynoylamino, aroylamino, aralkanoylamino, aralkenoylamino, heteroaroylamino, heteroarylalkanoylamino, any of which is optionally substituted on the aromatic ring; or alkoxycarbonylamino, aralkoxycarbonylamino, aryloxycarbonylamino, wherein any of the aryl containing groups is optionally substituted on the aromatic ring; or formylamino, H(S)CNH—, or thioacylamino;

$R^3$ is hydrogen, $C_{1-6}$ alkylthio, $C_{1-6}$ alkyl optionally substituted with OH, $NH_2$, COOH, aminocarbonyl, or $C_{1-6}$ alkoxy; and $R^4$, $R^5$ and $R^6$ are independently hydrogen, $C_{1-4}$ alkyl, aryl, hydroxyalkyl, aminoalkyl, monoalkylamino($C_{2-10}$)alkyl, dialkylamino($C_{2-10}$)alkyl, carboxyalkyl, cyano, amino, alkoxy, or hydroxy, or —$CO_2R^w$, where $R^w$ is alkyl, cycloalkyl, phenyl, benzyl,

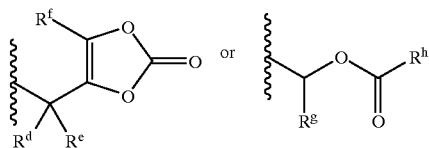

where $R^d$ and $R^e$ are independently hydrogen, $C_{1-6}$ alkyl, $C_{2-6}$ alkenyl or phenyl, $R^f$ is hydrogen, $C_{1-6}$ alkyl, $C_{2-6}$ alkenyl or phenyl, $R^g$ is hydrogen, $C_{1-6}$ alkyl, $C_{2-6}$ alkenyl or phenyl, and $R^h$ is aralkyl or $C_{1-6}$ alkyl.

2. A compound of Formula III,

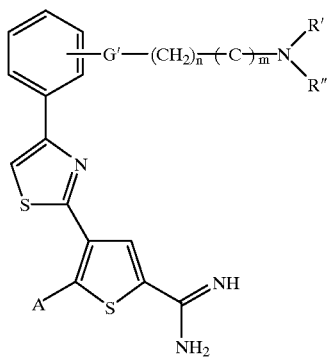

or a salt thereof, wherein

A is methylthio or methyl;

$G^1$ is —O—, —S—, —NH—, or a covalent bond;

n is an integer from 1–10;

m is an integer from 0–1; and

R' and R" are independently selected from hydrogen, alkyl, aryl or aralkyl, or R' and R" taken together with the N atom to which they are attached form a 3–8 membered heterocyclic ring optionally containing an additional O, N, or S atom.

3. A compound according to claim 2, wherein said 3–8 membered heterocyclic ring contains an additional N atom, said additional N atom optionally substituted by hydrogen, $C_{1-4}$alkyl, $C_{6-10}$aryl, $C_{6-10}$ar($C_{1-4}$)alkyl, $C_{1-6}$alkoxy, alkoxycarbonyl or benzyloxycarbonyl.

4. A compound according to claim 2, wherein said 3–8 membered heterocyclic ring is piperazinyl, pyrrolidinyl, piperidinyl or morpholinyl, which is further optionally substituted by 1–4 substituents selected from halogen, hydroxy, amino, monoalkylamino, dialkylamino, formylamino, acylamino, aminoacyl, monoalkylaminocarbonyl, dialkylaminocarbonyl, thiocarbonylamino, thioacylamino, aminothiocarbonyl, alkoxy, aryloxy, aminocarbonyloxy, monoalkylaminocarbonyloxy, dialkylaminocarbonyloxy, monoarylaminocarbonyloxy, diarylaminocarbonyloxy, monoarakylaminocarbonyloxy, diaralkylaminocarbonyloxy, alkylsulfonyl, arylsulfonyl, aralkylsulfonyl, alkylsulfonylamino, arylsulfonylamino, arakylsulfonylamino, alkoxycarbonylamino, aralkoxycarbonylamino, aryloxycarbonylamino, mono alkylaminothiocarbonyl, dialkylaminothiocarbonyl, aralkoxy, carboxy, carboxyalkyl, alkoxycarbonyl, alkoxycarbonylalkyl, nitro, cyano, trifluoromethyl, alkylthio and arylthio.

5. A compound of Formula IV

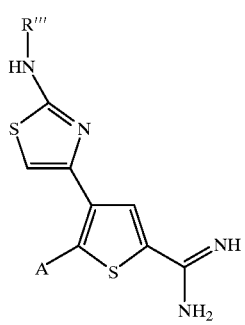

wherein

A is methylthio or methyl; and

R'" is hydrogen, $C_{6-14}$aryl, $C_{1-6}$alkyl, alkoxy($C_{6-4}$)aryl, amino($C_{6-14}$)aryl, monoalkylamino($C_{6-14}$)aryl, dialkylamino($C_{6-14}$)aryl, $C_{6-10}$ar($C_{1-6}$)alkyl, $C_{1-6}$alk($C_{6-14}$)aryl, amino($C_{1-6}$)alkyl, monoalkylamino ($C_{1-6}$) alkyl, dialkylamino ($C_{1-6}$)alkyl, hydroxy($C_{6-14}$)aryl, or hydroxy($C_{1-6}$)alkyl, any of which is further optionally substituted by 1–4 non-hydrogen substituents selected from halogen, hydroxy, amino, monoalkylamino, dialkylamino, formylamino, acylamino, aminoacyl, mono- or di-alkylaminocarbonyl, thiocarbonylamino, thioacylamino, aminothiocarbonyl, alkoxy, aryloxy, aminocarbonyloxy, mono- or di-alkylaminocarbonyloxy, mono- or diarylaminocarbonyloxy, mono- or diarakylaminocarbonyloxy, alkylsulfonyl, arylsulfonyl, aralkylsulfonyl, alkylsulfonylamino, arylsulfonylamino, arakylsulfonylamino, alkoxycarbonylamino, aralkoxycarbonylamino, aryloxycarbonylamino, mono- or di-alkylaminothiocarbonyl, aralkoxy, carboxy, carboxyalkyl, alkoxycarbonyl, alkoxycarbonylalkyl, nitro, cyano, trifluoromethyl, alkylthio and arylthio.

6. A method of treating a disease selected from benign prostatic hypertrophy, prostatic carcinoma, tumor metastisis, restenosis and psoriasis, comprising administering to a patient in need of such treatment an effective amount of a compound of Formula I:

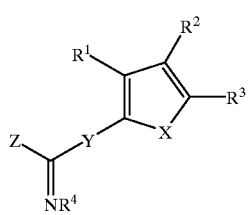

or a solvate, hydrate or pharmaceutically-acceptable salt thereof, wherein:

X is oxygen, sulfur or $NR^7$;

$R^7$ is hydrogen, alkyl, aralkyl, hydroxy($C_{3-4}$)alkyl, alkoxy ($C_{3-4}$)alkyl;

Y is a covalent bond, $CH_2$ or NH;

Z is $NR^5R^6$;

$R^1$ is a hydrogen, amino, hydroxy, halogen, cyano, $C_{1-4}$alkyl, —$CH_2R$ where R is hydroxyamino, or $C_{1-3}$ alkoxy;

$R^2$ and $R^3$ are independently:
  i. hydrogen;
  ii. halogen;
  iii. hydroxy;
  iv. nitro;
  v. cyano;
  vi. amino, monoalkylamino, dialkylamino, monoarylamino, diarylamino, monoalkylmonoarylamino, monoaralkylamino, diaralkylamino, alkarylamino, alkoxycarbonylamino, aralkoxycarbonylamino, aryloxycarbonylamino, alkylsulfonylamino, aralkylsulfonylamino, arylsulfonylamino, formylamino, acylamino, H(S)CNH—, or thioacylamino;
  vii. aminocarbonyl, monoalkylaminocarbonyl, dialkylaminocarbonyl, acyl, arylaminocarbonyl, or aminoacyl;
  viii. aminothiocarbonyl, monoalkylaminothiocarbonyl, dialkylaminothiocarbonyl, thioacyl, or aminothioacyl;
  ix. aminocarbonylamino, monoalkylaminocarbonylamino, dialkylaminocarbonylamino, monoarylaminocarbonylamino, diarylaminocarbonylamino, monoaralkylaminocarbonylamino, or diaralkylaminocarbonylamino,
  x. aminocarbonyloxy, monoalkylaminocarbonyloxy, dialkylaminocarbonyloxy, monoarylaminocarbonyloxy, diarylaminocarbonyloxy, monoaralkylaminocarbonyloxy, or diaralkylaminocarbonyloxy,
  xi. aminosulfonyl, monoalkylaminosulfonyl, dialkylaminosulfonyl, monoarylaminosulfonyl, diarylaminosulfonyl, or monoaralkylaminosulfonyl, or diaralkylaminosulfonyl,
  xii. alkoxy or alkylthio, wherein said alkyl portion of said alkoxy or alkylthio group may be optionally substituted;
  xiii. aralkoxy, aryloxy, aralkylthio, or arylthio, wherein the aryl portion of said aralkoxy, aryloxy, aralkylthio or arylthio group may be optionally substituted;
  xiv. alkylsulfonyl, wherein the alkyl portion may be optionally substituted;
  xv. aralkylsulfonyl, or arylsulfonyl, wherein the aryl portion of each group can be optionally substituted,
  xvi. alkenyl or alkynyl;
  xvii. optionally substituted aryl;
  xviii. optionally substituted alkyl;
  xix. optionally substituted aralkyl;
  xx. optionally substituted heterocycle; or
  xxi. optionally substituted cycloalkyl; and
  $R^4$, $R^5$ and $R^6$ are independently hydrogen, $C_{1-4}$ alkyl, aryl, hydroxyalkyl, aminoalkyl, monoalkylamino($C_{2-10}$)alkyl, dialkylamino($C_{2-10}$)alkyl, carboxyalkyl, cyano, amino, alkoxy, or hydroxy.

7. A compound of claim 1, which is one of:
5-methylthio-4-(6-quinolylamino)thiophene-2-carboxamidine;
5-methylthio-4-[(3-phenylphenyl)amino]thiophene-2-carboxamidine;
5-methylthio-4-(3-quinolylamino)thiophene-2-carboxamidine;
5-methylthio-4-(pyrimidin-2-ylamino)thiophene-2-carboxamidine;
4-[(4-cyclohexylphenyl)amino]-5-methylthiothiophene-2-carboxamidine;
methyl 4-amino-5-methylthiothiophene-2-carboxylate;
methyl 4-[(aminothioxomethyl)amino]-5-methylthiothiophene-2-carboxylate;
5-methylthio-4-[(4-phenyl(1,3-thiazol-2-yl))amino]thiophene-2-carboxamidine;
5-methylthio-4-{[4-(4-phenylphenyl)(1,3-thiazol-2-yl)]amino}thiophene-2-carboxamidine;
4-[(5-methyl-4-phenyl(1,3-thiazol-2-yl))amino]-5-methylthiothiophene-2-carboxamidine;
4-{[4-hydroxy-4-(trifluoromethyl)(1,3-thiazolin-2-yl)]amino}-5-methylthiothiophene-2-carboxamidine;
5-methylthio-4-(2-naphthylamino)thiophene-2-carboxamidine;
4-[(4-chlorophenyl)amino]-5-methylthiothiophene-2-carboxamidine;
4-[(3-methylphenyl)amino]-5-methylthiothiophene-2-carboxamidine;
4-[(3-methoxyphenyl)amino]-5-methylthiothiophene-2-carboxamidine;
4-{[3-(methylethyl)phenyl]amino}-5-methylthiothiophene-2-carboxamidine;
5-methylthio-4-[(3-nitrophenyl)amino]thiophene-2-carboxamidine;
4-{[4-(methylethyl)phenyl]amino}-5-methylthiothiophene-2-carboxamidine;
4-[(3,4-dimethylphenyl)amino]-5-methylthiothiophene-2-carboxamidine;
5-methylthio-4-[(4-phenylphenyl)amino]thiophene-2-carboxamidine;
4-[(3-fluoro-4-phenylphenyl)amino]-5-methylthiothiophene-2-carboxamidine;
4-(2H-benzo[d]1,3-dioxolen-5-ylamino)-5-methylthiothiophene-2-carboxamidine;
4-[(4-butylphenyl)amino]-5-methylthiothiophene-2-carboxamidine;
5-methylthio-4-[benzylamino]thiophene-2-carboxamidine;
4-(indan-5-ylamino)-5-methylthiothiophene-2-carboxamnidine;
4-(2,3-dihydrobenzo[b]furan-5-ylamino)-5-methylthiothiophene-2-carboxamidine;
5-methylthio-4-[(2-phenylimidazol-4-yl)amino]thiophene-2-carboxamidine;
5-methylthio-4-[(2-quinolylmethyl)amino]thiophene-2-carboxamidine;
4-{[(3-hydroxyphenyl)methyl]amino}-5-methylthiothiophene-2-carboxamidine;
5-methylthio-4-(phenylcarbonylamino)thiophene-2-carboxamidine;
4-((2E)-3-phenylprop-2-enoylamino)-5-methylthiothiophene-2-carboxamidine;
4-[(4-chlorophenyl)carbonylamino]-5-methylthiothiophene-2-carboxamidine;
4-(cyclohexylcarbonylamino)-5-methylthiothiophene-2-carboxamidine;
methyl 4-[(4-methyl-3-nitrophenyl)carbonylamino]-5-methylthiothiophene-2-carboxylate;
4-(2-furylcarbonylamino)-5-methylthiothiophene-2-carboxamidine;
4-(2,2-dimethylpropanoylamino)-5-methylthiothiophene-2-carboxamidine;
4-{[5-(3,5-dichlorophenoxy)(2-furyl)]carbonylamino}-5-methylthiothiophene-2-carboxamidine;
5-methylthio-4-(1-naphthylcarbonylamino)-thiophene-2-carboxamidine;
5-methylthio-4-(2-quinolylcarbonylamino)thiophene-2-carboxamidine;

4-[(3-methoxyphenyl)carbonylamino]-5-methylthiothiophene-2-carboxamidine;

4-[2-(2-hydroxy-5-methoxyphenyl)acetylamino]-5-methylthiothiophene-2-carboxamidine;

4-[(4-ethoxyphenyl)carbonylamino]-5-methylthiothiophene-2-carboxamidine;

5-methylthio-4-(2-phenoxyacetylamino)-thiophene-2-carboxamidine;

4-[(3-methylphenyl)carbonylamino]-5-methylthiothiophene-2-carboxamidine;

5-methylthio-4-{[3-(phenylmethoxy)phenyl]amino}thiophene-2-carboxamidine;

5-methylthio-4-[(3-phenoxyphenyl)amino]thiophene-2-carboxamidine;

5-methylthio-4-[(4-phenoxyphenyl)amino]thiophene-2-carboxamidine;

4-[(2-methoxyphenyl)amino]-5-methylthiothiophene-2-carboxamidine;

4-[(2-methylphenyl)amino]-5-methylthiothiophene-2-carboxamidine;

4-[(3-chlorophenyl)amino]-5-methylthiothiophene-2-carboxamidine;

4-(methylphenylamino)-5-methylthiothiophene-2-carboxamidine;

5-methyl-4-(phenylamino)thiophene-2-carboxamidine;

4-{[4-(dimethylamino)phenyl]amino}-5-methylthiothiophene-2-carboxamidine;

4-[(4-ethylphenyl)amino]-5-methylthiothiophene-2-carboxamidine;

5-methylthio-4-{[4-(phenylmethoxy)phenyl]amino}thiophene-2-carboxamidine;

5-methylthio-4-{[4-(phenylamino)phenyl]amino}thiophene-2-carboxamidine;

4-[(4-methoxyphenyl)amino]-5-methylthiothiophene-2-carboxamidine;

4-[(3-fluoro-4-methylphenyl)amino]-5-methylthiothiophene-2-carboxamidine;

4-(indan-5-ylamino)-5-methylthiothiophene-2-carboxamidine;

4-[(9-ethylcarbazol-3-yl)amino]-5-methylthiothiophene-2-carboxamidine;

5-methylthio-4-{[(4-phenylphenyl)sulfonyl]amino}thiophene-2-carboxamidine;

4-{bis[(4-phenylphenyl)sulfonyl]amino}-5-methylthiothiophene-2-carboxamidine;

5-methylthio-4-[(2-naphthylsulfonyl)amino]thiophene-2-carboxamidine;

4-[bis(2-naphthylsulfonyl)amino]-5-methylthiothiophene-2-carboxamidine;

4-{[(6-bromo(2-naphthyl))sulfonyl]amino}-5-methylthiothiophene-2-carboxamidine;

4-{bis[(6-bromo(2-naphthyl))sulfonyl]amino}-5-methylthiothiophene-2-carboxamidine;

5-methylthio-4-[(2-naphthylsulfonyl)amino]thiophene-2-carboxamidine;

4-[bis(2-naphthylsulfonyl)amino]-5-methylthiothiophene-2-carboxamidine;

4-{[(2-methylphenyl)sulfonyl]amino}-5-methylthiothiophene-2-carboxamidine;

4-{bis[(2-methylphenyl)sulfonyl]amino}-5-methylthiothiophene-2-carboxamidine;

4-{[(3-methylphenyl)sulfonyl]amino}-5-methylthiothiophene-2-carboxamidine;

4-{bis[(3-methylphenyl)sulfonyl]amino}-5-methylthiothiophene-2-carboxamidine;

4-{[(4-methylphenyl)sulfonyl]amino}-5-methylthiothiophene-2-carboxamidine;

4-{bis[(4-methylphenyl)sulfonyl]amino}-5-methylthiothiophene-2-carboxamidine;

5-methylthio-4-{[benzylsulfonyl]amino}-thiophene-2-carboxamidine;

4-{[(4-methoxyphenyl)sulfonyl]amino}-5-methylthiothiophene-2-carboxamidine;

4-{bis[(4-methoxyphenyl)sulfonyl]amino}-5-methylthiothiophene-2-carboxamidine;

4-{[(4-iodophenyl)sulfonyl]amino}-5-methylthiothiophene-2-carboxamidine;

4-{[(3,4-dimethoxyphenyl)sulfonyl]amino}-methylthiothiophene-2-carboxamidine;

4-{bis[(3,4-dimethoxyphenyl)sulfonyl]amino}-5-methylthiothiophene-2-carboxamidine;

4-{[(2-chlorophenyl)sulfonyl]amino}-5-methylthiothiophene-2-carboxamidine;

4-{[(3-chlorophenyl)sulfonyl]amino}-5-methylthiothiophene-2-carboxamidine;

4-{bis[(3-chlorophenyl)sulfonyl]amino}-5-methylthiothiophene-2-carboxamidine;

4-{[(4-chlorophenyl)sulfonyl]amino}-5-methylthiothiophene-2-carboxamidine;

4-bis[(4-chlorophenyl)sulfonyl]amino}-5-methylthiothiophene-2-carboxamidine;

5-methylthio-4-[(phenylsulfonyl)amino]thiophene-2-carboxamidine;

4[bis(phenylsulfonyl)amino]-5-methylthiothiophene-2-carboxamidine;

4-({[4-tert-butyl)phenyl]sulfonyl}amino)-5-methylthiothiophene-2-carboxamidine;

4-(bis{[4-tert-butyl)phenyl]sulfonyl}amino)-5-methylthiothiophene-2-carboxamidine;

4-{[((1E)-2-phenylvinyl)sulfonyl]amino)-5-methylthiothiophene-2-carboxamidine;

5-methylthio-4-({[4-(phenylsulfonyl)(2-thienyl)sulfonyl}amino)thiophene-2-carboxamidine;

or pharmaceutically acceptable salts or prodrugs thereof.

8. A compound of claim 2, which is one of:

5-methylthio-4-[4-(3-{[N-benzylcarbamoyl]methoxy}phenyl)(1,3-thiazol-2-yl)]thiophene-2-carboxamidine;

4-{4-[3-({N-[(3,4-dimethoxyphenyl)methyl]carbamoyl}methoxy)phenyl](1,3-thiazol-2-yl)}-5-methylthiophene-2-carboxamidine;

5-methylthio-4-[4-(3-{[N-(2-morpholin-4-ylethyl)carbamoyl]methoxy}phenyl)(1,3-thiazol-2-yl)]thiophene-2-carboxamidine;

5-methylthio-4-{4-[3-(2-morpholin-4-yl-2-oxoethoxy)phenyl](1,3-thiazol-2-yl)]thiophene-2-carboxamidine;

5-methylthio-4-{4-[3-(2-oxo-2-piperazinylethoxy)phenyl](1,3-thiazol-2-yl)}thiophene-2-carboxamidine;

4-[4-(3-{[N-(2-aminoethyl)carbamoyl]methoxy}phenyl)(1,3-thiazol-2-yl)]-5methylthiothiophene-2-carboxamidine;

4-(4-{3-[2-(4-acetylpiperazinyl)-2-oxoethoxy]phenyl}(1,3-thiazol-2-yl))-5-methylthiothiophene-2-carboxamidine;

4-(4-{3-[2-(4-methylpiperazinyl)-2-oxoethoxy]phenyl}(1,3-thiazol-2-yl))-5-methylthiothiophene-2-carboxamidine;

5-methyl-4-{4-[3-(2-oxo-2-piperazinylethoxy)phenyl](1,3-thiazol-2-yl)}thiophene-2-carboxamidine;

5-methylthio-4-[4-(3-{(2-oxo-2-[benzylpiperazinyl]ethoxy}phenyl)(1,3-thiazol-2-yl)]thiophene-2-carboxamidine;

(D,L)-4-(4-{3-[2-(3-aminopyrrolidinyl)-2-oxoethoxy]phenyl}(1,3-thiazol-2-yl))-5-methylthiothiophene-2-carboxamidine;

5-methylthio-4-{4-[3-(2-oxo-2-piperidylethoxy)phenyl](1,3-thiazol-2-yl)}thiophene-2-carboxamidine;

(D,L)-ethyl 1-(2-{3-[2-(5-amidino-2-methylthio-3-thienyl)-1,3-thiazol-4-yl]phenoxy}acetyl)piperidine-2-carboxylate;
5-methylthio-4-{4-[3-(2-oxo-2-pyrrolidinylethoxy)phenyl](1,3-thiazol-2-yl)}thiophene-2-carboxamidine;
5-methylthio-4-[4-(3-{2-oxo-2-[4-benzylpiperidyl]ethoxy}phenyl)(1,3-thiazol-2-yl)]thiophene-2-carboxamidine;
(D,L)-4-(4-{3-[2-(3-methylpiperidyl)-2-oxoethoxy]phenyl}(1,3-thiazol-2-yl))-5-methylthiothiophene-2-carboxamidine;
4-(4-{3-[2-(4-methylpiperidyl)-2-oxoethoxy]phenyl}(1,3-thiazol-2-yl))-5-methylthiothiophene-2-carboxamidine;
4-(4-{3-[2-(2-azabicyclo[4.4.0]dec-2-yl)-2-oxoethoxy]phenyl}(1,3-thiazol-2-yl))-5-methylthiothiophene-2-carboxamidine;
(D,L)-ethyl 1-(2-{3-[2-(5-amidino-2-methylthio-3-thienyl)-1,3-thiazol-4-yl]phenoxy}acetyl)piperidine-3-carboxylate;
5-methylthio-4-{4-[3-(2-oxo-2-(1,2,3,4-tetrahydroquinolyl)ethoxy)phenyl](1,3-thiazol-2-yl)}thiophene-2-carboxamidine;
ethyl 1-(2-{3-[2-(5-amidino-2-methylthio-3-thienyl)-1,3-thiazol-4-yl]phenoxy}acetyl)piperidine-4-carboxylate;
4-(4-{3-[2-((3R)-3-hydroxypiperidyl)-2-oxoethoxy]phenyl}(1,3-thiazol-2-yl))-5-methylthiothiophene-2-carboxamidine;
D,L-4-(4-{3-[2-(2-ethylpiperidyl)-2-oxoethoxy]phenyl}(1,3-thiazol-2-yl))-5-methylthiothiophene-2-carboxamidine;
4-(4-{3-[2-((3S)-3-hydroxypyrrolidinyl)-2-oxoethoxy]phenyl}(1,3-thiazol-2-yl))-5-methylthiothiophene-2-carboxamidine;
5-methylthio-4-(4-{3-[N-(5,6,7,8-tetrahydronaphthyl)carbamoyl)methoxy]phenyl}(1,3-thiazol-2-yl))thiophene-2-carboxamidine;
D,L-4-[4-(3-{2-[3-hydroxymethyl)piperidyl]-2-oxoethoxy}phenyl)(1,3-thiazol-2-yl)]-5-methylthiothiophene-2-carboxamidine;
4-{4-[3-(2R)-2-[(phenylamino)methyl]pyrrolidinyl}-2-oxoethoxy)phenyl](1,3-thiazol-2-yl)}-5-methylthiothiophene-2-carboxamidine;
4-[4-(3-{2-[(3R)-3-(methoxymethyl)pyrrolidinyl]-2-oxoethoxy}phenyl)(1,3-thiazol-2-yl)]-5-methylthiothiophene-2-carboxamidine;
1-(2-{3-[2-(5-amidino-2-methylthio-3-thienyl)-1,3-thiazol-4-yl]phenoxy}acetyl)piperidine-3-carboxamide; and
2-{3-[2-(5-{[(tert-butoxy)carbonylamino]iminomethyl}-2-methyl-3-thienyl)-1,3-thiazol-4-yl]phenoxy}acetic acid;
or pharmaceutically acceptable salts or prodrugs thereof.

9. A compound of claim 5, which is one of:
4-(2-amino(1,3-thiazol-4-yl))-5-methylthiophene-2-carboxamidine;
5-methylthio-4-[2-(phenylamino)(1,3-thiazol-4-yl)]thiophene-2-carboxamidine;
4-{2-[(2-chlorophenyl)amino](1,3-thiazol-4-yl)}5-methylthiothiophene-2-carboxamidine;
4-(2-amino-(1,3-thiazol-4-yl))-5-methylthiothiophene-2-carboxamidine;
4-{2-[(2,5-dimethoxyphenyl)amino](1,3-thiazol-4-yl)}-5-methylthiothiophene-2-carboxamidine;
4-{2-[(3-methoxyphenyl)amino](1,3-thiazol-4-yl)}5-methylthiothiophene-2-carboxamidine;
4-{2-[(4-methoxyphenyl)amino](1,3-thiazol-4-yl)}-5-methylthiothiophene-2-carboxamidine;
4-(2-{[4-(dimethylamino)phenyl]amino}(1,3-thiazol-4-yl))-5-methylthiothiophene-2-carboxamidine;
4-{2-[(4-chloro-2-methylphenyl)amino](1,3-thiazol-4-yl)}-5-methylthiothiophene-2-carboxamidine;
4-{2-[(diphenylmethyl)amino](1,3-thiazol-4-yl)}-5-methylthiothiophene-2-carboxamidine;
5-methylthio-4-{2-[(3-phenylpropyl)amino](1,3-thiazol-4-yl)}thiophene-2-carboxamidine;
5-methylthio-4-{2-[(2,4,5-trimethylphenyl)amino](1,3-thiazol-4-yl)}thiophene-2-carboxamidine;
4-{2-[(2-fluorophenyl)amino](1,3-thiazol-4-yl)}-5-methylthiothiophene-2-carboxamidine;
4-{2-[(3-chloro-2-methylphenyl)amino](1,3-thiazol-4-yl)}-5-methylthiothiophene-2-carboxamidine;
4-(2-{[(2-methylethyl)phenyl]amino}(1,3-thiazol-4-yl))-5-methylthiothiophene-2-carboxamidine;
5-methylthio-4-(2-{[4-(phenylmethoxy)phenyl]amino}(1,3-thiazol-4-yl))thiophene-2-carboxamidine;
4-{2-[(2-bromophenyl)amino](1,3-thiazol-4-yl)}-5-methylthiothiophene-2-carboxamidine;
4-{2-[(2,6-dichlorophenyl)amino](1,3-thiazol-4-yl)}-5-methylthiothiophene-2-carboxamidine;
4-{2-[(2-bromo-4-methylphenyl)amino](1,3-thiazol-4-yl)}-5-methylthiothiophene-2-carboxamidine;
5-methylthio-4-{2-[(2-morpholin-4-ylethyl)amino](1,3-thiazol-4-yl)}thiophene-2-carboxamidine;
4-{2-[(2,3-dichlorophenyl)amino](1,3-thiazol-4-yl)}-5-methylthiothiophene-2-carboxamidine;
5-methylthio-4-{2-[(3,4,5-trimethoxyphenyl)amino](1,3-thiazol-4-yl)}thiophene-2-carboxamidine;
5-methylthio-4-{2-[(2-piperidylethyl)amino](1,3-thiazol-4-yl)}thiophene-2-carboxamidine;
4-(2-{[(4-methylphenyl)methyl]amino}(1,3-thiazol-4-yl))-5-methylthiothiophene-2-carboxamidine;
4-(2-{[4-(4-chlorophenoxy)phenyl]amino}(1,3-thiazol-4-yl))-5-methylthiothiophene-2-carboxamidine;
4-(2-{[4-phenoxyphenyl]amino}(1,3-thiazol-4-yl))-5-methylthiothiophene-2-carboxamidine;
5-methylthio-4-(2-{[4-(phenylamino)phenyl]amino}(1,3-thiazol-4-yl))thiophene-2-carboxamidine;
5-methylthio-4-(2-{[4-benzylphenyl]amino}(1,3-thiazol-4-yl))thiophene-2-carboxamidine;
5-methylthio-4-(2-{[4-(piperidylsulfonyl)phenyl]amino}(1,3-thiazol-4-yl))thiophene-2-carboxamidine;
5-methylthio-4-[2-(3-quinolylamino)(1,3-thiazol-4-yl)]thiophene-2-carboxamidine;
5-methylthio-4-[2-(2-naphthylamino)(1,3-thiazol-4-yl)]thiophene-2-carboxamidine;
4-[2-(2H-benzo[3,4-d]1,3-dioxolan-5-ylamino)(1,3-thiazol-4-yl)]-5-methylthiothiophene-2-carboxamidine;
4-{2-[(7-bromofluoren-2-yl)amino](1,3-thiazol-4-yl)}-5-methylthiothiophene-2-carboxamidine;
4-{2-[(4-cyclohexylphenyl)amino](1,3-thiazol-4-yl)}-5-methylthiothiophene-2-carboxamidine;
5-methylthio-4-(2-{[4-(phenyldiazenyl)phenyl]amino}(1,3-thiazol-4-yl))thiophene-2-carboxamidine;
5-methylthio-4-(2-{[3-(hydroxymethyl)phenyl]amino}(1,3-thiazol-4-yl))-thiophene-2-carboxamidine;
4-[2-({3-[(3-methylpiperidyl)methyl]phenyl}amino)(1,3-thiazol-4-yl)]-5methylthiothipohene2-carboxamidine;
4-{2-[(3-hydroxyphenyl)amino](1,3-thiazol-4-yl)}-5-methylthiothiophene-2-carboxamidine;
4-(2-{[4-(carbamoylmethoxy)phenyl]amino}(1,3-thiazol-4-yl))-5-methylthiothiophene-2-carboxamidine;
5-methyl-4-{2-[(3,4,5-trimethoxyphenyl)amino](1,3-thiazol-4-yl)}thiophene-2-carboxamidine;
5-methyl-4-[2-[(4-phenoxyphenyl)amino](1,3-thiazol-4-yl)}thiophene-2-carboxamidine;
5-methyl-4-[2-(phenylamino)(1,3-thiazol-4-yl)]thiophene-2-carboxamidine; and
4-(4-isoxazol-5-yl(1,3-thiazol-2-yl))-5-methylthiothiophene-2-carboxamidine;

or pharmaceutically acceptable salts and prodrugs thereof.

10. A compound of claim 1, wherein the optional substituents on the aromatic ring of any group containing an optionally substituted aromatic ring is selected from halogen, $C_{1-6}$alkyl, $C_{1-6}$alkoxy, hydroxy, nitro, trifluoromethyl, optionally substituted $C_{6-10}$aryl, optionally substituted $C_{6-10}$aryloxy, optionally substituted $C_{6-10}$arylmethoxy, $C_{1-6}$aminoalkyl, carboxy, 3,4-methylenedioxy, 3,4-ethylenedioxy, 3,4-propylenedioxy, amino, mono- or di-($C_{1-6}$)alkylamino, mono- or di-$C_{6-10}$ arylamino, $C_{1-6}$alkylsulfonylamino, $C_{6-10}$arylsulfonylamino, $C_{1-8}$acylamino, $C_{1-8}$alkoxycarbonyl, $C_{1-6}$alkanoylamino, $C_{6-14}$aroylamino, $C_{1-6}$-hydroxyalkyl, methylsulfonyl, phenylsulfonyl, optionally substituted thienyl and tetrazolyl.

11. A compound of claim 1, wherein $R^2$ is $C_{1-6}$ alkylsulfonylamino, $C_{6-10}$ar($C_{1-6}$)alkylsulfonylamino, $C_{6-10}$ar($C_{2-6}$)alkenylsulfonylamino, $C_{6-10}$arylsulfonylamino, heteroarylsulfonylamino, di($C_{6-10}$ar($C_{1-6}$)alkylsulfonyl)amino, di($C_{6-10}$ar($C_{2-6}$) alkenylsulfonyl)amino, di($C_{6-10}$ arylsulfonyl)amino, or di-(heteroarylsulfonyl)amino, wherein any of the aryl or heteroaryl containing groups are optionally substituted on the aromatic ring.

12. A compound of claim 11, wherein $R^2$ is $C_{6-10}$arylsulfonylamino, di-($C_{6-10}$arylsulfonyl)amino, $C_{6-10}$ar($C_{1-3}$)alkylsulfonylamino, di-($C_{6-10}$ar($C_{1-3}$) alkylsulfonyl)amino, or thienylsulfonylamino, any of which is optionally substituted on the aromatic ring.

13. A compound of claim 1, wherein $R^2$ is biphenylsulfonylamino, bis(biphenylsulfonyl)amino, naphth-2-ylsulfonylamino, di(naphth-2-ylsulfonyl)amino, 6-bromonaphth-2-ylsulfonylamino, di(6-bromonaphth-2-ylsulfonyl)amino, naphth-1-ylsulfonylamino, di(naphth-1-ylsulfonyl)amino, 2-methylphenylsulfonylamino, di-(2-methylphenylsulfonyl)amino, 3-methylphenylsulfonylamino, di-(3-methylphenylsulfonyl) amino, 4-methylphenylsulfonylamino, di-(4-methylphenylsulfonyl)amino, benzylsulfonylamino, 4-methoxyphenylsulfonylamino, di-(4-methoxyphenylsulfonyl)amino, 4-iodophenylsulfonylamino, di-(4-iodophenylsulfonyl) amino, 3,4-dimethoxyphenylsulfonylamino, bis- (3,4-dimethoxyphenylsulfonyl)amino, 2-chlorophenylsulfonylamino, di-(2-chlorophenylsulfonyl) amino, 3-chlorophenylsulfonylamino, di-(3-chlorophenylsulfonyl)amino, 4-chlorophenylsulfonylamino, di-(4-chlorophenylsulfonyl)amino, phenylsulfonylamino, di-(phenylsulfonyl)amino, 4-tert-butylphenylsulfonylamino, di-(4-tert-butylphenylsulfonyl) amino, 2-phenylethenylsulfonylamino, or 4-(phenylsulfonyl)thien-2-ylsulfonylamino.

14. A compound of claim 1, wherein $R^2$ is amino, mono ($C_{1-6}$)alkylamino, di($C_{1-6}$)alkylamino, mono($C_{6-10}$) arylamino, di($C_{6-10}$)arylamino, mono($C_{1-6}$)alkylmono ($C_{6-10}$)arylamino, monoar($C_{1-6}$)alkylamino, di($C_{6-10}$)ar ($C_{1-6}$)alkylamino, mono($C_{1-6}$)alkylmono($C_{6-10}$)ar($C_{1-6}$) alkylamino, monoheteroarylamino, diheteroarylamino, or mono($C_{1-6}$)alkylmonoheteroarylamino, wherein any of the aryl or heteroaryl containing groups are optionally substituted on the aromatic ring.

15. A compound of claim 14, wherein $R^2$ is mono($C_{6-10}$) arylamino, mono($C_{1-6}$)alkylmono($C_{6-10}$)arylamino, mono ($C_{6-10}$)ar($C_{1-3}$)alkylamino, mono($C_{1-6}$)alkylmono($C_{6-10}$)ar ($C_{1-3}$)alkylamino, monoheteroarylamino, or mono($C_{1-6}$) alkylmonoheteroarylamino.

16. A compound of claim 1, wherein $R^2$ is anilino, naphtha-2-ylamino, naphtha-1-ylamino, 4-(biphenyl) thiazol-2-ylamino, 4-(phenyl)thiazol-2-ylamino, 4-phenyl-5-methylthiazol-2-ylamino, 4-hydroxy-4-trifluoromethylthiazol-2-ylamino, 3-phenylphenylamino, pyrimidin-2-ylamino, 4-isopropylphenylamino, 3-isopropylphenylamino, 4-phenylphenylamino, 3-fluoro-4-phenylphenylamino, 3,4-methylenedioxyphenylamino, n-butylphenylamino, N-methyl-N-(2-methylphenyl)amino, 3-nitrophenylamino, 4-methoxyphenylamino, 3-methoxyphenylamino, 2-methoxyphenylamino, 2-methylphenylamino, 3-methylphenylamino, 3,4-dimethylphenylamino, 3-chlorophenylamino, 4-chlorophenylamino, 4-(3-fluoro-4-methylphenyl)amino, 4-(indan-5-yl)amino, benzylamino, indanylmethylamino, 2,3-dihydrobenzofuranylmethyl, 2-phenylimidazol-5-yl, 3-hydroxybenzyl, 3-phenoxyphenylamino, 4-phenoxyphenylamino, 3-benzyloxyphenylamino, 4-benzyloxyphenylamino, quinolin-6-ylamino, quinolin-3-ylamino, 4-(phenylamino)phenylamino, 4-(4-ethylphenyl) phenylamino, 4-(dimethylamino)phenylamino, 4-cyclohexylphenylamino, 4-(9-ethylcarbazol-3-yl)amino, 4-(t-butyl)phenylamino, or 4-methylthiophenyl amino.

17. A compound of claim 1, wherein $R^2$ is alkanoylamino, alkenoylamino, aroylamino, aralkanoylamino, aralkenoylamino, heteroaroylamino, or heteroarylalkanoylamino, any of which is optionally substituted on the aryl or heteroaryl moiety.

18. A compound of claim 17, wherein $R^2$ is ($C_{6-10}$) arylcarbonylamino, $C_{6-10}$ar($C_{1-3}$)alkylcarbonylamino, $C_{6-10}$ar($C_{2-3}$)alkenylcarbonylamino, $C_{6-10}$aryloxy($C_{1-3}$) alkylcarbonylamino, $C_{3-8}$cycloalkylcarbonylamino, $C_{1-6}$alkylcarbonylamino, or heteroarylcarbonylamino.

19. A compound of claim 17, wherein $R^2$ is 3-hydroxyphenylcarbonylamino, 2-phenylethenylcarbonylamino, phenylcarbonylamino, cyclohexylcarbonylamino, 4-methyl-3-nitrophenylcarbonylamino, furan-2-ylcarbonylamino, tert-butylcarbonylamino, 5-(3,5-dichlorophenoxy)furan-2-ylcarbonylamino, naphth-1-ylcarbonylamino, quinolin-2-ylcarbonylamino, 4-ethoxyphenylcarbonylamino, phenoxymethylcarbonylamino, or 3-methylphenylcarbonylamino.

20. A method of treating a disease selected from benign prostatic hypertrophy, prostatic carcinoma, tumor metastasis, restenosis and psoriasis, comprising administering to a patient in need of such treatment an effective amount of a compound of claim 2, for a solvate, hydrate or pharmaceutically-acceptable salt thereof.

21. A method of treating a disease selected from benign prostatic hypertrophy, prostatic carcinoma, tumor metastasis, restenosis and psoriasis, comprising administering to a patient in need of such treatment an effective amount of a compound of claim 8, or a solvate, hydrate or pharmaceutically-acceptable salt thereof.

22. A method according to claim 20, wherein said effective amount is between about 0.01 and about 50 milligrams per kilogram per day.

23. A method according to claims 22 wherein said effective amount is between about 0.1 and about 20 milligrams per kilogram per day.

24. A method of inhibiting urokinase, comprising contacting urokinase with a compound of claim 8.

25. A pharmaceutical composition comprising a compound of claim 2, or a solvate, hydrate or pharmaceutically-acceptable ester, salt or ether thereof, and a pharmaceutically-acceptable carrier.

26. A pharmaceutical composition comprising a compound of claim 8, or a solvate, hydrate or pharmaceutically-acceptable ester, salt or ether thereof, and a pharmaceutically-acceptable carrier.

27. A pharmaceutical composition according to claim 25, wherein said compound is present in an amount between about 0.01 and 100 milligrams.

28. A pharmaceutical composition according to claim 25, suitable for parenteral, oral, subcutaneous, intravenous, intramuscular, intraperitoneal, transdermal, buccal or ocular administration.

29. A pharmaceutical composition according to claim 28, suitable for oral administration, wherein said compound is present in an amount between about 0.01 and 100 milligrams.

30. A pharmaceutical composition according to claim 28, suitable for parenteral administration, wherein said compound is present in an amount between about 0.01 and 100 milligrams.

31. A method of treating a disease selected from benign prostatic hypertrophy, prostatic carcinoma, tumor metastasis, restenosis and psoriasis, comprising administering to a patient in need of such treatment an effective amount of a compound of claim 5, or a solvate, hydrate or pharmaceutically-acceptable salt thereof.

32. A method of treating a disease selected from benign prostatic hypertrophy, prostatic carcinoma, tumor metastasis, restenosis and psoriasis, comprising administering to a patient in need of such treatment an effective amount of a compound of claim 9, or a solvate, hydrate or pharmaceutically-acceptable salt thereof.

33. A method according to claim 31, wherein said effective amount is between about 0.01 and about 50 milligrams per kilogram per day.

34. A method according to claim 33, wherein said effective amount is between about 0.1 and about 20 milligrams per kilogram per day.

35. A method of inhibiting urokinase, comprising contacting urokinase with a compound of claim 9.

36. A pharmaceutical composition comprising a compound of claim 5, or a solvate, hydrate or pharmaceutically-acceptable ester, salt or ether thereof, and a pharmaceutically-acceptable carrier.

37. A pharmaceutical composition comprising a compound of claim 9, or a solvate, hydrate or pharmaceutically-acceptable ester, salt or ether thereof, and a pharmaceutically-acceptable carrier.

38. A pharmaceutical composition according to claim 36, wherein said compound is present in an amount between about 0.01 and 100 milligrams.

39. A pharmaceutical composition according to claim 37, suitable for parenteral, oral, subcutaneous, intravenous, intramuscular, intraperitoneal, transdermal, buccal or ocular administration.

40. A pharmaceutical composition according to claim 39, suitable for oral administration, wherein said compound is present in an amount between about 0.01 and 100 milligrams.

41. A pharmaceutical composition according to claim 39, suitable for parenteral administration, wherein said compound is present in an amount between about 0.01 and 100 milligrams.

42. A method of treating a disease selected from benign prostatic hypertrophy, prostatic carcinoma, tumor metastasis, restenosis and psoriasis, comprising administering to a patient in need of such treatment an effective amount of a compound of claim 1, or a solvate, hydrate or pharmaceutically-acceptable salt thereof.

43. A method of treating a disease selected from benign prostatic hypertrophy, prostatic carcinoma, tumor metastasis, restenosis and psoriasis, comprising administering to a patient in need of such treatment an effective amount of a compound of claim 7, or a solvate, hydrate or pharmaceutically-acceptable salt thereof.

44. A method according to claim 42, wherein said effective amount is between about 0.01 and about 50 milligrams per kilogram per day.

45. A method according to claim 44, wherein said effective amount is between about 0.1 and about 20 milligrams per kilogram per day.

46. A method of inhibiting urokinase, comprising contacting urokinase with a compound of claim 7.

47. A pharmaceutical composition comprising a compound of claim 1, or a solvate, hydrate or pharmaceutically-acceptable ester, salt or ether thereof, and a pharmaceutically-acceptable carrier.

48. A pharmaceutical composition comprising a compound of claim 7, or a solvate, hydrate or pharmaceutically-acceptable ester, salt or ether thereof, and a pharmaceutically-acceptable carrier.

49. A pharmaceutical composition according to claim 7, wherein said compound is present in an amount between about 0.01 and 100 milligrams.

50. A pharmaceutical composition according to claim 47, suitable for parenteral, oral, subcutaneous, intravenous, intramuscular, intraperitoneal, transdermal, buccal or ocular administration.

51. A pharmaceutical composition according to claim 50, suitable for oral administration, wherein said compound is present in an amount between about 0.01 and 100 milligrams.

52. A pharmaceutical composition according to claim 50, suitable for parenteral administration, wherein said compound is present in an amount between about 0.01 and 100 milligrams.

53. A method according to claim 6, wherein said effective amount is between about 0.01 and about 50 milligrams per kilogram per day.

54. A method according to claim 53, wherein said effective amount is between about 0.01 and about 20 milligrams per kilogram per day.

55. A method according to claim 53, wherein X is sulfur.

56. A method according to claim 6, wherein said disease is benign prostatic hypertrophy.

57. A method according to claim 6, wherein said disease is prostatic carcinoma.

58. A method according to claim 6, wherein said disease is tumor metastisis.

59. A method according to claim 6, wherein said disease is restenosis.

60. A method according to claim 6, wherein said disease is psoriasis.

* * * * *